US009957510B2

(12) United States Patent
Lee et al.

(10) Patent No.: US 9,957,510 B2
(45) Date of Patent: May 1, 2018

(54) **TRANSCRIPTIONAL CONTROL IN *ALICYCLOBACILLUS ACIDOCALDARIUS* AND ASSOCIATED GENES, PROTEINS, AND METHODS**

(71) Applicant: Battelle Energy Alliance, LLC, Idaho Falls, ID (US)

(72) Inventors: Brady D. Lee, West Richland, WA (US); David N. Thompson, Idaho Falls, ID (US); William A. Apel, Jackson, WY (US); Vicki S. Thompson, Idaho Falls, ID (US); David W. Reed, Idaho Falls, ID (US); Jeffrey A. Lacey, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days. days.

(21) Appl. No.: 15/347,936

(22) Filed: Nov. 10, 2016

(65) Prior Publication Data

US 2017/0058281 A1 Mar. 2, 2017

Related U.S. Application Data

(62) Division of application No. 14/920,598, filed on Oct. 22, 2015, now Pat. No. 9,499,824, which is a division of application No. 14/256,819, filed on Apr. 18, 2014, now Pat. No. 9,187,753, which is a division of application No. 12/380,008, filed on Feb. 20, 2009, now Pat. No. 8,716,011.

(60) Provisional application No. 61/030,820, filed on Feb. 22, 2008.

(51) Int. Cl.
C07K 14/195 (2006.01)
C12N 15/63 (2006.01)
C12N 15/74 (2006.01)

(52) U.S. Cl.
CPC .......... *C12N 15/635* (2013.01); *C07K 14/195* (2013.01); *C12N 15/74* (2013.01)

(58) Field of Classification Search
None
See application file for complete search history.

(56) References Cited

U.S. PATENT DOCUMENTS

| | | | |
|---|---|---|---|
| 4,237,226 A | 12/1980 | Grethlein | |
| 4,581,333 A | 4/1986 | Kourilsky et al. | |
| 4,624,922 A | 11/1986 | Horikoshi et al. | |
| 5,098,825 A | 3/1992 | Tchen et al. | |
| 5,643,758 A | 7/1997 | Guan et al. | |
| 5,882,905 A | 3/1999 | Saha et al. | |
| 5,916,795 A | 6/1999 | Fukunaga et al. | |
| 5,948,667 A | 9/1999 | Cheng et al. | |
| 6,083,733 A | 7/2000 | Gronberg et al. | |
| 6,268,197 B1 | 7/2001 | Schulein et al. | |
| 6,426,211 B1 | 7/2002 | De Buyl et al. | |
| 6,506,585 B2 | 1/2003 | Danielsen et al. | |
| 6,777,212 B2 | 8/2004 | Asakura et al. | |
| 6,833,259 B2 | 12/2004 | Bhosle et al. | |
| 7,727,755 B2 | 6/2010 | Thompson et al. | |
| 7,858,353 B2 | 12/2010 | Thompson et al. | |
| 7,923,234 B2 | 4/2011 | Thompson et al. | |
| 7,960,534 B2 | 6/2011 | Thompson et al. | |
| 8,071,748 B2 | 12/2011 | Thompson et al. | |
| 8,202,716 B2 | 6/2012 | Thompson et al. | |
| 8,298,799 B2 | 10/2012 | Bomscheuer et al. | |
| 8,431,379 B2 | 4/2013 | Thompson et al. | |
| 8,492,114 B2 | 7/2013 | Thompson et al. | |
| 9,222,094 B2 | 12/2015 | Thompson et al. | |
| 9,499,824 B2 * | 11/2016 | Lee ...................... | C07K 14/195 |
| 2003/0134395 A1 | 7/2003 | Shetty | |
| 2003/0233674 A1 | 12/2003 | Gabor | |
| 2003/0233675 A1 | 12/2003 | Cao et al. | |
| 2004/0029129 A1 | 2/2004 | Wang et al. | |
| 2005/0112742 A1 | 5/2005 | Thompson et al. | |
| 2006/0105442 A1 | 5/2006 | Wu et al. | |
| 2006/0211083 A1 | 9/2006 | Katzen et al. | |
| 2007/0082381 A1 | 4/2007 | Wilting et al. | |
| 2007/0099282 A1 | 5/2007 | Thompson et al. | |
| 2007/0134778 A1 | 6/2007 | Benning et al. | |
| 2007/0148728 A1 | 6/2007 | Johnson et al. | |
| 2009/0203107 A1 | 8/2009 | Thompson et al. | |
| 2009/0215168 A1 | 8/2009 | Lee et al. | |
| 2009/0221049 A1 | 9/2009 | Shaw, IV et al. | |
| 2009/0226978 A1 | 9/2009 | Thompson et al. | |
| 2009/0253205 A1 | 10/2009 | Thompson et al. | |
| 2009/0263859 A1 | 10/2009 | Thompson et al. | |
| 2009/0269827 A1 | 10/2009 | Thompson et al. | |
| 2010/0203583 A1 | 8/2010 | Thompson et al. | |
| 2010/0311110 A1 | 12/2010 | Thompson et al. | |
| 2011/0081683 A1 | 4/2011 | Thompson et al. | |
| 2011/0275135 A1 | 11/2011 | Lee et al. | |
| 2012/0015407 A1 | 1/2012 | Thompson et al. | |
| 2016/0046911 A1 | 2/2016 | Thompson et al. | |

FOREIGN PATENT DOCUMENTS

| | | |
|---|---|---|
| DE | 19717893 A1 | 1/1999 |
| WO | 8100577 A1 | 3/1981 |
| WO | 9906584 A1 | 2/1999 |
| WO | 2003068926 A2 | 8/2003 |
| WO | 2005066339 A2 | 7/2005 |
| WO | 2006117247 A1 | 11/2006 |
| WO | 2010014976 A2 | 2/2010 |

OTHER PUBLICATIONS

Auerbach et al., "Lactate dehydrogenase from the hyperthermophilic bacterium Thermotoga maritima: the crystal structure at 2.1 ? resolution reveals strategies for intrinsic protein stabilization," Structure (London, England:1993) 1998; 6(6):769-81.

(Continued)

*Primary Examiner* — Padmavathi Baskar
(74) *Attorney, Agent, or Firm* — TraskBritt

(57) ABSTRACT

Isolated and/or purified polypeptides and nucleic acid sequences encoding polypeptides from *Alicyclobacillus acidocaldarius* are provided. Further provided are methods of modulating transcription or transcription or transcriptional control using isolated and/or purified polypeptides and nucleic acid sequences from *Alicyclobacillus acidocaldarius*.

8 Claims, 196 Drawing Sheets

(56) References Cited

OTHER PUBLICATIONS

Iwata et al., "T and R states in the crystals of bacterial L-lactate dehydrogenase reveal the mechanism for allosteric control," Nature Structural Biology 1, 176-185 (1994).
Olive et al., "The Crystal and Molecular Structure of Yeast L-Lactate Dehydrogenase (Cytochrome b2)" Int. J. of Peptide Protein Res, 5:219-228 (1973).
Uchikoba et al., "Crystal Structure of Non-Allosteric L-Lactate Dehydrogenase From Lactobacillus pentosus at 2.3 ? Resolution: Specific Interactions at Subunit Interfaces," Proteins: Structure, Function, and Genetics, 46:206-214 (2002).
Vieille and Zeikus, 2001, Micro. and Mol. Biol. Rev., vol. 65, No. 1, p. 1-43.
Viikari et al., "Xylanases in bleaching: From an idea to the industry," FEMS Microbiology Reviews 13 (1994) 335-350.
Walker, G. T. et al., 1992, NAR 20: 1691-1696.
Walker, G. T. et al., 1992, PNAS. USA, 89:392-396.
Walseth, Curtis S., Occurrence of Cellulases in Enzyme Preparations from Microorganisms, TAPPI vol. 35, No. 5, May 1952, pp. 228-233.
Ward et al., "Characterization of a new bacteriophage which infects bacteria of the genus Acidiphilium," Journal of General Virology (1993) 74: 2419-2425.
Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.
Whisstock et al. "Prediction of Protein Function from Protein Sequence and Structure" Quarlty Reviews of Biophysics 36, 3 (2003) pp. 307-340 (35 pages).
Witkowski et al. "Conversion of a β-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).
Wright et al., "Ethanol from Biomass by Enzymatic Hydrolysis," Chemical Engineering Progress, Aug 1988, pp. 62-74.
Yuan et al., Expression of acidophilic alpha-amylase from Alicyclobacillus acidocaldarius, Sheng Wu Gong Cheng Xue Bao, Jan. 2005, 21(1)78-83. Abstract only.
Office Action and Examination Report for Canadian Patent Application No. 2,708,279, dated Jul. 6, 2015, 4 pages.
Office Action and Examination Report for Canadian Patent Application No. 2,708,280, dated Jan. 26, 2015, 4 pages.
Office Action and Examination Report for Canadian Patent Application No. 2,712,127, dated Feb. 25, 2015, 8 pages.
Office Action and Examination Report for Canadian Patent Application No. 2,627,334, dated Feb. 2, 2012, 2 pages.
Office Action and Examination Report for Canadian Patent Application No. 2,627,334, dated Oct. 22, 2012, 2 pages.
Office Action for Chinese Patent Application No. 200980106013.4 dated Feb. 14, 2012, 9 pages.
Office Action for Chinese Patent Application No. 200980106043.5 dated Jan. 11, 2013, 7 pages.
Office Action for Chinese Patent Application No. 200980107073.8 dated Aug. 3, 2012, 7 pages.
Office Action for Chinese Patent Application No. 200980106149.5 dated Apr. 20, 2012, 11 pages.
Office Action for Chinese Patent Application No. 200680050210.5 dated Feb. 23, 2011, 11 pages.
Office Action for Chinese Patent Application No. 200980101404.7 dated Aug. 15, 2011, 11 pages.
Office Action for Chinese Patent Application No. 200680050210.5 dated Mar. 28, 2012, 12 pages.
Office Action for Chinese Patent Application No. 200980101404.7 dated Mar. 20, 2012, 7 pages.
Jeffries, 1996, Curr. Op. in Biotech., 7:337-342.
Jones et al., "Cloning and transcriptional analysis of the Thermoanaerobacter ethanolicus strain 39E maltose ABC transport system," Extremophiles 2002, 6:291-299.
Keller et al., "Microbial Pretreatment of Biomass: Potential for Reducing the Severity of Thermochemical Biomass Pretreatment," Applied Biochemistry and Biotechnology, vol. 105-108, 2003.
Kenealy et al., "Rapid 2,2?-bicinchoninic-based xylanase assay compatible with high throughput screening," Biotechnology Letters 25: 1619-1623, 2003.
Kievitis, T. et al., 1991, J. Virol. Methods, 35: 273-286.
Knappert et al., "Partial Acid Hydrolysis of Cellulosic Materials as a Pretreatment for Enzymatic Hydrolysis," Biotechnology and Bioengineering, vol. XXII, pp. 1449-1463 (1980).
Kohler, G. et al., 1975, Nature, 256(5517): 495497.
Kulkarni et al., "Molecular and biotechnological aspects of xylanases," FEMS Microbiology Reviews 23 (1999) 411-456.
Kwoh, D. Y. et al., 1989, PNAS. USA, 86: 1173-1177.
Lau et al., "PCR ligation mutagenesis in transformable streptococci: application and efficiency," Journal of Microbiological Methods 49 (2002) 193-205.
Lauro et al., "Characterization of a β-glycosidase from the thermoacidophilic bacterium Alicyclobacillus acidocaldarius," Extremophiles (2006) 10:301-310.
Lauro et al., "Isolation and characterization of a new family 42 beta-galactosidase from the thermoacidophilic bacterium Alicyclobacillus acidocaldarius: Identification of the active site residues," Biochimica et Biophysica Acta 1784 (2008) 292-301.
Lavarack et al., "The acid hydrolysis of sugarcane begasse hemicellulose to produce xylose, arabinose, glucose and other products," Biomass and Bioenergy 23 (2002) 367-380.
Lee et al., "Oxygen Effects on Thermophilic Microbial Populations in Biofilters Treating Nitric Oxide Containing Off-Gas Streams," Environmental Progress, vol. 20, No. 3, Oct. 2001.
Lin et al., "Purification, Characterization, and Gene Cloning of Thermopsin, a Thermostable Acid Protease from Sulfolobus acidocaldarius," The Journal of Biological Chemistry, 1990, vol. 265, No. 3, pp. 1490-1495.
Liu C, and CE Wyman, 2003, The effect of flow rate of compressed hot water on xylan, lignin, and total mass removal from corn stover, Ind. Eng. Chem. Res., 42:5409-5416.
Lucas et al., C4-Dicarboxylate Transporter/Malic Acid Transport Protein [Alicyclobacillus acidocaldarius LAA1], GenBank Direct Submission, Accession No. EED06059, Dec. 17, 2008 (Retrieved from the Internet Dec. 15, 2009: <URL:http://www.ncbl.nlm.nlh. gov/.
Luckow, V. A., 1993, Baculovirus systems for the expression of human gene products. Curr. Op. Biotechnology 4: 564-572.
Lynd, Lee R., "Overview and Evaluation of Fuel Ethanol from Cellulosic Biomass: Technology, Economics, the Environment, and Policy," Annu. Rev. Energy Environ. 1996, 21:403-65.
Lynd et al., 2002, Micro. and Mol. Biol. Rev., vol. 66, No. 3, p. 506-577.
MacKenzie et al., "Multiple Chromosomes in Bacteria: The Yin and Yang of trp Gene Localization in Rhodobacter sphaeroides 2.4.1," Genetics 153: 525-538 (Oct. 1999).
Malherbe and Cloete, 2002, Re/View in Environmental Science and Bio/Technology, 1: 105-114.
Manchenko, Gennady P., "Handbook of Detection of Enzymes on Electrophoretic Gels," CRC Press, Inc. 1994, pp. 220-240.
Matthews, J. A. et al., 1988, Anal. Biochem., 169: 1-25.
McCoy, Michael, "Chemical Makers Try Biotech Paths," Chemical Engineering News, Jun. 22, 1998, pp. 13-19.
Merrifield, R. D., 1966, J. Am. Chem. Soc., 88(21): 5051-5052.
Michel et al., "Specificity of the protein secretory apparatus: secretion of the heat-labile enterotoxin B subunit pentamers by different species of Gram bacteria," Gene 152 (1995) pp. 41-45.
Miele, E. A. et al., 1983, J. Mol. Biol., 171: 281-295.
Mielenz, 2001, Curr. Op. in Micro., 4:324-329.
Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.
Neddleman and Wunsch, J. Mol. Biol. 48: 443 (1970).
Ng et al., 1981, Applied and Environmental Microbiology, 41(6):1337-1343.

(56) References Cited

OTHER PUBLICATIONS

Ohta et al., "Purification and Characterization of an Acidophilic Xylanase from Aureobasidium pullulans var. melanigenum and Sequence Analysis of the Encoding Gene," Journal of Bioscience and Bioengineering, vol. 92, No. 3, 262-270, 2001.
Olins, P. O., and Lee, S. C., 1993, Recent advances in heterologous gene expression in *E. coli*. Curr. Op. Biotechnology 4: 520-525.
Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.
Pajunen et al., Microbiology (2005) 151, 1209-1218.
Patel et al., (2006), "Medium and long-term opportunities and risks of the biotechnological production of bulk chemicals from renewable resources: The potential of white biotechnology". The BREW Project. Final Report prepared under the European Commission's Growth Programme (DG Research), (publica.fraunhofer.de/eprints/N-48834.pdf).
Examination Report for Australian Patent Application No. 2006312031 dated Jun. 1, 2011, 2 pages.
EC-PDB Database, EC 3.2.1.37 Xylan 1 ,4-beta-xylosidase, Hydrolysis of (1->4)-beta-D-xylans, to remove successive D-xylose residues from teh non-reducing termini, www.ebi.ac.uklthornton-srv/databases/cgi-bin/enzymes/GetPage.pl?ec_number=3.2.1.37, accessed Jan. 28, 2012.
Edwards, C. P., and Aruffo, A., 1993, Current applications of COS cell based transient expression systems. Curr. Op. Biotechnology 4: 558-563.
Ehrman, Tina, "Standard Method for Determination of Total Solids in Biomass," Chemical Analysis and Testing Task, Laboratory Analytical Procedure, Oct. 28, 1994, 242 total pages.
EMBL Submission CP001728, Sep. 2009. [Retrieved from the internet: URL:http://www.ebi.ac.uk/Tools/dbfetch/embifetch?style=html&id=CP001728&Submit=Go], 51 pages.
Erlich, H.A., J Clin. Immunol., Nov. 1989; 9(6):437-47.
Extended Supplementary European Search Report for EP 09 74 3132, dated Apr. 19, 2013, 4 pages.
Extended Supplementary European Search Report for EP 09 70 3173, dated Mar. 25, 2011, 7 pages.
Extended Supplementary European Search Report for EP 09 70 9191, dated Mar. 29, 2012, 6 pages.
Extended Supplementary European Search Report for EP 09 75 5307, dated Apr. 18, 2012, 4 pages.
Extended Supplementary European Search Report for EP 09 75 5308, dated Jun. 18, 2013, 3 pages.
Extended Supplementary European Search Report for EP 10 74 6882, dated Aug. 27, 2012, 9 pages.
Extended Supplementary European Search Report for EP 09 82 3952, dated Sep. 20, 2011, 7 pages.
European Office Action for EP 06 82 7231, dated Mar. 2, 2010, 3 pages.
European Office Action for EP 06 82 7231, dated Dec. 7, 2010, 5 pages.
European Office Action for EP 06 82 7231, dated Feb. 7, 2012, 10 pages.
Fan et al., "The Nature of Lignocellulosics and Their Pretreatments for Enzymatic Hydrolysis," Advances in Biochemical Engineering/Biotechnology, 1982, vol. 23/1982, 157-187.
Fillinger et al., "Two Glyceraldehyde-3-phosphate Dehydrogenases with Opposite Physiological Roles in a Nonphotosynthetic Bacterium", The Journal of Biological Chemistry, vol. 275, No. 19, Issue of May 2000, pp. 14031-14037.
Flanagan, et al., "Development of gas phase bioreactors for the removal of nitrogen oxides from synthetic flue gas streams," Fuel 81 (2002) 1953-1961.
Fushinobu et al., "Crystallographic and mutational analyses of an extremely acidophilic and acid-stable xylanase: biased distribution of acidic residues and importance of Asp37 for catalysis at low pH," Protein Engineering vol. 11, vol. 12, pp. 1121-1128, 1998.

Garrote, G, H Dominguez, and JC Parajo, 2001, Manufacture of xylose-based fermentation media from corncobs by posthydrolysis of autohydrolysis liquors, Appl. Biochem. Biotechnol., 95:195-207.
GenBank: AJ252161.1 *Alicyclobacillus acidocaldarius* maltose/maltodextrins transport gene region(malEFGR genese, cdaA gene and glcA gene), NCBI, Hulsmann, A. http://www.ncbi.nlm.nih.gov/nuccore/AJ252161 (Jan. 6, 2000).
GenBank: E17054.1 Direct Submission *Alicyclobacillus acidocaldarius* genomic DNA clone pOP3 containing acyl carrier protein gene. Nov. 5, 2005 [Retrieved from the Internet Jan. 23, 2010: http://www.ncbi.nlm.nih.gov/nuccore/E17054.1?ordinalpos=2&tool=Entr.
Gessesse, Amare, "Purification and Properties of Two Thermostable Alkaline Xylanases from an *Alkaliphilic bacillus* sp.," Applied and Environmental Microbiology, Sep. 1998, pp. 3533-3535.
Glenn et al., "Transformation of Acidiphilium by electroporation and conjugation," Can J Microbial. May 1992;38 (5):387-93.
Goldstein et al., "The Hydrolysis of Cellulose with Superconcentrated Hydrochloric Acid," Biotechnology and Bioengineering Symp. No. 13, pp. 17-25 (1983).
Grassin et al., "Chapter 2.13, Fruit Juices," (T. Godfrey and S. West, eds.), Industrial Enzymology, 2nd Ed., pp. 227-264 (1996).
Grethlein, H. E., "Pretreatment for enhanced hydrolysis of cellulosic biomass," Biotechnol. Adv. 1984. 2:43-62.
Grethlein, Hans E., "Comparison of the Economics of Acid and Enzymatic Hydrolysis of Newsprint," Biotechnology and Bioengineering, vol. XX, pp. 503-525 (1978).
Guateli, J. C. et al., 1990, PNAS. USA, 87: 1874-1878.
Hamelinck, CN, G van Hooijdonk, and APC Faaij, 2005, Ethanol from lignocellulosic biomass: techno-economic performance in short-, middle-, and long-term, Biomass Bioenergy, 28:384-410.
Hanselmann, K.W., "Lignochemicals," Experientia 38 (1982) pp. 176-189.
Houghton et al., "Fungal Upgrading of Wheat Straw for Straw-Thermoplastics Production," Applied Biochemistry and Biotechnology, vol. 113-116, 2004, pp. 71-93.
Hulsmann et al., "Maltose and maltodextrin transport in the thermoacidophilic gram-positive bacterium *Alicyclobacillus acidocaldarius* is mediated by a high-affinity transport system that includes a maltose binding protein tolerant to low pH," J. Bacteriology, Nov. 2000, p. 6292-6301.
Huygen, K. et al., 1996, Nature Medicine, 2(8): 893-898.
International Preliminary Report on Patentability and Written Opinion of the International Searching Authority for PCT/US06/42566 dated Apr. 23, 2009, 7 pages.
International Search Report and Written Opinion of the International Search Authority for PCT/US09/32333, dated Jun. 19, 2009, 9 pages.
International Search Report of the International Searching Authority for PCT/US06/42566, dated Jul. 25, 2008.
Ito et al., "Purification and properties of acid stable xylanases from Aspergillus kawachii," Bioscience Biotechnology and Biochemistry 56 (4):547-550, Apr. 1992.
Examination Report for Malaysia Patent Application No. PI 20081221 dated Aug. 30, 2010, 5 pages.
Examination Report for New Zealand Patent Application No. 587185 dated Jun. 21, 2011, 2 pages.
Examination Report for New Zealand Patent Application No. 587188 dated Mar. 8, 2011, 3 pages.
Examination Report for New Zealand Patent Application No. 595377 dated Nov. 7, 2011, 2 pages.
Examination Report for New Zealand Patent Application No. 586498 dated Mar. 1, 2011, 2 pages.
Examination Report for New Zealand Patent Application No. 585947 dated Feb. 28, 2011, 1 page.
Examination Report for New Zealand Patent Application No. 585950 dated Feb. 24, 2011, 2 pages.
Examination Report for New Zealand Patent Application No. 587062 dated Mar. 8, 2011, 3 pages.
Examination Report for New Zealand Patent Application No. 567774 dated Mar. 18, 2010, 2 pages.
Examination Report for New Zealand Patent Application No. 587062 dated Jul. 18, 2011, 2 pages.

(56) References Cited

OTHER PUBLICATIONS

Examination Report for New Zealand Patent Application No. 567774 dated May 27, 2011, 2 pages.
Accession C8WVP7. Nov. 3, 2009.
Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.
Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).
Badger, P.C., "Ethanol from cellulose: A general review," In: J. Janick and A. Whipkey (eds.), Trands in new crops and new uses. ASHS Press, Alexandria, VA, 2002, pp. 17-21.
Bailey et al., "Interlaboratory testing of methods for assay of xylanase activity," Journal of Biotechnology, 23 (1992) 257-270.
Barany, F., 1991, PNAS. USA, 88: 189-193.
Bergquist et al., "Molecular diversity of thermophilic cellulolytic and hemicellulolytic bacteria," FEMS Microbiology Ecology 28 (1999) 99-110.
Bertoldo et al., 2004, Eng. Life Sci., 4, No. 6.
Bhatia et al., "Microbial beta-Glucosidases: Cloning, Properties, and Applications," Critical Reviews in Biotechnology, 22(4):375-407, Jan. 1, 2002.
Blast Search of Seq. ID. 464, accessed Apr. 22, 2009, 45 pages.
Blast Search of Seq. ID. 36, accessed Apr. 22, 2009, 54 pages.
Blast Search of Seq. ID. 456, accessed Apr. 22, 2009, 48 pages.
Blast Search of Seq. ID. 458, accessed Apr. 22, 2009, 59 pages.
Blast Search of Seq. ID. 460, accessed Apr. 22, 2009, 37 pages.
Blast Search of Seq. ID. 462, accessed Apr. 22, 2009, 35 pages.
Bork, Peer, "Powers and Pitfalls in Sequence Analysis: The 70% Hurdle," Genome Research, 2000, 10:398-400.
Borman, S., 2006, Glycosylation Engineering. Chem. Eng. News, 84(36): 13-22.
Bowie et al., "Deciphering the Message in Protein Sequences: Tolerance to Amino Acid Substitutions," Science, 1990, 247:1306-1310.
Breves et al., "Genes Encoding Two Different beta-Glucosidases of Thermoanaerobacter brockii Are Clustered in a Common Operon," Applied and Environmental Microbiology, vol. 63, No. 10, Oct. 1997, pp. 3902-3910.
Broun et al. "Catalytic Plasticity of Fatty Acid Modification Enzymes Underlying Chemical Diversity of Plant Lipids" Science vol. 282 Nov. 13, 1998 pp. 1315-1317 (4 pages).
Buckholz, R. G., 1993, Yeast systems for the expression of heterologous gene products. Curr. Op. Biotechnology 4: 538-542.
Burg, J. L. et al., 1996, Mol. and Cell. Probes, 10: 257-271.
Chu, B. C. F. et al., 1986, NAR, 14: 5591-5603.
Collins et al., "Xylanaes, Xylanase Families and Extremophilic Xylanses," FEMS Microbiology Review, 2005, pp. 3-23.
Cowling, Ellis B., "Physical and Chemical Constrains in the Hydrolysis of Cellulose and Lignocellulosic Materials," Biotechnol. & Bioeng. Symposium No. 5, 163-181 (1975).
Crout et al., "Glycosidases and glycosyl transferases in glycoside and oligosaccharide synthesis," Current Opinion in Chemical Biology, Current Biology LTD, London, GB, vol. 2, No. 1, Feb. 1, 1998, pp. 98-111.
Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.
Database EMBL [Online]. Mar. 16, 2007. XP-002627757. Database accession No. ER073884, 1 page.
Database UniProt [Online]. Feb. 10, 2009. XP-002695727. Database accession No. B7DUZ1, 1 page.
Database UniProt [Online]. Feb. 10, 2009. XP-002698982. Database accession No. B7DRM6, 1 page.
Database SCORE [Online]. Feb. 10, 2009. Database accession No. B7DQJ6, 2 pages.
Database SCORE [Online]. Nov. 3, 2009. Database accession No. C8WYA8, 2 pages.
Database Geneseq [Online]. May 21, 1998. XP-002627734. Database accession No. AAW35004, 1 page.
Database UniProt [Online]. May 1, 1997. XP-002630045. Database accession No. P96090, 1 page.
Database UniProt [Online]. Oct. 1, 2001. XP-002627736. Database accession No. Q97UI4, 1 page.
Database UniProt [Online]. Feb. 10, 2009. XP-000002659383. Database accession No. B7DT70, 1 page.
Database UniProt [Online]. Jun. 26, 2007. XP-002627735. Database accession No. A5IKZ4, 1 page.
Database UniProt [Online]. Nov. 3, 2009. XP-002627733. Database accession No. C8WTP2, 1 page.
Database Uniprot [Online]. Nov. 3, 2009. Database accession No. C8WVZ2, 2 pages.
Database UniProt [Online]. Feb. 10, 2009. XP-002674095. Database accession No. B7DM51, 1 page.
Devos et al. "Practical Limits of Functiona Prediction" Proteins: Structure, Function, and Genetics 41 (2000) pp. 98-107 (10 pages).
Doan et al., "Regulation of the central glycolytic genes in Bacillus subtilis: binding of the repressor CggR to its single DNA target sequence is modulated by fructos-1,6-bisphosphate", Molecular Microbiology, 47(6), 2003, pp. 1709-1721.
Duck, P. et al., 1990, Biotechniques, 9: 142-147.
EC-PDB Database, EC 3.2.1.21 Beta Glucosidase, Hydrolysis of terminal, non-reducing beta-D-Giucosyl Residues with release of Beta-D-glucose, www.ebi.ac.uklthornton-srv/databases/cgi-bin/enzymes/GetPage.pl?ec_number=3.2.1.21, accessed Jan. 28, 2012.
EC-PDB Database. EC 3.2.1.23 Beta Galactosidase. Hydrolysis of terminal non-reducing beta-D-galactose residues in beta-D-galactosides, www.ebi.ac.uklthornton-srv/databases/cgi-bin/enzymes/GetPage.pl?ec_numbers=3.2.1.23, accessed Jan. 28, 2012.
EC-PDB Database, EC 3.2.1.55 Alpha-N-arabinofuranosidase, Hydrolysis of terminal non-reducing alpha-L-arabinofuranoside residues in alpha-L-arabinosides, www.ebi.ac.uklthornton-srv/databases/cgi-bin/enzymes/GetPage.pl?ec_number=3.2.1.55, accessed Jan. 28, 2012.
EC-PDB Database, EC 3.2.1.91 Cellulose 1,4-beta-cellobiosidase (non-reducing end), Hydrolysis of (1->4)-beta-D-glucosidic linkages in cellulose and cellotetraose, releasing cellobiose from the non-reducing ends of the chains, www.ebi.ac.uklthornton-srv/databases/cgi-bin/enzymes/GetPage.pl?ec_number=3.2.1.91, accessed Jan. 28, 2012.
Eckert et al., "A Thermoacidophilic Endoglucanase (CelB), etc.," Eur. J. Biochem. 270, 2003, pp. 3593-3602.
Eckert et al., "Gene cloning, sequencing, and characterization of a family 9 endoglucanase (CelA) with an unusual pattern of activity from the theremoacidophile Alicyclobacillus acidocaldarius ATCC27009," Applied Microbiology and Biotechnology, vol. 60, pp. 428-436 (2002).
Eckert, Kelvin, "Dissertation, Cloning and Characterization of two glycosidases from the acidothermophile Alicyclobacillus acidocaldarius ATCC27009," Berlin, Dec. 18, 1971, 113 pages.
Chica et al., "Semi-rational approaches to engineering enzyme activity: combining the benefits of directed evolution and rational design", Curr Opin Biotechnol, (Aug. 2005) 16(4): 378-84.
Singh et al., "Protein Engineering Approaches in the Post-Genomic Era", Curr Protein Pept Sci. (2017) 18, pp. 1-11.
Dilauro et al. "Characterization of a p-glycosidase from the thermoacidophilic bacterium Alicyclobacillus acidocaldarius", Extremophiles (2006) 10:301-310.
Supplemental European Search Report for EP 06 82 7231, dated Nov. 11, 2009, 6 pages.
PCT International Search Report and Written Opinion of the International Searching Authority for PCT/US10/51095, dated Dec. 2, 2010, 11 pages.
PCT International Search Report and Written Opinion of the International Searching Authority for PCT/US09/35275, dated Feb. 25, 2010, 13 pages.

(56) References Cited

OTHER PUBLICATIONS

PCT International Search Report and Written Opinion of the International Search Authority for PCT/US09/35307, dated Jun. 10, 2010, 10 pages.
PCT International Search Report and Written Opinion of the International Searching Authority for PCT/US09/35331, dated Feb. 23, 2010, 10 pages.
PCT International Search Report and Written Opinion of the International Searching Authority for PCT/US09/00442, dated May 18, 2009, 8 pages.
PCT International Search Report and Written Opinion of the International Search Authority for PCT/US10/25521, dated Jul. 14, 2010, 12 pages.
PCT International Search Report and Written Opinion of the International Searching Authority for PCT/US09/34701, dated Jan. 12, 2010, 10 pages.
PCT International Search Report and Written Opinion of the International Search Authority for PCT/US11/34852, dated Oct. 21, 2011, 12 pages.
Pearson and Lipman, Proc. Natl. Acad. Sci. (U.S.A.) 85: 2444 (1988).
Perlack et al., "Biomass as Feedstock for a Bioenergy and Bioproducts Industry: The Technical Feasibility of a Billion-Ton Annual Supply," USDA and DOE, Apr. 2005, 78 pages.
Peyton et al., "Biotransformation of Toxic Organic and Inorganic Contaminants by Halophilic Bacteria," Halophilic Microorganisms, Antionio Ventosa (Ed.), Springer, 2004, pp. 315-331.
UniProtKB/TrEMBL Q9JRQ1 [online]. Oct. 1, 2000. Available on the Internet at <<URL://http://www.uniprot.org/uniprot/Q9JRQ1>>.
Uniprot Direct submission Q9RHZ5_ALIAC, "Putative maltose transport membrane protein malF," Nov. 13, 2007. Retrieved from the Internet Jan. 22, 2010: <http://www.uniprot.org/uniprot/Q9RHZ5.txt?version=30?].
Ragauskas et al., "The Path Forward for Biofuels and Biomaterials," Science, Jan. 27, 2006, vol. 311, pp. 484-4589.
Ramos et al., "Biomechanical and Biochemical Pulping of Sugarcane Bagasse with Ceriporiopsis subvermispora Fungal and Xylanase Pretreatments," J. Agric. Food Chem. 2001, 49, 1180-1186.
Rezacova et al., "Crystal structures of the effector-binding domain of repressor Central glycolytic gene Regulator from Bacillus subtilis reveal ligand-induced structural changes upon binding of several glycolytic intermediates", Mol Microbiol., 69(4): Aug. 2008, pp. 895-910.
Sa-Pereira et al., "Rapid production of thermostable cellulose-free xylanase by a strain of Bacillus subtilis and its properties," Enzyme and Microbial Technology, 30 (2002) 924-933.
Saeman et al., "Quantitative Saccharification of Wood and Cellulose," Industrial and Engineering Chemistry, Jan. 1945, vol. 17, No. 1, pp. 35-37.
Saha et al., "Dilute Acid Pretreatment, Enzymatic Saccharification, and Fermentation of Rice Hulls to Ethanol," Biotechnol. Prog. 2005, 21, 816-822.
Sanchez-Pescador, R., 1988, J. Clin. Microbiol., 26(10): 1934-1938.
Schafer et al., "X-ray Structures of the Maltose-Maltodextrin-binding Protein of the Thermoacidophilic Bacterium *Alicyclobacillus acidocaldarius* Provide Insight into Acid Stability of Proteins," J. Mol. Biol. 2004, 335:261-274.
Schäffer, C. et al., 2001, Prokaryotic glycosylation. Proteomics, 1: 248-261.
Scheffel et al., "Functional reconstitution of a maltrose ATP-binding cassette transporter from the thermoacidophilic gram-positive bacterium *Alicyclobacillus acidocaldarius*," Biochem Biophy Acta, 2004, 1656(1):57-65.
Schell et al., "Dilute-Sulfuric Acid Pretreatment of Corn Stover in Pilot-Scale Reactor," Applied Biochemistry and Biotechnology, vol. 105-108, 2003, pp. 69-85.
Schneider, "Import of solutes by ABC transporters—the maltose system. ABC protein: from bacteria to man," Elsevier Science, London 2003, p. 157-185. [Retrieved from the Internet on Jan. 24, 2010; <http://www2.hu-berlin.de/biologie/baktphys/paper/1_ABC/r.
Schwarz, Wolfgang H., "A list of cellulolytic bacteria," Technische Universitat Munchen, Apr. 24, 2003, 8 pages.
Schwermann, B. et al., 1994, Puri?cation, properties and structural aspects of a thermoacidophilic a-amylase from *Alicyclobacillus acidocaldarius* ATCC 27009, insight into acidostability of proteins. Eur. J. Biochem. 226: 981-991.
Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).
Shallom et al., "Microbial hemicellulases," Current Opinion in Microbiology, Current Biology Ltd, GB, vol. 6, No. 3, Jun. 1, 2003, pp. 219-228.
Simpson et al., "An extremely Thermostable xylanase from the thermophilic eubacterium Thermotoga," Biochem. J. (1991) 277, 413-417.
Skolnick et al. (Trends in Biotechnology 18: 34-39, 2000).
Smook, G.A., "Handbook for Pulp & Paper Technologists," Tappi Pr; 2nd Ed. (Jun. 1992) pp. 65-88.
Somogyi, M., "Notes on Sugar Determination," Journal of Biological Chemistry (1952) pp. 195:19-23.
Subramaniyan et al., "Cellulase-free xylanases from Bacillus and other microorganisms," FEMS Microbiology Letters 183 (2000) 1-7.
Sunna et al., "Glycosyl hydrolases from hyperthermophiles," Extremophiles (1997) 12-13.
Techapun et al., "Production of a cellulose-free xylanase from agricultural waste materials by a thermotolerant *Streptomyces* sp.," Biotechnology Letters 23: 1685-1689, 2001.
Thompson et al., "Comparison of Pretreatment Methods on the Basis of Available Surface Area," Bioresource Technology 39 (1992) 155-163.
Thompson et al., "In Vitro Degradation of Natural Insoluble Lignin in Aqueous Media by the Extracellular Peroxidases of Phanerochaete chrysosporium," 1998 John Wiley & Sons, Inc. pp. 704-717.
Thompson et al., "Measurement of fumonsins in corn with a fiber-optic fluoroimmunosensor," SPIE vol. 2980, (2010) pp. 532-538.
Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.
Thompson et al., "Purification and Characterization of a Novel Thermo-Alkali-Stable Catalase from Thermus brockianus," Biotechnol. Prog. 2003, 19, 1292-1299.
Thompson et al., "Thermoacidophilic Cellulases and Hemicellulases from *Alicyclobacillus acidocaldarius*," Idaho National Laboratory, 2006, 1 page.
Thompson, et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.
Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.
Tsao, GT, MR Ladisch, and HR Bungay, 1987. Biomass Refining, In Advanced Biochemical Engineering, Wiley Interscience, N.Y., 79-101.
Turner et al., "Potential and utilization of thermophiles and thermostable enzymes in biorefining," Microbial Cell Factories, Biomed Central, London, NL, vol. 6, No. 1, Mar. 15, 2007, p. 9.
Uhl et al., "The first description of an archaeal hemicellulase: the xylanase from Thermococcus zilligii strain AN1," Extremophiles (1999) 3:263-267.

(56) References Cited

OTHER PUBLICATIONS

Upreti et al., 2003, Bacterial glycoproteins: Functions, biosynthesis and applications. Proteomics, 3: 363-379.
Urdea, M. S., 1988, Nucleic Acids Research, II: 4937-4957.

* cited by examiner

FIG. 1

```
ref|YP_001210812.1|      ---------------------------------------MKEKEVILTVNGLKKL
ref|YP_001111548.1|      ---------------------------------------MKEKDVMLTVTGLKQL
ref|ZP_01666866.1|       ---------------------------------------MAEKQTILTVDGLKKI
RAAC01465                MTIPFFRTMVSSMAHSARAARDGMHASRYSGSLEAPTGSKGETAMADKEVLLTPEGLRKL
ref|YP_001039288.1|      ---------------------------------------NKEVVLTYEGLQKL
ref|ZP_01576004.1|       ---------------------------------------MSAKEVVLTYEGLKKL
                                                                *:..:**   **:::

ref|YP_001210812.1|      ESELELLKSVKRREVAERIKQAIEFGDITENSEYEDAKNEQAFIEGRILTLEKMLRNAKI
ref|YP_001111548.1|      EDELEQLKTVKRRQVAERIKQAIEFGDISENSEYEDAKNEQAFIEGRILTLEKMLRNAKI
ref|ZP_01666866.1|       EQKLEHLKSVRRREVAERIKQAIEFGDISENSEYEDAKNEQAFIEGEILTLEKMLRNAKV
RAAC01465                EEELELLKSVKRREVAERIKVAISYGDISENSEYEDAKNEQAFIEGRIMTLEKQLRNARV
ref|YP_001039288.1|      EQELENLKTVKRREVAERIKQALSFGDISENSEYDEAKNEQAYIEGRIFQLENMLKNAKV
ref|ZP_01576004.1|       EEELEFLRGTKRKEVAERIKQALSFGDISENSEYDEAKNEQAQVEGRIVQLESMLKHARI
                         *.:**  *:  .:*::******  *:.:***:*****::****** :**.*. **. *::*::

ref|YP_001210812.1|      IDDENIGTEVVSIGSTVLLKDLECGDEYKYTIVGSAEADPGANKISNESPVGRAILGQPK
ref|YP_001111548.1|      IDDENLDNEVVSLGSKVILKDLEFGDELEYSIVGSVEADPDANKISNESPVGRAILGQSK
ref|ZP_01666866.1        IDEGEISTDTVTIGSTVVLKDLEFGDELEYTLVGSAEADPMEFKISNESPVGQAIMGQKV
RAAC01465                INEDEVDTNVVSIGSTVKVLDLDLDEEVEYTIVGSAEANPAENKISNESPVGKALLGKQI
ref|YP_001039288.1|      IDEEDIQTDVVSIGSKVKVLDMEFDEEVEYYIVGSTEADPSQYKISNESPVGKALIGGKI
ref|ZP_01576004.1        IDEDEVNTDVVSIGSKVRIFDIEFDEEVEYLIVGSTEANPLKSKISNESPVGAALIGHTK
                         *::  ::  .:.*::**.*  :  *::   .:*  :*  :*.:*     ********* *:.:* ref|YP_001210812.1|      GSVVEVTVPAGQLKYQIIDILR
ref|YP_001111548.1|      GSVVEVNVPAGILKYEIVDILR
ref|ZP_01666866.1        GSVVEVNVPAGILKYKILEIKR
RAAC01465                GSIVEVNVPAGVIKFKILEIKR
ref|YP_001039288.1|      GDIVEVTVPDGVIKFKILEIRK
ref|ZP_01576004.1|       GETVEVQVPDGVLKFKILEISK
                         *. *** ** * :*::*::* :
```

FIG. 2

```
ref|YP_145986.1|         ---------------MIEIEKPKIETVELSEDAKYGKFVVEPLERGYGTTLGNSLRRILL
ref|YP_001124263.1       ---------------MIEIEKPKIETVELSEDAKYGKFVVEPLERGYGTTLGNSLRRILL
ref|NP_241028.1|         ---------------MIEIEKPVIETIEISEDAKYGKFVVEPLERGYGTTLGNSLRRILL
RAAC00371                ---------------MIEIEKPRIEIVEQTGD--YGKFVCEPLERGYGTTLGNSLRRILL
ref|YP_001210899.1       ---------------MLEIEKPKIEIVEMSDDNTYGKFVVEPLERGYGITLGNSLRRILL
ref|YP_001111617.1       ---------------MLEIEKPKIEIVEQSEDNTYGKFVVEPLERGYGITLGNSLRRILL
                                        *:***  :* : *  *** **** ********** ref|YP_145986.1|         SSLPGAAVTSVQIDGVLHEFSTIDGVVEDVTAIILNIKKLALKIYSDEEKTLEIDVQGEG
ref|YP_001124263.1|      SSLPGAAVTSVQIDGVLHEFSTIEGVVEDVTAIILNVKKLALKIYSDEEKTLEIDVQGEG
ref|NP_241028.1|         SSLPGAAVTSVQIDGVLHEFSTIEGVVEDVTTIVLNLKQLALKIYSDEDKTLEIDTQGEG
RAAC00371                SSIPGAAVRSVKIEGVLHEFSTIPGVVEDVTEIILNLKRLSLKIHSDEEKTLIIDAVGPG
ref|YP_001210899.1|      SSLPGAAVTSVKIDGVLHEFSTIPGVVEDVTDIILNLKNLCLKIYGDEEKVLRVEASTEG
ref|YP_001111617.1|      SSLPGAAVTSVKIEGVLHEFATVPGVQEDVTDIILNLKNLCLKIHSDEEKVLRVEAQTEG
                         :* :*:****** *:*   ** *:**:*.*.*:.:*.*  ::.  * ref|YP_145986.1|         VVTAADITHDSDVEILNPDLHIATLAEGGRLRMRMTAKRGRGYVPAEANKREDQPIGVIP
ref|YP_001124263.1|      VVTAADITHDSDVEILNPDLHIATLAEGGRLRMRMTARRGRGYVPAEANKREDQPIGVIP
ref|NP_241028.1|         VVTAGDLTHDSDVDVLNPDLHIATLTTGAHLRMRITAKRGRGYVPAEGNKSDELAIGVIP
RAAC00371                VVTAGDIRADSDVDIMNPDLHIATLTEGARIYMEMRAGRGRGYVPAHRNKPEEQEIGLIP
ref YP_001210899.1       VVKAKDIIHDADVEIMNPDLTIATLAENARLYMEITVAKGRGYVSAERNKKGDHIIGVIP
ref YP_001111617.1       PVTAGDIIHDADVEILNPDLHLATLDTGGRLFMEISVNKGRGYSSAEKNKKGEHIIGVIP
                          *.* *:  *:**:::****  :*** ...:: *.:  . :****  .*.  **  :   **:**

ref YP_145986.1|         IDSIYTPVSRVSYQVENTRVGQVTDYDKLTIDVWTDGSIGPKEAISLGAKILTEHLNIFV
ref|YP_001124263.1|      IDSIYTPVSRVSYQVENTRVGQVTDYDKLTIDVWTDGSIGPKEAISLGAKILTEHLNIFV
ref|NP_241028.1|         IDSIYTPVSRVNYQVENTRVGQVTNYDKLTLDVWTDGSIRPEEAVSLGAKILTEHLNIFV
RAAC00371                IDSLYSPISRVNFSVENTRVGQITDYDKLTLEVWTDGSVAPDEAVSIGAKILTEHLMLFV
ref|YP_001210899.1       VDSVFTPVRKVNYTVENTRVGQITDYDKLTLEVWTDGSIRPDEATSLSAKILSEHLRLFI
ref|YP_001111617.1       IDSIYTPVRRVNYNVENTRVGQITDYDKLTLEVWTNGSIRPDEATSLSAKILSEHLRLFI
                         :**:::*: :*.: ********:*:*****::***.**: *.** *:.****:*** :*:

ref|YP_145986.1          GLTDEAQNAEIMVEKEDDQKEKVLEMTIEELDLSVRSYNCLKRAGINTVQELTQKTEEDM
ref|YP_001124263.1|      GLTDEAQNAEIMVEKEDDQKEKVLEMTIEELDLSVRSYNCLKRAGINTVQELTQKTEEDM
ref|NP_241028.1          GLTDQAQNAEIMVEKEDDQKEKVLEMTIEELDLSVRSYNCLKRAGINTVQELTQKTEEDM
RAAC00371                GLTDRARDTDLMVEKENAHNDKILDMPIEELDLSVRSYNCLKRAGINTVAELCAKSEEEM
ref|YP_001210899.1       GLTETVSDVEIMVEKEEEHKDRVLEMTIEELDLSVRSYNCLKRAGINTVEELIQRNEEDM
ref|YP_001111617.1       GLTETVNDVEIMVEKEEEQKDKILEMTIEELDMSVRSYNCLKRAGINTVEELIQRNEEDM
                         *: . :.::***  :::::*:* ***  :. :.**:* ref|YP_145986.1|         MKVRNLGRKSLEEVKAKLAELGLSLRKDD
ref|YP_001124263.1       MKVRNLGRKSLEEVKAKLAELGLSLRKDD
ref|NP_241028.1|         MKVRNLGRKSLEEVQEKLGELGLGLRKEE
RAAC00371                MKVRNLGRKSLEEVVEKLHALGLSLRKDD
ref|YP_001210899.1       MKVRNLGKKSLEEVINKLHELGLSLRKDD
ref|YP_001111617.1       MKVRNLGKKSLEEVINKLHELGLSLRQED
                         *******:****** ** ***.**:::
```

FIG. 3A

```
ref|NP_240992.1|        ---MTGQLIQYGRHRQRRSYARINEVLELPNLIEIQTASYQWFLDEGLREMFQDISPIQD
ref|YP_173646.1|        ---MTGQLIQYGRHRQRRSYARINEVLELPNLIEIQTASYQWFLDEGLREMFQDISPIQD
ref|YP_001124230.1|     ---MTGRLVQYGRHRQRRSYARISEVLELPNLIEIQTSSYQWFLDEGLREMFKEISPIED
ref|YP_145951.1|        ---MTGRLVQYGRHRQRRSYARISEVLELPNLIEIQTSSYQWFLDEGLREMFREISPIED
ref|ZP_02326346.1|      ---LAGHLVQYGR-RKRRTYARINEVLEIPNLIEIQQKSYQWFLDEGLREMFQDISPIQD
RAAC00408               MTVLQGHMVKYGW-AERRSYARIREVLDLPNLIEIQQKSYEWFLREGLRETFADISPITD
                           :  *::::    ::** *::*****  :* *** * :**** * ref|NP_240992.1|        FTGNLVLEFIDYSLGEPKYPVDESKERDVTYAAPLRVKVRLINKETGEVKEQEVFMGDFP
ref|YP_173646.1|        FTGNLVLEFIDYSLGEPKYPVDESKERDVTYAAPLRVKVRLINKETGEVKEQEVFMGDFP
ref|YP_001124230.1|     FSGNLSLEFIDYSLGEPKYSVEEAKERDVTYAAPLRVKVRLINKETGEVKEQDVFMGDFP
ref|YP_145951.1|        FSGNLSLEFIDYSLGEPKYTVEEAKERDVTYAAPLRVKVRLINKETGEVKEQDVFMGDFP
ref|ZP_02326346.1|      FTGNLVLEFIDYSLGEPKYTVDDSKERDVTYAAPLRVKVRLINKETGEVKEQEVFMGDFP
RAAC00408               FTGNLVLEFVDYSLGEPKYDVEESKERDVTYAAPLRVKVRLLNKETGEVKEQEVFLGDFP
                        *:*.*:********* *::.******:*******.*******:*:**** ref|NP_240992.1|        LMTDTGTFIINGAERVIVSQLVRSPSVYYSEKIDKNGKKGYTATVIPNRGAWLELETDAK
ref|YP_173646.1|        LMTETGTFIINGAERVIVSQLVRSPSVYYSQKLDKNGKKGFTATVIPNRGAWLELETDAK
ref|YP_001124230.1|     LMTETGTFIINGAERVIVSQLVRSPSVYYSDKVDKNGKRGYSATVIPNRGAWLEYETDAK
ref|YP_145951.1|        LMTETGTFIINGAERVIVSQLVRSPSVYYSDKVDKNGKRGYSATVIPNRGAWLEYETDAK
ref|ZP_02326346.1|      IMTETGTFIINGAERVIVSQLVRSPSVYYNTKVDKNGKKAFTATVIPNRGAWLELETDAK
RAAC00408               LMTETGTFIINGAERVIVSQLVRSPSVYYSSKIDKNGKRTFAATVIPNRGAWLEFETDAK
                        ::******************** *. *:**:   ::********** *** ref|NP_240992.1|        DIVYVRIDRTRKIPVTVLLRALGFGSDQEIIDLLGEDEYLRNTLEKDNTDSAEKALLEIY
ref|YP_173646.1|        DIVYVRIDRTRKIPVTVLLRALGFGSDQEIVDLLGENEYLRNTLEKDNTDSTDKALLEIY
ref|YP_001124230.1|     DVVYVRIDRTRKLPVTVLLRALGFSSDQEIIDLLGDNEYLRNTLEKDNTDSTEKALIEIY
ref|YP_145951.1|        DVVYVRIDRTRKLPVTVLLRALGFSSDQEIIDLLGDNEYLRNTLEKDNTDSTEKALIEIY
ref|ZP_02326346.1|      DIIYVRIDRTRKIPVTVLLRALGFGTDAEILDLLGDDEYIRNTLDKDNTDSTDKALIEIY
RAAC00408               DVVYVRIDRTRKLPITVLLRALGLSSDAEIIELLGEDEYLQNTLDKDTTDSTERALIEIY
                        *::*********:*:*******:..:*.::*::*::.*.*.::.:*** ref|NP_240992.1|        ERLRPGEPPTVENAKSLLDSRFFDPKRYDLANVGRYKVNKKLHIKNRLFNQRLAETLIDP
ref|YP_173646.1|        ERLRPGEPPTVENAKSLLESRFFDPKRYDLANVGRYKINKKLHIKNRLFNQRLAEKLVDP
ref|YP_001124230.1|     ERLRPGEPPTLENAKSLLASRFFDPKRYDLASVGRYKINKKLHIKNRLFNQRLAETIADP
ref|YP_145951.1|        ERLRPGEPPTLENAKNLLASRFFDPKRYDLASVGRYKINKKLHIKNRLFNQRLAETIIDP
ref|ZP_02326346.1       ERLRPGEPPTLDNARSLLYARFFDPKRYDLANVGRYKINKKLHIKNRLFNQRLAETLVHP
RAAC00408               ERLRPGEPPTVENARALLASRFFDPKRYDLAAVGRYKINKKLHLKNRLLNQRLAETLVDE
                        **********::.::  **  ***********.******:*****:**** ******. .

ref|NP_240992.1|        ETGEVIAEEGSIIDRRTLDRILPYLENNVGFRTVRMSGGVVEEDEVRLQSVKIYAPDDQD
ref|YP_173646.1|        ETGEVLAEEGTLLDRRTLDKLIPHLEKNVGFRTARTSGGVLEESDVEIQSVKIYVADDYE
ref|YP_001124230.1|     ETGEIIAEAGTMIDRRTLNRLLPYLEKGAGLQTYRPTEGVAD-GQISVQTVKIYAPNDPD
ref|YP_145951.1|        ETKEVIAEAGAMIDRRTLNRLLPYLEKGVGLQTYRPAEGVVDGD-ISVQTIKIYAPNDPD
ref|ZP_02326346.1|      ETGEIIAEAGQLVDRRLLDEILPCLEEGVGFKEYSVPNGVLESDHIPMQTIDVFSP--IE
RAAC00408               ETGEIIAEAGTVLDRRTLDRIIPRLSGKVGRFTIRGTRDLFEQDEIPLQMVKIFSP--AE
                        ** **::** *  ::***   *:.::* *.    .*   .:: .  :* :.::.    :

ref|NP_240992.1|        GEHVIRVIGNGLVEKEIKHITPADIIASINYFFNLLHSVGGTDDIDHLGNRRLRSVGELL
ref|YP_173646.1|        GERVISVISNGMVERDVKHIAPADIIASISYFFNLLHGVGDTDDIDHLGNRRLRSVGELL
ref|YP_001124230.1      NEKVINIIGNGFIAEDVKHITPADIIASISYFFNLLHGVGDTDDIDHLGNRRLRSVGELL
ref|YP_145951.1|        GEKVINVIGNGFIAEDVKHITPADIIASISYFFNLLHGVGDTDDIDHLGNRRLRSVGELL
ref|ZP_02326346.1|      DGKVVKVISNGVIDKNVKNITPADIISSINYFINLLHGIGNTDDIDHLGNRRLRSVGELL
RAAC00408               DGKVLHVISNGELPADVKYITPSDIIAAVSYFFNLLRGVGTTDDIDHLGNRRLRSVGELL
                        . :*: :*.**  :   :* *:****::::.**:****:. **:***************
```

FIG. 3B

```
ref|NP_240992.1|       QNQFRIGLSRMERVVRERMSIQDPNSITPQALINIRPVIASIKEFFGSSQLSQFMDQTNP
ref|YP_173646.1|       QNQFRIGLSRMERVVRERMSIQDPNVITPQALINIRPVIASIKEFFGSSQLSQFMDQTNP
ref|YP_001124230.1|    QNQFRIGLSRMERVVRERMSIQDANTITPQQLINIRPVIAAIKEFFGSSQLSQFMDQTNP
ref|YP_145951.1|       QNQFRIGLSRMERVVRERMSIQDTNTITPQQLINIRPVIAAIKEFFGSSQLSQFMDQTNP
ref|ZP_02326346.1|     QNQFRIGLSRMERVVRERMSIQDANVITPQALINIRPVIASIKEFFGSSQLSQFMDQTNP
RAAC00408              QNQFRIGLSRMERVVRERMSIQDASAITPQALINIRPVIAAIKEFFGSSQLSQFMDQTNP
                       ********************..   *****.**************** ref|NP_240992.1|       LAELTHKRRLSALGPGGLTRERAGFEVRDVHYSHYGRMCPIETPEGPNIGLINSLSTYAK
ref|YP_173646.1|       LAELTHKRRLSALGPGGLTRERAGMEVRDVHYSHYGRMCPIETPEGPNIGLINTLSSYAK
ref|YP_001124230.1|    LAELTHKRRLSALGPGGLTRERAGFEVRDVHYSHYGRMCPIETPEGPNIGLINSLSTYAK
ref|YP_145951.1|       LAELTHKRRLSALGPGGLTRERAGFEVRDVHYSHYGRMCPIETPEGPNIGLINSLSTYAK
ref|ZP_02326346.1|     LAELTHKRRLSALGPGGLTRERAGFEVRDVHHSHYGRMCPIETPEGPNIGLINSLSTFAR
RAAC00408              LAELTHKRRLSALGPGGLTRERAGFEVRDVHYSHYGRMCPIETPEGPNIGLINSLSTYAC
                       **********************:*:*******************:::* ref|NP_240992.1|       VNEFGFMETPYRRVDPETGKVTAQIDYLTADEEDNYVVAQANMKLAEDGSFIDENIIARF
ref|YP_173646.1|       VNEFGFMETPYRRVDPETGKVTSRIDYLTADEEDNYVVAQANAKLNDDGSFVDDNIIARF
ref|YP_001124230.1|    VNKFGFIETPYRRVDPETGKVTDQIDYLTADEEDNYVVQANVPLAEDGTFLEENVIARF
ref|YP_145951.1|       VNKFGFIETPYRRVDPETGRVTDQIDYLTADEEDNYVVAQANVPLAEDGTFLEENVVARF
ref|ZP_02326346.1|     INEYGFIEAPYRRVDPKTGVVTDEIVYMTADEEDNYVVAQANAELNEDGTFAADNVYVRY
RAAC00408              VNEYGFIETPYRRVDPETGVVTDQIDYLTADEEENYLIAQANEPLTEDGHFVAEEITVRS
                       :*::**:*:*****:  ** .*  *;***:::****   *  :**  *    ::: .* ref|NP_240992.1|       RGENIVVSRDRVDYMDVSPKQVVSAATSCIPFLENDDSNRALMGANMQRQAVPLLVPEAP
ref|YP_173646.1|       RGENTVVPCDRVDYMDVSPKQVVSAATSCIPFLENDDSNRALMGANMQRQAVPLLVPEAP
ref|YP_001124230.1|    RGENIVVKRDRVDYMDVSPKQVVSAATACIPFLENDDSNRALMGANMQRQAVPLLQPEAP
ref|YP_145951.1|       RGENIVVKRDRVDYMDVSPKQVVSAATACIPFLENDDSNRALMGANMQRQAVPLLEPEAP
ref|ZP_02326346.1|     KDEILTLPKERVDYMDVSPKQVVSVATALIPFLENDDSNRALMGSNMQRQAVPLLMPKAP
RAAC00408              REDVITVSRDRIDYMDVSPKQVVSVATALIPFLENDDANRALMGSNMQRQAVPLLVTDSP
                       :  :  .:  :*:**********.:  ******:**:*********   ..:* ref|NP_240992.1|       IVGTGMEHVSAKDSGAAIVSKHRGIVERVTAKEIWVRRLEEVDGKEIKGDLDKYRLQKFI
ref|YP_173646.1|       LVGTGMEHVSAKDSGAAVVSKYAGIVERVTAKEIWVRRIEEVDGKETKGDLDKYKLQKFV
ref|YP_001124230.1|    IVGTGMEYVSAKDSGAAIICKHRGIVERVEAKEIWVRRLIEVDGKEVKGDLDKYRLLKFV
ref|YP_145951.1|       IVGTGMEYVSAKDSGAAVICKHRGIVERVEAKEIWVRRLIEVDGKEVKGDLDKYRLLKFV
ref|ZP_02326346.1|     LVGTGMEYKAAKDSGVCVVAKHDGIIEKVSGNEIWLRRQEEVDGRLVSGNITKFKLHKFM
RAAC00408              LVGTGMEYQAAKDSGVCVVSKHNGVVERVTAREIWVREEAVVDGQVVKGNVHKYKLIKFA
                       :****:  :**... ::.*: *::*:* ..:***:*.  ***  .*:: *::* ** ref|NP_240992.1|       RSNQGTSYNQRPIVKEGDVVEKREILADGPSMEKGEMALGRNVLVGFMTWEGYNYEDAII
ref|YP_173646.1|       RSNQGTSYNQRPIVREGDRIEKREILADGPSMEMGEMALGRNVLAFMTWDGYNYEDAII
ref|YP_001124230.1|    RSNQGTCYNQRPIVKKGDIVEKGEILADGPSMDKGELALGRNVLAFMTWDGYNYEDAII
ref|YP_145951.1|       RSNQGTCYNQRPIVKKGDIVEKGEILADGPSMDKGELALGRNVLAFMTWDGYNYEDAII
ref|ZP_02326346.1|     RSNQGTCINQRPLVLEGQRVKAGDILADGPSTEQGELALGRNVVVAFMTWEGYNYEDAIL
RAAC00408              RSNQNTCLNQRPIVREGDRVKVGDILADGPATQNGELALGRNVLAFMTWEGYNYEDAIL
                       ****.*. ****.*  :*:  ::   :******:  :  **:******:*.****:********:

ref|NP_240992.1|       LSERLVKDDVYTSIHIEEYESEARDTKLGPEEITRDIPNVGEDALRNLDERGIIRVGAEV
ref|YP_173646.1|       LSERLVKDDVYTSIHIEEYESDARDTKLGPEEITRDIPNVGEDALRNLDERGIIRIGAEV
ref|YP_001124230.1|    MSERLVKEDVYTSIHIEEYEAESRDTKLGPEEITRDIPNVGEDALKNLDERGIVRIGAEV
ref|YP_145951.1|       MSERLVKEDVYTSIHIEEYEAESRDTKLGPEEITRDIPNVGEDALKNLDERGIVRIGAEV
ref|ZP_02326346.1|     LSEKLVKEDVYTSIHIEEYESEARDTKLGPEEITRDIPNVGEDALKNLDERGIIRVGAEI
RAAC00408              ISEKMVKEDVYTSIHIEEYEIEARDTKLGPEEITRDIPNVGEDALKNLDERGIIRIGAEI
                       :**::**:***********  ::*******************.*******:*:***:
```

FIG. 3C

```
ref|NP_240992.1|       KDGDILVGKVTPKGVTELTAEERLLHAIFGEKAREVRDTSLRAPHGGDGIVLDVKIFNRE
ref|YP_173646.1|       KDGDILVGKVTPKGVTELTAEERLLHAIFGEKAREVRDTSLRAPHGGDGIVLDVKIFNRE
ref|YP_001124230.1     KDGDILVGKVTPKGMTELTAEERLLHAIFGEKAREVRDTSLRVPHGGGGIVLDVKVFNRE
ref|YP_145951.1|       KDGDILVGKVTPKGMTELTAEERLLHAIFGEKAREVRDTSLRVPHGGGGIVLDVKVFNRE
ref|ZP_02326346.1|     GAGDILVGKVTPKGVTELTAEERLLHAIFGEKAREVRDTSLRVPHGTDGIVVDVKVFTHE
RAAC00408              TTNDILVGKVTPKGVTELTAEERLLHAIFGEKAREVRDTSLRVPHGGAGIVVDVKVFTRE
                       .*:*******:*******************.*  *:*.*.:* ref|NP_240992.1|       DGDELPPGVNQLVRVYIVQKRKIHEGDKMAGRHGNKGVISRILPEEDMPYLPDGTPIDIM
ref|YP_173646.1|       DGDELPPGVNQLVRVYIVQKRKINQGDKMAGRHGNKGVISRILPEEDMPFLPDGTPVDIM
ref|YP_001124230.1     DGDELPPGVNQLVRVYIVQKRKISEGDKMAGRHGNKGVISRILPEEDMPFLPDGTPIDIM
ref|YP_145951.1|       DGDELPPGVNQLVRVYIVQKRKISEGDKMAGRHGNKGVISRILPEEDMPFLPDGTPIDIM
ref|ZP_02326346.1|     NGDELPPGVNQLVRVYIAQKRKISQGDKMAGRHGNKGVIARILPEEDMPFLPDGTPVEVV
RAAC00408              NGDELPAGVNQLVRVYVAQKRKISEGDKMAGRHGNKGVVARILPEEDMPFLEDGTPVEIV
                       :*****.*********:.*****.**************::*********.* ****.::.:

ref|NP_240992.1|       LNPLGVPSRMNIGQVLELHLGMAARRLGLHVASPVFDGASEEDVWATLEEAGMARDGKTI
ref|YP_173646.1|       LNPLGVPSRMNIGQVLELHLGMAARKLGIHVASPVFDGASEEDVWGTLEEAGMARDGKTI
ref|YP_001124230.1     LNPLGVPSRMNIGQVFELHLGMAAKKLGLHIASPVFDGATEEDVWNILEEAGMARDAKTV
ref|YP_145951.1|       LNPLGVPSRMNIGQVFELHLGMAAKKLGLHIASPVFDGATEEDVWNILEEAGLARDAKTV
ref|ZP_02326346.1|     LNPLGVPSRMNIGQVLEVHLGMAAKQLGIHVATPVFDGAHEYDVFDTMEEAGMQRNGKTK
RAAC00408              LNPLGVPSRMNIGQVLETHLGMAAKVLGLKMATPVFDGAKPEDVFETLREAGLPEDGKQV
                       ***************:*  ****:  ::*:**** .:   :  :.***  .:.* ref|NP_240992.1|       LYDGRTGEPFDNRVSVGIMYMIKLAHMVDDKLHARSTGPYSLVTQQPLGGKAQFGGQRFG
ref|YP_173646.1|       LYDGRTGEPFDNRVSVGIMYMIKLAHMVDDKLHARSTGPYSLVTQQPLGGKAQFGGQRFG
ref|YP_001124230.1     LYDGRTGEPFDNRVSVGIMYMIKLAHMVDDKLHARSTGPYSLVTQQPLGGKAQFGGQRFG
ref|YP_145951.1|       LYDGRTGEPFDNRVSVGIMYMIKLAHMVDDKLHARSTGPYSLVTQQPLGGKAQFGGQRFG
ref|ZP_02326346.1|     LYDGRTGEEFEREVTVGVMYMIKLAHMVDDKIHARSTGPYSLVTQQPLGGKAQFGGQRFG
RAAC00408              LYDGRTGEPFENRVTVGYVYMMKLHHLVDDKIHARSTGPYSLVTQQPLGGKAQFGGQRFG
                       ********  *:..*: ::** *:**:********************* ref|NP_240992.1|       EMEVWALEAYGAAYTLQEILTVKSDDVVGRVKTYEAIVKGENVPEPGVPESFKVLIKELQ
ref|YP_173646.1|       EMEVWALEAYGAAYTLQEILTVKSDDVVGRVKTYEAIVKGENVPEPGVPESFKVLIKELQ
ref|YP_001124230.1     EMEVWALEAYGAAYTLQEILTVKSDDVVGRVKTYEAIVKGENIPEPGVPESFKVLIKELQ
ref|YP_145951.1|       EMEVWALEAYGAAYTLQEILTVKSDDVVGRVKTYEAIVKGENIPEPGVPESFKVLIKELQ
ref|ZP_02326346.1|     EMEVWALEAYGAAYTLQEILTVKSDDVVGRVKTYESIVKGENVPEPGVPESFKVLIKELQ
RAAC00408              EMEVWALEAYGAAYTLQELLTVKSDDVVGRVKTYEAIVKGENVPEPGVPESFKVLIKELQ
                       ****************:*********** .***:****************** ref|NP_240992.1|       SLGMDVKMLSSTEEEIEMKELDDEDEQASDKLNLNIDSTE---
ref|YP_173646.1|       SLGMDVKMLSSNEEEIEMRELDDEEDQTSEKLNLNLETNE---
ref|YP_001124230.1     SLGMDVTILT---------------------------------
ref|YP_145951.1|       SLGMDVTILT---------------------------------
ref|ZP_02326346.1|     SLGMDVKILSGDEEEIEMKELDDEDDAGSDKLNLNLEGAEMG-
RAAC00408              SLGMDVKILSGDEREIEMKEMDDDED-SPDKLNLNLEYNEVGD
                       ******.:*:
```

FIG. 4A

```
ref|YP_001124231.1|    VYPLLDVNKFEYMKIGLASPEKIRSWSYGEVKKPETINYRTLKPEKDGLFCERIFGPTKD
ref|YP_145952.1        ---MLDVNKFEYMKIGLASPEKIRSWSYGEVKKPETINYRTLKPEKDGLFCERIFGPTKD
ref|NP_976431.1        ---MIDVNNFEYMKIGLASPDKIRSWSYGEVKKPETINYRTLKPEKDGLFCERIFGPQKD
ref|NP_240993.1        ---MIDVNNFEYMKIGLASPNKIRSWSRGEVKKPETINYRTLKPEKDGLFCERIFGPQKD
ref|ZP_02326345.1|     ---MMDVNNFEFMKIGLASPDKIRSWSRGEVKKPETINYRTLKPEKEGLFCEKIFGPTKD
RAAC00407              MHKLFDLNNFEFMKIGLASPEKIRSWSHGEVKKPETINYRTLRPEKEGLFCEKIFGPTRD
                          :*:*::** :** ********:*;***:** :* ref|YP_001124231.1|    WECHCGKYKRVRYKGVVCDRCGVEVTRSKVRRERMGHIELAAPVSHIWYFKGIPSRMGLV
ref|YP_145952.1        WECHCGKYKRVRYKGVVCDRCGVEVTRSKVRRERMGHIELAAPVSHIWYFKGIPSRMGLV
ref|NP_976431.1        WECHCGKYKRVRYKGVVCDRCGVEVTRAKVRRERMGHIELAAPVSHIWYFKGIPSRMGLV
ref|NP_240993.1        WECHCGKYKRVRYKGVVCDRCGVEVTRAKVRRERMGHIELAAPVSHIWYFKGIPSRMGLV
ref|ZP_02326345.1|     WECHCGKYKRVRYKGVVCDRCGVEVTRQKVRRERMGHIELAAPVSHIWYFKGIPSRMGLA
RAAC00407              WECHCGKYKRIRYKGVVCDRCGVEVTRSKVRRERMGHIELAAPVSHIWFFKGIPSRMGLI
                       ********:*********** ****************:******* ref|YP_001124231.1|    LDMSPRALEEVIYFASYVVTDPGDTPLEKKQLLSEKEYRAYREKYGQSFQASMGAEAIKK
ref|YP_145952.1        LDMSPRALEEVIYFASYVVTDPGDTPLEKKQLLSEKEYRAYREKYGQSFQASMGAEAIKK
ref|NP_976431.1        LDMSPRALEEVIYFASYVVTESGDTPLDKKQLLSEKEYRAYRDRYGSTFQAAMGAEAIKK
ref|NP_240993.1        LDMSPRSLEEVIYFASYVVTDPGDTPLEKKQLLSEKEFRAYLDKYGRSFTAQMGAEAIRK
ref|ZP_02326345.1|     LDMSPRSLEEIIYFASYVVTDPGDTPLEKKQLLSEKEYRSYREKYGYAPQAGMGAEAVKK
RAAC00407              LDMSPRALEEVIYFASYVVTDPGDTPLEKKQLLSEKEYRSYREKYGYAPKAGMGAEAIRT
                       ******:***:*********:.*****:*********:*:* ::** :* *.*****::.

ref|YP_001124231.1|    LLQDIDLDKEVATLKEELKTAQGQRRARIIKRLEVLESFRSSGNDPAWMVLDVLPVIPPE
ref|YP_145952.1        LLQDIDLDKEVAALKEELKTAQGQRRARIIKRLEVLEAFRSSGNDPAWMVLDVLPVIPPE
ref|NP_976431.1        LLQDIDLDKEVDFLKEELKTAQGQRRTRAIKRLEVLEAFRNSGNEPSWMILDVLPVIPPE
ref|NP_240993.1        LLMDIDLDKEVDGLKEELQTAQGQRRTRAIKRLEVLEAFRNSGNEPSWMILDVLPVIPPE
ref|ZP_02326345.1|     LLQDIDIDKEVDVLKEELRTAQGQRRNRAIKRLEVMEAFRNSKNKPDWMILDVLPVIPPE
RAAC00407              LLQEIDLDREVEILREELRTAQGQRRNRAIKRLEVIEAFRQSGNKPSWMILEALPVIPPD
                       ** :**:*:** *:***:*******.* ******:*.** **:*: .******:

ref|YP_001124231.1|    LRPMVQLDGGRFATSDLNDLYRRVINRNNRLKRLLDLGAPNIIVQNEKRMLQEAVDALID
ref|YP_145952.1        LRPMVQLDGGRFATSDLNDLYRRVINRNNRLKRLLDLGAPNIIVQNEKRMLQEAVDALID
ref|NP_976431.1        LRPMVQLDGGRFATSDLNDLYRRVINRNNRLKRLLDLGAPSIIVQNEKRMLQEAVDALID
ref|NP_240993.1        LRPMVQLDGGRFATSDLNDLYRRVINRNNRLKRLLDLGAPSIIVQNEKRMLQEAVDALID
ref|ZP_02326345.1|     LRPMVQLDGGRFATSDLNDLYRRVINRNNRLKRLLDLGAPDIIVQNEKRMLQEAVDALID
RAAC00407              LRPMVQLDGGRFATSDLNDLYRRVINRNNRLKRLLDLGAPDIIVQNEKRMLQEAVDALID
                       **************************************.**************** ref|YP_001124231.1|    NGRRGRPVTGPGNRPLKSLSHMLKGKQGRFRQNLLGKRVDYSGRSVIVVGPNLKMYQCGL
ref|YP_145952.1        NGRRGRPVTGPGNRPLKSLSHMLKGKQGRFRQNLLGKRVDYSGRSVIVVGPNLKMYQCGL
ref|NP_976431.1        NGRRGRPVTGPGNRPLKSLSHMLKGKQGRFRQNLLGKRVDYSGRSVIVVGPNLKMYQCGL
ref|NP_240993.1        NGRRGRPVTGPGNRPLKSLSHMLKGKQGRFRQNLLGKRVDYSGRSVIVVGPNLKMYQCGL
ref|ZP_02326345.1|     NGRRGRPVTGPGNRPLKSLSHMLKGKQGRFRQNLLGKRVDYSGRSVIVVGPSLKMYQCGL
RAAC00407              NGRRGRPVTGPGNRPLKSLSHMLKGKQGRFRQNLLGKRVDYSGRSVIVVGPELRMYQCGL
                       ***************************************************.*:****** ref|YP_001124231.1|    PKEMALELFKPFVMKELVERGLAHNIKSAKRKIERVHPEVWDVLEDVIKEHPVLLNRAPT
ref|YP_145952.1        PKEMALELFKPFVMKELVERGLAHNIKSAKRKIERVHPEVWDVLEDVIKEHPVLLNRAPT
ref|NP_976431.1        PKEMALELFKPFVMKELVEKGLAHNIKSAKRKIERVQPEVWDVLESVIKEHPVLLNRAPT
ref|NP_240993.1        PKEMALELFKPFVMKELVSKGLAHNIKSAKRKVERVQPEVWDVLEEVIKEHPVLLNRAPT
ref|ZP_02326345.1|     PKEMALELFKPFVMKELVNKQLAHNIKSAKRKVERVSPEVWDVLEEVIKEHPVLLNRAPT
RAAC00407              PKEMALELFKPFVMKELVARGLAHNIKSAKRKVERVSDEVWDVVEDVIKQHPVLLNRAPT
                       ****************** : *********** *****:*.***:**********
```

FIG. 4B

```
ref|YP_001124231.1|    LHRLGIQAFEPTLVEGRAIRLHPLVCTAYNADFDGDQMAVHVPLSAEAQAEARLLMLAAQ
ref|YP_145952.1|       LHRLGIQAFEPTLVEGRAIRLHPLVCTAYNADFDGDQMAVHVPLSAEAQAEARLLMLAAQ
ref|NP_976431.1|       LHRLGIQAFEPTLVEGRAIRLHPLVCTAYNADFDGDQMAVHVPLSSEAQAEARLLMLAAQ
ref|NP_240993.1|       LHRLGIQAFEPTLVEGRAIKLHPLVCTAYNADFDGDQMAVHVPLSAEAQAEARILMLAAQ
ref|ZP_02326345.1|     LHRLGIQAFEPILVEGRAIMLHPLVCTAYNADFDGDQMAVHVPLSAEAQAEARILMLAAG
RAAC00407              LHRLGIQAFEPVLVEGRAIKLHPLVCTAYNADFDGDQMAVHVPLSAEAQAEARLLMLAAH
                       ******** ** ***********************:**:*** ref|YP_001124231.1|    NILNPKDGKPVVTPSQDMVLGNYYLTMEREGAIGEGMVFKDTDEALLAYHNGYVHLHSRI
ref|YP_145952.1|       NILNPKDGKPVVTPSQDMVLGNYYLTMEREGAIGEGMVFKDTDEALLAYHNGYVHLHSRI
ref|NP_976431.1|       NILNPKDGKPVVTPSQDMVLGNYYLTLEREGAIGEGMVFKDANEALLAYQNGYVHLHTRV
ref|NP_240993.1|       NILNPKDGKPVVTPSQDMVLGNYYLTMEREGAKGEGSVFKDTNEALIAYQNGYVHLHTRI
ref|ZP_02326345.1|     NILNPKDGKPVVTPSQDMVLGSFYLTTDNKHAKGSGMILRSVHEAFSVYQNGTAELHARV
RAAC00407              NILNPKDGKPVVTPTQDMVLGSYYLTIEREGAPGEGKVFASVSEVEYALHQRLITLQTRI
                       ************** :****** :*** :.: *.*.* :: .. *.   . ::    *::*:

ref|YP_001124231.1|    AIHAGSLKNETFTPEQNNKLLLTTVGKLIFNEILPKSFPYINEPTTENIEGRTP-DKYFL
ref|YP_145952.1|       AIHAGSLKNETFTEEQNNKLLLTTVGKLIFNEILPNSFPYINEPTTENIEGRTP-DKYFL
ref|NP_976431.1|       AVAASAVNNATFTEEQKSMLLLTTVGKLIFNEILPESFPYINEPTNSNLEKETP-AKYFV
ref|NP_240993.1|       AIPVASLGKTTFKEEQNSQLLLTTVGKLIFNEILPESFPYVNEPTAHNLEVETP-SKYMV
ref|ZP_02326345.1|     AIPAKALNKISFTDKQQDAYLITTIGKIIFNEIFPKDFPYINQSTTSNLMHGPS-DDYFA
RAAC00407              ALPAKAVGKTSFTEKQANALLITTPGKLIFNSIFPSDFPYLNSAAKSNLLGGPP-DDTFI
                       *:.  . ::    :*.  :*.   *:** **:*** .*:*..***:*..:   *:     .. . :

ref|YP_001124231.1|    -DKGVDVREEIRKRELVPPFKKKVLGQIIAEVFKRFKITETSKMLDRMKDLGFQYSTKAG
ref|YP_145952.1|       -DKGVNVREEIRKRELVPPFKKKVLGQIIAEVFKRFKITETSKMLDRMKDLGFQYSTKAG
ref|NP_976431.1|       -EKGANIKEIIASREEVAPFSKKILGNIIAEVFKRFKITETSRMLDRMKNLGFKYSTKAG
ref|NP_240993.1|       -PTSTNVKELFQERDVVAPFKKGFLGNIIAEVFKKFKITETSKMLDRMKDLGFKYSTKAG
ref|ZP_02326345.1|     FEKGSDIRAKMEELPECKAVGKDYLGSIIAECFRKYHTTETSIILDKVKQLGFTYSTKAG
RAAC00407              FEKGVDIREAILKRPIPKAVIKKDLGNILAECFRRYGTTMTAEILDKVKRLGFHYSTLAG
                         .. :::  : .      .. *  **.*:** *:::   * *: :**::* * * ** ref|YP_001124231.1|    ITIGVSDIVVLPEKQEILDEAQAKVDTVLKQFRRGLITDEERYERVISVWSAAKDKIQDR
ref|YP_145952.1|       ITIGVADIVVLPEKQEILDEAQAKVDTVLKQFRRGLITDEERYERVISIWSAAKDKIQDR
ref|NP_976431.1|       ITVGVSDILVLGEKDEILHEAQAKVDNVIKQFRRGLITEEERYDRVISIWSNAKDVIQGK
ref|NP_240993.1|       ITVGVADIVVLPEKKEILAEAEKKVDRVLKQFRRGLITEEERYDRVISIWSEAKDVIQDK
ref|ZP_02326345.1|     ITVAVADVIVPKEKQEILKESEQKVQTITNQYRRGLITDDERYDRVIAIWSKAKDDITDI
RAAC00407              ITISISDIVVPEEKKRIIAEAEAKEHKLKLQYRRGLITEEEQYVTFSQIWSEAKEQISSI
                       **:.::*::*  **..*: *:: *  . : *:*****::*:*  .  :** **: * .

ref|YP_001124231.1|    LMKSLDKRNPIFMMSDSGARGNASNFTQLAGMRGLMANPAGRIIELPIKSSFREGLTVLE
ref|YP_145952.1|       LMKSLDKRNPIFMMSDSGARGNASNFTQLAGMRGLMANPAGRIIELPIKSSFREGLTVLE
ref|NP_976431.1|       LMKSLNKRNPIFMMSDSGARGNASNFTQLAGMRGLMANPSGRIIELPIKSSFREGLTVLE
ref|NP_240993.1|       LMGSLDKRNPIFMMSDSGARGNASNFTQLAGMRGLMANPSGRIIELPIKSSFREGLTVLE
ref|ZP_02326345.1|     LMKSLDKYNSINMMVESKARGNKSQITQLGGMRGLMANPAGKIIELPIKSNFREGLTVLE
RAAC00407              LMESMDQFNPIYMMATSGARGSNSQITQLAGMRGLMANPSGEIIQLAIKSNFREGLSVLE
                       ** *::: *.* **   * ***. *::*.*******:*.**:*.*.** ;* ref|YP_001124231.1|    YFISTHGARKGLADTALKTADSGYLTRRLVDVAQDVIVREEDCGTDRGILARALTDGTEV
ref|YP_145952.1|       YFISTHGARKGLADTALKTADSGYLTRRLVDVAQDVIVREEDCGTDRGILARALTDGTEV
ref|NP_976431.1|       YFISTHGARKGLADTALKTADSGYLTRRLVDVAQDVIVREDDCGTDRGLLIGAIKEGNEV
ref|NP_240993.1|       YFISTHGARKGLADTALKTADSGYLTRRLVDVAQDVIVREDDCGTDRGLEVEAIKEGNEI
ref|ZP_02326345.1|     YFISTHGARKGLADTALRTADSGYLTRRLVDVAQDVIVREEDCGTDKGFVVSKIQDGKEV
RAAC00407              YFISTHGARKGLADTALRTADSGYLTRRLVDVAQDTIVREHDCGTDKGLRVMEIRDGSEV
                       *****************:*****************.****.*****:*.     : :*.*:
```

FIG. 4C

```
ref|YP_001124231.1|   VVKLEERLVGRYAHKTVHHPETGEVIVRKDEMITEDIANEIIKAGITEVWIRSVFACNTR
ref|YP_145952.1|      VVKLEERLVGRYAHKTVRHPETGEVIVRKDEMITEDIANEIMKAGITEVWIRSVFACNTR
ref|NP_976431.1|      IESLYDRLVGRFARKTVKHPETGEVLVAENQLITEDIAHIVENSGVETVNIRSAFTCNTR
ref|NP_240993.1|      IEGLYDRLVGRVAFKTVRHPETGEPIVKKNELIHEDLAKQIVEAGVEQVTIRSVFTCDTR
ref|ZP_02326345.1     IEDLFDRIEGRYAFETVRHPETGEIIVHRNELIDANLASRIVEAGVEKIQIRSVMSCRAR
RAAC00407             IEDLRDRLEGRVAFQDVYHPETGEKIVGKNEMIDEEAADKIVAAGIKEVTIRSVLTCRTR
                       *  *:  ** *  : * ****** :*  .:::*  :  *  :  :*:  :***.::* :* ref|YP_001124231.1|   HGVCKKCYGRNMATGMDVEVGEAVGIIAAQSIGEPGTQLTMRTFHTGGVAGDDITQGLPR
ref|YP_145952.1|      HGVCKKCYGRNMATGMDVEVGEAVGIIAAQSIGEPGTQLTMRTFHTGGVAGDDITQGLPR
ref|NP_976431.1|      HGVCKKCYGRNLATGTDVEVGEAVGIIAAQSIGEPGTQLTMRTFHTGGVAGDDITQGLPR
ref|NP_240993.1|      HGVCKKCYGRNLATGSDVEVGEAVGIIAAQSIGEPGTQLTMRTFHTGGVAGDDITQGLPR
ref|ZP_02326345.1     YGVCKKCYGRNLATGQHVEIGEAVGIIAAQSIGEPGTQLTMRTFHTGGVAGDDITQGLPR
RAAC00407             HGVCQLCYGRNLATGDMVEVGEAVGIIAAQSIGEPGTQLTMRTFHTGGVAGDDITQGLPR
                      :*: *:*  :************************************** ref|YP_001124231.1|   VQELFEARNPKGQAVISEIDGTVVAINETRDNQYEIVVQSEVETRSYVAPYNARLKVEEG
ref|YP_145952.1|      VQELFEARNPKGQAVISEIDGTVISINKTRDNQYEVVVQGEVETRTYVAPYNARLKVEEG
ref|NP_976431.1|      IQEIFEARNPKGQAVISEIDGVIAAINDVKDRQ-EVVVQGEVETRTYAIPYGARLKVIPG
ref|NP_240993.1|      IQELFEARNPKGQAVITEIEGEVTNINEA-DKR-EITVKGEMETKTYSIPYGARIKVELG
ref|ZP_02326345.1     IQELFEARNPKGQAIITEIDGMVKDIREAKDRR-EIEVEGEAESRVYSVPFGSIRVAVN
RAAC00407             VQELFEARNPKGQAVIAEFDGVITDIREGKDKR-EIELTGESETKTYQIPYGSIRVSVG
                      :**:**********:*:*::*  :  *..  *.:  *:  :  .* *::  *  *:.:*::*  .

ref|YP_001124231.1|   QHVERGQELTEGSVDPKQLLRVRDITSVQEYLLREVQKVYRMQGVEISDKHIEVMVRQML
ref|YP_145952.1|      QRVERGQELTEGSVDPKQLLRVRDITSVQEYLLREVQKVYRMQGVEISDKHIEVMVRQML
ref|NP_976431.1|      QQISHGKELTEGSIDPKELLKVTDITAVQEYLLREVQKVYRMQGVEIGDKHVEVMVRQML
ref|NP_240993.1|      EQVVPGQSLTEGSIDPKELLKVQGMTGVQEYLLREVQKVYRMQGVEIGDKHVEVMVRQML
ref|ZP_02326345.1     DHIEAGDELTEGSIDPKEMLRIKGIRGVQNYILQEVQRVYRNQGVEINDKHVEVMIRQML
RAAC00407             QQLEAGEELTEGSVDPKEMLRVKGLQGVQNYLLREVQRVYRLQGVDINDKHIEVMIRQML
                      :::  *..***:*::*::  .:  .**:*:*:*:*  *.*:*:**** ref|YP_001124231.1|   RKVRVIDAGDTDVLPGTLLDVHQFTDVNAQAIREGKRPATARPVLLGITKASLETDSFLS
ref|YP_145952.1|      RKVRVIDAGDTDVLPGTLLDVHQFTDVNAKALREGKRPATARQVLLGITKASLETDSFLS
ref|NP_976431.1|      RKVRVSDAGETDVLPGTLLDIHQFTDANAKVLLQGKQPATARPVLLGITKASLETDSFLS
ref|NP_240993.1|      RKIRVIDAGDTEVLPGSLIEIQHFNDENKKVLLSGKRPATGRPVLLGITKASLETDSFLS
ref|ZP_02326345.1     RKIRIVDAGDTNLLPGSFVDMHEYEEANKTALLEGREPAVAKPILLGITKASLETDSFLS
RAAC00407             RKVRILDAGDTDLLPGTYVDLFEYEAANREALLSGKEPAVARPALLGITKASLETDSFLS
                      **:*:  ***:*::***:  :::  .:  *  .:  .*::..:  ************** ref|YP_001124231.1|   AASFQETTRVLTDAAIKGKRDELLGLKENVIIGKLVPAGTGMARYRNVKPAV--------
ref|YP_145952.1|      AASFQETTRVLTDAAIKGKRDELLGLKENVIIGKLVPAGTGMARYRKVKPAV--------
ref|NP_976431.1|      AASFQETTRVLTDAAIKGKRDELLGLKENVIIGKLVPAGTGMNRYRKVD-----------
ref|NP_240993.1|      AASFQETTRVLTDAAIKGKRDELVGLKENVIIGKLVPAGTGMNRYRNLD-----------
ref|ZP_02326345.1     AASFQETTRVLTDAAIKGKVDQLLGLKENVIIGKLIPAGTGMQRYRNI------------
RAAC00407             AASFQETTRVLTEAAIKGKVDRLLGLKENVIIGKLIPAGTGMVRYRNVEPEVVRPGDAEA
                      ************:*****  *.*:***********:******  ***::

ref|YP_001124231.1|   ----------------
ref|YP_145952.1|      ----------------
ref|NP_976431.1|      ----------------
ref|NP_240993.1|      ----------------
ref|ZP_02326345.1     ----------------
RAAC00407             AATGEEVAETEAVSSAE
```

FIG. 5

```
ref|NP_244660.1|        --------------------SKEEIQELSMVEVAYLVMKETKEPFNYQDLLKKVAELKG
ref|NP_693930.1|        --------------------THDEIDHLSMIELGVKILKEENKAMNYKVIFNKIAELKD
RAAC00480               MATGLSRAGREDSKMAISLARTEHEIQEMPLVELVYEILKARKEPMYFRDIMKEIQELRH
ref|ZP_01168478.1|      ---------------------TKEELQEMSFIDIAYELLKGTKQQVSFTDIMNEYKTRLE
ref|ZP_01860921.1|      --------------MSLKQLSTE-ELRQKSFIELAHELLTEKKQAVTFNDLLKEIGDLLK
ref|YP_001127419.1|     --------------MSLQQQYSPEELQEMSFVELANLILLNKREALPFDQIVREAAALTG
                                        :  *:  . .::::     ::      .:  .  :   :..:

ref|NP_244660.1|        MSEEQMLDRIGYLYTDLNIDGRFVTLGDNRWGLRSWYPLEQVEEEITGPTK---------
ref|NP_693930.1|        FTDEQKQNMMAQFYTDMNVDGRFLTLGSGMWGLKRWYPVEQAEEEIT-------------
RAAC00480               MTDEQVADVIARVFTEINVDGRFVCIGHNVWGLNRWYPTDRNAERLSGGKKFIRKTGDAF
ref|ZP_01168478.1|      VSDEEIRSRIAQFYTDLNLDGRFIAMGENRWGLRSWYPVDTMEE----------------
ref|ZP_01860921.1|      LSKEEVRSRMVQFYTDLNVDGRFIALGENRWGIRAWYPVDQIEEETVPTIKPRKKKAKKT
ref|YP_001127419.1|     ATEDDIAARLAQYYTDLNIDGRFICVGENVWGLRAWYPFDQTED----------------
                        :.::      :     :*::*:****: :* .  **:. ***  :     :

ref|NP_244660.1|        ------------------------------------------------------------
ref|NP_693930.1|        ------------------------------------------------------------
RAAC00480               GDEEDDEEEYEEEDVLEDDELDYDEVEAVDEEPEFDDVEVVEDEDEILPEDEYDDAPLFD
ref|ZP_01168478.1|      ------------------------------------------------------------
ref|ZP_01860921.1|      DD----------------------------------------------------------
ref|YP_001127419.1|     ------------------------------------------------------------ ref|NP_244660.1|        -----------
ref|NP_693930.1|        -----------
RAAC00480               EEEEVEEDEED
ref|ZP_01168478.1|      -----------
ref|ZP_01860921.1|      -----------
ref|YP_001127419.1|     -----------
```

FIG. 6

```
ref|NP_465351.1|     ---MLYPSIDNLLLKIDSKYSLVTVAAKRARYMQLENDKGVLPSYQSDKFVGKALEEIHA
ref|NP_471274.1|     ---MLYPSIDNLLLKIDSKYSLVTVAAKRARYMQLENDKGVLPSYQSDKFVGKALEEIHA
ref|YP_014447.1|     ---MLYPSIDNLLLKIDSKYSLVTVAAKRARYMQLENDKGVLPSYQSDKFVGKALEEIHA
ref|YP_850042.1|     ---MLYPSIDNLLLKIDSKYSLVTVAAKRARYMQLENDKGVLPSYQSDKFVGKALEEIHA
RAAC00147            ---MIYPSIDRLLERCNSKYALVVLAAKRAR--KLQNETLNQPGASTTRNVSRALWEIHD
ref|NP_268055.1|     ---MLEPSIDKLLDQVDSKYSLVVLEAKRAH--ELRDKERPTKEFKAVKNTLRALEEIAD
                        *: ****.**  : :***:**.: ****:   :*.:.       .: : . :** **

ref|NP_465351.1|     GKLVLQNDD--
ref|NP_471274.1|     GKLVLQN----
ref|YP_014447.1|     GKLVLQNDD--
ref|YP_850042.1|     GKLVLKN----
RAAC00147            GVVRCKNFDGE
ref|NP_268055.1|     GTVK-------
                     *  :
```

FIG. 7

```
ref|YP_074981.1|         ------ETEARPAEAAVEAWIQQHGEAVLRLAYASLLNRAQAEDVFQEVFIRAYRHADRL
ref|YP_001275817.1|      ------------DHDAFAQLMGRYAGSVFNLAYRMLGNAQEAEDASQEIFLRAYTNLARF
RAAC01826                MRHARRNETPAEDAALLAEWMELYGGDVIRLAYSYVHNFHKAEDIAQDVFLRAWQHYGEF
ref|YP_074736.1|         MSQSDRAALPSDRTAAIDHLMREYGTKVLHLAYSYLKDRHLAEDVAQEVFIKAYRNWENF
ref|YP_001394390.1|      ----------------LERLMNCYGNDILRTAYIYLKDIHLAEDVFQDVFIKVYNNFDKF
ref|NP_244228.1|         ---------------LIAWMEEYGTAILRVVYSYVKDKQIAEDLTQEVFVRAFQSYHTY
                                          .   :.  ::. .*  : :    ***  *::*::.:

ref|YP_074981.1|         RDPDRVRPWLLQVTMNACRDLRRSWWWRRTREGSGL--EGLAEAGEGPAADPAAAAVRAD
ref|YP_001275817.1|      DQERRFSTWLLSIGSNYCIDRLR----RRRFAWLTL--DDVVLSVPTSAKGPERSAVERE
RAAC01826                QGQSSIKTWLLSITANRARDVLRSGAERREFAD-----EGEAFAREIEPCDPADLVADKL
ref|YP_074736.1|         RGESSAYTWLYRITVNLCRDKARSAWWRRLLPTDDPRAAGTPVEPDTAGDDPEEAVVLSD
ref|YP_001394390.1|      NGKSSEKTWILTITINTCRDMLRSCWIKKVLRFDDT-EYGIFNSTDDLN-DTEDTVIKNI
ref|NP_244228.1|         QTRSSAKAWLYRIAINRSKDFLKSWHAKHVYPSE------VAEEIETTEQTPEYEVLLKS
                             .*:   :  * .* .      ::               . .

ref|YP_074981.1|         VSQAVARAVRALPDGFRETVVLHYFEGLDAAEIARITGVRVGTVHSRLHRARQLLRRQLE
ref|YP_001275817.1|      ERDAVQRALLSLPPTYREVAVLRYWNDLSYEEITQVTGLPESTIKTRLHRARRMLAEALR
RAAC01826                ARDAVWRAIRVLPETYREVMELYYGNDLTTHEVAEILGIRDQTVRTRLHRGRQMLERALA
ref|YP_074736.1|         QRERLLDYVMQLSDAYREVIILYYYHDLTTVEIABVTGQNENTVKTRLFRARAMLKQMLQ
ref|YP_001394390.1|      EYEDILKKVMDLPKKYKEVILLYYYQELSTSEISKILKIPEGTVRSRLYRARGILK----
ref|NP_244228.1|         DEERLAAAVFSLPLSYREVIYFYYYEELSVKEVASFTGLNENTVKTRLRKGRLLLKNLLE
                          :  :    :  *.  ::*.  : * . *   *::  .      *:::**  :.*  :* ref|YP_074981.1|         AWG-------
ref|YP_001275817.1|      AEG-------
RAAC01826                EQGGMGVDHA
ref|YP_074736.1|         KGG-------
ref|YP_001394390.1|      ----------
ref|NP_244228.1|         KE--------
```

FIG. 8

```
ref|YP_001126509.1|    ---------------TLEQAKEQLAELGKKRGILTYEEIAERLSGFDLDSDQMDEYYEYL
ref|YP_148335.1|       ----------EAAGESLEQVKEQLAELGKKRGILTYEEIAERLSGFDLDSDQMDEYYEYL
ref|ZP_01173341.1|     MAEKSARSKEVDSELTMEQVKEQLTEVGKKTGVLAYDDIAERLSNFELDSDQMDEFYEFL
ref|YP_001376241.1|    ---------------MTLEQVKEQLTELGKKRGVLTYEEIAERMNGFEIESEQMDEYYEYL
ref|ZP_02328521.1|     ----NDQHTELETELTLEQVKDQLIELGKKRSSLTYKEIMDRLAPYDQDAEQIDDFFEHL
RAAC00896              MAKTNDEIRDEDQGITLQEAKQQLIELGKKQGSLTYEEISDRLSSFDMDADAMDDFFEQL
                           :::: .*:** *:***  . *:*..* :*:   ::  :::  :*:::* * ref|YP_001126509.1|    ADQGIEVISESDIETDPDIDELVK-EEEFDLN---DLSVPPGVKINDPVRMYLKEIGRVP
ref|YP_148335.1|       AEQGIEVISESDLEADPDIDDLAK-EEEFDLN---DLSVPPGVKINDPVRMYLKEIGRVP
ref|ZP_01173341.1|     GDQGVELVGD-NDDADPNVQELAKGEEEFDLN---DLSVPPGVKINDPVRMYLKEIGRVD
ref|YP_001376241.1|    GEQGIDLVGD-NDEG-PNNHQITKTEEEFDLN---DLSVPPGVKINDPVRMYLKEIGRVD
ref|ZP_02328521.1|     SEMGIDVGNE-NDDDEDNIRPGNTDNEDEDFNFEDDLTLPPGIKINDPVRMYLKEIGRVP
RAAC00896              AELGIDVVNE-RDEE------GGREDDDYDL---DDLSVPPGVKISDPVRMYLKEIGRVP
                        .: *:::  .:      :       :::  *:    ::*:.********** ref|YP_001126509.1|    LLSAEEEIELAKRIEQGDEEAKRRLTEANLRLVVSIAKRYVGRGMLFLDLIQEGNMGLIK
ref|YP_148335.1|       LLSAEEEIELAKRIEQGDEEAKRRLTEANLRLVVSIAKRYVGRGMLFLDLIQEGNMGLIK
ref|ZP_01173341.1|     LLSAQEEISLAKRIEQGDEEAKRRLAEANLRLVVSIAKRYVGRGMLFLDLIQEGNMGLIK
ref|YP_001376241.1|    LLSAEEEIQLATRIEEGDEEAKRRLAEANLRLVVSIAKRYVGRGMLFLDLIQEGNMGLIK
ref|ZP_02328521.1|     LLSAEDEVELAKRIEQGDEEAKRRLTEANLRLVVSIAKRYVGRGMLFLDLIQEGNMGLIK
RAAC00896              LLSAQEEIELAKRIEQGDEEAKQRLAEANLRLVVSIAKRYVGRGMLFLDLIQEGNLGLLK
                       ****:.:*:..*:**** ::******************************:.* ref|YP_001126509.1|    AVEKFDYRKGYKFSTYATWWIRQAITRAIADQARTIRIPVHMVETINKLIRVQRQLLQDL
ref|YP_148335.1|       AVEKFDYRKGYKFSTYATWWIRQAITRAIADQARTIRIPVHMVETINKLIRVQRQLLQDL
ref|ZP_01173341.1|     AVEKFDYRKGYKFSTYATWWIRQAITRAIADQARTIRIPVHMVETINKLIRVQRQLLQDL
ref|YP_001376241.1|    AVEKFDYRKGFKFSTYATWWIRQAITRAIADQARTIRIPVHMVETINKLIRVQRQLLQDL
ref|ZP_02328521.1|     AVEKFDHTKGYKFSTYATWWIRQAITRAIADQARTIRIPVHMVETINKLIRVSRQLLQEL
RAAC00896              AVEKFDYRKGYKFSTYATWWIRQAITRAIADQARTIRIPVHMVETINKLIRVSRQLLQEL
                       ****: :***********************************.***:* ref|YP_001126509.1|    GREPTPEEIAEEMDLTPEKVREILKIAQEPVSLETPIGEEDDSHLGDFIEDQEATSPSEH
ref|YP_148335.1|       GREPTPEEIAEEMDLTPEKVREILKIAQEPVSLETPIGEEDDSHLGDFIEDQDATSPSEH
ref|ZP_01173341.1|     GREPTPEEIAEDMDLTPDKVREILKIAQEPVSLETPIGEEDDSHLGDFIEDQDATSPSEH
ref|YP_001376241.1|    GREPTPEEIGEEMDLAPEKVREILKIAQEPVSLETPIGEEDDSHLGDFIEDQEATSPADH
ref|ZP_02328521.1|     GREPTPEEIAKEMELSTDKVREIMKIAQEPVSLETPIGEEDDSHLGDFIEDQEALAPADA
RAAC00896              GREPTPEEIAAEMDLTPEKVREIQKIAQEPVSLETPIGEEDDSHLGDFIPDDEAPAPADA
                       *********. :*.*:.:***** *********************** *::* :*::

ref|YP_001126509.1|    AAYELLKEQLEDVLDTLTDREENVLRLRFGLDDGRTRTLEEVGKVFGVTRERIRQIEAKA
ref|YP_148335.1|       AAYELLKEQLEDVLDTLTDREENVLRLRFGLDDGRTRTLEEVGKVFGVTRERIRQIEAKA
ref|ZP_01173341.1|     AAYELLKEQLEDVLDTLTDREENVLRLRFGLDDGRTRTLEEVGKVFGVTRERIRQIEAKA
ref|YP_001376241.1|    AAYELLKEQLEDVLDTLTDREENVLRLRFGLDDGRTRTLEEVGKVFGVTRERIRQIEAKA
ref|ZP_02328521.1|     AAYELLKEQLEDVLDTLTDREENVLRLRFGLDDGRTRTLEEVGKVFGVTRERIRQIEAKA
RAAC00896              AAYELLKEQLEDVLDTLTEREENVLRLRFGLDDGRTRTLEEVGKVFGVTRERIRQIEAKA
                       ****************:*************************************** ref|YP_001126509.1|    LRKLRHPSRSKRLKDFLE
ref|YP_148335.1|       LRKLRHPSRSKRLKDFLE
ref|ZP_01173341.1|     LRKLRHPSRSKRLKDFLE
ref|YP_001376241.1|    LRKLRHPSRSKRLKDFLE
ref|ZP_02328521.1|     LRKLRHPSRSKRLKDFLE
RAAC00896              LRKLRHPSRSKRLKDFLE
                       ******************
```

FIG. 9

```
ref|YP_146980.1|         --------------------------------DEIYYIGGSEALPPPLTKEEEEQLIAR
ref|YP_001125115.1|      --------------------------------DEIYYIGGSEALPPPLTKEEEERLIER
ref|ZP_01862300.1|       --------------------------------DEIYYIGGSEALPPPLSKEEEAVLLKK
ref|ZP_01172495.1|       --------------------------------DEIFYIGGSEALPPPLSKEEEEVLLIK
ref|NP_243422.1|         --------------------------------DEIYYIGGSEALPPPLSKEEEAHLLKK
RAAC00120                MYAFQFLETKRRLALLRLRLLYIRLRIRLLGQPDEVYYVGGSEALPPPLTKEEEQYLLER
                                                         **::*:**********:**** *: :

ref|YP_146980.1|         LAAGDDTARSLLIERNLRLVVYIARKFENTGIHIEDLISIGTIGLIKAVNTFNPEKKIKL
ref|YP_001125115.1|      LAVGDKTARSLLIERNLRLVVYIARKFENTGIHIEDLISIGTIGLIKAVNTFNPEKKIKL
ref|ZP_01862300.1|       LPNGDKTARSLLIERNLRLVVYIARKFENTGINIEDLISIGTIGLIKAVNTFNPEKKIKL
ref|ZP_01172495.1|       LPKGDKAARSMLIERNLRLVVYIARKFENTGINIEDLISIGTIGLIKAVNTFNPEKKIKL
ref|NP_243422.1|         LPSGDKAVRSMLIERNLRLVVYIARKFENTGINIEDLISIGTIGLIKAVNTFNPEKKIKL
RAAC00120                LPSGDPSVRSMLIERNLRLVVYIARKFENTGVNIEDLVSIGTIGLIKAVNTFDPSKKIKL
                         *.   :.:*****************.:.**********:*.***** ref|YP_146980.1|         ATYASRCIENEILMYLRRNNKVRAEVSFDEPLNIDWDGNELLLSDVLGTDDDVITKDLEA
ref|YP_001125115.1|      ATYASRCIENEILMYLRRNNKVRAEVSFDEPLNIDWDGNELLLSDVLGTEDDVITKDLEA
ref|ZP_01862300.1|       ATYASRCIENEILMYLRRNNKIRSEVSFDEPLNIDWDGNELLLSDVLGTEEDIITKDLEA
ref|ZP_01172495.1|       ATYASRCIENEILMYLRRNNKIRSEVSFDEPLNIDWDGNELLLSDVLGTEEDIITKDLEA
ref|NP_243422.1|         ATYASRCIENEILMYLRRNNKIRSEVSFDEPLNIDWDGNELLLSDVLGTDDDIITRGIEE
RAAC00120                ATYASRCIENEILMYLRRNNKLRAEVSLDEPLNVDWDGNELLLSDVLGTDSDTIYRNLED
                         *********************:*:*:*:**********:.* *  :.:* ref|YP_146980.1|         DVDRRLLLNALRQLSDREKQIMELRFGLSGGEEKTQKDVADLLGISQSYISRLEKRIIKR
ref|YP_001125115.1|      DVDRRLLLNALRQLSDREKQIMELRFGLSGGEEKTQKDVADLLGISQSYISRLEKRIIKR
ref|ZP_01862300.1|       TVDRKLLFNALTELSDREKQIMELRFGLMGGEEKTQKDVADMLGISQSYISRLEKRIIKR
ref|ZP_01172495.1|       NVDKKLLLKALHQLTDREKQIMELRFGLGSGEEKTQKDVADMLGISQSYISRLEKRIIKR
ref|NP_243422.1|         KVDRKLLMKALHTLTDREKQIMELRFGLAGGEEKTQKDVADLLGISQSYISRLEKRIIKR
RAAC00120                EVDRELLYDALDKLSERERTIMELRFGLGTGQEMTQKDVADLLGISQSYISRLEKRILKR
                          **:.** .**   *::** :********   *:* *******:************:**

ref|YP_146980.1|         LRKEFNKMM
ref|YP_001125115.1|      LRKEFNKMM
ref|ZP_01862300.1|       LKKEFNKMV
ref|ZP_01172495.1|       LKKEFNKMV
ref|NP_243422.1|         LQKEFNKMV
RAAC00120                LQREFNKMM
                         *::*****:
```

FIG. 10

```
ref|YP_001126333.1|      -----MPMDVDVKQDQSPIKDQEMKELIRRSQEGDQEARDEIIEKNMRLVWSVVQRFLNR
ref|YP_148161.1|         ------------------IKDQEMKELIRRSQEGDQEARDEIIEKNMRLVWSVVQRFLNR
pdb|1L00|C               -----------HMQGQSPIKDQEMKELIRRSQEGDQEARDEIIEKNMRLVWSVVQRFLNR
gb|AAB81194.1|            ------------------IKDQEMKELIRRSQEGDQEARDEIIEKNMRLVWSVVQRFLNR
ref|YP_001487306.1|      -----------------QLSNDEVKELIKKSQDGDQQARDLLVEKNMRLVWSVVQRFLNR
RAAC02146                MDQAKERPVPHHVDEYEKLSDEEVRELLERSHNGDAEARERLIVHNQRLVWAVVQRFLGR
                                          :.::*::**:..:*::  :. ::  :* **:****.* ref|YP_001126333.1|      GYEADDLFQIGCIGLLKSVDKFDLSYDVKFSTYAVPMIIGEIQRFLRDDGTVKVSRSLKE
ref|YP_148161.1|         GYEADDLFQIGCIGLLKSVDKFDLSYDVKFSTYAVPMIIGEIQRFLRDDGTVKVSRSLKE
pdb|1L00|C               GYEADDLFQIGCIGLLKSVDKFDLSYDVKFSTYAVPMIIGEIQRFLRDDGTVKVSRSLKE
gb|AAB81194.1|            GYEADDLFQIGCIGLLKSVDKFDLSYDVKFSTYAVPMIIGEIQRFLRDDGTVKVSRSLKE
ref|YP_001487306.1|      GYEPDDLFQIGCIGLLKSVDKFDLSYDVKFSTYAVPMIIGEIQRFIRDDGTVKVSRSLKE
RAAC02146                GYEAEDLFQIGCIGLMKAVDKFDLSYDVKFSTYAVPMIIGEIQRFLRDDSTVKVSRSLKE
                         *.:********.*:.***********************:.******** ref|YP_001126333.1|      MGNKIRKAKDELSKTRGRAPTITEIADHLGVSPEEVVLAQEAVRSPASIHETVYENDGDP
ref|YP_148161.1|         MGNKIRKAKDELSKTRGRAPTVTEIADHLGISPEDVVLAQEAVRSPTSIHETVYENDGDP
pdb|1L00|C               MGNKIRKAKDELSKTRGRAPTVTEIADHLGISPEDVVLAQEAVRLPTSIHETVYENDGDP
gb|AAB81194.1|            MGNKIRKAKDELSKTRGRSPTITEIADHLGISPEDVVLAQEAVRLPTSIHETVYENDGDP
ref|YP_001487306.1|      LGNKIRRARDELSKSHGRMPTVQEIAEYLDITPEDVVLAQEAVRTPSSIHETVYENDGDP
RAAC02146                TAKQIRHVRDRLAKELGRQPHITEIAEAMGMEPSEIVFAQEALRAPASIHETVYENDGDP
                          .::**:.:*.*:*  ** * : ***. :.: *.::*:****:* *:************ ref|YP_001126333.1|      ITLLDQIADADEASWFEKIALKKAIEELDERERLIVYLRYYKDQTQSEVAARLGISQVQV
ref|YP_148161.1|         ITLLDQIADADEASWFDKIALKKAIEELDERERLIVYLRYYKDQTQSEVASRLGISQVQV
pdb|1L00|C               ITLLDQIADADEASWFDKIALKKAIEELDERERLIVYLRYYKDQTQSEVASRLGISQVQM
gb|AAB81194.1|            ITLLDQIADADEASWFDKIALKKAIEELDERERLIVYLRYYRDRTQSEVASRLGISQVQV
ref|YP_001487306.1|      ITLLDQIADHSEERWFDKIALKEAIKELEEREKLIVYLRYYKDQTQSEVAERLGISQVQV
RAAC02146                IYLMDQIADEETEGKFDKVELHEIIGRLPERERFIVYMRFFRDKTQSDVARVLGISQVQV
                         * *:***** .    *:*: *:: * .* ***::***:*:::*:***:**  *******:

ref|YP_001126333.1|      SRLEKKILQHIKEKMD
ref|YP_148161.1|         SRLEKKILQHIKDKMD
pdb|1L00|C               SRLEKKILQHIK----
gb|AAB81194.1|            SRLEKKILQHIKDKMD
ref|YP_001487306.1|      SRLEKKILKQIQMQMD
RAAC02146                SRLEKRILQQIRQELE
                         *****:**::*: :
```

FIG. 11

```
ref|YP_001212395.1|      ------------NKVEICGVNTSKLPVLTGSQMKALFEAMHK-GDASARTKLINGNLRLV
ref|ZP_01667054.1|       ------------NKVEICGVNTAKLPVLSANKMRELFEIMQQ-GNPEAREQLIYGNLRLV
RAAC00121                MTGRLGGTSLKRNKVEICGVNTSQLPVLTNAQMRELFEQLRA-GDPSAREKLVNGNLRLV
ref|YP_001125116.1|      ----MGGNNLTRNKVEICGVDTSKLPVLKNEEMRELFQRMHE-GDLEAREKLVNGNLRLV
ref|NP_243420.1|         ---------MTRNKVEICGVDTSKLPVLKNQEMRELFARLQS-GDTSARETLVNGNLRLV
ref|ZP_02330758.1|       ---------MTRNKVEICGVDTAKLPVLTNTEMRELFALLQTKNERAAREKLVNGNLRLV
                                     ********:*::****.  :*:   ::   .:    *: ****** ref|YP_001212395.1|      LSVIQRFTNRGEYVDDLFQVGCIGLMKAIDNFDLSQNVKFSTYAVPMIIGEIRRYLRDNN
ref|ZP_01667054.1|       LSVIQRFNNRGEYVDDLFQVGCIGLMKAIDNFDLSQNVKFSTYAVPMIIGEIRRYLRDNN
RAAC00121                LSVIQRFNNRGEYVDDLFQVGCIGLMKAIDNFDLNQNVRFSTYAVPMIVGEIRRYLRDNN
ref|YP_001125116.1|      LSVIQRFNNRGEFVDDLFQVGCIGLMKSIDNFDLNQNVKFSTYAVPMIIGEIRRYLRDNN
ref|NP_243420.1|         LSVIQRFNNRGEYVDDLFQVGCIGLMKSIDNFDLSQNVKFSTYAVPMIIGEIRRYLRDNN
ref|ZP_02330758.1|       LSVIQRFNNRGEFVDDLFQVGCIGLMKAIDNFDLSQNVKFSTYAVPMIIGEIRRYLRDNN
                         *****.:**********:**.:****:********* ref|YP_001212395.1|      PIRVSRSLRDVAYKALQVRDALVNKY--SREPSINEIACELKMPREEIVFALDAIQEPIS
ref|ZP_01667054.1|       PIRVSRSMRDIAYKALQVRDALVSKF--SREPSINEIADELKIPREEIIFALDAIQEPVS
RAAC00121                PIRVSRSLRDIAYKALQVRDMLASKN--LREPSIVEIANEMNLPKEEVVFALDAIQDPVS
ref|YP_001125116.1|      PIRVSRSLRDIAYKALQVRERLMGET--AKEPSTEEIAKELGVAHEEVVLALDAIQDPVS
ref|NP_243420.1|         PIRVSRSLRDIAYKALQVRDLMGEKQREKEPTVQEIAKELGVPKEDVVFALDAIQDPVS
ref|ZP_02330758.1|       PIRVSRSLRDIAYKALQVRDQLTNRN--SREPTIYEISEVLNVPKEDVVFALDAIQDPVS
                         *****::********:  *    :: :   : :.:*:::********:*:* ref|YP_001212395.1|      LFEPIYHDGGDPIFVMDQISDEKNQDQNWLEGIAIRDALRKLSDREKLILTLRFYEGKTQ
ref|ZP_01667054.1|       LFEPIYHDGGDPIFVMDQISDDKNQDMNWLEGVAIKEALRKLSDREKHILTLRFFEGKTQ
RAAC00121                MFEPIYHDGGDPIYVMDQIHDEREKDSAWVEGIALREAMRKLSDREKKILAKRFYEGKTQ
ref|YP_001125116.1|      LFEPIYNDGGDPIYVMDQLSDERNRDSQWIEEIALKEGLRRLNEREKMIIRKRFFQGKTQ
ref|NP_243420.1|         LFEPIYNDGGDPIYVMDQISDDRNKDVQWVDEIALKEAMVRLNDREKLILNMRFYQGKTQ
ref|ZP_02330758.1|       LFEPIYHDGGDPIYVMDQISDERNKDLFWIEGIALREAMRKLGSREKMILSMRFFEGKTQ
                         :*****:******:****: *:::*  *:: :*::::.: :*.. ***  *:   **::****

ref|YP_001212395.1|      MEVAEEIGISQAQVSRLEKAALNHMKKHI--
ref|ZP_01667054.1|       MEVADEIGISQAQVSRLEKAALGHMRKYI--
RAAC00121                MEVADEIGISQAQVSRLEKAAIHRMYKHIQS
ref|YP_001125116.1|      MEVAEEIGISQAQVSRLEKAAIRQMNKNIQ-
ref|NP_243420.1|         MEVAEEIGISQAQVSRLEKAAIQQMSKHAQS
ref|ZP_02330758.1|       MEVADEIGISQAQVSRLEKSAINQMQKHVKT
                         ****:**************.:*  :* *
```

```
FIG. 12 ref|NP_842661.1|         ------------------------------------------------------------
ref|NP_829995.1|         ------------------------------------------------------------
ref|NP_976421.1|         ------------------------------------------------------------
ref|YP_001373458.1|      ------------------------------------------------------------
ref|YP_001512033.1|      ------------------------------------------------------------
RAAC02546                -------MTDQSLGRSPARLEDTAQASVPERRSRDLRRSFQLKCTISRIFVN-------- ref|NP_842661.1|         --------------------------------------------DEAIVELVRKGNT
ref|NP_829995.1|         --------------------------------------------DEAIVELVRKGNT
ref|NP_976421.1|         --------------------------------------------DEAIVELVRKGNT
ref|YP_001373458.1|      --------------------------------------------DEAIVELVRKGNI
ref|YP_001512033.1|      --------------------------------------------VLDEVMVEIAKEGDL
RAAC02546                -----------------------------ALLPCTSLTIGGDFVMDTTLVLSAKRGDQ
                                                              *  .:*   .:.*:

ref|NP_842661.1|         DALEYLIHKYKNFVRAKSRSYFLVGADREDIVQEGMIGLFKAIRDYKEDKLSSFKAFAEL
ref|NP_829995.1|         DALEYLIHKYKNFVRAKSRSYFLVGADREDIVQEGMIGLFKAIRDYKEDKLSSFKAFAEL
ref|NP_976421.1|         DALEYLIHKYKNFVRAKSRSYFLVGADREDIVQEGMIGLFKAIRDYKEDKLSSFKAFAEL
ref|YP_001373458.1|      DALEYLIHKYKNFVRAKSRSYFLVGADREDIVQEGMIGLFKAIRDYKEDKLSSFKAFAEL
ref|YP_001512033.1|      EALEYLIKKYKNFVRAKARSYFLIGADREDIVQEGMIGLYKAIRDFKPDKLSSFRAFAEL
RAAC02546                DSFMALYREFHARIRSWIRNYWIPGADREDLMQHAWIGFWEAIRDYDVRGKVPFRAFAKM
                         ::: * :::: :*: *.*:: ******::*.. **:::****:.    .*:***::

ref|NP_842661.1|         CITRQIITAIKTATRQKHIPLNSYVSLDKPI-YDEESDRTLLDVISEAKVTDPEEMIIS-
ref|NP_829995.1|         CITRQIITAIKTATRQKHIPLNSYVSLDKPI-YDEESDRTLLDVISEAKVTDPEEMIIS-
ref|NP_976421.1|         CITRQIITAIKTATRQKHIPLNSYVSLDKPI-YDEESDRTLLDVISEAKVTDPEEMIIS-
ref|YP_001373458.1|      CITRQIITAIKTATRQKHIPLNSYVSLDKPI-YDEESDRTLLDVISEAKVTDPEEMIIS-
ref|YP_001512033.1|      CITRQIITAIKTATRQKHIPLNSYVSLNKPI-YDEESDRTLLDVISGQKVTDPEELVVS-
RAAC02546                CVMREIQAALKMARRQKHVSHLTALSLDAECPWIEDAERTVLDVFVDRAAPSVDDMVFGP
                         *: *:* :*:* * ****:.  : :**:   : *::*****:.   ... :::::..

ref|NP_842661.1|         ------QEEYTDIESKISELLSDLER----------KVLSLYLDGRSYQEISEQLNRHV
ref|NP_829995.1|         ------QEEYTDIESKISELLSDLER----------KVLSLYLDGRSYQEISEQLNRHV
ref|NP_976421.1|         ------QEEYTDIESKISELLSDLER----------KVLSLYLDGRSYQEISEQLNRHV
ref|YP_001373458.1|      ------QEEYSDIELKISELLSDLER----------KVLSLYLDGRSYQEISEQLNRHV
ref|YP_001512033.1|      ------REELGHIEDKIGEILSDLEL----------KVLMLYLEGRSYQEIAGDLERHV
RAAC02546                PPSAGPEELVAWAERHWGLRLTELER----------EVWRLRVEGHSYAEIQRMLGCGY
                          .*       * : . *::**                :*  *  ::*:    * ref NP_842661.1          KSIDNALQRVKRK------------
ref NP_829995.1          KSIDNALQRVKRK------------
ref NP_976421.1          KSIDNALQRVKRK------------
ref YP_001373458.1       KSIDNALQRVKRK------------
ref YP_001512033.1       KSIDNALQRVKRK------------
RAAC02546                KAVDNAVQRLRRKAKMLVNNANLQT
                         *::***:**::**
```

FIG. 13

```
ref|YP_077384.1          ----------------------LEDEQVIEMVHVGDSDALDYLITKYRNFVRAKARSYF
ref|YP_001419777.1|      ----------------------LEDEQVIEKVHVGDSDALDYLITKYRNFVRAKARSYF
emb|CAA41793.1|          ----------------------EQQEDETVVDLVHKGDIDALEYLIHKYKNFVRAKARSYF
ref|ZP_01173595.1|       ----------------------LEDEEIIELVHRGESEALDYLIQKYRNFVRAKARSYF
ref|NP_240981.1          ----------------------DVGLVNRVRNGDGAALEYLIHKYKNFVRAKARSYF
RAAC00418                MSTQPTPRDADAAPPYDTAPYENMTDEELVEAVHRGDTDALDYLIHKYKNFVRAKARSYF
                                               *  :::  *:  *:   :*  ;********* ref|YP_077384.1          LIGADREDIVQEGMIGLYKSIRDFREDKLTSFKAFAELCITRQIITAIKTATRQKHIPLN
ref|YP_001419777.1|      LIGADREDIVQEGMIGLYKSIRDFREDKLTSFKAFAELCITRQIITAIKTATRQKHIPLN
emb|CAA41793.1|          LIGADREDIVQEGMIGLYKAIRDFREDKLTSFKAFAELCITRQIITAIKTATRQKHIPLN
ref|ZP_01173595.1|       LIGADKEDIVQEGMIGLYKAIRDFKEDKLSSFKAFAELCITRQIITAIKTATRQKHIPLN
ref|NP_240981.1          LIGADHEDIVQEGMIGLYKAIRDFKGDKLSSFKAFAELCITRQIITAIKTATRQKHIPLN
RAAC00418                LIGADREDIVQEGMIGLYKSIRDFRGDKLSSFKAFAELCITRQIITAIKTATRQKHIPLN
                         ***:********:.: *:******************************* ref|YP_077384.1          SYVSLDKPIYDEESDRTLLDVISGAKVMNPEELIINQEEFDDIELKMGELLSDLERKVLA
ref|YP_001419777.1|      SYVSLDKPIFDEESDRTLLDVISGAKTLNPEEMIINQEEFDDIEMKMGELLSDLERKVLV
emb|CAA41793.1|          SYVSLDKPIYDEESDRTLMDVISGTKVANPEELIINREKFDDIELKMAELLSDLERKVLV
ref|ZP_01173595.1|       SYVSLDKPIYDEESDRTLMDVISGAKVMDPEELIINQEEFDNIEVKMSELLSDLERKVLA
ref|NP_240981.1          SYVSLDKPLYDEESDRTLLDVVCGSRVTDPEELLINQEEFDDIEVKMGELLSDLERKVLM
RAAC00418                SYVSLDKPIYDEDSDRTLLDVICTVRVADPEELIINQEEFDDIEGKMSELLSDLERQVLM
                         ********::**:*****:**:.   :. :***::**:*:** ** **:*******:**

ref|YP_077384.1          LYLDGRSYQEISEELNRHVKSIDNALQRVKRKLEKYLELREI-
ref|YP_001419777.1|      LYLDGRSYQEISDDLNRHVKSIDNALQRVKRKLEKYLEIREI-
emb|CAA41793.1|          LYLDGQSYQEISEELNRHVKSIDNALQRVKRKLERYLEIREI-
ref|ZP_01173595.1|       LYLDGQSYQEISEELNRHVKSIDNALQRVKRKLERYLEVR---
ref|NP_240981.1          LYLDGRSYQEISAELNRHVKSIDNALQRVKRKLERYMELKGV-
RAAC00418                LYLDGRSYQEIAVDLARHVKSIDNALQRVKRKLEKYLTVRNVI
                         *****:*****:  :* *******************:*: ::
```

FIG. 14

```
ref|YP_181606.1|         ------------------------------------------------------------
RAAC02968                ------------------------------------------MLDVLVDRTAPSVED
ref|YP_001409756.1|      ------------------------------------------------------------
ref|NP_976421.1|         ---------------------------------------------LLDVISEAKVTDPEE
ref|NP_842661.1|         C--------------------------------------------LLDVISEAKVTDPEE
ref|YP_001485343.1|      ---------------------------------------------LLDVISGAKALNPED ref|YP_181606.1|         ----------------WLEPAKGMN------ISHRELEVFVLMIEGHNNKEIGALLGIQY
RAAC02968                VVFGPPKGVSAEELVAWAERHWRLN------LSELEREVWRLRIEGHSYTEIQRMLGCGY
ref|YP_001409756.1|      ------------------------------LNEEETQIFELWLDGYSYKEIEEMVGVNF
ref|NP_976421.1|         MI------ISQEEYTDIESKISEL-------LSDLERKVLSLYLDGRSYQEISEQLNRHV
ref|NP_842661.1|         MI------ISQEEYTDIESKISEL-------LSDLERKVLSLYLDGRSYQEISEQLNRHV
ref|YP_001485343.1|      LI------ISKEEFDDIEMKMGEL-------LSELERKVLVLYLDGRSYQEISEDLNRHV
                                         :..  *  ::   *  ::*  .  **    :.

ref|YP_181606.1|         QSVKN--------------------
RAAC02968                KAVDNAVQRLRKKARRALMRQEGAAL
ref|YP_001409756.1|      KKVDNTV-------------------
ref|NP_976421.1|         KSIDNAL-------------------
ref|NP_842661.1|         KSIDNAL-------------------
ref|YP_001485343.1|      KSIDNAL-------------------
                         : :.*
```

FIG. 15  RAAC03263

```
ref|YP_001666100.1|       ---------- ---------- ---------- ---------- ---------- ----------
ref|NP_621806.1|          ---------- ---------- ---------- ---------- ---------- ----------
ref|NP_346951.1|          ---------- ---------- ---------- ---------- ---------- ----------
ref|YP_001181188.1|       ---------- ---------- ---------- ---------- ---------- ----------
ref|YP_001317994.1|       ---------- ---------- ---------- ---------- ---------- ----------
RAAC03236                 MSGCVSSLPF ILALCVSSAA PRVRALGGAW LRLGHRLAIG AAFTVCATAS HCCPTRCRMD
Clustal Consensus ref|YP_001666100.1|       ---------- -----TGIVR KVDELGRVVI PIELRRTLNI AERDALEIYV DGEQIVLKKY
ref|NP_621806.1|          ---------- -----TGIVR KVDELGRVVI PIELRRTLNI AERDALEIYV DGEQIVLKKY
ref|NP_346951.1|          ---------- --MKSTGVVR RVDELGRIVI PIELRRTLNI AEKDALEIYV DGEQIILKKY
ref|YP_001181188.1|       ---------- --MKSTGVVR KVDELGRIVL PIELRRTLDI AEKDALEIFV DGDKIILRKY
ref|YP_001317994.1|       ---------- --MKSTGIVR KVDELGRIVL PIELRRTLTI AEKDSLEIYV DGESIILKKY
RAAC03236                 DHEAAKLRRR IRMLVTGYVR KVDHLGRLVI PKRLRKDLAI GQDDSIEIYV EGDAVVLSKY
Clustal Consensus                               :.*:*: * .**: * *  .: *::**:*  :*: ::* ** ref|YP_001666100.1|       EPACIFCGNA ENVINYKGKN ICKNCLEELK ------
ref|NP_621806.1|          EPACIFCGNA ENVINYKGKN ICKNCLEELK ------
ref|NP_346951.1|          EPACIFCGDA SDVINYRGKN ICKHCLEELK ------
ref|YP_001181188.1|       EPACIFCGNA KDVIYYKGKN ICKDCMEELK ------
ref|YP_001317994.1|       EPACIFCGNA KDVTVYKTKN VCEDCLEEFR ------
RAAC03236                 EPKCVFCG-E KAEKVFHERG VCGTCLEELK AKSKVS
Clustal Consensus         ** *:***    .         :: :. :*  *:**::
```

FIG. 16

```
ref|YP_001126560.1|    -----GIFSAFAFLLKELTFLVSYIKNNAFPQPLSPKEEEKYLELMAKGDEQARNRLIEH
ref|YP_148388.1|       -----GIFTAFTFLLKELTFLVSYIKNNAFPQPLSAQEEEKYLALMAKGDEQARNRLIEH
ref|ZP_01861605.1|     ------IATAIGYFLKELVFLVSYVKNNAFPQPLSSQEEKKYLRKMANGDEDARNILIEH
ref|NP_242151.1|       ------IIAALTYFFKEVLVFVSYVKNNAFPQPLSKEEERHYLKRMAEGDEEARNRLIEH
ref|YP_175113.1|       -----GILAALTYFMKEVFVFVSYVKNNAFPQPLSKEDEKKYLARMAEGDASARNMLIEH
RAAC00856              MDQVPGLLTLLALVFKDVSLFVSYVKQGAFPHPLSPEEEERAIRDYLAGDADARNRLIEH
                           :   :   ..:*::  .:***:*:.*:*  ::*.: :     .* **** ref|YP_001126560.1|    NLRLVAHIVKKFENTGEEVEDLISIGTIGLIKAIESYSPNKGTKLATYAARCIENEILMH
ref|YP_148388.1|       NLRLVAHIVKKFENTGEEVEDLISIGTIGLIKAIESYSPGKGTKLATYAARCIENEILMH
ref|ZP_01861605.1|     NLRLVAHIVKKFENTGEDPEDLISIGTIGLIKAIESYSEGKGTKLATYAARCIENEILMH
ref|NP_242151.1|       NLRLVAHIVKKFENTREHTEDLISIGTIGLIKAIESFSEGKGTKLATYAARCIENEILMH
ref|YP_175113.1|       NLRLVAHIVKKFENTREDVEDLISIGTIGLIKAIESYSEGKGTKLATYAARCIENEILMH
RAAC00856              NLRLVAHLAKKYESSGEEMDDLISIGTIGLIKAVESYRPDKGTKLATYAARCIENEILMY
                       *******:.**:*.: *. .:************.**:  .*******************:

ref|YP_001126560.1|    LRSLKKTRKDVSLHEPIGQDKEGNEISLLDILKSEGQDIVDEIQLNMELEQVKKYISVLD
ref|YP_148388.1|       LRSLKKTRKDVSLHEPIGQDKEGNEISLLDILKAEGEDIADEIHLNMELEQVKQYISVLD
ref|ZP_01861605.1|     LRALKKTKKDVSLHDPIGQDKEGNEISLIDILKSDADDVIETIQLSMELEKVRKYICVLD
ref|NP_242151.1|       LRALKKVKKDVSLHDPIGTDKEGNEITLIDVLQEDSEDIADSIQLKMEKKQIYEYIHVLD
ref|YP_175113.1|       LRALKKVKKDVSLHDPIGTDKEGNEITLIDILKDDGEDIVDVLQTEMEKKQIYEYIHVLD
RAAC00856              LRSSKKHRRDAFLSDPVGTDKDGNEMTLADLLGSDPDDVIDAVDMSWEKQKMFECLPLLA
                       :   ::*. * :*:* :*::* *:*   : :*: : :..  * ::: : :* ref|YP_001126560.1|    EREKEVIVNRFGLGRQREKTQREIAKELGISRSYVSRIEKRALMKMFHEFYRQEK-----
ref|YP_148388.1|       EREKEVIINRFGLGRQREKTQREIAKELGISRSYVSRIEKRALMKMFHEFYRQEK-----
ref|ZP_01861605.1|     DREKEVIIGRFGLDMKEEKTQREIAKELGISRSYVSRIEKRALMKMFHEFYREEK-----
ref|NP_242151.1|       DREKEVIVGRFGLDLEEERTQREIAKELGISRSYVSRIEKRALMKLF-------------
ref|YP_175113.1|       EREKEVIIGRFGLNMEEERTQREIAKELNISRSYVSRIEKRALMKLF-------------
RAAC00856              PREREVLCKRFGLPDGEERTQREIAKELGISRSYVSRIEQKAIVKLYENMRQRKPAGSGA
                        **:**:    ****    .*:*********.**********::*:.*:

ref|YP_001126560.1|    --
ref|YP_148388.1|       --
ref|ZP_01861605.1|     --
ref|NP_242151.1|       --
ref|YP_175113.1|       --
RAAC00856              DA
```

FIG. 17

```
ref|YP_148388.1|         VKKFENTGEEVEDLISIGTIGLIKAIESYSPGKGTKLATYAARCIENEILMHLRSLKKTR
ref|YP_001126560.1|      VKKFENTGEEVEDLISIGTIGLIKAIESYSPNKGTKLATYAARCIENEILMHLRSLKKTR
ref|YP_896655.1|         VKKFENTGEDAEDLISIGTIGLIKAIESYSAGKGTKLATYAARCIENEILMHLRVLKKTK
ref|NP_980714.1|         VKKFENTGEDAEDLISIGTIGLIKAIESYSAGKGTKLATYAARCIENEILMHLRVLKKTK
gb|ABY76244.1            VKKFENTGEDAEDLISIGTIGLIKAIESYSAGKGTKLATYAARCIENEILMHLRVLKKTK
RAAC01814                MKKFDTSGIDQDDLISIGTVGLIKAVDTYQPSKGTKFATYAARCIQNEILMQLRAQRKSR
                         :***:.:*  :  :******:*****:::*...****:*********:*****.**   :*::

ref|YP_148388.1|         KDVSLHEPIGQDKEGNEISLLDILKAEGEDIADEIHLNMELEQVKQYISVLDEREKEVII
ref|YP_001126560.1|      KDVSLHEPIGQDKEGNEISLLDILKSEGQDIVDEIQLNMELEQVKKYISVLDEREKEVIV
ref|YP_896655.1|         KDVSLHDPIGQDKEGNEISLIDILKSESEDVIDMIQLSMELEKIKEYIDILDEREKEVIV
ref|NP_980714.1|         KDVSLHDPIGQDKEGNEISLIDILKSESEDVIDMIQLSMELEKIKEYIDILDEREKEVIV
gb|ABY76244.1            KDVSLHDPIGQDKEGNEISLIDILKSESEDVIDMIQLSMELEKIKEYIDILDEREKEVIV
RAAC01814                KDVSLYSPIGTDKEGNEITIGDILFSESDSTEDEVSRRMELNTMRQLLDVLDERERKVIE
                         *****:.*** *******:: *** :*.:.  * :   ***: :::  :..*****::**

ref|YP_148388.1|         NRFGLGRQREKTQREIAKELGISRSYVSRIEKRALMKMFHEFYRQEKEKR---------
ref|YP_001126560.1|      NRFGLGRQREKTQREIAKELGISRSYVSRIEKRALMKMFHEFYRQEKEKR---------
ref|YP_896655.1|         KRFGLGLDKEKTQREIAKALGISRSYVSRIEKRALMKMFHEFVRAEKEKKA--------
ref|NP_980714.1|         KRFGLGLDKEKTQREIAKALGISRSYVSRIEKRALMKMFHEFVRAEKEKKA--------
gb|ABY76244.1            KRFGLGLDKEKTQREIAKALGISRSYVSRIEKRALMKMFHEFVRAEKEKKA--------
RAAC01814                LRFGLADGREWTQNEVADSLDISRSYVSRLEKRALLKMFHQSHVAKERKQAIRNARLQP
                         ****.  :* **.*:*. *.*******:*****:****:      :::.*:
```

FIG. 18

```
ref|YP_001486125.1|     ---FHDQPILPAVRNMKQFEEFLKSPFTYGVLLDVHLGRLKGIMNEANAHHKKMFVHVDL
ref|NP_388808.1|        MMSFHNQPILPAIRNMKQFDEFLNSSFSYGVILDIHLGQLKGVIKEAQKHGKNMMVHVDL
ref|NP_830819.1|        ---FHEQKILPAVRQIKDLEKLLHSSYEYIVILDIHVGQLKSVISLAKQYCKKVFLHVDL
ref|YP_001643827.1|     ---FHEQKILPAVRQIKDLEKLLHSSYEYIVILDIHVGQLKSVVSLAKQHNKKVFLHVDL
ref|ZP_01696681.1|      ------QRILPASVNMKEFERFLKSDYEIGIFLELHISQLKYVAAMAKAEGKKMIYHVDL
RAAC02673               MNPFEGRRVLPAVRSLKDFEELMQGPHPVVVLLETNLTALPSLMRMANKAGKRLILHADL
                           : :***   .:*:::.:::.  .  ::*: ::  *   :  *:   *.:: *.**

ref|YP_001486125.1|     IHGIKHDEYGTEFICQEMKPAGIISTRSSVIVKAKQKKVYAIQRMFLLDTSAMEKSMEFV
ref|NP_388808.1|        IQGIKHDEYGAEFICQDIKPAGIISTRSNVIAKAKQKKIYAIQRLFLLDTSAMEKSMEFI
ref|NP_830819.1|        IHGLQSDGHATEYLCQEFRPYGLLSTKASVIMKAKQKGVVAIQRIFLIDSSAMEKSCNLL
ref|YP_001643827.1|     IHGLQSDGHATEFLCQEYKPYGLLSTKASVIMKAKQKGVVSIQRIFLIDSSAMEKSCNLL
ref|ZP_01696681.1|      IQGLKSDDYATEYLCQEYQPFGLISTKANVIQKAKQKGVVSIQRMFLIDSHALEKSYKLI
RAAC02673               IQGLKHDEAGTQFLCQMIRPYGIISTHASVIATAKKQGVIAIQRVFLIDSHSLRTSYRVL
                        *:*::  *    .:::::**    :* *::**::.**  .**::  : :***:**:*:  ::..*   ..:

ref|YP_001486125.1|     GKHRPDFIEVLPGVVPNLITEVRERAGIPIFAGGFIRTKEDVERALEAGATAVTTSNTTL
ref|NP_388808.1|        GKHKPDFIEVLPGIVPSLIQEIKEKTGIPIFAGGFIRTEEDVEQALKAGAVAVTTSNTKL
ref|NP_830819.1|        DKTKPDYIEVLPGALTDVIAEVKERTGVPILAGGFIRTVEDVERALNAGATAITTSKREL
ref|YP_001643827.1|     EKTKPDYIEVLPGALTGVIAEVKERTGVPILAGGFIRTVEDVERALNAGATAITTSKKEL
ref|ZP_01696681.1|      ERTKPDYIEVLPGIAPWMITEVKERLGIPIFAGGLIRTREDVEKALKAGAEGITTSDTEL
RAAC02673               QQAKPDFLEVLPGVVPQLIAEIREQTGLPVLAGGFVRTKEDVERAVAAGATAVTTSVKAL
                         : :::***   . :* *::*: *:*:;*:: ****:*: * .:*   * ref|YP_001486125.1|     WK-
ref|NP_388808.1|        WK-
ref|NP_830819.1|        WK-
ref|YP_001643827.1|     WK-
ref|ZP_01696681.1|      WE-
RAAC02673               WQL
                        *:
```

FIG. 19

```
ref|ZP_01725195.1|        MKRHEAREKALQVLFQLD-NT------DLTVEEAMGH------IKGQPTNA-----FYEK
RAAC02112                 MTRHEARECALQALCVLDVQR------DLGSAEAIASA-----LAERGTDAGGDFTYIEE
ref|ZP_00538565.1|        MKRHMARELAVQSLFQMELS-------DLSAQEAIEFA-----VEGKEYD-----TFVTR
ref|YP_148250.1|          MKRHEAREKALQALFQIDVGR------IPPDEALHNV-----TGGGDIDP-----FLRQ
ref|YP_001126420.1|       MKRHEAREKALQALFQIDVGH-------IPPDEAIGNV-----TGSGEVDP-----FLRQ
ref|NP_390312.1|          MKRRTAREKALQALFQIDVS-------DIAVNEAIEHA-----LDEEKTDP-----FFEQ
                          *.*: *** *:* *   ::            :    **:                :    .

ref|ZP_01725195.1|        IVTGTAEHLEEIDATLEQHLEKWSLARLPKIERTVLRLAVYELLYMPETPKRVVLNEAIE
RAAC02112                 LVDGTRRHLDEIDELLARHMERWSPERIGRVERNVLRLATYELLFEPELPIASAIDEAVE
ref|ZP_00538565.1|        LVEGVEANKPEIDQKLRAALVNWSFERIGNIERTILRLAVYELLFEAKIPVRVTINEAIE
ref|YP_148250.1|          LVFGVVEHQEEIDELLRANLEKWTLERVANVDRAILRMATYEMKYADDVPVSVSLDEAVE
ref|YP_001126420.1|       LVFDVIEHRAEIDELLRSNLEKWKLERVANVDRVILRMATYEMKYVDDVPVSVSLDEAVE
ref|NP_390312.1|          LVHGVLEHQDQLDEMISKHLVNWKLDRIANVDRAILRLAAYEMAYAEDIPVNVSMNEAIE
                          :*  .. :  ::*   :  .*.  *: .::* :**:*.**:  .  .  *   ::**:* ref|ZP_01725195.1|        LCKTFGDDSSSKFVNGVLSK----------------------------------------
RAAC02112                 IAKTFATEQSGRPVNGVLAKLLPAVADRRRADTREAGQEKRTASAAEPAREGVDDGA
ref|ZP_00538565.1|        LTKAFADEEATKIVNGVLGKVAQEV-----------------------------------
ref|YP_148250.1|          LAKKFGDWKSGSFVNGVLSKVKAAL-----------------------------------
ref|YP_001126420.1|       LAKKFGDWKSGSFVNGVLSKVKAAL-----------------------------------
ref|NP_390312.1|          LAKRFGDDKATKFVNGVLSNI---------------------------------------
                          : * *.  .:  :*****.:
```

FIG. 20

```
ref|YP_147113.1|          ------------------------MNTQLLEALADLMREKGISKEVVMEAIEAAIVSAY
ref|YP_001125233.1|       ------------------------MNTQLLEALADLMREKGISKEVIMEAIEAALVSAY
ref|NP_243282.1|          ------------------------MNSEFMDALTTLEKEKGISKEVIIEAIEAALISGY
ref|YP_175727.1|          ------------------------MNSEFMEALSTLEADKGIKKEVIIEAIEAALISGY
ref|ZP_02330483.1|        ------------------------MNSEFIEALSEIEREKGISKDLLIDAIEAAMISSY
RAAC02902                 MRTRGWLWSGDPNAPEISRRGGSLVMNVDFLEALDQLAREKGIDKEVLLEAIEAALIASY
                                                    ::::   :  :***.*::::*****:::.* ref|YP_147113.1|          KRNFGQAQNVRVDLNMDTGTIRVFARKDVVEEVADPRLEISLEDAQRINPNYQIGDVVEL
ref|YP_001125233.1|       KRNFGQAQNVRVDLNMDTGTIRVLARKDVVEEVTDPRLEISLEEAQRLNPNYQIGDVVEL
ref|NP_243282.1|          KRNFNQAQNVRVDVNRENGSIRVFARKEVVEEVPDARLEISLDEAKGINPNYEVDDVVEI
ref|YP_175727.1|          KRNFGQAQNVRVDVNRDNGSIRVFARKVVVEEVFDKRLEISEAEAQRINPHYEVDDIVEI
ref|ZP_02330483.1|        KRNFNTAQNVRVDINRQTGVIRVFARKTVVEDVLDPRLEISLTAAREINQNYQLGDIVEI
RAAC02902                 RRNFHSAANVRVEVKRDTGEVHVYARKTVVEEPKDTRLEISLDAARDINPSYQIGDVVEI
                          :***   * ****:::  :.*  ::* *** ***   * ******   *:  :*  *::.*:**:

ref|YP_147113.1|          EVTPRDFGRIAAQTAKQVVTQRVREAERSIIYAEFVDREEDIMTGIVQRVDPRFVYVSLG
ref|YP_001125233.1|       EVTPRDFGRIAAQTAKQVVTQRVREAERSIIYAEFVDREEDIMTGIVQRIDPRFVYVSLG
ref|NP_243282.1|          EVTPDFGRIAAQTAKQVVTQRVREAERGIIYADFIDREEDIMTGIVQRQDNRFIYVDLG
ref|YP_175727.1|          EVTPKDFGRIAAQTAKQVVTQRVREAERGIIYSDFIDREEDIMNGIVQRQDHRFIYVDLG
ref|ZP_02330483.1|        EVTPRDFGRIAAQTAKQVVTQRIREAERGLIYNAFIDKEEDIVTGIVQRQDQRSYYVDLG
RAAC02902                 EVTPRDFGRIAAQAAKQVVMQRVKEAERSVIYSKFADREEEVVSGIVSRLEPRVAYIDLG
                          ****:********:***** **::****.:**  * *:**:::.***.*  :  *   *:.**

ref|YP_147113.1           KAEALLPANEQMPNETYKPHDRLKVYITKVEKTTKGPQIFVSRTHPGLLKRLFELEVPEI
ref|YP_001125233.1|       KAEALLPANEQMPNETYKPHDRLKVYITKVEKTTKGPQIFVSRTHPGLLKRLFELEVPEI
ref|NP_243282.1|          KVEALLPLSEQMPNESYRHNDRIKAYITKVEKTTKGPQIMISRTHPGLLKRLFELEVPEI
ref|YP_175727.1|          KVEALLPLSEQMPNETYKHNDRIKAYITKVEKTTKGPQILISRTHPGLLKRLFELEVPEI
ref|ZP_02330483.1|        KVEAVLPLNEVMPTEKFKHGDRVKAYITKVENTTKGPQIILSRTHPGLLKRLFELEVPEI
RAAC02902                 DTEAILPQSEQMASDKLQVGKRLKVFIARVERTSKGPQIVVSRTHPGLLRRLFELEVPEI
                          ..:  .* *...: :  .*:*.:*::**.*:***.:*****:******** ref|YP_147113.1|          YDGTVEIKSIAREAGDRSKISVHSDNPEVDPVGACVGPRGQRVQAIVDELNGEKIDIVRW
ref|YP_001125233.1|       YDGTVEIKSIAREAGDRSKISVHSDNPEVDPVGACVGPKGQRVQAIVDELHGEKIDIVRW
ref|NP_243282.1|          YDGTVELKSVAREAGDRSKISVHAENPEVDPVGACVGPKGSRVQTIVNELKGEKIDIVRW
ref|YP_175727.1|          YDGTVEIKSVSREAGDRSKIAVHSDNPEVDSVGACVGPQRGQRVQTIVDELKGEKIDIVEW
ref|ZP_02330483.1|        FDGVVEIRSVAREAGFRSKIAVDSRNEEVDPVGSCVGPKGLRVQTIVNELRGEKIDIVRW
RAAC02902                 YEGIVEIKAVAREAGSRSKIAVHSRNPEVDPIGACVGARGSRVQAIVNELNGEKVDIVEW
                          ::* :::: **.*.: * ***.:*:***   :* *::.*:***.* ref|YP_147113.1|          SADPVEFVANALSPAKVLRVIVNEEQKATTVIVPDYQLSLAIGKRGQNARLAAKLTGWKI
ref|YP_001125233.1|       SADPVEFVANALSPAKVLRVIVNEEQKATTVIVPDYQLSLAIGKRGQNARLAAKLTGWKI
ref|NP_243282.1|          SEDPVEYVANALSPSKVVKVNVNEEEKTTQVIVPDYQLSLAIGKRGQNARLAAKLTGWKI
ref|YP_175727.1|          SEDPVVYVANALSPAKVMKVNVLEGEKMTQVIVPDYQLSLAIGKRGQNARLAAKLTGWKI
ref|ZP_02330483.1|        MESTEEYVANALSPSKVLEVNIFEDEKMARVIVPDYQLSLAIGIKGQNARLAAKLTGWKI
RAAC02902                 SEDPATFVANALSPAKVIDVHIYEDERVARTVVPDYQLSLAIGKEGQNARLAARLTGWKI
                          ..  :*****:: * :  *  ::  .:*********  .*****:**** ref|YP_147113.1|          DIKSESE-------------------------------
ref|YP_001125233.1|       DIKSESE-------------------------------
ref|NP_243282.1|          DIKSESEAQELGLLED-EAASHE---------------
ref|YP_175727.1|          DIKSESEARELGLLDE-ENENDELEEF-----------
ref|ZP_02330483.1|        DIKSETQ-------------------------------
RAAC02902                 DIKSESQMASHSLLDQLEDTNEEEPEFATLSDDWLNEP
                          *****::
```

FIG. 21

```
ref|ZP_01173598.1|        -------------MEKNWYVVHTYSGYENKVKANLEKRVETMAMQDKIFRVIVPEEEETD
ref|YP_848410.1|          -------------MEKNWYVVHTYSGYENKVKANLEKRVESMGMSDKIFRVIVPEEEETE
ref|YP_089786.1|          -------------MEKKWYVVHTYSGYENKVKANLEKRVESMGMQDKIFRVVVPEEEETD
ref|NP_691027.1|          -------------MEKNWYVVHTYSGYENKVKMNLEKRVESMGMEDKIFRVIVPEDEEAE
ref|YP_173640.1|          -------------MEKNWFVVHTYSGYENKVKANLEKRVESMEMTDHIFRVLVPVEEETE
RAAC00415                 MGVAGCSPCSMENLEKQWYVIHTYSGYENKVKSNLESRVQTMGMEDRIFRVVVPTEEAVE
                                       :**:*:*:***********   ***.**::*  *  *:****:** .:*  .:

ref|ZP_01173598.1|        IKNGKKKVVKRKVFPGYVLVEIVMTDDSWYVVRNTPGVTGFVGSAGSGSKPTPLLPEEVN
ref|YP_848410.1|          VKNGKTKTIKRKVFPGYVLVEIVMTDDSWYVVRNTPGVTGFVGSSGSGSKPTPLLPEEAE
ref|YP_089786.1|          IKNGKKKVVKKKVFPGYVLVELVMTDDSWYVVRNTPGVTGFVGSAGSGSKPTALLPGEAE
ref|NP_691027.1|          IKNGKKKMVKKKSFPGYVLTEMVMTDDSWYVVRNTPGVTGFVGSSGHGAKPTPLMPGEID
ref|YP_173640.1|          IKNGKTKQVSRKVFPGYVLVEMVMTDDSWYVVRNTPGVTGFVGSAGAGSKPTPLMPDEVE
RAAC00415                 IKNGKKRVVQRKTYPGYVLVEMIMTDDSWYVVRNTPGVTGFVGSPGAGSKPVPLMPHEVE
                          :****.:  :.:*  :*****.*::*********************.*  *:**..*:* * :

ref|ZP_01173598.1|        VILKRMGVDEKRVDIDFEIGETVKVNEGPFANFTGSIEEIDKDKAKIKVLVNMFGRETPV
ref|YP_848410.1|          RILKSMGMVEKRAEADFEIGETVMVKEGPFADFSGKVDEMDNDKGKAKVMVNMFGRETPV
ref|YP_089786.1|          KILKRMGLEERKTEIDFELKETVKVIDGPFADFTGTIEEIDHDKNKVKVFVNMFGRETPV
ref|NP_691027.1|          VVLKRMGVSEPTVQVDFEIKENVRVTDGPFTDFTGSIEHIDTDKQKIKVHVNMFGRETPV
ref|YP_173640.1|          RILKQMGVVEAQEEVDFELKESVKVKSGPFADFVGTIEEIQVEKRKLKVHVNMFGRETPV
RAAC00415                 QILSSMGVNEAKPVAQFKVGDVVRLTSGPFADMVGTVEEVHPEHQKLKVLVSMFGRETPL
                          :*. **: *      :*:: : * : .***:::  *.::.:.  ::  *  ** *.*******:

ref|ZP_01173598.1|        ELDFTQIEKL-
ref|YP_848410.1|          EVDFNQIEKL-
ref|YP_089786.1|          ELEFTQVDKL-
ref|NP_691027.1|          ELDFSQVEKL-
ref|YP_173640.1|          ELEFGQVEKI-
RAAC00415                 EADFTQVEHLP
                          *  :*  *::::
```

FIG. 22A

```
ref|YP_149235.1|         ------------------------------------------------------------
ref|YP_001127411.1|      ------------------------------------------------------------
ref|YP_001377035.1|      ------------------------------------------------------------
ref|YP_039325.1|         ------------------------------------------------------------
gb|AAU09403.1|           ------------------------------------------------------------
RAAC00475                --------------------------------MPPGHECEGRCLDIRELEEKKLTEL ref|YP_149235.1|         ---AKQYKISYYSKLTKKELIFAILKARAEQDGLFFMEGILEIIPSEGFGFLRPINYSPS
ref|YP_001127411.1|      ---ARQYKISYYSKLTKKELIFAILKARAEQDGLFFMEGVLEIIPSEGFGFLRPINYSPS
ref|YP_001377035.1|      ---AKEYKISYYSKLTKKELIFAILKARAEKEGFFFMEGVLEIIQSEGFGFLRPINYSPS
ref|YP_039325.1|         ---AKEFKISYYSKLTKKELIFAILKARAEKEGFFFMEGVLEIIQSEGFGFLRPINYSPS
gb|AAU09403.1|           ---AREYKVSYYSKLTKKELVFAILKAQAEQDGLLFMEGVLEIIQSEGFGFLRPINYSPS
RAAC00475                YKYAREFQIPHYGSMKKKELIFAILKAQAERDGLMFAEGVLEIMP-EGYGFLRPVGYLPS
                            * :::::.:*...:.**:**.::*::* :*:    :***:.* ** ref|YP_149235.1|         SEDIYISASQIRRFDLRNGDKVSGKVRPPKENERYFGLLHVEAVNGEDPEVAKERVHFPA
ref|YP_001127411.1|      SEDIYISASQIRRFDLRNGDKVSGKVRKPKENERYFGLLHVEAVNGEDPEIAKERVHFPA
ref|YP_001377035.1|      SEDIYISASQIRRFDLRNGDKVSGKVRPPKENERYFGLLQVEAVNGDDPESAKERVHFPA
ref|YP_039325.1|         SEDIYISASQIRRFDLRNGDKVSGKVRPPKENERYFGLLQVEAVNGDDPESAKERVHFPA
gb|AAU09403.1|           SEDIYISASQIRRFDLRNGDKVSGKVRPPKENERYYGLLHVEAVNGEDPETSKDRVHFPA
RAAC00475                QEDIYVAASQIRRFDLRTGDLVSGKVRPPKENERYFGLLHVEAVNGYSPEVAAERLHFAA
                         .**::******. **** ***:*.****  .  :  :*:**.* ref|YP_149235.1|         LTPLYPNRQMKLETTPDKLSTRIIDLIAPVGFGQRGLIVAPPKAGKTMLLKEIANSITTN
ref|YP_001127411.1|      LTPLYPNRQMKLETTPDKLSTRIIDLIAPVGFGQRGLIVAPPKAGKTMLLKEIANSITAN
ref|YP_001377035.1|      LTPLYPNRQMKLETEPKKLSTRIMDLIAPVGFGQRGLIVAPPKAGKTILLKEIAHSITTN
ref|YP_039325.1|         LTPLYPDRQMKLETEPKKLPTRIMDLIAPVGFGQRGLIVAPPKAGKTSLLKEIAHSVTTN
gb|AAU09403.1|           LTPLYPNEQMLLETQPRSFSTRIIDLISPIGFGQRGLIVAPPKAGKTMLLKEIANSITTN
RAAC00475                LTPLFPSKRIVLETTPENLATRLIDLFAPIGFGQRGMIVAPPKAGKTVLLKEIAHSIATN
                         ***::*...::  *** *  .::::*:****:******  ****:*::* ref|YP_149235.1|         HPDVELIVLLIDERPEEVTDIERSVQGDVVSSTFDEVPENHIKVAELVLERAMRLVEHKR
ref|YP_001127411.1|      HPDVELIVLLIDERPEEVTDIERSVQGDVVSSTFDEVPENHIKVAELVLERAMRLVEHKR
ref|YP_001377035.1|      HPEAELIVLLIDERPEEVTDIERSVKGDVVSSTFDEVPENHIKVAELVLERAMRLVEHKK
ref|YP_039325.1|         HPEAELIVLLIDERPEEVTDIERSVKGDVVSSTFDEVPENHIKVAELVLERAMRLVEHKK
gb|AAU09403.1|           HPDAELIVLLIDERPEEVTDIERSVDGDVVSSTFDEVPENHIKVAELVLERAMRLVEHKK
RAAC00475                YPDVHLFVLLIDERPEEVTDMQRSVKGEVIASTFDEVPENHIKVSELVLERALRLVEHKQ
                         :*:..*:************:***..*.*:::**************:******.******.:

ref|YP_149235.1|         DVVILMDSITRLARAYNLVIPPSGRTLSGGIDPAAFHRPKRFFGAARNIEEGGSLTILAT
ref|YP_001127411.1|      DVVILMDSITRLARAYNLVIPPSGRTLSGGIDPAAFHRPKRFFGAARNIEEGGSLTILAT
ref|YP_001377035.1|      DVVILMDSITRLARAYNLVIPPSGRTLSGGIDPAAFHRPKRFFGAARNIEEGGSLTILAT
ref|YP_039325.1|         DVIILMDSITRLARAYNLVIPPSGRTLSGGIDPAAFHRPKRFFGAARNIEEGGSLTILAT
gb|AAU09403.1|           DVVILMDSITRLARAYNLVIPPSGRTLSGGIDPAAFHRPKRFFGAARNIEDGGSLTILAT
RAAC00475                DVVILLDSLTRLTRAYNLVVPPSGRTLSGGIDPAAFHRPKRFFGAARNVEEGGSLTILAT
                         **:**:**:***:*****:************************:*:*********
```

FIG. 22B

```
ref|YP_149235.1|         ALIDTGSRMDDVIYEEFKGTGNMELHLDRSLAERRIFPAIDIRRSGTRKEELLIPKEHLE
ref|YP_001127411.1|      ALVDTGSRMDDVIYEEFKGTGNMELHLDRSLAERRIFPAIDIRRSGTRKEELLIPKEHLD
ref|YP_001377035.1|      ALVDTGSRMDDVIYEEFKGTGNMELHLDRSLAERRIFPAIDIRRSGTRKEDLLIPKEHLD
ref|YP_039325.1|         ALVDTGSRMDDVIYEEFKGTGNMELHLDRSLAERRIFPAIDIRRSGTRKEDLLIPKEHLD
gb|AAU09403.1|           ALIDTGSRMDDVIYEEFKGTGNMELHLDRSLAEKRIFPAIDIRRSGTRKEELLIPKEHLD
RAAC00475                ALIDTGSRMDDVIYEEFKGTGNMELHLDRRLAEKRVFPSIDIRRSGTRREEALMPKEELE
                         **:*********************** ***:*:**:*********:*: *:***.*:

ref|YP_149235.1|         KLWAIRKTMADSPDFIERFLNKLRRTKSNEEF----------------------------
ref|YP_001127411.1|      KLWAIRKTMADSPDFIERFLNKLRRTKSNEEF----------------------------
ref|YP_001377035.1|      KLWGIRKTMRDTPDFVESFLRKLRQTKTNEEFLQNI------------------------
ref|YP_039325.1|         KLWGIRKTMRDTPDFVESFLRKLRQTKTNEEFLQNI------------------------
gb|AAU09403.1|           HLWAIRKSMADAPDFAEKFLKRLRQTKTNEEFFSMLT-----------------------
RAAC00475                KVWAIRKSMGDNQDFTEMFLRKFRHYKTNKEFLDSLSLNRVERKPVASAEKPAAQPVTSE
                         ::*.***:*  ** * **.::*: *:*:**

ref|YP_149235.1|         -
ref|YP_001127411.1|      -
ref|YP_001377035.1|      -
ref|YP_039325.1|         -
gb|AAU09403.1|           -
RAAC00475                T
```

FIG. 23A

```
ref|YP_001488275.1|        --------------LYKQMLDLIDVGVHAIDENGHTVVYNKKMMEIESLKRSDVLHKNVL
ref|YP_173520.1|           --------------LYQMLIDEINVGIHVIDQDGHTIIYNKKMMEIESMVDTDVLHKNLL
ref|ZP_01173129.1|         --------------ILEQILEHVDAGIHAIDHEGRTIIYNRKMAEIEGMDPESVIGRSLL
ref|ZP_01696484.1|         --------------LYETIMNLVDAGIHAVDEEGRTMIYNQKMRDIEGMDSREVLYKKLE
ref|ZP_02171541.1|         MQPEKLTDTAFIHPVYRKLLDYLDIGIHMINTEGRSVIYNRKMSEMEDMNPKEVLNKRIM
RAAC02984                  ---MEPSVVADVWKLYQEILEFAPVGVHAVDREGRTRVYNRVMGEIDGYRPDEVLEKNVF
                                         :  . :::    *:*  :: :*::  :**: *  :::.     .*:  : :

ref|YP_001488275.1|        DFFAFQDEMHSTLVQALRTGKQTVHAKQTYHNYNGKEITTINHTYPLVRDG---------
ref|YP_173520.1|           EVFTFHDDERSTLVQALKTGKVTKDVKQTYFNNKGEEITTINNTFPFIENG---------
ref|ZP_01173129.1|         EVFPFSRREDSTLLLALQNGKGTQPAKQTYFNSKGKEITAINHAIPILAAG---------
ref|ZP_01696484.1|         DVFRFRSSEESTLLKALKTGEESHLVKQTYFNNKGREITSVNHTYPFYYKG---------
ref|ZP_02171541.1|         EIFLFDSEEESRLLQALNNNVVHKDAKQVYFNFKGQEITTVNNTFPLTVDG---------
RAAC02984                  ELYELD-EETSTLWRALKTGHPVQIDEQVYVARNGRRVVTQNRTKPVVIAG---------
                            :.:  :         *  * **...        :*.*     :*..:.:  *.: *.     * ref|YP_001488275.1|        --LIQGAVE--ISNDVTKLERLIHHNMKKKGSTRFTFESIIGQSPAFLEVIEHAKRATRT
ref|YP_173520.1|           --KITAAVE--IAKDMTQLDHVIKKNVLRKRESHYTFDQIIGNSKAFLAVIEEAKRAART
ref|ZP_01173129.1|         --KSLGAIE--IAKDVSRIERLVKENLSRKNSDRYTFESIIGSSKAILEVVEAAKRAVRT
ref|ZP_01696484.1|         --KLAGAVE--IAEDITKIERLIRRN--HESHTGYTFHHIIGKSKAISEVIEFSRRAART
ref|ZP_02171541.1|         --EKIGAVE--IARDITKLERLSRETSRGASDARFTFDQIIGNSPAIEDVVENARRATRT
RAAC02984                  --EIIGAME----IAVPREAGGAQEAADARIRRRYSFADILGESRAMQRALDLAERAARM
                               .*:*        :.:                   ::*  *:*.*  *:   .:  :.**.* ref|YP_001488275.1|        SSYVLIVGETGTGKELFAQSIHNGSSRSSGPPITQNCAALPDNLIESLLFGTQKGAFTGA
ref|YP_173520.1|           SSSVLIVGETGTGKELFAQSIHYASPRSHAPPLAQNCAAIPENLMESLLFGTKKGAFTGA
ref|ZP_01173129.1|         TSPILIAGETGTGKELFAQSIHSGSLRSPGPFVAQNCAALPENLVESILFGTKKGAFTGA
ref|ZP_01696484.1|         SSYVLIIGETGTGKELFAQSIHYESERSRGPFIAQNCAALPDNLIESILFGTKKGAFTGA
ref|ZP_02171541.1|         TSSVLIYGETGTGKELFAQSIHNGSSRASKPFISQNCAALPDTLIEGILFGSVKGAFTGA
RAAC02984                  DLPVLLVGETGTGKELFAQAIHGASARKHGPFLAQNCAAWPEGLAESVLFGTRRGGFTGA
                             :*: **********:    *  *    ::***  *: * *.:***  :*.**** ref|YP_001488275.1|        ADQPGLFEQAQGGTLLLDEINSLNPHLQAKLLRVLQEKRVRRLGSTKEIAVDVRVIANMN
ref|YP_173520.1|           LDTPGLFEQADGGTLLLDEINSLDPALQAKLLRVIQEKTIRRIGDTKDKKVDVRIIATIN
ref|ZP_01173129.1|         VDRPGLFEQAEGGTLLLDEINSMPAPLQAKLLRVLQEKKVRRIGDTKDREIDVRVVAAIN
ref|ZP_01696484.1|         VDRAGLFEQADGGTLLLDEINALNIHLQAKLLRVLQEKKVKRIGGTQEKPVDVRVIATMN
ref|ZP_02171541.1|         TDHPGLFEQANGGTLMLDEINSLSASLQAKLLRAIQEKTIRRIGDTKSRSVDVRIIATMN
RAAC02984                  VDRAGVFELACGGTLLLDEVHAMSPSVQAKLLRALQDGEVWPIGARRSVQTDVRVIAAMN
                             *   .*:**  *  **:*::::     :******. :*:     : :*  :.    ***::*  :* ref|YP_001488275.1|        EDPVDAIASGRMRKDLFYRLGIVTLFIPPLSERKEDIPTFVNHFIQKYNELFQMKVKAAD
ref|YP_173520.1|           EDPIDMIAKQRLRKDLYYRLSVVTLFIPPLRERKEDILPLIEEFIHKYNTLFQMNVKTIS
ref|ZP_01173129.1|         EDPVDAIAEGRLRKDLYYRLSAVSLFIPPLRERKEDILLLSSFFIQKYNDWFGMEVPGLD
ref|ZP_01696484.1|         ETPYEAIANHRLRKDLYYRLGVVTLFIPPLRDRLEDLPLLTGHFIQKYNPLFQMNVRGIT
ref|ZP_02171541.1|         EDPVDALSKNKLREDLYYRLSVVSIVIPPLRHRKEDLTVLIAHFIRKYNRLFQMNIQEVT
RAAC02984                  VPPSAALSRGLVRPDLLYRIGAIAIHLPPLRERPEDIPLLAQAFLRRYG---EARAVRLS
                             *     ::     :* ** **:.  :::  :***  .* **:    :    *:::*.

ref|YP_001488275.1|        EEVLALFKAYDWPGNVRELEHVIEAGMNMMMDEDELSMHHLPYHFRFKQMEGRPPAQLQT
ref|YP_173520.1|           EEAKAILFQHDWPGNARELEHTIEGTMNFISDETEIHIHNLPFRLRNR------------
ref|ZP_01173129.1|         EETEEQFLRYDWPGNIRELEHVIEGAMNMAEDDARITSEILPHHFRQK------------
ref|ZP_01696484.1|         PEVLTFFRSYRWPGNIRELEHMIEAAMNVMLDEDMIELRHLPMQYRQSGH----------
ref|ZP_02171541.1|         DDVFNLFSEYDWPGNVRELEHTIEGAMNLIYDDEPIGFQHLPLHLKHKFTQP--------
RAAC02984                  SDAMAFLTSHDWPGNVRELEQTVRSALALWPEAREITSEMLRS-----------------
                            :.     :  :   ****  ****:   :...  :  .   :     :  . *
```

FIG. 23B

```
ref|YP_001488275.1      NSLQQTVAADTFVYTSPEQTTDFQTQMERFEKQYIVHYLEKMDDNISQTAKLLGMSRQSL
ref|YP_173520.1|        ---YQKEVKDTETGNLPAKT--LQEKMAEVEKLYILQALRENNNNVSQTAKNLGMSRQNL
ref|ZP_01173129.1|      -AETSHSFPGRNLGEPAGPQPSLSDYVASAEKAYINKVWREQDGNITRTAKILGMSRQNL
ref|ZP_01696484.1       -----------FNSPAEKSPLLKDRLFEYEKHCILEALEANGSNISKAAEQLGLSRQSL
ref|ZP_02171541.1|      --PATSEGTERLFTQQPEPGLPLETYMDTVEKAYIQKSLTEAGGNISQAARTLGLKRQSL
RAAC02984               --------AHPLLGEGAPRELERVARAARPSDDAIRRAYEAASGNLTHAAQALGISRQRM
                                   .        .. * .    ..*::::*. **:.** :

ref|YP_001488275.1      QYRMKKL---------
ref|YP_173520.1|        QYRLKKFHL-------
ref|ZP_01173129.1|      QYRIKKHGL-------
ref|ZP_01696484.1       QYRMKRLGI-------
ref|ZP_02171541.1|      QYRMRKFNL-------
RAAC02984               QYHVRRLGLRTSSQPK
                        **::::
```

FIG. 24A

```
ref|YP_090070.1|     ------------------------------------------------------------
ref|YP_077660.1|     ------------------------------------------------------------
ref|NP_244812.1|     ------------------------------------------------------------
ref|ZP_02171541.1|   ------------------------------------------------------------
ref|ZP_01173129.1|   ------------------------------------------------------------
RAAC02994            MIRRARIRAGSTCTIEANFVPNGQRRCRAGGAADRTGAKRALRFSDSDCKLGLHADLDRR ref|YP_090070.1|     --------------------------------------------GLHVVDENGTSVVYNKKM
ref|YP_077660.1|     --------------------------------------------GLHVVDENGTSVVYNKKM
ref|NP_244812.1|     --------------------------------------------GIHVIDTFGQTIIYNKKM
ref|ZP_02171541.1|   --------------------------------------------GIHMINTEGRSVIYNRKM
ref|ZP_01173129.1|   --------------------------------------------GIHAIDHEGRTIIYNRKM
RAAC02994            HKALCILMQARLEHAERRRGMRAQDAEARRTLLEAALDALDEGVHVVDAEGVTVFYNRKM
                                                                 *:*  ::  * ::.**:**

ref|YP_090070.1|     SQIEGMDVGDVLGKNVLDVFTFASQHDSTLLQALHHGKTNKNVKQTYFNNKGQEITTVNH
ref|YP_077660.1|     SQIEGMDVGDVLGKNVLDVFTFASQHDSTLLQALHHGKTNKNVKQTYFNNKGQEITTVNH
ref|NP_244812.1|     MEIESLTKEDVENKDFLDIFMFEEGQGSTLLEALYKKKHSKDVKQTYFNNRGKEITTINN
ref|ZP_02171541.1|   SEMEDMNPKEVLNKRIMEIFLFDSEEESRLLQALNNNVVHKDAKQVYFNFKGQEITTVNN
ref|ZP_01173129.1|   AEIEGMDPESVIGRSLLEVFPFSRREDSTLLLALQNGKGTQPAKQTYFNSKGKEITAINH
RAAC02994            ADIEAMSRQDVMGRRIDDVFSFPDAAGSTLLDAVRRGVRRDDVRQTYFNRRGQAITTVNR
                      :*  :   .* .: .  ::* *       * ** *:.    . .:*.*** :*: **::*.

ref|YP_090070.1|     TFPIMENGNTKGAVEIAKDVTKLERLIRENMNKTESTKYTFDSLIGVSPAFKEVIEHAKR
ref|YP_077660.1|     TFPIMENGNTKGAVEIAKDVTKLERLIRENMNKTESTKYTFDSLIGVSPAFKEVIEHAKR
ref|NP_244812.1|     TFPLYENGQVIGAIEISKDVTKLERLIRKNMESKGNTRYTFDSIIGESTAIREVIENTKR
ref|ZP_02171541.1|   TFPLTVDGEKIGAVEIARDITKLERLSRETSRGASDARFTFDQIIGNSPAIEDVVENARR
ref|ZP_01173129.1|   AIPILAAGKSLGAIEIAKDVSRIERLVKENLSRKNSDRYTFESIIGSSKAILEVVEAAKR
RAAC02994            TFPVYADGRILGAVEIARDVTSVEQLRSTAFGQAG-VRYTFASIIAESLAMREVLEQARR
                     ::*:   *. :::*::  :*:*         ::**  .:*. * *: :*:* ::* ref|YP_090070.1|     ATRTSSSILIVGDTGTGKELFAQSIHNGSQRSTGPPFISQNCAALPESLVEGLLFGTVKGA
ref|YP_077660.1|     ATRTSSSILIVGDTGTGKELFAQSIHNGSQRSTGPPFISQNCAALPESLVEGLLFGTVKGA
ref|NP_244812.1|     ATRTASSVLIVGETGTGKELFAQSIHNGSDRSKGPPFISQNCAAMPETLIESLLFGTKKGA
ref|ZP_02171541.1|   ATRTTSSVLIYGETGTGKELFAQSIHNGSSRASKPFISQNCAALPDTLIEGILFGSVKGA
ref|ZP_01173129.1|   AVRTTSPILIAGETGTGKELFAQSIHSGSLRSPGPFVAQNCAAPENLVESILFGTKKGA
RAAC02994            AARTDSSVLIIGETGTGKELLAQGIHAASPRRDGPPFVSQNLAAIPDTLVEGILFGTARGA
                     * ** *.:** *:******:**:*  .* *      **::** **:*:.*:*.:*** .:**

ref|YP_090070.1|     FTGAVDRPGLFEQADGGTLLLDEINSLDFRLQAKLLRAIQEKTIRRIGASKDTPIDVRII
ref|YP_077660.1|     FTGAVDRPGLFEQADGGTLLLDEINSLDFRLQAKLLRAIQEKTIRRIGASKDTPIDVRII
ref|NP_244812.1|     YTGAIERPGLFEEAEGGTLLLDEINSLPPLQAKLLRAIQEKQIRRVGDTVDRKVNVRIL
ref|ZP_02171541.1|   FTGATDHPGLFEQANGGTLMLDEINSLSASLQAKLLRAIQEKTIRRIGDTKSRSVDVRII
ref|ZP_01173129.1|   FTGAVDRPGLFEQAEGGTLLLDEINSMPAPLQAKLLRVLQEKKVRRIGDTKDREIDVRVV
RAAC02994            FTGAVDRPGLIEQANGGTLLLDELNAMPAPLQAKLLRVLQERVVRRVGDLKDRPVDVRIL
                     :*** :.***:*.*:******:***:*.:      *******..:**: :**:*   ::**::

ref|YP_090070.1|     ATMNEDPVDAVSGQRLRKDLYYRLSVVTLFIPPLKDRKEDIMPLTQHFIDKYNALFQMEV
ref|YP_077660.1|     ATMNEDPVDAVSGQRLRKDLYYRLSVVTLFIPPLKDRKEDIMPLTQHFIDKYNALFQMEV
ref|NP_244812.1|     STINEDPIEAIASGRLRKDLYYRLGVVTLFIPPLRERKEDIVPLVDHFIAKYNERFQMEV
ref|ZP_02171541.1|   ATMNEDPVDALSKNKLREDLYYRLSVVSIVIPPLRHRKEDLTVLIAHFIRKYNRLFQMNI
ref|ZP_01173129.1|   AAINEDPVDAIAEGRLRKDLYYRLSAVSLFIPPLRERKEDILLLSSFFIQKYNDWFGMEV
RAAC02994            ATMNEDPGRAIREGRLRADLFYRLSVVTLTVPPLRSRREDIPPLVAHFIRRLNGAFGLRV
                     :::****  *: :  :** **:***..*:: :***: :**:.  *   *   *  * :.:
```

FIG. 24B

```
ref|YP_090070.1|      KGFEEEVRRFLLSYDWPGNVRELEHLIEGAMNLMSYEDKIELTHLP--LQYRTKPAAKEQ
ref|YP_077660.1|      KGFEEEVRRFLLSYDWPGNVRELEHLIEGAMNLMSYEDKIELTHLP--LQYRTKPAAKEQ
ref|NP_244812.1|      KGLSDEVTQLLLQYDWPGNVRELEHIIEGAMNLMIGEDLIDVRHLP--FHFRQKSLSAPL
ref|ZP_02171541.1|    QEVTDDVFNLFSEYDWPGNVRELEHTIEGAMNLIYDDEPIGFQHLP--LHLKHKFTQPPA
ref|ZP_01173129.1|    PGLDEETEEQFLRYDWPGNIRELEHVIEGAMNMAEDDARITSEILP--HHFRQKAET---
RAAC02994             EGCEPRLMDAFLAYEWPGNVRELEHVIEGAMNLMEDEAKIGFQHLPGHVRRRLEQALDEM
                           *:****:***** ******:    *    **    : : :

ref|YP_090070.1|      L---PQQGYDLFA-----PLPSASAAPL---------------KEQIENAE---KYYIQK
ref|YP_077660.1|      L---PQQGYDLFA-----PLPSASAAPL---------------KEQIENAE---KYYIQK
ref|NP_244812.1|      S----SQITSVYETGPSDAIEHSVEEQQP----------LRDLKDYLLEAE---KMYIKK
ref|ZP_02171541.1|    T----SEGTE--------RLFTQQPEP-----------GLPLETYMDTVE---KAYIQK
ref|ZP_01173129.1|    -----SHSFPGRN------LGEPAGPQ------------PSLSDYVASAE---KAYINK
RAAC02994             QGNEDQGGRDARAEVVREPTPQGASDEIP----------RGRPSFRDLVRDYARTVLQA
                          .                                          ..   :  ::

ref|YP_090070.1|      TVKKCNYNVSQAARVLGISRQSLQYRLKK----------
ref|YP_077660.1|      TVKKCNYNVSQAARVLGISRQSLQYRLKK----------
ref|NP_244812.1|      ALERNKYHVTKTAEKLGLSRQSLQYRMKRLGI-------
ref|ZP_02171541.1|    SLTEAGGNISQAARTLGLKRQSLQYRMRK----------
ref|ZP_01173129.1|    VWREQDGNITRTAKILGMSRQNLQYRIKK----------
RAAC02994             ALEETRGNVSEAARRLGMSRQNLQYWLREVAVDPARYRR
                      .    :::.:*. **:.**.***  ::.
```

FIG. 25

```
ref|YP_177603.1|         --KKGLGKGLQAFFPEQE--DKQEEQ-IVQVDLADVRPNPYQPRKTFSEEALKELSNSIR
ref|NP_244925.1|         ---KGLGKGLNAFFPEAA--DETTEQ-VEEVKLLELRPNPYQPRKTFLEEALQELADSIK
ref|ZP_02172038.1|       ---KGLGKGIGAFFPDSERYEESDSQGAQNIKIKDLRPNPYQPRKHFDDEAIDELRQSIE
ref|YP_001423363.1|      MAKGGLGKGINALFNQVD---LSEET-VEEIKISDLRPNPYQPRKQFDDESLAELKESII
RAAC00039                MAKRGLGRGLDALIPQLN---VSDEDQIVQIDIRDLRPNPYQPRRTFNEEKLQELCNSIR
ref|ZP_02327875.1|       MSKR-LGRGLDALLPSMD---IEDDDKVIEIPLSKLRANPYQPRKSFNEDGIQELAASIK
                              **:*: *::  .            ::  :  .:*.******:  *  ::  ** **

ref|YP_177603.1|         EHGILQPVTVRKA-IKGYEIVMGERRVKAAKQAGLTQIPVIVQELDENKMMEIALIENLQ
ref|NP_244925.1|         EHGILQPIVVRKSSVKGYEIVVGERRFRAAERAGLVKVPVVIRELDDQKMMEMALIENLQ
ref|ZP_02172038.1|       QHGILQPLVVRKS-IKGYEIVVGERRYRAAKAAKLDSVPAIVRELTDDEMMELALIENLQ
ref|YP_001423363.1|      QHGILQPIIVRKS-LKGYDIVAGERRYRAAKLAGKETVPAIVRDLSESLMREIALLENLQ
RAAC00039                EHGILQPLIVRRSQVKGFDIVAGERRYRAAKMAGLQVVPAVVRDLSDVLLMEIALIENLQ
ref|ZP_02327875.1|       EHGVIQPIIVR-SVLKGYEIIAGERRFRASQACGLKSIPAVVKKFSDQQVMEIALIENVQ
                          ::::   : :::*: ****  :*::     .:*.:::.:  :  *:::* ref|YP_177603.1|         REDLNPIEEAIAYEKLMEHTNSTQEQLAKRLGKSRPHIANHMRLLQLPKVVQEFISVGKL
ref|NP_244925.1|         REDLNPIEEANAYEKLMTHLQMTQEQLAVRLGKSRPHIANHLRLLQLPKVVQEFISEGKL
ref|ZP_02172038.1|       REDLNPLEEAKAYKKLMEHLSLTQDQLSVKLGKSRPHIANYLRLLQAPQIVQQYLQEEKI
ref|YP_001423363.1|      REDLSPLEEEALAYDSLLKHLDLTQEQLAKRLGKSRPHIANHLRLLTLPESIQNLIAEGTL
RAAC00039                REDLNPIEIADAYAKLIEKCHLTQDELAKRVGQSRSHITNMLRLLQLPAQIQDMVSRGTL
ref|ZP_02327875.1|       REDLNALEIAIAYQAIIDQFSLTQEELSAKVGKSRSHIANFLRLLTLPDSIKQHVSRGTL
                         ****..:* * **   :: :    **::*: ::*:**.**:*  :***   *   :::  ..:

ref|YP_177603.1|         TMGHGRALLGLQDKQKLSQLLEKVLQDKLSVREVEQLVQRLNEHVPRETKQVK-VKLPPI
ref|NP_244925.1|         SMGHGRALLGLANKNEISSVLNKILEEKLSVRQVEALVQQMNERVSRGTKKAK-PKLSPF
ref|ZP_02172038.1|       STGHARALLGLKEDKKLSPLLQKTIKEQWSVRHLESVIHDMNENVSRETSKGK-PALDVY
ref|YP_001423363.1|      SMGHGRTLLGLKNKDKLEPLVKKVVEEQLNVRQLEQLIQQLNNNVPRETKKKE-PVQDVV
RAAC00039                TMGHARALLSVEDAEEQLRLAEQTVKEAWSVRKLEMVIYQP-KKVSRETDK---PALPTE
ref|ZP_02327875.1|       SMGHARAIVGVKDNQKKQILADACIREQWSVRQLEEEIKKLEGNSGNAKKKSKDKKRDPY
                         : **.*:::: :  .:      :   .:  .**.:*  :           .::

ref|YP_177603.1|         IKEQQERLRDTLGTSVLIKPGKKKGKIEIDYFSEDDLERILSLLV----
ref|NP_244925.1|         LKERQDFLRSHFGTSVAIKKGKKKGKIEIEFFSDDDLERILEML-----
ref|ZP_02172038.1|       LKDREAFLKSYFGTNVTIKPGKKKSKIEIDFFDDDDLQRILRLMSA---
ref|YP_001423363.1|      LKERESYLQNYFGTTVNIKRQKKKGKIEIEFFSNEDLERILELL-----
RAAC00039                YRRYQEQVQAYLGTSVRIQPGKKRGKIEIDYYSEDDLRRIMDLMLAHAP
ref|ZP_02327875.1|       IQQVEDQLRDVYRTTVKIKHQKNKGKIELLYYSNDDLERLLDML-----
                           :    :  ::      *.*  *:   *::.***:  ::.::**.*::   ::
```

FIG. 26

```
ref|NP_243941.1|         ---------------KPLLTKREREVFELLVQDKTTKEIAEQLFISEKTVRNHISNTMQK
ref|YP_176156.1|         ---------------KPLLTKREREVFELLVQDQTTKEIANHLFISEKTVRNHISNTMQK
ref|YP_080133.1|         ----------KEFQSKPLLTKREREVFELLVQDKTTKEIASELFISEKTVRNHISNAMQK
ref|YP_001376422.1|      -------------QSKPLLTKREREVFELLVQDKTTKEIASELFISEKTVRNHISNAMQK
ref|YP_001422137.1|      ----------KDFQSKPLLTKREREVFELLVQDKTTKEIASELFISEKTVRNHISNAMQK
RAAC02034                ------MAPVKDGRGKSLLTNREREVFELLVQDKTTKEIASQLFVSEKTVRNHISNVMKK
                               *.*:********:**..:***********.*:* ref|NP_243941.1|         LGVKGRSQAVIELIRLGELEI
ref|YP_176156.1|         LGVKGRSQAVIELIRLGELTI
ref|YP_080133.1|         LGVKGRSQAVVELLRMGELEL
ref|YP_001376422.1|      LGVKGRSQAVVELLRMGELEL
ref|YP_001422137.1|      LGVKGRSQAVVELLRMGELEL
RAAC02034                LNVKGRSQAVVELVRLGEITI
                         *.********:**:*:**:  :
```

FIG. 27

```
ref|NP_242122.1|          ----------VRQDAWSHEDDVFLAETVLKHIEEGSTQLRAFDEVGDVLNRTSAACGFRW
RAAC00092                 MSETRQKDRAMRQDAWTTEDDEILAEIVLKHIKQGSTQLAGFNEAARRLGRTAAACGFRW
ref|ZP_01697682.1|        ----------AVRQDAWTQEEDLLLSDIVLRHIREGSTQLRAFEEAGKRMNRTAAACGFRW
ref|ZP_01860230.1|        -----------RQDAWSQDEDLLLAEVVLRHIREGGTQLQAFEEVGRKLSRTAAACGFRW
ref|YP_146960.1|          ----------VRQDAWTKEEDELLANVVLQYIREGGTQLEAFAEVGRRLSRTAAACGFRW
ref|YP_001125095.1|       ----------VRQDAWTKEEDELLANVVLEYIRTGGTQLEAFAEVGRRLSRTAAACGFRW
                                    *****: ::* :*:: **.:*. *.*** .* *..   :.:***** ref|NP_242122.1|          NAVVRQRYVKQIAEAKKERKRRKRAASYAYQLYPTA-------SQQPVVLTGEATSLTLP
RAAC00092                 NACVRKQQRYRIELAKEERKKNK-SQRVQAQLEGGD-------ADHP-----TATLMTWA
ref|ZP_01697682.1|        NSYVRKQYASEIEAAKKERKE-KKQLVRDSGRAPAE--------------EGQQTEATLF
ref|ZP_01860230.1|        NSFVRKQYKSGIELAKRQRKESKKQPVPSPAREVKQPDVKHEVASADKKVEPQSSKVTLN
ref|YP_146960.1|          NSCVRKQYKEEIEQAKQERKMRKKETPSTKESEGQE----------KVEAAVKSHLSWA
ref|YP_001125095.1|       NSYVRKQYKEEIEQAKQERKTRKKETASEKDGRGQP----------EMEAAVESKLSWA
                          *: **::    *  **.:**  *                               : :

ref|NP_242122.1|          ---MVIEFL-QQLATHQVA---DGQTRKEQEELMK---QNEQLQERNKELEKEL---QKI
RAAC00092                 ---QVLRFLRQEKNTAQEW---ASRWRSTERQLNEWKAKYEALEADYKRVCEEL---REL
ref ZP_01697682.1|        ---DAIRILQQLAEKSRHE---SGQLSASRRGTEEWKSK---YEALLQKY-------LEE
ref ZP_01860230.1|        ---GVIEFLEGLKDNLNQ----DKELESAYKKLEEYVGK---IEQQLEKLKEEN---SVY
ref YP_146960.1|          ---EVLAFLQAEEQKARD----ARRTADENRAL---KNDMEQLQQMVTKLQMEK---ESL
ref YP_001125095.1|       ---EVLAFLQAEGQKARE----IRRTADENRAL---KNDMEQLQQMVTKLQMEK---EAL
                             .: :*      ..         ..          .

ref|NP_242122.1|          KQEHSIIEEDYQSMIQIMNRARRMAILQDD--EPASTQAF--KMDKNGNLEKI-------
RAAC00092                 KSTHDAITRDYKALLEIMERARKAALLDDDLIGPKFAEGFMYRIDEYGNLERITTGERME
ref|ZP_01697682.1|        KEKHEQLQKEYSALLSIMEKARQLS---EQD-----------------------------
ref|ZP_01860230.1|        KEKLELLEEDHQSLLSIFEKARKMALLQESDDKVKF------QMDKNGNLQRL-------
ref|YP_146960.1|          QKQLAAIQEEYKTLLSIMERARK-------------------------------------
ref|YP_001125095.1|       QKQLAAVQEEYKTLLTIMERARK-------------------------------------
                          :.       :  .::.::: *:::**:

ref|NP_242122.1|          ---
RAAC00092                 QAE
ref|ZP_01697682.1|        ---
ref|ZP_01860230.1|        ---
ref|YP_146960.1|          ---
ref|YP_001125095.1|       ---
```

FIG. 28

```
ref|YP_001125095.1      --------VRQDAWTKEEDELLANVVLEYIRTGGTQLEAFAEVGRRLSRTAAACGFRWNS
ref|YP_146960.1|        --------VRQDAWTKEEDELLANVVLQYIREGGTQLEAFAEVGRRLSRTAAACGFRWNS
ref|YP_896293.1|        ----EMATTRQDAWTDDEDLLLAEVVLRHIREGGTQLSAFKEVGRHLSRTPAACGFRWNS
ref|ZP_02261942.1|      ---------RQDAWTDDEDLLLAEVVLRHIREGGTQLSAFKEVGRHLSRTPAACGFRWNS
ref|NP_389392.1|        ---------RQDAWTQDEDLLLAEVVLRHIREGGTQLSAFEEVGRALTRTAAACGFRWNS
RAAC02454               MASVEKSPVRSDAWTAEDDERLAQLVLRHIRTGSTQLKAFEEAAEQLGRTAAACGYRWNG
                               *.****  ::*   **::**.:**  *.***.**  *...  * **.****:***.

ref|YP_001125095.1      YVRKQYKEEIEQAKQERKTRKKETASEKDGRGQP-----EMEAAVESKLSWAEVLAFLQA
ref|YP_146960.1|        CVRKQYKEEIEQAKQERKMRKKETPSTKESEGQE-----KVEAAVKSHLSWAEVLAFLQA
ref|YP_896293.1|        YVRKQYKERIEEAKQLRKVEHYEVKETKVLEP--------------KSITLNDVIDFLQN
ref|ZP_02261942.1|      YVRKQYKERIEEAKQLRKVEHYEVKETKVLEP--------------KLITLNDVIDFLQN
ref|NP_389392.1|        YVRKQYQSGIELAKKQRKELRKQIGVHSVNMPNSMKQTASASSEGKRDLSIQDVIQFLEQ
RAAC02454               VIRKRYRDEIEAAKAERKALHVKTQTQKAATAP-------------TASMQEVIRFLQT
                         :**:*:. ** ** **  :  :          .             : :*:  **:

ref|YP_001125095.1      EGQKAREIRRTADENRALKNDME-QLQQMVTKLQMEKEALQKQLA-----------AVQE
ref|YP_146960.1|        EEQKARDARRTADENRALKNDME-QLQQMVTKLQMEKESLQKQLA-----------AIQE
ref|YP_896293.1|        YKD---------------ENSLM-VLQQQIESLQTEKESLLERLS-----------VYEE
ref|ZP_02261942.1|      YKD---------------ENSLM-VLQQQIESLQTEKESLLERLS-----------VYEE
ref|NP_389392.1|        FKETP-SAQEFQLEREKLKEQIQ-SLQKELEDLRSENQTLRNQLE-----------MTEE
RAAC02454               YDEQYQRLREYVSAIEREKSELEARVRALESQLREGGPELPLSPE-----------QLEE
                                  :           :..:   ::    .*:     *                   :* ref|YP_001125095.1      EYKTLLTIMERARKMM--------
ref|YP_146960.1|        EYKTLLSIMERARKMVTDS-----
ref|YP_896293.1|        EYR---------------------
ref|ZP_02261942.1|      EYR---------------------
ref|NP_389392.1|        DYKALIDIMDRARKMV--------
RAAC02454               DSRTLFAIMERARKLLAENRSAGT
                         : :
```

FIG. 29

```
ref|ZP_01666183.1|      MKSTGIVRRVDELGRVVIPIELRRTLDIEEKDALEIYVDNDRIILRKYEPACVFCGNADE
ref|YP_077079.1|        MKSTGIVRKVDELGRVVIPIELRRTLNIEEKDSLEIYVDGDKIILRKYEPACVFCGNAAN
RAAC00212               MKSTGIVRKVDELGRVVIPIELRRTLGIGEKDALEIYVDGDRIILKKYEPACIFCGQADE
ref|YP_001666100.1|     LKSTGIVRKVDELGRVVIPIELRRTLNIAERDALEIYVDGEQIVLKKYEPACIFCGNAEN
ref|NP_621806.1|        LKSTGIVRKVDELGRVVIPIELRRTLNIAERDALEIYVDGEQIVLKKYEPACIFCGNAEN
ref|YP_752777.1|        LKSTGVVRKVDELGRIVIPIELRRTMGIEEKDALEIYVDSEKIILKKYEPACIFCGNAEE
                        :****:**:******:*********:.* *:*:******.::*:*:******:***:* :

ref|ZP_01666183.1|      VTNFKGKNVCRECLEAM---
ref|YP_077079.1|        VENFKGKNVCQSCLASM---
RAAC00212               IIHFKGKNICPSCIAEMQHA
ref|YP_001666100.1|     VINYKGKNICKNCLEELK--
ref|NP_621806.1|        VINYKGKNICKNCLEELK--
ref|YP_752777.1|        VVNYKGKNLCKSCLTEL---
                        : ::****:* .*:   :
```

FIG. 30

```
ref|YP_001666100.1|    ------------------------------------------------------------
ref|NP_621806.1|       ------------------------------------------------------------
ref|YP_001317994.1|    ------------------------------------------------------------
ref|YP_001181188.1|    ------------------------------------------------------------
ref|NP_346951.1|       ------------------------------------------------------------
RAAC03236              MSGCVSSLPFILALCVSSAAPRVRALGGAWLRLGHRLAIGAAFTVCATASHCCPTRCRMD ref|YP_001666100.1|    ---------------TGIVRKVDELGRVVIPIELRRTLNIAERDALEIYVDGEQIVLKKY
ref|NP_621806.1|       ---------------TGIVRKVDELGRVVIPIELRRTLNIAERDALEIYVDGEQIVLKKY
ref|YP_001317994.1|    ------------MKSTGIVRKVDELGRIVLPIELRRTLTIAEKDSLEIYVDGESIILKKY
ref|YP_001181188.1|    ------------MKSTGVVRKVDELGRIVLPIELRRTLDIAEKDALEIFVDGDKIILRKY
ref|NP_346951.1|       ------------MKSTGVVRRVDELGRIVIPIELRRTLNIAEKDALEIYVDGEQIILKKY
RAAC03236              DHEAAKLRRRIRMLVTGYVRKVDHLGRLVIPKRLRKDLAIGQDDSIEIYVEGDAVVLSKY
                                        :.*:*:* .**: * *.: *::**:*:*: ::* ** ref|YP_001666100.1|    EPACIFCG-NAENVINYKGKNICKNCLEELK------
ref|NP_621806.1|       EPACIFCG-NAENVINYKGKNICKNCLEELK------
ref|YP_001317994.1|    EPACIFCG-NAKDVTVYKTKNVCEDCLEEFR------
ref|YP_001181188.1|    EPACIFCG-NAKDVIYYKGKNICKDCMEELK------
ref|NP_346951.1|       EPACIFCG-DASDVINYRGKNICKHCLEELK------
RAAC03236              EPKCVFCGEKAEKVFHERG--VCGTCLEELKAKSKVS
                       ** *:*** .*..*   :    :*  *:**::
```

FIG. 31

```
ref|YP_001666100.1|       ------------------------------------STGIVRKVDELGRVVIPIELRR
ref|NP_621806.1|          ------------------------------------STGIVRKVDELGRVVIPIELRR
ref|NP_346951.1|          -----------------------------------MKSTGVVRRVDELGRIVIPIELRR
ref|YP_001181188.1|       -----------------------------------MKSTGIVRKVDELGRIVLPIELRR
ref|YP_001317994.1|       -----------------------------------MKSTGIVRKVDELGRIVLPIELRR
RAAC02603                 MAVSAAFAVCAIASHCCRDRCRMGDDETTVLRRKSRMIATGYVRKVDRLGRLVVPNRIRS
                                                             : :.*:*:*  .:* ref|YP_001666100.1|       TLNIAERDALEIYVDGEQIVLKKYEPACIFCG-NAENVINYKGKNICKNCLEELK-----
ref|NP_621806.1|          TLNIAERDALEIYVDGEQIVLKKYEPACIFCG-NAENVINYKGKNICKNCLEELK-----
ref|NP_346951.1|          TLNIAEKDALEIYVDGEQIILKKYEPACIFCG-DASDVINYRGKNICKHCLEELK-----
ref|YP_001181188.1|       TLDIAEKDALEIFVDGDKIILRKYEPACIFCG-NAKDVIYYKGKNICKDCMEELK-----
ref|YP_001317994.1|       TLTIAEKDSLEIYVDGESIILKKYEPACIFCG-NAKDVTVYKTKNVCEDCLEEFR-----
RAAC02603                 DLHLAKEDPVEIYVEADSIVLTKYEPKCVFCG--EKAEKVFHERAVCGTCLEELKTRSKR
                            :*:.*.:**:*:.:.*:* **** *:***  .    :: : :*  *:**::
```

FIG. 32

```
ref|YP_001374031.1|    ------------------------------------------MANQNSS--NQLVVPGAT
ref|NP_830661.1|       ------------------------------------------MANQNSS--NQLVVPGAT
gb|AAC62407.1          ------------------------------------------MANNNSS--NQLVVPGVQ
RAAC00161              ------------------------------------------MMANQNGS--NKVLVQGAN
ref|YP_037204.1|       ------------------------------------------MANKNSGSRNELLVRGAE
ref|NP_979446.1|       ------------------------------------------MANNNSGNRNELLVRGAE
                                                                 ***:*..  *::* *.

ref|YP_001374031.1|    AAIDQMKYEIAQEFGVQLGADTTARANGSVGGEITKRLVAMAEQSLGG-
ref|NP_830661.1|       AAIDQMKYEIAQEFGVQLGADSTARANGSVGGEITKRLVAMAEQSLGG-
gb|AAC62407.1          QALDQMKYEIASEFGVQLGPDATARANGSVGGEITKRLVQMAEQQMGGY
RAAC00161              RALDQMKYEIATEFGVQLGPDTTARQNGSVGGEITKRLVAYAEQQLAGH
ref|YP_037204.1|       QALDQMKYEIAQEFGVQLGADTTARSNGSVGGEITKRLVAMAEQQLGG-
ref|NP_979446.1|       QALDQMKYEIAQEFGVQLGADTTARSNGSVGGEITKRLVAMAEQQLGG-
                       *:******* ******.*:*** *************   ***.:.*
```

FIG. 33

```
ref|YP_001422239.1|         --------------------------------------------QQSNSGNSNQLLVPGAAQ
ref|YP_001420593.1|         --------------------------------------------MANNNSSNQLVVPGAAQ
ref|YP_001486165.1|         --------------------------------------------MANSNSSNQLLVPGAEQ
ref|ZP_01170670.1|          --------------------------------------------MANNNSSNQLLVPGVSQ
ref|ZP_01697004.1|          --------------------------------------------QMANNSNSNQLLVSGAEQ
RAAC00923                   MYSLFEAIATPAESTFGAPRGAYGRMARSHYRCHHHHIRRECKMANNSGSNRTLVPQASK
                                                                         :*...**: :*.  . :

ref|YP_001422239.1|         AIDQMKYEIASEFGVNLGPETTSRANGSVGGEITKRLVSFAQQSMGG--
ref|YP_001420593.1|         AIDQMKYEIASEFGVNLGGETTSRANGSVGGEITKRLVSFAQQNMGGQ-
ref|YP_001486165.1|         AIDQMKYEIASEFGVNLGAETTARANGSVGGEITKRLVSYAQQHMGG--
ref|ZP_01170670.1|          ALDQMKYEIANEFGVNLGAETTARANGSVGGEITKRLVQMAEQQLGG--
ref|ZP_01697004.1|          ALDQMKYEIAQEFGVNLGADTTSRANGSVGGEITKRLVQMAEQQLGG--
RAAC00923                   ALDQMKYEIATEFGVNLGPDTTSRQNGSVGGEITKRLVAYAEQSLAGRA
                            *:******** ******* :**:* ************* *:*  :.*
```

FIG. 34

```
ref|ZP_02330525.1|        ---SNVLVVPQANQALEQLKYEVAQELGIQIPQDGYYGYMATRDTGAIGGNITRRLVQIA
ref|ZP_02330045.1|        ---SNVLVVPQANAALDQLKYEVAQELGIVIPQDGYYGNMATRDTGAIGGHITRRLVQIA
ref|YP_001665292.1|       ----NPLVVKEAKQVMSQWKYEIANELGITPPADGYWGNLTSRDCGAVGGHMVRKMIQMA
ref|YP_001665293.1|       ----NPLVVKEAKQVMSQWKYEIARELGITPPADGYWGNLTSRDCGAVGGHMVRKMIQMA
ref|NP_623103.1           ----NPLVVKEARQVMNQWKYEIANELGITPPADGYWGYLTSRDCGAVGGHMVRKMIQMA
RAAC00643                 MAKSNRLLLGQASRALQDMKYEIAGELGITPPADGYWGFVSSYENGSIGGSITKRLVRYA
                             *::  :*    .:.: ***:* ****  * ***:*  ::: :  *::**  :.::::: * ref|ZP_02330525.1|        EQSLA-------
ref|ZP_02330045.1|        EQQLS-GTQGS-
ref|YP_001665292.1|       ESQMA-------
ref|YP_001665293.1|       ESQMA-------
ref|NP_623103.1           ESQMA-------
RAAC00643                 QERLAQGDAGSP
                          :.  ::
```

FIG. 35

```
ref|NP_829946.1|           ----------------------------------------MSRRRGVMSNQFKEELAKE
ref|NP_842611.1|           ----------------------------------------MSRRRGVMSNQFKEELAKE
ref|YP_001419725.1|        ----------------------------------------MGRRRGVMSDEFKYELAKD
ref|NP_240926.1|           ----------------------------------------MSRRRGIMSDRLKEEIAKE
ref|ZP_02330558.1|         ----------------------------------------RRRSTMSDQLKNELAKD
RAAC01427                  ----------------------MPCRRIVSVSPLTREGFGMARRRSTMSDAFKVELAKE
                                                                   ***. **: :* *:**:

ref|NP_829946.1|           LGFYDVVQKEGWGGIRAKDAGNMVKRAIEIAEQQLMKRN---
ref|NP_842611.1|           LGFYDVVQKEGWGGIRAKDAGNMVKRAIEIAEQQLMKQN---
ref|YP_001419725.1|        LGFYDTVKNEGWGGIRARDAGNMVKRAIEIAEQQMAAQN---
ref|NP_240926.1|           LGFYDTVQQEGWGGIRARDAGNMVKRAIELAEQQLAERESSR
ref|ZP_02330558.1|         LGFYDTVQKEGWGGIKAKDAGNMVKRAIQIAEQAAQKK----
RAAC01427                  LGFYDTVQREGWGGIKARDAGNMVKRAIEIAEQALAEKSGQR
                           *****.*:.******:*:**********::***    :
```

FIG. 36

```
ref|YP_173696.1        -----------LLFAAVLLWVQYDSTL---KDSSSTWHLPMS------------GKVIV
ref|NP_241105.1        -----------------------------------LS------------GKVII
ref|ZP_01696660.1|     ------------------------------------------------------------
ref|YP_001124272.1|    ------------------------------------------------------------
ref|ZP_02329530.1|     ----------------VALLVMIYAYKLPATETWTEWTQPLA------------GKTIA
RAAC00365              MIMHGKHRHVPLAFAAMAMLVGATSLVVPVQDARAAWFRPLQHRVNPGVQATGIQGKVIV ref|YP_173696.1        LDPGHGGMDGGAVSKTGTLEKEVTLAVALKLRDYLQEAGALVIMTREEDVDLADAGTAKI
ref|NP_241105.1        LDPGHGGIDGGATSRAGALEKDITLAVSLELRDYLQEAGALVLMTREEDRDLADATTAKV
ref|ZP_01696660.1|     ------------------EKDVALSVAAKIKDYLQQQGALVIMTRETDTDLADNETKGY
ref|YP_001124272.1|    ------------------VVEKEIALNVAKKLRDYLQQQGALVLMTRETDRDLASPSTRGY
ref|ZP_02329530.1|     LDAGHGGPDGGASSKSGVIEKDINLIISLYVRDYLQQAGAIVVMTREMDKDLANPDTKGY
RAAC00365              VDAGHGGRDSGARGVGGIEEKDITLSVALKLARYLQQGGAIVIMTRTTDTDLATERDRAM
                                         **::  *   ::     :   *: .*:.***   * *** ref|YP_173696.1        RQRKTEDLRKRAMIINDSEADAFLSIHMNAIPSERWNGAQTFYHLKNQRNEDMAVFIQEE
ref|NP_241105.1        RQRKVQDLKRRVEIVNGSGADMFVSIHLNAIASPRWSGAQTFYNRAIPENEPLARFVQDQ
ref|ZP_01696660.1|     SRRKVEDLRKRLSLINESEADLFISIHLNAIPQSQWHGAQTFYAPTMIENKRIATFIQAE
ref|YP_001124272.1|    SRRKTEDLRERTTFINKSDADLFISIHLNAIPSPRWRGAQTFYYGSLIENERLAKFIQAE
ref|ZP_02329530.1|     SKRKTEDLLKRAEFVIQKKADLFLSIHLNSVPSPKWRGAQAFYYPNNQDNYRLASLIQEE
RAAC00365              RQRHLGDLRGRLNVVRRQRVDAFVSIHCNSAPSPDWRGAQVLYLKTNPHAKQLATVMQEA
                       :*:  **   *  .:   .* *:*** *:  ..  * ***.:*         :*  .:* ref|YP_173696.1        IKRNLQNTNRYPKPIHHVYLLKEAEIPGALVEAGFLSNPQEAALLATEEYQDKMAASIYE
ref|NP_241105.1        LKRNLENTSRYAKPINNVFLLKHAEIPGLLVEAGFLSNPSEAELLETEDYQQKVAASIYQ
ref|ZP_01696660.1|     LVRNLENTNRASKTLSNVYLLKHAKKPGCLVEIGFLSNPGEREQLKSDAYQTKVAASIYE
ref|YP_001124272.1|    LRRNLENTHRVAKMIDTVYLLKHAKKPGALVEIGFLSNPDERELLASDHYQTQLAASIYK
ref|ZP_02329530.1|     IKRNMENTDRVAKQEESVYLLKTLKMPSTLIELGFLSNPDEARMLADDKYQKKLAASIYQ
RAAC00365              FRTELLPTHRDVQSNRTLFLLKRIEGPTVLAEIGFVSNPEEARALTTDAYQERVAFAMYE
                       :   ::  *   :       ::***   :   *   * **:***  *    :  **   ::*  ::*:

ref|YP_173696.1        GMLRFFTD-----------
ref|NP_241105.1        GIMRYYTN---EDAPE---
ref|ZP_01696660.1|     GIMRYFT------------
ref|YP_001124272.1|    GVLRYFSN-----------
ref|ZP_02329530.1|     GILRYYAGEKV--------
RAAC00365              ALVRYFSDPAVEQVPEDDG
                       .::*:::
```

FIG. 37A

```
ref|YP_036745.1|      ------------------------------------------------------------
ref|YP_083969.1|      ------------------------------------------------------------
ref|YP_028716.1|      ------------------------------------------------------------
ref|ZP_02259717.1|    ------------------------------------------------------------
ref|ZP_01665476.1|    ------------------------------------------------------------
RAAC01563             MFAMPSKVVVTLGSAYAPMASKDNDFCRPDEVSGATSPPRLRAPYLLVRASAREMSFFEF ref|YP_036745.1|      ------------------------------------------------------------
ref|YP_083969.1|      ------------------------------------------------------------
ref|YP_028716.1|      ------------------------------------------------------------
ref|ZP_02259717.1|    ------------------------------------------------------------
ref|ZP_01665476.1|    ------------------------------------------------------------
RAAC01563             VRDLAATHPDPDPFLCLVLDAEGGVMTSAAHGEWEKDEMAACLSAASREFPAVAAQETSM ref|YP_036745.1|      ------------------------------------------------------------
ref|YP_083969.1|      ------------------------------------------------------------
ref|YP_028716.1|      ------------------------------------------------------------
ref|ZP_02259717.1|    ------------------------------------------------------------
ref|ZP_01665476.1|    ------------------------------------------------------------
RAAC01563             SPRTEFGLSAVALLRTDGWHTAWTRLPMAVGRARHLAVIRRASDEDPRSLGRLALHLAHA ref|YP_036745.1|      -------------------RKKTEELLNKSDTLAAIGQLAAGVAHEVRNPLTVIKGFIQL
ref|YP_083969.1|      -------------------RKKTEELLNKSDTLAAIGQLAAGVAHEVRNPLTVIKGFIQL
ref|YP_028716.1|      -------------------RKKTEELLNKSDTLAAIGQLAAGVAHEVRNPLTVIKGFIQL
ref|ZP_02259717.1|    -------------------RKKTEELLNKSDTLAAIGQLAAGVAHEVRNPLTVIKGFIQL
ref|ZP_01665476.1|    -------------------IREVRHRMHHLETLAALGQLAAGTAHEIRNPLTSIRGFTQL
RAAC01563             ATQAWTSCERTLVRRSQCVIERMRKKLQEFEKVSALAQLCAGIAHEIRNPLTTARGFLQL
                                         .. .. ::. :.::*:.**.** ***:*****  :** **

ref|YP_036745.1|      FQIN----KEDQEK-YFDLMLSEIERIEAILQEFLSIAKTDEISTEKKNIYQIFKNVVSL
ref|YP_083969.1|      FQIN----KEDQEK-YFDLMLSEIERIEAILQEFLSIAKTDEISTEKKNIYQIFKNVVSL
ref|YP_028716.1|      FQIN----KEDQEK-YFDLMLSEIERIEAILQEFLSIAKTDEISTEKKNIYQIFKNVVSL
ref|ZP_02259717.1|    FQIN----KEDQEK-YFDLMLSEIERIEAILQEFLSIAKTDEISTEKKNIYQIFKNVVSL
ref|ZP_01665476.1|    IQTRALRRNDATTADYCRLIMQEIDHINNLTDILSLARPTTRQLSLLNIVKIVHDVIAF
RAAC01563             FAER----CDDKDRGYLELTISELDRIRELLEDFMGLCRPDREEAAEVDMVEIARSVHRF
                      :  .    :     *  *  :.*:::*. :* ::::...     ::  :* .*  :

ref|YP_036745.1|      INTKAIMTNIQVELYTDSKDIIIECSENQLKQVFINILQNSIEAMPDGGRISIHIKEIGK
ref|YP_083969.1|      INTKAIMTNIQVELYTDSKDIIIECSENQLKQVFINILQNSIEAMPDGGRISIHIKEIGK
ref|YP_028716.1|      INTKAIMTNIQVELYTDSKDIIIECSENQLKQVFINILQNSIEAMPDGGRISIHIKEIGK
ref|ZP_02259717.1|    INTKAIMTNIQVELYADSKDIIIECSENQLKQVFINILQNSIEAMPDGGRISIHIKEIGK
ref|ZP_01665476.1|    MYGEAILSGITLRPELPPEELWVQGHIDKLKEVLINICRNAFQAMG--PGGVLTLSVAAD
RAAC01563             LVPEASLCDIAFELNVPAHPIPAAVRPAQIKQVLINLVQNALQACRGQAHAVVRLDVAEK
                        :* : .* ..       ..  :      ::*:*:**: :*::: *      :  :.  .

ref|YP_036745.1|      -DGIIISVIDKGIGIPEERIKRLGEPFYSTKEKGTGIGLMLSYKIIESHQGNISIMSEVG
ref|YP_083969.1|      -DGIIISVIDKGIGIPEERIKRLGEPFYSTKEKGTGIGLMLSYKIIESHQGNISIMSEVG
ref|YP_028716.1|      -DGIIISVIDKGIGIPAERIKRLGEPFYSTKEKGTGIGLMLSYKIIESHQGNISIMSEVG
ref|ZP_02259717.1|    -DGIIISVIDKGIGIPEERIKRLGEPFYSTKEKGTGIGLMLSYKIIESHQGNISIMSEVG
ref|ZP_01665476.1|    TATVKIVLADTGCGMTKEVMDQIFTPFFTTKETGTGLGLAICQQIMHEHGGDIQVESTPG
RAAC01563             EDRVLVQVVDNGCGI--EHMDRIFRPFYTTKSTGTGLGLFVCKHIIESHGGSISVRSQVG
                       :  : *.* *: *:  *   ..::*:**  .* :*: ..::: . *.*.: * *
```

FIG. 37B

```
ref|YP_036745.1|        VGTTVTIYLPKIQSKK-
ref|YP_083969.1|        VGTTVTIYLPKIQSKK-
ref|YP_028716.1|        VGTTVTIYLPKIQSKK-
ref|ZP_02259717.1|      VGTTVTIYLPKIQSKK-
ref|ZP_01665476.1|      QGSTFTLLLPRC-----
RAAC01563               AGTTVTVEIPKCASRRA
                        *:*.*:  :*:
```

FIG. 38

```
ref|YP_145847.1|         ------TITMGIQKGGCGKSTTTGVLAYLLSRDGYRVLAVDMDSQGN-LTELLSRKP---
RAAC02315                MERVGCTISVGLQKGGVGKSTTTALTSYILAEQGHRVLAVDFDSQGN-LTQLLTQRS---
ref|YP_536482.1|         ---MGTVIAIANQKGGVGKTTTSVNLGACLARAGQKVLLIDTDAQGNATSGIGVRKH---
ref|YP_799230.1|         ---MGKIVSISNQKGGVGKTTTSINLAANLASIGKKVLIIDMDPQGNSGSGLGIEIN---
gb|ABG00342.1|           ------TIIIGNQKGGVGKTTNTYLIAYTLAKLGIKTLVCDLDPQSNSTKALILTKS-QN
ref|YP_891181.1|         MLKMAITITVGNYKGGVGKTTNAVLNSYEFAKKGKRTLLVDLDPQSNATKSLMLTKSILN
                                : :.  *** **:*.:   .  ::   * :.*  * *.*.*   . :

ref|YP_145847.1|         --SNEFTEKSVLEAMQERDPEPYIVKVND-----RLDLLPANNFLAT-----FPRWIYTG
RAAC02315                --PYDFVHRTSLEACKERDPRPYIHAISD-----NLHLLPAEDFLSQ-----FDKWIYT-
ref|YP_536482.1|         --NIENDVYDVI--VSELPIREAIMPTYI----DNLDVVPATIQLAG------AEIELTA
ref|YP_799230.1|         --TLVKTSYELL--LGESSTNECIQRTNV----SNLHIIPSNINLSG------AEADLLV
gb|ABG00342.1|           SNEIMTIDKTLMWGVQQRDLKDLPVSIIE-----NLDLLPSYIDPED-----PAKYLYKN
ref|YP_891181.1|         PDEIVTVEKTLMKGIQEGNLDGLEVEITD-----NLYLIPSYVDFQD-----PAKFLYQN
                             :           :           .* ::*:   :          .

ref|YP_145847.1|         ETYLGKYIRYKGKPTLILDDTLDKIRHRYDFIVIDTPPSLSEQTTNALCASQYVIMMFEC
RAAC02315                EVHVS-------QQMVILKNTLDVVKSDYDYILIDLPPNLGGLTLNGVCASDYCVVVCQS
ref|YP_536482.1|         QMAREKK---------LYDAVQDVKEEYDFILIDCPPSLGLLTINAFTASDSILIPVQS
ref|YP_799230.1|         EDQREYR---------LKNAVSELRSEYDYILIDCPPSLGILTINALCAADSVMITLQT
gb|ABG00342.1|           TSNEYEET-------HLLEPLFEPLKEDYDIILIDVPPLSVEVTSNAVMFSDYVLISLQT
ref|YP_891181.1|         CASEAEED-------HYFKGLLEKIKHKYDYIFIDVPPMSLEVTKNAVVASDYVLIALQT
                                      .. ::  ** *.** **      * *..  ::  ::  :

ref|YP_145847.1|         SNWCYSAVPNFMESVEGARVHGRHNTRLLGILRTMNDVRRNDAKAFNEMIEEDY-PNEVF
RAAC02315                EPFAYDALDRYMEIIQAAQQRVNPNLRIAGILISLLDARTAIGNYITERIREEY-QDFVF
ref|YP_536482.1|         EYYALEGLSQLMNTIQLVQKHFNPDLQIEGVLMTMLDARTNLGNQVVEEVKKFF-KEKVY
ref|YP_799230.1|         EYFALEGLTQLMKIISLVQNQLNPSLELEGVLLTMFDKRTNLANQVAEDVKSYF-KDKVY
gb|ABG00342.1|           QDDSMTGAIEYIKTLVKLKMKYELGIEVLGALPMLSNSRGSVDKLIIESAKEEWGEDLVF
ref|YP_891181.1|         QERSLTGAENYVNELIKLKEQYDLDIEVVGILPVLLKNNGKVDEYIMENAREIFGEENLF
                              .  . ::   :    :   ..:  * *    :    .   :  *  .. :  : ::

ref|YP_145847.1|         KTIITRKAPIGRLSLYGFEENN-ELN-QALEQYENFYKEMMERV--
RAAC02315                DTVIRRKSRIIEFSVEGIKIQT-KADREAIAMYESFVEELKARVSR
ref|YP_536482.1|         KTVIPRNVRLSEAPSHGMSIIDYDPRSRGAEEYEALAKEV------
ref|YP_799230.1|         TTIIPRNVKLSE----------------------------------
gb|ABG00342.1|           ETVIPQMERIKRFSINGITDED-RFDRKVLEMYEKVVSEMLSKL--
ref|YP_891181.1|         KNIVPQMERIKRFDVNGITEKD-RHDMNVIELYETISDELLSRI--
                          .::  :    :  .
```

FIG. 39

```
ref YP_001423364.1|     ----KIIAITNQKGGVGKTTTSVNLGACLAYIGKRVLLVDIDPQGNATSGLGIEKADVDH
ref NP_391977.1|        ----KIIAITNQKGGVGKTTTSVNLGACLAYIGKRVLLVDIDPQGNATSGLGIEKADVEQ
ref YP_093870.1|        ----KIIAITNQKGGVGKTTTSVNLGACLAYIGKRVLLVDIDPQGNATSGIGVEKADVDQ
ref YP_081433.1|        ----KIIAITNQKGGVGKTTTSVNLGACLAYIGKRVLLVDIDPQGNATSGIGVEKADVDQ
ref YP_001488932.1|     ----KIIAITNQKGGVGKTTTSVNLSACLAYIGKRVLLVDIDPQGNATSGIGIEKADVEK
RAAC00040               MSSARVIAIANQKGGVGKTTTAVNLGACLATLGKRVLLIDIDPQGNTTSGVGINKADVKY
                            ::***.***********.***.****  .:******:*******.***.*::****.

ref YP_001423364.1|     CVYDILVDDADVTDIIKPTSVENLDVIPATIQLAGAEIELVPTISREVRLKRALESVKQN
ref NP_391977.1|        CVYDILVDDADVIDIIKATTVENLDVIPATIQLAGAEIELVPTISREVRLKRALEAVKQN
ref YP_093870.1|        CVYDILVDDADVKDVIKTTSVENLDVIPATIQLAGAEIELVPTISREVRLKRALESVKQN
ref YP_081433.1|        CVYDILVDDADVKDVIKTTSVENLDVIPATIQLAGAEIELVPTISREVRLKRALESVKQN
ref YP_001488932.1|     CVYDILVDDADVLDVIKTTEVENLDVIPATIQLAGAEIELVPTISREVRLKRALESVKQN
RAAC00040               CVYDVIINDVNIADAIMPSGLDNLDVLPATIQLAGAEIELVPTISREVRLRRAIQGMRSR
                        ****::::*.::  *  *  .:  ::****:***********************:**::.:..

ref YP_001423364.1|     YDYMIIDCPPSLGLLTINALTASDSVVIPVQCEYYALEGLSQLLNTVRLVQKHLNTDLMI
ref NP_391977.1|        YDYIIIDCPPSLGLLTINALTASDSVVIPVQCEYYALEGLSQLLNTVRLVQKHLNTDLMI
ref YP_093870.1|        YDFMIIDCPPSLGLLTINALTASDSVVIPVQCEYYALEGLSQLLNSVRLVQKHLNTDLMI
ref YP_081433.1|        YDFMIIDCPPSLGLLTINALTASDSVVIPVQCEYYALEGLSQLLNTVRLVQKHLNTDLMI
ref YP_001488932.1|     YDYMIIDCPPSLGLLTINALTASDSVLIPVQCEYYALEGLSQLLNTVRLVQKHLNTDLAI
RAAC00040               YDYIVIDCPPSLGLLTVNALTAADSVMIPIQCEYYALEGLSQLLNTVRLVQKHLNTSLEV
                        **:::***********:*****.***:**:***********************.*  :

ref YP_001423364.1|     EGVLLTMLDARTNLGIQVIEEVKKYFRDKVYQTIIPRNVRLSEAPSHGKPIILYDPRSRG
ref NP_391977.1|        EGVLLTMLDARTNLGIQVIEEVKKYFRDKVYKTVIPRNVRLSEAPSHGKPIILYDPRSRG
ref YP_093870.1|        DGVLLTMLDARTNLGIQVIEEVKKYFRDKVYKTVIPRNVRLSEAPSHGKPIILYDPRSRG
ref YP_081433.1|        DGVLLTMLDARTNLGIQVIEEVKKYFRDKVYKTVIPRNVRLSEAPSHGKPIILYDPRSRG
ref YP_001488932.1|     EGVLLTMLDARTNLGIQVIEEVKKYFRDKVYQTVIPRNVRLSEAPSHGKPIILYDPRSRG
RAAC00040               EGVVLTMLDARTNLGLQVIEDVKKFFRDKVYKTIIPRNVRLSEAPSHGRPIIHYDPKSRG
                        ::*******::*:******:*:***********:*  *:* ref YP_001423364.1|     AEVYLDLAKEVAANG
ref NP_391977.1|        AEVYLDLAKEVAANG
ref YP_093870.1|        AEVYLELAKEVAA--
ref YP_081433.1|        AEVYLELAKEVAA--
ref YP_001488932.1|     ADVYLDLAKEVDANG
RAAC00040               AESYMELAKEVIARG
                        *:  *::*****  *
```

FIG. 40

```
ref ZP_01697918.1|      ----------------------------------FFMLVMLIIYLESPLSRVHRIQIE
ref ZP_01172488.1|      ----------------------------------LLLLFFSMIVFVIYFQSPLSRVKEISIS
emb CAJ75583.1|         ----------------------------------FFLFILCVLYFQSPLGAVGHVEVS
ref YP_146973.1|        ----------------------------------FFLFILCVLYFQSPLGAVGHVEVS
ref YP_001125108.1|     ----------------------------------FFLFILCVLYFQSPLSAVRHVEVS
RAAC00113               MNRGRTGGERRESMPRQETAEERERRKARNRRIVVSFFAPIGLVAVLESPLARVRHIEVS
                                                          **  ::  :   ::***. *  .:.:.

ref ZP_01697918.1|      GNEAVSKPYILKKSGIATGENIWNI-RKDAVRKRIASIPEVDSVKVGISLPN-TLYIKVK
ref ZP_01172488.1|      GNQTYTTKELIAVSGLSKKTNIWKVD-KGAIEGRLKELPEISGAEIKTRLPN-TVDIKVA
emb CAJ75583.1|         GNRHLTAERIISLSGITKRTSFWKVNEQNVEKKL-TRHPEIKEATVEKQLPN-TIAIHVR
ref YP_146973.1|        GNRHLTAERIISLSGITKRTSFWKVNEQNVEKKL-TRHPEIKEATVEKQLPN-TIAIHVR
ref YP_001125108.1|     GNRHLPAERIISLSGITKRTSFWKVNEQNVEAKI-ARHPEIKEATVKKRLPN-TIVIDVR
RAAC00113               GNTTIPMAQIVACSGVVYGESLWEVNRKRAASEIVAKLPMVDRAAISVSWPSGTVSIHVH
                           .  ::  :   .:*::  :  .      * :. .:   *. *: *.* ref ZP_01697918.1|      EHQKIGYLQQKGGFLPVLDNGSVV-KRTVKEIPAAS----LIFTGFKQDT---------H
ref ZP_01172488.1|      EHNRIAYIAKEKSFLPVLENGMILSKQEITDIPVNA----PLLLGFKEGD---------V
emb CAJ75583.1|         EWRRIAYVYDRQTFFPLLENGRLLKQEGTKTAPSDA----PVLVGWKDGD---------A
ref YP_146973.1|        EWRRIAYVYDRQTFFPLLENGRLLKQEGTKTAPSDA----PVLVGWKDGD---------A
ref YP_001125108.1|     EWRRVAYVYNRQTFFPLLENGQLLKQEAVKTAPSDA----PVLVGWKS----------GEA
RAAC00113               ERDVVAVYADPNGFYELMSNGYVYQKIPSAAGLPYP-----IVTGQDSELS---------
                        *  :.  .  *  ::.**  :  .        .    :. *  ..

ref ZP_01697918.1|      LHEM---------IRQMQKLPDSITNAISEVRYTPSNVDRDLVTLYMNNGFEVRASIPSF
ref ZP_01172488.1|      LLEMIDS---------LESLPKEVLNAISEIHYSPKETDEYHITLYMNDGFEVSATLRSF
emb CAJ75583.1|         IAEMTG---------QLAELPAAVLGAMSEIHYKPTREYEDRVIVYMNDGYEVSATI---
ref YP_146973.1|        IAEMTG---------QLAELPAAVLGAMSEIHYKPTREYEDRVIVYMNDGYEVSATI---
ref YP_001125108.1|     IAEMTG---------QLAELPAAVLGAISEIHYKPTGEYKDRVVVYMNDGYEVSATIHN-
RAAC00113               VHQMASAAVSS-VCRQLASVPASELTGVSEIHVN----GDGTVTIYLDNDFEVLADVANL
                        : :*           :  .:*    .:**::  .       : :*:::.:** * :

ref ZP_01697918.1|      AEKMAHYPSIISQLDPK--KKGVIDL----------------------------------
ref ZP_01172488.1|      SEKMAHYPSIISQLDPG--VSGVIDL----------------------------------
emb CAJ75583.1|         ------------------------------------------------------------
ref YP_146973.1|        ------------------------------------------------------------
ref YP_001125108.1|     ------------------------------------------------------------
RAAC00113               RGSVAAIQPTIRYFEGKGYRPGVIDLTGSPPYRYTPFSSLPSSNAKTSSASGRGGPVEGT ref ZP_01697918.1|      --------
ref ZP_01172488.1|      --------
emb CAJ75583.1|         --------
ref YP_146973.1|        --------
ref YP_001125108.1|     --------
RAAC00113               SSKTASHP
```

```
FIG. 41A
emb CAJ75587.1|         MSSNEIVVSLDVGTSSVKVIIGEMLGSSINIIGVGNVKAEGLKKGAIVDIDKTVQSIRRA
ref YP_146977.1|        MSSNEIVVSLDVGTSSVKVIIGEMLGSSINIIGVGNVKAEGLKKGAIVDIDKTVQSIRRA
ref YP_001125112.1|     MSSNEIVVSLDVGTSSIKVIIGEMLGSSINIIGVGNVKSEGLKKGAIVDIDKTVHSIKRA
ref NP_243425.1|        MNNNEIYVSLDIGTSNVRIIIGEITDGSINIIGVGNAPSEGIKKGSIVDIDETVRSIRRA
ref ZP_02330014.1|      MSSSDIIVSLDIGTSKVRAIIGEVNNGTINIIGVGSADSEGIRKGAIVDIDQTVSSIRAA
RAAC00117               MAKEDYIVSLDIGTSKVRVIIGESTGNNLNIIGVGSASSQGLRHGAIVDIDKTVDSIREA
                        *  .:  **:*.::  **    ...:****..  ::*::*:***:  **:  * emb CAJ75587.1|         VEQAERMVGLSIRRVIVGVAGSHIQLHDCHGIVAVASENREISDEDVARVIDAAQVVSIP
ref YP_146977.1|        VEQAERMVGLSIRRVIVGVAGSHIQLHDCHGIVAVASENREISDEDVARVIDAAQVVSIP
ref YP_001125112.1|     VEQAERMVGLSIRRVIVGVAGSHVQLQDCHGIVAVASENREISDEDVARVIDAAQVVSIP
ref NP_243425.1|        VEQAERMVGLSIRQVIVGVNGNHVQLQPCHGVVAVSSPDREIGDEDIARVIDAAQVVSIP
ref ZP_02330014.1|      VDHAERMVGLQISEVYVGITGNHIALQTSHGVVAVSNEDREIGEEDIERVNQAARVIALP
RAAC00117               VDHAERMVGIRIPSAYVGISGEHIQLHSSHGVVAVSSADREITDEDIERVLQQARVVALP
                        *:  :******:   *    **:  *.*:  *:   ..*:.  :* ::     *: *::  :* emb CAJ75587.1|         PDREIIGVVPRQFIVDGLDGIHDPRGMLGVRLEMEGTMVTGAKTVLHNLLRCVERAGLEI
ref YP_146977.1|        PDREIIGVVPRQFIVDGLDGIHDPRGMLGVRLEMEGTMVTGAKTVLHNLLRCVERAGLEI
ref YP_001125112.1|     PDREIIGIVPRQFIVDGLDGIHDPRGMLGVRLEMEGTMITGAKTILHNLLRCVERAGLEI
ref NP_243425.1|        PEREIIDVIPKQFIVDGLDEINDPRGMIGVRLEMEGTIITGSKTLLHNLLRCVERAGLEV
ref ZP_02330014.1|      PEREIIGIVPKQYIVDGQEGIQDPRGMIGVRLEVEATIITGAKTGIHNLLRVVEKSGLKV
RAAC00117               PEREVIDVVAKEFVVDGLRGIMDPRGMLGVRLEVDAYLITGSRTAIHNIVRCVERAGLEV
                        *:**:*.::.:::***    * *****:*****::. ::**::*  :**::* **::**::

emb CAJ75587.1|         SDICLQPLAAGSLVLSDDERHLGAALVDLGGGSTTVAVFEQGTLQAVSSLPVGGEHITKD
ref YP_146977.1|        SDICLQPLAAGSLVLSDDERHLGAALVDLGGGSTTVAVFEQGTLQAVSSLPVGGEHITKD
ref YP_001125112.1|     SDICLQPLAAGSLALSDDERHLGAVLVDLGGGSTTVAVFEQGTLQAVSSLPVGGEHITKD
ref NP_243425.1|        ADICLQALAAGSVAISKDEKSLGVCLIDIGGGSMTISCFEQGSLVDTSVIPVGGDHVTND
ref ZP_02330014.1|      SGLILMSLAAGQLALSKDEKQIGTVLVDVGAGTTTISVFDQGSLVATSTLPIGGDFITTD
RAAC00117               ANLVLAPMAASQIALTQDERKLGVALVDVGAGVTSVSVFANGVLMGTSIIPIGGDYVTQD
                        :.: *  .:..:..::::  :*. *:*:*.*  ::: *  :* *  .* :*:**:.:* * emb CAJ75587.1|         LAIGLRTTTDDAEKIKLKHGHAFYDYASEEEVFSVPIMGTDQHQQFSQLEIADIIEARLE
ref YP_146977.1|        LAIGLRTTTDDAEKIKLKHGHAFYDYASEEEVFSVPIMGTDQHQQFSQLEIADIIEARLE
ref YP_001125112.1|     LAIGLRTTTEDAEKIKLKHGHAFYDYASEEEVFTVPIMGTDQHQQFSQLEIADIIEARLE
ref NP_243425.1|        IAVGLRISTEEAIKIKHTHGHAYIDEASEEDRFEVKAIGSTEPEAFSQFELAHIIEPRME
ref ZP_02330014.1|      ISIGLRTQMDIAEKIKLKFGCASIADSAPDQMFKVNRIGSNVDKEFSQVDLANIVEPRVQ
RAAC00117               IAIGLRTNTVAAEQVKLRHACAMVEQASEHETFRVPRMGSNKEAEFTQYDLATIIEPRMQ
                        :::***    * ::*  ..  *   ::  .:  * *  :*:    *:* ::* *:*.*::

emb CAJ75587.1|         EILQMVQQEVRRLGFRD-LPGGYVLTGGVANMPGLLELAHVVLGTSVRIAMPDYIGVRDP
ref YP_146977.1|        EILQMVQQEVRRLGFRD-LPGGYVLTGGVANMPGLLELAHVVLGTSVRIAMPDYIGVRDP
ref YP_001125112.1|     EILQMVQHEVRRLGFRD-LPGGYVLTGGVANMPGVLELAHVVLGTSVRVALPDYIGVRDP
ref NP_243425.1|        EMFELINRELRRLGQHD-FPGGYVLTGGSVMMPGVLELAKETLGRNVRVAIPDYIGVREP
ref ZP_02330014.1|      EIFQLIRGEVHRMGYSD-LAGGYVLTGGTVNLPATLVIAQEELAATVRIATPDYIGVRDP
RAAC00117               EIFGLVRKEVEKMGYADELPAGYVFHGGVMSTPSAAELAGEELQAPVRIAVPEFLGVRDP
                        *::  ::. *:.::*    *  :..*:*: **    *.    :*    *    **:*  *::.***:* emb CAJ75587.1|         QYTIGVGLLKFAYR----------------------------------------------
ref YP_146977.1|        QYTIGVGLLKFAYR----------------------------------------------
ref YP_001125112.1|     QYTIGVGLLKFAYR----------------------------------------------
ref NP_243425.1|        QYTTGVGLIQFAYKNVKIQGKEVAAAVAEAGVEQEQRPKKEKERSRTNEGPGVKSKVKNW
ref ZP_02330014.1|      AYTSGVGIIQFVIKYIR------NRPASLNKKQPIKAAASKSGSQEKEGEGFFDRVKNF
RAAC00117               SFVNGVGMIVYAAR--------------TGLRPSSADYNAGARQVRSSNHVGVFARIKDW
                        :. ***:: :.. :
```

```
FIG. 41B emb|CAJ75587.1|          -----
ref|YP_146977.1|         -----
ref|YP_001125112.1|      -----
ref|NP_243425.1|         FKVFL
ref|ZP_02330014.1|       LKEFI
RAAC00117                LRDFV
```

FIG. 42

```
ref|YP_001646530.1|     ------------------------MLEFDTTQDQLANIKVIGVGGGGNNAVNRMIEHG
gb|AAN04557.1|          ------------------------MLEFDTTQDQLANIKVIGVGGGGNNAVNRMIEHG
ref|YP_001375784.1|     ------------------------MLEFDTTQDQLANIKVIGVGGGGNNAVNRMIEHG
ref|YP_078922.1|        ------------------------MLEFETNIDGLASIKVIGVGGGGNNAVNRMIEND
ref|ZP_02171874.1|      ------------------------MLEFEMDTDQLATIKVIGVGGGSNAVNRMIENG
RAAC00118               MCARTCALTPYCRRGSAEPNRLGGPTVLEFDFETDSLANIKVIGVGGGGCNAVNRMIESG
                                                  :***:    * **.********* *******  .

ref|YP_001646530.1|     VQGVDFIAVNTDAQALNLSKAETKMQIGGKLTRGLGAGANPEVGKKAAEESKEQIQEALR
gb|AAN04557.1|          VQGVDFIAVNTDAQALNLSKAETKMQIGGKLTRGLGAGANPEVGKKAAEESKEQIQEALR
ref|YP_001375784.1|     VQGVDFIAVNTDAQALNLSKAETKMQIGEKLTRGLGAGANPEVGKKAAEESKEQIQEALR
ref|YP_078922.1|        VQGVEFIAVNTDAQALNLSKAETKMQIGAKLTRGLGAGANPEVGKKAAEESKEQIEEALK
ref|ZP_02171874.1|      LQGVEFIAVNTDAQALQLSKAEHKLQLGGKLTRGLGAGANPDIGKKAAEESRDQLEEYLT
RAAC00118               VKGVEFIVVNTDAQALKLSKAETKLQIGEKLTRGLGAGANPEIGKKAAEESREMLANALK
                        :::.******:**.*:*:* **********: :*****:: : :  * ref|YP_001646530.1       GADMVFVTAGMGGGTGTGAAPVVAQVAKELGALTVGVVTRPFTFEGRKRATQAASGIASF
gb|AAN04557.1|           GADMVFVTAGMGGGTGTGAAPVVAQVAKELGALTVGVVTRPFTFEGRKRATQAASGIAAF
ref|YP_001375784.1       GADMVFVTAGMGGGTGTGAAPVVAQVAKELGALTVGVVTRPFTFEGRKRATQAASGIAAF
ref|YP_078922.1          GADMVFVTAGMGGGTGTGAAPVIAQIAKDLGALTVGVVTRPFTFEGRKRQLQAAGGISAM
ref|ZP_02171874.1        GADMVFITAGMGGGTGTGAAPVIAEIAKEAGALTVGVVTKPFTFEGRRRMNQAQTGISDL
RAAC00118                GADMVFVTAGMGGGTGTGAAPVIAEIAKELGALTVGVVTKPFRFEQRRRMIQAEQGVNEL
                         ******:************** :.:**: ********.** ** *:*  **  *:   :

ref|YP_001646530.1|     KENVDTLIVIPNDRLLEIVDKNTPMLEAFREADNVLRQGVQGISDLIATPGLINLDFADV
gb|AAN04557.1|          KENVDTLIVIPNDRLLEIVDKNTPMLEAFREADNVLRQGVQGISDLIATPGLINLDFADV
ref|YP_001375784.1|     KENVDTLIVIPNDRLLEIVDKNTPMLEAFREADNVLRQGVQGISDLIATPGLINLDFADV
ref YP_078922.1|        KEAVDTLIVIPNDRLLEIVDKNTPMLEAFREADNVLRQGVQGISDLIATPGLINLDFADV
ref|ZP_02171874.1|      KEKVDTLIVIPNDRLMEIVDKNTPMIEAFREADNVLRQGVQGISDLIAVPGLINLDFADV
RAAC00118               KQKVDTLIVIPNDRLLEIVDRNTPVLEAFREADNVLRQGVSGISDLIATPALINVDFADV
                        *:  ********: :*::*********** *****.*  **.*** ref|YP_001646530.1|     KTIMSNRGSALMGIGSGNGENRAAEEAAKKAISSPLLETSIDGAQGVIMNITGGANLSLYE
gb AAN04557.1           KTIMSNRGSALMGIGSGNGENRAAEEAAKKAISSPLLETSIDGAQGVIMNITGGANLSLYE
ref|YP_001375784.1|     KTIMSNRGSALMGIGSGNGENRAAEEAAKKAISSPLLETSIDGAQGVIMNITGGANLSLYE
ref|YP_078922.1|        KTIMSNKGSALMGIGVATGENRAAEEAAKKAVSSPLLETAIDGAQGVLMNITGGTNLSLYE
ref|ZP_02171874.1|      KTIMSEKGSALMGIGIATGESRAAEEAAKKAISSPLLETSVDGAQGVLMNITGGTNLSLFE
RAAC00118               KAIMTERGSALMGIGIASGENRAAEEAAKKAISSPLLETSDGARGILMHVAGGTNLSLWE
                        *:::::*****  ..*******.***::*:*::*:::**.* ref|YP_001646530.1|     VQEAADIVASASDPEVNMIFGSVINEGLKDDIVVTVIATGFDDSASTQPPKPIIRPTANH
gb|AAN04557.1|          VQEAADIVASASDPEVNMIFGSVINEGLKDDIVVTVIATGFDDSAATQPPKPIIRPTANH
ref|YP_001375784.1|     VQEAADIVASASDPEVNMIFGSVINEGLKDDIVVTVIATGFDDSIVAQQQKTLVRPKINS
ref|YP_078922.1|        VQEAADIVAAASDQDVNMIFGSVINENLKDEIVVTVIATGFIE--QDQDSSKPQRPLNQG
ref|ZP_02171874.1|      VHEAAEIVSSASDEEVNMIFGSVINDNLKDEIIVTVIATGFDEASQQKAQPKRSKPNAQK
RAAC00118               VNEAADIVSMTADPDVNMIFGAAIDPNLEDEIVVTVIATGFDGSNQQQQARQNHLHHEPH
                        *:****:**:  ::* :******:.*:  .*:*:*:********     :

ref|YP_001646530.1|     TQQQQQPVAQPSKQREVKREMKREEPVVHDRHTDS---DDIDIPAFLRNRRRR-----
gb|AAN04557.1|          TQQQQQPVAQPTKQREVKREMKREEPVVHDRHTDS---DDIDIPAFLRNRRRR-----
ref|YP_001375784.1|     SHVQQQAAVQPPKHREVKREVKREEPVIHDRNTDA---DDIDIPAFLRNRRRR-----
ref|YP_078922.1|        LKQHHQP--------APKREPKREEPSMPHRSPSQPAEDTLDIPTFLRNRNKR-----
ref|ZP_02171874.1|      SGRQEQK------DQPQQKAAEVEETSQEEI-------DTLDIPTFLRNRRQR-----
RAAC00118               DNVVRGT---------VQRHPSAQDPVINVPNTGN----PWEIPAFMRRQNSRFGRDR
                                        ::  ::.               :**:*:*.:.  *
```

FIG. 43

```
ref|YP_001395809.1|      ---KDSITVSLCMIVKNEEDTIGRCLDSVKDVIDEFIIVDTGSSDNTKDVIKKYTDNIYD
ref|YP_001309701.1|      -------TISLCMIVKNEEDVIANCLESVKDIVDEMIIVDTGSDDKTKKIVKRYTDKIYD
ref|YP_001643660.1|      -------TISLCMIVKDEEQTISKCLESVKSVVDEIIIVDTGSTDGTKEIVKKYDAKVYD
ref|YP_520670.1|         ----------SLCMIVRNEEKTIARCLDSVCDIADEIIIVDTGSTDRTKEIVARYTDKIFD
ref|YP_147952.1|         -------TISLCMIVKNEEDVLARCLDSVQHLVDEIVIVDTGSTDRTKEIARSYTARVID
RAAC01377                MSAKTENTWSLCMIVKDEEAVLDRCLQSIADIVDEIVIVDTGSQDRTQEIARKYTDLVFD
                                     ****::  .:  .**.*:    :  :: ****   *  *:.:       *       :  * ref|YP_001395809.1|      FEWIDDFSAARNFAFSKATKDYIFWLDADDVLLPEDVEKFKALKKNLDTSIDSVTMRYNV
ref|YP_001309701.1|      FKWIDDFSAARNFAFSKATKDYILWLDADDVVLPEDGEKFKDLKETLDPTVDSVTAKYNT
ref|YP_001643660.1|      FQWIEDFSAARNFAFSKATKEYILWLDADDIIDTEDIKKLLQLKHTLDRSTDAVSMKYYL
ref|YP_520670.1|         FAWIDDFAAARNYAFSLGTKEYLLWLDADDVILESDRLKFHNLKKNLNPSIDVVNMHYLL
ref|YP_147952.1|         FPWSDDFSAARNFSFSHATMDYIFWLDADDILPAEEQTKFLTLKRTLSSDIDSVTMIYSL
RAAC01377                FEWVDDFSEARNESFRHASMDYVLWLDADDVVSDVDRIKLAEFKKNLSSDVDAVTMWYHL
                         *  *   ::   *  :*     .:  :*:;*******:    :     *:    :*..*.    * *.   * ref|YP_001395809.1|      SFDEYSNVTTSYRRNRLVKKEKNFKWIGFVHEYLEVYGNIINSEISVTHKKINYSPNRNL
ref|YP_001309701.1|      AFDEYGNVTASYRRNRLVKRSNNFQWFGFVHEYLAVGGNIINSEIAITHRKLKQTPKRNL
ref|YP_001643660.1|      TFDIEGNPTHSLRRYRLVNRSKNFQWYGFVHEYLEVYGNLINSDVGVSHKKEKAYTNRNL
ref|YP_520670.1|         AFDSSENPTFTLRRNRLVRRGKNFRWKGAVHEYLEVSGNIMNSDIAIAHKSEEHDSERNL
ref|YP_147952.1|         AQDEYGKTISSVRRNRLVKRSSGFRWHGMVHEYLEVWGTILNSDITIIHQPNRCASDRNL
RAAC01377                AFQGDQPTVSS-RLVRLVKRSRGFVWRGRVHEYLEINGNILNSDIAIIHRPVEHDAARNL
                          : :       : *   ***.:   .* *  * ***** : *.:;:**.::  : *:   .   . *** ref|YP_001395809.1|      EIFQNKLKEGVEFTPRDILYYGNELYEHRMFEDALKYYNDFLDSKRGWYEDNIHVCGKIC
ref|YP_001309701.1|      EIYQNKLKEGVVFTPRDILYYGNELYDHRMFDEALQYYNKFLDSKQGWFEDNIRVCEKIC
ref|YP_001643660.1|      KIYEKHLESGKEFSPRDVYYYANECKDHRLFDKAVKGYSRFLDEEKGWVEDNIQACLKRA
ref|YP_520670.1|         RIYEKRLEQGEEFSPRDLYYFANELYDHKQYEKAVEYYEKFLNTEKGWVEDNISACGKLA
ref|YP_147952.1|         QIYEKQLAQGKEFSPRDLFYFANELFDHQQYERAIQYYEQFLQTKKGWVEDCIAACGKVA
RAAC01377                RIYEKKLALGEDFSPRDMLYYANELLDHAQYEKAVQWYKRFLATGQCWKEDAITACFKLA
                         .*::::*   *  *:***: *:.**  :*   ::  *::  *. ** :   * ** *  .* *   .

ref|YP_001395809.1|      DYYQSINNGEECRKYAFKSFEYDSPRAEACCRLGPSFLQENKINQAIFWYETAANLKKPI
ref|YP_001309701.1|      DYYQSIDKVEDGRRYAFRSFEYDTPRAEACCKIGFSFLHEKKYKQSAFWYEQATKLEKPK
ref|YP_001643660.1|      ECYLELGDLKKSIQSCLQSFTYDTPRGELCCHLGRVFLQQGEYSKAIYWYHAAIDGPRPK
ref|YP_520670.1|         DIYKLLGDSANAQAYLYKSFDYDTPRAEFCCRIGFNHLNAGKYQQAIFWYKLASELEKPT
ref|YP_147952.1|         DCFDALGDEEQALRYALRSFEYDTPRAECCCRLGYYFLQRKQYRLAAFWYHLATQLTMPS
RAAC01377                ECFRAMNQPEQSKQAVLHSFLYDTPRAEACCRIGYGYLEEGKIDQAIFWYDLATKCRRPA
                          :       :..  .             :  :**.*  **::*.   .*.     :   :**. *.    * ref|YP_001395809.1|      NSLGFFSDACWTWLPHLQLCVCYDRIGKHQLAYEHNEIAGKFRPNDKKILYNRNYFQS--
ref|YP_001309701.1|      DSWGFFNDACWTWLPHLQLCVCYDRLGDHNLAYEHNEIAAKFRPNDSRILYNRNYFKS--
ref|YP_001643660.1|      D-SPFVREECHTWLPHIQLCICYDRIKEYEKAIYHNEQAALFIPNNPSIEYNR-------
ref|YP_520670.1|         NSWGPKSEACWTYLPHLQLCVCYDRLGMHELAYKHNEIARDYRPDNPQILHNKKYL----
ref|YP_147952.1|         DSWGFVHHACWTWLPHLQLCVCYFYMGEYELAYQHNEKAKQYVPHHPAVLHNECLLQSIL
RAAC01377                NFVGFVNHACETWLPHIQLCVCYSRLGQYRKAYDHNERAAEYLGEDPMIVHNRSVLRAWM
                          :         .  * *:***:***:**   :   :  *    *** **:        : ..  .   : :*.

ref|YP_001395809.1|      -------
ref|YP_001309701.1|      -------
ref|YP_001643660.1|      -------
ref|YP_520670.1|         -------
ref|YP_147952.1|         AAE----
RAAC01377                DGELEKP
```

FIG. 44A

```
ref|NP_470039.1|        ------LISICMIVKNEAHILRQSLASFRKFTEEIIIVDTGSTDDTKEIAKEFTDFVYDF
ref|ZP_01929325.1|      ------LISICMIVKNEAHILRQSLASFRKFTEEIIIVDTGSTDETKEIAQEFTDFVYDF
ref|YP_848858.1|        ------LISICMIVKNEAHILRQSLASFRKFTEEIIIVDTGSTDETKEIAKEFTDFVYDF
ref|YP_001374688.1      -------ISACLIVKNEEDMLRKCLESLQGGVDEIVVVDTGSTDTTKEIAKEFTDKVYDF
ref|NP_622177.1|        -------LSLCLITKNEEKNISRCINSVKDIVDEIVVVDTGSTDRTIEIAKSFGAKVIQI
RAAC02381               MRRIVVLLSACLIVKNEAHVLPRCLGSLQGVADEIVVVDTGSTDDTPRIAESFGARVYHF
                             :* *:*.***  .: :.: *.:  ..:**::******* * .**:.*   *  .:

ref|NP_470039.1|        EWTGNFSDARNFAAKHATGKWILAIDADECLEEESYRKLEKQLKSPIEP--IQMAQIISF
ref|ZP_01929325.1|      EWTGNFSDARNFAAKHATGKWILAIDADECLEEESYRKLEKQLKSPTEP--IQMAQIISF
ref|YP_848858.1|        EWTGNFSDARNFAAKHATGKWILAIDADECLEEESYLQLKKQLKAPTEP--IQMAQIISF
ref|YP_001374688.1      EWTNDFAEARNFAASKASGEWILAIDADECVDPKNLAAAIEEIQSHDNKFDVYAVEINSF
ref|NP_622177.1|        KWEDDFSKARNTAIESATGDWILFLDADEEIKKEDVSKIKSLLYDDTVEAYLFKFVNYAG
RAAC02381               EWTGDFAVARNESLRYALGEYVLVIDADEFLPKEDGVRLRQALQERRADAYTVDLVNYLG
                        :*  .:*: ***  :   *  *.::* :****  :   :.       . :

ref|NP_470039.1|        TGEKGRVTTTNQMARVYKNDGTICFRGVIHEQ-----LEAVDKHAIEAGLAEVKIYHYGY
ref|ZP_01929325.1|      TGEKGRVTTTNQMARVYKNDGTICFRGVIHEQ-----LEAIDKRPIAAGVAEVKIYHYGY
ref|YP_848858.1|        TGEKGRVTTTNQMARVYKNDGTICFRGVIHEQ-----LEGIDKHAVETGFAPVKIYHYGY
ref|YP_001374688.1      SDKYGENLSMNHMQRIYKNNGEFHFSGAIHEQI----VEKGEGR-QELVFSALKLYHYGY
ref|NP_622177.1|        SSINSGLTEINYNYRLFRNNGKLKYIYPVHEN----LRNIEENRPPIAKKADVTILHYGY
RAAC02381               SVARFVRSPGVRVVRVFRRG--FSYMGSIHEQ----ILYDVIAKGGQIEVLDVEIHHLGY
                        :             *::.. *        :**:    ::   .               : : * ** ref|NP_470039.1|        MSEIVEKQDKSDRNLRLLEKEVKNNKNSGFVHFNIGQEMNRLGNKKEALKEFSEAFRL--
ref|ZP_01929325.1|      MSEIVEKQDKSDRNLRLLEKEVKNNKNSGFVHFNIGQEMNRLGNKKEALKEFSEAFRL--
ref|YP_848858.1|        MSEIVEKQGKSDRNLRLLEKEVKNNKNSGFVHFNIGQEMNRLGDKKEALKEFTKAFRL--
ref|YP_001374688.1      LPNVVKKKNKRKRNMDILKKALKSNNNDGFTYFNYGQELRSLGKTKEALESFIKAY----
ref|NP_622177.1|        LADIRKEKNKSERYIKLISKYLESHPEDKFQHANLAVEYFNIGDYQKALKHLLIATKGMD
RAAC02381               LAEFVALKGKSDRNLEILNQALAIDPDNFFHITNLMABEYARLGDPKKVVELGERAYDLFQ
                        :.:.   :.* .* :  ::.: :   . :.  *     *     *  :*. ::.::   * ref|NP_470039.1|        --RDNNHYIWAKLSAYHISELLEQE-KRYDESLAIIEEAKVIWPNVPEFPLKKANILYVN
ref|ZP_01929325.1|      --RDHNHYIWAKLSAYHIAELLEQE-KRYDESLAIIEEARVIWPNVPEFPLKKANILYVN
ref|YP_848858.1|        --RDNNQYIWAKLSAYHISELLEQE-KRYEESLAIIEEAKVIWPNVPEFPLKKANILYLH
ref|YP_001374688.1      QNKEDVYEEWVSRCLYFIVEMLVEL-KRYEEAIVIINDAEEVFSTAPDFPFWKGEIYFKQ
ref|NP_622177.1|        VNSVN----ATRLLRYLIGCYIGLK--DYSTALKIIKDAKDYYKDIPDFSFLEGLMYMDQ
RAAC02381               RGRVNQPHLVLRMYRMMIAAHGDLG--NYDRVEALAREAELFFPNIPDVPFVHALYVMQR
                                      .          *     *.  : ..:*.  :    *:...   ..   .

ref|NP_470039.1|        HQLEDAKEI---YKSLLENTAIDYQPI-VLYEATNFMPHKMLGTIYLEEKDYTRAMTHFS
ref|ZP_01929325.1|      HQLEDAKEI---YQSLLENAAIDYQPI-VLYEATNFMPHKMLGTIYLEEKDYTRAMTHFS
ref|YP_848858.1|        HQLEDAKEI---YHSLLDNKVIDYQPI-VLYEATNFMPHKMLGTIYLEEKDYTRAMTHFS
ref|YP_001374688.1      KRFDDAKEV---YTHIISNNMIYQNAVFN-AGAKTFLPHVRLGEIYTQERQHQQALQHYV
ref|NP_622177.1|        KRYEKAIEA---FKESLSIGEYDGLFI-TMGGTGSYRARYMIGLCKEKLNQLNDAVKEYI
RAAC02381               GDWRKAIRL---FERSREIGEIRSEIIDTIAGAGSYVAAAKLGELWLLEGDVELAREYFV
                         .*  .     :          :     :  :.:   :*    :    *    :

ref|NP_470039.1|        KAYAENSSDYGVMFQMIMLL----------------------------------------
ref|ZP_01929325.1|      KAYAENSSDYGVMFQMIMLL----------------------------------------
ref|YP_848858.1|        KAYAENSSDYGVMFQMIMLL----------------------------------------
ref|YP_001374688.1      EALNEN------------------------------------------------------
ref|NP_622177.1|        EVLKENPNYQEVFIKLFDLFIKNEP-----------------------------------
RAAC02381               QSLRENLRQEGTFFFLASLLPLNDPSVFEQLRALASHDPVCLAYLALAGAVWRVDHAWRL
                        :   **
```

FIG. 44B

```
ref|NP_470039.1|        ------------------------------------------------------------
ref|ZP_01929325.1|      ------------------------------------------------------------
ref|YP_848858.1|        ------------------------------------------------------------
ref|YP_001374688.1|     ------------------------------------------------------------
ref|NP_622177.1|        ------------------------------------------------------------
RAAC02381               INEIEQTPVTAPIVAKLRALGAVLGILPANDVRVDSTVEREIQWYEALFALERGDRDQAE ref|NP_470039.1|        ------------------------------------------------------------
ref|ZP_01929325.1|      ------------------------------------------------------------
ref|YP_848858.1|        ------------------------------------------------------------
ref|YP_001374688.1|     ------------------------------------------------------------
ref|NP_622177.1|        ------------------------------------------------------------
RAAC02381               RCLRDQPERWERLSEWLTSKQGLCISPILDELLLARVDELLLAWLPRAEDRDLALSRVLA ref|NP_470039.1|        ------------------------------------------------------------
ref|ZP_01929325.1|      ------------------------------------------------------------
ref|YP_848858.1|        ------------------------------------------------------------
ref|YP_001374688.1|     ------------------------------------------------------------
ref|NP_622177.1|        ------------------------------------------------------------
RAAC02381               SPLREEVWKAAWLGERGWECDFLALGAFRRRDIQASLNWLERGLTYEPTVRRAIVEIDLA ref|NP_470039.1|        ------------------------------------------------------------
ref|ZP_01929325.1|      ------------------------------------------------------------
ref|YP_848858.1|        ------------------------------------------------------------
ref|YP_001374688.1|     ------------------------------------------------------------
ref|NP_622177.1|        ------------------------------------------------------------
RAAC02381               LCHKNIAHAQEVASQASRLFPESKLLEGIAGSLGVSPRPMRSLDDLLGGGSGLNPHRAYQ ref|NP_470039.1|        ------------------------------------------------------------
ref|ZP_01929325.1|      ------------------------------------------------------------
ref|YP_848858.1|        ------------------------------------------------------------
ref|YP_001374688.1|     ------------------------------------------------------------
ref|NP_622177.1|        ------------------------------------------------------------
RAAC02381               SSVNSMPLKVKIMKLHERAVECVDQVKALVDQGDIMGARTYIQYVQDIITFLRSNLDTST ref|NP_470039.1|        --------------------------------------------------
ref|ZP_01929325.1|      --------------------------------------------------
ref|YP_848858.1|        --------------------------------------------------
ref|YP_001374688.1|     --------------------------------------------------
ref|NP_622177.1|        --------------------------------------------------
RAAC02381               EAGKAADAAYAYFYKMLVEWFLQPSKVESEYKEMRDFWQSWADTWAKVEA
```

FIG. 45

```
ref|NP_831314.1|        ---------------------LKIGITCYPSVGGSGVVGTELGKQLAERGHEIHFITSG
ref|NP_844008.1|        ---------------------LKIGITCYPSVGGSGVVGTELGKQLAERGHEIHFITSG
ref|ZP_01172765.1|      ---------------------LKIGITCYPTVGGSGVVATELGKLLAERGHEIHFISSS
ref|YP_001487207.1|     ---------------------LKVGITCYPSVGGSGIIATELGKRLAEKGHDVHFITSS
ref|ZP_02327412.1|      ---------------------LKIGITCYPSLGGSGVVATELGKLLAEQGHEVHFIAHS
RAAC00991               ---------------------MRVGISCYPTVGGSGAVATELGKALARRGHEVHFIVTD
                                             ::.:**:***:**** :.***** **:.**::***  .

ref|NP_831314.1|        LPFRLNKVYPNIYFHEVTVNQYSVFQYPPYDLALASKMAEVAQRENLDILHVHYAIPHAI
ref|NP_844008.1|        LPFRLNKVYPNIYFHEVTVNQYSVFQYPPYDLALASKMAEVAQRENLDILHVHYAIPHAI
ref|ZP_01172765.1|      LPFRLNRMYHNIFYHQVEVSQYSVFQYPPYDIALASKMAEVINREKLDLMHVHYAVPHAV
ref|YP_001487207.1|     IPFRLNKVYPNIYFHEVDVNQYAVFQYPPYDLALASKLAEVARREKLDIIHAHYAVPHAV
ref|ZP_02327412.1|      MPFRLGRFDKNVFYHEVEVSDYYVFKYPPYDLSLASKLAQVARMQELDLLHVHYAIPHAV
RAAC00991               VPFRLGAFVEHVYIHQIEPITYPVLKTPPYDFALASLMARVADEYQLDVLHAHYALPFAV
                         :****.  .  :::  *::     *  *:: ****::*** :*.*     :**::*.***:*.*:

ref|NP_831314.1|        CAYLAKQMIGERIKIVTTLHGTDITVLGSDPSLNNLIRFGIEQSDVVTAVSHSLINETHE
ref|NP_844008.1|        CAYLAKQMIGERIKIVTTLHGTDITVLGSDPSLNNLIRFGIEQSDVVTAVSHSLINETHE
ref|ZP_01172765.1|      CAILAKQMSGRDVKIATTLHGTDITVLGYEPSLKDSIRFGIEKSDRVTAVSKSLISQTNE
ref|YP_001487207.1|     CAYLAKQMTGHSVKVVTTLHGTDITVLGYDPSLKEVIRFAIESSDRVTAVSHSLAAQTYD
ref|ZP_02327412.1|      CALLAKQMVGDHLKVVTTLHGTDITVLAQDASISNMIRFAINESDAVTAVSEDLIRETRQ
RAAC00991               CAHLAREMAKHPIRVVTTLHGTDITVLAQDPSLKSIIKLGIERSDAVTAVSQSLVRDTAR
                         ::*    :::.***********. .:*:.. *::.*:  ***.*  :* ref|NP_831314.1|        LVKPSKEIQTVYNFIDERVYFKRNMSQLKKEYGISESEKVLIHISNFRKVKRVQDVVQAF
ref|NP_844008.1|        LVKPNKDIQTVYNFIDERVYFKRDMTQLKKEYGISESEKILIHISNFRKVKRVQDVVQAF
ref|ZP_01172765.1|      LIHPEKEIQAVYNFIDHRVYQKTGSDHLKKEYGITEDEKTVIHVSNFRAVKRVQDVVKVF
ref|YP_001487207.1|     LIKPNKKIETIHNFVDERVYLRDDHNVLKRHYGLLDHEKVVIHVSNFRKVKRVHDVIHVF
ref|ZP_02327412.1|      TLDIQKPIHKIYNFVDKRMYYPRPVEDLKREVTRP-GEKLFIHISNFRPVKRVHDVVQIF
RAAC00991               LFETDKPIRCIYNFVDPDVFRPGCGGELKRHFAPN-GERVLLHISNFRPVKRLHDVIAVF
                         .. .*  *. ::**:*   ::      **:.       *:  .:*:**  *::**:    * ref|NP_831314.1|        AKIVKEVDAKLLLVGDGPEFCTILQIVKNLHIEDRVLFLGKQDNVAELLAMSDLMLLLSE
ref|NP_844008.1|        AKIVTEVDAKLLLVGDGPEFCTILQLVKNLHIEDRVLFLGKQDNVAELLAMSDLMLLLSE
ref|ZP_01172765.1|      ARIESEMPAKLLLVGDGPEMSNVCKLVKELGLKEKVLFLGKQDKVEELYSISDLMLLLSE
ref|YP_001487207.1|     KKISEQVNAKLLLIGDGPEKSVVCELVKKLGLTDRVLFLGKQDEKVEELYSISDLKLLLSE
ref|ZP_02327412.1|      ARVHREIPSRLLLVGEGLELSRIVSEVRELGLQDFVFWGKQDDVAQVISLADVMLLPSE
RAAC00991               ERVARRMPAKLLLVGEGPDLGAAKRQVEEAGLGDRVHFLGRQDEVAPLFAAADLFLLPSE
                           ::    .:  ::***:*:*  :       *.:  ::  * * *:*:.*   : : :*:  ** **

ref|NP_831314.1|        KESFGLVLLEAMACGVPCIGTRVGGIPEVIQHGETGYLCEVGDTTGVANQAIQLLKDEEL
ref|NP_844008.1|        KESFGLVLLEAMACGVPCIGTRVGGIPEVIQHGDTGYLCEVGDTTGVADQAIQLLKDEEL
ref|ZP_01172765.1|      KESFGLVALEAMACGVPCIGTNIGGIPEVISDGETGYICKLGDIGSMAEKAAGLLADADK
ref|YP_001487207.1|     KESFGLVLLEAMACGVPCIGTDVGGIPEVITHGETGFLVPLGDIDAAAKHAVSILKDKAL
ref|ZP_02327412.1|      KESFGLVALEAMACGVPTVGSNAGGIPELITHGETGPMAEVGDVDTMSKYTIRLLEDEEL
RAAC00991               SESFGLVALEAMSCGVPVVGSTAGGIPEVVHGETGFLAPVGRVDDMADLACKLLQDEAT
                        .**** :**  :*:  *****::   .*:**::  :*   :.  :  :* * ref|NP_831314.1|        HRNMGERARESVYEQFRSEKIVSQYETIYYDVLRDDK----------
ref|NP_844008.1|        HRNMGERARESVYEQFRSEKIVSQYETIYYDVLRDDK----------
ref|ZP_01172765.1|      HTSFSHRAVQTAREKFSAEQIVSEYERLYFDML--------------
ref|YP_001487207.1|     HEQVSAAAQSSVQAHFSSEKIVSEYEELYLELIEGD-----------
ref|ZP_02327412.1|      LKRVSEACVQRARKKFCNDSLRARYEQVYYEVL--------------
RAAC00991               YRAFSARARERAVRAFHVDEKVSEYEALYREVMAAERGEHAHPRPGA
                        ..  .  .     *  :.  :.** :*  :::
```

FIG. 46

```
ref|YP_001647987.1|        -----------AGAEDGGGKTHIISLLDQFPDGEVE-------LAVFEDGIVAKEARELG
ref|NP_835081.1|           -----------AGAEDGGGKTHIISLLDQFPTGEVE-------LAVFEDGIVAKEARELG
ref|YP_001377114.1|        -----------AGAEDGGGKTHIISLLDQFPTDEVE-------LAVFEDGIVAREAREIG
ref|YP_001127183.1|        ------VLHVISGGETGGSRKHVVTLLSKFAPGTAT-------LVVFQDGPLAAEARQAG
ref|ZP_02038504.1|         ------VIHLISGGDSGGAKTHVHMLLQNLSRTPGVEVT----MVCFMEGPFSQEARELG
RAAC00650                  MASERTVIVFFAGNEVGGAATHLATWAKALKGAQVDYRYR---FVSLGDGPLADELRQMG
                                            :*  :* **. .*:      . :     :. : :* .: * *: * ref|YP_001647987.1|        IKVHVFSQKSRYDLSILKNISEFINKEKFDVVHTHGPRANFFVSLMKKKFAAKWVTTIHS
ref|NP_835081.1|           IKVHVFSQKSRYDLSILKNISEFINKEKFDVVHTHGPRANFYVSLMKKRIKAKWVTTIHS
ref|YP_001377114.1|        IKVHVFSQKSRYDLSILKNISRFINEEQFDIVHTHGPRANFYVSLMKKRIAAKWVTTIHS
ref|YP_001127183.1|        IDVRLLAQSSRYDLSVLSKLVALIRRERFDILHTHGPRANLYGALIKRKIAIPWMTTVHS
ref|ZP_02038504.1|         ISTVVLPGKN--IFRTFHTLKNMIREGGYEIIHCHGARGNMMGALLRKATGLPVVTTVHS
RAAC00650                  MLHGAVAGTVG----AIRDLARVLRRERAWILHSHGPRMNMLASFAASSAGAIWTATIHS
                           :        ..    .            : :   .:..     ::* **.* *:  ::           :*:**

ref|YP_001647987.1|        DPFQDFTKQGLKGWIFTKLNLKALKNIDLFFVVTNRLKKSLAALGISNEKMHVIYNGIEY
ref|NP_835081.1|           DPFQDFTKQGLKGWIFTKLNLKALKNIDLFFVVTNRLKKSLAALGISNEKMHVIYNGIEY
ref|YP_001377114.1|        DPFQDFTKQGLKGWIFTKLNLKALKDIDLFFVVTNRLKKSLEQLGISSEKMRVIYNGIEY
ref|YP_001127183.1|        DPRLDFMKSGWKGKWFTRLNVWALQKVDYFFAVSERFKESLMELGIAAERIQTIYNGIDF
ref|ZP_02038504.1|         DYRLDYMGRPISRITYGTINTLALRLLDYRIGVSDAMTDLLISRGFDPDKLFTIYNGIDF
RAAC00650                  HPRYDFEGHPLKAALFPSLHLWRLSRARGLFVVQPALGDALPCR-TILEVPNAFFPRLPR
                             . *:          .   :  ::    *     :  *   :. * .       .  ::  :

ref|YP_001647987.1|        DQEKADGYN--------KKEMFNIDEDVFTAIQVARLHPVKGHEVLFDALQQTKL--EKI
ref|NP_835081.1|           DKEKAEGYN--------KKEMFNIDEDVFTAIQVARLHPVKGHEVLFDALQQTKL--EKI
ref|YP_001377114.1|        DKEKAQGYD--------KKEKFHIEEDVFTAIQVARLHPVKGHEVLFDALNNTSL--TKI
ref|YP_001127183.1|        DDAPRPHM---------LQRADLGLREDDLVIAMVARLHPIKGHALVFEALASLSD--PDM
ref|ZP_02038504.1|         TPRTPSMTR----SEYLKSVGANWPEDCVVAGIAARLNPVKDIPTLIRGFAQARQSCPKL
RAAC00650                  ASRDVCAAE--------WRRRLGLNPESRLIGIAARLDPVKQIDVAIAALALLSD--LDV
                                                   :       .***.*:*    :  .:        .:

ref|YP_001647987.1|        KVLLVGDGPLERELKALATEKGINDKVEFLGHRQDVKQLFASSHVNLLTSHSEGFPLVLL
ref|NP_835081.1|           KVLLVGDGPLEENLKSLATEKGINDKVEFLGHRQDVKQLFASSHVNLLTSHSEGFPLVLL
ref|YP_001377114.1|        KVLLVGDGPLEEDLKALAKEKGIDDKVQFLGHRQDVKQLFASAHINLLTSHSEGFPLVLL
ref|YP_001127183.1|        KLLVVGDGPLASELREKATQSGIGRQVQFLGFRRDVADIYALSDVALMASYSESFPLALL
ref|ZP_02038504.1|         RLLIAGDGEQMNELKALAADLGVAEDVCFAGWVSDVDSFYGALDINTLTSLSETFPYSLT
RAAC00650                  HLLVAGDGRDRIRLEAAAEDCGVRHRVHFLGHLQDVRDLYCAIDVHVLPSKSEGAPTSML
                           ::*:.***    *.  *  *:     *     ** .::   .:   :.*  **   *  :

ref|YP_001647987.1|        EAANQRVPSIVTRAGEIEPLIADETYGWIVPTGDGKALASAL------------------
ref|NP_835081.1|           EAANQRVPSIVTRAGEIEPLIVDETYGWIVPTGDGKALALAL------------------
ref|YP_001377114.1|        EAANQRVPSIVTRAGEIEPLIVDDTYGWVVPVGDGKALANALEQ----------------
ref|YP_001127183.1|        EAANERLPVISTDVGGVSQLIASSDMGWIVPVGDRAALAQAMREARSRRHELKTMGKRLY
ref|ZP_02038504.1|         EGARAGLPTVASRVGGVPYLIDHGVNGLLFEAGDYETLAKHLTALASDETMRTHMGQRLY
RAAC00650                  EAGYYGAANIGSDVPGIRRMLLDGEAGALVPSGDVQALAHAVRRLLTDTKARDAYVERFQ
                           *..        .:  :.   :  ::      *   :.  **  :**   :

ref|YP_001647987.1|        ------------------------------------------
ref|NP_835081.1|           ------------------------------------------
ref|YP_001377114.1|        ------------------------------------------
ref|YP_001127183.1|        EHASTHFSLQRLYEETM-ATYER-------------------
ref|ZP_02038504.1|         QKGKNDYSLESTLQRQLEIYSVI-------------------
RAAC00650                  RLVLPRYRPERMVVAYERGYTVIEEDAVRSGWRLPANSEQTR
```

FIG. 47

```
ref|YP_001486101.1|      --QFIVSQEDWSLHRKGYDDQQRHQKKVKEAIKNNLPDLVTEESIIMSNGKDVVKIPIRS
ref|ZP_01170532.1|       --QFVISEEDWSLHRKGHDDQQRHQEKVQDAIRNNLPDLITEESIIMSNGREVVKIPIRS
ref|NP_241897.1|         ---FVVSQENWTLHRKGYQDQRRHQEKVKEAIRKNLPDLVSEENIIMSNGREVIKIPIRS
ref|ZP_01721811.1|       ---FVISQENWSLHRKGHQDQQRHMEKVKDAIKNNLPDLVSEESIVMSNGREVIKIPIRS
ref|ZP_02327994.1|       ---FIVSRENWSLHRKGYQDQTRHQQKIKDAIKQNLPDLVTEENIILSNGKQIIKIPIRS
RAAC02421                MVEFTLQREDWSLHRKGHIDQERHREKVREAIREHLADLVSDESLIMSDGKQIIKIPIRS
                            * :..*:*:***:  ** :*::.**:::*.**::*.:::*:*::*:****** ref|YP_001486101.1|      LDEYKIRYNYDKNKHVGQGDGDSEVGDIVARDG--SDSKQGQGKGQSAGDQAGE--DYYE
ref|ZP_01170532.1|       LDEYKIRYNYDKNKHVGQGDGDSQVGDVVARDG--SSGQKGPGKGQGAGDQPGE--DYFE
ref|NP_241897.1|         LDEYKIRYNYDKNKHVGQGDGDSQVGDVIARDP--SAGQQGPGKGQGAGDQPGE--DYFE
ref|ZP_01721811.1|       LDEFKIRYNYDNSKHVGQGDGDSNVGDVVARDG--SKANQTQGKGKEAGDKPGQ--DYYE
ref|ZP_02327994.1|       LDEYRFRFNYNKSKHVGQGDGDSQVGDVLG-----IDPYTQQGKGAGAGDQAGE--DYYE
RAAC02421                LEEYRIRYNFQKGKHVGSGSGDTAVGDLVARGKPDADGQPGPGQGEGAGSEPGV--DYAE
                         *:*:::*:*::::.****.*.: *::.       *:*  **.:.*    ** * ref|YP_001486101.1|      AEVSLMDLEEALFRELELPNLKQKELDDIIVEQIEFNDIRKTGLTGNIHKKRTMLSAFKR
ref|ZP_01170532.1|       AEVSMMELEEALFKQLELPNLKRKEQEEHLVENIEFNDIRKTGLMGNIDKKRTMMTAFKR
ref|NP_241897.1|         AEVSILELEELLFRELELPNLQQKEEDHLVVEHIEFNDIRKKGLMGNIDKRRTILSAIKR
ref|ZP_01721811.1|       AEVSLEEIQNVLFHELELPNLQQKEKAEIVTEKIEFNDIRKKGLMGNVDKKRTILNALKR
ref|ZP_02327994.1|       AEVDMEELQSLLFEELELPYLNPKERLDISTQDIIFNDIRKKGIMSNIDKKRTILENIRR
RAAC02421                AEVTLEDIQQELFRELELPDLAEKDEADMVVDTVEFRDVRKKGITANIDKKRTLLQALRH
                         ***   :  ::. **.:***** *  *:     .:  : *.*:**.*: .*:.*:**:: :::

ref|YP_001486101.1|      NAMTGSPSFYPIYPEDIKYKTWNEVTKPESKAVVLAMMDTSGSMGLWEKYMARSFFFWMT
ref|ZP_01170532.1|       NAMTGKPAFYPIYQEDLKFKTWNEIVKPDSKAVVLAMMDTSGSMGLWEKYMARSFFFWMT
ref|NP_241897.1|         NALEGRPGLIPIYNDDLRFKTWNEVVRPESKAVVLAMMDTSGSMGRWEKYMARSFFFWMT
ref|ZP_01721811.1|       NAMHGKAEITPIHNDDLRFKIWDEVVKPESKAVVLAMMDTSGSMGAFEKYCARSFFFWMT
ref|ZP_02327994.1|       NASSGTPGIHGISPDDLRFKTWDEIEKPHSNALILAMMDTSGSMGSFEKYIARSFFFWMT
RAAC02421                AKKDDR---VVITPDDLRYKTWETIVKPDSNAVILAMMDLSGSMGLFEKYCARTFFFWMT
                         .    *   :*::*  *:   :*.*:*:***  * :* :**** ref|YP_001486101.1|      RFLRTKYETVDIEFIAHHTEAKVVDEEHFFSRGESGGTICSSVYRKALELIDERYPPSRY
ref|ZP_01170532.1|       RFLRTKYETVEIEFIAHHTEAKVVSEEDFFSKGESGGTICSSAYRKALELINEKYNPRRF
ref|NP_241897.1|         RFLRTKYETVDIEFIAHHTEAKVVSEEDFFSKGESGGTICSSAYRKALELINEKYDPARY
ref|ZP_01721811.1|       KFLRSKYETVEIEFIAHHTEAKVVTEEEFFTKGESGGTICSSAYKKALELIKEKYSPSRY
ref|ZP_02327994.1|       RFLRSKYEHVDIVFIAHHTEARIVSEEEFFTKGESGGTICSSAYQAALDVIDRSYPPSKY
RAAC02421                RFLRTKYANVQIRYIAHHTEAHEVDEEYFFTKGESGGTICSSAYQYALDMVNREYPPERY
                         :***:**    *:*  *******:   * **   **:.**********.*: **:::.. * *   ::

ref|YP_001486101.1|      NIYPFHFSDGDNLTSDNARCVKLVSEIMKKANLFCYGEVNQYNRHSTLMSAYKHIQDEKF
ref|ZP_01170532.1|       NIYPFHFSDGDNLTSDNARCVKLVEELIAVSSMFGYGEVNQYNRHSTLMSAYKNIKNEHF
ref|NP_241897.1|         NIYPFHFSDGDNLTSDNARCLKLVHELMESSSMFGYGEVNQYSRHSTLMNAYKNLKDPRF
ref|ZP_01721811.1|       NIYPVHFSDGENISMDNEKCLKLVAELMDVSSMFGYGEVNQHNRFSTLMYTYKKIDDPKF
ref|ZP_02327994.1|       NIYPFHFSDGDNLTSDNERCVKLIQRLMERSNMFGYGEVNQYNRSSTLMQTYRHIQDPKF
RAAC02421                NIYSIHFSDGDNLTSDNEKCVQLVKELSSVSRMFGYAEVNQYSRSSTLMSAYGKLQIPRF
                         *..***:*:: **  :*:*:  .:    :  :* *.****.*.***** :*  ::.  :* ref|YP_001486101.1|      KHYILKQKSDVFLALKKFFQQEE-----
ref|ZP_01170532.1|       RYYILKQKADVFHAMKSFFQNEE-----
ref|NP_241897.1|         RSYVLKEKGDVYRAMKTFFKKEE-----
ref|ZP_01721811.1|       RHHILRKKGDVYDALKSFFKKNE-----
ref|ZP_02327994.1|       LYYIIREKGEVYKALKTFFAKPEG----
RAAC02421                RTYVIRDKSEIYGALRHFFSQQQGVKSA
                         : :::.*.::: *:: ** : :
```

FIG. 48A

```
ref|ZP_01860158.1     ------------------------------------------------------------
ref|YP_001421751.1|   ------------------------------------------------------------
ref|YP_148164.1|      ------------------------------------------------------------
ref|YP_001126336.1|   ------------------------------------------------------------
ref|NP_242401.1|      ------------------------------------------------------------
RAAC02142             MTLRGIGCVVPLRLAHTNADFDSVDSERGGCRMKRHSRALGLGLGALCLVATSAAPQVAR ref|ZP_01860158.1     ----------------PFASAEEKKT-ELAAGAKSAILIERDTGTVLYDKNSHEKLPPAS
ref|YP_001421751.1|   ----------TASAPSAFAKPDGKHTSELAHEAKSAVLIERDTGSILYNKNSRERLAPAS
ref|YP_148164.1|      ----------------------AKVKLADEAKSAILIERDTGKVLYEKNAHEPLPPAS
ref|YP_001126336.1|   -------------------------ELADEAKSAILIERDTGKVLYEKNPHEKLPPAS
ref|NP_242401.1|      ----------------PVGLAAEKQPNLAKEASSAIVIERDTGQVLFEKNSDEKLPPAS
RAAC02142             AASAPGIVQIREAADAGPTQSAPAASVDLAKQARSAVLMDFATGKVLYAKNAHERLPMAS
                                         .**   * **:::   **  :*: **.  * *. **

ref|ZP_01860158.1     MTKIMTMILIMEALDKGQIKWEDEVRTSEYAASMGGSQIFLEPGEVMTVKEMLLGISIGS
ref|YP_001421751.1|   MTKIMTMLLIMEALDKGKIKMSDKVRTSEHAASMGGSQIFLEPGEEMTVKEMLKGIAIAS
ref|YP_148164.1|      MTKIMTMLLVMEAIDEGKLSYDEKVRASEYAASMGGSQIFLEPGEEMTVDELLRGIAIGS
ref|YP_001126336.1|   MTKIMTMLLIMEAIDEGKLSYDEKVRTSEYAASMGGSQIFLEPGEEMTVDELLRAIAIGS
ref|NP_242401.1|      MTKIMTLLLIMEAIDSGKITYDDMVRTSENAASMGGSQVFLEPGEEMSVRDMIKAIAIAS
RAAC02142             ITKIMTLLLIFEAIDSGKLKWTDRVQASERAASMGGSQIFLEPGETMTVRDLVKGIAIAS
                      :*****::*::**:*.*::.   : *:: *****:***  *:*  ::: .*:*.* ref|ZP_01860158.1     ANDASVAMAEHIAGSEEGFVEKMNNKVKDLGLKDTNFKNPTGLPASEHYSSAHDMAMMAK
ref|YP_001421751.1|   GNDASVAMAEYIAGSEEDFVSRMNKKAKELGLKDTSFKNPTGLPEKDHYSSAYDMAKMAK
ref|YP_148164.1|      ANDASVAMAEQIAGSEEAFVEMMNEKAKQLGLKNTHFANATGLPAEHHYSSAYDMAMMAR
ref|YP_001126336.1|   ANDASVAMAERIAGSEEAFVEMMNEKAKELGLKETKFANTTGLPAEGHYSSAYDMAIMAR
ref|NP_242401.1|      GNDASVAMAEHLAGTEEEFVGMMNEKARQLGLKNTNFVNTNGLPEKDHYTSAYDLAMISK
RAAC02142             ANDACVAMAEHLDGSEEAFVARMNQRAKELGMTDTHFANCNGLPAPNHYSSAHDIAVMSR
                      .***.*****  :  *:** **    **::.::**:.:*  *  * .***   **:**:*:*  :::

ref|ZP_01860158.1     ELLKYQEITKYTGTYESYLREDTDKKFWLVNTNKLVRFYPGVDGLKTGFTNEAKYCLTAT
ref|YP_001421751.1|   ELLKYDKITQFTGTYEDYLRENTDKKFWLVNTNRLIKFYPGVDGVKTGFTGEAKYCLTAT
ref|YP_148164.1|      ELLKYEDITKYTSKYEDYLRENTDKKFWLVNTNRLVKFYPGVDGLKTGYTAEAKYCLTAT
ref|YP_001126336.1|   ELLKYEGITKYTSKYEDYLRENTDKKFWLVNTNRLVKFYPGVDGLKTGFTSEAGYCLTAT
ref|NP_242401.1|      ELLKYEDITEFTSVYEDYLRKGTDKEFWLVNTNRLVKFYPGVDGLKTGFTKEAKYCLTAT
RAAC02142             ALLMHPEITAFTSVYSDYLRKDTDHPLWLVNTNKLVRFYDGVDGLKTGYTQEAKYCLSAT
                       **  :  ** :*. *..***:.**: :******:*::** ****:***:* ** ***:**

ref|ZP_01860158.1     AKKDNMRVIAVVFGEPTPKDRNAEISKMFDYAFSQYQTQPLFEKGASVGKAEISKGKAKE
ref|YP_001421751.1|   AKKGNMRVIAVVFGASTPKERNAQVTKMLDYAFSQFKTHPLYKRDQIVGTVKVKKGKQKL
ref|YP_148164.1|      AKKNGMRVIAVVFGAPTPKSRNAQITKMLDYAFSQYRTHPVYKRNETVARVNISKGKRSS
ref|YP_001126336.1|   AKKNGMRVIAVVFGAPTPKSRNAQITKMLDYAFHHYQAHPVYKRNETVARVDVSKGKQKS
ref|NP_242401.1|      AVKNGMRVITVVMGAPTPKERNSQITEMLDFAFSQYQTHQVYERDTYMMDLNVRKGNKKS
RAAC02142             AKRDGFRVIAVVMGEPKPTVRNAEIAAMLNYAFAHYKSVQVYPRGHVVGQVAVKRGTRDR
                      * :..:***:**:*  ..*.   **::::   *:::**  ::::   ::  :.    :  :*. .

ref|ZP_01860158.1     VEAMTNEPISLLAKKGEKLDGIEKKVKLQK--LKAPVKKGDTIGKLVVEKDGKTLSETPL
ref|YP_001421751.1|   IKLTTSEPISLLAKKGENMDKVKKEVKING-NVTAPVKKGEVLGSLVLKKDGKVLVESPV
ref|YP_148164.1|      VEAVTSEPVSVLTKKGQSVEQIEKVIKVKD-NVKAPVRKGDELGVLILKQDGKEILHSPI
ref|YP_001126336.1|   VAAVTSEPVSVLTKKGQSVEQIEKVVKVKD-GVKAPVRKGDELGVLILKQDGKEILRSPL
ref|NP_242401.1|      VPIFTSESVSLVTKKGESIDNVTERVEWKE-SLLAPVHKGDVVGTLYLERDGEILSETPL
RAAC02142             VEAVTAEPVAFVTERS-SKTAYTTEIQWMT--LKAPVSRGQVVGHVLVKSGGQIVANVPV
                       :   * *.::::::.. .        ::     :  :  : *** :*: :*   : :: .*:   . *:
```

FIG. 48B

```
ref|ZP_01860158.1|      IAKEDVPQASFWQ----------------
ref|YP_001421751.1|     TAKDDMEKAGFLTFLKRTM----------
ref|YP_148164.1|        VAKQTVEEASFWDLFKRVFGRFVQAG---
ref|YP_001126336.1|     VAKQTVAEASFWDLFKRVFGRFVQAG---
ref|NP_242401.1|        IAGEDVASASFWQMFKRIVGK--------
RAAC02142               VAKDDVPKATFFQSLGKTVKKVITFGQAQ
                         *  :  :  .*  *
```

FIG. 49A

```
emb|CAA04971.1|       ------------------------VQLLRPLPDPVLTLRDSASSTTLGGDRISIPWPKEG
gb|AAC32488.1|        ------------------------VQLLRPLPDPVLTLRDSASSTTLGGDRISIPWPKEG
ref|NP_824958.1|      ------------------------VAQAVRPLPTPTLGLTADETYTFEGG-KLDLPWPGQG
ref|NP_628606.1|      ------------------------VVQSMRPLPAPTLDLTAQDSFSFDGG-KPQIPWPESG
ref|ZP_02061285.1|    --------------------------------------------------ISWPTDI
RAAC03015             MVVRSLRGFVIAIVIAIIVIGVPVLQLVRPIPQAASDVAAPLPRAIPGE-KPVIHWPSQG
                                                                          : **  .

emb|CAA04971.1        QGAVTVAGSGVYETFGP-EKSVPTASTAKIMTAYVLLRKHPLKRGEPGPTITV---DAQT
gb|AAC32488.1|        QGAVTVAGSGVYETFGP-EKSVPTASTAKIMTAYVLLRKHPLKRGEPGPTITV---DAQT
ref|NP_824958.1       QSAVEVEGVGTVGTAGK-QAPKPIASVAKIMTAYVILEEHPLKGTAAGDKITV---DQQA
ref|NP_628606.1       QAALDVQGIGSFGSSGD-QKPVPIASVAKVMTAYLVLRDHPLKSGAEGPKIKI---DQAA
ref|ZP_02061285.1     RYGVIGTLQSGIISKNPNQGQWPLASVAKIMTAYIILKDHPLPIGQDGPTITVTQKEVNE
RAAC03015             EAALMADGVGSFGSSGP-QVPVPIASVTKVMTAYLVLQKHPLQLGQQGPSITITPDDVKV
                      . .:    .       :  . :      * **.:*:****::*..***     *  .*.:     :

emb|CAA04971.1|       VAEGKAKDESRIEGLTEGQTFSQQDMLKMLMIPSGNNIGRLLARWSTKTDDQTAFVREMN
gb|AAC32488.1|        VAEGKAKDESRIEGLTEGQTFSQQDMLKMLMIPSGNNIGRLLARWSTKTDDQTAFVREMN
ref|NP_824958.1|      EDESKNEDES-TAAMTKGQKFTERQMLQMLMIPSGNNAARLLARW---DSDSETFVGKMN
ref|NP_628606.1|      EDQSQAGQES-TVDVFAGDSISQREALQAILIASANNVARLLARWD--AGSEKAFVEKMN
ref|ZP_02061285.1|    YEAFKKDGQS-VVKVALGEKLTERQLLEGLMIPSANNFAYILARWD--AGSVKAFVDKMN
RAAC03015             YERDKALGQS-VVKVAAGEQITEYQALEGLLLPSGNNMGTLLAKWC--DGSVQAFVQEMN
                      :       :*     :    *:  ::: :   *:  :::.*.**   .:**:*       ..  :** :**

emb|CAA04971.1|       EAAKDLGMKNTVYTDPSGLDKGTVSTAVDQLKLAEAVMEYDVFRDVVALPNAEIPG-HGR
gb|AAC32488.1|        EAAKDLGMKNTVYTDPSGLDKGTVSTAVDQLKLAEAVMEYDVFRDVVALPNAEIPG-HGR
ref|NP_824958.1|      AAAKKLGMTNSTYTDPSGLEKTTVSTATDQLKLAKAVMQKEVFRSIVGMAKADIPGLKGT
ref|NP_628606.1|      GAAKDLGMTNTTYTDPSGLNNTTVSTAVDQVKLAKAAMKEPAFREVAAMMSYNDYK--GE
ref|ZP_02061285.1     KTAQSLGLKDTRYEDPSGASAGTVSTPKDQFKLTQLAMQIPTFRHMVAMPQVNLPI-AGI
RAAC03015             ATAKRLGMTETHYADPTGYSPASQSDAVDQMKLFALAMQNPVFRQIVGEAQAELPV-AGL
                      :*: **:.::  * **:*  .   : *  . .    .*:  .** :..   .:        * emb|CAA04971.1|       IYNNNDRLILAGLG-IVGIKTGSNTPAGGTLSWAAYKTFDGEDRLILGTMMAQHAPGPDI
gb|AAC32488.1|        IYNNNDRLILAGLG-IVGIKTGSNTPAGGTLSWAAYKTFDGEDRLILGTMMAQHAPGPDI
ref|NP_824958.1|      IYNNND-LLVKQVG-VIGLKTGSSTPAGGNLVWAATKTVNGKVRTIYGAVLNQDAGTG--
ref|NP_628606.1|      NHGNWN-QLVGHNG-VVGIKTGTTTSALGNLVFAAKKEVGGETRTIVGAVVRQPDVGG--
ref|ZP_02061285.1|    QYNVNY---DLGKDNIVGKTGSSLPAGANFVFDSKQ--GNIDIL--GVIFGASGKSS--
RAAC03015             VYNVDS---VVGHGTIIGGKTGSTLEAGGCFVFAARKVIGNREVLIIGAVLGQKGPQP--
                      :.           . ::* ***:.  *   :..*  .      *.:.

emb CAA04971.1|       NGGDSLVLVQDNSRKVVASVREMLTSANVVKKGEVVGHVDDRFGR-RIPVVTTKSLDLVG
gb AAC32488.1|        NGGDSLVLVQDNSRKVVASVREMLTSANVVKKGEVVGHVDDRFGR-RIPVVTTKSLDLVG
ref NP_824958.1       RVWDSLQLALTNSQKLIDKVQQGLISAPVVKKGQVVGYVDDQLGG-RTPVVATENMTAVG
ref|NP_628606.1|      ---GILDAALDASDELIRAAQDTLKSSTIIKKGSVVGYVDDGLGG-RTPVVASQDVKAVG
ref|ZP_02061285.1|    -----LMTALKDAIILIDTTKTQISTEKLISKNQQIGFIKVSWMKKEIPMLASQDFSTVV
RAAC03015             -----LAEALTAAVAMSQDAQKALRSVQLVSAGQTVGTLSAPWAK-PVSLVATEPVQVIG
                           *          .  :    :    .:  : :  ::.. ...  :* :.      .:::::. . :

emb CAA04971.1|       LSGQKVTLTYGRKGDGALSRTARAGAVVGELTVGNGPDAHRIPLALKEGLTEPSLGTRLT
gb|AAC32488.1|        LSGQKVTLTYGRKGDGALSRTARAGAVVGELTVGNGPDAHRIPLALKEGLTEPSLGTRLT
ref|NP_824958.1       WPGLKTKISIG-AGDTTVPHEAKAGKVVGELTVGDGS---------------------
ref|NP_628606.1       WGGLTVKLTFTAD-----------------------------------------------
ref|ZP_02061285.1|    YPGMKI--TYSLYPIKDMKFPIKSNEVIGTLVINYG-----------------------
RAAC03015             WGGLPVQQTYRAD-VLDPKKPIAADQVVGQLQIQVGAQTVRVPVAAASSVPAPTLSWRMK
                      *                  :
```

FIG. 49B

```
emb|CAA04971.1|      RL
gb|AAC32488.1|       RL
ref|NP_824958.1|     --
ref|NP_628606.1|     --
ref|ZP_02061285.1|   --
RAAC03015            RL
```

FIG. 50A

```
ref|YP_001663198.1|    ------------------------------------------------------------
ref|YP_001665129.1|    ------------------------------------------------------------
ref|YP_430213.1|       ------------------------------------------------------------
ref|YP_001212426.1|    ------------------------------------------------------------
ref|YP_360920.1|       ------------------------------------------------------------
RAAC02227              MHVYESRFWRWLGRMTSRLIRLGCAALAAAASLAVYQPAVRAERSTSPPVATESLIPRED ref|YP_001663198.1|    ----------------AESYPSISAKAAIVMDQETGRVLYEKNPHEKLPMASTTKIMTLL
ref|YP_001665129.1|    ----------------AESYPSISAKAAIVMDQETGRVLYEKNPHEKLPMASTTKIMTLL
ref|YP_430213.1|       ------------------PDIQAESYVLMDFRTGQVLMAKNPHERRPQAITTKITTAI
ref|YP_001212426.1|    ------------------ASSGPEIVGEAAVVIDIKNGQVLFEKNPDRRVYPASTTKIMTAV
ref|YP_360920.1|       ------------------PQIIGRAAAVINVNSGKFVYLKNADQKMYPASTTKIMTTL
RAAC02227              VLNVQSGPIPYVVGEDASSWPSIVSQAAVVMDMDTGAVVYAKHSTAPHYPASITKIMTAL
                                       *.*  ..:  :::   .* .: *:.      *  ***  * :

ref|YP_001663198.1|    VALEKGNLNDIVTVSKRAASVGGSSIWLSPGEKIDMESLLYGLMLNSGNDAATAIAEHIG
ref|YP_001665129.1|    VALEKGNLNDIVTVSKRAASVGGSSIWLSPGEKIDMESLLYGLMLNSGNDAATAIAEHIG
ref|YP_430213.1|       LALERGNLNDQVIASKNAAETPESSIYLQEGETLTLEELLYALLLRSANDAAVAIAEHIG
ref|YP_001212426.1|    IALENGRLDAAVAVPGEACNIEGSSIGLQEGEKISLEDLLYALMLNSGNDTAVAIACHVG
ref|YP_360920.1|       IALEKGNLSDRVYIDKEACYVEGSAIWLNPGEQLSLEDLLYSIMLNSANDSAIAVAKYIG
RAAC02227              LALRLGHLTDVLTASTDAVRQPPDKLYMRAGEKATLKDLLYGLLIDSANDAAVEIAERYG
                       :**. *.*    :     *      . :      ::.*.::: *.**:*  :*  * ref|YP_001663198.1|    GSVENFIEIMNQKAREIGAYNTHFVTPSGLDIGIDDHYTTAYDLALITRYAFRYPKFAEI
ref|YP_001665129.1|    GSVENFIEIMNQKAREIGAYNTHFVTPSGLDIGIDDHYTTAYDLALITRYAFRYPKFAEI
ref|YP_430213.1|       GSVENFARMMMNAKVQEIGARDTHYVNPHGLTA--PDHYSSAYDLALIGRYAMMNPKFREI
ref|YP_001212426.1|    GSVEAFVSMMNKKAAELGAVNTHFNNPNGLPD--PGHYSTAYDMALISRYAMQNPEFRKI
ref|YP_360920.1|       GDVATFVQEMNDKARELGAKNTHFVNPNGLPN--DDHYTTARDLALIARAAMQNPKFREI
RAAC02227              GSVAHFADMMNAEARALGATHTHFVNPSGLPD--PRHVTTAYDMAVIARAAMQIPEFRTI
                       *.*   *      :.  : .**:.* **       * ::* *:*;* * *:  *:* * ref|YP_001663198.1|    VSTKEKTIPWEGKEWDRYLRNKNKLLW---IYEGADGVKTGFTNKAGRCLVSSATRDGRR
ref|YP_001665129.1|    VSTKEKTIPWEGREWDRYLRNKNKLLW---IYEGADGVKTGFTNKAGRCLVSSASREGRR
ref|YP_430213.1|       VATRQRIIPWAGKPWPRLLINENRLLWGYYAYPGADGVKNGYTTPAGQVLVASATRDNWR
ref|YP_001212426.1|    VSTRVKTIRRSVPDAQVYLENHNRLLW---LYEGATGVKTGYTVEAGQCLVSSAARQGRE
ref|YP_360920.1|       AATKTKVINR-DPKYLRFLQNHNKLLW---RYEGANGIKTGYTVKARQCLVASAARDGEE
RAAC02227              VDTRS--FDWKGTAWQATLTNLNRMLF---TYPGAIGVKTGFTSVAHETLVVAATRGGTT
                       . *:   :       *  *::*:      *  *** *:*.*:*  *  .  ** :*:* .

ref|YP_001663198.1|    FIAVVLNSP---PMWEDSMKILDYAFSKYKPYKVLEKG----------------------
ref|YP_001665129.1|    FIAVVLNSP---PMWEDSMKILDYAFSKYKPYKVLEKG----------------------
ref|YP_430213.1|       LIAVVMKSP---NMYRETSAILDYGFNNFHQVKLMPAGGQVALAGVRGGIAANIPAVTAD
ref|YP_001212426.1|    LLAVVMK-SEGSNIWSDSTSLMDYCFKEFRPVCLVEAGAFVADVPVKFGEPAAVAVQTGS
ref|YP_360920.1|       FIAVVLG-SEGRNVYDDATKLLDYAFNNFKTVKLVSKGQEFGKVEVAGGK----------
RAAC02227              FLAVLMDCPTDAEIRQDATNLLNYAFLHDETQRILPAGYRAGFVLARDGED---PVVTSE
                       ::***::   .     :  :: :::*  *  . .    ::  * ref|YP_001663198.1|    ------------------------------------------------------------
ref|YP_001665129.1|    ------------------------------------------------------------
ref|YP_430213.1|       DVLVVEPKNETWTWQQRVELNPDLNAPV---KKGDRIGR--IIFTSHDQEV-SVDLIAAG
ref|YP_001212426.1|    SFTYNFPADKPLEIKKEVLLEKEFCAPV-RA--GEKLGEMAFYDGE--RELGRVDLV---
ref|YP_360920.1|       ------------------------EPV------KLIAAEDLYDTV--------------
RAAC02227              PVLATVPIGHPLDVIERVR----VSAPLDRAPKGAAAGELDLVDAATGRKLGSVPLVLAA
```

FIG. 50B

```
ref|YP_001663198.1|      ------------------------------------------------------------
ref|YP_001665129.1|      ------------------------------------------------------------
ref|YP_430213.1|         DVAPRP------------------------------------------------------
ref|YP_001212426.1|      ------------------------------------------------------------
ref|YP_360920.1|         ------------------------------------------------------------
RAAC02227                PFEPVPKPIPWPRLAAPAAAVILMAALVLGWRRRRRSRMAPRARVVRVQPWQESWQSARR ref|YP_001663198.1|      ---
ref|YP_001665129.1|      ---
ref|YP_430213.1|         ---
ref|YP_001212426.1|      ---
ref|YP_360920.1|         ---
RAAC02227                GRR
```

FIG. 51

```
ref|NP_622598.1         ------------------------RTDLALEAREL---YKEREIPGVSIREEGEEGIKI
ref|YP_001665389.1|     ------------------------SIRTDLAVEAREL---YKGREIPGVRVDEKHLEGIKV
ref|YP_001320854.1|     ------------------------RTDLALEVRELYQEEKQQEIPGVKVDQEEDTDVLV
ref|YP_001512768.1|     ------------------------PNTDLAIEARELYSEKTSGEIPGVTMDNEEIEDVLI
ref|YP_001037463.1|     ------------------------------------------------------------
RAAC00872               MVISWNAARRVRLKPCHLPISRSSPRTDLAVEARELA--LREGHIRGVEEEREEHEGVVI ref|NP_622598.1         TRVKILDERGEKAMGKPVGDYITIEAPGLLERDLDLEERVAKVLANIISELAQLKKDSHV
ref|YP_001665389.1|     TKVKILNEEGEKAMGKPVGDYITIEAPGLIERDLDLEEEVAKVLADIIKEIANLTENTQV
ref|YP_001320854.1|     TRVDVMDQQGAEIMGKKQGMYITLESPGLRKADADLKDHISQVLAKELKALLPERKNLKA
ref|YP_001512768.1|     TRVEVFNETGVSIIGKPIGKYITLESNSLRKADADFKDEMSKLLAKELRRIIPQKDDIKV
ref|YP_001037463.1|     TRVRVTSPTGEAAIGKPMGNYITLEVPRLKENDQELYEETCKALAKELTRVLNLKDDSTI
RAAC00872               TRVRVSTQVAARRLGKRKGTYVTIEAPGMRRRDFDLEDRLTRILADELKRLLPER-AETA
                        *:*  :          .  :** * *:*;*     :  . * ::  :. : **. :  :

ref|NP_622598.1         LVVGLGNWNVTPDALGPRVVSNIVVTRHLKEYAPLQFGDE-----IRSVSAFSPGVLGIT
ref|YP_001665389.1|     LVVGLGNWNVTPDALGPRVVSNIVVTRHLKEYAPQQFGDE-----IRSVSAISPGVLGIT
ref|YP_001320854.1|     LVVGLGNWNVTPDALGPKAVAKIHVTRHLFK-MYQKESDDH----MIEVSAISPGVMGTT
ref|YP_001512768.1|     LVVGLGNWNVTPDALGPKVVSKIFVTRHLFQ-MYNKEGDVD----LSEVSAISPGVMGTT
ref|YP_001037463.1|     LVIGLGNWNVTPDALGPKVVSRLMVTRHLLE--YVPDQVD--E-GVRPVCAVSPGVLGIT
RAAC00872               LVIGLGNEHVTADALGPMVVNRLFVTRHLFSYMPEVLGDGE---GYRSIAALAPGVLGLT
                        :  ..*****  . *  .: *****  .              :.*.:***:* * ref|NP_622598.1         GIETAEILKGVVDRVKPDLVITIDALASRRLERLSTTIQISNTGISPGSGVGNRRLSITS
ref|YP_001665389.1|     GIETAEILKGVVDRIKPDLIITIDALASRRLERLSTTIQISNTGISPGGGIGNRRLSITE
ref|YP_001320854.1|     GLETGEIIKGIVEHSRPDVVVVVDALASRKMERVNATIQISTTGISPGSGVGNKRMALDE
ref|YP_001512768.1|     GLETGEVIKGIVDNSKPDLVIVVDALASRKMERVNATIQISTTGITPGSGVGNKRKALNR
ref|YP_001037463.1|     GIETGEIVRGIVDRVKPDVVIAIDALASRKMERVNTTIQIADTGISPGSGVGNKRMELSR
RAAC00872               GIETSEVVLGVVERIKPDVVLAVDALAARSLERLHRTIQLSDVGIQPGAGVGNHRKAIDK
                        *:**.*:: *:*:. :**::::.:****:*  :**:   ***:: .**  **:*:**:*   :

ref|NP_622598.1         ESLGVPVIAIGVPTVVDAVTIAHDTIEYLVKELSEQTSKESVFYKVLENMNKQEKYSLIE
ref|YP_001665389.1|     QSLGIPVIAIGVPTVVDAVTIANDTIEYLTEELLKHTKEESPFYEVLKNMSQQEKYSLIQ
ref|YP_001320854.1|     ESLGVPVIAVGVPTVVDAATLTNDTIQLVIKAFSKQAQAGSEFYSMLEKLKEEEKYGLIR
ref|YP_001512768.1|     ETLGVPVIAIGVPTVVDAATLTNDTIDKVIDAFSRQAKVGSQFYNMLRELKEEEKYSLIT
ref|YP_001037463.1|     ETLGVPVIAIGVPTVVDAATMANDTIDLVIDNLIREAKEDSHFYNMLKNIDRNEKYQLIQ
RAAC00872               ETLGVPVIAIGVPTVVDAATIASDAIELVFRELGRQVP-GNAANRLLDQLTGQEKWQLVR
                         :**:****:********.*::  *:*:  :     :  .    . :*  ::  :**: *:

ref|NP_622598.1         EVLSPYVQNLVVTPKEIDLLIKNIALVISRGINLALQPGLTEKEMNQLLH
ref|YP_001665389.1|     EVLTPYVHNLVVTPKEIDLLVRNIASIISRGINLALQPGLTEREMNQLLH
ref|YP_001320854.1|     EVLEPYNANVMVTPKEIDDIILDLSQIIANGINIALHPGIDLKDVNRYIH
ref|YP_001512768.1|     EVLEPYSANIIVTPKEVDEVIVNLSQIIANGINIAVHPGIDLKDVN----
ref|YP_001037463.1|     EVLQPYVGNLVVTPKEIDDVVDRIAKVIANGLNIALHQGITLNDVN----
RAAC00872               EVLEPIEQNLVVAPKEVDEFMENVAYLIAKSMNVALHPAMTLEDADLVTH
                        *** *   *::*:***:*  .:   :: :*:...:*:*::   .:  :
```

FIG. 52

```
ref|ZP_02172045.1|         ---------MKKVTVSGKTVEEAVQNGLDRLEVTAEQVDYTVLEEPEKGFLGFLGNKPAL
ref|NP_244931.1|           ---------MTKRRVSGKTVEEAVEQAIIELGTTRERITYTVVEEPKSGLFGILGSKPAV
RAAC00045                  MRRVGGLGEMRKVVATGKTIEEAVMSALVRLGVPRSQAQVRVIREPARGFLGWLSGREAE
ref|YP_001213468.1|        ---------MKAIEKSGKTVEEAVELALKDLGVTRKDVEVEVIEEPSKGIFGILGVKPAR
ref|YP_358877.1|           ---------MREIEVTGKTVEEAVSLGLEQLGVDRSLVEIEILEQPSKGILGLFGQKPAK
ref|ZP_01189194.1|         ----------------GKTVEDAVEQALQKLNITRDEAEIKVIDEGSKGIFGLIGGKNAV
                                           ***:*:**  .:  *    .     ::  :  *::*  :. : * ref|ZP_02172045.1|         VEVRLKPDPLKEALVFLRDTIDKMGITASVEAEER----KEG-MYLTISGAE--IGVLIG
ref|NP_244931.1|           IEVVVKPDPVDRAKAFLEELLQEMDMEVEVTIEKD-----PATVLFNISGEQD-LGTLIG
RAAC00045                  VEVTVIETPLDAAKEFLRTAISKMGLGQAVIVADDVD--EEGHVKLSISADEDALPILIG
ref|YP_001213468.1|        VRVLLREGPLQKAEKFLKSVFEAMNIQVEMSLQEN-----EREVVINLRGPE--MGVLIG
ref|YP_358877.1|           VKLTIKSKVMEKARKFLDDVISAMGVNVGYEVLERDD-----HLLINLYGSD--VGILIG
ref|ZP_01189194.1|         VEVKPKVNPASIALDFLEDVLEKIPVATRVEVIEEKT--DYDQVYLNISGDN--LGIIIG
                           :.:    .  *  **    :. : :       .           :  :. .:  :  :**

ref|ZP_02172045.1|         KRGQTLDSLQYLVNLVANRQSDNYMKFYLDAEGYRDRRREALETLAKRLSEKAVRTGREV
ref|NP_244931.1|           KRGQTLDSLQYLVNLVANKEEGEFIRIKLDAENYRARRKEALVQLAERLASKALRTKRPV
RAAC00045                  RRGATLDALQYLVNIVANRDASEKMRFTLDAAGYRDRRLESLRRLADEAADKAVRLGRPV
ref|YP_001213468.1|        RRGETMEALQYLVNLSANKNQEVRKKIIDIEGYRSRREETLQKLALKLADKAKQRGRNV
ref|YP_358877.1|           YRGETLDALQYITNLAANKNEITPRRIILDAQGYRERREKTLIRLAEKVAEKVRQKGRPF
ref|ZP_01189194.1|         YRGETLDALQYLTSLVVNRELKKYTRVLLDAEGYRERRKKTLERLANKLARKAIRVGRKV
                            **  *:::***:..: .*::      :. :*  .** ** ::*  **  . : *. :  * .

ref|ZP_02172045.1|         KLEPMNAHERKIIHTALQHIHTVSTYSEGREPHRRIVVVP-------
ref|NP_244931.1|           SLEPMSAHERKIIHTALQELGDVETYSEGQGIGRHVVIAPKR-----
RAAC00045                  ALDPMPRKDRKWVHAHLQSRGDVVTVSEGQEPYRRVKIIPKRHDWIE
ref|YP_001213468.1|        VLEPMNSQERRIIHTALQGRDDIYTFSEGEEPYRKIVISPKK-----
ref|YP_358877.1|           ALEPMTPQERRIIHTALQNFEGVYTYSEGEDPNRKVIIAPKR-----
ref|ZP_01189194.1|         VLEPMPPHERRIIHMTLKDSEQVYTYSEGQEPYRRVLIAPR------
                           *:**  ::*: :*  *:      : * ***.   *:: :  *
```

FIG. 53A

```
dbj|BAB83769.1|            ----EFKLPDIGEGIHEGEIVKWFVKPGDEVNEDDVLCEVQNDKAVVEIPSPVKGKVLEI
ref|YP_146913.1|           ----EFKLPDIGEGIHEGEIVKWFVKPGDEVNEDDVLCEVQNDKAVVEIPSPVKGKVLEI
sp|P11961|ODP2_BACST       ----EFKLPDIGEGIHEGEIVKWFVKPGDEVNEDDVLCEVQNDKAVVEIPSPVKGKVLEI
ref|YP_001125047.1|        ----EFKLPDIGEGIHEGEIVKWFVKPGDEVNEDDVLCEVQNDKAVVEIPSPVKGKVLEI
ref|ZP_01696305.1|         ----EFRLPDIGEGIHEGEIVKWFIKPGDKVSEDDVLCEVQNDKSVVEIPSPVEGTVEDI
RAAC02428                  MAVVEFRLPELGEGLHEGRISKWLVQPGDTVQEDDPIABVENDKSLVELPSPVSGKVKEI
                               ::*:*.* ::*  *.*  :.:*:::****.*.*  :* dbj|BAB83769.1|            LVPEGTVATVGQTLITLDAPGYENMTF---------KGQEHEE-VKKEEKAETVS----K
ref|YP_146913.1|           LVPEGTVATVGQTLITLDAPGYENMTF---------KGQEHEE-VKKEEKAETVS----K
sp|P11961|ODP2_BACST       LVPEGTVATVGQTLITLDAPGYENMTF---------KGQEQEE-AKKEEKTETVS----K
ref|YP_001125047.1|        LVPEGTVATVGQTLITLDAPGYENMTF---------KGQEHEEEAKKEEKTETVS----K
ref|ZP_01696305.1|         LVEEGSVAVVGDVLVKFDAPGYENLKFKG------DHGQDQKEEAAESAKPEPAKPEPAK
RAAC02428                  KVPEGTTCVVGDVLLTFEVEGDAPAEA----------GADEKPTDKSAQKAEADAHQNAK
                            * :...:.*:.::. *              * :.:    . *.*.        * dbj|BAB83769.1|            KEMVETAAPSAPAAE------AEADPNRRVIAMPSVRKYAREKGVDIRLVQGTGKNGRIL
ref|YP_146913.1|           KEMVEIAAPSAPAAE------AEADPNRRVIAMPSVRKYAREKGVDIRLVQGTGKNGRIL
sp|P11961|ODP2_BACST       EEKVDAVAPNAPAAE------AEAGPNRRVIAMPSVRKYAREKGVDIRLVQGTGKNGRVL
ref|YP_001125047.1|        EESVGATAPAAAAEAA-----AEADPNRRVIAMPSVRKYAREKGVDIRLVQGTGKNGRIL
ref|ZP_01696305.1|         QETAETAKPAEKEAEH-----GSESADRRVIAMPSVRKYAREKGVDIQLVSGTGKNGRVL
RAAC02428                  ADEAPAAKPAPDAAKAD----TQESAAHEVLATPAVRKYAREQGVDIRTVKGTGNHGKVT
                            :  .  *              . .. :.*:* *:******:****: *.***::*::

dbj|BAB83769.1|            KEDIDAFLAGGAKAAAEPTPQAAEEKAAPQAPAAKPVVPEGEFPETRE-KMSGIRRAIAK
ref|YP_146913.1|           KEDIDAFLAGGAKAAAEPTPQAAEEKAAPQAPAAKPVVPEGEFPETRE-KMSGIRRAIAK
sp|P11961|ODP2_BACST       KEDIDAFLAGGAK----PAPAAAEEKAAP--AAAKPATTEGEFPETRE-KMSGIRRAIAK
ref|YP_001125047.1|        KEDIDAFLAGGAKAAAQPAPAAEAEEKAAPQAAATPVVPEGEFPETRE-KMSGIRRAIAK
ref|ZP_01696305.1|         REDIDAYVNGPQQP------EAETGKTEAQAPASQNAIPEGEFPETRE-PMSGIRKVIAK
RAAC02428                  KEDIDRAKSGTQAP-----QQAAEDKEQRPAQAQQAPAAYGEEYEERV-PMPMIRQAIAR
                           :****   *        *   *  :    *    *  .  ** * *  *. **:.**:

dbj|BAB83769.1|            AMVHSKHTAPHVTLMDEADVTKLVAHRKKFKAIAAEKGIKLTFLPYVVKALVSALREYPV
ref|YP_146913.1|           AMVHSKHTAPHVTLMDEADVTKLVAHRKKFKAIAAEKGIKLTFLPYVVKALVSALREYPV
sp|P11961|ODP2_BACST       AMVHSKHTAPHVTLMDEADVTKLVAHRKKFKAIAAEKGIKLTFLPYVVKALVSALREYPV
ref|YP_001125047.1|        AMVNSKHTAPHVTLMDEVDVTKLVAHRKKFKAIAAEKGIKLTFLPYVVKALVSALREYPT
ref|ZP_01696305.1|         AMVNSKQTAPHVTLMDDVDVTALVAHRKKFKEIAAEKGIKLTFLPYVVKALVSTLREYPV
RAAC02428                  AMVKSKYTAPHVTLMDEVDVTELVKLRNEVKPLAQERGIKITYLPFIVKALIAALRTKPQ
                           *:  ******* :* **  *:::*  *::***:*::::::   * dbj|BAB83769.1|            LNTSIDDATEEIIHKHYYNIGIAADTDRGLLVPVIKHADRKPIFALAKEINELAEKAREG
ref|YP_146913.1|           LNTSIDDATEEIIHKHYYNIGIAADTDRGLLVPVIKHADRKPIFALAKEINELAEKAREG
sp|P11961|ODP2_BACST       LNTSIDDETEEIIQKHYYNIGIAADTDRGLLVPVIKHADRKPIFALAQEINELAEKARDG
ref|YP_001125047.1|        LNTSIDDQTEEIIHKHYYNIGIAADTDRGLLVPVIKHADRKPIFALAQEINELAVKARDG
ref|ZP_01696305.1|         LNSSIDDETNEIIHKHYYNIGIAADTERGLLVPVVKHADRKPVFAVSKEINELAEKARDG
RAAC02428                  LNASYDEEKQELVIKHYYHIGIATDTERGLLVPVVRHADRKNIWTIAQEINDLATRGRAG
                           **:*  *:  .:*:: ****:****:.****** :****  :::::***:**  .* *
```

FIG. 53B

```
dbj|BAB83769.1|           K_MPNEMKGASCTITNIGSAGGQWFTPVINHPEVAILGIGRIAEKPIVRDGEIVAAPMLA
ref|YP_146913.1|          K_MPNEMKGASCTITNIGSAGGQWFTPVINHPEVAILGIGRIAEKPIVRDGEIVAAPVLA
sp|P11961|ODP2_BACST      K_TPGEMKGASCTITNIGSAGGQWFTPVINHPEVAILGIGRIAEKPIVRDGEIVAAPMLA
ref|YP_001125047.1|       K_APNEMKGASCTITNIGSAGGQWFTPVINHPEVAILGIGRIAEKPIVRDGEIVAAPVLA
ref|ZP_01696305.1|        K_APNEMKGASITISNIGSAGGQWFTPVINRPEVAILGIGRIAEKPVVKNGEIVAAPVLA
RAAC02428                 K_KPEEMKGSTISITNIGSAGGLFFTPIINYPEVAILGVGRITEKPIIKNGEFAVGQMMS
                          ** * ****:: :*:*******  :***:** *******:***:***::::**:... :::

dbj|BAB83769.1|           LSLSFDHRMIDGATAQKALNHIK-------------
ref|YP_146913.1|          LSLSFDHRMIDGATAQKALNHIK-------------
sp|P11961|ODP2_BACST      LSLSFDHRMIDGATAQKALNHIK-------------
ref|YP_001125047.1|       LSLSFDHRMIDGATAQKALNHVK-------------
ref|ZP_01696305.1|        LSLSFDHRIIDGATAQNALNHIK-------------
RAAC02428                 LSLSFDHRVIDGALGQQFINDIKRLLENPRLLLLEV
                          ********:****  .*: :*.:*
```

FIG. 54A

```
ref|ZP_02326222.1|     MEFKLPDVGEGIHEGEIGKWLIKEGEQVNCDQPIVEVMTDKVNAELTAPAKGVVRRLMFA
ref|NP_241081.1|       VEFRLPDVGEGMHEGEIISWFVQEGDHVKQDEPVVEVQTDKMNAELTAPVSGKIKRVYYK
RAAC01659              MEFKLADIGEGIHEGEILRWLVKEGDQVEQDAPLVEVQTDKVTAELPSPVAGVIERIMAR
ref|YP_074242.1|       -EFKLPDVGEGLHEAELLRWLVKEGDTVTEDQPIMEVQTDKATVEITSPVNGRVVKLLGQ
ref|YP_001153408.1|    IEFKFPDLGEGLVEGEIVKWHVKEGDFVKEGDPLVDVMTEKANVTLPAPATGKVVKIFAK
ref|NP_560158.1|       MEFKFPDLGEGLVDGEVIKWHVKEGDFVKEGDPLVDVMTEKATVTLPAPTTGRVVKILVR
                        **::.*:***: *.*:   * ::**: *  . *:::* *:* .. ::*. * : ::

ref|ZP_02326222.1|     EGDKVEVGQVLFLL----------DVEEHETLGRTGEAEQAATASPPASPPAGESSFAPV
ref|NP_241081.1|       VGEVAEVGSLLFTID-----------ENLSTFKSETHERTKRENSTEQTRPISNISLTSQ
RAAC01659              EGQVVPVGTVLAVIR-----------EAGAKAAAASGAPGAQASLQEKPAAQAHSEAQP
ref|YP_074242.1|       PGDILKVHSVVVIFDDGSPGALPTAGEVASGVAAAAPAGAQPQASLDVPAPAAQPAPAPA
ref|YP_001153408.1|    EGEIVKVGQVLCVIEEV--------------------AAQEASPKAPAAEASTSQKV-
ref|NP_560158.1|       EGEVVKVGQTLCVIEP----------------------AEGPAAGPQTEAPARP-REVA
                       *:   *   :   :                                         :

ref|ZP_02326222.1|     H-----TP-----------RRVR-------AAPYVRQLARQLKIDIEQVTVSGADGRISE
ref|NP_241081.1|       Q----KAP----------VRKGL-------ATPYVRQLAREMNINLEDVVGTGPGGRVLE
RAAC01659              GRE-AAAPQASGAAHRGGRRRAL-------ATPHVRALARKLGVDIDEIDGTGPVGRVTE
ref|YP_074242.1|       APPAPAPAPAAGAGPADRPRRA-------LATPATRRLARELGVDINQVPGTGPAGRVTS
ref|YP_001153408.1|    ------------------------------VAMPAARRLARELGIDLSKVKGTGPGGVITV
ref|NP_560158.1|       ------------------------------AMPAARRLAKELGIDLSKVKGTGPGGVITV
                                                    * * .* **::: :::..: :*. * :

ref|ZP_02326222.1|     EDLRRYADS-------------------RETAEPVVPALASEAAESDHNGSAGGSKLL
ref|NP_241081.1|       QDLQNDTN--------------------LQKVKTVPSGVANVQESIERTGSS------
RAAC01659              EDVRRFAEGG------------------REPAVEPARAHAEHAAEAQPTAALR-----
ref|YP_074242.1|       DDVRAFAARR------------------TAPAPAQAPTQAPTEAAAPTPATPAP----
ref|YP_001153408.1|    EDVRRAAEEL------------------ARQEKAPPAPPPAAVQPPPAIAQPQA---
ref|NP_560158.1|       EDVKRYAE--------------------ETAKATAPAPAPKAVEK------------
                       :*::  :                              .

ref|ZP_02326222.1|     YSPPEAKGNFVNATHMNSEAPSCAEERIPLRGVRLKIAERMVKAVTVIPHVTQVDELEAD
ref|NP_241081.1|       ----------------------AEKRIPLKGIRKAIAEKMIKSVATIPHVTHVDEIEMD
RAAC01659              --------------VATPAASGEPVEQVPLRGLRRRIAEHMVQAKRIIPHATHIDEVEMD
ref|YP_074242.1|       ----------------AAPAEADD--ERIPLRGIRKVIAERMVKSKYTAPHVTTVEEVDMT
ref|YP_001153408.1|    ------------PAAAQLPQPVAEEERIPVRGIRRAVAEKMAKSASAIPHAYHFEEVDVT
ref|NP_560158.1|       --------------------AEEEAEVVPVRGIRRAVAEKMSKAKRLIPHAYHLEEVDFT
                                              : :*::*:* :**:* ::    **.  ..:*::

ref|ZP_02326222.1|     ALQALRERLQSIAAERQLKLTYLPFFIKALIIALKEFPVFNASLDDERKEILLKRYYHIG
ref|NP_241081.1|       ALKELREQLKHYSEQKGIKLTFLPFFIKAIVSALKEFEYFNASIDEETNEIVLKKDYHIG
RAAC01659              GIEALRERLRPYABARGVKLTSLAFFVKAVAIALKEFPYVNASVDEAQENVLLRRYYHIG
ref|YP_074242.1|       ELMAFRAQAKELAARKGIKLSFMPFIIKAVVAALREFPYLNASIDDEAQEIVLHKRYHIG
ref|YP_001153408.1|    ELVSLRERLRQEAERLGVKLTYLPFVAKAVAVALREFPMLNSSFDEERGEIVVKRRIHLG
ref|NP_560158.1|       ELIKLRERVKAEAEKRGIRLTLLPFIAKAVAMALREYPMLNSEYDEEKNAIVVKKEVNLG
                        :  :* : :    ::*: :.*. : :*:  .*:. *:   ::::: ::* ref|ZP_02326222.1|     IAVDTPDGLIVPVIRHADRKTVFQLAEEISQLTMQAWEGKLTLNQITGGTFTISNVGPIG
ref|NP_241081.1|       IATDTEKGLIVPVIQNADQKSLLELAGEITQLSTQARKGTLNVQQMTGSTFTISNVGPIG
RAAC01659              IAVDTEQGLIVPVVKHADEKSVFEIAREVSDLARRARENRLSLDEVTGSTFTISNAGALG
ref|YP_074242.1|       FALDTDAGLLVPVIKDADRKPVFAIAQEMNDLIARGREGKLAPDEMRGSTFTISNQGSIG
ref|YP_001153408.1|    FAVDTEQGLMVVVVRDADKKSVLEIARELNALAERARAGKASVDEVRGSTFTITNIGAIG
ref|NP_560158.1|       IGVDTEQGLVVVVVKNADKKGLLEMAKEINELAQKAREGKLELQDVRGSTFTISNIGAVG
                       :. **  **:* *:::.**.* ::  :* *:. *  :.    ::: *.****:* *.:*
```

FIG. 54B

```
ref|ZP_02326222.1|      SLLATPIINHPEAAILTLHKMEPRMVVRNREGVIRLMMNMALSFDHRIIDGADAIRFTNR
ref|NP_241081.1|        GLHATPIINYPEVAILALHKMEPRNVVREWESVIKLMMNMSLSFDHRLVDGATAVRFTNR
RAAC01659               GLYATPIINYPESAILGIHKMEPRPVVRNNEIVIRNIAHVSLSFDHRIIDGGMAIRFTNR
ref|YP_074242.1|        GLFFTPVINYPEVAILGIGKTQPRPVVRDGEIVIRQMAHLALSFDHRLIDGGMATRFLNR
ref|YP_001153408.1|     GVGGLPIINYPEAAIMALGKIRKIPRVVNGAVVPRDVMNVVVGFDHRVVDGAYVARFTNR
ref|NP_560158.1|        GLGGLSILNYPEAGILAVGQARKKPWAVGDRIEIRDIALLAVSFDHRVVDGAYVARFMNR
                        .:    .::*:**  .*:  :  :  .       .      : :   : :.****::**.  . ** **

ref|ZP_02326222.1|      MRQLLENPDLLWAEM-
ref|NP_241081.1|        MKELIENPNLLLMELR
RAAC01659               VRELLEEPDRLWAELR
ref|YP_074242.1         LAELLSDPTLLMME--
ref|YP_001153408.1|     VKELLEDVGKL-----
ref|NP_560158.1         VKELLENP--------
                        :  :*:.:
```

FIG. 55

```
ref|YP_001127228.1|         ----------------QILDENGN--GDEAKIAAFSDE---WLLDAYRAMRRARVVDERL
ref|YP_149070.1|            FDPDKLP-----VEIVRILDENGN--GDEEKLAAFSDE---WLLRAYREMRRARVIDERL
RAAC01745                   MDDVQVYRFTGDTKPDQVLNEAGE---MVGELPENAAD---LALEWYPFMIFCRKFDERA
ref|ZP_02326224.1|          ----------GLQEPYQVLKPDGE-LRHR-IGGEVDEA---LMIKMYENMMHVRMFDRKA
ref|NP_241079.1|            ----------------QVLTPKGE-CQYE-GSEFLDKT---FVLSMYKQMINCREFDEKA
ref|ZP_00539127.1|          ----------------RILDDAGQ-VTDTSKTDLLTKD---LSLALFTHMNRIRTFDRKA
                                            ::*    *:              : *    *.* .*.:

ref|YP_001127228.1|         LRMQRQGRIGTYAPFSGQEAAQIGSVLALQKDDWIFPSYREVAVCLTHG-MPLEQFFHYV
ref|YP_149070.1             LRMQRQGRIGTYAPFSGQEAAQIGSALALHKDDWIFPSYREVAVCLMHG-MPLEQFFHYV
RAAC01745                   QLLQRQGRLGTYAPFRGQEAAQIASFAVLRPSDWVFPTYRELAGMMYHG-LEPVHALLKS
ref|ZP_02326224.1|          VNLQRQGRIGTYAPYEGQEAAQVGSAMALSPEDWLFPSYRDHAATITHG-QSLSRVLLYW
ref|NP_241079.1|            LKLQRQGRIGTYASFKGQEACQIGGALALRPTDWLFPTYRDHAAISTHG-QPWHRIFLYW
ref|ZP_00539127.1|          INLQRQGRLGTYAPFEGQEAAQVGSAYALQDKDWVFPTYRDHGATLTFG-ADMVRTFLYW
                             :*****:****.:  ****.*:..   .*    **:**:**: .    .*      : :

ref|YP_001127228.1|         RGRLSGKRMPEELNIFPTQIIIAAQTLHAVGCAWATKLKGESHVSVAYFGDGATSEGDFH
ref|YP_149070.1|            QGRLSGKRMPEGVNIFPTQIIIAAQTLHAVGCAWASKLKGEPHVSVAYFGDGATSEGDFH
RAAC01745                   RGHPDAGRMPEEIHMAPPQIAIAAQILHAVGAGWACKLQEKDDIAVAYFGDGATSEGDFH
ref|ZP_02326224.1|          MGHMEGSVSPEGLKIMPPCVPIATQLVHAVGTSWAAKLKGEKQASIAYFGEGATSEGDFH
ref|NP_241079.1|            MGHMDGSLSPDDRNILPPAVPIATQMLHAVGTAWADKLKGNPHVSLVFFGDGATSEGDFH
ref|ZP_00539127.1|          NGRVEGCVATDELHIFPPAVPIATQIPHAVGAAWAEKRKGSTQVAVAYFGDGATSEGDFH
                             *:  ..    .:   ::  *. :  **:*   ** .  .   ::.: :******* ref|YP_001127228.1|         EAMNFAAVYNVPVIFFCQNNQYAISVPYAKQTASRTIAQKALAYGMKGVLVDGNDVLAVY
ref|YP_149070.1|            EAMNFAAVYNVPVIFFCQNNQYAISVPYRKQTASRTIAQKALAYGMKGVLVDGNDVLAVY
RAAC01745                   EGMNFASVMRLPVVFFCQNNQYAISVPVHRQMASPTIAQKAIAYGMEGLRVDGNDAFAVY
ref|ZP_02326224.1           EALNFAGVYQTATIFFCQNNQYAISVPFHAQSASRTIAQRAAAYDIVGVRVDGNDIFAVW
ref|NP_241079.1|            EALNFAGVYQTPTIFFCQNNGYAISVPFEKQSASKTIKQRSVAYDMRGERVDGNDIFAVY
ref|ZP_00539127.1|          EGMNFASVFQAPVILFNQNNGYAISVPIQKQMHSETIAQKALAYGMPSVRIDGNDVFAVY
                            *.:***.*    . ..::*  *** ******    *   *  **  **.:  . :**** :**:

ref|YP_001127228.1           ETMKQAVEAARRGEGPMLIEALTYRLGPHTTADDPTKYRHPEE-VETW-RRKDPLHRLRV
ref|YP_149070.1|            ETMKQAVEAARRGEGPMLIEALTYRLGPHTTADDPTKYRRPEE-VETW-RAKDPLRRLRL
RAAC01745                   QAMCYAVERARRGDGPTLIEAVTYRLGPHTTADDPGRYRDAVD-VERWAAAKDPLVRLRL
ref|ZP_02326224.1|          LTVREAIKRGLAGGGPTLVEAVTFRYGAHTTSDDPRKYRDQERLASEWREQRDPVHRLRL
ref|NP_241079.1|            LTVKRAIEQARKGRGPTLIEAVTTRFGSHTTADDAKKYRDQEEIERTWKEMQDPLTRLKA
ref|ZP_00539127.1|          FTMQKALERARSGGGPTLIEAVTWRFGAHTTADDPSKYRDQ----ERSRDRVDPLERLEA
                              ::    *::    .  * **  *:**: *  *    ***:**   :**        **: **.

ref|YP_001127228.1|         LLERRGLWTDAKEEEFVAKVNEEVTAAYEAAVASESGSIADVFDYVYSEAPKLLA-----
ref|YP_149070.1|            LLERRGLWTEAQEDALVAQVNDEVTAAYEAAIASKSGSIVDAFDCVYSEAPKLLA-----
RAAC01745                   WLTRQGLWDDERQAACEEEAEARVRQAVADMEAYPHKSLEEAARHVYAEVPEALALHLAK
ref ZP_02326224.1|          FLQKRGLWNEKDEERMLERLTGLIEDAVSEAESYPKSRPADMFKHVFADVP--------
ref NP_241079.1|            YIQAKGWLSEEEEAQMKAKIRETIDEELSMAEQYPKPSISQMFEHVYENQP---------
ref ZP_00539127.1|          FMKEQGFYDEQEIETIRSRHQEEVEAAVKTMESFPPPDVNDLFDHTFATLPDDL------
                                  :*        :         :                  :   .: * ref YP_001127228.1|         ------
ref|YP_149070.1|            ------
RAAC01745                   RGKEAR
ref|ZP_02326224.1|          ------
ref|NP_241079.1             ------
ref|ZP_00539127.1|          ------
```

FIG. 56

```
ref|ZP_00539126.1|        ----TLVQAVTDALRTKLTDDETTLVLGEDVGKNGGVFRATDGLQEEFGEDRIIDTPLSE
RAAC01746                 MPKWTMIEAIRDALAIALRDDPRVLVFGEDVGKNGGVFRATDGLQAEFGEARVADTPLAE
ref|YP_149069.1|          MAELTMIEAINEAMRQEMERDPRIIVLGEDVGENGGVFRATDGLLAQFGEGRVFDTPLAE
ref|YP_001127227.1|       MAELTMIEAINEAMRQEMERNSRVIVLGEDVGENGGVFRATDGLLEQFGSGRVFDTPLAE
ref|YP_001125046.1|       MAQMTMVQAITDALRIELKNDPNVLIFGEDVGVNGGVFRATEGLQAEFGEERVFDTPLAE
ref|NP_833691.1|          MAQMTMIQAITDALRVEMKNDPNVLVFGEDVGVNGGVFRATEGLQAEFGEDRVMDTPLAE
                              *:::*: :*:    :  :    ::***  ****:   :**. *: ****:* ref|ZP_00539126.1|        AGIVGTSIGLAVNGFKPIVEIQFLGFIYPAYEQIMTHVSRIRMRTMGRYGVPMVIRAPYG
RAAC01746                 KAIVGTAVGLAMAGMKPVAEIQFLGFAYEAMDQIAAQLARIRFRTQGRFTAPAVIRAPYG
ref|YP_149069.1|          SGIIGTSIGLAINGMRPIAEIQFLGFVYQAMDQLAAQAARIRFRSAGRFSCPIVVRSPYG
ref|YP_001127227.1|       SGIIGTSIGLAINGMRPIAEIQFLGFVYQAMDQLAAQAARIRFRSSGRFSCPIVVRSPYG
ref|YP_001125046.1|       SGIGGLAVGLALQGFRPVPEIQFFGFVYEVMDSISGQMARIRYRTGGRYHMPITVRSPFG
ref|NP_833691.1|          SGIGGLAVGLALEGFRPVPEIQFFGFVYEVMDSISGQLARMRYRSGGRWTAPVTVRSPFG
                           .* *  ::***:  *::*: **:  *  . :.:   : :*:*  *: **:  * .  :*:*:* ref|ZP_00539126.1|        AGIRAPEIHSDSTEALFTSMPGLKVVCPSTPYDAKGLLIAAIEDPDPVLFLESMRSYRAF
RAAC01746                 GGVRTPELHSDSLEALFAHTPGLVVVTPSRPYDAKGLLLSAIRSPDPVVFLEPIRLYRAF
ref|YP_149069.1|          GGVRTPELHSDALEALFTHSPGLKVVMPSNPYDAKGLLISAIRDEDPVLFLEPMKLYRAF
ref|YP_001127227.1|       GGVRTPELHSDALEALFTHSPGLKVVMPSNPYDAKGLLISAIRDDDPVLFFEPMKLYRAF
ref|YP_001125046.1|       GGVHTPELHSDSLEGLVAQQPGLKVVIPSTPYDAKGLLISAIRDNDPVIFLEHLKLYRSF
ref|NP_833691.1|          GGVHTPELHADSLEGLVAQQPGLKVVIPSTPYDAKGLLISAIRDNDPVIYLEHMKLYRSF
                           .*::**:*:*: *.*.: *   ****::.. ***:::* :: **:* ref|ZP_00539126.1|        KEPVPSEAYTIEIGKANCITEGQDVTLIAWGAMVQVAQKAATEAATRGISCEVIDLRTLY
RAAC01746                 REEVPEGDYQVPLGRAAVRREGSDVTLVAWGPTVPVAESAAAQVASRGISCEVLDLRTLA
ref|YP_149069.1|          RMEVPEEPYTIPLGQARVVKEGDDVTIIAWGATVPLAAKVAAEMQAKGVNAEVIDLRCLQ
ref|YP_001127227.1|       RMEVPEEPYTIPLGQARIVKEGDDVTILTWGATVPLVAKLADEMRMRGVDAEVIDLRCLQ
ref|YP_001125046.1|       RQEVPEGEYTIPIGKADIKREGKDITIIAYGAMVHESLKAAAELEKEGISAEVVDLRTVQ
ref|NP_833691.1|          RQEVPEGDYTIDLGKADIKREGTDVSVIAYGAMVHAALKAAEELEKEGISLEVVDLRTVQ
                          :  **.    *  :  :*:*      **  *:::::::*. *     . *  :  .*:. **;*** :

ref|ZP_00539126.1|        PLDRETISASVQKTGRAVIIHEAQATGGLGNDLLALINDTSFLYLRAPVARVTGFDVPVP
RAAC01746                 PLDRSALKASVEKTGRAVIVHEAVRYAGLGAEIAASIMDLAFYHLRAPIERVAGLDTPYP
ref|YP_149069.1|          PLDIDTIITSVEKTGRVMIVHEAVKTGGFGAEVAALISERALFSLSAPIVRIAGYDTPYP
ref|YP_001127227.1|       PLDIDTIIASVEKTGRVMIVHEAVKTSGFGAEVAALISERALFSLSAPIVRIAGYDTPYP
ref|YP_001125046.1|       PLDIETIIGSVEKTGRAIVVQEAQRQAGIAANVVAEINERAILSLEAPVLRVAAPDTVYP
ref|NP_833691.1|          PLDIETIIASVEKTGRVVVVQEAQKQAGIAANVVAEINDRAILNLEAPVVRVAAADTVFP
                          * .::  :**.:::::  .*:.  :: * :  ::   *  **: *::. *.  * ref|ZP_00539126.1|        LFALEDHYIPTPTRVLEAIQRTVD-
RAAC01746                 PPALEDAWLPSVTRVVEAIERVMED
ref|YP_149069.1|          VPSVEDDWLPNAERIAEGIETLL--
ref|YP_001127227.1|       VPSVEDDWLPNPARIVEGIETLM--
ref|YP_001125046.1|       FAQAESVWLPNFKDVIETAKKVM--
ref|NP_833691.1|          FSQAESVWLPNHKDIVEAVNKVM--
                                *. ::*.   : *  : :
```

FIG. 57

```
pdb 1W85|A              ---------------------------------QFPT--FQILNEEGEVVNEEAMPELSDE
sp|P21873|ODPA_BACST    ---------------------------------QFPT--FQILNEEGEVVNEEAMPELSDE
ref YP_146911.1         ---------------------------------QFPT--FQILNEEGEIVNEEAMPELSDE
ref YP_001421036.1|     ---------------------------------QILNAEGEVVNKDAMPDLSDD
ref NP_243521.1         ------------------------LEKVEGQFET--FQILNEEGEVVNEAAMPDLSDE
RAAC02426               ----------------------MTMLSQVVARFEIPYVQIVDENGNVVNPDLVPELSDD
                                                            **::  :*::**    :*:***:

pdb 1W85|A              QLKELMRRMVYTRILDQRSISLNRQGRLGFYAPTAGQEASQIASHFALEKEDFILPGYRD
sp|P21873|ODPA_BACST    QLKELMRRMVYTRILDQRSISLNRQGRLGFYAPTAGQEASQIASHFALEKEDFILPGYRD
ref YP_146911.1         QLKELMRRMVYTRILDQRSISLNRQGRLGFYAPTAGQEASQIASHFALEKEDFILPGYRD
ref YP_001421036.1|     QLKELMRRMVYIRILDQRSISLSRQGRLGFYAPTAGQEASQIASHFALEQDDFILPGYRD
ref NP_243521.1         QLQELMKRMVYTRIWDQRAISLNRQGRLGFYAPVAGQEASMLGSQFALDKEDWILPGYRD
RAAC02426               DLRELMKRMVFTRIWDQRAIRLSRQGRLGFYAPVSGQEASMIGSEFATKKEDFLLPGYRD
                        :*:*:*:  *:* *.********.:*** :.*.** ..:*::****** pdb 1W85|A              VPQIIWHGLPLYQAFLFSRGHFHGNQIPEGVNVLPPQIIIGAQYIQAAGVALGLKMRGKK
sp|P21873|ODPA_BACST    VPQIIWHGLPLYQAFLFSRGHFHGNQIPEGVNVLPPQIIIGAQYIQAAGVALGLKMRGKK
ref YP_146911.1         VPQIIWHGLPLYQAFLFSRGHFHGNQIPEGVNVLPPQIIIGAQYIQAAGVALGLKMRGKK
ref YP_001421036.1|     VPQIIWHGLPLHQAFLFSRGHFKGNQMPEGVNALSPQIIIGAQIIQTAGVALGLKKRGKK
ref NP_243521.1         IPQIVFHGLPLYQAFLYSRGHFEGGQIPDGVNVLMPQIIIGAQIVQAAGVAMGLKRKGKQ
RAAC02426               IPQLYFHGYPLHQLFLYSRGHQLGGKVPEGVNCMVPQIIIGAQIVQAAGVGLAFKLRGEK
                        :**: :** **:* **:****  *.::*:*** : ********.:*:***.:..:* :*::

pdb 1W85|A              AVAITYTGDGGTSQGDFYEGINFAGAFKAPAIFVVQNNRFAISTPVEKQTVAKTLAQKAV
sp|P21873|ODPA_BACST    AVAITYTGDGGTSQGDFYEGINFAGAFKAPAIFVVQNNRFAISTPVEKQTVAKTLAQKAV
ref YP_146911.1         AVAITYTGDGGTSQGDFYEGINFAGAFKAPAIFVVQNNRFAISTPVEKQTIAKTLAQKAV
ref YP_001421036.1|     AVAITYTGDGGASQGDFYEGMNFAGAFKAPAIFVVQNNRYAISTPVEKQSSAQTIAQKAV
ref NP_243521.1         NVAITYTGDGGASQGDFYEGMNFAGAYNSPAIFVVQNNRFAISVPVEKQSAAKTIAQKAV
RAAC02426               RVAVTYTGDGGTSQGDFYEGMNFAGAMNLPVVFFVQNNQYAISVPRELQTRAQTLAQKAI
                        **:*******:******:***** : *.:*.****::***.* * *: *:*:****:

pdb 1W85|A              AAGIPGIQVDGMDPLAVYAAVKAARERAINGEGPTLIETLCFRYGPHTMSGDDPTRYRSK
sp|P21873|ODPA_BACST    AAGIPGIQVDGMDPLAVYAAVKAARERAINGEGPTLIETLCFRYGPHTMSGDDPTRYRSK
ref YP_146911.1         AAGIPGIQVDGMDPLAVYAAVKAARERAINGEGPALIETLCFRYGPHTMSGDDPTRYRSK
ref YP_001421036.1|     AVGITGVQVDGMDALAVYAATAEARQRAINGEGPTLIETLTFRYGPHTMSGDDPTKYRTK
ref NP_243521.1         AAGIEGIQVDGMDVLAVYAATKQARERALAGDGPTLIETLCYRYGPHTMAGDDPTRYRSS
RAAC02426               AAGIPGVQVDGMDVLAVYHVMHEALERARNGEGPTMIEAVTFRYGPHTMSGDDPTRYRTK
                        *.** *:******.****   .  * :**  *:**::**::  :.*******:*****.**:.

pdb 1W85|A              ELENEWAKKDPLVRFRKFLEAKGLWSEEEENNVIEQAKEEIKEAIKKADETPKQKVTDLI
sp|P21873|ODPA_BACST    ELENEWAKKDPLVRFRKFLEAKGLWSEEEENNVIEQAKEEIKEAIKKADETPKQKVTDLI
ref YP_146911.1         ELENEWAKKDPLVRFRKFLEAKGLWSEEEENRVIEQAKEDIKEAIKKADETPKQKVTDLI
ref YP_001421036.1|     EIENEWEQKDPLVRFRKFLENKGLWSEEEENKVIEQAKEEIKQAIKKADGESKPKVTELI
ref NP_243521.1         DLDDEWEKKDPLVRFRKFLEGKGLWSEEQENEVVVEKAKEDIKAAIKKADAAPKQKVTDLI
RAAC02426               DVQEEWEKKDPLIRFRKYLEEKGLWSQEEEEAYIEEAKETVNNALKEADAAEKMTIPGLI
                        :::::**.:****:****:** *****:*:*:  :*:***  :: *:*:**   * ... **

pdb 1W85|A              SIMFEELPFNLKEQYEIYKEKES-
sp|P21873|ODPA_BACST    SIMFEELPFNLKEQYEIYKEKES-
ref YP_146911.1         SIMFEELPANLKEQYEIYKEKES-
ref YP_001421036.1|     ENMFEEPTFNLKEQLEIYKAKES-
ref NP_243521.1         GFMFEEAPQHLREQLEEYTAKES-
RAAC02426               DSMFEELTPTLKRQRAEFAGEEAN
                            ****  . *:.*   :  :*:
```

FIG. 58

```
sp|P21874|ODPB_BACST    --------------------------------------------------MAQMTMVQAI
pdb|1W85|B              --------------------------------------------------SAQMTMVQAI
ref|YP_001125046.1|     --------------------------------------------------MAQMTMVQAI
ref|YP_146912.1         --------------------------------------------------MAQMTMVQAI
ref|ZP_01696304.1|      --------------------------------------------------MAQLTMIQAI
RAAC02427               ------------------------------------------MPARRRTDMAQMTMIQAI
                                                                          ::*** sp|P21874|ODPB_BACST    TDALRIELKNDPNVLIFGEDVGVNGGVFRATEGLQAEFGEDRVFDTPLAESGIGGLAIGL
pdb|1W85|B              TDALRIELKNDPNVLIFGEDVGVNGGVFRATEGLQAEFGEDRVFDTPLAESGIGGLAIGL
ref|YP_001125046.1|     TDALRIELKNDPNVLIFGEDVGVNGGVFRATEGLQAEFGEERVFDTPLAESGIGGLAVGL
ref|YP_146912.1         TDALRIEMRNDPNVLVFGEDVGVNGGVPRVTEGLQAEFGEERVFDTPLAESGIGGLAIGL
ref|ZP_01696304.1|      TDALRTELKNDENVLVFGEDVGVNGGVFRATEGLQKEFGKDRVIDTPLAESGINGLAIGL
RAAC02427               THALDLELARDERVLVFGEDVGKNGGVFRATEGLQQKYGPNRVFDTPLAESGIIGLANGL
                        *.**   *:  .* .:* **.***  ::*  ::***** * ** sp|P21874|ODPB_BACST    ALQGFRPVPEIQFFGFVYEVMDSICGQMARIRYRTGGRYHMPITIRSPFGGGVHTPELHS
pdb|1W85|B              ALQGFRPVPEIQFFGFVYEVMDSICGQMARIRYRTGGRYHMPITIRSPFGGGVHTPELHS
ref|YP_001125046.1|     ALQGFRPVPEIQFFGFVYEVMDSISGQMARIRYRTGGRYHMPITVRSPFGGGVHTPELHS
ref|YP_146912.1         ALQGFRPVPEIQFFGFVYEAMDAICGQMARIRYRTGGRYHVPITIRSPFGGGVHTPELHS
ref|ZP_01696304.1|      ALQGFRPVPEIQFFGFVFETMDSIHGQMARYRFRTGDLKMPITIRAPFGGGVHTPEMHA
RAAC02427               AIQGFRPVPEIQFFGFVFEAFDQIAGQLARTRYRTGGRYTAPVTIRSPFGGGVHTPEMHA
                        *:*************:*.:* * **:** *:****    *:*:*:*********:*:

sp|P21874|ODPB_BACST    DSLEGLVAQQPGLKVVIPSTPYDAKGLLISAIRDNDPVIFLEHLKLYRSFRQEVPEGEYT
pdb|1W85|B              DSLEGLVAQQPGLKVVIPSTPYDAKGLLISAIRDNDPVIFLEHLKLYRSFRQEVPEGEYT
ref|YP_001125046.1|     DSLEGLVAQQPGLKVVIPSTPYDAKGLLISAIRDNDPVIFLEHLKLYRSFRQEVPEGEYT
ref|YP_146912.1         DSLEGLVAQQPGLKVVIPSTPYDAKGLLISAIRDNDPVIFLEHLKLYRSFRQEVPEGEYT
ref|ZP_01696304.1|      DSLEGLMAQTPGIKVVIPSTPYDAKGLLISAIRDNDPVVFLEHMKLYRSFREEVPEEEYT
RAAC02427               DSLEGLFVQTPGIKVVIPSTPYDAKGLLLSAIRDPDPVIFLEHMKLYRSFRQEVPEDDYT
                        ******..* **:***************.***** ***:****:*******.**** :**

sp|P21874|ODPB_BACST    IPIGKADIKREGKDITIIAYGAMVHESLKAAAELEKE-GISAEVVDLRTVQPLDIETIIG
pdb|1W85|B              IPIGKADIKREGKDITIIAYGAMVHESLKAAAELEKE-GISAEVVDLRTVQPLDIETIIG
ref|YP_001125046.1|     IPIGKADIKREGKDITIIAYGAMVHESLKAAAELEKE-GISAEVVDLRTVQPLDIETIIG
ref|YP_146912.1         IPIGKADIKREGKDITIIAYGAMVHESLKAAAELEKE-GISAEVVDLRTVQPLDIETIIG
ref|ZP_01696304.1|      IPLGKADVKREGKDISIIAYGAMVHESLKAADELEKE-GYSAEVVDLRTVSPLDVETIVA
RAAC02427               IPLGVANVVREGKHATVIAYGAMVHVALKAAEQWSKEKGLEAEVIDLRTVNPIDIDTIVA
                        **:*  *:: ****.  ::******** :****   :  .** *  .***:*****.*:*:**:.

sp|P21874|ODPB_BACST    SVEKTGRAIVVQEAQRQAGIAANVVAEINERAILSLEAPVLRVAAPDTVYPFAQAESVWL
pdb|1W85|B              SVEKTGRAIVVQEAQRQAGIAANVVAEINERAILSLEAPVLRVAAPDTVYPFAQAESVWL
ref|YP_001125046.1|     SVEKTGRAIVVQEAQRQAGIAANVVAEINERAILSLEAPVLRVAAPDTVYPFAQAESVWL
ref|YP_146912.1         SVEKTGRAIVVQEAQRQAGIAANVVAEINERAILSLEAPVLRVAAPDTVYPFAQAESVWL
ref|ZP_01696304.1|      SVEKTNRAIVVQEAQVAANVVAEINERAILSLEAPVLRVTAPDTVYPFSQAEGVWI
RAAC02427               SVKKTNRAIVVQEAQRSAGAAAEIVAQINENAIYYLEAPVLRATPPDTVYPFGMIEDEWL
                        **:**.**********.** **:::**:.*** ******.:.*******.  *. *:

sp|P21874|ODPB_BACST    PNFKDVIETAKKVMN-
pdb|1W85|B              PNFKDVIETAKKVMN-
ref|YP_001125046.1|     PNFKDVIETAKKVMN-
ref|YP_146912.1         PNFKDVIETAKKVIN-
ref|ZP_01696304.1|      PTYKDILEKAKETLT-
RAAC02427               PTPEYVLKTLDKVMSL
                        *. :  :::. .:.:.
```

FIG. 59

```
dbj|BAB40585.1|        ----------------EHQFPKIQIVDENGNIVDSKYEDKLTPEFIKELYERLMFVRTF
ref|ZP_01171269.1      ------------------------MIDENGNEVSG--TSGFDTELALEFYRQLVRIRVF
ref|YP_001126012.1|    ------------------------VLNEEGTVVQPEYRERITKELTMVMYRHLIRTRTF
ref|ZP_02326224.1      -----EKEEMAMKHDKLHGLQEPYQVLKPDGE-LRHRIGGEVDEALMIKMYENMMHVRMF
ref|NP_241079.1|       --------------------------------------------VLSMYKQMINCREF
RAAC01657              MLAEHDRAERLMEIAKAEGLYEEIHLLKEDGT-LAGAVD-DIPPEVMVAMYRHMVFARAF
                                                                    :*..::  *  * dbj|BAB40585.1|        DRKAISLQRQGRLGTYAPFEGQEAAQVGSALALEKDDWLFPTYRDHAATITFGHKLSTVF
ref|ZP_01171269.1      DRKAVSLQRQGRIGTYAPFEGQEAAQIGSAMALEESDWMFPTYRDHGAALAFGHSMRNVL
ref|YP_001126012.1|    DRKCVSLQRQGRIGTYVPYEGQEACQVGSALALNDEDWMFPTYRDHGAMMTFGRSLVNTL
ref|ZP_02326224.1      DRKAVNLQRQGRIGTYAPYEGQEAAQVGSAMALSPEDWLFPSYRDHAATITHGQSLSRVL
ref|NP_241079.1|       DEKALKLQRQGRIGTYASFKGQEACQIGGALALRPTDWLFPTYRDHAAISTHGQPWHRIF
RAAC01657              DRKAIALQRQGRIGTYAPFEGQEAAQVASAMALAPEDFVFPSYRDHAATMVLGQSPANVL
                       *.*.: ******:***..::****.*:..*:**   *:.**:****.*   .*:    :

dbj|BAB40585.1|        LYWNGRVEGCVPPEGKKIFPPAVPIATQLPHATGAAMAEKYKGTKNAAIVYFGDGATSEG
ref|ZP_01171269.1      LFWNGRNEGCIPPEGKNIFPPGIPIATQIPHAAGAAYAEKRKGTKKAAIVYFGDGATSEG
ref|YP_001126012.1|    LYWKGRTEGCVPPEGKKIVPPSVPIATQLPHAAGAACAEKWKGTKNAVIVYFGDGATSEG
ref|ZP_02326224.1      LYWMGHMEGSVSPEGLKIMPPCVPIATQLVHAVGTSWAAKLKGEKQASIAYFGEGATSEG
ref|NP_241079.1|       LYWMGHMDGSLSPDDRNILPPAVPIATQMLHAVGTAWADKLKGNPHVSLVFFGDGATSEG
RAAC01657              LYWSGRVEGIRSPEGRHILPPSVPIATHVLHAVGAAWASRYRKESAVSIAYFGDGATSEG
                       *:*  *: :*  .*:. :*. ::: .*:: * :   . :.::**** dbj|BAB40585.1|        DFHEGLNFASVFKAPVVFFNQNNSFAISVPIHKQMNSKTIAQKSVAYGIPGIRLDGNDIF
ref|ZP_01171269.1      DFHEGLNFASIVKAPVVFFNQNNQYAISVPLSKQMNTKTIAQKSLAYDIPGVRVDGNDVF
ref|YP_001126012.1|    DFHEGLNFASVFNAPVVFFNQNNQYAISVPITRQMRSKTIAQKALAYDIPGVRIDGNDVF
ref|ZP_02326224.1      DFHEALNFAGVYQTATIFFCQNNGYAISVPFHAQSASRTIAQRAAAYDIVGVRVDGNDIF
ref|NP_241079.1|       DFHEALNFAGVYQTPTIFFCQNNGYAISVPFEKQSASKTIKQRSVAYDMRGERVDGNDIF
RAAC01657              DFHEALNFAGVFHLPVLFFCQNNGYAISVPFSRQSASRTIAQRAIAYDIVGVRVDGNDAF
                       **..: :  ..: * :***:    *   ::** *:: **.:  * *:**** * dbj|BAB40585.1|        AVYFYTKEALDRARNGEGPTLIEAVTWRYGAHTTADDPTKYRNQE-ESLERREKYDPILR
ref|ZP_01171269.1      AVYRETKKALERAREGGGPTLIEAVTWRYGAHTTADDPAKYRDQQ-ESSVLRGKIDPILR
ref|YP_001126012.1|    AVYFQTAEALERARHGGGPTLIEAVTWRYGAHTTSDDPSRYRDQE-ESKKRRETTDPIKR
ref|ZP_02326224.1      AVWLTVREAIKRGLAGGGPTLVEAVTFRYGAHTTSDDPRKYRDQERLASEWREQRDPVHR
ref|NP_241079.1|       AVYLTVKRAIEQARKGRGPTLIEAVTTRFGSHTTADDAKKYRDQEEIERTWKEMQDPLTR
RAAC01657              AVYRAVKEARSRALHGLGPTLIEAVTFRMGAHTTADDPTRYRDQKAVVEAWQK-RDPIVR
                       **:    .* .::   * **:**.* *:*::. :**:.*        **: * dbj|BAB40585.1|        VERLMKNKGIWDEKWAASVEEKASQTIEEAVKEMEAFPAPDVNDLFDHVFEKPTW-----
ref|ZP_01171269.1      MERWLKNKDLYDENWAKRAESEAAAEIDLAIAEMEAYPPADPADIFDHVFAELIWPL---
ref|YP_001126012.1|    VVRLMQREGWWNEQWANQVQEEVNAEIEQAVAEMERYPKANASDMFDYVFAEPTWTIA--
ref|ZP_02326224.1      LRLFLQKRGLWNEKDEERMLERLTGLIEDAVSEAESYPKSRPADMFKHVFADVPWSI---
ref|NP_241079.1|       LKAYIQAKGWLSEEEEAQMKAKIRETIDEELSMAEQYPKPSISQMFEHVYENQPWYV---
RAAC01657              LRLYLESQKLWSESDEAKLQDEVKARVEAAVEEALSIAPPDMEMMFDHVYAEEPWHLAAE
                       :    ::.   .*.     .    ::  :     ..   :*.:*: . * dbj|BAB40585.1|        -------------
ref|ZP_01171269.1      -------------
ref|YP_001126012.1|    -------------
ref|ZP_02326224.1      -------------
ref|NP_241079.1|       -------------
RAAC01657              REEYRRTREGVSV
```

FIG. 60

```
dbj|BAB40586.1|         ----LTLVQAVTDGLRTMLKEKKEVIVLGEDVGKNGGVFRATDGLQEEFGEDRVIDTPLS
ref|NP_693798.1|        -TKQLTLIQAITDGMRTMLHEREEVVVLGEDVGKNGGVFRATDGLQEEFGEKRVFDTPLS
ref|YP_001126011.1|     -TKSLTLVQAVNDALRIMLKERDDVVLLGEDVGRNGGVFRATDGLLQEFGEERVIDTPLS
ref|ZP_02326223.1|      MSRSLTILQAVTEALDQKLAHDHRVVLLGEDIGVNGGVFRATDGLFVKYGEERVLDTPLA
ref|NP_241080.1|        -SQQQTMLQAINQTLDDLLATNDDVMLLGEDIGINGGVFRATDGLYEKYGKDRVVDTPLA
RAAC01658               MSRMLNLVQAINEALDLKLADDPRVVLLGEDIGKNGGVFRATDGLLEKYGEERVIDTPLA
                          .::**:.:  :   *      *::****:* ***********  ::*:.**.****:

dbj|BAB40586.1|         EAGIVGVSIGMAINGMLPVAEIQFLGFIYPAYEQIMTHASRIRMRTMSKFHVPLVIRAPY
ref|NP_693798.1|        EAGIIGSSIGMAINGLLPVAEIQFSGFIYPAYEQIMTHATRMRYRTKGVFTVPLVIRAPY
ref|YP_001126011.1|     EAGFTGAAIGMALNGFRPVVEIQFLGFIYPAYEQIMTHAARMRSRTRGHFTVPLVIRAPY
ref|ZP_02326223.1|      ESGIIGSAIGFALNGLLPVIEIQFLAFIYPGFEQLVSHAARMRYRTRGQFSVPIVIRTPY
ref|NP_241080.1|        ESGIIGSAIGLAMNGKRPIVEIQFLAFIYPGFEQLISHAARMRYRTRGQYNVPMVIRTPY
RAAC01658               ESAIIGTSIGMAVNGLIPVPEIQFLAFIFPALDQLFSHVARMRYRSQGQFPVPMTIRTPY
                        *:.:  *  :**:*:**  *:  ****  .**:*. .:*: :*.:*:*  *:  . :  **:.**:**

dbj|BAB40586.1|         GAGVRAPEIHSDSVETLFTHMPGIKVVCPSTPYDAKGLLIAAIEDPDPVLFMESMKLYRS
ref|NP_693798.1|        GAGVRAPEIHSDSMEALFTHMPGIKVVCPSSPYDAKGLLISAIEDPDPVLFLEPLKLYRA
ref|YP_001126011.1|     GAGVRAPEIHSDSTEALFTHMPGVKVVCPSSPYDAKGLLIAAIEDPDPVLFLEPMRNYRA
ref|ZP_02326223.1|      GTGIRGPELHSDSIEAFFVHTPGIKVAVPSNPYDAKGLLISAIEDPDPVIFLEPAQIYRA
ref|NP_241080.1|        GAGIRGPELHSESVEAFFAHTPGLKVVAPSNPYDAKGLLTAATSDPDPVIFLEDTKLYRA
RAAC01658               GAGIHGPELHAESVESFFAHTPGLKVVPSGPYDAKGLLISAIEDPDPVVFLEPTKLYRA
                        *:*:.**:**:* *::*.* **:**.  ** ********  :*  .****:*:*    : **:

dbj|BAB40586.1|         SREDVPEGKYTVEIGKARKVRDGKDVSIFAWGAMVPVATKAAEEMEK-KGVTCDVIDLRT
ref|NP_693798.1|        VRGEVPEEKYEIEIGKGKYLREGDDVTVIAWGAMVPVAMKAAEQ-AAEKGITCEVIDLRT
ref|YP_001126011.1|     FREDVPEGKYTVDIGKGKKLREGEDVTVIAWGAMVPVAMKAAEAAAK-KGIDADVIDLRT
ref|ZP_02326223.1|      FKTKVPEDMYRVPLGKASIVQEGNDVTIISWGAMMRVALTAAQQMERENGWSCEVIDLRS
ref|NP_241080.1|        FKEDVPNTLYEIPLGQAKVVQEGEDVTVIAWGGMVREALQAAKEBAEKAHGWSCEIIDLRT
RAAC01658               FREEVPEGLYRVPIGKAKRVREGEDVSVFAWGSMLHTALKVAEAIERERGWTCDVIDLRT
                           :.**:   *   :  :*:.   :::*.**::::**.*:   *    .*:     .  .:::****:

dbj|BAB40586.1|         LYPLDKDAIAESVQKTGRVVIVHEAHATGGVSNDVMAVINDTAFLYLKAPIERVTGFDVP
ref|NP_693798.1|        LYPIDRAIIAESVQKTGRCVVVHEAPATGGLGNDIISIVNDTSFLYMKSPIERVTGADVH
ref|YP_001126011.1|     LYPLDKDMIAESVQKTGRTVIVQEAHATGGLANDILAVINDTSFFYQKAPAERVTGFDVP
ref|ZP_02326223.1|      LYPLDRDTIVASVQKTGRALIVHEAHKTAGVGAEIISLINEEALMYLRAPVKRITGFDVP
ref|NP_241080.1|        IAPIDRETIIESVKKTGRAIIIHEAHKTAGLGGEITALINEEALIYLKAPVKRIAGFDIP
RAAC01658               LYPLDRDAIVESVQKTGRAVVVHEAHKTAGLGAEIVSLINEEALLYLRAPIKRIAGFDVP
                        :  *:*:  *   **:****  :::  :**   *.*.:  ::   :::*:   ::* :*::* *:

dbj|BAB40586.1|         VPFFTLEEHYLPNTGRVVKAIEKVIHF
ref|NP_693798.1|        VPFWALEEHNIPTPARVMDAINQVINF
ref|YP_001126011.1|     VPFFAHEDDYLPTPARVLHAIEKVM--
ref|ZP_02326223.1|      VPQFSLENFYVPTVKRVKDGIADTIRF
ref|NP_241080.1|        VPQFLSENQYLPTIERMFRGIEETVSF
RAAC01658               VPFFALEDEYMPTEARIRAGIEETITF
                        **  :   *:   :*.   *:     .*   ..:
```

FIG. 61A

```
ref|YP_001125466.1|      ------------------------------------------------------------
ref|YP_147353.1|         ------------------------------------------------------------
RAAC00484                MCGEGRECLAGTAGGRVLGLPRYLAPARAGARRRAGAVSNHPRRGEGRALAPDQGRPPAL
ref|ZP_01697095.1|       ------------------------------------------------------------
ref|YP_077737.1|         ------------------------------------------------------------
ref|ZP_01886631.1|       ------------------------------------------------------------ ref|YP_001125466.1|      ------------------------------------------------------------
ref|YP_147353.1|         ------------------------------------------------------------
RAAC00484                VPGRRGDVRRADGARSRPHGAPRRSLAHTGLRRGQVAGSRPSRLREGAAGPRRDAICPGV
ref|ZP_01697095.1|       ------------------------------------------------------------
ref|YP_077737.1|         ------------------------------------------------------------
ref|ZP_01886631.1|       ------------------------------------------------------------ ref|YP_001125466.1|      ------------------------------------------------------------
ref|YP_147353.1|         ------------------------------------------------------------
RAAC00484                CGRGGRPRARDLRPDLRGRRRAVGRSRLSVGPPILSAGGLARDEIGHIEPPLRVRLPHNL
ref|ZP_01697095.1|       ------------------------------------------------------------
ref|YP_077737.1|         ------------------------------------------------------------
ref|ZP_01886631.1|       ------------------------------------------------------------ ref|YP_001125466.1|      ------------------------------------------------------------
ref|YP_147353.1|         ------------------------------------------------------------
RAAC00484                VGISPLAHHPLVHRLLDGVEARPLLGPREIRRVQADVVQHAIHVQESADGGELEEDEFVL
ref|ZP_01697095.1|       ------------------------------------------------------------
ref|YP_077737.1|         ------------------------------------------------------------
ref|ZP_01886631.1|       ------------------------------------------------------------ ref|YP_001125466.1|      ------------------------------------------------------------
ref|YP_147353.1|         ------------------------------------------------------------
RAAC00484                VVAALAVRIALKTSDAQDGLRAVKARHEIRSVAKNVELVRKRTPAQDVIAHQAAAVFSPV
ref|ZP_01697095.1|       ------------------------------------------------------------
ref|YP_077737.1|         ------------------------------------------------------------
ref|ZP_01886631.1|       ------------------------------------------------------------ ref|YP_001125466.1|      ------------------------------------------------------------
ref|YP_147353.1|         ------------------------------------------------------------
RAAC00484                LGVGGGDDRVGGSLVHGGGQFGEGRWREPVVAVQGDEVRRSHVRQRRLQRVAKALVFPER
ref|ZP_01697095.1|       ------------------------------------------------------------
ref|YP_077737.1|         ------------------------------------------------------------
ref|ZP_01886631.1|       ------------------------------------------------------------ ref|YP_001125466.1|      --------------------------------------------------------
ref|YP_147353.1|         --------------------------------------------------------
RAAC00484                QHAHARVPQVAPRDLARSVRRSVIHDDEIPCRRGLCEHACDGHRQIARPVVHGEHHRAR
ref|ZP_01697095.1|       --------------------------------------------------------
ref|YP_077737.1|         --------------------------------------------------------
ref|ZP_01886631.1|       --------------------------------------------------------
```

FIG. 61B

```
ref|YP_001125466.1|    ----------------------------------------------------------------
ref|YP_147353.1|       ----------------------------------------------------------------
RAAC00484              LSPGAHGEPLLCAEHDAKIRYNECKSSRKAWESAVIEDKVRLEFMGVQALLLRLPEEVPI
ref|ZP_01697095.1|     ----------------------------------------------------------------
ref|YP_077737.1|       ----------------------------------------------------------------
ref|ZP_01886631.1|     ---------------------------------------------------------------- ref|YP_001125466.1|    -----------------------EGIKEIVPAFSSLTVY--YDPVVAGNYADVCAWLREN
ref|YP_147353.1|       -----------------------EGIEEIVPAFSSLTIY--YDPLVID-YIGIGAWLRKN
RAAC00484              ETGEALDRLLSLRAALLRELEGVDGIEDITIGYRSVAVYARFEDVSPD---DVLARARRA
ref|ZP_01697095.1|     ---------------------------VTVLYDPFKVYAKFG-------EYPYRYVSRY
ref|YP_077737.1|       ----------------------VPAFTSVTVFYQPFEVYRKMESGKAV--DSPYEKVKAL
ref|ZP_01886631.1|     -------------------------------PTEV-------------------------
                                                        .  :

ref|YP_001125466.1|    I-GSTGQA---ARHSTR---TIVIPVCYGGEFGPDLADVARFHGMTEDEVVALHSSGRYR
ref|YP_147353.1|       I-RRSEQA---VRRSAR---TVVIPVCYGGEFGPDLPDVARFHGMTEDEVIALHSAGRYR
RAAC00484              IQGSQGSP-VPATRPEA---VVTLPVVYGGSFGPDLDAVAERAGLSPQDVIRLHQEAVYR
ref|ZP_01697095.1|     FTRLLEKAQPAFIPEPR---TVDIPVCYGGEFGPDLENVARINDLTPEEVIRIHASGDYT
ref|YP_077737.1|       LDHHLQELTMEEETDQR---TVEIPVCYGGRFGPDLEEVADINGLTAQEVIDIHTSGEYL
ref|ZP_01886631.1|     --------------------VEIPVIYGGEYGPDLDVVAQHTGLSVAEVIRRHSDVEYL
                                           :  : *.**    .:: .*: *    * ref|YP_001125466.1|    VYMIGFSPGFAYLGGLSPRLATPRRPVPRTTVPAGSVGIAGGQTGVYPLATPGGWQLIGR
ref|YP_147353.1|       VYMIGFSPGFAYLGGLSPRLATPRRSVPRTKVPAGSVGIAGGQTGVYPLATPGGWQLIGR
RAAC00484              VAMIGFSPGFAYLIGLPEPLRVPRRETPRSRVERGSVGIAGFQTGVYSFATPGGWQIIGR
ref|ZP_01697095.1|     VYMIGFAPGFPYIGGMPEKIAAPRKKTPRLKIPERSVGIAGKQTGIYPIETPGGWQIIGR
ref|YP_077737.1|       VYMIGFAPGFPYLGGMSEKIAAPRRSSPRTSIPAGSVGIAGMQTGVYPLSTPGGWQLIGN
ref|ZP_01886631.1|     VYMIGFTPGFPYLGGMDPALAVPRKDSPRAKIASGAVGIAGQQTGIYPMESPGGWQIIGR
                       * ****:***.*: *:   .  .**:  **    :*****.***:*.:  :*****:**.

ref|YP_001125466.1|    TPLRLFDPHREKPSLLSAGDIVEFRRITAEEF--------
ref|YP_147353.1|       TPLKLFDPHREKPSLLAAGDIVAFQPIGADEF--------
RAAC00484              TPVALFDVHRPSPSLLSPGDEVRFEAVTEEEYHGRFGAYT
ref|ZP_01697095.1|     TPVKLFRPDRDGPSLLQAGDKIRFRPVSLEEY--------
ref|YP_077737.1|       TPLELFKPYEQPPSLLRAGDIVKFVSVTEEEYH-------
ref|ZP_01886631.1|     TAADLFDRNRNPPALLKAGDRLRFVSITEDNYH-------
                       *.  **     .  :*:**  **  :   :::
```

FIG. 62

```
ref|YP_001420062.1|      ---------------MKVVKPGLLTTVQDTGRTGYQKYGVLGSGAMDTISLRIANLLAGNQ
ref|NP_242684.1|         ---------------IFRPGLLTTIQDLGRTGYLKYGVIVSGPMDEYAHRMANLLVGND
ref|NP_886151.1|         ---------------VIKPGMLSTFQDGGRHGYQHQGIPVAGAMDPRAHRLANLLAGNA
ref|YP_147354.1|         ---------------IDVIEAGLFTTVQDGGRFGYRHAGVPAGGAMDAWAYRLANALVGNN
ref|YP_001125467.1|      ---------------VIDGGFFTTVQDGGRIGYRNAGVPVGGVMDAWAYRLANALVGNE
RAAC00483                MAALARTHEPGIARVRVLAPGLFTTVQDGGRPHHRHLGVPLGGALDVLAFRSANRLVGNA
                                         : .  *::*.** **   : :  *:   .*  :*  : * ** *.**

ref|YP_001420062.1|      EKEAGLEITLMGPGPSFEFSEPAVIAVTGADFALHINGEPAPLWKPVLIKENSVVSFGPC
ref|NP_242684.1|         EKAALLEMTFIG--PTIQFTSDQLIAMTGGDLSPTIDGHSVPMYRPVFVKKGAVLSFGRC
ref|NP_886151.1|         ADTATLEITVAG--PTLRFEAPACVALGGADLGATLGGLPAPVLRPLVARAGDVLSFARP
ref|YP_147354.1|         GDEAVLEATMAG--PTLRFRVEAVVAVCGGDFPCTLNGQPISLWKPEIVKSGDVLEVGVC
ref|YP_001125467.1|      GDEAVLEATMSG--PTLRFHVETVIAVCGGDFPCTLNGEPMAMWKPVIIRPGDVLKVGVC
RAAC00483                EDCAALEVTGAG--PKLAFEAPAAVALCGADFLAYVDGEPLPVQRPVWLGGGAVLEIRNA
                         .  * **   *   *.: *       :*: *.*:    :.* .  .: :*    . *:..

ref|YP_001420062.1|      KMGSRAYLAVAGGFDVPAVMESKSTYVRAGIGGFCGRALQKDDELPLG-----RMTPCSE
ref|NP_242684.1|         KTGCRSYLAIGGGIDVPKVMNSRSTYLRAKIGGFQGRALVEGDELICG-----APPEQTE
ref|NP_886151.1|         GQGARAYLAVHGGYDLPMVMGSQSTYLRSAFGGYHGRALAKGDQVGLR-----RPLADDA
ref|YP_147354.1|         RTGFRAYIAVSGGIDVPPVMGSRSTYVPAQLGGLSGRPLQRGDAL-----------PVGV
ref|YP_001125467.1|      QAGWRAYIAVSGGIGVPSVMGSRSTYVPAQLGGLSGRPLQPGDVL-----------PIGT
RAAC00483                RRGFRGYLAIRGGFLVEQVLDSRSALPRYGIG----KLLAAGDEMTYQ-----PGPAAPP
                           *  *.*:*:  **   :   *: *:*:     :*   .*   .*:

ref|YP_001420062.1|      SIAYCLSDSFGQHGFSAPDWSVSSRGFLP-LKKNPVIRVLEGAQFHAFTEEAKLRFYQES
ref|NP_242684.1|         RLVKTCQKGI-VHSFATTKWSVVSSQRSR-DGAEKVVRVTVGSHYEQFSEASQHKFFSET
ref|NP_886151.1|         ARLDALAQQLWQLRFY-----LAATLSSP-PRD--VLRILPGPHWEAFDAASRQALLDQA
ref|YP_147354.1|         THGRRVIG-RMRWGLASAARRYIGG-------KTKTVRAVPGPEYDEFTPASRRQFFAAR
ref|YP_001125467.1|      AREHNIRK-PFRWGLSSDAGRYIDG-------KTKTVRAVPGPEYSEFTPESRRQFFAAR
RAAC00483                AGFRAISPRAAVAPFQVGGWLDQIED------EIVILRVVRGEQADWFEKGSRRAFFDRT
                                   :                        :*   *  . *      ::   :

ref|YP_001420062.1|      YTVTPQSDRMGYRLKGAPLELREP-LEMVSEAVTFGTVQVPPDGNPIILLADRQTTGGYP
ref|NP_242684.1|         FQVTSKSDRMGYRLKGPTLERLEE-QELISEPISVGTIQVPADGNPIILMADRQTTGGYP
ref|NP_886151.1|         FRIGAQSDRMGYRLEGPRLRLSER-REMLSEATCFGTVQVPADGAPIVLMADRQTTGGYP
ref|YP_147354.1|         YEVTTQSDRIGYRLSGRALALVRE-REMVSEAVVFGTVQVPASGQPIVLMADSQTTGGYP
ref|YP_001125467.1|      YHVTPQSDRIGYRLSGPALVLGRE-REMVSEAVVFGTVQVPTSGQPIVLMADSQTTGGYP
RAAC00483                WQVAPRSDRMGLRLRGEPLRAPSR--QLASEPVVPGSVQVPQDGLPIVLMRECQTTGGYP
                         :  : ..:***:* ** * *      :: **.  *:::*** .* **:*:. * ******* ref|YP_001420062.1|      RMAHIISADLPLVAQTMPGEHITFRAVSLEEAELLLLEKEQQLKE-LKARL----KMEWL
ref|NP_242684.1|         RIAHVIAVDLPIIAQAKPGAAIRFQQASLKEAERL------------------------
ref|NP_886151.1|         KLAQVATVDLPSLAQAMPGQALRFALIELEQAQRL------------------------
ref|YP_147354.1|         RIAQVASVDLPILAQARPGDFIQFQPIEPEEAMWLYREQQQRLAR-WIAAI----RRQWE
ref|YP_001125467.1|      RIAQVAAADLPVLAQARPGDRIQFQPVAPEEAVQLYIEQQRRLGC-WIAAI----RRQWG
RAAC00483                KLATVISADLDKLAHLRPGSSVRFVEVSFEEAFRLRRVHDR-LARVWLRFVAERARQAWG
                         ::* : :.** :*:  **   *        ::*    * ref|YP_001420062.1|      -----
ref|NP_242684.1|         -----
ref|NP_886151.1|         -----
ref|YP_147354.1|         GE---
ref|YP_001125467.1|      EK---
RAAC00483                SEGGD
```

FIG. 63

```
ref|ZP_01860800.1|        ------MAQKTVVLDQPAIRRALTRIAHEIIERNKGIQDCVLVGIKTRGIHLAKRLANRI
ref|ZP_01695960.1|        ------MAQKAVVMDEIMIRRALTRIAHEIIERNKGIEDTMLIGIKTRGIYLADRLAERI
ref|YP_147000.1|          --------QKAVVMDEQAIRRALTRIAHEIIERNKGIDGCVLVGIKTRGIYLARRLAERI
ref|YP_001125127.1|       --------QKAVVMDEQAIRRALTRIAHEIIERNKGIDGCVLVGIKTRGIYLARRLAERI
ref|YP_806677.1|          ------MAQSKQVVDEVTMKRALTRISYEIIEQNKGLNDLVLVGIKTRGIYLAHRIAKRL
RAAC00134                 ------MAQKTQIMDEAAMRRSLTRMAHEILERNKGLDDLVLVGIVTRGAILAERLGRKL
                                *.  ::*:    ::*:***:::**:*:***::. :*:** ***   ** *:..::

ref|ZP_01860800.1|        EEIEGAKMPVGEIDITLYRDDLTVKTANEEPEVKGSDLPVDVTDKKVILIDDVLFTGRTV
ref|ZP_01695960.1|        ERIEGRKVEVGELDITLYRDDLSKKTVDGEPEVKGANLPSSITGKKIVLVDDVLYTGRTV
ref|YP_147000.1|          EQIEGASVPVGELDITLYRDDLTVKTDDHEPLVKGTNVPFPVTERNVILVDDVLFTGRTV
ref|YP_001125127.1|       EQIEGTSVPVGELDITLYRDDLTMKTEDHEPLVKGTNVPFPVSEQKVILVDDVLFTGRTV
ref|YP_806677.1|          EQLEGLQVPVGELDIQFYRDDVHKIDHDHQPDVEGAQLPVNITGKHVILVDDVIFTGRTI
RAAC00134                 FEIEGQVVPCHRLDPRPYRDDRDRTVSPEAPAPN-----IDVADRKVILVDDVLYTGRTV
                          .:**   :   ..:*  ****        *  :      ::  ::::*:***::****:

ref|ZP_01860800.1|        RAALDALMDVGRPSNIQLAVLVDRGHRELPIRADFVGKNIPTSSSEKIVVELTEVDDEDQ
ref|ZP_01695960.1|        RAAMDALMDIGRPSRIQLAVLVDRGHRELPIRPDFIGKNIPTSQSERIVVQLTDVDGRDL
ref|YP_147000.1|          RAAMDAVMDLGRPARIQLAVLVDRGHRELPIRADFVGKNVPTSRSELIVVELSEVDGIDQ
ref|YP_001125127.1|       RAAMDAVMDLGRPARIQLAVLVDRGHRELPIRADFVGKNVPTSSAEVIVVELAEVDGVDQ
ref|YP_806677.1|          RAALDALMDEGRPRKISLAVLVDRGHRELPIRPDFVGKNIPTSLDEQIQVQVSELDGKDG
RAAC00134                 RAALDAMMRAGRARCVQLATLVDRGHRELPIRPDFVGKNVPTARDEQVIVRLAEVDGLDG
                          *::*  .   :..**********.:*::   * : *.::::*. * ref|ZP_01860800.1|        VTI-----
ref|ZP_01695960.1|        VTI-----
ref|YP_147000.1|          VSIHE---
ref|YP_001125127.1|       VSIHE---
ref|YP_806677.1|          ISI-----
RAAC00134                 VWIAEGRA
                          : *
```

FIG. 64

```
ref|YP_145879.1|        ----------MYTVVGVRFKKAGKIYYFDPGDAVIPVGEFVIVETVRGIEYGKVVIANKQ
ref|YP_001124157.1|     ----------MYTVVGVRFKKAGKIYYFDPGDFVIPAGEFVIVETARGIEYGKVVIANKQ
ref|ZP_01174007.1|      ----------MYDVVGVRFKKAGKIYYFDPGDLSIQKDDFVIVETVRGVEYGKVVIARKQ
ref|YP_001642924.1|     ----------MYDVVGVRFKKAGKVYYFDPNQFDISENEFVIVETVRGIEYGKVVITKKQ
ref|ZP_01697513.1|      ----------MFNVVGIRFKKAGKVYYFDPGDFPVKKNDAVIVETARGIEYGFVVTNPKV
RAAC00215               MRPFAGGYNLMVTIVGVRFKPAGKIYYFDPGDLPIEKGADVIVETTRGIECGRVVVGPKQ
                                    *  ::* *:*.:   :   .  *.:* * **    * ref|YP_145879.1|        VDENDIVLPLKKVIRVANEKDKWVVEENKKAAREAYDICLRKVEEHGLEMKLVDVEYTFD
ref|YP_001124157.1|     VDENDIVLPLKKVIRVANEKDKWVVEENKKAAREAYDICLRKVEEHGLEMKLVDVEYTFD
ref|ZP_01174007.1|      VDENDVVLPLKKVLRIADQKDRMIVEENKEAAHEAYEVCCEKVSTHQLDMKLVDVEYTFD
ref|YP_001642924.1|     VDENDVVLPLKKVIRIANENDRTIVEENRHAAKEAYQVCQQKVGEHNLDMKLVDVEYTFD
ref|ZP_01697513.1|      VGEHDVVLPLKKIIRIADQKDHMTVDENKAAAKEAYGICMKKIAEHQLEMKLVDVEYTFD
RAAC00215               VAEDDVVLPLKEVMRIATEADRAVVEENRRRAKQAMGVFREKVAKHGLEMKLVDAEYTFD
                        * *.*:*****:::*:*  : *:  *:**:   *::*   :  .*:  * *:***.*** ref|YP_145879.1|        RNKVIFYFTADGRVDFRELVKDLASIFRTRIELRQIGVRDEAKMLGGIGPCGRMLCCSTF
ref|YP_001124157.1|     RNKVIFYFTADGRVDFRELVKDLASIFRTRIELRQIGVRDEAKMLGGIGPCGRMLCCSTF
ref|ZP_01174007.1|      RNKVIFYFTADGRVDFRELVKDLAAIFRTRIELRQIGVRDEAKMLGGIGPCGRMLCCSTF
ref|YP_001642924.1|     RNKIIFYFTADGRIDFRELVKDLAAIFRTRIELRQIGVRDEAKMLGGIGPCGRMLCCSTF
ref|ZP_01697513.1|      RNKIIFYFTADGRVDFRELVKDLASIFRTRIELRQIGVRDEAKMLGGIGPCGRMLCCSTF
RAAC00215               RNKLIFYFTADGRVDFRELVKDLASVFRVRIELRQIGVRDEAKILGGIGPCGRLLCCSTW
                        ***:*********:**********::.**.**************:********:*****:

ref|YP_145879.1|        LGDFEPVSIKMAKDQNLSLNPTKISGLCGRLMCCLKYENEEY-------
ref|YP_001124157.1|     LGDFEPVSIKMAKDQNLSLNPTKISGLCGRLMCCLKYESEEY-------
ref|ZP_01174007.1|      LGDFDPVSIKMAKDQNLSLNPTKISGLCGRLMCCLKYENDEY-------
ref|YP_001642924.1|     LGDFEPVSIKMAKDQNLSLNPAKISGLCGRLMCCLKYENDEY-------
ref|ZP_01697513.1|      LGDFEPVSIKMAKDQNLSLNPAKISGLCGRLMCCLKYENDEY-------
RAAC00215               MGEFDPVSIRMAKDQSLSLNPSKISGLCGRLMCCLKFENDAYHDQDAMA
                        :*.*:****:*****.*****.**************:*.:  *
```

```
FIG. 65
pdb|1M2N|A              ------------------------YLVALTGAGVSAESGIPTFRGKDGLWNRYRPEELAN
pdb|1M2K|A              ------------------------YLVALTGAGVSAESGIPTFRGKDGLWNRYRPEELAN
ref|ZP_02127016.1|      ------------------------VVFTGAGVSAESGIPTFRGAGGLWERYRAEDLAT
ref|YP_359129.1|        ------------------------HAIAFTGAGVSTESGIPDFRGNSGLWEQYPVEKVAS
ref|YP_001540277.1|     ------------------------HAIAFTGAGISTESGIPDFRGPQGLWRRFDP-ALAS
RAAC02164               MLYYCSGKPPAKRVHRHLWTWPKSHLVAITGAGISVESGLPTV---DDMVAGVPLRSLFQ
                                                 :.:****:*.***:*    .:        :

pdb|1M2N|A              PQAFAKDPEKVWKWY----AWRMEKV----FNAQPNKAHQAFAELERLGVLKCLITQNVD
pdb|1M2K|A              PQAFAKDPEKVWKWY----AWRMEKV----FNAQPNKAHQAFAELERLGVLKCLITQNVD
ref|ZP_02127016.1|      PEAFARDPKLVWEWY----RWRQTLA----YNARPNPAHYAIAQLEEAGLVKAVITQNVD
ref|YP_359129.1|        RRALMENPAFFLNFY----RERFKSY----ANVKPNRAHEALARMEKAGIIKGIVTQNID
ref|YP_001540277.1|     IDYLNTDPKGFWEFY----IERFRVL----NNARPNKAHLALAELEKLGIIKYVITQNID
RAAC02164               PNIWREQPLEAFHAFR--VIAREWQ------RKRPNRAHLALAQAEIP-----IITQNID
                         :*        . :       *         . :  *:*. *        ::***:* pdb|1M2N|A              GLHERAGSRNVIHLHGSLRVVRCTSCNNSFEVESAP----KIPPLPKCDKCGSLLRPGVV
pdb|1M2K|A              DLHERAGSRNVIHLHGSLRVVRCTSCNNSFEVESAP----KIPPLPKCDKCGSLLRPGVV
ref|ZP_02127016.1|      GLHQRAGSRRVVELHGSLWRARCVQCGAVYKLEKPV----EETP-PRCPRCRGLLRPDVV
ref|YP_359129.1|        GLHQKAGSKNVIEIHGTLKRVRCDRCG-KYYLPEKL----DEEEVPRC-NCGGVIRPDVV
ref|YP_001540277.1|     NLHQSAGSINVIELHGNYTTVYCMRCKTQYPFTLALRKYEEGENPPRCPKCGGILRPNVV
RAAC02164               GLHRAAGSTRVIELHGNLRELRCDACGGIFQSELAWR-----EQLPKCPTCGELLRPGFV
                        .. *  .*:.:**.       *  *    :         *:*  *  ::**..* pdb|1M2N|A              WAGEMLPPDVLDAAMREVERADVIIVAGTSAVVQPAASLPLIVKQR--------------
pdb|1M2K|A              WAGEMLPPDVLDRAMREVERADVIIVAGTSAVVQPAASLPLIVKQR--------------
ref|ZP_02127016.1|      WFGEPLPREAWEEAVQLASSADVVLVVGTSGAVYPAAAIPQIAKRRGAAVVEV-------
ref|YP_359129.1|        LFGEALPRREWQIALELAERSDLVLVVGSSLVVTPANQI---------------------
ref|YP_001540277.1|     LFGEPVN--EINRALEIAALSDVALVVGSSLTVYP-------------------------
RAAC02164               LEGEEVR--HIARALDWVTEARGLLVGTELQMTPVRELYEVARRRNVPIAWVRDHAEDW
                         ** :       *:    .  :    :*.*::.   : * pdb|1M2N|A              --------------------
pdb|1M2K|A              --------------------
ref|ZP_02127016.1|      --------------------
ref|YP_359129.1|        --------------------
ref|YP_001540277.1|     --------------------
RAAC02164               VPYLLGQEGGSDSLFCPGEV
```

FIG. 66A

```
ref|YP_173587.1|        ---------GLQQLVGSVKEVRAVAKGIENDMNEQLLTGLTGSARTVVSAALF----RET
ref|NP_240935.1|        ---------GLQRFIQEQEDTQAIVQGLEVNMKEQLVSGLSGSARPAVMAALY----KET
ref|YP_892975.1|        ------KMIGLLEQFYKNEEIQSVINGLEDGLKEQLVSGMATSSRSLLMAALY----KKT
ref|NP_976379.1|        ---------GLLEQFYKNEEIQSVINGLEDGLKEQLVSGMATSSRSLLMAALY----KKT
ref|YP_001373418.1|     ---------GLLEQFYKNKEVQSIINGLEEGLKEQLVSGMATSSRSLLMAALY----KKT
RAAC01438               MCWEGDKVKGLVELMAADGALSSLADGMGPRRNDILITGVTGAGRQLVMAALYH--LRNR
                                 **  .      ::  .*     ::  *::*:: :.*  : ***:   ::

ref|YP_173587.1|        GRSQ--LVVTHNLYQAQKIYEDLVELLDEDTVYLYPVNELISAEIAVASPEMKAQRLDLL
ref|NP_240935.1|        RRPQ--LVITYNLYQAQKIFEDLVELVGADHVLLYPVNDLISSEIAIASPEMKAQRIDVL
ref|YP_892975.1|        KKSQ--LIVTHNLYQAQKVHEDLVALLGEKDVWLYPVNELIASELGVASPELKAQRIEVL
ref|NP_976379.1|        KKSQ--LIVTHNLYQAQKVHEDLVALLGEKDVWLYPVNELIASELGVASPELKAQRIEVL
ref|YP_001373418.1|     KQSQ--LVVTHNLYQAQKIYEDLVSLLGEKDVWLYPVNELIASEVGVASPELKAQRIEVL
RAAC01438               RLPESMIVVTHTASHAQTIWEDLKEYLPDARVYLYPERDNALVDYLASSSDVLADRLHVL
                         .:   :::*:. :.: * .:    * ***.:     :  :*.::  *:*:.:* ref|YP_173587.1|        NALVQDFKGIVVAPLAGIRRLLPPKALWQSSQLHLKTGEDIGDLEEFIKNFVTMGYRRSD
ref|NP_240935.1|        NQLVAGFSGIVVVPLAGMRRLLPPSSLWKESQIRLSVGDDIGDLESLIRRLVRNGFTRVD
ref|YP_892975.1|        NRLAAGEHGIIVAPVAGLRRFLPMKELWKQRQIEISLGQEI-DLDTFLHTLHHIGYERKS
ref|NP_976379.1|        NRLAAGEHGIIVAPVAGLRRFLPMKELWKQRQIEISLGQEI-DLDTFLHTLHHIGYERKS
ref|YP_001373418.1|     NRLAAGENGIIVAPVAGLRRFLPMKELWKQKQIEINLGQEV-DLDALLHTLHHIGYERKS
RAAC01438               EALAQEGPVVVVTTLLAAWQPVTKKSHFLHSLVNLAVGESK-PIDDVVAQLVRGGYERVS
                         : *.       ::*...:   :  :..   :  :.: *::    :: .: :   *: * .

ref|YP_173587.1|        MVSAPGEFSVRGGIVDLYPLTKEHPLRIELFDTEVDSMRYFSLETQRSEGMIDEVTIGPA
ref|NP_240935.1|        MVTTPGECSVRGGIIDLYPLTEEDPIRIELFDTEIDSIRTFTIEDQRSKDSLSEVVIGPA
ref|YP_892975.1|        MVEAPGEFSLRGGILDIYPLTEELPFRIEFFDTEVDSIRLFDVDEQRSQDKKESVRFGPA
ref|NP_976379.1|        MVEAPGEFSLRGGILDIYPLTEELPFRIEFFDTEVDSIRLFDVDEQRSQDKKESVRFGPA
ref|YP_001373418.1|     MVEAPGEFSLRGGILDIYPLTEELPFRIEFFDTEVDSIRLFDVEEQRSQDKRESVKFGPA
RAAC01438               LVESRGQFSVRGGILDVFPMGHDLPYRIEWFDTDIDSIRTFDPATQRSQDKRDRVSFGPA
                        :*  :  *: *:****:*::*: .: * * *::**:* :    ***:.   . * :*** ref|YP_173587.1|        QEVLLHHSHYSHGAKLLEEKYEATLKKVASKQTRDKLQEHIPFEIAQLKQSATFEGMYKY
ref|NP_240935.1|        AEIIMDEEHPIQGASRLEDRLSQTLKKVKKKEVKEKLTEQISFDISELKQKHPFPSMYKY
ref|YP_892975.1|        TEFLFSQEELKSGIKHLEEGLTKTMQKLSDDKLKTTVLETVSHEIEMLKNGQSIEQMFKY
ref|NP_976379.1|        TEFLFSQEELKSGIKHLEEGLTKTMQKLSDDKLKTTVLETVSHEIEMLKNGQSIEQMFKY
ref|YP_001373418.1|     TEFVFSPEELRVGIEHLEKGLMKTMQKLSDDKIKTAVLETVSHEIELLKNGQNIEQMFKY
RAAC01438               FDLMLPQPVADKVADELEARLEARLKTVTDAALRDRLEQSISADIRKLREGQPFAGVARY
                         : .::       . **   :  :::  : ::.  . : .  : .         . : .:* ref|YP_173587.1|        MSLYYETPQSLLSYMPEDAFVWVDEMNRVKEMAEHLQKEEAEWHTAMLEQGSIVHGTHLS
ref|NP_240935.1|        ISLFYDDTYSLFSYVPSNGVIFVDEMSRVKEMSESLEKEEAEWHTTLIEQGEIVHDVTLA
ref|YP_892975.1|        LSIFYNEPASLIDYLPEDGVVILDEISRIQETASHLESEEEAEWYISLLGEGTIIQDLSFS
ref|NP_976379.1|        LSIFYNEPASLIDYLPEDGVVILDEISRIQETASHLETEEEAEWYISLLGEGTIIQDLSFS
ref|YP_001373418.1|     LSIFYKEPASLIDYLPENGVVILDEISRVQETASHLETEEEAEWYTSLLSEGAIIQDLVFS
RAAC01438               QLLYPEHADTLFDHVPQPAFVCFDETARILERADVLEKEFREWLSGAMMRGEVLSGTVDA
                         ::  .  .:*:..:*.  ..:.** *:  *  :. *:.* **       : .* ::  .  :

ref|YP_173587.1|        LDALARLQQAPQPVLYTSLFQKQVPSTKPEQIINLSCKSMQNFHGQMDLLTSEVNRWLSN
ref|NP_240935.1|        HSVLEQMKQGVLPIVYLSLFVRHVPSTNPQNIISFQCKSMQNFHGQMPLLQSEVKRWISS
ref|YP_892975.1|        HSFEEEFLHHKKRSFVYLTLFLRHIAHTHPQNIVNVTCKTMQDFHGQMQLLKTEIDRWNEG
ref|NP_976379.1|        HSFEEEFLHHKKRSFVYLTLFLRHIAHTHPQNIVNVTCKTMQDFHGQMQLLKTEIDRWNEG
ref|YP_001373418.1|     HSFEEEFLRHKKRSFVYLTLFLRHIAHTHPQNIVNVTCKTMQDFHGQMQLLKTEIDRWNEG
RAAC01438               IHYEAKFQELNRPKVHFATFAHTRGSQRYQQVLNISARSMQNFHGQMNVLKQELARWEKA
                        ::.    . ::  : * :      . :::::.. .::**:*****   *:  **  .
```

FIG. 66B

```
ref|YP_173587.1|         DYTVLFIAGTEDRANRLALNLEDEKIDAHLIEAITDLTPSKV--QIYTGHLHTGFELSEQ
ref|NP_240935.1|         QFATVFIAATRERAKRLNHVLAEEGIEALVVDGEAPLTPGQA--QIMVGALTSGFELTLH
ref|YP_892975.1|         HFTTVVLGTDDERVKKLQHILSDYDIDADIVEGTDILLPGRL--QIAVGDLHAGFEMPMQ
ref|NP_976379.1|         HFTTVVLGTDDERVKKLQHILSDYDIEADIVEGTDILLPGRL--QIAVGDLHAGFEMPMQ
ref|YP_001373418.1|      QFTTVILGTDEERAKKLQHILSDYDIEADIIESTDILLPGRL--QIAVGDLHAGFEMPMQ
RAAC01438                HTQVVFAAATKERADHLARVLDDYRIQADQVE---VFTPGSKVPQIVVANLSSGFELPMH
                           .::..  :*...*   *  :  *:*   ::       : *.   **  ..  * :***:.. :

ref|YP_173587.1|         KLVVVTEEEVFSKRAKRPKRRQKLSNAERIKSYSELAVGDLVVHTNHGVGKYLGVETLEI
ref|NP_240935.1|         KLVVITEEEIFAKKVKRPQRKQKLSNAERIKNYSELKVGDLVVHTNHGIGKYLGIETLEI
ref|YP_892975.1|         KLVVITEKELFHKKVKKSQRKQKLSNAERIKSYSELKVGDYVVHVNHGIGKFLGIETLEI
ref|NP_976379.1|         KLVVITEKELFHKKVKKSQRKQKLSNAERIKSYSELKVGDYVVHVNHGIGKFLGIETLEI
ref|YP_001373418.1|      KLVVITEKELFHKKVKKSRRKQKLSNAERIKSYSELKVGDYVVHVNHGIGKFLGIETLEI
RAAC01438                RIAVIVETEVFTAKRKHRQTRAQVSDAERIKSYQELNVGDYVVHVNHGIGRYMGIKTLEV
                         ::.*:.* *:*   : *:  :  ::*:*****.*.** *** ***.***:*:::*::***:

ref|YP_173587.1|         NGVHKDYLNLRYAGNDKLYVPVEQIDQVQKYVGTEEKDPKIYALGGSDWKKVKKKVQTSV
ref|NP_240935.1|         NGVHKDYLHIRYAGNDKLYVPVEQIDQVQKYVGAEDKDPKLYSLGKSDWKKVKRRVQSSV
ref|YP_892975.1|         NGVHKDYLNIKYQGNDKLYVPIEQIDQVQKYVGSEGKDPKVYKLGGNDWKKVKTKVEKSV
ref|NP_976379.1|         NGVHKDYLNIKYQGNDKLYVPIEQIDQVQKYVGSEGKDPKVYKLGGNDWKKVKTKVEKSV
ref|YP_001373418.1|      NGVHKDYLNIKYQGNDKLYVPIEQIDQVQKYVGSEGKDPKVYKLGGNDWKKVKTKVEKSV
RAAC01438                DGRRNDYLYLSYAGGDSLYVPVDQIDQIQRYIGSGEKEPKLHSLGSSEWQKTKNRVKKSV
                         :*  ::*** :  * *.*.****::****:*:*:*:   *:**:: ** .:*:*.* :*:.**

ref|YP_173587.1|         EDIADDLIKLYAEREASVGHRFSSDGPEQAEFESSFPYQETEDQLRAIKEIKEDMEKQRP
ref|NP_240935.1|         EDIADDLIKLYAEREASKGFAFAPDGPEQAEFEASFPYQETEDQLRAIQEIKEDMEKERP
ref|YP_892975.1|         QDIADDLIKLYAEREASKGYAYTPDTAEQQEFESSFPYQETEDQLRSIEEIKKDMERGRP
ref|NP_976379.1|         QDIADDLIKLYAEREASKGYAYTPDTAEQQEFESSFPYQETEDQLRSIEEIKKDMERGRP
ref|YP_001373418.1|      QDIADDLIKLYAEREASKGYAFTPDTAEQREFESSFPYQETEDQLRSIEEIKKDMERSRP
RAAC01438                RDIAGDLLKLYAKREATPGHAFSPDTPWQADFENMFPYEETEPDQLRAIAEIKRDMEKPRP
                          .***.**:****.***:  *.  ::.*  .* :**  ***:** ****:* ***.***:  **

ref|YP_173587.1|         MDRLLCGDVGYGKTEVAIRAAFKAIMDGKQVAILVPTTILAQQHFETISDRFSDFPITVG
ref|NP_240935.1|         MDRLLCGDVGYGKTEVAIRAAFKAIMNGKQVAILVPTTILAQQHFETIQERFADYPINIG
ref|YP_892975.1|         MDRLLCGDVGYGKTEVAIRAAFKAIMDEKQVAILVPTTILAQQHYETIRERFQDYPINIG
ref|NP_976379.1|         MDRLLCGDVGYGKTEVAIRAAFKAIMDEKQVAILVPTTILAQQHYETIRERFQDYPINIG
ref|YP_001373418.1|      MDRLLCGDVGYGKTEVAIRAAFKAIMDEKQVAILVPTTILAQQHYETIRERFQDYPINIG
RAAC01438                MDRLLCGDVGYGKTEVAMRAAFKAVMDGKQVAVLVPTTVLAQQHYETFKERFAGFPVKIE
                         ****************:******.*:  ****:*****:*****::: :**  .*:..:

ref|YP_173587.1|         VLSRFRSRKEQTEVLKGLKAGSVDLVVGTHRLLSKDVQFRDLGLLIVDEEQRFGVTHKEK
ref|NP_240935.1|         VLSRFRSRKEQSQTLKGLKAGSVDLVVGTHRLLSKDVQFKDLGLLIVDEEQRFGVTHKEK
ref|YP_892975.1|         LLSRFRTRKQQNETIKGLKDGTVDIVIGTHRILSKDVTYKDLGLLIIDEEQRFGVTHKEK
ref|NP_976379.1|         LLSRFRTRKQQNETIKGLKDGTVDIVIGTHRILSKDVTYKDLGLLIIDEEQRFGVTHKEK
ref|YP_001373418.1|      LLSRFRTRKQQNETIKGLKDGTVDIVIGTHRILSKDVTYKDLGLLIIDEEQRFGVTHKEK
RAAC01438                MLSRFRTRKETQEVLKGLKEGTIDIVIGTHRLLQNSVQFKDLGLLIVDEEQRFGVTHKEK
                         :***::   :..:**** *::*:*:****.::.* ::****:************ ref|YP_173587.1|         IKRMKANIDVLTLTATPIPRTLHMSMLGVRDLSVIETPPENRFPVQTYVVEFNPAIVREA
ref|NP_240935.1|         IKQLKANIDVLTLTATPIPRTLHMSMLGVRDLSVIETPPENRFPVQTYVVEYNSPLVREA
ref|YP_892975.1|         IKQLKANVDVLTLTATPIPRTLHMSMLGVRDLSVIETPPENRFPVQTYVVEYNPALMREA
ref|NP_976379.1|         IKQLKANVDVLTLTATPIPRTLHMSMLGVRDLSVIETPPENRFPVQTYVVEYNPALMREA
ref|YP_001373418.1|      IKQLKANVDVLTLTATPIPRTLHMSMLGVRDLSVIETPPENRFPVQTYVVEYNPALIREA
RAAC01438                LKQLRANVDCLTLTATPIPRTLHMSMLGVRDLSIIETPPENRFPVQTYVVEYNEGLVKEA
                         :*:::**:* ************************:*****************.*   :::**
```

FIG. 66C

```
ref|YP_173587.1|       IERELSRGGQVYVLYNRVEDIERMTEQISTLVPDARVSYAHGQMNERELESIILDFLEGE
ref|NP_240935.1|       IERELSRGGQVYFLYNRVENIERMANEISMLVPDARVSFAHGQMKESELESIMLAFLEGE
ref|YP_892975.1|       IERELARGGQVYFLYNRVEDIERKADEISMLVPDARVTYAHGKMNESELESVMLSFLEGQ
ref|NP_976379.1|       IERELARGGQVYFLYNRVEDIERKADEISMLVPDARVTYAHGKMNESELESVMLSFLEGQ
ref|YP_001373418.1|    IERELARGGQIYFLYNRVEDIERKADEISMLVPEARVTYAHGKMNESELESVMLSFLEGQ
RAAC01438              IERELARGGQVYFVYNDVQTIHRMAERVQSLVPDARVSVAHGQMAEAELERVMLDFLEGE
                       *****:****:*..** *: *.*  ::.:. ***:***: ***:* * *** ::* ****:

ref|YP_173587.1|       SDVLVTTTIIETGVDIPNVNTLIVCNADKMGLSQLYQIRGRVGRSNRVAYSYFTYQPDKV
ref|NP_240935.1|       SDVLVTTTIIETGVDIPNVNTLIIHGADKMGLSQLYQIRGRVGRSNRVAYAYFTYQRDKV
ref|YP_892975.1|       HDVLVSTTIIETGVDIPNVNTLIVFDADRMGLSQLYQLRGRVGRSNRVAYAYFAYKRDKV
ref|NP_976379.1|       HDVLVSTTIIETGVDIPNVNTLIVFDADRMGLSQLYQLRGRVGRSNRVAYAYFAYKRDKV
ref|YP_001373418.1|    YDVLVSTTIIETGVDIPNVNTLIVYDADRMGLSQLYQLRGRVGRSNRVAYAYFAYKRDKV
RAAC01438              YDVLVTTTIIETGLDIPNVNTLIVYDADKFGLSQLYQLRGRVGRSNRIAYAYFTYQPAKV
                       ****:*******.********:  .**::*******:**********:**:**:*:  **

ref|YP_173587.1|       LTEVAEKRLQAIKEFTELGSGFKIAMRDLTIRGAGNLLGSQQHGFIDSVGFDLYSQMLKE
ref|NP_240935.1|       LSEVAEKRLQAIKEFTELGSGFKIAMRDLAIRGAGNLLGAQQHGFIESVGFDLYSQMLKE
ref|YP_892975.1|       LSEVAEKRLQAIKEFTELGSGFKIAMRDLSIRGAGNLLGAEQHGFIDSVGFDLYSQMLKD
ref|NP_976379.1|       LSEVAEKRLQAIKEFTELGSGFKIAMRDLSIRGAGNLLGAEQHGFIDSVGFDLYSQMLKD
ref|YP_001373418.1|    LSEVAEKRLQAIKEFTELGSGFKIAMRDLSIRGAGNLLGAEQHGFIDSVGFDLYSQMLKD
RAAC01438              LSEVAEKRLAAIKEFTELGSGFKIAMRDLSIRGAGNLLGAEQHGFINSVGFDMYTELLQQ
                       *:******* ******************:.*********::.****.*****:*::*::

ref|YP_173587.1|       AIEERKGEKPKEPPFKAELNVNIDAYIPERYIPDAKQKIEMYKRFKGVETLEEIADLQDE
ref|NP_240935.1|       AIEKRKGEQPKEEPRNVEIDVQVDAYIPDSYIQDAKQKIEMYKRFGVETIEEINDLKDE
ref|YP_892975.1|       AIEQRRGTDGVENTVNVEIDLEVDAYLPDAYISDSKQKIMMYKQFRGVSAIEDIEELQEE
ref|NP_976379.1|       AIEQRRGTDGVENTVNVEIDLEVDAYLPDAYISDSKQKIMMYKQFRGVSAIEDIEELQEE
ref|YP_001373418.1|    AIEQRKGKQGIENTIDVEIDLEVDAYLPDSYISDSKQKIMMYKQFRGVSTLEDIEELQEE
RAAC01438              AIRELRGEQ-LEKPVEPTIDVPVEAYIPDTYISDPSQKVAMYKRFRAIQAVSEADDLEDE
                       **.: :*  .  *  . ::: ::**:*: **  *..: *:*:.:.::.:  :*::* ref|YP_173587.1|       LVDRFGEYPKQVAYLFEMTKIKLIADQEKVEKI-TEGKDAVTILLTEETTNRIHVATLVD
ref|NP_240935.1|       MFDRFGEYPQEVSDLLQLTTIKIIAYQEGVESI-VESKGQWIILLSPETTEGIDGAKLFE
ref|YP_892975.1|       MIDRFGDYPQEVGYLLQIANIKVLAMKEQIELI-KQNKFEVTILFSEQASQNIDGGKLFM
ref|NP_976379.1|       MIDRFGDYPQEVGYLLQIANIKVLAMKEQIELI-KQNKFEVTILFSEQASQNIDGGKLFM
ref|YP_001373418.1|    MIDRFGDYPQEVGYLLQIANIKVLAMKEQIELI-KQTKSEVTFLFSEQASQNIDGGKLFM
RAAC01438              LIDRYGDPPQEVRNLLDVTRLKSLAMQAHADHIATQGAD-TTVRFPNEKHAPVDYPKLLS
                       ::**:*: *::*  *:::: :* :*  :  * .    .:. :.   .*.

ref|YP_173587.1|       AAQKIGRDVSIGSQGNQIKLVIKTKQLSDETLLAYIIELLEALIRADKSKK--------
ref|NP_240935.1|       VIHKLDQQVGLGTEGERIKLTLKTKQLGTNQLLEVTETLLASLAD---------------
ref|YP_892975.1|       LGNSFGRMIGLGMEGSQLKIVMKTNGL---------------------------------
ref|NP_976379.1|       LGNSFGRMIGLGMEGSQLKIVMKTNGL---------------------------------
ref|YP_001373418.1|    LGNK--------------------------------------------------------
RAAC01438              MAVKHKAQVTSRPNG-MIFVAFRTKGLAGDEIVRRIIAFLTDYLEMVRQSKKQEEVAGV
```

```
FIG. 67 ref YP_117520.1|         ------------------VIAASLRRERTRAGLSLSEVAARAGIAKSTLSQLESGSGNPSL
ref YP_707186.1|         -----------------IGPSLRRERERSGMSLTEVARRAGVAKSTLSQLESGGGNPSV
ref YP_046943.1|         ----------------IEIVAKGLHREROKAGLSLAELARRAGIAKSTLSQLEAAQGNPSL
ref YP_001337847.1|      ---------------ISVIAKSLVRERARTGLSLAEVARRAGIAKSTLSQLESGNGNPSL
ref YP_001105447.1|      ----------------MLAANLRALRERAGLSLSEVARRSGIAKGTLSQLESGAGNPTI
RAAC03184                MILFDISNILIHMNIMKIVSNNLRALRLARGWSISELERRSGVAKGTISQLESGYGNPTV
                                         :. .*    *    * *::*:  *:*:**.*:****:. ***::

ref YP_117520.1|         ETLWALCVALDMPFSRLLD-----PPRPVVHVIRAGEGPAVAAERS-DYHATLLAAGPSN
ref YP_707186.1|         ETLWALCVALDVQMSQLLD-----PPRPRVQVIRADEGPELTSDRS-DYRATLVASSPPS
ref YP_046943.1|         ETLWSLCVALEIPFAKLME-----SNIPQTQVIRFGEGPSVASEIA-HYQAILLANCPTG
ref YP_001337847.1|      ETLWSLCVALDIPFARLLE-----PQVNKTQVIRRGEGTKVVAEQA-NYQAILLAACPPG
ref YP_001105447.1|      ETVFSLSNALSVPVSSLLT-----ERLDPEVVLVRSRGLEVLSSNAVDLRMLRRMDLTET
RAAC03184                ATLWSLASALSVPFSDLIQ-----TAKETESVHESP----VLAEPSGTTRFVDRVTM-EG
                         *:::*. **.: .: *:          *           : :. :    :

ref YP_117520.1|         TRR----------DLFRITAE----------PGQPRESQPHIPGVIEHILLAAGRALV
ref YP_707186.1|         ARR----------DLYRLAVE----------PGPARESEPHMPGVVEHVILSAGRALV
ref YP_046943.1|         ARR----------DVYILNTQ----------PGEPRLSHPHPIGSIEHIIIMKGCAKV
ref YP_001337847.1|      ARR----------DIYLLLTQ----------PGADRISHPHPPGSVEHIIVTQGRARV
ref YP_001105447.1|      VFE-----------LYDQRVR----------PGEVQRSEGHP--GREHVVVTSGVLRV
RAAC03184                MIE-----------IYEMVLS----------KDDERVSEAHPLGIMEHILVVQGRMEV
                                     ::                .  : *. *     **::: *   * ref YP_117520.1|         GPTGEPVELAPGDYIAYPGDAPHVFEALEPGTWATLVIEY---------------
ref YP_707186.1|         GVAGDPVELGPGDYIAYPGDVAHVFEALEAGTRAVL-----------------
ref YP_046943.1|         GLTAEPVVLNEGDYICYPADQEHIFEALDEDTRAIL------------------
ref YP_001337847.1|      GLTSAPEELGEGDYICYPADQEHVFQALEPDTQALL------------------
ref YP_001105447.1|      GPPDSPFELEAGDYVCFPARQPHIYETVGGPVVSVLLLEYPA------------
RAAC03184                GPIGQEIALNPGSYTTFPGYVRHVYRSLDEEARAVLWLVYPSIRAGHEGEGATL
                         *         *  *.*  :*.   *::.::   . : *
```

FIG. 68

```
ref|NP_391246.1              ---------- -----SFGEQ LRALREERKL TVNQLATYSG VSAAGISRIE NGKRGVPKPA
ref|NP_391246.1              ---------- ---------Q LRALREERKL TVNQLATYSG VSAAGISRIE NGKRGVPKPA
ref|YP_001488252.1|          ---------- ----MKFGAY LRALREEKKL SVNQLAMYSE VSAAGISRIE NGKRGIPKPP
ref|NP_244416.1              ---------- -MEGKQFGSF IRALRKKKGF TVNQLALYSG VSSAQISRIE NGLRGVPKPE
ref|YP_001488252.1|          ---------- ---------- LRALREEKKL SVNQLAMYSE VSAAGISRIE NGKRGIPKPP
RAAC02740                    MYNSDVRGGE SMDTLNFGEY LRSLRLARKL SINQLAEKTG ISAAHISRLE RNVREVPRPD
Clustal Consensus                                   :*:   : : ::**   :  :*:* ***:* .. * :*:* ref|NP_391246.1              TIKKLAEALK IPYEGLMYKA GYIEEVHEA- ---------R APYETKCKLL EKAEAYDLKN
ref|NP_391246.1              TIKKLAEALK I--------- ---------- ---------- ---------- ----------
ref|YP_001488252.1|          TIKKLASALK VPYEDMMQAA GYIEE----- ---------- ---------- ----------
ref|NP_244416.1              TIKKLSEALG HPYEDLMQAA GYIDDNTKT- ---------D LP-----ALT ERDER-----
ref|YP_001488252.1|          TIKKLASALK V--------- ---------- ---------- ---------- ----------
RAAC02740                    TLRKLALGLG VPFDELLRAA GYSEEQYEYN TKVLSRRLQR LRESKGLSLS DVAHIAGISE
Clustal Consensus            *::**: .* ref|NP_391246.1              LAL------- ---------- ---------- ---------- ---------- ----------
ref|NP_391246.1              ---------- ---------- ---------- ---------- ---------- ----------
ref|YP_001488252.1|          ---------- ---------- ---------- ---------- ---------- ----------
ref|NP_244416.1              ---------- ---------- ---------- ---------- ---------- ----------
ref|YP_001488252.1|          ---------- ---------- ---------- ---------- ---------- ----------
RAAC02740                    AYLARLESAE GRLPGVTTLH RLAQVFDVTP AYLVGDTPDP KDNGPLDAWY QPKDLIQWLE
Clustal Consensus ref|NP_391246.1              ---------- ---------- ---------- -------
ref|NP_391246.1              ---------- ---------- ---------- -------
ref|YP_001488252.1|          ---------- ---------- ---------- -------
ref|NP_244416.1              ---------- ---------- ---------- -------
ref|YP_001488252.1|          ---------- ---------- ---------- -------
RAAC02740                    ESEVMFEGQP LTDEDKLKIK QILAVVFMDA KRKNQRP
Clustal Consensus
```

FIG. 69

```
ref|YP_075413.1|          --EEIGRRLK AARLAKGLTL EQVEEETRIR KKYLDALESG RTVLIPGEVY VKGFLRSYGN
ref|YP_001662816.1|       --KELGEFLK SERIKMGLTL EEIQEITKIR IRYLKAIEDG DFSVMPALVY AKGFVKSYAE
ref|YP_001662816.1|       PQQNQSEAST ISEDKTNLPQ ESNVSQLTVK TSIEKVAETS KKIEYKVVPF G----ESYKV
ref|YP_001664674.1|       --KELGEFLK SERIKMGLTL EEIQEITKIR IRYLKAIEDG DFSVMPALVY AKGFVKSYAE
ref|YP_001664674.1|       PQQNQSEAST ISEDKTNLPQ ESNVSQPIVK TSIEKVAETS KKIEYKVVPF G----ESYKV
RAAC02937                 MHEQLGQILR ARRESLGLTV EDIEERTKIR KRYIEALESG QWDVLPGRVY ARGFVRSYAE
Clustal Consensus         ::  ..        . .*. *. .     ::      .. * .            :      .**

ref|YP_075413.1|          FLGLDGEGLV EEYKALKARP AAEDGAGNGG PAEAPAREPE AAIAASAPRA -SAEPRQPAF
ref|YP_001662816.1|       ALGLDGNELV KKY------- ---------- ---------- ---------- ----------
ref|YP_001662816.1|       EISVPGEKCW FSVKVDGN-- ---------- ---------- ---------- ----------
ref|YP_001664674.1|       ALGLDGNELV KKY------- ---------- ---------- ---------- ----------
ref|YP_001664674.1|       EISVPGEKCW FSVKVDGN-- ---------- ---------- ---------- ----------
RAAC02937                 VLGLDGSELL EKYVDGGDAG SAEP----GV RAESPALTSE NRAADRKPAA RMVEPRSLN-
Clustal Consensus         :.: *.      .

ref|YP_075413.1|          ATPPRRSSRS RPKRRRNGPG PGVYFLRRLM VALILILPLA AAGWWFWGRQ AAAPPPQEPG
ref|YP_001662816.1|       ---------- ---------- ---------- ---------- ---------- ----------
ref|YP_001662816.1|       ---------- ---------- ---------- ---------- ---------- ----------
ref|YP_001664674.1|       ---------- ---------- ---------- ---------- ---------- ----------
ref|YP_001664674.1|       ---------- ---------- ---------- ---------- ---------- ----------
RAAC02937                 ---EMERTRS RAHERHERSR RETYDRPVRS VGSWVGQGLL IVGALVVVGG LYVLLHHHHG
Clustal Consensus ref|YP_075413.1|          QVAQEPGTTA QQPEPEPEPE PEPEPEPEQP PASGQPVPAK PVITVGAPQG DEVD--ITIT
ref|YP_001662816.1|       ---------- ---------- ---------- ---------- ---------- ----------
ref|YP_001662816.1|       --VVYEGLMT KDMSKIFDVK DSITILMGYP PAVKITVDGE ELPTVQTPSP VTI-------
ref|YP_001664674.1|       ---------- ---------- ---------- ---------- ---------- ----------
ref|YP_001664674.1|       --VVYEGLMT KDMSKIFDVK DSITILMGYP PAVKITVDGE ELPTVHTPSP VTI-------
RAAC02937                 QATERINTTT SSPQKTQAIK P-AIHQTAPP KRTTQPIQKA QTVVVALPYA NGMYIYKVLF
Clustal Consensus ref|YP_075413.1|          ASEVQLEMDF TQGFPWLEVY SGGETLY--- WSKASGPLSF TGKD-FRIRI GFVAGFQLAL
ref|YP_001662816.1|       ---------- ---------- ---------- ---------- ---------- ----------
ref|YP_001662816.1|       ---------- ---------- ---------- ---------- ---------- ----------
ref|YP_001664674.1|       ---------- ---------- ---------- ---------- ---------- ----------
ref|YP_001664674.1|       ---------- ---------- ---------- ---------- ---------- ----------
RAAC02937                 AASLQVVVTV NSGELWFSAT ADGQAVAPNV ILNQGQSKSF SAQNNVTFHL GHVQGVSITV
Clustal Consensus ref|YP_075413.1|          NGEPV----- ---------- -
ref|YP_001662816.1|       ---------- ---------- -
ref|YP_001662816.1|       ---------- ---------- -
ref|YP_001664674.1|       ---------- ---------- -
ref|YP_001664674.1|       ---------- ---------- -
RAAC02937                 DGQPVQLPNI TWAPVVVIER G
Clustal Consensus
```

FIG. 70

```
ref|YP_034761.1|        ----LSKLIKKLLKERALSMRQLGMLTNIDPATISRIMNGKQPPKQKHLQKFAECLQVPP
ref|ZP_00237972.1       --------------------QLGMLTNIDPATISRIMNGKQPPKQKHLQKFAECLQVPP
ref|YP_893335.1|        --------------------QLGMLTNIDPATISRIMNGKQPPKQKHLQKFAECLQVPP
ref|YP_001373772.1      --------------------QLGTLTNIDPSTISRIISGKQQAKQKHLQKFAECLKVPP
ref|ZP_02329595.1       ----LGSTIKALLKERSLSMRKLSALTGIDTATISRIVNGKQAAKPDHLKVFALHLGVPV
RAAC00675               MMGHLEETVKSLLRRRSMSMRQLATATGISVSTISKMIAGKQRVNLDYLRRIADALGVPP
                                             :*.  *.*. :*::: *   : .:*: :*   *  ** ref|YP_034761.1|        QLLFDE--MYPDSPHINKEKT-----DMYTSLDTIQQTLQSSNLFDFDYTTTRVKQELEN
ref|ZP_00237972.1       QLLFDE--MYPDSPHINKEKT-----DMYTSLDTIQQTLQSSNLFDFDYTTTRVKQELEN
ref|YP_893335.1|        QLLFDE--MYPDSPHINKEKT-----DMYTSLDTIQQTLQSSNLFDFDYTTTRVKQELEN
ref|YP_001373772.1      QLLYGA--LHSASSPIKKEKI-----DMYNSIDTIQDTLQSSNLFDYDYTTIRVKQELEN
ref|ZP_02329595.1       ERLFQA-----AGYDVGTNKTS-TEIGIHTSINRIKEVLQSSNFFDYELTTELVQKELFK
RAAC00675               LTLAEA-----AGLPLIKEPIGPTDGDRQTSMNALLEYLGLGNLN---VLRTEIERELEK
                           *            .  .*:: : : *  .*:               :::**  :

ref|YP_034761.1|        YERYAQTTEGEKRIHESFASKLEQIDSAGPFIEQLTDMYQQFCNETIPKEERAVLGGALL
ref|ZP_00237972.1       YERYAQTTEGEKRIHESFASKLEQIDSAGPFIEQLTDMYQQFCNETIPKEERAVLGGALL
ref|YP_893335.1|        YERYAQTTEGEKRIHESFASKLEQIDSAGPFIEQLTDMYQQFCNETIPKEERAVLGGALL
ref|YP_001373772.1      YERYAQTTEGQMRIHESFSTKLKQIDSTGPFIEQLTEMYQQFCKDTISETERAVIGSALL
ref|ZP_02329595.1       YEQYALTEEGQRVIHNEFSSKVEKVNGSGPFIDELRQMHELFCSREVSQDTRAIAGSALL
RAAC00675               YEAYAQTEEGRQFIAEKYLAKRGQIQGIGDFLRDLDDIYDRFSRPDTPEDERRILASGIL
                          * **.   *  .:  :*    :::. * *: :* ::::  *.    .:   * :  ...:* ref|YP_034761.1|        YFILSTDIIPDYLFPIGYLDDAIAVELAKEKL---------------
ref|ZP_00237972.1       YFILSTDIIPDYLFPIGYLDDAIAVELAKEKL---------------
ref|YP_893335.1|        YFILSTDIIPDYLFPIGYLDDAIAVELAKEKL---------------
ref|YP_001373772.1      YFVLSTDIIPDYIFPIGYLDDAIAVELVKEKLAHFRK----------
ref|ZP_02329595.1       YFILSADIIPDYVFPIGYLDDAIAVQMVRNRLS--------------
RAAC00675               YFLLATDAIPDYLFPAGYLDDAIAMQMVRERLARRREMKDQGAEGS
                        **:*::* ****:** ********:::.::::*
```

FIG. 71

```
gb|AAB91591.1|         MSPFGQQLRELRRARKLTVNQLAVYSGISSATISKIENGKRGTPKPATIKKLAAVLKVPY
ref|NP_391247.1        MSPFGQQLRELRRARKLTVNQLAVYSGISSATISKIENGKRGTPKPATIKKLAAVLKVPY
ref|YP_001422657.1|    MNTFGKQLRELRRARKLTVNQLAVYSGVSSATISRIENGHRGIPKPATIRKLADTLKIPY
ref|YP_093160.1        MTNFGHHLRQLRERKKLTVNQLAMYSGVSSAGISRIENGKRGVPKPATIRKLADALKVPY
ref|NP_391246.1        MESFGEQLRALREERKLTVNQLATYSGVSAAGISRIENGKRGVPKPATIKKLAEALKIPY
RAAC02292              MSQFGQYLRKLRKERNLTINQLALYSGVSSALISRIENGQRGRPKPDTLKKLASALKVPY
                       *  **. ** **. ::**:****  ***:*:*  **:****:**  *** *::***  .**:**

gb|AAB91591.1|         ENLMAAAGHIRAFPEEIREASES---------------------------------------
ref|NP_391247.1        ENLMAAAGHIQAFPEEIREASE----------------------------------------
ref|YP_001422657.1|    EELMARAGHIKAFQEEIRETSES---------------------------------------
ref|YP_093160.1        EELMASAGYISAS--TVQEARS----------------------------------------
ref|NP_391246.1        EGLMYKAGYIEE--------------------------------------------------
RAAC02292              EDLLLHAGVLNEQISRTSESRDLKPVDPSWYKRQVPIPVLGSIRAGTPVEMLALNSSEFV
                       * *:   **  :

gb|AAB91591.1|         ------------------------------------------
ref|NP_391247.1        ------------------------------------------
ref|YP_001422657.1|    ------------------------------------------
ref|YP_093160.1        ------------------------------------------
ref|NP_391246.1        ------------------------------------------
RAAC02292              LVDSDLLGNHEGFALEVVGDSMIGDYIFPGDLVIVKYTSNFSPQDICVVAINGEEATLKR gb|AAB91591.1|         --------------------------------------------
ref|NP_391247.1        --------------------------------------------
ref|YP_001422657.1|    --------------------------------------------
ref|YP_093160.1        --------------------------------------------
ref|NP_391246.1        --------------------------------------------
RAAC02292              VKCQGDICILTPSNPSMEPMVYNSVDVHVIGVVVEVRRRLRNK
```

FIG. 72

```
ref|NP_845841.1       ------------------------------MYIPKYFAIQDEKMKYEIMEQNSFATLFSQH
ref|ZP_02260616.1     ------------------------------MYIPKYFAIQDEKMKYEIMEQNSFATLFSQH
ref|ZP_02256143.1     ------------------------------MYIPKYFAIQDEEMKYEIMEQNSFATLFSQH
ref|ZP_00235680.1     ------------------------------MYIPKYFAIQDEEVKYEIIEQNSFAILFSQH
ref|NP_241278.1       ------------------------------MYIPKAFHVDDVNELITFIRNHSFGIMVSQT
RAAC01655             ------------------------------MYIPRSFELKDAQLIETVLREHSFAVLVTSV
                                                    ****: *  :.*  :    .:.::**. :.:.

ref|NP_845841.1       NGEPYATHLPLLLNR---ETLTLHGHFARPNEQWKDIGTQQVLAIFQGPHSYISPSWYET
ref|ZP_02260616.1     NGEPYATHLPLLLNR---ETLTLHGHFARPNEQWKDIGTQQVLAIFQGPHSYISPSWYET
ref|ZP_02256143.1     NGEPYATHLPLLLNR---ETLTLHGHFARPNEQWKDIGNQQVLAIFQGPHSYISPSWYET
ref|ZP_00235680.1     NEESYATHLPLLLNR---ETLTLHGHFARPNDQWKDSGNQQVLAIFQGPHSYISPSWYET
ref|NP_241278.1       EEEPFATHLPFLLDEQKGENGVLISHLARANPHWQGLQDQKVLVVFQGPHAYISPTWYDE
RAAC01655             GEDIMATHVPLVYDP---AEAALFGHLARANPQAKHLHEAQCLAVFQGPHAYVSPAWYGL
                       :  ***:*:: :    .*  .*:**.*  :  :    : *.:******:*:**:**

ref|NP_845841.1       KNAVPTWNYVAVHVYGELELVEDEQELIDSLQDLVDTYEDPQSTYSLNDVDPNYMEGLSK
ref|ZP_02260616.1     KNAVPTWNYVAVHVYGELELVEDEQELIDSLQDLVDTYEDPQSTYSLNDVDPNYMEGLSK
ref|ZP_02256143.1     NNAVPTWNYVAVHVYGELKFVEDEQELIDSLQELVHKYEDPESAYSLNDVDPNYMGGLSK
ref|ZP_00235680.1     NNAVPTWNYVAVHVYGELEIVEDEQELIDSLQKLVYKYEDPKSTYSLNDVDPNYMTGLSK
ref|NP_241278.1       PRTVPTWNYVAVHVYGTFRQIQDKHKVKEWIEKTVNVYEQTMNPPWEAVFDEPFMEGLLN
RAAC01655             ADQVPTWNYIAVHVYGRARVIEDEEAVADLLQRLLLTYDP--QSPLPADRDRPYYRNLMR
                           ******:******  .  ::*:. : :: :   *:   ..    *   :  .* .

ref|NP_845841.1       GIVGFKIKISKIEGKAKLSQNHSVARRKLVVEELEKVGSEGSRGIAELMRK---------
ref|ZP_02260616.1     GIVGFKIKISKIEGKAKLSQNHSVARRKLVVEELEKVGSEGSRGIVELMRK---------
ref|ZP_02256143.1     GIVGFKVKINKIEGKAKLSQNHSVERRNLVVEKLEKVGSEGSKGIAELMKETK-------
ref|ZP_00235680.1     GIVGFKIKINKIEGKAKLSQNHSVERRKLVVEKLEKVGSEGSREIAELMR----------
ref|NP_241278.1       GIVAFEIEVERMEGNWKLNQNHPIERQERVVKKLKSINEPNAQKMAELMEK---------
RAAC01655             GIVAFRIDIARIKAAAKLSQNKPLEVRARVVEALESQDDANSRAVAAWMRRLKLTHLGDD
                      ***.*.:.:  :::. **.**::.:  :  **: *:.. ..::  :.   *.

ref|NP_845841.1       -----------
ref|ZP_02260616.1     -----------
ref|ZP_02256143.1     -----------
ref|ZP_00235680.1     -----------
ref|NP_241278.1       -----------
RAAC01655             DGNESKPKGAS
```

FIG. 73

```
ref|ZP_02329455.1|      ---NVSEIIEHYLKHILQQSPNGAIEIQRNELADQFQCVPSQINYVISTRFTLEKGYLVE
RAAC00436               MASNISDIIEAYLKRLMEESGLDVIEIQRNELAEQFHCVPSQINYVISTRFTTDHGYIVE
ref|YP_077369.1         MGKNISDIIEQYLKQILEQNGKEILEIKRSEIADKFQCVPSQINYVINTRFTSERGYIVE
ref|YP_001419762.1      MGHNISDIIEQYLKQVLDQNGKEILEIKRSEIADKFQCVPSQINYVINTRFTSERGYIVE
ref|YP_001485328.1      MAQNISDIIEQYLKEVLDQNGREILEIKRNEIADKFQCVPSQINYVINTRFTSERGYIVE
ref|ZP_02171828.1|      ---NISDVIEGYLKQIIEKNDQELIEVKRSELAEQFDCVPSQINYVIRTRFTVEKGYMVQ
                           *:*::** ***.::::.     :*::*.*:*::*.********** **** ::**:*:

ref|ZP_02329455.1|      SKRGGGGYVRIQKIELNSHGSILDYILTTINQSIDQSTSEGLIYRLEEGEFLTAREAKLI
RAAC00436               SKRGGGGYIRIRRVKLDKDHLLWD-VLRSLGDEVSQSASEALIERLHRDGWLTDREAALI
ref|YP_077369.1         SKRGGGGYIRIIKIKMNDKIDLINNIMNQIYTRLSQAASDDIILRLLENGVITESEAKLM
ref|YP_001419762.1      SKRGGGGYIRIIKIKMNNEVVLINNIISQIHTHLSQAASDDIILRLLEDGVISEREAKMM
ref|YP_001485328.1      SKRGGGGYIRIIKVKMNDEVDLLNNIISQIYHRLSQAASDHIIMRLVENNILSEREAKMM
ref|ZP_02171828.1|      SKRGGGGYIRITRVTPDNHLQLYDQLIDLSGDEISQTAAMHLIGRLLEEEAITKREANLM
                        ********:**  ::   :..   : : ::       :.*::: :* **    ::  ** ::

ref|ZP_02329455.1|      RAAISRDVLQFKLP---------------------
RAAC00436               SAMLRREVLALGLPYRDRLRAKLLASALQALAAHRKP
ref|YP_077369.1         VSVMDRSVLYIDLP---------------------
ref|YP_001419762.1      VSVMDRSVLYIDLP---------------------
ref|YP_001485328.1      ISVMDRSVLHIDLP---------------------
ref|ZP_02171828.1|      ESVMNREVLSIRLPY--------------------
                          : : *.** : **
```

FIG. 74

```
ref|YP_001485324.1      -DVWGRRIRAYRKLKGYTQEGFAKRLGISVSVLGEIERGNRLPTNQLVGQIADALNITVE
ref|YP_077366.1|        -EIWGRRIRAYRKLKGYTQEGFAKALGISVSVLGEVERGNRMPTESMLRDVANTLNITVE
ref|NP_829977.1|        -EKWGRRIRAFRKLKGYTQEGFAKELGVSVSVLGEVERGNRSPSQDFVVEVAKALNVSIE
ref|YP_001124204.1      -ERWGRRIRAFRKLKGYTQERLAKELGVSVSILGEIERGNRMPSDSLVEQIAELLNISIE
ref|YP_145925.1|        -ERWGRRIRAFRKLKGYTQERLAKELGISVSILGEIERGNRMPSDSLVGQIAERLNISVE
RAAC01464               MDAFGRRLRAFRKLKHMTQADLARALGVSLATIGGIERGTRQPTAHLVSAIASALSVDVE
                         : :*::**      :*: **:*::  :*  :***.* *:    ::    :*.  *.:  :* ref|YP_001485324.1      EL----------------------------------------
ref|YP_077366.1|        EL----------------------------------------
ref|NP_829977.1|        EL----------------------------------------
ref|YP_001124204.1      ELTPP-------------------------------------
ref|YP_145925.1|        ELAPP-------------------------------------
RAAC01464               ELCGPTWPGDGWDRGAAEDAADSRAGHGHATVDGPHSPLDQGAMVR
                        **
```

FIG. 75

```
ref|ZP_01440002.1|      -----DRSEEVAA-ILSLIANPARLRILCLLAEGEMQVGALAERVGLSQSALSQHLAKLR
ref|ZP_01419169.1|      --------DDACA-LLKALANPHRLMIVCALIDGEQSVGALAHLLGVRETLASQHLGLLR
RAAC00579               MTHGPDMPEDVCMRCLAVLGEPQRLRILRALAEGEQTAGALSERLGVRQNTLSHHMRQLR
ref|YP_001623237.1|     ---------------LEAIAEPTRRRILDAIRTGERSVGDLVEIVGMHQPGISRHLKVLR
ref|NP_896891.1|        ---------------LKALADPTRLDVIHALAEGERCVCDLTADLGITQSRLSFHLRVLR
ref|ZP_01084741.1|      --------DQARALLKALGDPVRLRVIEALGGGERCVCDLVTDLGLAQSKLSFHLKVLK
                                     *  :.:*  *    ::  :  **    *    :*: :    *  *: *:

ref|ZP_01440002.1|      AGGAVETRR---DRQTIYYRL---------------------------------
ref|ZP_01419169.1|      RDGVVAARR---DGQTIYYGLRGGQARALV----ETLS-----------------
RAAC00579               EHGLVEVRRHPHDERFTFYRLNGRRLRALS----AVLTDWAARADAECETSGRWSS
ref|YP_001623237.1|     DSGLVEVRQ---DAQRRLYRLRAEPLKELD----QWLEPYRLEWAGRLDA------
ref|NP_896891.1|        DCGLLTDR---HSGRWTYYRLQPDALSALE----DWLAALRQHCSRS---------
ref|ZP_01084741.1|      QAGLLADRQ---EGRWIYYRLRPETLGALQ----AWLTDLGAHCGA----------
                              *  :   *         .  :         *  *
```

FIG. 76

```
ref YP_954024.1|         -----VPAERLAATFKALADPARVKLLSLIAA------------ARDGE--------ACI
ref ZP_00050136.2|       ---------ELARTFKALADPTRVQLLAIVAAQ------------EGHE--------ACV
ref YP_001156989.1|      --------ERLAGVLKALADPARLRLLSLIQS------------APEGE--------ACV
ref YP_001360254.1|      --------------LKALADPARLRLLSLVA------------AHEGGE--------ACV
RAAC03156                MMVIDVTNEEVLTCLHALADKSRFQILQMMAKG---SIATCCDRIEAYEN------GCCV
ref YP_591607.1|         --------------LRAVADPTRRRILRMLGEK--------GHCSIGE-----STGLCA
                                       ::*:**  :*  ::*  ::              *         * ref YP_954024.1|         CDLTAPLGLSQPTVSHHMKLLVDAGLVSRQQRGKW-AYY---RIQRDALDRVAQDVAALT
ref ZP_00050136.2|       CDLTGPVGLSQPTVSHHLKILVDAGLLTREQRGRW-AYY---SLVPGALARVAG---SLT
ref YP_001156989.1|      CDLTAPLGLSQPTVSHHLRILTEAGLLEREKRGVW-AYY---RLVPTAIATIAD---LLT
ref YP_001360254.1|      CDLTEPLGLSQPTVSHHLKVLVEAGLLTRDKRGVW-AYF---AVVPETLNALAA--VLVT
RAAC03156                ADVVAVTGLSQPTVSHHLKVLEKAGLVRRESRGPWTCYFPNSQALEEVVKALTSELMMPA
ref YP_591607.1|         RDIEAKIKLSQPTVSHHMKILADAGLITGQRRGQW-TWY---RRDETAVRQMTKKFREEL
                           *:     *********::*  .***:   : ** *  ::        .:   ::

ref YP_954024.1|         S------------------------
ref ZP_00050136.2|       -------------------------
ref YP_001156989.1|      -------------------------
ref YP_001360254.1|      PA-----------------------
RAAC03156                NVHNHEKGECCPCPDGSPMSPSTCET
ref YP_591607.1|         -------------------------
```

FIG. 77

```
ref|YP_001309477.1|    ------------------------------MIHITNLKESLPLFKALSSDVRMNILEILSQYK
ref|YP_001180339.1|    ------------------------------IDNLKEAKILFEALASDARLEIINLLSKHR
RAAC00603              MSPCRPLSESSGLFYTHVKIMAGVGDRVIHIKELRSGLPLFKALGSEVRVALLELLEHG
ref|NP_242735.1|       -------------------------------------LPVYEALASKVRLAIIQQLTRKS
ref|YP_173905.1|       ---------------------------------KQSLPVYEALASRIRLNVLQLLAERS
ref|ZP_00603386.1|     -------------------------------------LPVYEALASKTRIKIIQLLSKK-
                                                            :::**.*  *: ::: * .

ref|YP_001309477.1|    QLNMNELSEKLDLTNGAVTMHIKKLEECGLIKTTNLTGKHGLQKICSLHEDKFVIDI--G
ref|YP_001180339.1|    EMNMNEIAQKLGLTNGAVTQHMKKLIAAGIVTISAASGKHGNQKICRLVEDKIIINI--V
RAAC00603              RLNMDEIAKRLGITNGAVTQHVRKLEECGLVVTETAGARHGLQKFCYVNEQKILVEL--A
ref|NP_242735.1|       -MNIRELAEAVGLSSAIMTMHIKKLEKAGIIRTEMVPGKAGIQKLCILDTDHIEINFPPK
ref|YP_173905.1|       -MNIKELAESQQVSSAIMTKHVQKLEKAGLIDTTHVRGKAGVQKMCSLRVRHAQIAFPNK
ref|ZP_00603386.1|     KMNVKDLAKELGVSSAITTMHVKKLEEANIIKTEKVGQ----QKISSLRVDKIDISFPEK
                         :*:  ::::    ::..  * *::**   ..::        **:. :   :  : :

ref|YP_001309477.1|    KQDVENS-YHIDLNIGHYSNYDITPTCGIATKDSIIGEVDNPNYFADPERINADILWFTK
ref|YP_001180339.1|    TK-HPQKLYECEIKVGNYSIFEVYPTCGLATKDKLIGEVDDPKYFAHPEHVNCDIIWFTK
RAAC00603              PETKDQDVYEVDIRVGHYVSFEVWPTCGLATAETIIGTFDDPRYFADPQHIDAEIVWLTK
ref|NP_242735.1|       KE-SLKLYHQTILSVGHYTDFLVEPTCGLATAEKIIGEFDEPRYFLDPERVNAKILWFSK
ref|YP_173905.1|       ENGPTRAFHESHVSVGHFTDFYVEPTCGLATPETIVGEFDEPRYFLDPMRVNARILWFYK
ref|ZP_00603386.1|     IFNAFDT-KETSIPIGHYTNYAIEPTCGLATIHDFIGKVDEPRYFMDPRRMDARILWFTS
                            .  :  :*::    : :  ****:**  .  ::*  .*:*.**  .*  :::. *:*: .

ref|YP_001309477.1|    GSIEYRIPNYLKPSEVFSELQISMEISSEAPGVCSIWPSDIHFYLNNVNVGRWTSPGDFG
ref|YP_001180339.1|    GYVEYIIPNFLRQNQKAVEIQISFEISSEAPGVSENWPSDIYFYLNGVELGYWTSPGDFG
RAAC00603              GYLEYWIPNFIRTDRPVEEIQIIAELASEAPSYNNDYPSDIHFSINGVDIGYWTSPGDFG
ref|NP_242735.1|       GYIEYKIPNFLHHSENPKELEISLELSSEAPFTNDNWPSDISFYFNNVKIGIWTSPGDFG
ref|YP_173905.1|       GFVEYKLSNFIHGGETPKELEISMELSSEAPFTNDNWPSDVSFTPNGVSLGYWRSPGDFG
ref|ZP_00603386.1|     GFVEYQAPNFLNTEDTLEMLEVSVEISSEFPFSNDNWPSDITFSLNGVELGTWTSPGDFA
                       * :**  .*::.        :::  *::** *. :*: **** *.*:*.:*:* *  * *****.

ref|YP_001309477.1|    -DSKGILTPSWWNPHWNQYGLLKLLTINSFGTFIDGIKISDVTLEDLELTYKSDILLKLA
ref|YP_001180339.1|    GETKGIFTPDWWFPNWNQYGLLKLLSVSEDGTYIDGFKISNVTIKDIDIESKNEIRFRVA
RAAC00603              -DERGRQNPSWWPPHLNQYGHLKLVRVNHEGTFIDGCKISDVTIEDLQPFQGHAIPLRFS
ref|NP_242735.1|       -DSPGKYTPDWWPKVINQYGLLKPFIRITKEGTFIEGAKISDVTIDDVH-IRSKQWSFRVA
ref|YP_173905.1|       -DQKGKYTPAWWPRGINQYGLLKVIRITEAGTFIDGKQLSDVKLADVS-IREKVWTFRVA
ref|ZP_00603386.1|     -DIRGKYTPDWYPDNLNQYGLLKTIRITKHLTNMNGEPLSNITINDI-PKEQDTWHLRIE
                        :   *  .* *:   **** ** : :.    * ::*  :*::.: *:          ::.

ref|YP_001309477.1|    VPEETKHVGGLTIFGKNFGNYNQGISVRLVY------
ref|YP_001180339.1|    VPDHAKNIGGVTLFGRNFGNYDQDIKFRIFY------
RAAC00603              VPENARHVGGMTIFGRRFGHYDQDIKVRVIYGRGARD
ref|NP_242735.1|       VPDDAENVGGVTIFGEGFGNYNQDIIFRLYY------
ref|YP_173905.1|       VGEEGVHIGGVTLFGSSFGNYDQDIVFRLYY------
ref|ZP_00603386.1|     VKDDAKHVGGCTLFGKGFGNYDQDIKLKVYY------
                       *  :.    ::** *:**  **:*:*.*  .:: *
```

FIG. 78

```
ref|YP_001664041.1|      -----KRIKELRKKKGITQKELASYLGISDRAVGYYESGQRTPPPDILQKIADFFNVSTD
ref|YP_085042.1|         ------RIKSLRKKENLTQKQLAEKIGVSQRMIGYYESEERFPPHDVLSKLADCFSVSAD
ref|NP_242309.1|         ---FPERLRYLRKKHGLTMKELGKKINVAESTISGYENGNRKPDMDTLVKMAEYFNSSTD
RAAC03180                MSSFPERLSELLSATNSTKRALARAIGISERMIQYYITGAKSPTLDVLVAMADYFNVGLD
ref|ZP_02038515.1|       ---FEERLYQLRRERGISQEELANIIGVSRQAVQKWESGASQPNIDNLVAISEYFGVTLD
ref|YP_001210714.1|      ---FAKRLSFLITKNKLSKQAVANAINVSRPAVSQFANGENLPSVEKLIALADFFDVSLD
                            *:  *          : . :.  :.::    :   :  .   *   : *  ::: *.   * ref|YP_001664041.1|      YLLG-----------------
ref|YP_085042.1|         YLLG-----------------
ref|NP_242309.1|         YLLG-----------------
RAAC03180                YLAGRSDDPTPPPRSPSSGWDP
ref|ZP_02038515.1|       YL-------------------
ref|YP_001210714.1|      YLVG-----------------
                         **
```

FIG. 79

```
ref|ZP_02309926.1|        ----FSKRLSELRKKKGFSQYKLADELGFSRGQVANYEQGTREPDYQTLLKIAEFFNVST
ref|ZP_01941236.1|        ----FSKRLSELRKKKGFSQYKLADELGFSRGQVANYEQGTREPDYQTLLKIAEFFNVST
ref|ZP_01926077.1|        ----FSKRLSELRKKKGFSQYKLADELGFSRGQVANYEQGTREPDYQTLLKIAEFFNVST
ref|NP_469419.1|          ----FSKRLSELRKKKGFSQYKLADELGFSRGQVANYEQGTREPDYQTLLKIAEFFNVST
RAAC02417                 MMMTFGERLAQLRRSKGLSQYALAEQLKMTRGQIANYEQGTREPDIETLKKLADFFDVSI
ref|YP_001111866.1|       ---------------MTQEQLAQQLGFTRGQVSNYEQGSREPDFETLKKIADFFKVTT
                            :*   **::*  ::***::*****:****  :**  *:*:**.*:

ref|ZP_02309926.1|        DYL-LGR----DDNNLADTIAAHID--SNATEEDIKEILAYIEEKR--KEHANEKEINIT
ref|ZP_01941236.1|        DYL-LGR----DDNNLADTIAAHID--SNATEEDIKEILAYIEEKR--KEHANEREINIT
ref|ZP_01926077.1|        DYL-LGR----DDNNLAETIAAHID--SNASEEDIKEILAYIEEKR--KEHVNEEEINIT
ref|NP_469419.1|          DYL-LGR----DDNNLADTIAAHID--SNASEEDMKEILAYIEEKR--KEHANEEEIDIT
RAAC02417                 DFLVLGKPNVSDFNGLTNEVKRTLEALSQMSVEKQQEVADFAEYLRS-KEEQPVVEYDVR
ref|YP_001111866.1|       DYM-LGR---------------TD--DPTPVDKLIELSALAGQQK--FDPMK-------
                          *::  **:                    :   . .:.  *:        :   :

ref|ZP_02309926.1|        EIASKEDEEINKFVDEN--EDFKVVAARVM--------------
ref|ZP_01941236.1|        EIASKEDEAVDKFVEEN--EDFKAVAARVM--------------
ref|ZP_01926077.1|        EIASKEDDAVDKFVEEN--EDFKAVAARVM--------------
ref|NP_469419.1|          DIAAKKDADVAKFVEEN--PDFKAVAARVM--------------
RAAC02417                 EIAANMEKALYAHGDEDLIQHFEEIMRRVIRRYDERASQDQQNR
ref|YP_001111866.1|       ELPPEAQRSL---------EDFIDYLMRK---------------
                          ::..:  :   :          .*      *
```

FIG. 80

```
ref|NP_625321.1|           ------------EQRRALILDEVRRGGVRVNELTRKLGVSDMTVRRDLDALSRQGVLEK
ref|NP_822608.1|           -----ENQNLLAEQRRALILDEVRRGGVRVNELTRKLGVSDMTVRRDLDALARQGVLEK
ref|YP_001103030.1|        ------------RQRQEVILNEVRRTGAVQVSALVLQLGVSDMTIRRDLDALARRGLVEK
ref|ZP_00996757.1|         ------------QRRAAILSMVQDSGAVRVSDLVEHLGVSDMTVRRDIERLDTDGLLER
ref|YP_001363698.1|        ------------QRQEVILDAVRTHGGVRVADLVERLGVSEMTVRRDIGELSRRGLVAR
RAAC01912                  MIKRREVRTVYPKERQRVLLELLAQHGFASYRQLAERLGVSEITVRRDMKALEAQGLVET
                                        :*:  :*. :   *  .    *,.:****::*:***:    *  *::

ref|NP_625321.1|           VHGGAVPVAEASTHEPGFEAKSGLEPTAKEDIARAAAELVAPGAAIALSGGTTTYALAHR
ref|NP_822608.1|           VHGGAVPVVEASTHEPGFEAKSGLETAKEDIARAAAELVAPGTAIALSGGTTTYALAHQ
ref|YP_001103030.1|        VYGGATSMVGRSTDEPGFEAKSVRQLAEKEAIAMLAAEQVRPGTAIGLSAGTTTWTLARH
ref|ZP_00996757.1|         VHGGALALLPRATDEPGFTAKSSLMTAAKHAIALAAARLVDPGATIGISAGTTTYEFARA
ref|YP_001363698.1|        VHGGAAS-VARSSEEPGFAAKAGLRPDAKRAIARAAADLVPDGASVALSAGTTTAEVARE
RAAC01912                  AFG--GGQVARAARELPYTDKRILQIPEKIAIAKAALRQIESGMTIAIAAGTTTWVLAQH
                           ..*        ::  * :  *       * ** *    : *::::.****    .*:

ref|NP_625321.1|           LVDVPDLTVVTNSVRVADVFHVAQRTSGARQGGATVVLTGG-VRTPSDSLVGPVADQAIA
ref|NP_822608.1|           LVDVPDLTVVTNSVRVADVFHAAQRTSGQRQGAATVVLTGG-VRTPSDSLVGPVADQAIV
ref|YP_001103030.1|        LDDVADLTVVTNSIRVADALQQRGRTDR------TVVLTGG-VRTPSDALVGPVAVQSLR
ref|ZP_00996757.1|         IRNIPHLTVVTNSVPVAQLLHESG-------GNHVVVLTGG-VRTPSDALVGPVAVAALQ
ref|YP_001363698.1|        LRDVSDLTVVTNSPRVADLLHDPADHSR------TVVLSGGT-RTPSDALVGPVARAGLR
RAAC01912                  IAGFQNLTPLTNSVNVATELSKNGYR--------DIFLTGGQFRTPSDALVGPVAEHMIR
                           :  .. **.:***  **  :               :.*:**  *****:******   :

ref|NP_625321.1|           TLHFDALFLGVHGISAEAGLSTPNLAEAETNRRLVQSARRVVVVADHTKWGVVGLSSFAA
ref|NP_822608.1|           ALHFDVLFLGVHGISVEAGLSTPNLAEAETNRRLVQSARRVVVVADHTKWGTVGLSSFAS
ref|YP_001103030.1|        SLHLDLVFLGVHGIAARAGFTTPNLNESETNRALAEAANRLVVVADHSKWSTVGISTIVD
ref|ZP_00996757.1|         GLHVDRLFLGAHGIDRNAGLTTPNLVEAETNRALVRASRSVCVLADHSKVGIVGLSTFMA
ref|YP_001363698.1|        GLHVDLLFLGVHGLDAAAGLSTPNLSEADTNRALMDCAARVVVVADASKWGVVGLTSFAD
RAAC01912                  QFRADILFVGASGLHVDHGLSTPNVLEAAVNRAMMERAARVVVLADHTKWGVESLMSFAK
                             :: *  :*:*. *:   *::***: *: .**   :  :*:**  *  .  .: ::

ref|NP_625321.1|           LEQVDTLVTD--SGLSADARAEVAE-HLGLVVAGEPEPEA-------
ref|NP_822608.1|           LDQVDTLVTD--AGLPAGARAEVSEHLRRLVVAGEP-----------
ref|YP_001103030.1|        LHEVDLLISD--DGLPQEARQVLSENVPELVLAEVP-----------
ref|ZP_00996757.1|         LHEVDTLITD--PGTPARVRALLEDSVDHLVLAEVASA---------
ref|YP_001363698.1|        LGSVDLVLTD--AALDPSARPVISDLVGELVVAGTPQEE--------
RAAC01912                  LSEIDALITD--RWPGEAEAAALAECDVDLIVADAPNAESSKRGDAQ
                           *  .:* *::*       :  :      *:* .
```

FIG. 81

```
ref|YP_001169444.1|      ------------------------------IRRRIVSLNYPPGLMIFENAVAAEFGVSRTP
RAAC02663                MGLRGGGDVIAGVTYGVAKKTLGEQAYEVIREEILSLRLHPGQTVYESDFTRMLNMSRTP
ref|NP_435364.1          -------------------ETAAAQVERDLRESIIRLELAPGMRLSEQEIATRMGVSRQP
ref|YP_001313948.1|      -------------------ETAAAQVERDLRESIIRLELAPGSRLSEQEIATRMGVSRQP
ref|ZP_01509063.1|       -------DLTASVSFD-SHEPIGKQIFRALRQAIFVGQLVPGTPLSEKEVSDMFQVSRQP
ref|YP_527240.1          ------------------------QIFEYLRDAIVSMELRPGQMIAETSLAEQFGVSRTP
                                                   :*  *. .  ** : * .:  : :** * ref|YP_001169444.1|      VHQAFMRLSHEGLLDVLPQRGARVSFLSRSTIIHAQYVRECLEAAAFFDAAR--IWDAAD
RAAC02663                VREAVRALAMERLIEVLPQRGMKVALISERQVEETRFVRESLELSVIRRVAEDVAQDASV
ref|NP_435364.1          VREALIALGKSKLVDIRPNRGTVVVRISARQMMEARFVREAIEVAVARRASETF--DSWT
ref|YP_001313948.1|      VREALIALGKSKLVDIRPNRGTVVVRISARQMMEARFVREAIEVAVAQRASE--AFDSWT
ref|ZP_01509063.1|       VREAFIKLVEAGVLQVLPQRGTFVKRISPRQVREGRFIREAIETAVVKKAAVSIS-DEQL
ref|YP_527240.1          VREALIKLSNIGFVEVLPQRGTYVTKFSTQKILEARFIREALEVAVAADLAS-----NVT
                         *::*.  *      .:::  *:**   *   :*    :  . :::**.:*  :.    :

ref|YP_001169444.1|      AAHLQ---RERRAQDLIEAQREAVARGDYLRFTELDVAFHTEILGVLGNDLLLACVSQMR
RAAC02663                RARLE---REMARS--LQDQREAAEAGDALQFMHADDAFHQIFLQHFDNETLTAIVAQMR
ref|NP_435364.1          RR-----KIDTILAR----QKAANEAHDHNAFRREDEQFHIAIAEGAGCGLAWNAVSDIK
ref|YP_001313948.1|      RG-----RIDTILSR----QRAAEEINDHNAFRREDEQFHIAIAEGAGCGLAWNAIADIK
ref|ZP_01509063.1|       QA------LADNLRD----QKIAAKANDTAAFLALDEAFHYAIAQAIDCTAAWETIQDIK
ref|YP_527240.1          EE------LVEACQAIIEAQSKAADEDDSITFQKLDDEFHQMLAQHTQYARVGSLIEAEK
                                            *    *    *    *  **   :              :    :

ref|YP_001169444.1|      NQLNRLRLLELREAHHEKRMIADHEALLAAVSAGRADEARRRLITHLKTLEDFREEIFGR
RAAC02663                GHLNRVRMLSLFEPERMKRLVGEHERVAEAVLSGNADRSAEAMHHLAKLMEDLPGIKAR
ref|NP_435364.1          AHMDRVCNLQLRHPDSMKKLIAEHEAIITAIDARDADAAAAAMRSHLNGILADLPQIEAD
ref|YP_001313948.1|      AHMDRVCNFQLRHPDLMKNLIAEHEAIIIAIDARNAEAAANAMRRHLNGILSDLPQIEAD
ref|ZP_01509063.1|       AQMDRVRYLSLPDVSPLDLLIKQHAKILAGLRAHDASAAEEAMRNHLREILMSLGPIAAR
ref|YP_527240.1          AHMDRVRNLSLQEAGQFKRVLAQHKAIVKAIKAGDANKAQEAMSTHMREVYKILTVIPAE
                         :::*:  :.*  .     . :: :*    :  .: :   *. :    :    *:  :        *  .

ref|YP_001169444.1|      HPDLFRP
RAAC02663                HPAFFGP
ref|NP_435364.1          NPDLF--
ref|YP_001313948.1|      NPDLF--
ref|ZP_01509063.1|       NPAWF--
ref|YP_527240.1          HPEYF--
                         :*  *
```

FIG. 82

```
ref|YP_643029.1|         --------LRRPEPLYRQVYEVLRRRILAGEYGAGEVLQESRAAEELRVSRTPVREALRQ
RAAC01158                MERRSVTAIQRSEPLVKQVYKYLYHAILSGEFRPRDKVVETHIAERLQVSRSPVREAIRL
ref|YP_077724.1|         --------SIQRAVSYHDQVHHYLKDMIIKGGYQPGERIYESKIAKELQVSRSPVREAIRT
ref|YP_001308645.1       --------IEKAPSYYDQAYNSIKAMIFNGILKPGDRIYESKLASEFQISRSPVREAIRS
ref|YP_174340.1|         --------VERPIPYYEQFYHSIKKMIFTGHFKPGDRIVETQLAKEFNVSKSPIREAIRI
ref|YP_516602.1|         -----MSAITKSLPFHLQIYEILKGKILNGEISRGERLYENKISQELGVSRSPVREALRM
                                   :  ..   *  :. :    *:  *       :  : *.: :..: :*::*:***:* ref|YP_643029.1|         LEREGLLVARGTE-RVVADPSREEFVDLYTCRAALEGLVAERAARLAEEEELREMEEALE
RAAC01158                LIQRDLLVEDADG-VRVFQPTQRDFAELYEMRLALEPVAAERAAENAHSTCVAALHENVK
ref|YP_077724.1|         LEQEGLLLIDDKSKITVYEPTIKDLEEIYQCRQALESLAVSLATRLASNETLELISETLS
ref|YP_001308645.1       LEKDGLLVIGDKSKITIYKPTKEDIENIYECRQALESQAAKLTTLKASNKELDKIEKILL
ref|YP_174340.1|         LEKEGLVIVDEKSRVIVYKPTQKDVEEVYFCRMALESFAVSEATKIASDEDIHELEKLLI
ref|YP_516602.1|         LEQDELVVVTSTG-LIVNPMEFSDMEEIYQCRMALEPFAAKISADKLTNEDLAALRNLVI
                         *  :  *::         :        :.. ::*   *  ***   ... ::    .   :   : : :

ref|YP_643029.1|         EARRAVAAGDHGGV-------LSANTRFHDLMVRSARMPPLERLMDTLRGQILVARRHIL
RAAC01158                QTEQALALGDWDSI-------VALNKEFHECIWQMSGNRRILKAMQEITDLVQFYWRALL
ref|YP_077724.1|         EAHKHQKSQGPESA----NALLRLNTQFHDAIIEASENERLQKQLLDLRSLTFFYRSKNL
ref|YP_001308645.1       EIKKNIDNFDDTLT----KNIIELNTKFHDLILDFSQNNHLKKLSKDLSSLTYFYRSIDV
ref|YP_174340.1|         RTDQAISSKKEEDR------IISLNELPHSTIIDYTKNLRLKKQINDLKALIYYFRILNF
ref|YP_516602.1|         QARVYHNQKAYEKV-------VESNTQFHDIIIQSSGNSRLIGIIEKIRSLIILSRKTEF
                               :        *   **.    :           .     .

ref|YP_643029.1|         SDERIEAEICEEHASILEAIRRRDVGAARERMQRHMQNDIR-------------------
RAAC01158                DIPNLDIQIVGDHQQIVQYIERRDSAGAHTAMKQHVAKDLRVISERFRDAKNAFKEQILD
ref|YP_077724.1|         EKPERTLEIINQHEEILRHMQDRNDAKAAESMRKHIEADLCYLKE---------------
ref|YP_001308645.1       YEPERNIDIFNHHLEIFNYIKQRDEEKAYKAMYNHIDNDLK------------------
ref|YP_174340.1|         QGDNRANVILEQHYRIFEFIKKRDPEKAAKAMISHLELDL-------------------
ref|YP_516602.1|         ECYQREEGYLDEHEGVLEALTQRNGDEAERLLRIHIMNDPEFYS---------------
                              .    .*  :.. :  *:   *     :  *:  *:

ref|YP_643029.1|         --
RAAC01158                EA
ref|YP_077724.1|         --
ref|YP_001308645.1       --
ref|YP_174340.1|         --
ref|YP_516602.1|         --
```

FIG. 83

```
ref|ZP_02082978.1|        ----------------SRPLYEQVAERLRELMFKGALPQDAQLPSVRSLATELSINPNTI
ref|ZP_01962813.1|        ----------------RPIYEQITEKFRTLIYQGALPAGCRLPSVRQLAMELSINPNTI
RAAC00068                 MTLDPPWQPPAWELDPSQPLYEQIAHRLRVEIAASRLPGGARLPSVRDLAAHLRVTPNTV
ref|YP_001420528.1|       ------------EFQSSKPIYLQIADRVYYRLIRSELSPGDKLPSVREMAVQMKVNPNTI
ref|YP_430032.1|          ------------EFDNSRPIYLQIIAAIKKQLARGELQPGQKLPSQREMAEELQVNPNTV
ref|ZP_02328287.1|        ------------PNLDLSKPLYEQVLSQIRSSIAKGEIALGEKIPSVREMAQALKITPNTV
                                          :*:* *:    :   .: . .::**  *.:*   : :.***:

ref|ZP_02082978.1|        QRAYTELERQGYIYSIKGKGSFVADNS---------------------------------
ref|ZP_01962813.1|        QRAYMTLEQEGLIYPVKGKGNFVAETRQIQEKSKEDFRKEFL-ELVRR------------
RAAC00068                 MRAYAELEQDGLLETFRGQGTFVARGSGVEARARARIARQAF-EHVRRVAADLGMRVEDL
ref|YP_001420528.1|       QRTYSEMERLGIVETRRGQGTFIAERSDLKAELKDRLTKDVFKRFIQEM-AELGL-----
ref|YP_430032.1|          QRAYREMEAMGLLETLRGQGTFISNRPGL-------------------------------
ref|ZP_02328287.1|        MRAYQELERDQLTVTRRGQGTFITSNAETVEQIKYNLAEIATGEYVRKM-TDIG------
                           *:*   :*       . :*:*.*::

ref|ZP_02082978.1|        ------------------
ref|ZP_01962813.1|        ------------------
RAAC00068                 LRLGAEAEGGAEDDASSH
ref|YP_001420528.1|       ------------------
ref|YP_430032.1|          ------------------
ref|ZP_02328287.1|        ------------------
```

FIG. 84

```
ref|YP_642998.1|        ------GSLS-----------------------------DVAYEKLYGDITGGRLQPN
RAAC01035               MGQQDGGKLSPLWHACGITVPDDKSTGGVAHVEVPSQGYTEEECYRRLRDAIIDGTLMPS
ref|NP_822795.1|        ---PSTGEQAK----------------------------QHALTQLRQAILHGEMAPA
emb|CAJ88752.1|         ---------------------------------------------QLRQAILRGDMAPA
ref|YP_001191149.1|     ----TRGKKS-----------------------------DYIYERLKTDIQRGKFLPG
ref|YP_752794.1|        VDLDSYKPLR-----------------------------ELVLEAIREAIKNGVLKPR
                                                                      :  *  * : * ref|YP_642998.1|        ERLIELDIARELGVSRAAVRNALIRLEQEGLVKREPNRGARVRLVSEEEAVEILEARMAL
RAAC01035               QRLVEMDLARWLGASRATIRTVLARLEQEGLVERERYRGARVRHVSHEEAVEILEVRMAL
ref|NP_822795.1|        QRLVENELAEQFGVTRASIRAALIDLAAEGLVERIRNRGSRVRVVTVEEAVAITECRMVL
emb|CAJ88752.1|         QRLVENELAEQFGVTRASIRAALIDLESQGLVERIRNRGSRVRVVTVEEAVAITECRLVL
ref|YP_001191149.1|     QRLVEDALAKEYGSSRNTIRLALTRLENDGIVKRTT-SGVIVSFIDLKEAVEILEVREVI
ref|YP_752794.1|        ERLMEIQLAEELGVSRTPIREALRKLELEGFIVMVPRKGAYVADISLKDVADVFEIRAAL
                        :**:*   :*.  *  :*  .:*  .*   *  :*::    *   *  :  ::..: * *  .:

ref|YP_642998.1|        ECVAVRHAALNRTQEDIAGLREILSQMESRLEAGDLLGASDLNGQFHRRLVEISNHATIS
RAAC01035               ECLIARYAALRATDEDVRRLEDIISWMRRQYEGNDLLSYSDGNARLHRTIAEISRHNTAK
ref|NP_822795.1|        EGLCAAKAAVAASDEQLTELADLGAAMTKAVADGEPVTYSELNHELHDRIREFSGQQTAV
emb|CAJ88752.1|         EGLCAAKAASAVDDGQLGELKDLGTAMRKAVADGEPLVYSDLNHELHARIREFSGQRTAV
ref|YP_001191149.1|     EGFLARKAATRISEESLQRLESTLMEMKTALENREFLRYSQLNERFHSIIYEASGNTTAQ
ref|YP_752794.1|        EALAAGLAAERITDEELEAMERLLVEKVEAISSNDMDKLVDVDTKFHEAIYRASRNQRLF
                        *  .  .  **      :   .: :            :         : :.:*  :  . *:

ref|YP_642998.1|        KLLKMLNSQLIRFQYRTILTPGRPASSLAEHRAIFEAVEAGDPERAEQAMRRHLSGVTEA
RAAC01035               RLLDTLNSQSVRYQYRTILAPNRSAASMQEHERIVDAIRRRDPDSAEQAMRVHLSQVCDT
ref|NP_822795.1|        ELLERLNAQLVRHRFQLALRPGRPQHSLNEHLSMIEAIRDRDPQAAEVAVRAHLTSVIEA
emb|CAJ88752.1|         ELLERLNAQLVRHRFQLALRPGRPQQSLNEHLAMIEAIEARDPQAAEAAVRAHLTSVIEA
ref|YP_001191149.1|     LLLSTLKLKMIRYQFRTVMVPGRAEVSWNEHFRIFQALKNHDENEAELWARTHVKNVREL
ref|YP_752794.1|        AIINNLREQIQRFRSTSLSYPGRMQQSMQEHRDIVEAIQSRDIQLSRQLAQEHI------
                        :: . *.  :  *.:       *.*   *  **  . :*:.   *  :  :.   : *:

ref|YP_642998.1|        LR------
RAAC01035               LRSMRQGF
ref|NP_822795.1|        LR------
emb|CAJ88752.1|         LR------
ref|YP_001191149.1|     IQNNKE--
ref|YP_752794.1|        --------
```

FIG. 85

```
ref|YP_148128.1|        ------------IPIYYQLEQYMKEKIEKGEWQPGEMIPSERELAEMYDISRMTVRQAVN
ref|YP_001126297.1|     ------------VPIYYQLEQYMKEKIEKGEWQPGEMIPSERELAETYDISRMTVRQAVN
ref|ZP_01697892.1|      ------------IPIYFQIQEEIRKKIREGEWKTGEAIPSERVLSDLFEVSRMTVRQAVQ
RAAC02031               MTKGSIRSMRESVPLYKQLKSELLEKILSGEWPPGEQIPSEAELASMYDVSRTTVRQAVG
ref|ZP_01662088.1|      ------------PLYERIKGTLREGILSGHYAPASLLPSEAALGEQFNASRITVRQALA
ref|YP_900875.1|        ------------MPLYHQVESHLKENIGNGTWKAGEAIPPERMLVDQYGVSRITIRQALA
                                    *:*  ::    :  :  * .* :  ... :*.*   *  . :  ** *:***:

ref|YP_148128.1|        NLVNDGYLIRRRGKGTFVAAQKIEQPLKGLT---SFSEDMRARGMEPGTIVLSFEMVPAS
ref|YP_001126297.1|     NLVNDGYLVRRRGKGTFVAAKKIEQPLKGLT---SFSEDMRARGMEPDTVVLGFETVPAS
ref|ZP_01697892.1|      GLVDEGILMRKRGSGTFISEHKVEQPLEGR--M-SFTRLMEERGMKASNKIVAFFEREAS
RAAC02031               DLVTSGFIVRRQGKGTFVAE--VDHPATSTTLY-GFAEELRAAGLPVDVRVDVIEMRTCP
ref|ZP_01662088.1|      DLQNEGLIFRRHGKGTFVSQPKAFQNVTALQ---GFAEAMSAQGHAIRNRVLKLRTLPAP
ref|YP_900875.1|        NLVAAGLLYRKHGKGTFVAGAQDRPITESLANLTGHLEELQLRGLNPQVRVLALETRTLA
                         .*   *   * :*::*.***::      .     .    ...:  *       :  :   .

ref|YP_148128.1|        EKLAEGLGVTEGDDLYEVRRLRLADGLPMALETLYI--PVNLVPGLTRD-VVSGSVYEFI
ref|YP_001126297.1|     KKLAEWLAVKEGDALYEIRRLRLADGSPMALETLYI--PCALAPHLTRE-IVNGSVYEFM
ref|ZP_01697892.1|      VQEMEALTLKEPENVLHIERLRYGDEIPIVFES--IITPARIAAGLT-EEKLNRSFYQFL
RAAC02031               EDIARWLRMTRSKQVLYIERTAYVEDMAYFHERSYLVPPYQVSSRMTPDPKMYDSIYGFF
ref|ZP_01662088.1|      TDVAQALQLAPGTAVTELHRVRLLDQVPVSLEVTWLPEPLG--SSVARADLVTRDVFLVL
ref|YP_900875.1|        AEVAEALERSPAAPGWYLYRLVTVDRQPLMLSTVWL--PRDLEIELTED-ILKQHGMALL
                           .  *        : *    :  .     : *     ::   :      .:

ref|YP_148128.1|        EKEKGMIIGSAVQTLEASVARKVEAEHLKMKEGAPVLLLERRTHLVDGRPLEVVKSVYRG
ref|YP_001126297.1|     EKEVGLAIGTAVQVIEASVARKLEVEHLQVKEGAPVLLLERRTYLTDGRPLEVVKSVYRG
ref|ZP_01697892.1|      EREKGLRLGKGYQTIEAVAASARLAKLLKVAPGSPVLSIERVTSLSDGTPFEYVKAQYAG
RAAC02031               E-QNGVRINSGSQTISAELADEEDCARFGLTPPAAVLCIERITRDESGAPVEYSLVRYPS
ref|ZP_01662088.1|      EQDAGVALGHATLAIDAALADHATATALDTGAGAALLRVERLTHDAQGTPIDFERLYFRG
ref|YP_900875.1|        LTRNGIFPLRGRQRIGASSAGPEEAQLLGIRPGDAVLCVKRVIYGAASRPLVWFRTLYRS
                        *:.    .  :  *  *          :         .:*  ::*      . *.       :  .

ref|YP_148128.1|        DRYKFMIEMKR---
ref|YP_001126297.1|     DRYKFIVEMER---
ref|ZP_01697892.1|      SRFK----------
RAAC02031               DRYQLRVHLLRHPR
ref|ZP_01662088.1|      DAFQYRLRLDR---
ref|YP_900875.1|        DRYEYEVELKR---
                        . ::
```

FIG. 86

```
ref|YP_832996.1|         ------SKSEQAYAAVKARIVDGTYSPGYRLVLAKIAEDLGVSVVPVREAIRRLEAEGLV
ref|YP_950253.1|         ----PGSKSEQAYQAVKARIVNGAYSPGYRLVLGSIAKDLGFSVVPVREAIRRLEAEGLV
ref|YP_949591.1|         ------SKSQQAYAAVKARIVEGTYTPGYRLVLAKIAEDLGFSVVPVREAIRRLEAEGLV
ref|YP_001127075.1|      ------NKTQLAYEYILSHIESGAYGPGYRVVIDQIARELGLSSIPVREAIRQLEAEGLV
ref|YP_148880.1|         ------NKTQLAYEYILSRIENGVYGPGYRVVIDQIARELGLSSIPVREAIRQLEAEGLV
RAAC03005                MTKHPPSKQQVAYQTLKQRILEGTYGPGYRIVIDRIAKELGVSAIPIREAIRRLEAEGLV
                               .*  :  **    :    :*  .*.*  ****:*:   ...*  :*:***:***** ref|YP_832996.1|         TFERNVGATVSGIDPTEYLYTMQTLSIVEGAATALSAPLIGSADVARARAVNEEMRECLE
ref|YP_950253.1|         TFERNVGATVAGIDPTEYLYTMQTLSIVEGAATALSAPLIDSVAISRARAVNEEMRECLD
ref|YP_949591.1|         KFERNVGATVSGIDPTEYLYTMQTLSIVEGAATALSAPLIDSVAIARARAVNEEMRECLE
ref|YP_001127075.1|      EFKPYAGAVVSTINEKEYVETLSVLAVLEGYATALGSAKLTKEAIKQLEQLNEQMERALE
ref|YP_148880.1|         EFKPYTGAVVSNINEKEYIETLSVLAVLEGYATALGSAHLTKEAINELERLNEWMERALE
RAAC03005                EVERFSGAKVTRIDAKMYEDILSALAVLEGYATAQAYRNLTDEDFDALRQTNEAMRQARS
                           .:      **  *: *:  .  *      :..*:::**  ***  .    :  .   . **  *...  .

ref|YP_832996.1|         HFDPVRFTRLNQDFHSVLFEHCPNPHILDLVHRGWNRLASLRSSTFRFVPGRARDSVDEH
ref|YP_950253.1|         HFDPVRFTRLNQDFHSVLFEHCPNPHILDLVHRGWNRLASLRSSTFRFVPGRARASVDEH
ref|YP_949591.1|         HFDPVRFTALNQDFHSVLFEHCPNPHILDLVHRGWNRLASLRSSTFRFVPGRAQESVREH
ref|YP_001127075.1|      ELELERFSELNYAFHSLIYSHCGNAYLEEQIKQIWQRMKRIRVYGFTFVPQRAKASIGEH
ref|YP_148880.1|         ELELERFSELNYEFHSLIYAHCGNAYLEEQIKQIWQRMKRIRAYGFTFVPQRAKASIEEH
RAAC03005                DFDLTLYSRLNQQFHEIILRRCNNRYLVDEIHAVRERMDAMRVSVFNLIPHRASDSIAEH
                           .:: :  ::  **   **.::  :*  *  ::  :  ::    :*:  :*      *  :*  **    *:  **

ref|YP_832996.1|         EALLRLIESGAGADEIEKAARLHRSATLDAY------------------------------
ref|YP_950253.1|         EALLKLIETGADADTIEKAARLHRSATLNAY------------------------------
ref|YP_949591.1|         EALLRLIENAADADTIEKAARQHRAATLDAY------------------------------
ref|YP_001127075.1|      REMIRLLREQAPPHEVEQYARQHKMNTIEAFLR----------------------------
ref|YP_148880.1|         REIIRLLREQAPPHEIEQYVRQHKINTAEAFKR----------------------------
RAAC03005                DKLIQLMAVDVGEDAVERFARQHRLATLEAFRRWNEQHTRLVAERREWYRAPREIHRPGA
                           :::*:        .    . :*: .* *:   * :*:

ref|YP_832996.1|         --
ref|YP_950253.1|         --
ref|YP_949591.1|         --
ref|YP_001127075.1|      --
ref|YP_148880.1|         --
RAAC03005                DS
```

FIG. 87

```
ref|YP_073926.1            ------------RVSSQRIYQQIVDQITRMVQEGTLRPGDRLPPERQLAEEFGVSRSAVR
ref|YP_431134.1            ---------------TKKIYEEIVQQIKDLIGEGNLKPGDRLPSERELSERLAVSRASVR
emb|CAB08003.1|            ---------------------------------GELKPGDKLDSVQALAESFQVSRSAVR
ref|YP_001422711.1|        ---------------TKKIYEEVADALLEKIKAGELKPGEKLDSVQALSESFQVSRSAVR
ref|YP_080763.1            ---------------TKKIYEVAEALLESIKSGELEPGDKLDSVQALADSFQVSRSAVR
RAAC02459                  MNALDPEGDATMREASSKLYMEIAEEIRRQIEEGAFRPGDRLPTLRELADRFGVSRATVR
                                            *  :.**::*  . : *::  : ***::**

ref|YP_073926.1            EALSALRMLGLVEARVGEGTFVTQPPDERFISPLALVLTIEQSEAVGRELLELRAALEAE
ref|YP_431134.1            EALSALAAMGVIVIRPGEGTFVQNIRNGAIVEPLAMALLLDRQAAM--ELLEARQALEGE
emb|CAB08003.1|            EALSALKAMGLVEMKQGEGTYLKEFELNQISQPLSAALLMKKEDVK--QLLEVRKLLEIG
ref|YP_001422711.1|        EALSALKAMGLVDMKQGEGTYIREFEPSHVSQPLSSALLMKKEDVK--QLLEVRKLLELG
ref|YP_080763.1            EALSALKAMGMVEMKQGEGTYVKRFEPEQISIPLSAALLMKKKDVA--ELLEVRKILEIG
RAAC02459                  EALSALRGQGLVEFRHGMGTYVRAASVEMWMQPLDAAILLSYDNVR--DLVELQTAVLAQ
                           ******    *::   : * **::            **  .: :. .    :*:*  :  :

ref|YP_073926.1            SAALAAVRREAEDLAAMEEALGDMERDLQEGRLGAEADWRFHDAVASASGNSLLLQTMRS
ref|YP_431134.1            AAYLAARRAGPEDLEKMEELLKEMEHDLQRGILGEEADLRFHLAIAEAARNSVLARLMHT
emb|CAB08003.1|            VASLAAEKRTEADLERIQDALKEMGSIEADGELGEKADFAFHLALADASQNELLKHLMNH
ref|YP_001422711.1|        VAAMAAEKRTEDDLQKIRQALLEMKDIDGDEELGEKADFSFHMALAEASQNGLLKHLMNH
ref|YP_080763.1            AVSSAAQKRTEDDLGRMQEALEDMKLADGNGELGEKADLAFHLALAGASQNDLLKGLMNH
RAAC02459                  IAYRAAAQRMESDYSVLSHALFELEASPRRGEHRIASELKFFSVLAELAGNRLLENALRV
                            . **  *    *  :  .*  ::            ::  *. .:*  :   * :*    :.

ref|YP_073926.1            LSDTMKEALGLYRE-QL-------------------------------------------
ref|YP_431134.1            VSDTMRQALKTSRQ-RLYTTAGNP---------------EKLFAQHNQIYEAIKAHDPRA
emb|CAB08003.1|            VSSLLLETMRETRKIWLFSKKTSV---------------QRLYEEHERIYNAVAAGNGAQ
ref|YP_001422711.1|        VSALLLETMRETRKIWLFSKRTSV---------------QRLYEEHERIYSAVAAKDADE
ref|YP_080763.1            VSSLLIETMR--------------------------------------------------
RAAC02459                  LQEALRSSLRLLNPKLDLGVQACRRVYNAVQTGRPADARDAVYAYGEAILRAVAEKKGRG
                           :.    :  .::

ref|YP_073926.1            --------
ref|YP_431134.1            ARKAI---
emb|CAB08003.1|            AEAAMLAH
ref|YP_001422711.1|        AEAAMTAH
ref|YP_080763.1            --------
RAAC02459                  QSAMM---
```

FIG. 88

```
ref|YP_147389.1         ----------------MNAMERENTVKSVRRALQIIEIVSTKKDGLGVTEIAKQMDINKSS
ref|YP_001125502.1|     -----------------------VKSVSRALQIIDIVSTKKDGLGVTEIAKQMDINKSS
ref|NP_243003.1         -----------------------VKSVDRALTIISLVSEHKQGLGVTDVAAKLSLTKSS
RAAC01353               MCRSPAEKHRRARKDEVNRLEDYTVKSVDKALLLLEVVSEHPDGIAITELAQSVGMYKST
ref|YP_001665938.1|     -----------------------VQSLERALKILEVLGKNPNGLGVTELAREVDLPKST
ref|YP_360107.1         --------------------DTLIQSVDRALRILDTFSLKEKELGVTEIANRLGLHKST
                                             ::*:  :**  ::.  .. :  . ..:*::*  ..:  **:

ref|YP_147389.1         VYRILTTLAQYGYIEQHPETERYKLGYKFLELSSKLLDSIDLRQEAKPYLRELEKETNEV
ref|YP_001125502.1|     VYRILTTLAQHGYIEQHPETERYKLGYKFLEISSKLLDSIDLRQEARPYLRQLEKETNEV
ref|NP_243003.1         AYKLLATLVEHGFIEQDEETKKYRLGYRYLELSATLLESIDIRRQARPFLEQLEATTNEV
RAAC01353               VHRLLGTMMRRGYIEQDPVSGRYKLGYTVLDLGMKLLSSIDLRREAMPALQELALASGEV
ref|YP_001665938.1|     VYRLLSTLAKWGYVEQEKENEKYKLGLKIIELSSNILNNLELREVARQYLEELMEFANEV
ref|YP_360107.1         VFGLLRTLEHWGYVEQNQVTGKYRLGLKLLELGNRVKEGLDLRAVALPFLQDLVERYGET
                        .. :* *: . *::**.  . :*:**    :::.    :  ..:::*  *   *.:*     .*.

ref|YP_147389.1         IHLVVYDQGEVIYIEKLEGTETLRMHSKVGKRAPMHCTAVGKAILAHLPPAVAAEIIDRK
ref|YP_001125502.1|     VHLVVYDQGEVIYIEKLEGTETLRMHSKVGKRAPMHCTAVGKAILAYLPPTVTAEIIDRK
ref|NP_243003.1         VHLVLYDQGEMVYIDKLEGTKTLRTHSKIGRRAPIHCTSVGKVIMAYLPEKVQISLIERY
RAAC01353               VHLALLDRGSVVYIEKVESPNTIRMHSRVGTRVPVHATGLGKAILAFLPKREVQDIVRRY
ref|YP_001665938.1|     VHLCVLRDGEIVYIDKVESHNTIQMYSQIGKRAPVHCTAVGKAILAFLPQEEAISILKTK
ref|YP_360107.1         VHLAVHDRGEIVYIEKVEGPNAIRMYSQIGRRAPMHCTGVGKAILAFRPEKEIEEIIRTK
                        :** :   *.::**:*:*.  ::::  :*:* *.*:*.*.:**.*:*. *       .::

ref|YP_147389.1         GLPKHTDWTITDREAFFRELETVRQNGYALDLEENEYGIRCVAVPIFDYTGGVVAAISVS
ref|YP_001125502.1|     GLPKHTDLTITDREAFFRELDSVRQNGYALDLEENEYGIRCVAVPIFDYTGSVVAAVSVS
ref|NP_243003.1         GLPPHTERTITDKETFMKELEKIRLEGYGYEMEENEPGITCIAAPIFDYQGAITAAVSIS
RAAC01353               GLPRLTPHTITDADAFWASLEETRSTGFAFDMEEHQEGVCCVAAPIFAHDGRVMAAVSVS
ref|YP_001665938.1|     GLPRKTPNTITSLEEMLKHLEEIRRLGYAIDNVEHEEGIRCVAAPIFDYTGQVVASVSIS
ref|YP_360107.1         GLKYFTPNTITDPKKLHEELSLIRENGYSLDREEIEIGLRCVAAPIRDSQNTVVAAISVA
                        **   *  ***. .:  *. *   *:.  *   *  *: *:*.**       .  : *::*::

ref|YP_147389.1         GPTIRMTDDRITSLTVRMRQIGKELSARLGYR------
ref|YP_001125502.1|     GPTIRMTDDRIAGLAMRMRQIGKELSARLGHR------
ref|NP_243003.1         GPSIRLSKERLHELRPLIIAIGKKISQRLGYQ------
RAAC01353               GPALRMTRERMVELVPLVKRAGERISERLGYRRERVAP
ref|YP_001665938.1|     GPEYRVTWEKVPGLAVKVKEITKKISQRLGY-------
ref|YP_360107.1         GPSIRMTEEKIQELIVSVKEAALEISKRLGYQ------
                        **  *::  ::: *    :      .:* ***:
```

FIG. 89

```
ref|ZP_02329176.1|        ---------TVRSVERALDILLCFRDSSEL-TLTEISNQAGLHKSTVHRLLASLEGKGFL
RAAC02432                 MPHTPSGQTTVRAVERALDILLLFTHSPRAWSLSEIARATGLHKSTVHRLLLALQQKGFV
ref|YP_076367.1|          -------------MERALDVLLCFAGERGGLGVTQIAEKLGLYKSTVHRILAALESRGFV
ref|NP_694155.1|          MNDSPKG---IRTLQRSIDILNCFIEKNSELTLTEISLYTGLAKSTTTRLLSTLEMNNFV
ref|YP_001126042.1|       ----------LRTVQRAIDILYCFTLEEQELSLTEIANKISLAKSTTTRLLATLEQNRLV
ref|YP_643152.1|          -----------AAVRVADVLLLFASGPDALGVSEISRRLGLSKAVVHRILRSLASRGLV
                                        *  *:*   *        :::*:    .* *:.. *:* :*   . ::

ref|ZP_02329176.1|        LRDSSGDKYRLGFSVWELSANLSQGDDISMLLLPEMEWLRDQVGETISIYVRDGKERVRI
RAAC02432                 RRESESDRYVLGWSLYGLGANAALHDRWSDAAKPILRRLRDETNETVSLYVRNGLERIRI
ref|YP_076367.1|          RRDPATGRYHLGLRALELAQVYLSSGDLPTIALGEMLQLRDLAQETVSLYVRDGAERVRV
ref|NP_694155.1|          EKDEVNAKYRLGKQIYFLGFVAGQTFELNSLAKSTMERLREQTKETVNLYILDGKHRVCV
ref|YP_001126042.1|       IKNPETLKYRLGQGLYYLGHIAGKSIEVREIAKPVMERLRNETRETVNLYVLEQGARVCI
ref|YP_643152.1|          SHDAESRSYGLGPAAAALGARALAGLELRRVALPVLRRLQRETGETTTLSELVGTARVYL
                            ::      *  **    *.              :  *:   . **  .:       *: :

ref|ZP_02329176.1|        QAVQSKHAIRRVAPVGARMPLYVGASSKVLVAFGDEALQVELAHD----ARSSVGLDPTA
RAAC02432                 LAVESLQPIRNVASVGERYPLTIGASGKVLLAFSNSAVIEAACHP----DRLPNGVRQVD
ref|YP_076367.1|          QRAEGPLTVRRVVGLGERLPLYLGASGKVLLAWCPPEERARILDA-----QLPAGFDRTA
ref|NP_694155.1|          QQFESLQSVKHMISVGQKLPLTVGASGKVFLAYQSKEFIEDAM------DTQPLKKSKVD
ref|YP_001126042.1|       EQYEGLQSLRHMVKIGERLPLWAGAGGKVLLAYQSPSFQERIL------AQVPTEERRTR
ref|YP_643152.1|          DQVPSLKEIKMTVEVGRPFPLHAGASSKAILAFAPPEVREHVLEGPLEALTPLTVTDRAR
                              .    :: :*   **  **..*.::*:                       .

ref|ZP_02329176.1|        ---FLKQLAETREQGFATSMEEREPGAAALSAPILNRSGKLVAALAISGPISRLTPEQMQ
RAAC02432                 ---LRQQLEAIRREGYALSRQERDAGAAAIAAPVLNEDGSCLYAIAVSGPVERMTEDKMR
ref|YP_076367.1|          ---LEARLAEAREQGWALSLEEREEGVASVAAPVIDRAGRCVAALAISGPVSRFTDDRV-
ref|NP_694155.1|          ---LKNELDLIIKEKYAVSIEERESGTSAAAAPIFNFQNEVVAVLSVSGPASRL------
ref|YP_001126042.1|       ---LTAELEMIRQRGSTSSIDEREVGSAAVAAPIFNIHGEVNACLSISGPTHRFTPQAIR
ref|YP_643152.1|          ---LEVELGQIRESGTAVSCGERQSGAGSVAAPVIGVDGYAVGSISVCGPVDRFGEETVE
                             :  .*    .   :  *  **:  *  .: :**::.  .       :::.** *:

ref|ZP_02329176.1|        ------------------
RAAC02432                 DMVTPLKRAAEELSERLAE
ref|YP_076367.1|          ------------------
ref|NP_694155.1|          ------------------
ref|YP_001126042.1|       ------------------
ref|YP_643152.1|          RM----------------
```

FIG. 90

```
ref YP_001662226.1|        --TIKDVAKRANVAPSTVSRVIADNPRISKETKERVWKAMEELGYYPNAIARSLASKVTN
ref YP_001664166.1|        --TIKDVAKRANVAPSTVSRVIADNPRISKETKERVWKAMEELGYYPNAIARSLASKVTN
ref NP_624096.1|           --TIKDVAKRANVAPSTVSRVIADSPRISKETKERVWKAMEELGYYPNAIARSLASKVTN
ref ZP_02171282.1|         --TIKDVAKLANVAPSTVSRVIANSPRISERTKETVREAMKELGYHPNFNARSLANKSTN
emb CAB65654.1|            MATIKDVARLANVSPSTVSRVLANSPRISEETKRRVRAALEQLNYHPNAFARGLVTNSTG
RAAC00570                  MATIKDVARLANVSPSTVSRVLANSPRISEETKRRVRAALEQLNYHPNAFARGLVTNSTG
                             ******: ***:********:*:.****:.**. *  *::*.*:**  **.*..: *.

ref YP_001662226.1|        TLGLIMPRSTEEAFSNPFFPEVMRGISVVAHREKYDLLLSTSGNQEEEKEAVINMVKGKR
ref YP_001664166.1|        TLGLIMPRSTEEAFSNPFFPEVMRGISVVAHREKYDLLLSTSGNQEEEKEAVINMVKGKR
ref NP_624096.1|           TLGLIMPRSTEEAFSNPFFPEVMRGISVVAHREKYDLLLSTSGNKEEEKEAVIRMVKGKR
ref ZP_02171282.1|         TIGIVMPNSANKTFQNPFFPEVIRGISSKAHQLEYGLYLSTGQTEAEIFEEVQHMVQGKR
emb CAB65654.1|            AIGILIPPSAQEFFVNPFFAEWMAGVAEVARQRGVDTVLSTSARG--EIETLDHMIRGRR
RAAC00570                  AIGILIPPSAQEFFVNPFFAEWMAGVAEVARQRGVDTVLSTSARG--EIETLDHMIRGRR
                           ::*:::*  *::: * ****.*  *:::  *::    ***.        *  : .*::*:* ref YP_001662226.1|        VDGIILLSSRTTDELIPWLRDEKFPFVVIGKPLDAKG--VYWVDNDNIGASKLATNYLIK
ref YP_001664166.1|        VDGIILLSSRTTDELIPWLRDEKFPFVVIGKPLDAKG--VYWVDNDNIGASKLATNYLIK
ref NP_624096.1|           VDGIILLSSRTTDELIPWLRDEKFPFVVIGKPLDARG--VYWVDNDNIGASKLATNYLIK
ref ZP_02171282.1|         VDGIILLYSRVDDKVVDYLYKENFPFSVIGRPYDEKKRDITFVNNDNFKAAKTVTEYLLL
emb CAB65654.1|            VDGVLLIGARQGDPVLQEVAKLRCPAVLLGRPADPAP---ISWVNNDNQRAAYDATVHLLN
RAAC00570                  VDGVLLIGARQGDPVLQEVAKLRCPAVLLGRPADPAP---ISWVNNDNQRAAYDATVHLLN
                           ***::*:  :*   *  ::   :  .  *  ::*:*  *        : :*:***  *: .*  .*:

ref YP_001662226.1|        HGHREIAFISGSLEYVVSLDRLDGYKLALEENGIPFKRELAEQDEFSEDGGYRAMMRILE
ref YP_001664166.1|        HGHREIAFISGSLEYVVSLDRLDGYKLALEENGIPFKRELVEQDEFSEDGGYRAMMRILE
ref NP_624096.1|           HGHREIAFISGSLEYVVSLDRLDGYKLALEENGITFKRELVEQEEFSEDGGYRAMMKILE
ref ZP_02171282.1|         LGHKNIAFIGGNLDFVVTVDHMEGYRKALSNAGMELLDDYVVFHEELQEGGQEAVIDLMS
emb CAB65654.1|            LGHRRIGFLGGASDLVVTMDRVAGYRQALVDHGVEPDSRLEVSSFFLEQGGYLGMMRLLA
RAAC00570                  LGHRRIGFLGGASDLVVTMDRVAGYRQALVDHGVEPDSRLEVSSFFLEQGGYLGMMRLLA
                            **:.*.*:.*   :  **::*::  **:  ** : *:          ::**  .:: ::

ref YP_001662226.1|        -REKPTAVVVTDDVMAFGVIRAAIDKGYRVPEDISIVGFNNIPLSAFANPPLTTIDISTF
ref YP_001664166.1|        -REKPTAVVVTDDVMAFGVIRAAIDKGYRVPEDISIVGFNNIPLSAFANPPLTTIDISTF
ref NP_624096.1|           -RAKPTGVVVTDDVMAFGVIRATIDKGFRVPEDISIVGFNNIPLSAFANPPLTTIDISTF
ref ZP_02171282.1|         LNDPPTAMIVADDIMTFGVMRMLSEMEMKVPDDVSIISFNNVMISELSSPPMTTVDIHIY
emb CAB65654.1|            IPDRPTAVLCADDVLAFGGMRAAHELGFEVPGDLAIVGFNDIRLAELAHPALTSVRVHMH
RAAC00570                  IPDRPTAVLCADDVLAFGGMRAAHELGFEVPGDLAIVGFNDIRLAELAHPALTSVRVHMH
                             **.::  :**::** :*  :      .** *::*:.**::  ::   ::  *.:*::   : .

ref YP_001662226.1|        DLGIKSAELLIARLKQKEIDIDHIIVPVKLVERKSCVAR-------
ref YP_001664166.1|        DLGIKSAELLIARLKQKDVDTDHIIVPVKLVERKSCVAR-------
ref NP_624096.1|           ELGIKSAELLIARLKQKEIESDHIIVPVKLIERKSC----------
ref ZP_02171282.1|         NLGFEACNLLIDQILHPETGSKQVLIPHKMIKR-------------
emb CAB65654.1|            ELGVRSAELLLEEIDQGKPLQRHVIVKHELVIRYSCGAKPIGTLTT
RAAC00570                  ELGVRSAELLLEEIDQGKPLQRHVIVKHELVIRYSCGAKPIGTLTT
                           :**..:.:**:  .:  .    ::::  :::  *
```

FIG. 91

```
ref ZP_01188246.1|    MATIKDIAKIAGVSTATVSRVINNYPDVSEKTKKKILKIMKENNYRPNSVARSLSTSKSN
ref ZP_01188241.1|    MVTIKDIARIAGVSTATVSRVINNYPQVNEKTKKKVLEVMKENNYRPNSVARSLSTSRSY
ref ZP_01188890.1|    MATIKDIAKLAGVSVTTVSKVINNYPDISDKTKEKVIKIMEQQNYRPNAIARSLSTSRSR
ref NP_242794.1|      MATIYDIAKKTGYSITTVSKVLNNYTDVSDKARKKVMDAVTEMGYFPSSSARMLTTKKSW
RAAC00269             MTTIYDIARRAGVSATTVSKVLNGYPDVSQKTREKVQRITRELGYQPNAAARGLVTRRSM
ref NP_244559.1|      MTTIKDIAKVAGVSVTTVSRALNGYSDVNEKTRKKIKDIANELKYSPNVMARSLVMNRSK
                      *. *: :* *  :***:.:*.*.::..*:::*:    : * *. ** *   :* ref ZP_01188246.1|    IIGIFFTDHFNTGIHHPFFREVIYGLEKIFDEKGYDILYFTNRKWGENF---SYVEKCHD
ref ZP_01188241.1|    TIGIFFTDHFDTGLRHPFFREVIYGLEKIFGQKGYDILYFTKRNWDDKCS---YVDKCRD
ref ZP_01188890.1|    SIGVFFTDHLNSGLRHPFFRDIIYGIEKTFFRKGYDLILFAH-QWGDRFS---YTEKCKS
ref NP_242794.1|      TIGVVFVESAGIGMEHPFFSSVIENFKKNVERFGYDLLFASNQI-GNEAK--TYLEHFRY
RAAC00269             SIGVFFQDDARMGFRHPFLHDIVASFQDVVGESGYDLLFFSRTTPPNAPQG--FEARARH
ref NP_244559.1|      TIGLLVSEISREGAKDNFTFEVLCGINDRASESDYDIILFNTNTSKQKLKS--YTQLCRE
                      **:...:   * ... *  .::.::.  . .**::    :      :    :

ref ZP_01188246.1|    RQ--VDGVVLMGVPKTDSNIPKLLDSDIPTVFVDLDIVGKKASYVISDNYRGAEMAVNYL
ref ZP_01188241.1|    RH--VDGVVLMGVSREDTNLPQLLDSGIPTVFIDVDIIGKRASYVTLNNTDGAKMAVNYL
ref ZP_01188890.1|    RH--VDGAILMGMPRTDPNLDKLVNSNIPTVFIDLDIVGKNATYVISDNVQGAKQAVNYL
ref NP_242794.1|      RG--VDGIVVVCSLLNDPEVEKLMKADIPSVVIDLDSKGSSAVY--SDNEYGSELAVDYL
RAAC00269             RG--VDGLFLLGIPRTSPGLPSLVRSRIPIVSVDLDLFGPRASWLSSDNVGGARLAVEHL
ref NP_244559.1|      RC--VDGVILQGIKKEDPYLEEVIESDIPCVMVDIPITGESVSYVTTDNVDGAKKAVETL
                      *   *  .:       ..: .:::  * :*:   *  .:   :* *:. **: * ref ZP_01188246.1|    HSLGHTRIGMIMGISSTKVTNDRLLGYQTAIKNLGLVYNSQWILDG-RYTEEGGYQAMSK
ref ZP_01188241.1|    YSLGHTKIGMIMGISSTKIAHDRFLGYQMALKDLSLSYNPDWVLNG-LFSEEGGYRAMNK
ref ZP_01188890.1|    YSLGHIKIGMIMGQRITKPAQDRLIGFQEELTNLGLEYNPEWIIEA-EFGEEGGYQAMKR
ref NP_242794.1|      VSLGHRSIAHISGDQGLFVGVQRLKGFKDAIQKLNLSISDEYIVDGGFFTYEGGQRAMEA
RAAC00269             AAMGHTKIGFVGDRYGTKPGQDRALGYHMAMQELGLTFRSEWVAEG-DFMEESGEEAMHR
ref NP_244559.1|      IDFGHRKIAMMNGHERAYVSGKRKLGYEQALQEAGIPLQEEWVLNG-EFSEQVAEKEAYQ
                      :**  *. : .         .* *:. :  . :     :::  :    : ..

ref ZP_01188246.1|    YLEMDERPTAIFCQSDSMAIGAMQAIHEAGMSVPEDFSLIGFDDIEVSRYVNPALTTIKQ
ref ZP_01188241.1|    FLKMIDRPTAIFCQSDTMAIGAMKAIKEAKMNVPGDFSIIGFDDIEISKYVKPALTTIRQ
ref ZP_01188890.1|    IITQEIRPSAVFCQGDEMAIGAINAIKEHGYNVPQDFSIVGFDNIEISSYVSPGLTTIHQ
ref NP_242794.1|      LLRNRVRPTAVYAAGDLMALGAIDTIRKHGLSVPEDFSIVGFDDIQMIRYTAPALTTIRQ
RAAC00269             ILEAREWPTAVFFASDMMAIGAMKALRQRGLEPGRDISLVGFDDVAIARLVTPSLTTIRQ
ref NP_244559.1|      FLQKHSDVTAFFCASDLMALGVMKAAKLLNLRLPEQLSVIGFDDILLAQYTSPPLTTVAQ
                      :    :*.: .* **:*.:.: :       :*:::***:: :   . * ***: * ref ZP_01188246.1|    DKIGLGRAAGELLINIVENENESQAPVILPVELVKRDSCGR---
ref ZP_01188241.1|    DKVKLGRAAGKLLLNIINNDLDGYKPVILPVKLIKRKSCAKL--
ref ZP_01188890.1|    DKLTMGKKAASILLEMINNPNKTFSPVVLPTKLIERESCRKIG-
ref NP_242794.1|      NTDLIGKTAANLLLDQINENEKQSLSVKIPVTLIERDSCRKI--
RAAC00269             NTRAMGEEAARELLDLMQNPNRPPRVITIPVELVSRDSVARIGG
ref NP_244559.1|      NKYQMGYAAAGLLIDRLRMKEVPP-FHMLDNELIIRESVAK---
                      :.  :*   *.  *:: :.          :  *: *.*  :
```

FIG. 92

```
ref|YP_518526.1|         ------------------------------------------------------------
ref|ZP_01369294.1|       ------------------------------------------------------------
ref|YP_430255.1|         -------------------------------------------------ETGSTDTGG
ref|YP_001213325.1|      ------------------------------------------------------------
ref|YP_361384.1|         ------------------------------------------------------------
RAAC02012                MGGIALKRHGRRLAWVAVAAAAFGAWHAWPRPERPHAHAHGSHSVAPSSASWTATDPGTT ref|YP_518526.1|         -LKDRVTVLLIGMDNRPGE-ALSNTDTLMVASLDQKSKKMVLLSVPRDTQVIL-NQKKEK
ref|ZP_01369294.1|       -LKDRVTVLLIGMDNRPGE-ALSNTDTLMVASLDQKSKKMVLLSVPRDTQVIL-NQKKEK
ref|YP_430255.1|         SQPGTLNILLLGTDARPGE-KVGNTDTIILAHFDGE--RLALLSIPRDTRVNIPGHGVDK
ref|YP_001213325.1|      ----RLNVLLLGIDARQGE-TMARTDTMILASVDTKSKQMILLSIPRDTGVEIPGHGWDK
ref|YP_361384.1|         ---GRVNILLLGVDDRHSKNRRERTDTIIFASIDSNLKKVVLVSIPRDTRVNIPGHGWDK
RAAC02012                RLGGRETILVLGSDKRPED-PRGNADVLLVASLDDSHRRIELLSIPRDTQVAFPDGRYHK
                              .:*::*  * *   .  .:*.::.* .* .  :: *:*:**** * :   .* ref|YP_518526.1|         VNAIARLQKGPISTQQYLQELLGTPIDGYVLTNFQGFKNIVDGLGGITIDVEKDMYYDTG
ref|ZP_01369294.1|       VNAIARLQKGPISTQQYLQELLGTPIDGYVLTNFQGFKNIVDGLGGITIDVEKDMYYDTG
ref|YP_430255.1|         INAAYSIG-GPDLTTSIVADLTGVPISKYVLLRWDGFIKIIDLLGGVTVNIPRDMYYY--
ref|YP_001213325.1|      INSAAVYG-GPELSMKVVSNLLGIPVRYYVLTNFSGFKDIVDALGGVTLEVEQNM-YHEG
ref|YP_361384.1|         INAAHVVG-GIDLTKQVVSDLLGKPVDYYVLVNFEDFKKVIDTLGGVTIDVEKDM-YHAD
RAAC02012                INEALASG-GPEETCMLVERLIGLPIDHYAIIRFDALVHMVDRIGGLDIDVPRNMDYRTG
                         :*         *    :  :    *  *:  *. :: . ..:*  :**:  ::: ::* * ref|YP_518526.1|         EAQDR---FINLKKGVQRLNGTQALQYARFRNDELADITRTSRQQEVIKAIVAEATTPRN
ref|ZP_01369294.1|       EAQDR---FINLKKGVQRLNGTQALQYARFRNDELADITRTSRQQEVIKAIVAEATTPRN
ref|YP_430255.1|         DPVDGPQYKINLKKGLQHLDGHQALAFVRPRKEALGDIDRTGQQQELIKALLEKVRQPGT
ref|YP_001213325.1|      DEEYGGAYGINLKKGVQRLDGDKALQYVRYREYPMGDIDRTRAQQKFLVALAKEVLQPST
ref|YP_361384.1|         EYPY----TINLKKGRQHLNGEKALMYVRYRSDALGDISRTQRQQKFLKALAEQALQPGT
RAAC02012                DKVYG---VIRLRKGRHHLSGEQALQFVRYRHDALGDIGRTERQQAFLVALKDQLLRPQT
                         :           *.*:** ::*.* :**  :.*:*    :.** ** **  .: *:    *  .

ref|YP_518526.1|         IPKLPIIIPKVYQAIDTNLNLGQIWALAMAFKNKDTYEVINQTLPGQFS-----DEE---
ref|ZP_01369294.1|       IPKLPIIIPKVYQAIDTNLNLGQIWALAMAFKNKDTYEVINQTLPGQFS-----DEE---
ref|YP_430255.1|         LLKMPRLLPEIYKNVETNMGLDEMLTMARAGLHLKNMTVVSQTLPGYFQ-----TING--
ref|YP_001213325.1|      IPKLPKLIPEISRYVKTNLSVSEMYKLAAAAKNLENGNILTQTLPGR------PVEIGG--
ref|YP_361384.1|         LLKLPKLIPEIIQMVETDMSTKDLMSLLAFSRELNKDSIITQTLPGYFY-----NYN---
RAAC02012                LPRLPEVAFDAWKMIDTDMSLGDISRLAARAPQYKTYRTVHTTLPGSFHDP-DPSIPG--
                         :   ::*    :    :.*::. ::       :      .   ..   :    **** ref|YP_518526.1|         --GISYWKVNPKETKVILNQLF-QGKTSP-IFETIQKVHVPAQPPASKEAKP-------
ref|ZP_01369294.1|       --GISYWKVNPKETKVILNQLF-QGKTSP-IFETIQKVHVPAQPPASKEAKP-------
ref|YP_430255.1|         ---ISYWGVDPAQARQVAQALFEYGQTTK---------QVVLDAPASQT----------
ref|YP_001213325.1|      ---ISYWGVEPAEARQMVAKLF-NGETVT----------NVV-----------------
ref|YP_361384.1|         --GVSYWQADLEVAKNLVDMLFA-GQIEQ---------NIVLGTKE--------------
RAAC02012                --DLSYWVVNPAEARYVAKRFFADGEVPPRIIQDPRETRTWLPPEARAAQRPADRSTSG
                           :***  .:    :: : :   :*  *:                       .
```

FIG. 93

```
ref|NP_354021.1|         ----------CPVESALSFLDGKWKGVILYHLIN----EGTLRFNELRRHIPSVTQRMLT
ref|ZP_01074644.1|       ----------CPVERALEIIGGKWKGAILYHLLDSSNQGGSIRFNELRRIMPNITQRMLT
ref|NP_772010.1|         ----------CSVEATLDLIDGKWKGVILYHL-----QDGTQRFGELRRRMPGITQRMLT
RAAC01701                MSSGHRGDSPCSAVSTLQVLSGKWKWLILYHLFQ----HPSLRFSELMRRIPGITQRVLT
ref|NP_691275.1|         ----------CSVEDALGILVGKWKPIILLHLME----KGTVRFSDLKRSIPGITQKMLT
ref|YP_174284.1|         ----------CEVDTALEILVGKWKHKILFQLMT----HDVMRFNELKRAIPGITQKMLT
                                   *  .:* .: ****  ** :*        **.:* * :*.:**::**

ref|NP_354021.1|         KQLRELEEAGLISRTVFPVVPPRVDYALTPLGETMRPVISALKSWGDAHV----------
ref|ZP_01074644.1|       KQLRELAETSLISRTVYPEVPPRVEYAMTDYGKTLAPVIDSLRAWGISHL----------
ref|NP_772010.1|         KQLRALEEDKLVIRKVYAEVPPRVEYCLSELGESLRPVIDILKAWGESHQQR--------
RAAC01701                KQLRELEEEGIVERTVYPEVPPRVEYAITPYGQSLRPILDLMHAWGLEHLRRKAERALQE
ref|NP_691275.1|         KQLRELENEEIINRVVYPEVPPRVEYSISEYGRTLEDLLHAMHEWGQAHTIRKQQK-LQE
ref|YP_174284.1|         SQLRELESHDIVERKVYPQIPPKVEYSISEYGKSLQPVLDAMHEWGKNH-----------
                         .*** *  .::  * *:. :**:*:*.:: *.::  ::   :: **  * ref|NP_354021.1|         ---
ref|ZP_01074644.1|       ---
ref|NP_772010.1|         ---
RAAC01701                PKL
ref|NP_691275.1|         ---
ref|YP_174284.1|         ---
```

FIG. 94

```
ref|ZP_02330514.1|        --------------LCPRFEHAFEILGKRWTGLIIRVLLSGPKRFKDISDVIPGMSDRML
RAAC00927                 -----MIVMGNHEQICPRFEWAFALLGKRWTGLIIRVLLEGPKRFKDISDMIPNMSDRML
ref|YP_001376921.1|       --------MEHNSCLCPKFESAFTLLSKKWTGLIIKSLLEEPKRFREIADIIPNMSDRML
ref|YP_001253394.1|       --------------MCPKFENAFELLGKRWTGLIIRTLLNGQKRFSDIAEAIPNMSARML
ref|YP_001308605.1|       --------------MCPRFENAFELLGKRWTGLIIRTLLNGQNRFSDIEEAIPNMSARML
ref|NP_347485.1|          -------------KLCPHFEAAFELLGKRWTGLIIHSLLKGAKRFSDIQDIIPNLSARML
                                        :: ** :*.*:****: .  :** :* : **.:* *** ref|ZP_02330514.1|        SERFKELEAADIVVRKVYPETPVRIEYELTEKGKALRPVMDELQKWAEKW----------
RAAC00927                 AERPKELERAGLVVRRVYAETPVRIVYELTPKGEALRPVMEAVQKWGDEWVTDSDCDEYQ
ref|YP_001376921.1|       SERLKELESEGIVVRNVYPEVPVRIEYGLTDKGKALESVMNEVQNWAEKWV---------
ref|YP_001253394.1|       TERFKELEEEGIIIRKVYPETPVRIEYELTEKGLDLQAVMDEIQKWAEKW----------
ref|YP_001308605.1|       TERFKELEKEGIIIRKVYPETPVRIEYELTEKGRDLQSAMDEIQKWAEKW----------
ref|NP_347485.1|          TERFRELEKQGIVVRKVYAETPVRIEYELTEKGRELESVMQEIQKWAEKW----------
                          :::*  .:::*.**.*.**** *    *...*: :*:*.::* ref|ZP_02330514.1|        ------------
RAAC00927                 RRYKCSSRDRAL
ref|YP_001376921.1|       ------------
ref|YP_001253394.1|       ------------
ref|YP_001308605.1|       ------------
ref|NP_347485.1|          ------------
```

FIG. 95

```
ref|YP_001643469.1|      ----------------------------------SGLTPPQFYILKILDHYGASRATQLAE
RAAC00935                MRGDMDALTQRFAQSLGVLAQEFGPHLLNRLH-TGLTAGQFFTMQMIRREGRLKVSQLAE
gb|AAB87745.1|           ----------RLDQAFYKAMKTLGPKVYEKLE-HNLTGEQFFVLNTLEQKGRITSSQLAE
ref|NP_391166.1          -----DQLMSDIQLSLQALFQKIQPEMLESMEKQGVTPAQLFVLASLKKHGSLKVSEIAE
pdb|1S3J|A               -----DQLXSDIQLSLQALFQKIQPEXLESXEKQGVTPAQLFVLASLKKHGSLKVSEIAE
ref|YP_001422559.1|      -----DQYVSDIQKSLQTLLQNIQPEMVESMAKHEVTPAQLFVLASLKKHGSCKVSEIAE
                                            :*   *::  :   : : *      ::.**

ref|YP_001643469.1|      KMYVKPSAITVMTDRLIDHGLVERYHDDNDRRVVVIELTKKGKTTVEEAMAARNEHIAKY
RAAC00935                RLEVTPSAITVMIDRLEHHGYVSRVRDEEDRRVVVIELTEAGRAKLAEVERAWFEMMRQM
gb|AAB87745.1|           ELQVKPSAITAMVDRLLKNDFVIRERDEKDRRAVYVRISDEGRRALKSSVKKRNIIMEKY
ref|NP_391166.1          RMEVKPSAVTLMADRLEQKNLIARTHNTKDRRVIDLSLTDEGDIKFEEVLAGRKAIMARY
pdb|1S3J|A               RXEVKPSAVTLXADRLEQKNLIARTHNTKDRRVIDLSLTDEGDIKFEEV-----------
ref|YP_001422559.1|      RMEVKPSAVTLMADRLEQKGLIVRKHNQQDRRVIDISLTKKGETKFEDVVEGRKAILARN
                          . *.***:*     ***  .:. :  *  ::  :***.: : ::. *    . .

ref|YP_001643469.1|      FSHLE---------------------------------------
RAAC00935                VSRIEPGAFKQCVSALETMVAAAKQLRMESYGEETPRQEV----
gb|AAB87745.1|           MSKLTEEEMEQLTTVLEKLTS-----------------------
ref|NP_391166.1          LSFLTEEEMLQAAHITAKLAQAAE--------------------
pdb|1S3J|A               --------------------------------------------
ref|YP_001422559.1|      LSVLTDDELIQSVNIIRKVAEAAENTRLIKKKTNRKEELPKHE
```

FIG. 96

```
ref YP_001126687.1|     ---------------PSAMNEKTVAELEKLLRYIAANLKQRGREILTNYPITPPQFVALQ
ref YP_148522.1         ----------------------VAELEKLLRYIAANLKQRGREILTNYPITPPQFVALQ
ref NP_693030.1         ------------------ELSDSVNQMEKRLRYISGMIKQNGRKILNNYPITSPQFIALQ
RAAC02041               MVRFIGLWARTGCGYPLADYSPFVEEIEKALRLVAATVRRRGRVLLKDYDLTSPQFDALI
ref YP_001320949.1|     ------------------------EIEKELRYLCTVIKQKGREILTDFQITPPQFQALQ
ref YP_001512727.1|     -----------------ARYDDNIIBIEREIRYLCTKIKQKGREILADFSITPPQFEALQ
                                                 ::*: :* :.   :::.** :* :: :*.* ref YP_001126687.1|     WLLEEGDLTVGELSNKMYLACSTTTDLIDRMERNGLVSRVRDEHDRRVVRIHLLEKGERI
ref YP_148522.1         WLLEEGDLTVGELSNKMYLACSTTTDLVDRMERNGLVARVRDEHDRRVVRIRLLEKGERI
ref NP_693030.1         WLLEEGDLTIGELSNRISHAFSTTTDLVDRMEKNELVERVRDTNDRRVVRIHLLEKGKHI
RAAC02041               TLYNEGELTIGELSAKLYLAYSTTTDLVDRLERAGYVSRQRDLVDRRVVRVQLRDKGAQV
ref YP_001320949.1|     YLISEDSLTIGELSNKMFLACSTITDLVDRMEKNDLVKRARDEKDRRVVRIVVLDNGHEI
ref YP_001512727.1|     YLNNCQGITIGELSNKMFLACSTVTDLVDRMEKNDLVKRVRDEKDKRVVRPQVSEKGYQL
                         *  .   :*:****  ::  * ** ***:**.*:   * * ** *:****  : ::* .:

ref YP_001126687.1|     IEEVIEKRQRDLARVLENFSDEE------------------
ref YP_148522.1         IEEVIEKRQRDLASVLESFSDEE------------------
ref NP_693030.1         IEEVIDKRQAYLGEVLTKFSEEEKEQLNQLLDFLYTEM---
RAAC02041               IEAVLSARRAYLDSILKHVSIEQRRAILQALDLLLTNMGNS
ref YP_001320949.1|     INQVLHARRNYLEEVLLDVSSEQRDSVLQGISLI-------
ref YP_001512727.1|     IEEVLHARRNYLADVMKDVSEKDRKFILDGITMI-------
                        *: *:  *:  *  ::  .* ::
```

FIG. 97

```
ref|NP_629113.1|       ------------------------------------------------------------ET
ref|NP_824479.1|       ------------------------------------------------------------DT
ref|ZP_01169478.1|     --------------------------------------------------MSKEKQNDVEL
ref|NP_631123.1|       ------------------------------------------------------------ET
RAAC02241              MRGHEKFLLPSDTKCQLPVPNCSGTREMKSTQLLYYTTITLKMHPKEADMDQANMDSFEA
ref|YP_001508494.1|    --------------------------------------------------------DSLRD ref|NP_629113.1|       LQHEVALFARRAEQTRLGGVGQVRNSMDRAAYLLLNRLDKEGPMGVKALAASMGIDSSTV
ref|NP_824479.1|       LQHEVAVFARRAEQTRLGGVGQVRNSMDRAAYLLLNRLDKEGPMGVKALAASMGIDSSTV
ref|ZP_01169478.1|     IEYELATFIRKAVYLEQS--EKKIGQLERSAYLLLRQLDEFGPARVKELAEAFKLDISTL
ref|NP_631123.1|       IQREMTVFARRARAS----AGRMHPELSLVSYTLLGHLEERDGRRATDLAAHYALDKSTV
RAAC02241              LEREMAIFARRLEGARQS--WRKHREIDRSAYLILLALREEGELTAGQLAARFLLDISTI
ref|YP_001508494.1|    LERELMLLARHHIAPNAARRGRTR-HLDRSAYLLLSRLEAQGPMTIGQLAEAFSLDVSTV
                       ::  *:   : *:        :      :.  :*  :*   *     .   **    :* **:

ref|NP_629113.1|       TRQVAPLVDTGLVKRTSHPEDGRAVVLQLSPRGVARLEEVRSSRRQLMAELTHDWAPQER
ref|NP_824479.1|       TRQVAPLVDTGLVKRTSHPEDGRAVVLQLSPRGMSRLEEVRSSRRQLMSELTHDWAPQER
ref|ZP_01169478.1|     SRQAASLESKDLIKRCSDPKDGRVSVFSITDLGKEKLEADIANRRAHYFKVLNDWTEEEK
ref|NP_631123.1|       SRQVSALERAGLIERRVDPDDHRVQVLHLTESGRDVLDRVTERRRAAFRERLADWPEEEL
RAAC02241              SRQITPLVEAGWIAKERDEDDKRQLRLSITEAGVEALEATRASRIELYRELVGDWTEEER
ref|YP_001508494.1|    NRQTAAVLQAGLAERIPDPDGGLARKLSITPEGARRVADDRAFVIGELSGLVSTWSEDEL
                       .**  ::.   :       .  :  .  ..     : ::   *     :        *. :* ref|NP_629113.1|       ETFCALLARFNGALSAR------
ref|NP_824479.1|       EAFTALLTRFNTALSDR------
ref|ZP_01169478.1|     EIFGKLVVRLN------------
ref|NP_631123.1|       LRFAAYLERYNAWPDAAPGAER-
RAAC02241              RTFLGLLRRLNERIRARQQAERT
ref|YP_001508494.1|    RLFASMLERLNTSIETK------
                        *    :  *  *
```

FIG. 98

```
ref|NP_388620.1|            ---------------------IDQVAKRSGLTKRTIRFYEEIGLIPAPKRTDGGVRLYS
ref|YP_001420380.1|         ---------------------IDQVAKRSGLTKRTIRFYEEIGLIPAPKRTEGGVRLYS
ref|YP_090401.1|            ----------------DVEWMKIDQMAKRSGLTKRTIRFYEEIGLLSSPKRTEGGVRLYS
ref|YP_077997.1|            ---------------------IDQMAKRSGLTKRTIRFYEEIGLLSSPKRTEGGVRLYS
RAAC02671                   MAYTGVRQKMRRWKMDRDKAWTVEAVAERLGITPRTLHYYEEKGLIPEVPRTPGGHRVYD
ref|YP_714968.1|            ----GVRDKDQMKKAARELCGIGQA-AQELGVSVRALRYYQEVGLLTPSGRTSGGNRLYA
                                                 : *:. *:: *::::*:* :.     ** *:* ref|NP_388620.1|            EDDMEELEKVISTKEVLGFSLQELQHFMETSRQLELNKEGYLLSLDPKERKEKLEEIQET
ref|YP_001420380.1|         EDDMEELEKVTSTKEVLGFSLQELQQFMEMSRQLELNKEGYLLSLDPKERKEKLEEIQQA
ref|YP_090401.1|            EDDLEELERVISAKEVLGFSLQELQQFMETGKHLEMNKEGYLLSLDKRERKEKLEDIQRM
ref|YP_077997.1|            EDDLEELERVISAKEVLGFSLQELQQFMETGKHLEMNKEGYLLSLDKRERKEKLEDIQRM
RAAC02671                   EDTIERIEHILRLKEALGYSLQEIRSILSTEDQLKAYRARIAEGHEPEHNVQMLSESVRL
ref|YP_714968.1|            DSDLARVRRIRELQTLLGFNLDEIGTILAYEDRLAQVRVEFHAASDDGDRLRLLSEGETA
                            :. : .:.::   :   **:.*:*:  ::    :*    :    .  .  ... *.:

ref|NP_388620.1|            LNHQLDLIDEKIRTFQSFKE-------------------------
ref|YP_001420380.1|         LNHQLEMIDEKISTFQHFKTRLNGMKE-----------------
ref|YP_090401.1|            LNEQMRMIDEKIEKFQSFKK-------------------------
ref|YP_077997.1|            LNEQMRMIDEKIEKFQSFKK-------------------------
RAAC02671                   LEDVVRHIDEKMLRLGSMREHYMDRLARIRARLEREEAATRTVGFPDQEGE
ref|YP_714968.1|            YVKLRAEIDEKISRLAAFRD-------------------------
                              .     ****:    :  ::
```

FIG. 99

```
ref|YP_001141973.1|    --RTYSISELAREFDVTTRSIRFYEDQGLLNPARQGQTRIYSKQDRVRLKLTLRGKRLGF
ref|YP_856665.1|       --RTYSISELAREFDVTTRSIRFYEDQGLLNPARQGQTRIYSRQDRVRLKLTLRGKRLGF
ref|YP_927240.1|       ----YSISDLSKEFDITTRSIRFYEDQGLLKPKRRGQTRIYSLKDRVRLKLILRGKRLGF
ref|YP_001141729.1|    ----YSISELAHEFDITPRTIRYYEDEGLITPTREGQTRIYSHKDKIRLKLTLRGKRLGF
ref|YP_427081.1|       -RDSFSIADLAAEFSVTPRAIRFYEDKGLITPARDGMRRIYSPRDRVRLMLILRGKRLGF
RAAC00549              MRRYYTIRDLADMFDITPRTLRHYEDMGLLKPARRGAKRLYSERDRVRLQLILRGRRLGF
                        ::*  :*:   *.:*.*::*.***  **:.*  *  *   *:**  :*::**  * ***:****

ref|YP_001141973.1|    SLADIRDLFDLYDADKSSRTQLQTMLGLVADKRETLQQQLEDIKMVLLELDAAEQRCQQA
ref|YP_856665.1|       SLADIRDLFDLYDADKSSRTQLQTMLGLVADKRETLQQQLEDIKMVLLELDAAEQRCQQA
ref|YP_927240.1|       SLAETRRLFELYDADKTSVTQLNTMLALIEEKKAALQQQMDDIKVVLMELTSAEAQCRGA
ref|YP_001141729.1|    SLAEIRELFDMYDTDRSSKTQLHSMIQLINAKRQSLHQQLEDIQMVMAELEAAEQRCANS
ref|YP_427081.1|       SLKEIQEIIDLYDAEPTGEAQLRRLITTCQTSRAALRQQMEDIRITIDEIEAVEAQCRQA
RAAC00549              SLPEIAEMLDLYDADPTEITQLREVIRRGDEKLRHVELQISELEALRDELIAMRSLQQV
                       **  :    ::::**::  :  :**. ::        .   :. *:..:.     *:  :  . :

ref|YP_001141973.1|    L--------------
ref|YP_856665.1|       L--------------
ref|YP_927240.1|       LD-------------
ref|YP_001141729.1|    LN-------------
ref|YP_427081.1|       L--------------
RAAC00549              LDDKLKQCHQKGCDD
                       *
```

FIG. 100

```
dbj|BAA00729.1|            -----------------------------------------RRSMPLFPIGIVMQLTELSA
ref|NP_389627.1            -----------------------------------------RRSMPLFPIGIVMQLTELSA
ref|NP_833433.1            -----------------------------------------EDRRSAPLFPIGIVMDLTQLSA
ref|YP_001375615.1|        -----------------------------------------EDRRSAPLFPIGIVMDLTQLSA
ref|ZP_02328256.1|         -----------------------------------------RRNMALFPIGIVMKLTDLTA
RAAC01080                  --------------MSWRALHVTISFNRSHREGRAVDLEERRNMPLFSIGTVQKLTGLSA
                                                                    . ..** * .** *:* dbj|BAA00729.1|            RQIRYYEENGLIFPARSEGNRRLFSFHDVDKLLEIKHLIEQGVNMAGIKQILAKAEAEPE
ref|NP_389627.1            RQIRYYEENGLIFPARSEGNRRLFSFHDVDKLLEIKHLIEQGVNMAGIKQILAKAEAEPE
ref|NP_833433.1            RQIRYYEEHNLVSPTRTKGNRRLFSFNDVDKLLEIKDLLDQGLNMAGIKQVLLMKEN---
ref|YP_001375615.1|        RQIRYYEEHNLISPTRTKGNRRLFSFNDVDKLLEIKDLLDQGLNMAGVKQVLQMKEN---
ref|ZP_02328256.1|         RQIRYYEQHELVIPARTSGNQRLYSFNDVERLLEIKDLIEKGVNIAGIKQVLLPVSKDSE
RAAC01080                  RQIRYYEEHGLIQPARTPGNQRQFSFADVERLMQIRQLLDEGHNIASVKRNLLEKDRRPR
                           *******:: *: *:*: **:*  :** **::*::*:.*:::* *:*..*: *    .

dbj|BAA00729.1|            QKQNEKTKKPVKH-DLSDDELRQLLKNEL---MQAGRFQRGNTFRQGDMSRFF---
ref|NP_389627.1            QKQNEKTKKPMKH-DLSDDELRQLLKNEL---MQAGRFQRGNTFRQGDMSRFF---
ref|NP_833433.1            QTEAVKVKEETK--EISKTELRKILRDEL---QHTGRFNR-TSLRQGDISRFF---
ref|YP_001375615.1|        QTEAVKTKEETK--EISKAELRRILRDEL---QHTGRFNR-TSLRQGDISRFF---
ref|ZP_02328256.1|         EATYLNEASETKRKELTDSQLRQLLKQQI---VGARRPGQ-VSLIQGELSRFY---
RAAC01080                  SSRPLATR------DVPDSEVYQWLEREL---MERRQTGE----FQGDLSRFYRHR
                            .             ::.. ::  : *. ::         :   .    **::***:
```

FIG. 101

```
ref|YP_146517.1|        ----------------------QIIEAAAQSFAAFGYKATTMEQIAKLANVGKGTIYTF
ref|YP_001124699.1      ----------------------QIIEAAAQSFAAFGYKATTMEQIAKLANVGKGTIYTF
ref|ZP_00739458.1|      ------FGGEDVAIDRKRS------IIEAATKSFSAFGYKATTMDQVAKLANVGKGTIYTF
ref|NP_830863.1|        ----------MAIDRKRS------IIEAATKSFSAFGYKATTMDQVAKLANVGKGTIYTF
ref|YP_893832.1|        ------FGGDDVAIDRKRS------IIEAATKSFSAFGYKATTMDQVAKLANVGKGTIYTF
RAAC01126               MTKLEFWSECVAMRRKRGMTVRDRIEEAAKRAFSEFGYKGTTMDQIARLAGVSKGAIYLH
                                              * *** ::*: ****.***:*:*:**.*.**:** .

ref|YP_146517.1|        FKSKEELLDEIVSGLIMEIKAEAELAMDSSLPFSENVHRALYRILEFRQRHQLTAKLLQE
ref|YP_001124699.1      FKSKEELLDEIVSSLIAEIKVEAEQAMDSSLPFSENVHRALYRILEFRQRHQLTAKLLQE
ref|ZP_00739458.1|      FKNKEELFGEIISNLITEMKQVAESAIRSDVSFFENVHRALYSILEFRKEHQLMIKLIQE
ref|NP_830863.1|        FKNKEELFGEIISNLITEMKQVAESAIRSDVSFFENVHRALYSILEFRKEHQLMIKLIQE
ref|YP_893832.1|        FKNKEELFGEIISNLITEMKQVAENAIRSDVSFFENVHRALYSILEFRKEHQLMIKLIQE
RAAC01126               FPSKEALFQHMLRGVIAQVRDAFESAQVEGDDYFRNLERGLRALMRFRADHAMLSKLVQE
                        * .** *: .:: ..:* :::   * *  ..  : .*:.*.*  ::.** * :  **:**

ref|YP_146517.1|        VRNIGTAAVQEVLAKLDRAMVEFIRQKIDAAVEKGEIRPCNSEITAFLMLKTYIALIVDW
ref|YP_001124699.1      MRSIGTIAVQEVLTKFDRAMVEFIRQKIEAAVEKGEIRPCNAEITAFLMLKMYIALIVDW
ref|ZP_00739458.1|      ERDMGTKEVQEVMQQVDVEIVSVIQSYLKIAIEKGEISKCDPEITAFIMLRLYVSLIFDW
ref|NP_830863.1|        ERDMGTKEVQEVMQQVDVEIVSVIQSYLKIAIEKGEISKCDPEITAFIMLRLYVSLIFDW
ref|YP_893832.1|        ERDMGTKEVQEVMQQVDVEIVSFIQSYLKIAIEKGEISKCDPEITAFIMLRLYVSLIFDW
RAAC01126               VRQFGTAEARAGLGELEAAILDYLARHLKRGVELGVVRPCRANLVAFVLLRAYTAVLRDF
                         *.:**  .: ..:  :.: ::. :   :. ..:*  * :  * .::.**::*:*  * ::: *:

ref|YP_146517.1|        EKDHEPLTKEQIAELFTLYFLQGL-------------------
ref|YP_001124699.1      EKDHQPLTKEQIAELFALYFLQGL-------------------
ref|ZP_00739458.1|      EKNHEPLEKEKIAELFELYLLKGL-------------------
ref|NP_830863.1|        EKNHEPLEKEKIAELFELYLLKGL-------------------
ref|YP_893832.1|        EKNHEPLEKEKIAELFELYLLRGL-------------------
RAAC01126               PSAEGPLSEEDLYQLFTGVFVDGLRLRPGEGEPRNTQSEQER
                        .. ** :*.: :** :: **
```

FIG. 102

```
ref NP_832103.1        -----KQRPLGRPRQNKNTKSTKENILEVATRLFLTQNYQVVSMDEVAKVCGVTKATVYY
ref NP_978750.1        -----KQRPLGRPRQNKNTKSTKETILEVATRLFLTQNYQVVSMDEVAKVCGVTKATVYY
ref ZP_02215257.1|     -----KQRPLGRPRQNKNTKSTKETILEVATRLFLTQNYQVVSMDEVAKVCGVTKATVYY
ref NP_844783.1        -----KQRPLGRPRQNKNTKSTKETILEVATRLFLTQNYQVVSMDEVAKVCGVTKATVYY
ref YP_894956.1        -----KQRPLGRPRQNKNTKSTKETILEVATRLFLTQNYQGVSMDEVAKVCGVTKATVYY
RAAC01138              -MRNARSRRPGRPPQVEMEEPTAEKILRAAAECFMDQGFAAVSMDDVAERAGVTKAVVYY
                         .*  ***  *  :    :.* *.**..*:.  *:  *.:    **::  .***.* ref NP_832103.1        YYSTKADLFTATMIEMMVRIRENMSQILSTNKTLEERLLDFAKVYLHATMDIDMKNFMKD
ref NP_978750.1        YYSTKADLFTATMIQMMVRIRENMFQILSTNKTLKERLLDFAKVYLHATMDIDMKNFMKD
ref ZP_02215257.1|     YFSTKADLFTATMIQMMIRIRENMSQILSTNNTLEERLLNFAKVYLHATMDIDMKNFMKD
ref NP_844783.1        YFSTKADLFTATMIQMMIRIRENMSQILSTNNTLEERLLNFAKVYLHATMDIDMKNFMKD
ref YP_894956.1        YFSTKADLFTATMIQMMIRIRENMSQILSTNNTLEERLLNFAKVYLHATMDIDMKNFMKD
RAAC01138              YYGSKTELFQRAMMEVMRASRERTQAILRENGPLRERLQKLTRTRLAIPATLDMNHILRG
                       *:..*::**   :*:::*    **.    **   * .*.***  .::.  *    .  :**::::.

ref NP_832103.1        AKLSLSEEQLKQLKNAEDNMYEVLEKALDNAMHIGEIPKGNAKFAAHAFVSLLSIGNFKD
ref NP_978750.1        AKLSLSEEQLKQLKHAEDNMYEVLEKALDNAMQIGEIPKGNAKFVAHAFVSLLSIGNFKD
ref ZP_02215257.1|     AKLSLSEEQLKELKKAEDSMYEVLEKALDKAMQLGEIQKGNPKFAAHAFVSLLSIGNFKD
ref NP_844783.1        AKLSLSEEQLKELKKAEDSMYEVLEKALDKAMQLGEIQKGNPKFAAHAFVSLLSIGNFKD
ref YP_894956.1        AKLSLSEEQLKELKKAEDSMYEVLEKALDKAMQLGEIQKGNPKFAAHAFVSLLSIGNFKD
RAAC01138              SQRALRPDQVDEMHRAEEQLVEVIAQELHAEMEQGRLRPVDAMFVARSYLALLGMGQAEI
                       ::  :*   :*:..:::.**:..:  **:  :  *.   *.  *.:     :.  *.*:::::**.:*:  :

ref NP_832103.1        ENHNPILANIDELAQEIVSFYWNGL---
ref NP_978750.1        ENHNPILTNIDELAQEIVSFYWNGL---
ref ZP_02215257.1|     ENDNPIIISIDELAQEIVSFYWNGL---
ref NP_844783.1        ENDNPIIISIDELAQEIVSFYWNGL---
ref YP_894956.1        ENDNPIIVSIDELAQEIVSFYWNGL---
RAAC01138              RRRGGGQAAIDEIAEEIVDLLWRGIEPR
                       ..  .     ***:*:***.:  *.*:
```

FIG. 103

```
ref|YP_001309939.1|    MDRRIEKSKQAIMGAFIKLMSEKDFEKITINEIAEEANVNRGTVYLHYEDKFDLMNKCID
ref|YP_001643723.1|    VDRRIIKSKEAIKNAFIELMAEKGFDKITVKDICSGADVGNRTFYLHYLDKFDLLDKLVI
RAAC00354              MDRRVQKSRQAIRDAFVALMKEKDFDHITVQDITERANVSRKTFYLHFLDKYDLLDRVME
ref|YP_001647188.1|    -DPRVKRTRQLIQDAFVALVGEKGFENVTVQHIAERAPVNRATFYSHYHDKYDLLEKSIE
ref|NP_980994.1|       -DPRVKRTRQLIQDAFVALVGEKGFENVTVQHIAERAPVNRATFYSHYHDKYDLLDKSIE
ref|YP_079403.1|       -DRRVKRTKKMIRDALSELMKNKAFEEISVTDITKKADINRGTFYLHYEDKYDLLDQSEE
                        * *: :::: * .*:   *:  :* *:.::: .* . * :.. *.* *: **:**:::

ref|YP_001309939.1|    THLNQLCD------SCISDGESSNFDSKA---SLLQTFQYLEKHAIFYSNMLTNKAMPAF
ref|YP_001643723.1|    ERIEALKT------LCAP---LHDLSFRE---ACIAWFENMEQHYFFFSTMLAGKGASAF
RAAC00354              DAIRDMDEFG----QCVS-----ELDWVP---ATEQCFQYLADRYDFFGTMLTQAGAPYF
ref|YP_001647188.1|    EMLEKLAAVIKPQNRNKEDF-QLTFDSPH--PTFLALFEHIADNTNFYNVMLGDKAAGNY
ref|NP_980994.1|       EMLEKLTKVIKQKNRNKEDF-QLTFDSPH--PSFLALFEHIAENANFYNVMLGDKAAGNY
ref|YP_079403.1|       EIIQEINKIAKRSIHSMDVLNQDVIDHPL--TFVVDIFQYIKENEVFMKAVLGPKGPGSF
                        : . :                   :.         *: :  .. *    :*   .   :

ref|YP_001309939.1|    RERILTMALKSMEEHL-DMTGSNE--NISKNIMAQYVASAAVGVMEWWIVNSMPYPAAYM
ref|YP_001643723.1|    RKHFFDYIIEQIKDDVDIKEGINK--GFSEDMIITFFGSAIVGVVETYFMKGLPDPPEIV
RAAC00354              RRRYVESCKASFTREIRRVVGRDP--LPEEDAILQFVVNAYVGTVEWWLQEGMPYPPRVM
ref|YP_001647188.1|    SYKMMKTIQTHLTLSLSISQPDDEDLMVPRDILISYVTGAHIGMIMSWLKRGMIYTPHFM
ref|NP_980994.1|       TYKMMKAIQTHLTLSLSISQPNDEKLMVPRDILISYVTGAHLGMIMSWLKKGMIYTPHFM
ref|YP_079403.1|       RLKF-KSVLISNLKRLKTAIRTDP--IVPEDYLISYITGAHISVMQQWLENGMKETPHDM
                                 :       :        .: : :..* :. : :: ..:  .. :

ref|YP_001309939.1|    AEQLWQLLK------------------------
ref|YP_001643723.1|    AEQLGMLLD------------------------
RAAC00354              ADRIGRMLESVYTQLPSLAEKPASPRETSQVRPA
ref|YP_001647188.1|    AMQLTRLI-------------------------
ref|NP_980994.1|       AMQLTRLI-------------------------
ref|YP_079403.1|       A--------------------------------
                       *
```

FIG. 104

```
ref|YP_036650.1|       ------------------------------------------------------------
ref|NP_844911.1|       ------------------------------------------------------------
ref|NP_978853.1|       ------------------------------------------------------------
ref|ZP_02256518.1|     ------------------------------------------------------------
ref|ZP_01173627.1|     ------------------------------------------------------------
RAAC02712              ----------MTGGVPHPSVSHLRDGVAECFLDG------------NLSKGEYPMSERMD ref|YP_036650.1|       -WLEELIAATNTDKRNERQMRILEAAVDMFGEKGYASTSTSEIAKRAGVAEGTIFRYYKT
ref|NP_844911.1|       -WLEELIAATNTDKRNERQMRILEAAVDMFGEKGYASTSTSEIAKRAGVAEGTIFRYYKT
ref|NP_978853.1|       -WLEELIAATNTDKRNERQMRILEAAVDMFGEKGYASTSTSEIAKRAGVAEGTIFRYYKT
ref|ZP_02256518.1|     -WLEELIAATNTDKRNQRQMRILEAAVDMFGEKGYASTSTSEIAKRAGVAEGTIFRYYKT
ref|ZP_01173627.1|     --------------LTEKQRSILLAAIQMFSEKGYSATSTNEIAKLAGVAEGTIFRHYKT
RAAC02712              QWLTELVRLNEDDRVTDRQLNILRAAVEVFAEKGFAAASTSEIAQRAGVAEGTIFRHYKT
                        .::*    :::*.*:::..*. ******:* ref|YP_036650.1|       KKDLLLAVVMPTLMKFAAPFFVQAFAKEIFKSEYESYEGLLRVVIHNRFDFAKKHFPMIK
ref|NP_844911.1|       KKDLLLAVVMPTLMKFAAPFFVQAFAKEIFKSEYESYEGLLRVVIHNRFDFAKKHFPMIK
ref|NP_978853.1|       KKDLLLAVVMPTLTKFAAPFFVQAFAKEIFESEYESYEGLLRVVIHNRFEFAKKHFPMIK
ref|ZP_02256518.1|     KKDLLLAVVMPTLTKFAAPFFVQAFAKEIFKSEYESYEGLLRVVIHNRFEFAKKHFPMIK
ref|ZP_01173627.1|     KKDLLLAIVEPIMSDLVAPYLIQD-IEQVLKQRPIRYEDFLRSLLDNRIAFLKKNLPIVK
RAAC02712              KKDLLLSITVPVIDEFVGPFLLRD-LETILTAQHERFEDFLRAVLFNRLQFAKKYAQVLR
                       ******::.  *  : .:...*:::.    :  ::   .   :*.:**  :: **: * **   :::

ref|YP_036650.1|       ILIQEVPFHPELKNEIQQLVETELLLHFKKLIEKFQEKGEIIE-MPPATVLRLTLSAVLG
ref|NP_844911.1|       ILIQEVPFHPELKNEIQQLVETELLLHFKKLIEKFQEKGEIIE-MPPATVLRLTLSAVFG
ref|NP_978853.1|       ILIQEVPFQPELKNEIQQLVETELLSHFKKLIEKFQEKGEIIE-MPPVTVLRLTLSAVLG
ref|ZP_02256518.1|     ILIQEVPFQPELKNEIQQLVETELLSHFKKLIAKFQEEGEIIE-MPPSSVLRLTLSAVLG
ref|ZP_01173627.1|     ILIQEIPFHPDLKKRFIEQIAEKVFQQFAKIVEYYQEQGQIISGIPPKSIVRMTFSALIG
RAAC02712              ILAQEIPFHPELKAQLKQYVTENVLKRLVGIIEHFQEKGEIAR-IPARTVIRLTVSVILS
                       ** **:**:*:**  .: :  :  :::  ::     ::   :**:*:*    :*.  :::*:*.*.::.

ref|YP_036650.1|       LLLTRFLLLPEEKWDDETEIENTIQFILYGLTP-------
ref|NP_844911.1|       LLLTRFLLLPEEKWDDETEIENTIQFILYGLTP-------
ref|NP_978853.1|       LLLTRFLLLPEEKWNDEAEIENTIQFILYGLTP-------
ref|ZP_02256518.1|     LLLTRFLLLPEEKWDDEVEIEHTIQFILFGLTP-------
ref|ZP_01173627.1|     HLAIRYLFLPEAQWDDEAEVERTIRFVMNGLSP-------
RAAC02712              HVVLRHILFHDAPWRDDEEIEMTVRFIVQGLRPDASRDQK
                        :  *.::: :   * *: *:* *::*:: ** *
```

FIG. 105

```
ref|ZP_02327699.1|      MTS----KKREKYQLILDAALKVFAEHGFHRSQVSKIAKAAGVADGTIYLYFKRKEDILI
RAAC01059               MTSGLAEKRREKYEAILKAALKMFAEHGFFNSQVSKIAREAGVADGTIYLYFKNKEDILI
ref|YP_001126706.1      -------REKPKFKQIIDAAVVVIAEHGYHQAQVSKIAKQAGVADGTIYLYFKNKEDILI
ref|YP_148542.1|        -------REKPKFKQIIDAAVVVIAEHGYHQAQVSKIAKQAGVADGTIYLYFKNKEDILI
ref|NP_243968.1|        ----MGKKKGPKYDQIIDAAVQVIAEHGYHQAQVSKIAKAAGVADGTIYLYFNNKEDVLI
ref|YP_360433.1|        ----MAKKSIDKYEAILDAAAKIIGEVGYHKAQISKIAREANVAEGTIYLYFKNKQDLLL
                            *:. *:.**   ::.* *:...*:****: *.**:*******:.*:*:*:

ref|ZP_02327699.1|      SLFREKLGELVSKFNQSIETSTDMKQALYHICRIHYTELEQDVDLAFVTQIELRQSSLEL
RAAC01059               SLFREKLGSLVRKFHEHVHEDDRADEAIRKICELHFTELEKDVQLAKVTQLELRQSSREL
ref|YP_001126706.1      SLFQEKMGSFIEKIEQEIEGISSPLEKLYVLVRTHFSALADDPHMAVVTQLELRQSNKEL
ref|YP_148542.1|        SLFQEKMGAFIEKIEQETEGISSPLEKLYVLVKTHFSALAADPHMAVVTQLELRQSNKEL
ref|NP_243968.1|        SLFQEKMGRFVDKIRSQMNEATDVEEKLKILVNMHFKQLAADHKLAIVTQLELRQSNTEL
ref|YP_360433.1|        SLFQKRYGEFISNLKVEIAAAKTPLDKLKKLITMHLENSEKDRNFAQVTQIELRQADRDL
                        ***::: * :: ::.            : :  :  *      * .:* *:**:. :* ref|ZP_02327699.1|      RREIGKAVKPYIVLIEQLLLKGIEEEVFRPDLDVKLTRSLIFGAMDEVVTSWLVSGRKYS
RAAC01059               HSEISKALKPYIQLIEDVLVRGIEQGIFRRDLDVKLTRLLIFGAMDEVVSSWLISGRRYS
ref|YP_001126706.1      RQRINEVLKGYLRLIDSIIIEGMEKGEFRNDLDVRLTRQMIFGTIDETVTTWVMNEQKYD
ref|YP_148542.1|        RHRINEVLKGYLRLIDRIIMEGMEKGEFRQDLDVRLTRQMIFGTLDETVTTWVMNEQKYD
ref|NP_243968.1|        RLKINEVLKGYLNLLDELLMEGKEKGYFFQELDTRLARQMIFGTLDEVVTNWVMKDCKYD
ref|YP_360433.1|        RQKLSELLKDYFYIIESVIEEGKEQGIFRKDISTKVIRRMIFGTLDETVSSWLLSSRRYS
                        : .:.: :* *: ::: :: .* *:  *  ::..:: * :***::**.*:.*::. .:*.

ref|ZP_02327699.1|      LSDQVEGTVQFFLRGI--
RAAC01059               LSAQVDKTVDFFLRGLRA
ref|YP_001126706.1      LAALAEPVYELLAKGCAA
ref|YP_148542.1|        LAALADPVYELLVKGCAA
ref|NP_243968.1|        LTALVKPVHQLLLGGLR-
ref|YP_360433.1|        LAKLSDDVFQLFCYGI--
                        *:     . . ::: *
```

FIG. 106

```
ref|YP_076316.1|    ----------MGRNRRREAMLQAAIGLFSDKGYHATTVREIAQAVGILPGSLYAHMASK
RAAC01638           MLSGSAGGETRMPRPSQKDQILAAARRLFSEKGYHGTTIREIAVEAGVLSGSLYAHIESK
ref|YP_603589.1|    ---------PAKTR---REQIYDVASRLFSERGYHATSMRDLAGELGMQGGSLYAHISGK
ref|NP_296097.1|    ---------ETTKPR---REQIHDVASRLFSERGYHATSMRDLAGQLGMQGGSLYAHISGK
ref|YP_004584.1|    -------------R---RSQILTIAGHLFSRKGYHATSMRELARHLNLQGGSLYAHIQSK
ref|YP_144239.1|    -------------R---RSQILTIAGHLFSQRGYHATSMRELARHLNLQGGSLYAHIQSK
                                 *   :. :   *   * :*.*::*::*    .:  ******: .* ref|YP_076316.1|    EDLLYEAVVQASERFQEAVAPIAESPGHAGERLRQAMAAHIRVVAESPAAATVFLHEWRA
RAAC01638           EDLLFEIADEGAEAFLLAARAVESKWQHPVDRLREGLRAHIRVVADKQESAKVFFHEWRA
ref|YP_603589.1|    EDLLIEIVNRAARQFDAALFTLRDDPRPADHKLREAMYRHIRVVADNMESATVFFHEWKH
ref|NP_296097.1|    EELLVEIVRGASQQFDEALFSLRDVNLPADEKLREAMFRHIQVVADNMDSATVFFHEWKH
ref|YP_004584.1|    EELLLEVVRQAAERFQKVLEELPSG--DPVTRMKALVKGHLRVIAEELPRATVFFHEWKH
ref|YP_144239.1|    EELLLEVVRQAAERFQKVLEELPSG--DPVTRMKALVKGHLRVIAEELPRATVFFHEWKH
                    *:** *  .  .:. *    .    :.    . :::  : *:::*:*:.   *.**:***:

ref|YP_076316.1|    LSPQRRAMAVAHRRAYEELLARIIREGVESGVFRPVD-EKFVRLLVLSAVNWTYQWYRAD
RAAC01638           LSDDRRKVIQSKRDRYEAHWRKWIEEGMAQGAVRKAD-PKFVRLCLLSVANWVYQWYRPG
ref|YP_603589.1|    LSPAAYARVTAWRDTIDTFYRELVRQGIDEGLFRHDLDVKMTANLILSAVNWTYTWYRPG
ref|NP_296097.1|    LSAEPYAQVVAWRDTIDIFYRDLVAQGVRDGTFRADLDVRAAANLILSAVNWTYTWYRPG
ref|YP_004584.1|    LSPPLLEEAKALRRRYEEGVQAVVEEGVRAGVFRVEN-VRLATLFVLSALNWTYQWYRPD
ref|YP_144239.1|    LSPPLLEEAKALRRRYEEGVQAVVEEGVRAGVFRVEN-VRLATLFVLSALNWTYQWYRPD
                    **       :   *    :  :*:   * .*      :  .   :**. **.* ***..:

ref|YP_076316.1|    GPLSPEQVADQFYAIIAGGL--------------
RAAC01638           GEFTPEDIAEHFWTLLFNGIGTGQPAACELLGEA
ref|YP_603589.1|    GTLTPRDVAEGYADMLLGGL--------------
ref|NP_296097.1|    GRLSPRDVAEQFADMLLSGLMAGE----------
ref|YP_004584.1|    GPLSLEALAEAYAELVLKALG-------------
ref|YP_144239.1|    GPLSLEALAEAYAELVLKALG-------------
                    *  ::   .:*:  :    ::    .:
```

FIG. 107

```
ref|YP_148132.1|        ----RILVVDDEERIRRLLKMYLERENYVIDEAGDGNEALEKALTNDYDVILLDLMLPGK
ref|YP_001126301.1|     -----ILVVDDEERIRRLLKMYLERENYVIDEAGDGNVALEKALANDYDVILLDLMLPGK
ref|NP_242446.1|        --EAKILVVDDEDRIRNLLKMYLEREAYDVEEASDGKEALEKALAFDYDVILLDLMMPEM
ref|YP_175331.1|        -----LLVVDDEERIRRLLRMYLEREEYQIEEASNGEEALELALAKEYDLILLDVMMPGM
ref|ZP_02330236.1|      -----ILVVDDEERIRRLLRMYLEKEGYDIEESQDGETALKLAMDKDYDLILLDIMLPGM
RAAC02161               MAQTRILVVDDEERIRRLVRMYLERNGFEVDEAADGKEALHKALNQAYALIILDLMLPGM
                             :****.*.*::****:: : ::*: :*: **. *:  * :*:**.*:* ref|YP_148132.1|        DGIEVCKEIRAQKTTPIMMLTAKGEESNRVQGFEVGTDDYIVKPFSPREVVLRVKALLRR
ref|YP_001126301.1|     DGIEVCKEIREHKTTPIIMLTAKGEESNRVQGFEVGTDDYIVKPFSPREVVLRVKALLRR
ref|NP_242446.1|        DGIEVCQKLRKQKATPIIMLTAKGEEANRVQGFEVGTDDYIVKPFSPREVVLRVKALLRR
ref|YP_175331.1|        DGVEMCQELRKKKATPVMMLTAKGEEANRVQGFEVGADDYIVKPFSPREVVLRVKALLRR
ref|ZP_02330236.1|      DGTEVCARLRQFKTTPVIMLTAKGEETNRVHGFEVGADDYVVKPFSPREVIYRVKAILRR
RAAC02161               DGRDVCAQIRQHSNVPIMMLTAAGDEANRVHGFELGADDYVVKPFSPRELVLRVKAMLKR
                        **  ::* .:*   .*::****  *:*:*:*:*:*:****::  **:*:* ref|YP_148132.1|        AANAAYAPVETTAKDVLVFPHLTIDNDAHRVTVDGKEVSLTPKEYELLLFLARSPDKVFD
ref|YP_001126301.1|     AANATYAPVETTTKDVLVFPHLTIDNDAHRVTVDGKEVSLTPKEYELLLFLARSPDKVFD
ref|NP_242446.1|        SSSTKFLQTDTQAKDVLVFPHLSIDNDAHRVTVADQEINLTPKEYELLYYLAQSPDKVFS
ref|YP_175331.1|        ASATKFLQTDTQTKDVLVFGPLTIDNDAHRVTVDKTEISLTPKEYELLFYLAQSPDKVFS
ref|ZP_02330236.1|      SSATAFLSKDSNSSNNIVFPHLVIEHDAHRVTAGGQEVALTPKEYELLHYLAVSPDKVFS
RAAC02161               TGEMEYAR---NAIQTLTFPGLEIQIDARRVEVNGQEVNLTPKEFDLLVYMAQRPDKVFS
                        :.       :   :  : :.*  * *: **:**  .  *: ****::** ::*  *****.

ref|YP_148132.1|        REQLLKEVWHYEFFGDLRTVDTHIKRLREKLNKASPQAGKMIVTVWGVGYKFEAVS
ref|YP_001126301.1|     REQLLKEVWHYEFFGDLRTVDTHIKRLREKLNKASPQAGKMIVTVWGVGYKFEAVS
ref|NP_242446.1|        REQLLKDVWNYDFFGDLRTVDTHIKRLREKLNRVSPQAASMISTVWGVGYKFEV--
ref|YP_175331.1|        REQLLKDVWNYEFFGDLRTVDTHVKRLREKLNRVSPEVAAIISTVWGVGYKFE---
ref|ZP_02330236.1|      REELLKDVWNKYEFFGDLRTVDTHVKRLREKLNKVSPEAAVMITTVWGVGYKLEV--
RAAC02161               REELLRDVWNYQFFGDQRTVDTHIKRLREKLGQASPEVSRYIVTVWGVGYKFEVAS
                        **:**::**:*:**** ******:*******  .:.**:..  *  ********:*
```

FIG. 108

```
ref|YP_001213400.1|        -------EILELLEGNARLTPGQIATMLGMEEGEVTRIIKEMEEKKVILGYYTLVNWEKA
ref|YP_001114520.1|        ------LEILELLQSNSRLTAKEIAVLTGQEEDEVKGIIERLEADKTIIKYFTLINWEKA
ref|YP_358986.1|           -------EILQLLHENAKLTPKQIATMLGVTEKEVRAKIKELEERKAIIKYHTLINWEKT
ref|YP_430046.1|           ----MRKKILDLLENNGRLTAKEIAIMLALPVDQVAKEIAAMEQEKIILRYHTLINWEKA
RAAC00349                  MNDALRLKICDLLHENAKLSAETIARMLGETPDVIESTIRELEEEKVILRYSAVVNWDKL
ref|ZP_02330078.1|         --DDFKLKVLELLKEDARRGSDLIATMLGANEEQVAKAIKEMEEENIIVKYATVLNWAKV
                             : :. :.:   .   : .      :    *   :*   :  *: * :::** * ref|YP_001213400.1|        GEEKVSALIEVKISPQREVGFDAVAERIYRFPEVKTVRLMSGAYDLAVMVEGQNLKEVAN
ref|YP_001114520.1|        GLEKVSALIEVKMSPQRDVGFDSVAERIYRFPEVKSVHLMSGAYDLAVFLEGATMKEVAL
ref|YP_358986.1|           EYEPVMALIEVKVTPQREVGFDGIARRIYQFAEVKDVYLMSGDYDLAVMVEGSSMKEVAL
ref|YP_430046.1|           GEEEVAALIDVKVIPQRDLGFDEIASRIYRYPEVKSVFLMSGGYDLSVLVQGKSLKEVAS
RAAC00349                  PVNQVTAVIDVKVLPQREVGFDAIARKIYRFDEVKSVALMSGGYDLQVTVVGRDLREVSR
ref|ZP_02330078.1|         DSDKVTALIEVQITPERGTGFDAIAERIYLFPEVKAVYLMSGSYDLQVEIEGRTLQEVSS
                            : * *:*:*:: *:*  ***  :* :**  : *** * **** ***  * :*   ::**:

ref|YP_001213400.1|        FVAQKLASLDNVLSTTTHFVLKTYKNQGVIVEDGEEDRRLVVTP
ref|YP_001114520.1|        FVAQKLATIDNVLSTATHFVLKTYKQDGFIFEDRENDQRLVIQP
ref|YP_358986.1|           FVALKLSTIEGVQSCATHFILKTYKHEGVILDDEEEDRRLVITP
ref|YP_430046.1|           FVSQKLATLEHVQSTMTHFILKRYKQDGVIFEDQEADRRQALQP
RAAC00349                  FVSEKLATLENVTSTATHFLLKTYKSDGVIYDDTDGERRLMITP
ref|ZP_02330078.1|         FVSTKLSTLDRVLSTKTHFILKKYKHDGIIFEDHEDDHRMLISP
                           **: **:::: * *  ***:** **  :*.*  :*  : ::*   : *
```

FIG. 109

```
ref YP_001634921.1|     ----------MELRHLRYFEAVARHSHVTRAAAELHIAQPALSKQISQLERELGITLFDR
ref YP_290510.1|        ----------MQLQQLAYFLAVAETRHFTRAAELSRVAQPSLSKQIKALEEELGAPLFVR
RAAC01375               MNTRRIGRMRMELVQLEYFLAVAEYQSFRRAADAIRVSQPALSRAIQKLEGDLGAPLFVR
ref YP_079987.1|        ----------MELYQIDHFIAVSRHKHFTKAALEQRISQPALSRSIKKLEEELGVPLFIR
ref YP_001422015.1|     ----------MELHQIDNFIAAAAHQHFTNAAKERMISQPALSRSIIRLEEELGAPLFFR
ref YP_001423330.1|     ----------MDWHQINYFQTVAQVQHITQAAKQLSISQPALSRSISKLEDELGVQLFDR
                                  *:  ::  *  :.:    . .      :::**:   *    :  ** * ref YP_001634921.1|     VGRSLRLTEAGEALLPYARAILAQVEEARAAMAERIGLKAGRVTIGAPPTVGAHLLPPLL
ref YP_290510.1|        ARGNITLTPAGEILLPLAQRILADVETARREIQELAGMRRGWVRLGATPSLCAGLLADAL
RAAC01375               TAQGVRLTPCGEAFLPHARQALAEVAAGARKVAELAGQARGVLHVGLIYSLGTRFLPDVI
ref YP_079987.1|        KTKSIRLTKYGEQFLIKAKQARLALDEGVQQIRESVNPNAGEISVSFLHTLGSRLMPQLI
ref YP_001422015.1|     DTKAVRLTRHGEQFLIKAKQARRALNEGVEQVKKNMSLEHGEISVSFLHTLGLRLMPQLI
ref YP_001423330.1|     KGRNIYLNRYGKMFLHRVEQSIRQIEIGKQEVWNEIHPNSGTILLSFLPSLGMSMVPDVI
                           :  *.   *:  :*    ..       :        .    : :   *  : :.    ::   ::.    :

ref YP_001634921.1|     TIFHQRYPGITLRLHEAGIQSLLDLLEAGITDLAVVALPVT--DEQLTVTPLLNEPLVLI
ref YP_290510.1|        VRFHERYPGIELHVEEGGSRDLIRALGGGELDLALIILPLHSSDPAFVTVPILRESLVVA
RAAC01375               RTFTRTHPGVTVRLSEAPTQKLLQQLDAGEIDIAFCT-PQH--APHLTLVEILQEELVAI
ref YP_079987.1|        AEFKKKYPNVAFRLYQAANEHLQHMVETGEADICLSSPPLP--NEHLEWTVLDTEPLYLV
ref YP_001422015.1|     AEFKKLYPNVTFRLYQGANETLRKMVETGDADICLSSPPLP--SELLQWTVLEKEPLYAV
ref YP_001423330.1|     SSFQHMYPHVNFQLTQASNQQIIEQLTSREVDIALTSLRDE--NDDVICQPLLTEELYLA
                          *    .:*    :  .::  :.    . :         *:..        .   :    * * ref YP_001634921.1|     VSTTHPLARRSEVM-MTELRHERWILSPSSYELREATLKACREAGFTPQTVLEGGETETL
ref YP_290510.1|        SPISQPPPTNGGAMRITDLRDQPLVMFRRGYDVRETTLSACRAAGFEPRLAVEGGEMDAV
RAAC01375               VPLDHPLAAKDQCH-LSDLAGEPFVAYARESGIRHVIERYCAEAGFTPRVAMEGVEDLTV
ref YP_079987.1|        LPADHPLADRKEVA-IRSIAHEDFVCFKPGYGLRYVFDQMCRGLSISPKLAFEGEEVSTI
ref YP_001422015.1|     LPENHPLAGNKSIQ-MKEMQDEDFVGFKPGYGLRYMFDLMCRDLNIHPHLAFEGEEVSTI
ref YP_001423330.1|     VSAEHPLASYDEID-LKMAEHEPFISFKDTNVLHGMIKELCEKAGFSPDVVFEGEDIVTA
                         .    :*  .           :       :      :        ::          *     .: *    ..**   :    :

ref YP_001634921.1|     VRFVAAGLGVSLVPALAVAGCTDVVRLTVSDQHLTRSLGLVWRSDRTASPAARALREFL-
ref YP_290510.1|        LRFVEAGLGLAVVPSMVLRNRPGLRGTPLAEPRLLRTIALAHRKDVALSRTARAF-----
RAAC01375               AGLVAAGVGVAVVPLHAQLDQLPVHVLRLCEP-CKRSVYMAWHTHTTLSPVARAFIAFVK
ref YP_079987.1|        LGLVSAGLGVAILPKTAEHVHSPVAFCRVSDYRSERTIGLAVLKDHYLSPAARNFKEFV-
ref YP_001422015.1|     LGLTAAGLGAAVLPKTAEHSYFPVVFLPVADYQCERTIALAQLKNHALSPAAERFKQF--
ref YP_001423330.1|     SGLVGAKLGVSLIPDLHVFDKTKVKLLSVTNPICEREIGLAWRKDGYLSPAAENFIAFIQ
                         :. *  :* :::*         :  : :.    * ::.  ..   * .*. :

ref YP_001634921.1|     -----
ref YP_290510.1|        -----
RAAC01375               RMCAP
ref YP_079987.1|        -----
ref YP_001422015.1|     -----
ref YP_001423330.1|     -----
```

FIG. 110

```
ref|ZP_02255842.1        --------LKIFVTVVEQKHFSRAAELLNLSQPGVSMHIRNLENEFGTTLIQRSPKHVQVT
ref|YP_897365.1|         --------LKIFVTVVEQKHFSRAAELLNLSQPGVSMHIRNLENEFGTTLIQRSPKHVQVT
ref|NP_981573.1|         --------LKIFVTVVEQKHFSRAAELLNLSQPGVSMHIRNLENEFGTTLIQRSPKHVQVT
ref|YP_001647744.1|      --------LKIFVTVVEQKHFSRAAELLNLSQPGVSMHIRNLENEFGTTLIQRSPKHVQVT
ref|YP_146744.1|         ---MDQLLYVFVKVVEKGNFTKAAEELHMTQPAVSQHIQTLERLFDTKLLDRTNKYVKLN
RAAC00013                MKRVDLQLRVFVTVVEENSFTRAAEKLHISQPAISQHVQTLEQRLGVRLIDRGRRRLQVN
                                  * :**.***:   *::***  *:::**.:* *::.**.  :..  *::*     :  :::.

ref|ZP_02255842.1        EAGNILYIHAKQMLSLYEDAKQEINELHNVVTGTLRIGASFTIGEYLLPKILANYANENP
ref|YP_897365.1|         EAGNILYIHAKQMLSLYEDAKQEINELHNVVTGTLRIGASFTIGEYLLPKILANYANENP
ref|NP_981573.1|         EAGNILYIHAKQMLSLYEDAKQEINELHNVVTGTLRIGASFTIGEYLLPKILANYANENP
ref|YP_001647744.1|      EAGNILYIHAKQMLSLYEDAKQEINALHNVVTGTLRIGASFTIGEYLLPKILARFANENA
ref|YP_146744.1|         KAGEIVYHYAKEILGLYTRMNQLLDDLMNRASGELSIGASYTYGEYVLPQMIAKLHQHYP
RAAC00013                PAGRIVYEHAKEILALYRRMERLIADMQEMPAGPVHVGASLTYGEYVLPHVIARFRKAYP
                         **.*:* :**::*.**   :: :    : :*  :  *** * ***:**::*.  :  .

ref|ZP_02255842.1        RVEVHTFISNTEDVLQSLRSNQIDIGLVEGQVVYADVDVET-FMQDEMKLVVPPNHPLLR
ref|YP_897365.1|         HVEVHTFISNTEDVLQSLRSNQIDIGLVEGQVVYADVDVET-FMQDEMKLVVPPNHPLLR
ref|NP_981573.1|         RVEVHTFISNTEDVLQSLRSNQIDIGLVEGQVVYADVDVET-FMQDEMKLVVPPNHPLLD
ref|YP_001647744.1|      HVEVHTFISNTEEVLQSLRSNQIDIGLVEGQVVYADVDVET-FMQDEMKLVVPPNHPLLH
ref|YP_146744.1|         LIKPTITIGNSNEIVEMVRDHQLDVGIIE-MDIEPKNVYIEPFAKDQMVVVASAHHPYAQ
RAAC00013                AVQPSVSIANTQTIAHAVAVRQLDIGIVEGQDVVEDEVVLTPFAEDEMLVVASPASPWYA
                          ::      *.*:: :  .: .*:*:*::*    :  .     * :*:* :*... * ref|ZP_02255842.1        TNEINERTLQDQ-VWVLRESGSGTRAYSDRFIHQHHLKMKRFFTFSSIQSVKEAVAAGLG
ref|YP_897365.1|         TNEMNESTLQDQ-VWVLRESGSGTRAYSDRFIHQHHLKMKRFFTFSSIQSVKEAVSAGLG
ref|NP_981573.1|         TKEVNERTLQDQ-VWVLRESGSGTRAYSDRFIHQHHLKMKRFFTFSSIQSVKEAVAAGLG
ref|YP_001647744.1|      IKGINENTLQDQ-VWVLRESGSGTRAYSDRFIHQHHLKMKRFFTFSSIQSVKEAVAAGLG
ref|YP_146744.1|         KETVQMEDLCNA-TWIVRETGSGTRKATDEFFLKHNFFPSSIMEFGSTQLIKEAVEAGLG
RAAC00013                -EAPDRSLLERA-TWFIREPGSGTREMTDRLFTQLGIQPRDLVEYTSSQVIKESVAAGLG
                          :    :   *   .*.:.*** :*.::  :      :. : * * :**:* **** ref|ZP_02255842.1        IAILSDWTVRKELLAKELFHVEVPDEQLIRPFSIVRGKYFIPSKA---------------
ref|YP_897365.1|         IAILSDWTVRKELLAKELFHVEVPNEQLIRPFSIVRGKYFIPSKA---------------
ref|NP_981573.1|         IAILSDWTVRKELLAKELFHVEIPNEQLIRPFSIVRGKYFIPSKA---------------
ref|YP_001647744.1|      IAILSDWTVRKELLAKELFHIPVPNEELIRPFSIVRGKYFIPSKA---------------
ref|YP_146744.1|         LTFLSLWTIKKELSFGTLKIIPINDEPFFRHFSLVTPKTPFYTKAMEVFLTIVRTHQPSI
RAAC00013                LACLSRWVVARELAWGMLRTLPIPCAPVKRTFSIVTPKSAFETKASKLLYSFLMEHGSPE
                         ::  ** *.: :**   * : :  . * **:* *  : **

ref|ZP_02255842.1        --------
ref|YP_897365.1|         --------
ref|NP_981573.1|         --------
ref|YP_001647744.1|      --------
ref|YP_146744.1|         SHSPQPPS
RAAC00013                NPSLAGE-
```

FIG. 111

```
ref YP_075596.1           ---------------LLQHLTTFCRVVEEGSFTRAAQVLNLTQPSVTKQVGALEDYLQVQ
ref YP_478499.1           -----------------------IAQQGSFRRAADSLFVSQPAVSLQVQNLERQLGVV
ref YP_430668.1           -------------------LITFITTVEKGTLSAAAEELHLTQPAVSKQLQALEDYFGLR
ref YP_001668480.1|       -----------------EQLITFATVAEHGNISHAAQALHLSQPAVSGQLKLLQEAFGEP
RAAC01493                 MICIIFMLNLYGVMDMFEALRALVTVVSLGSVSEAARALHVTQPTVTRQIQQLERHFGQA
ref YP_590553.1           ---------------FDQLLTFLEVAKLGNFSRAGEKVYRSQSAVSAQIRQLEQEYGER
                                         ..  *..   *.  :  :*.:*: *:   *:

ref YP_075596.1           LFTRQGKRVHLTPVGELVYDYA-RQVIHLVQRCEEAVREYRSPGSGSVTVGCVHTIGLFT
ref YP_478499.1           LFDRSGRKVELTDAGKVVLQYS-ERILKLCREAVEALADLQKMEGGHLVLGASQTVGTYV
ref YP_430668.1           LLERRGREVRLTAAGEICYRHA-RIIASHLNQTRRELAELTQLVRGRLLLGASTTPGQYI
ref YP_001668480.1|       LYQRAGRGVRLTAAGEQLLAHA-ERLRETFRQAQALREAMRGLERGTLRIGASTTPASYL
RAAC01493                 LFDRSGKRLALTPAGERVHAYALEVLRKQE-ELAESLLEMSNPEAGLVRMGAGLSPTLYR
ref YP_590553.1           LFDRSGKIVRLSPAGEVLLEYA-QRMVALRNESLRAVADQGETPRGVLSIGANEATCLYV
                          *  *  *:  : *:  .*:    ::  . .                *  :  :*.    :  .

ref YP_075596.1           LPELLAAYVREHPRVK---INVKTGNNRETVTMLLHGEVDVGLVT--TPQVHER-IEVVP
ref YP_478499.1           MPSLIAQYHRRYPQIS---VQLLVQSTRRIAQKLVDGQLDVAIVGGEIPFELQRHLKVMA
ref YP_430668.1           LPRLIGAFRREYPRV---EVILTIADTQEVVQRLQEGEIDLGVVGAAGGRGKNLSYSRLA
ref YP_001668480.1|       LPYLIADFHARHPEV---LVTTSHGNTAEIVAALDS--VDIALIEGPPGQELPLGTAVTA
RAAC01493                 LPAMVARYASMHPRVR---FQVVTGSSKVTLERLASRVVDLAIVTTPPEDE--AGVEQVA
ref YP_590553.1           LPDIFTEYCQQFPQVQ---ITVYRNFSRKILQAVEDGVIDLGIAT--LPVKSPS-LKVHP
                          :*  :.   :  .*.:   .          :          :*::.:        .

ref YP_075596.1           LFEDPLVVVAGPSFAADLPPVVSNADLAQLPFIG-YVRGARFRMTTDQVLEEMGIQPQF-
ref YP_478499.1           LAEDEYVLVGAPGCAI---DSPALVDLLALPFIT-LDPQSSTRQTIDRVLNRHGINPAQL
ref YP_430668.1           G--DELVLIVPPGHRLAGATAISPGELKEEPLVW-RESGSGTRRVVEERLAAAGFTVDPE
ref YP_001668480.1|       WREDEIVAIVPSGHPLAGSDQQALASLGAYPLVL-RESGSGVRQIVERAFARDGVAMRV-
RAAC01493                 LWRDELVAVAPSYHALAG-KRATIVELAQYPLVV-MHGESGLRRQIDDLLHRAGVERPAP
ref YP_590553.1           IFRDRLELMVPVRHPLAAKESVTIEEIAEYPQI--FPKTGYTRQQLDKLFRP---YNSKL
                                *       :           :  .:   *   :      *     :    :

ref YP_075596.1           --VMEFDNHEAIKTMVALGFGIALEPVSAVQRELISGQLVRLNVPGLPRLSRTTSLILRR
ref YP_478499.1           NVRLELSSIEAIKNAVQAGLGVAFLSTVAVGSDVEQGRFRKLAVEGLQI-RRTLWLAFNP
ref YP_430668.1           QIVMELGSTEAIVSAVEAGLGISLVTSWAVEKSVKLGRLAVVTLQGVDL-KRDLYLVRRR
ref YP_001668480.1|       --ALEIAGVEGVKEAVRAGMGV--------------------------------------
RAAC01493                 P-VMETDSLEAMNRFVQAGLGLAVVPWPAVADDVTQGRLKLVHIVGCDLGQRTVTLVWRK
ref YP_590553.1           RVAMEIPSVGLIKSFVVSGVGVTLLSSTFAQDEVRAGKAKMLPIAGVDM-WRELGLIYRN
                           :*   .   :      *  *.*:

ref YP_075596.1           GERRSEAVRAFLSLL------------
ref YP_478499.1           ERYQSQAATRFLQGL------------
ref YP_430668.1           QPLSP-AAEAFVNFAA-----------
ref YP_001668480.1|       ---------------------------
RAAC01493                 ESHIPAAARAFIEWLASVGAASSSELR
ref YP_590553.1           DRTLPRSATAFIDLMRHRPVAKKSK--
```

FIG. 112

```
ref|YP_896056.1|     --------------------------------------------ELRHLQYFV
ref|NP_845992.1|     --------------------------------------------ELRHLQYFV
ref|ZP_02254866.1    --------------------------------------------ELRHLQYFV
ref|ZP_00743391.1    --------------------------------------------ELRHLQYFV
ref|YP_001375561.1   --------------------------------------------ELRHLQYFI
RAAC01653            -------------------------------------------MDTELRQLEYFV
                                                                 ***:*:**:

ref|YP_896056.1|     VVAEELHFGRAAARLQMTQPPLSQQIQQLEKEMGVMLFSRTKRKVELTEAGEMPLKEVKK
ref|NP_845992.1|     VVAEELHFGRAAARLQMTQPPLSQQIQQLEKEMGVMLFSRTKRKVELTEAGEMPLKEVKK
ref|ZP_02254866.1    VVAEELHFGRAAARLQMTQPPLSQQIQQLEKEMGVMLFSRTKRKVELTEAGEMPLKEVKK
ref|ZP_00743391.1    VVAEELHFGRAAARLQMTQPPLSQQIQQLEKEMGVTLFSRTKRKVELTEAGEMPLKEVKK
ref|YP_001375561.1   VVAEELHFGRAAARLQMTQPPLSQQIQQLEQEMGVMLFERTKRKVELTEAGEMPLKEVKK
RAAC01653            AVAEELHFGRAAKRLGLTQPPLSQQIQKLEDEIGVTLFDRTNRRVQLTHAGRVLLEEARK
                     .*********   :*******:.*: .**:*:*:..::*:*.:* ref|YP_896056.1|     AFEQIEKAVEIAQSAQRGEVGSLSIGFVGAAIYDILPSIVREYRKKFPRVSVALHELSTP
ref|NP_845992.1|     AFEQIEKAVEIAQSAQRGEVGSLSIGFVGAAIYDILPSIVREYRKKFPRVSVALHELSTP
ref|ZP_02254866.1    AFEQIEKAVEIAQSAQRGEVGSLSIGFVGAAIYDILPSIVREYRKKFPRVSVALHELSTP
ref|ZP_00743391.1    AFEQIEKAVEVAQSAQRGEVGSLSIGFVGAAIYDILPSIVREYRKKFPRVSVALHELSTP
ref|YP_001375561.1   AFDQIEKAVEVAQSAQRGEVGSLSIGFVGAAIYDILPSIVREYRKKFPRVSVALHELSTP
RAAC01653            VLAHVQTAVKAARDAAAGRVGRLSVAFVGSATYGWLPEVIRAYQERHPDVELVLREMSTP
                     .: ::::**: *:.*  *. :.***:*  *..**.::* *:::.* *.:.*:*:*** ref|YP_896056.1|     DQVHALHDNRIDIGFLRPPIPTQLLELEPIQKLSCTLCLPKAHPLAEKDEIHIEDLRDEP
ref|NP_845992.1|     DQVHALHDNRIDIGFLRPPIPTQLLELEPIQKLSCTLCLPKAHPLAEKDEIHIEDLRDEP
ref|ZP_02254866.1    DQVHALHDNRIDIGFLRPPIPTQLLELEPIQKLSCTLCLPKAHPLAEKDEIHIEDLRDEP
ref|ZP_00743391.1    DQVHALHDNRIDIGFLRPPIPTQLLELEPIQRLSCTLCLPKAHPLAEKDEIHIEDLRDEP
ref|YP_001375561.1   EQVHALHENRIDVGFLRPPISTQLLELEPIQKLPCTLCLPKAHPLAEKEEIHIEDLRDES
RAAC01653            AQMEALTAGELDVGVLRLPAQHPDLHVRLVERDDCVAVVPSEHPLATRSSLFLVELAEEP
                      *:.**   ..:*:*.** *    *.:. ::: *. :*.  **** :..:.:  :* :*.

ref|YP_896056.1|     FVFITRPVWPALYDTILSLCREVGFSPRIVQEATEYQTVMGLVAAGIGITVIPVSANKLY
ref|NP_845992.1|     FVFITRPVWPALYDTILSLCREVGFSPRIVQEATEYQTVMGLVAAGIGITVIPVSANKLY
ref|ZP_02254866.1    FVFITRPVWPALYDTILSLCRDVGFSPRIVQEATEYQTVMGLVAAGIGITVIPVSANKLY
ref|ZP_00743391.1    FVFITRPVWPALYDTILSLCREVGFSPRIVQEATEYQTVMGLVAAGIGITVIPVSANKLY
ref|YP_001375561.1   FVFITRPVWPALYDTILSLCRGVGFSPRIVQEATEYQTVMGLVAAGIGITVIPVSANKLY
RAAC01653            FVLVSRAIWPGLYDGFITLARALGFEPRVRLEVTEVQTAVGLVAAGLGVSIVPSATERVH
                     **::*.:**.***  :*:*.* .:**.**:.   *.** **.******:*::::*  ::::::

ref|YP_896056.1|     KTEVVYKELYDSNFVAEMSVAYKKMNSNPELLEFLKIA--------
ref|NP_845992.1|     KTEVVYKELYDSNFVAEMSVAYKKMNSNPELLEFLKIA--------
ref|ZP_02254866.1    KTEVVYKELYDSNFVAEMSVAYKKMNSNPELLEFLKIA--------
ref|ZP_00743391.1    KTEVVYKELYDSNFVAEMSVAYKKMNSNPELLEFLKIA--------
ref|YP_001375561.1   KTEVVYKDIYDSNFIAEMSVAYRKTNSSPELLEFLKIA--------
RAAC01653            RRDVRYLHIDGQSPTVELGVAWRRRDTSPLVAAFLAMAESVRPGLS
                     : :* *  .: ...  .*:.**::: ::.*  :  ** :*
```

FIG. 113

```
ref|YP_001210836.1|      ---EEKVDGNLLKVLRSLAPGTHLREGLENILRAKAGALIVIGDTPEVMEIAEGGFAINA
ref|YP_001111557.1|      MVKDEKIEDKLIKLLRLVAPGTPLREGLENILRAKTGALIVIGDIPEVMELAEGGFAINA
RAAC00430                MKDDAKREAAINKILRMVAPGTVLREGIENILRAKTGGLIVVGATETVLSMMDGGFAIQC
ref|YP_001485333.1|      ------RELDLLDIVQFVAPGTPLRAGIENVLRANTGGLIVVGYNDKVKSVVDGGFHINS
ref|NP_387969.1|         -KKGAKHELDLSSILQFVAPGTPLRAGMENVLRANTGGLIVVGYNDKVKEVVDGGFHINT
ref|NP_240971.1|         --DSEVKERFARNILKMVAPGTALRTGIDNVLRAKTGGLIVLGYNENMKGIVDGGFYLDC
                               .::: :****  ** *::*:***::*.***:*    :  : :*** ::

ref|YP_001210836.1|      DFTPSSLYELAKMDGAIILSKDAKKILAANTQLVPNQNIPSAETGIRHRTAERVAKQTGA
ref|YP_001111557.1|      DFTPAGLYELAKMDGAIILSEDAKKIIAANTQLIPDLIIPSSETGIRHRTAERVAKQCDM
RAAC00430                DLTPSHLYELAKMDGAIIISEDAKKVHYANTTLNPDHTIPTSETGTRHRTAERVARQSGQ
ref|YP_001485333.1|      AFSPAHLYELAKMDGAIILSDSGQKILYANTQLMPDATIHSSETGMRHRTAERVAKQTGC
ref|NP_387969.1|         AFSPAHLYELAKMDGAIILSDSGQKILYANTQLMPDATISSSETGMRHRTAERVAKQTGC
ref|NP_240971.1|         PFSPASLYELAKMDGAIILNEDGTKILYANTQLNPDNAISSNETGIRHRTAERVAKQTGN
                         ::*: ************:.... *: *** * *: * : *** ********:*  .

ref|YP_001210836.1|      LVIAISQRRGVITIYKGASKYVLRDIGVILSKANQAIQTLEKYRTVLDKVLVELSVLEFE
ref|YP_001111557.1|      PVISISQRRSVITVYKGSIKYFLRDISVILAKANQAVQTLEKYRSVSDRVINELSMMELQ
RAAC00430                LVICISQRRNVITLYQGNLKYVLRDISVILAKANQALQTLEKYKTVLEQELTDLSALEFE
ref|YP_001485333.1|      LIIAISERRNVITLYQGNRRYTLKDIGFILTKANQAIQTLEKYKTILDHAISALSALEFE
ref|NP_387969.1|         LVIAISERRNVITLYQENMKYTLKDIGFILTKANQAIQTLEKYKTILDKTINALNALEFE
ref|NP_240971.1|         LVISISQRRNVITLYHGHLRYALRDIGVILTKANQAIQTLDKYKSVLDQDITDLGALEFE
                         :*.**:**.***:*:    :* *:**.,**:*****:***.**::: ::  :  *. :*::

ref|YP_001210836.1|      EVVTLFDVAKAIQRVEMVLRVVKEIERYTSELGAEGRLITMQMEELVANVESEGLLVIQD
ref|YP_001111557.1|      EVVTLFDVTKAIQRIEMVLRVKKEIDRYISELGTEGRLIAMQMEELVANVEEEGLLIIQD
RAAC00430                EAVTLEDVTRVLQRFETVLRVTNEIRRYIIELGNEGRLVSMQLEELVSDVDEQAYLLIKD
ref|YP_001485333.1|      ELVTFGDVLSVLHRYEMVLRIKNEINMYIKELGTEGHLIRLQVNELITDMEQEAALFIKD
ref|NP_387969.1|         ELVTFSDVLSVMHRYEMVLRIKNEINMYIKELGTEGHLIKLQVIELITDMEEEAALFIKD
ref|NP_240971.1|         ELVTFHEVSQVMQRIHMVLRIKNIKGEILNYVNELGSEGRLITMQLNELVSNLEKEVLLLIQD
                         * **: :*  .::* . .:  * * :*: :*: **::::::.: *.*:* ref|YP_001210836.1|      YATTIGEKTPSSILGVIGSWPAEDILDLSLIARALGYPGSASILEQHVSPRGYRILEKIP
ref|YP_001111557.1|      YATTLGEKTPESILKVIGSWPAEDLLDLVLIARALGYPGSASVLDQSVSPRGYRALRKIP
RAAC00430                FAHPECPHTPHQIMSQIHNLSSEELLDGALLARILGYPPSVNQLEESVPSRGYRILNKIS
ref|YP_001485333.1|      YV-KEKIKDPYVLLKQLQDMSSFELLDDSILYKLLGYPASTN-IDEYVYTRGYRLLHKIP
ref|NP_387969.1|         YV-KEKIKDPFVLLKELQDMSSYDLLDDSIVYKLLGYPASTN-LDDYVLPRGYRLLNKIP
ref|NP_240971.1|         YA-KEDDVDPEDVLEQMMKCSNEELLDDSNILKLLGYHKAFNVQEQQATPRGYRILHKIP
                         :.           *  ::   :   ..::**    : : ***  ::  ..****  *.**.

ref|YP_001210836.1|      RLPLPVIDNLVKTFGTLNRILVATIEELDDVEGIGEVRARSIKEGLNRYREQLLQER--
ref|YP_001111557.1|      RLPLPVIENLVSTFQYLRTILAASIAELDEVEGIGEVRARSIKDGLTRYGEMLLQDR--
RAAC00430                RLPQPVIENLVEHFGVLSNILKASMADLDKVEGVGPVRARMIQNGLGRIQEQVLIDRQI
ref|YP_001485333.1|      RLPMPIVENVVEAFGVLDRIMEADVQDLDEVEGIGEVRAKKIKKGLKRLQEKHYIDRQL
ref|NP_387969.1|         RLPMPIVENVVEAFGVLPRIIEASAEELDEVEGIGEVRAQKIKKGLKRLQEKHYLDRQL
ref|NP_240971.1|         RLPATIVRNLVHSFENINDMLRADLKELDEVEGIGEARAKLIKDGLSRIQEQLFMDRNI
                         ***  .:: *:*    *    :  :: *   :**.***:* .**: *:..** *   *      :*
```

FIG. 114

```
ref|NP_832076.1|              ------------------------------------MNKTELIKNVAQSADISQKDASAA
ref|YP_001645033.1            ------------------------------------MNKTELVKNVAQSADISQKDASAA
ref|NP_844759.1|              ------------------------------------MNKTELIKNVAQSADISQKDASAA
ref|YP_001375058.1            ------------------------------------MNKTELIKNVAQSADISQKDASVA
ref|YP_535778.1|              ---------------------------------------NKAALIERVAEKTGLTKKDATVA
RAAC02359                     ------------------------------------MNKRDLIRKTAEETGLSQKDCEAV
                                                                  **   *:...*:..:.::**.  ..

ref|NP_832076.1|              VQSVFDTIANALQSGDKVQLIGFGTFEVRERSARTGRNPQTGEEIQIAAGKVPAFKAGKE
ref|YP_001645033.1            VQSVFDTIANALQSGDKVQLIGFGTFEVRERSARTGRNPQTGEEIQIAAGKVPAFKAGKE
ref|NP_844759.1|              VQSVFDTIATALQSGDKVQLIGFGTFEVRERSARTGRNPQTGEEIQIAAGKVPAFKAGKE
ref|YP_001375058.1            VQSVFDTITNALQNGDKVQLIGFGTFEVRERAARTGRNPQTGEEIQIAAGKVPAFKAGKE
ref|YP_535778.1|              VDAVFETIQDALVDGEKVQLIGFGNFEVRERAARKGRNPQTGEEIEIPASKVPAFKPGKS
RAAC02359                     INTLFDTIRKTVESGEKVQIIGFGTFELRERAARTARNPRTGEAVEVPARRVPAFKPGAE
                              ::::*:**   ::  .*:***:****.**:***:**..***:***  :::.*  :*****.* .

ref|NP_832076.1|              LKEAVK-
ref|YP_001645033.1            LKEAVK-
ref|NP_844759.1|              LKEAVK-
ref|YP_001375058.1            LKEAVK-
ref|YP_535778.1|              LKDAVK-
RAAC02359                     LKQAVQV
                              **:**:
```

FIG. 115

```
ref|YP_375842.1|          --------------------MSKAELVEKIAAQAKLTKVDAERAVNAFINVVTSSLKGGD
ref|YP_001131112.1|       --------------------MSKAELVEKIAAQANLTKVDAEKSVNAFINVVTSSLKAGD
ref|ZP_00591928.1         -------------------LMSKAELVEKIASQAGLTKADAERAVNSFVSVVTDSLKAGE
ref|YP_001003150.1|       --------------------MNKADLAEKVAAETGVSKRVATDAVSAVFTGIEESLASGE
ref|NP_046614.1|          --------------------MNKTELIAKVAEKQGVSKKEGAPSVEKVFDTISEALKSGE
RAAC02589                 MCCLTGLERMRDLLEKERELVNKGELVAEVQARVGLPKSQVLQVLNTFCEVTTERLQAGE
                                              :.* :*  ::  .  :.*    :. .    . * .*:

ref|YP_375842.1|          DVTLVGFGTFTTGDRAARQGRNPQTGKAITIPAKKVVKFKPGKALKDEV-
ref|YP_001131112.1|       DVTLVGFGTFTTGDRAERQGRNPQTGKTITIPAKTVVKFKPGKALKDEV-
ref|ZP_00591928.1         DVTLVGFGTFSVGERAERQGRNPQTGETITIAARKAVKFKPGKALKEEVD
ref|YP_001003150.1|       DVSIPGFGKFAVVARPERQGRNPQTGELIDIPAGMNVRFKPGAPLKRSVD
ref|NP_046614.1|          KVSIPGFGTFEVRERAARKGRNPQTGEEIDIPATKAPAFKPAKALKDAV-
RAAC02589                 EVSLPPLGKFQYVMRSARRQRNPQTGEMIDVPEKATVRFRPSGALKGRVN
                          .*::  :*.*    *. *: *****: * :.     *:*. .** *
```

FIG. 116

```
ref|ZP_02170919.1|      MNKTELINAVAESADLSKKDATSAVDAVFEVITDSLKKGDKVQLIGFGNFEVRERAARKG
ref|ZP_01862118.1|      MNKTELINAVAEAAELSKKDATKAVDAVFESIQDALANGDKVQLIGFGNFEVRERAARKG
ref|NP_692713.1|        MNKTDLVNAVAEKSELSKKDATKAVDAVFESVMDSLKNGEKVQLIGFGNFEVRERSARKG
ref|YP_535778.1|        -NKAALIERVAEKTGLTKKDATVAVDAVFETIQDALVDGEKVQLIGFGNFEVRERAARKG
ref|YP_359077.1|        MNKAELVSVIAEKAEMTKKDAEKALNAVLAAIEEALKKGEKVQLVGFGTFEVRERAARKG
RAAC01442               MNKMELINRVAEKTNLKKKDAESAVNAVFEIIEEALANGEKVQIIGFGTFETRSRAARSG
                         **   *:.  :  : :.**   *::**:    : ::* .*:*::*.**.*.*:**.* ref|ZP_02170919.1|      RNPQTGEEIEIPASNVPAFKPGKALKDAVK
ref|ZP_01862118.1|      RNPQTGEEIEISASKVPAFKPGKALKDAVK
ref|NP_692713.1|        RNPQTGEEIEIPASKVPAFKPGKALKD---
ref|YP_535778.1|        RNPQTGEEIEIPASKVPAFKPGKSLKDAVK
ref|YP_359077.1|        RNPQTGQEIEIPASKVPVFKPGKLLKE---
RAAC01442               RNPQTGEVIEIPASTVPAFKPGNKLKEVTR
                        ******: ***.**.**.****: **:
```

FIG. 117

```
ref|YP_001213441.1|    MLNKVILIGRLTQDPELRYTPGGVAVARFTLAVNRARLNKQGERETDFIDVVWQKQAET
RAAC00027              MLNRVILIGRLTADPELRYTNNGTAVASFTLAVDRMRSGPNGERQTDFINVVVWQKQAEI
ref|YP_077145.1|       MLNSVVLIGRLTKDPELRYTPSGKAVATLRLAVDRGTVNQQGERETDFIDIVVWEKQAET
ref|NP_244917.1|       MLNRVVLVGRLTRDPELRYTPNGVAVANFTLAVNRPFSNQQGEREADFINCVVWRKQAEN
ref|YP_149334.1|       MINRVILVGRLTRDPELRYTPSGVAVATFTLAVNRPFTNQQGERETDFIQCVVWRRQAEN
ref|YP_001377189.1|    MMNRVILVGRLTKDPDLRYTPNGVAVATFTLAVNRAFTNQQGEREADFINCVIWRKQAEN
                       *.*  *:*:**  :****  .* *  :  *:*      . :*::*:  *:*.:*** ref|YP_001213441.1|    CANYIRKGRLVAVEGRLQVRSYDDSQGIRRKAAEVVAETVRFLDR---------------
RAAC00027              VAQYLQKGRLAAVDGRLQIRSYDNRDGQRVRVAEVVAETVRFLDRGPDQAQGSGYSAAG-
ref|YP_077145.1|       VANYLQKGRLVAVQGRLQIRQYTTQDGQKREKAEVVATTVRFLDSARD------------
ref|NP_244917.1|       VANYLKKGSLAGVDGRIQTRSYDNNEGR--------------------------------
ref|YP_149334.1|       VANFLKKGSLAGVDGRLQTRSYENQEGRRVYVTEVVADSVQFLEPKGT-SEQRGATAGGY
ref|YP_001377189.1|    VANYLKKGSLAGVDGRLQTRNYEGQDGRRVYVTEVLAESVQFLEPRNSGGEQRGSFNQQP
                       *::::**  *..*:**:*  *.*    :* ref|YP_001213441.1|    ------------------------------------------------
RAAC00027              --------AQTRQQRPTPSSAPPFEDDPFADDSQLIDISEDDLPF
ref|YP_077145.1|       ------------------------------------------------
ref|NP_244917.1|       ------------------------------------------------
ref|YP_149334.1|       YGDPFPFGQDQNHQYPNEKGFGRIDDDPFANDGQPIDISDDDLPF
ref|YP_001377189.1|    SGAGFGNQGSNPFGQSGNSGFTK-NDDPFSNVGQPIDISDDDLPF
```

FIG. 118

```
ref|YP_001038261.1|      ------------------------------------------------------------
ref|YP_001394883.1|      ------------------------------------------------------------
ref|NP_624000.1|         ------------------------------------------------------------
ref|YP_001662406.1|      ------------------------------------------------------------
ref|YP_001664279.1|      ------------------------------------------------------------
RAAC02508                MRLSSCASSKHNTRCQLQRLGQQPHCTGQCVACSLRHPFALHWNPADVDGRIIASVTLDC ref|YP_001038261.1|      --------------------------ILVVDDEKKIVEVVKSYLEHSGYEVYEAFTGKEA
ref|YP_001394883.1|      --------------------------ILVVDDEQKIVDVIRAYLEKAGYEVHSAYNGTEA
ref|NP_624000.1|         --------------------------ILVVDDEIKILEVVKSYLEREGFSVITETNGNNV
ref|YP_001662406.1|      --------------------------IFVVDDEIKILEVVKSYLEHEGFSVITETNGNNV
ref|YP_001664279.1|      --------------------------IFVVDDEIKILEVVKSYLEHEGFSVITETNGNNV
RAAC02508                EDGMKTADCRQIVTHAGGATMKRHHTILVADDEKKIADVLSLYLEQAGFGVVCVDNGSEV
                                                   *:*.*** ** :*:   ***: *: *    .*:.:.

ref|YP_001038261.1|      LYVFEKVPLSLIVLDLMLPDLSGEEICKIIRKKSRVPIIMLTAKAEEEDILKGLNIGADD
ref|YP_001394883.1|      VKLFEKISPALIVLDLMLPDISGEDICKMLRKKSRVPIIMLTAKVDEKTVLEGFNIGADD
ref|NP_624000.1|         LDTFKKEKPDLVILDLMLPGISGEELCKRLRQFSNVPILMLTAKVQESDKINGFSIGADD
ref|YP_001662406.1|      LDTFKKEKPDLVILDLMLPGISGEELCKRLRQFSNVPILMLTAKVQESDKINGFSIGADD
ref|YP_001664279.1|      LNTFKKEKPDLVILDLMLPGISGEELCKRIRQFSNVPILMLTAKVQESDKINGFSIGADD
RAAC02508                LRRLEGLHPSLIILDLMLPDIPGEEVCMAVRARSAVPILMLTAKHRDEDRLRGLQIGADD
                         : ::      *::****.:.::*   :*  *  *:***  :.   :.*:.***** ref|YP_001038261.1|      YITKPFSPKQLVARVTAVLRRTSDDPVPLSNIFSFNNGDLVIDSLKYEVRKGNNVVNLTP
ref|YP_001394883.1|      YVTKPFSPKQLVARVMAHLRRTEEEAIPLSNILSFNNGDLVLNVIKHEVRKNGITVNLTS
ref|NP_624000.1|         YITKPFSPRELVMRVKAILRRTTDD-VPLAEVMSFNNDDLVVDLRAHTVRKKGVVVNLTP
ref|YP_001662406.1|      YITKPFSPRELVMRVKAILRRTTDD-VPLAEVMSFNNDDLVVDLRAHTVRKKGVVVNLTP
ref|YP_001664279.1|      YLTKPFSPRELVMRVKAILRRTSDD-VPLAEVMSFNNDDLVVDFKAHTVKKKGVVVNLTP
RAAC02508                YVTKPFNPNEVVARVQAILRRTMLD-HPLADRLEYRDGDLVIDALSQVVYKGGINAELTA
                         *:****.*.::* ** * ****   :  **::  :.::.:***::          * *    .:**.

ref|YP_001038261.1|      NEYKILMTLVKYPGKTFTRDELINMALGDDFDGFDRTVDTHIKNLRQKIETDPKSPKYIL
ref|YP_001394883.1|      SEYNILMTLVKYPQKTFTREELVNLALEEDFNGFDRIIDAHVKNLRQKIEDNSREPKYIL
ref|NP_624000.1|         NEFKILKILIRNPNRVFTREELIEKVMGFDYEGYDRTIDAHIKNLRQKIEDDTKNPVYIK
ref|YP_001662406.1|      NEFKILKILIRNPNRVFTREELIEKVMGFDYEGYDRTIDAHIKNLRQKIEDDTKNPVYIK
ref|YP_001664279.1|      NEFKILKFLIRNPNRVFTREELIEKVMGFDYEGYDRTIDAHIKNLRQKIEDDTKNPVYIK
RAAC02508                TEYKLLVILSRHPRRVFSREELIERVFGMDFRGDVRTIDAHVKNLRAKIEDDPKSPVYIQ
                         .*:::*  * : * :.*:*:**:: .: *: *  * :*:*:** * :.:.* ** ref|YP_001038261.1|      TVHGVYRFEG---
ref|YP_001394883.1|      TVYKVGYRFGGE--
ref|NP_624000.1|         TVYGVGYKF-GDGN
ref|YP_001662406.1|      TVYGVGYKF-GDGN
ref|YP_001664279.1|      TVYGVGYKF-GDGN
RAAC02508                TVYGMGYRFGGDGN
                         **: :**:* *
```

FIG. 119

```
ref|ZP_00237866.1|         -----MRLLVVEDNASLLESIVQILRDE-FEVDTALNGEEGLFLALQNIYDAILLDVMMP
ref|YP_034830.1|           -----MRLLVVEDNASLLESIVQILRDE-FEVDTALNGEEGLFLALQNIYDAILLDVMMP
ref|ZP_00739566.1|         MEGESMRLLVVEDNTSLLESIVQILRDE-FEVDTALNGEDGLFLALQNIYDAILLDVMMP
ref|YP_001643379.1|        -----MRLLVVEDNASLLESIVQILRDE-FEVDTAMNGEDGLFLALQNIYDAILLDVMMP
ref|NP_830389.1|           MEGESMRLLVVEDNASLLESIVQILRDE-FEVDTAINGEDGLFLALQNIYDAILLDVMMP
RAAC00905                  MEG-AMRILLVEDDRGLSDALAELLREESFQVDVAHDGEEGLYLAETAVYDALVVDVMLP
                               **:*:***:  .*  ::::.::**:* *:**.* :::     :*:::***:* ref|ZP_00237866.1|         EMDGFEVIQKIRDEKIETPVLFLTARDSLEDRVKGLDFGGDDYIVKPFQAPELKARIRAL
ref|YP_034830.1|           EMDGFEVIQKIRDEKIETPVLFLTARDSLEDRVKGLDFGGDDYIVKPFQAPELKARIRAL
ref|ZP_00739566.1|         GMDGFEVIQKIRDEKIETPVLFLTARDSLEDRVKGLDFGGDDYIVKPFQAPELKARIRAL
ref|YP_001643379.1|        EMDGFEVIQKIRDEKIETPVLFLTARDSLEDRVKGLDFGGDDYIVKPFQAPELKARIRAL
ref|NP_830389.1|           GMDGFEVIQKIRDEKIETPVLFLTARDSLEDRVKGLDFGGDDYIVKPFQAPELKARIRAL
RAAC00905                  GLSGYDLVRTLRDKRVHVPVLFLTALGDVDHRVQGLNAGGDDYLPKPFATEEFLARLRAL
                           :.*:::::..::::..**  ..::.:: *: * : *: :* ref|ZP_00237866.1|         LRRSGSLTTKQTIRYKGIELFGKDKDVQVDGQSMKLTLKQYELLEYLIQNSGKILMREQI
ref|YP_034830.1|           LRRSGSLTTKQTIRYKGIELFGKDKDVQVDGQSMKLTLKQYELLEYLVQNSGKILMREQI
ref|ZP_00739566.1|         LRRSGSLTTQQTIRYKGIELFGKDKDVQVDGQGIKLTLKQYELLEYLIQNSGKILMREQI
ref|YP_001643379.1|        LRRSGSLTTQQTIRYKGIELFGKDKDIQVDGQGIKLTLKQYELLEYLIQNSGKILMREQI
ref|NP_830389.1|           LRRSGSLTTQQTIRYKGIELFGKDKDVQVDGKGMKLSLKQYELLEYLVQNSGKILMREQI
RAAC00905                  LRRNRELGTDMTLRSGLLVLDPLARRAAFGNEPIKLSDKEFDLLEYLLSHRGQILMRERI
                           ***. .* *. *:*       : *   :   ...: :**: *:::*****:.: *:*****:* ref|ZP_00237866.1|         FDRVWGFDSDTTVAIVEVYVHHLRKKLEPFGYQKDIQTVRGIGYI----
ref|YP_034830.1|           FDRVWGFDSDTTVAIVEVYVHHLRKKLEPFGYQKDIQTVRGIGYI----
ref|ZP_00739566.1|         FDRVWGFDSDTTVAIVEVYVHHLRKKLEPFGYQKDIQTVRGIGYI----
ref|YP_001643379.1|        FDRVWGFDSDTTVAIVEVYVHHLRKKLEPFGYQKDIQTVRGIGYI----
ref|NP_830389.1|           FDRVWGFDSDTTVAIVEVYVHHLRKKLEPFGYQKDIQTVRGIGYI----
RAAC00905                  FNRVWGIDSDVMDTTVDLYVHYLRKKLQPFGYDTAIRTVRNVGYMWSDP
                           *:****:***.  : *::***:*****:****:.  *:***.:**:
```

FIG. 120

```
ref|YP_001244333.1|    -IPDRILLKPGILTPEEFEIMKQHTTIGFKILSRSNSPILQLGAEIALTHHERWDGSGYP
ref|ZP_02128221.1|     -IPDRILLKPGILTPEEFEIMKQHTTIGFRILSRSNSPILQLGAEIALTHHERWNGAGYP
ref|NP_228001.1|       -IPDRILLKPGILTPEEFEIMKQHTTIGFRILSRSNSPILQLGAEIALTHHERWDGSGYP
emb|CAI44346.1         -IPDRILLKPGILTPEEFEIMKQHTTIGFRILSRSSSPILQLGAEIALTHHERWNGSGYP
RAAC01903              QIPDEILRKPGRLTPEEFDIMKMHTIYGRDMMNSPVHPFLHIGSTVAEQHHERYDGSGYP
ref|ZP_02171167.1|     QVPEEILLKPSKLTEEEWAIMKLHTSYGAEMLRETCISHFLLAAEVVEQHHERYDGSGYP
                        :*:. .  : *    *    ::   .   . : :.: :.    ****::*:*** ref|YP_001244333.1|    RGLKGREIPISGLIVAVADSFDAMVSKRPYKNPKPLEEAFREIESLSGKLYSPEVVEAFL
ref|ZP_02128221.1|     RGLKGREIPISGLIVAVADSFDAMVSKRPYKNPKPLEEAFREIESLSGKLYSPEVVEAFL
ref|NP_228001.1|       RGLKEREIPISGLIVAVADSFDAMVSRRPYKNPKPLEEAFREIESLSGKLYSPEVVEAFL
emb|CAI44346.1         KGLKGKEIPLSGLIVAVADSFDAMVSRRPYKKPKTLEEAFQEIEELSGKLYSPEVVKAFL
RAAC01903              YGLKGEEIYLPAAIVAVVDSYDAMTSQRPYQRPKSKHEAIEEIRALRGKLYDPRVVDAFL
ref|ZP_02171167.1|     RGLKKEEISLEAAIVGLVDSYDAITSERVYQHARSHESALNELRGLRGIKYQPDVVDAFT
                       *** .**   :  . **.:.**::**:.*.*  *:..:.  ..*:.*:.  *  *.  *.* **.**

ref|YP_001244333.1|    KLEKEITD-
ref|ZP_02128221.1|     KLEKEITD-
ref|NP_228001.1|       KLEKEITD-
emb|CAI44346.1         KL-------
RAAC01903              KVVDTFEDT
ref|ZP_02171167.1|     DVIE-----
                       .:
```

FIG. 121

```
ref|YP_290547.1|         ---------IKVLVVDDHEFFRRGLVSVLAEEPDIEVVGEAGDGEEAVARAKELRPDVVL
ref|NP_627230.1|         ------EEPIRVLVVDDHALFRRGLEIVLAAEEDIQVVGEAGDGAEAVEKAADLLPDIVL
ref|YP_480150.1|         ----EGSALIRVLVVDDHELFLQGLQTVLEIEEDISVVGRAGNGQEALTLASGTSPDIVL
ref|YP_001509772.1|      ----RDVMPIRVLVVDDHELFLQGLQTVLETEEDISVVGRAADGQEALTLASGTTPDIVL
RAAC00981                MGTWQDESVIKVLVVDDHELFRRGVVTVLRSTPGIYVVGEAGNGREAIECFQTLQPDVTL
ref|YP_074752.1|         ---------MKVLIVDDHLMLRKGVLSVLSNTD-LEVIGEASNGQEALELVPKLKPDLVL
                                  :::**  ::  :*:  **       : *:*.*.:* :       :.* ref|YP_290547.1|         LDVRMPKRSGIAACAGIKEAVPDAKIVMLTMSDEEEDLFEAIKAGATGYLLKEISVVELP
ref|NP_627230.1|         MDVRMPKRGGIEACTSIKEVAPSAKIIMLTISDEEADLYDAIKAGATGYLLKEISTDEVA
ref|YP_480150.1|         MDVRMPGRDGIAAAGAIKRAVPRTRIVMLTVSDEESDLFEAIKAGAVGYLLKSIPPHEVA
ref|YP_001509772.1|      MDVRMPGRDGIAAAGAIKRAVPRTRIVMLTVSDEESDLFEAIKAGAVGYLLKSIPPHEVA
RAAC00981                LDIHMPVCNGLETARKMREANPNTKILMLTVSETEEMLFEAVKSGASGYVLKSVSPERLI
ref|YP_074752.1|         MDINMPVLDGVEATRKLKQMYPDLKVVILTVSEIDKDLFEAIKAGADGYLLKNLGPEELV
                         :*:.**  .*:  :    ::.  *  :::**:*: :  *::*:*:** **:**.:   .:

ref|YP_290547.1|         EAVRAVCKGQSFINPSMATKLINEFAALARKGKDRRSQPTKP-PRLTERETEVLRLVARG
ref|NP_627230.1|         TAIRAVADGQSQISPSMASKLLTEFKSMIQRTDERRLVPA---PRLTDRELEVLKLVATG
ref|YP_480150.1|         DAVRAVHNGQSLISPSMASKLMVEFATMARGTEDRPRAHA---PHLTARELEVLKLVAEG
ref|YP_001509772.1|      DAVRAVHNGQSLISPSMASKLMVEFATMARGGEDRPRAHA---PHLTARELEVLKLVAEG
RAAC00981                ECVRQVYEGEPVVPSSLAMKMIAEFSRTAETRMPSSESVT----ELTEREREVLQYLSAG
ref|YP_074752.1|         SSLRAAISGEAPISSVMAAKMLKEF-RQPRANTTGKQPGQ----QLSPREIEVLRLASTG
                          . :*  . .:*. . :* *::  **    .         .*:   *:   :  * ref|YP_290547.1|         LNNRDIADRLYISDNTVKNHVRNILEKLQLHSRTEAAVYAIR-------------
ref|NP_627230.1|         MNNRDIAKELFISENTVKNHVRNILEKLQLHSRMEAVVYAMREKI----------
ref|YP_480150.1|         RANREIARKLFISENTVKNHVRNILDKLQLHSRMEAVMYAVRQGL----------
ref|YP_001509772.1|      RANREIARKLFISENTVKNHVRNILDKLQLHSRMEAVMYAVRQGL----------
RAAC00981                ASNKEIARALFISENTVRNHVRHILDKLHLSNRAQAAAYAVRNGIARGRQLTSDV
ref|YP_074752.1|         LTYKEIAAKLYVAESTVKNHMRHILEKLHLRNRSEAVGYAIRTGLA---------
                          ::** *::::.**:**:*:**:**:*  *  :*. **:*
```

FIG. 122A

```
ref|NP_937072.1|         ------------------------------------------------------------
ref|NP_762428.1|         ------------------------------------------------------------
ref|YP_001489923.1|      ------------------------------------------------------------
ref|ZP_01847462.1|       ------------------------------------------------------------
RAAC00986                MIVREAVHALWVALGVISALEFLNMRSSWLRRNHVYEFFTDWLPYGLIWIWIGWVDGVGN
ref|ZP_01964315.1|       ------------------------------------------------------------ ref|NP_937072.1|         ------------------------------------------------------------
ref|NP_762428.1|         ------------------------------------------------------------
ref|YP_001489923.1|      ------------------------------------------------------------
ref|ZP_01847462.1|       ------------------------------------------------------------
RAAC00986                VVMPLYATLSCALHTPNRWNRKISLLGMMIPAALYVIHERHFDPVESEILIGIAAGYVVF
ref|ZP_01964315.1|       ------------------------------------------------------------ ref|NP_937072.1|         ------------------------------------------------------------
ref|NP_762428.1|         ------------------------------------------------------------
ref|YP_001489923.1|      ------------------------------------------------------------
ref|ZP_01847462.1|       ------------------------------------------------------------
RAAC00986                HNRVRASYWAYGCANIVATGFCVLHMTPFTFGTFEETLIVSTIFALYEHDALIRARYKEE
ref|ZP_01964315.1|       --------------------------------------------------------YNRE ref|NP_937072.1|         ------------------------------------------------------------
ref|NP_762428.1|         ------------------------------------------------------------
ref|YP_001489923.1|      ------------------------------------------------------------
ref|ZP_01847462.1|       ------------------------------------------------------------
RAAC00986                RGLDPLTGLYNRRGAEEWLNLHEGNAGIAVLVDLDDPFKFINDFFGHDAGDEVLRKVGGLL
ref|ZP_01964315.1|       LYTDALTGIYNRRYYEERIKNSDMTAGIA-MIDLDDFKIYNDTFGHDAGDLALTTVVGIV ref|NP_937072.1|         ------------------------------------------------------------
ref|NP_762428.1|         ------------------------------------------------------------
ref|YP_001489923.1|      ------------------------------------------------------------
ref|ZP_01847462.1|       ------------------------------------------------------------
RAAC00986                LRFVSSPGIGVRWGGDEFLILAEHETAQSAEQFVEELFSQLSSLELS-LNERRLRLRCSV
ref|ZP_01964315.1|       KANVRRTDMLIRMGGDEFLLVMPDITDQIFADKLKQIQEKIHDTKVPGYSQLRLSVSIGG ref|NP_937072.1|         ------------------------------------------------------------
ref|NP_762428.1|         ------------------------------------------------------------
ref|YP_001489923.1|      ------------------------------------------------------------
ref|ZP_01847462.1|       ------------------------------------------------------------
RAAC00986                GVAYGPLGDLLITEADRALLRVKQSGKAHVEWYHSTIENQGEQLDINQYAFQKAFHQLTE
ref|ZP_01964315.1|       VLSAPGSTVENAIHKADQFMYQAKTCKNMVVTEHDEEVQDKAEGGETSKTYKYRILIVDD ref|NP_937072.1|         ------------------------------------------------------------
ref|NP_762428.1|         ------------------------------------------------------------
ref|YP_001489923.1|      --------TDLKGVITHASSAFCKISGYEKKELIGKPHNIIRHPETSKETFKKMWEE---
ref|ZP_01847462.1|       ------------------------------------------------------------
RAAC00986                FCSAPCLATDLEFRIIDLNEAYERVSGYTRHALRGQKPSMLAFGDWNRRWYPEIHET---
ref|ZP_01964315.1|       SEMNRAILSEILSEEYDIVEADSGESCIDKLRQYEREISLVLLDIVMPGMDGFGVLN---
```

FIG. 122B

```
ref|NP_937072.1|        ------------------------------------------------------------
ref|NP_762428.1|        ------------------------------------------------------------
ref|YP_001489923.1|     -IQKEKKFTT---ELKNLRKDGTY------------------YWVVAEIEPKYDKKGNHI
ref|ZP_01847462.1|      ---------------------------------------------------RAYREQEE
RAAC00986               -LQRGRSWTG---ILHNQREDGTIWSGEMVISPVRIGEITAGYWCMVR----RVFSGDKV
ref|ZP_01964315.1|      YMNRHHYLED----IPVIMISSEDSTEVVRRAYEMGVSDYINRPFDAGV--VHRRVYNTI ref|NP_937072.1|        ------ENLNLLLDVRETSKELVYN-----LANAVEARSKETGAHVQRV----SLISEKL
ref|NP_762428.1|        ------ENLNLLLDVRETSKELVYN-----LANAVEARSKETGAHVQRV----SLISEKL
ref|YP_001489923.1|     GYFAVREDITANKEIEEIQKEIIFT-----MGSIAESRSKETSEHIERV----AKYTELI
ref|ZP_01847462.1|      RAAWLAREVAAAVSLVEAREREIVT----LLMRAAEHRDTDTGDHVARV----AGYVGLI
RAAC00986               RTELLNYEIQVDQDTAEYIENIFLQ----VLAEVAEWGDPELHAHVLRV----RRYTNWL
ref|ZP_01964315.1|      KLYAKQRRLITLITNQVYEKEKNNRMMVEILSQIVEFRNGESGSHVLNINILTGMILESL
                                          :.     :.   .*  .:    *:. .:            :

ref|NP_937072.1|        AQLYG----LSDFEVNLIKHASPLHDVGKVAIPDNILHKPSKLDAQEWEIMKKHVEYGVN
ref|NP_762428.1|        AQLYG----LSDFEVNLIKHASPLHDVGKVAIPDNILHKPGKLDAQEWEIMKKHVEYGVN
ref|YP_001489923.1|     ALELG----LEPKEAKMLKLASPMHDIGKIAIPDYILNKPAKLTPEEFEIVKTHTIKGYE
ref|ZP_01847462.1|      AEAMG----FPPDRGRLISLASTMHDVGKIAIPDAILLKRGPLSAAERREMERHAERGER
RAAC00986               AAKLADRKLIDPRDVPILSSASIAHDIGKVAIAREILFKPNTLDDVEHLYIQRHTEIGEQ
ref|ZP_01964315.1|      VQKTDKYN-ITWSERLLITTASALHDIGKIGIDDKILNKPGKLTDEEFKIMQNHTIIGAR
                        .        :      ::. **  **:**:.*    **  *    *    ::  *.  * .

ref|NP_937072.1|        ILSK----------SKRRLFAIAKEIAGTHHEKWDGSGYPMGLKGEAIPISGRITGLADV
ref|NP_762428.1|        ILSK----------SKRRLFAIAKEIAGTHHEKWDGSGYPMGLQGEAIPISGRITGLADV
ref|YP_001489923.1|     ML------------IALTHHEKYDGTGYPKGLKGEEIPLYGRITAIADV
ref|ZP_01847462.1|      MLES----------SSSEVVRLAAEIAGTHHERWDGTGYPRGLKGEEIPLSGRIVAVADV
RAAC00986               ILQSVLDKLDDMHVHAKRVVEYAKVIAGSHEWWNGKGYPRGLRGNDIPLPGRLVAITDV
ref|ZP_01964315.1|      ILKNMEGYEDE------ELMMVAYQICRWHHERYDGRGYPDGLKGDEIPISAQVVSLADV
                        :*                :.  *  *.   ***  ::*  ***  **:*:   **:   .::. ..:**

ref|NP_937072.1|        FDALGAKRSYKEPWSDEQIRQEIEAQKGKHFDPRLVDLLLENWQAFIDI------------
ref|NP_762428.1|        FDALGAKRSYKEPWSDEQIRQEIEAQKGKHFDPRLVDLLLENWQAFIDI------------
ref|YP_001489923.1|     FDALAHERCYKKAWRVDKIVEYIKEERGKHFDPKLVDLFFENFDKILEIKK----------
ref|ZP_01847462.1|      FDALTSARPYKAAWSLEAARDHVRAQAGTHFDPAVVEAFLGRWPAVEAL-----------
RAAC00986               LDALLSRRPYKEPWSLEEVRNYIESHRGLQFDPKLVTILLEEWAAFEDLVKEVTLYEVRE
ref|ZP_01964315.1|      YDALVGERVYKKAYSHEKAVQMILNGECGAFNPILLECLID-------------------
                        ***    * **  .:     :     :  :     *:*  ::    ::

ref|NP_937072.1|        -
ref|NP_762428.1|        -
ref|YP_001489923.1|     -
ref|ZP_01847462.1|      -
RAAC00986               S
ref|ZP_01964315.1|      -
```

FIG. 123A

```
ref|ZP_01170738.1|        ------------------------------YNRFLKKLLINYIFGSLIAVLAIGATFIFTT
ref|ZP_01856429.1|        ------------------------------------------------------------
ref|YP_001114416.1|       ------------------------------------------------------------
RAAC03031                 MSAAGGIHSSEVCVRRDVGCGMSWTANYEFKRLVKRLILNYFAGSVIAVLGVGGVLIFTT
ref|ZP_00539543.1|        ----------------------------QKFERQLLKNYLIGSFVAVFGVGCLFIFET
ref|ZP_02168828.1|        ---------------------------------RMLINYMVGSLIAVFGVGSVFIFHT ref|ZP_01170738.1|        IDARGYDKALIWLILAGSMVIMFFTEGFFFRQHIRPIRAVFLSDGMDAESVRKAILRLKQ
ref|ZP_01856429.1|        ------------------------------------------------------------
ref|YP_001114416.1|       ------------------------------------------------------------
RAAC03031                 LHLSQEDLWVICGILGGSLVLMLTADSIAFRVQIRPIRKALLTAHPTEDVLAKGYKRALH
ref|ZP_00539543.1|        LTFDARERVTLLTIMFLSVVLMFSFEYTIYRKHMRPLYQFFQTSTPSQAQLTAAFRTTHR
ref|ZP_02168828.1|        LTLSSEETLILLGIMVLSGLIMISLELFVYSKHIRPLVHFFKKGMNPQDA----YMTAHS ref|ZP_01170738.1|        FPVLTVKRIMLPHLLGLTIPAASASLYLISAGELKLSYYMVLYAAIAAFLVASMHALVEF
ref|ZP_01856429.1|        ------------------------------------------------------------
ref|YP_001114416.1|       ------------------------------------------------------------
RAAC03031                 LPALAVLRVMGPHWLSFLIPGLVSSSILVRRGLLHLPMAYVWLASLGTLIVACMHAVIEF
ref|ZP_00539543.1|        FPLLTIKRILGPHFLGLSIPSSSLTALAIHFQWLEMPYYLIGLACFGAILVAILHALIEF
ref|ZP_02168828.1|        FPFMTVRRIMGPHLLGLSIPATVMTLFALSLGFLTLPHLYVLYAWIGAILIATLHAMIEF ref|ZP_01170738.1|        YLTLRAIKPVLAHFKAANKSGW---LVQETPSTIPIKKKFRLTVLVIGVLPVLIFMVAAQ
ref|ZP_01856429.1|        ------------------------------------------------------------
ref|YP_001114416.1|       ------------------------------------------------------------
RAAC03031                 FLTSRSIEPTLVTIRRRSEHMYGASVLLRGQVVVPLAFKFAMSAVVFGALPLLLFGLANA
ref|ZP_00539543.1|        FLTYRVTESMLAELTVQSQQYGHGELILTKKDFISLRKKMLISTLIIGVFPILLFVLASA
ref|ZP_02168828.1|        FMTSRAVQPLIASICARTDE----NLKLDGVKVISMKWKLLLSMLLIAVFPAALFLLAGQ ref|ZP_01170738.1|        IKLEGMGMETAVFWQWAAVVIFITVCYAMLTAKYMAEDIEEPISRLQTLMSEAENQNFAY
ref|ZP_01856429.1|        ------------------------------------------------------------
ref|YP_001114416.1|       ------------------------------------------------------------
RAAC03031                 VRLTHEGLGSSTYWTWAGGILALGSLFSAFGGYLLASDVQRPIRRLEALMRRVERGDFSL
ref|ZP_00539543.1|        VQLT-ENESLRSYWSWSTLILIVILCLATFCSLLLYENIQKPILALQEGVAQIESGQLNT
ref|ZP_02168828.1|        IRESAET--TTAYWNWAFLVIVVILFVSIAGAVVLYRNMEQPILELRKNLEQVQHGEFHref|ZP_01170738.1|        LKDNVYTDEFSEVFTGFNIMIAALKQREETNRQLLESFMTVLSAALDARDPYTSGHSMRV
ref|ZP_01856429.1|        -----------------------AQQEE----LMLSPVKSFISTLDAKDPYTRGHSERV
ref|YP_001114416.1|       -------------------------------KTMFKSFLVALASAIDARDPYTRGHSERV
RAAC03031                 RADDTYMDEFSDLIQGFNLMLNGLAHRDAMNRQLIDSYFATLAAALDARDPYTAGHSQRV
ref|ZP_00539543.1|        -INNPFSDEFSQLVGGFNLMVEGIQGRDQENEQLLDSLFTLFAATLDARDPYTAGHSLRV
ref|ZP_02168828.1|        EMPNYYADEFSTLINGFNSMVSGIKSRDAENERLLESPFSVFAATLDARDSYTAGHTTRV
                                                 ::  *  .   :  :::**:*.** **:  **

ref|ZP_01170738.1|        ASFSRDIGKRLGLHDEELKQLYQTALLHDIGKIGVPDGVLQKEGKLSDEEFEYIKAHPVI
ref|ZP_01856429.1|        ALIAQQLAKQLGYSGEFIQDIYLSGLLHDIGKIGVDDGILRKEGKLTDEEFSQIQKHPMI
ref|YP_001114416.1|       SQYSLMMGKALGLPEQDLELLERAAFLHDIGKIGIRDHILLKESPLDNEEFIIMKTHTTI
RAAC03031                 ARYAEAIGRKVNLSPQTVRELRQSALLHDIGKIGIRDEBILLKEGKLTDEEFAIIKQHPVI
ref|ZP_00539543.1|        AEYSVEIARAAGLADDQVELLRKSALLHDIGKIGIRDDVLLKEGRLTGEEFDKIQKHPVI
ref|ZP_02168828.1|        ADYSTQIARRSGLSGDELDLLRKSALLHDIGKIGIPDSVLLKDGKLTDEEFDKIKEHPVI
                          :   :  :.:   .    :  :  :..:*******:  *  :* *:. *  .***   ::   *.   *
```

FIG. 123B

```
ref|ZP_01170738.1|      GETILKQVQPAGEVASLLPGIRSHHERIDGKYPDGLQGEEIPYFGRIIAVADSYDAMTS
ref|ZP_01856429.1|      GYKILTGIKK---LKNILPGIRNHHEQIDGRGYPDGLRGSDIPLMARIIAVADAYDAMGS
ref|YP_001114416.1      GQNILQQIEPNYLVQEISQGAACHHERYDGKYPQGLQREEIPLAARIMAIADTFDAMVT
RAAC03031               GENIIRQIQPDDAMKPLLPGIRSHHERYDGKYPDGLAGEEIPLFGRILAVADAFDAMTS
ref|ZP_00539543.1|      GVHILSQVHLPEKLQPILPGVKYHHERYDGKYPEGLAGESIPVFGRIMAIADAYDAMTS
ref|ZP_02168828.1|      GGDILEKVNLPEHLRPLLDGVRHHHERFDGKYPDGLSGDRIPLYGRIIAVADAFDAMTS
                         *  *:  :.    :  : *   ***: **:***:**    **  .**:*:**::*** :

ref|ZP_01170738.1|      DRPYRKGMPPEKALHILESGKGTQWDPQVADAFIELARKM-------------------
ref|ZP_01856429.1|      DRPYRNGMPLERLENIFREGKGLQWDSDVIDAYFEIRDEI-------------------
ref|YP_001114416.1      DRPYRKGLPVKLALQEIKRCAGSQFDPQLAEIFL-------------------------
RAAC03031               DRPYRSGMPVERAIQVLREGRGTQWDPHFVDAFIEVYREVYIPDEAKSAAREAAASTSQ
ref|ZP_00539543.1|      DRPYRKGMPVAKALAILEEGSGTQWDASFTQLFLDLKR---------------------
ref|ZP_02168828.1|      NRPYRKAMSYEQARNILQNGRGSQWDPAFIDHFMDFYEE--------------------
                        :****..:.           :.    * *:*. . : ::
```

FIG. 124

```
pdb|1B4A A              ------------------------------------------------N
sp|O31408 ARGR_BACST    ------------------------------------------------N
ref|YP_001126414.1|     ------------------------------------------------N
ref|NP_243643.1|        ------------------------------------------------N
ref|ZP_00538558.1|      ------------------------------------------------T
RAAC01956               ---------------------------------------MKRRLSVQS
                                                                        .

pdb|1B4A A              KGQRHIKIREIIMSNDIETQDELVDRLREAGFNVTQATVSRDIKEMQLVKVPMANGRYKY
sp|O31408 ARGR_BACST    KGQRHIKIREIIMSNDIETQDELVDRLREAGFNVTQATVSRDIKEMQLVKVPMANGRYKY
ref|YP_001126414.1|     KGQRHIKIREIIMNSDIETQDELVDRLKEAGFNVTQATVSRDIKEMQLVKVPMANGRYKY
ref|NP_243643.1|        KGQRHIKIREIIANNDVETQDELVEQLKAAGYNVTQATVSRDIKELHLVKVPMMDGRYKY
ref|ZP_00538558.1|      KGQRLIKIREIITQSEIETQDELVEELRNAGYKVTQATVSRDIKELHLVKVPLNDGRYKY
RAAC01956               KEQRLMRIREIVSQNEIETQEDLVRALEEAGFPVTQATISRDIKELQLVKVVGSNGKYKY
                        *  :::  ...:*::**   *. : *:**::**    :*:*** pdb|1B4A A              SLPSDQRFNPLQKLKRALVDVFIKLDGTGNLLVLRTLPGNAHAIGVLLDNLDWDEIVGTI
sp|O31408 ARGR_BACST    SLPSDQRFNPLQKLKRALVDVFIKLDGTGNLLVLRTLPGNAHAIGVLLDNLDWDEIVGTI
ref|YP_001126414.1|     SLPSDQRFNPLQKLKRALVDVFIKLDGTGNLLVLRTLPGNAHAIGVLLDNLDWGEIVGTI
ref|NP_243643.1|        SLPADQRFNPLQKLKRGLVDSFVSIDRTDNLIVMKTLPGNAHAIGALIDNLDWTEIMGTI
ref|ZP_00538558.1|      SLPADQRFNPLGKLRRLLGDSFISIDSAQNLIVMHVLPGNANALGVLLDHLNWPELLGTV
RAAC01956               ALPTAVNKVSVDALQRRLAEVFISHARANNLIVIKVAPGNAHAIGALMDALDPPGLLGTI
                        :**:   .  .: *:* * : *:.     : **:*::. ****:*:*.*:* *:    ::**:

pdb|1B4A A              CGDDTCLIICRTPKDAKKVSNQLLSM-
sp|O31408 ARGR_BACST    CGDDTCLIICRTPKDAKKVSNQLLSM-
ref|YP_001126414.1|     CGDDTCLIICRTPKDAKKVSNQLLSM-
ref|NP_243643.1|        CGDDTILIICKDKQDGPVVTERFLNM-
ref|ZP_00538558.1|      CGDDTILMITRNEEAATEVTERILGM-
RAAC01956               CGDDTMLLVCQDEEAAVRLLNETLNIG
                        ***** *:: :  :  .   :  :. *.:
```

FIG. 125

```
ref|YP_001127098.1|        --------------AQKKLLPDLLEVMQKRYQILHSISLMAPIGRRALAASLGMSERVLR
ref|YP_148912.1|           --------------AQKKLLPDLLDVMQKRYQILHSISLMAPIGRRALAASLGMSERVLR
ref|ZP_01696601.1|         ----------------KKLYPDILAVMQKRYRILRSISFAEPVGRRTLAQMLGMSERVLR
ref|ZP_01171675.1|         ----------------KRLLPDLLTVMQKRYQILQYIGFMQPVGRRSLAVSLGSTERVLR
ref|YP_176517.1|           ----------------QIVPELMETMAKRYRLLQYIRLMQPIGRRSLATNLQTSERIVR
RAAC01498                  MTMRRSGMEWTVWAAVERVAPELVRAMEHRVRVMQRIDAHAPIGRRALAQAMGQSERTLR
                                          ::  *:::  .*  :*  :::: *     *:*:   :  :** :* ref|YP_001127098.1|        SETEFLKGQNLLSTDVSGMRLTEEGQALLHTLNDLMREALGLKELETALKQRLNVARVVV
ref|YP_148912.1|           SETEFLKGQNLLSADVSGMRLTEEGQALLHTLNDLMREALGLKELEAALQEQLGIPRVIV
ref|ZP_01696601.1|         SETDFLKNQKLIDVKPSGMSVTNDGAALLQNMESMMREISGINETEEKLKQALGLEDVVV
ref|ZP_01171675.1|         SEVDFLKNQNLISVASSGMNLTAEGKDLLERLESIMRDITGIDILEARLKEVLGVRQVIV
ref|YP_176517.1|           GEVTLLLKDQGLIELTTAGMRLTEAGEALFLELADMMAELLGHRRLEEKLKEKLGVSQAIV
RAAC01498                  TELDYLKQLGLVATSSSGVSLTPEGKALLGELEPLVAEIAGRSDLAWRVSALLRIPRVIV
                              *   **   *:    :*: :*  *  *:    :   ::  :  *      :.  *  : ..:* ref|YP_001127098.1|        VAGDSDRSPWVKKELGRACVACMKEQLRPGDIVAVAGGTTMAAVAEMMTPDPKLA-DVLF
ref|YP_148912.1|           VAGDSDRSPWVKKEMGRACVACMKELLEPGDIVAVAGGTTMAAVAEMMTPDSKLR-DVLF
ref|ZP_01696601.1|         VQGDSDKEPWVKNELGRACAVRMKAALTGNNIIAVTGGSTMAAVADVLTPDISAKRQLLF
ref|ZP_01171675.1|         VAGNSDESPWVKSELGRACAASMKQRLKGKNTVAVTGGSTMAAVAEMLTPNLFDD-ELLF
ref|YP_176517.1|           VAGDSDEEEWVKQELGRACVDELKRVAKKGDVFAVMGGTTLAAVANMVTPDETLA-TTTF
RAAC01498                  VEGDADEDAWVTDRIGQAGSDVLAEVLQDGDIIAVTGGTTVAAVAKAMSAKPLRQ-RITV
                           *  *::*..  **...:*:*         :       : .** **:*:****. ::..         .

ref|YP_001127098.1|        VPARGGLGEDVENQANTICAKMAEKATGRYRLLHVPDQLSGEAYASLIEEPAVKEVLELI
ref|YP_148912.1|           VPARGGLGEDVENQANTICAKMAEKAMGRYRLLHVPDQLSDEAYASLVEEPAVKEVLELI
ref|ZP_01696601.1|         VPARGGIGEDVANQANTICAKMAERTGGKHRVLYVPDQVSPEVYKSVVNEPSIKEVLTLI
ref|ZP_01171675.1|         VPARGIGEEVKNQANTICAMMAEHTASRHKFLHVPDQVSKTMYETIMKEPVINEVLNLI
ref|YP_176517.1|           VPARGGLGEKVEIQANTISAEFARRSGASYRLLHVPDQLSEEAYHSLVLERSVREILDVI
RAAC01498                  VPARGTVGEIVAYQANTIASELAAKLGGSSVLLQISDSLSQKALEQLLDDPYIQERLPII
                           ***.: *  *****.: :*  :    .* :.*.:*         :: :  :.* * :* ref|YP_001127098.1|        QSCRMVVHGIGEAVTMAKRRKTPPVEMEKIIARHAVAEAFGYYFNEHGDVVHKVKTVGIQ
ref|YP_148912.1|           QSCRMVVHGIGEAVTMAKRRKTPPVEMENIIARHAVAEAFGYYFNEYGDVVHKVKTVGIQ
ref|ZP_01696601.1|         KQADIVLHGIGEAMTMAERRKTGKEEMEKIIRGHAVGEAFGYYFNEQGEIVHKVRTIGLQ
ref|ZP_01171675.1|         QSAGMVLHGIGDAITMAERRKTTPEDLLKIQERKAVGEAFGYYFDEAGEVVHKVQTIGLQ
ref|YP_176517.1|           TSSAVVMHGIGDARRMAARRDSGQPFIETLKREEAVAEAFGYYFNANGEIIHKQRTIGLQ
RAAC01498                  RQATVVVHGVGDALAMARRRHATEEEIKLLEAREAKAEAFGHYFNARGEVVYAMRTIGLR
                           .. :*:**:*:*  ** **.:     :     .* .****:**:  *:::: :*:*::

ref|YP_001127098.1|        LENLPHVEHVIAVAGGASKAKAIQAYIKRAPHS-LLVTDEGAAKALV-------------
ref|YP_148912.1|           LEHLPHVEHVIAVAGGASKAKAIRAYMKRAPHS-LLVTDEGAAK----------------
ref|ZP_01696601.1|         LEDLHRIRHVFAVAGGASKAKAIKAYMNTKPESTVLITDEGAAKQIL-------------
ref|ZP_01171675.1|         LKDLADIEHVIAVAGGSSKAKAIRAYMKQAPSSTILITDEGAAKQLLK------------
ref|YP_176517.1|           LGE-LEGKYVISIAGGHTKANAILAYMKNRPSD-VLVTDEGAARRLL-------------
RAAC01498                  LDDVARARVVIAVAGGQKKAQAIASVANAYRID-VLVTDEGAARRILQLETPAGKERVEH
                           * .      . *:::*** .**:**  :    :       .  :*:******:

ref|YP_001127098.1|        ------
ref|YP_148912.1|           ------
ref|ZP_01696601.1|         ------
ref|ZP_01171675.1|         ------
ref|YP_176517.1|           ------
RAAC01498                  GSEGWY
```

FIG. 126

```
ref|YP_090740.1|      ----------------------------MATIKEIALQAKVSSTTVSRVLNHDQSLSVAP
ref|YP_078338.1|      ----------------------------MATIKEIALQAKVSSTTVSRVLNHDQSLSVAP
ref|YP_001422307.1|   ----------------------------MVRLKDIALQASVSSATVSRILNKDDSLAVTD
ref|NP_243093.1|      ----------------------------MATIKDIAKLANVSNATVSRVLNRDATLSVTE
ref|YP_001126180.1|   ----------------------------MATLKEIAEKVGVSVATVSRVLNYDTTLSVSD
RAAC01624             MEIFLCIFTRKIILSLSPVICVKGGGKVLATMKDVAELARVSIAVVSRVLNEDRSLSVPE
                                                  :. :*::*   . ** :.***:**  *  :*:*.

ref|YP_090740.1|      ETRQRILDIAARLGYKSTRRREVYASGSGESPRIGIVVCQSQEEELNDPYFYSIRQGIE
ref|YP_078338.1|      ETRQRILDIAARLGYKSTRRREVYASGSGESPRIGIVVCQSQEEELNDPYFYSIRQGIE
ref|YP_001422307.1|   ETREKVLRIADELGYQPSAKRR-KNRSRSDSAPLIGVVSCLSPEVERQDPYFSAIRKGIE
ref|NP_243093.1|      ETRERIYSIAKELGYKRIKERQ---ETKKQVAPNIGIIILQSPEEEIDDPYFNSIRNGVE
ref|YP_001126180.1|   ETRKRIFEVAQELNYKTLRERS---QQARESFR-LGLIHWYSERQEIDDPYYMAIRLGVE
RAAC01624             STRKRVIEAANQLNYKVKRRQN---RSATSKIKTIAIVDFHPEEQERDDPYFWPMVRGIE
                       .**::      *  .*.*:      .:              :..::    .  *  :***:  .:   *:* ref|YP_090740.1|      SECFERGAF--ITKFIQLSSIR--SNQPVGD--VDGLIVIGRINFAGLQQCMGALNN--V
ref|YP_078338.1|      SECFERGAF--ITKFIQLSSIR--SNQPVGD--VDGLIVIGRINFAGLQQCMGALNN--V
ref|YP_001422307.1|   EECFRQKVF--ITSSIHLGSFQ--EHMFHEL---DGVIVIGSLQDEALTNISAAFRH--A
ref|NP_243093.1|      QTLQAKGIY--STKVIHVQDST--TTSNIDG--LDGLIIIGGVTSDKIKQMTAPLEH--L
ref|YP_001126180.1|   KECFERG-IQLVKLFKQNGA-YPIERMKELD----GIIAVGKFGPKEVSDFARGAKQ--I
RAAC01624             LECQEKGLIHPVKFYVKTPAEF--SPSELSN--FDGVLVIGAEEWSGWDDFH--HPN--V
                                   :                    .               *:: :*         :

ref|YP_090740.1|      VYINHTDNEELRDSVVVDFEKATGRALNHLKSLGYTRIGYIGGREKEHFRISDQETSAIE
ref|YP_078338.1|      VYINHTDNEELRDSVVVDFEKATGRALNHLKSLGYTRIGYIGGREKEHFRISDQETSAIE
ref|YP_001422307.1|   VFVNGTPDPARYDSVSVDFYAAAQKAIEHLLSLGYQRLGYIGGREREHTVIDG-VNSNKT
ref|NP_243093.1|      VFVNRCPSEEEFDSVVIDFEKATSKALDYLFLKGFRRIGYIGGTERQLS-----DQGKVE
ref|YP_001126180.1|   VFVDCSPDERQFDSVVIDLRQATITVLDYLLQLGHTKIGYIGGRE--------YVDGETP
RAAC01624             VFLDHCPNVARYSSVLLNFSSAVKDVFNHFWRLGYRTFAYIGGTRRFG------------
                      *:::    .  .** :::  *.  .:::    *.    :.****  .

ref|YP_090740.1|      IEDKRLTAFL---EMAGSDNAKH-IYIGEYSMQQGYELMKKALLE-KNVPEAFFIASDSM
ref|YP_078338.1|      IEDKRLTAFL---EMAGSDNAKH-IYIGEYSMQQGYELMKKALLE-KNVPEAFFIASDSM
ref|YP_001422307.1|   IEDKRLTAFL---QMAG-AEPEH-VLIGEYSMHEGFRLMNEAIKGGS-LPDAFFIASDSM
ref|NP_243093.1|      IEDFRHTVYVKKMEELGLYEPSL-VFIGEYKMTEGYKLMKRAIEAG-NLPEAFFISSDPM
ref|YP_001126180.1|   IRDERETAFYEYLYVKGMYDSRD-VWIGAFTAEDGYRLMKEAIAKG-DLPTAFFIASDSM
RAAC01624             -MDERESTFR--TCVKSTVGAEPPVYHGDWSTGGGYEAMKLMLQEGAPLPRAIFVASDPM
                             *  * :.:     .   .  :    *  :.  *:.  *:   :        :*  *:*:;**.* ref|YP_090740.1|      AIGALRALRESGLKVPEDVAIVSFNGIEASEFANPPLTTVKVHTEEMGRTGVKLLLDRLK
ref|YP_078338.1|      AIGALRALRESGLKVPEDVAIVSFNGIEASEFANPPLTTVKVHTEEMGRTGVKLLLDRLK
ref|YP_001422307.1|   AVGALKALQEAGLQVPRDTAVVSFNGIDEAEYASTPLSTVKVYTEEMGRTGVKLLLDRLN
ref|NP_243093.1|      AVGALRALKEANIAVPRDVSLVSFNDNEMAQFVDPPLTTVKVFTEQMGEMAVQLLLDRLN
ref|YP_001126180.1|   AIGALRALHEAGIAVPQDVAIVGFNDLPTAAFLHPPLSTVKVYTEFMGETAVELLIERLT
RAAC01624             AIGVIRALTEIGKRVPEDVAVVGFDDIDMAAYVNPALTTIRVQPEVMGRIGVRMLMCPYD
                      *:*.::**  *  . **.*.::*:.      :   ..*:*:.:*  .*  **. .*.:*:

ref|YP_090740.1|      -GRELPLKVTVPSELIIRE----------------
ref|YP_078338.1|      -GRELPLKVTVPSELIIRE----------------
ref|YP_001422307.1|   -GRTVPLAVTLPTSLIVRQ----------------
ref|NP_243093.1|      -GRTLPLKVVVPTELVVRE----------------
ref|YP_001126180.1|   TKRTICKKVIVPTELVVR-----------------
RAAC01624             --PNVPVQVVMPYQLVIRESCGACGSLAAGGRDFGL
```

FIG. 127

```
ref|ZP_01696173.1|                    ---------------------------------------LGEQIANELRLLILTNEIKPGDI
ref|ZP_02327860.1|                    ---------------------------------------LGESIACELRLQIINGTIKPGEV
ref|ZP_00539488.1|                    ---------------------------------------GDRVAHELRMRIISGKIESGTV
ref|YP_034511.1|                      ---------------------------------------GDRVASELRMRIIAGAIESGTI
ref|NP_694112.1|                      ---------------------------------------GEQVVAELRMRIISQAIEPETV
RAAC00077                             ----------------------MRRNAGGERRLGDVIADVLRREIVWGEWPSGHV
                                                                             *:  :.  **  *:      .  :

ref|ZP_01696173.1|                    ISENQIARKYGTSRSPVRDALKALANDGLIQLERMGARVLGMGLTDIHELYDVREMIEIF
ref|ZP_02327860.1|                    ISENRVAADFGTSRSPVREALKTLSNEGLIRLERMGAVVLGLSSKDVEELYDVRFLIESF
ref|ZP_00539488.1|                    LSENKLAADFSVSRSPVRDALKVLASERIIRLERMGAVVVGLSKKDIQEIYDVRLLIETF
ref|YP_034511.1|                      LSENKIAADFSVSRSPVREALKLLASENIIRLERMGAVVIGLTEKEIEEIYDVRLLIETF
ref|NP_694112.1|                      LSENQLAKEFQVSRSPIREALKVLSSENIVRPERMGAVVIGISEKDIEEIYDVRLMMESF
RAAC00077                             FSENALARRFGTSRSPVREALRQLAHEGLISLGRNGARVVGLDLGDALELYDVRSLIEQF
                                      :***  :*     :  ****:*;**:  *:   : ::      *  **  *;*:     *: ****  ::* * ref|ZP_01696173.1|                    AQQRVSAAP---QE---QLIQFLNETIDKMKIAAKYENHSDFAYYDFSFHDRIIRHAGHK
ref|ZP_02327860.1|                    VQERLAS---INQE---PLMTKLNQIIDKMELAVKYNDIADFAYQDFSFHETTVAAAGHN
ref|ZP_00539488.1|                    VFERIV---KMDRQ---DLVRELSKVLEMMKIAIKYKDADEFSYQDVLFHETIIRSIDHG
ref|YP_034511.1|                      IFERL---GKMDTN---DLVRELNKIMEMMKIAIKYHDSDEFSYQDLLFHETIIRTIEHS
ref|NP_694112.1|                      TFQRLL---DMDNA---SLINDLEKVVEMMKIAIKYKDVDQFSFLDMEFHETIIRSINHH
RAAC00077                             TASRVCERPRAERE---SLAHTLSTLVLAMEEAASRRDWQSFSDLDLAYHDAIVRAANHR
                                        .*:                *   *:   *:  *  ..:   .*:   *. :*:   :      * ref|ZP_01696173.1|                    RILNLWNGMKSLIMAVLLVTTEHVFAHGPDHLAWVIEKHRKIVNSLLTGNEENVEQSVSA
ref|ZP_02327860.1|                    RIFYLWTSIRHIVMTVMLITTEEVFSMGERKKQSVIEKHRTIIRGLESKNGEIILKTVRT
ref|ZP_00539488.1|                    YVSMMWQNLKPVMESFILLSMRQRLDEDIEDFERILENHALYIEAIETGD----------
ref|YP_034511.1|                      YILMIWNNLKPVMESLILLSMRTRFKEKYEDFERIIKNHELYIKAIESKDRALMIEALHQ
ref|NP_694112.1|                      YIAMLWTNLKPVMECLVLLSMRYRMQEDENDFERIIENHRLIVESIKNKDANLVNNAFYK
RAAC00077                             RVLRMWDEMRSLVQLTLALVMRKRMQRGDADMRGALAQHRSLAEAILAGDAAWVRRVMQS
                                       :  :*  ::  ::    : :  .  :           . :*       ..:    :

ref|ZP_01696173.1|                    YFKDSKRTLD-----------
ref|ZP_02327860.1|                    YFADSRQTLHNSL---------
ref|ZP_00539488.1|                    ---------------------
ref|YP_034511.1|                      NFDDVQGKVE-----------
ref|NP_694112.1|                      NFNDVQNRVE-----------
RAAC00077                             HVEETRRLLEGGLRGHPAGDER
```

FIG. 128

```
ref|NP_980690.1         ---------MLTERQLLILQTIIDDFIGSAQPVGSRTLAKKDEITFSSATIRNEMADLEE
ref|ZP_02257686.1|      ---------MLTERQLLILQTIIDDFIGSAQPVGSRTLAKKDEITFSSATIRNEMADLEE
ref|YP_038371.1         ---------MLTERQLLILQTIIDDFIGSAQPVGSRTLAKKDEITYSSATIRNEMADLEE
ref|YP_079889.1         ---------MLTNRQLLILQVIVNDFIRSAQPVGSRTLSKKEDITFSSATIRNEMADLEE
ref|ZP_02170056.1|      ---------MLTERQLLILKAIIDDYVSHAEPVGSRSVSKRDDIHFSPATIRNEMSDLED
RAAC00876               ---------MLTPRQQLILSAIIEDYVRMAEPIGSRALAKHEEIQYSPATIRNEMADLEE
                                 *** ** ***..*::*::  *:*:***::*::* :*.*******:***:

ref|NP_980690.1         LGFIEKTHSSSGRVPSEKGYRFYVDHLLAPQNLPNDEIVQIKDLFAERIFEAEKIAQQSA
ref|ZP_02257686.1|      LGFIEKTHSSSGRVPSEKGYRFYVDHLLAPQNLPNDEIVQIKDLFAERIFEAEKIAQQSA
ref|YP_038371.1         LGFIEKTHSSSGRVPSEKGYRFYVDHLLAPQNLPNDEIVQIKDLFAERIFEAEKIAQQSA
ref|YP_079889.1         LGFIEKTHSSSGRIPSEKGYRYYVDHLLSPGKLSKTDLNIIHSIFKEKIFELEKAVQKSA
ref|ZP_02170056.1|      MGFLEKTHSSSGRIPSHKGYRHYVDHLLSPGQLSKEDIGNIQDVLRSRFHELEEVVRHSA
RAAC00876               MGYLTQPHASAGRFPSQKGYRFYVDNLLRLGQMDRETGEFLKSVFTKRIDEVEQVAREVA
                        :*:: :.*:*:..**.*:**  ::  . ::.:: .::  *  *:  .:. * ref|NP_980690.1         QILSELTNYTAIVLGPKLSTNKLKNVQIVPLDRQTAVAIIVTDTGHVQSKTITVPESVDL
ref|ZP_02257686.1|      QILSELTNYTAIVLGPKLSTNKLKNVQIVPLDRQTAVAIIVTDTGHVQSKTITVPESVDL
ref|YP_038371.1         QILSELTNYTAIVLGPKLSTNKLKNVQIVPLDRQTAVAIIVTDTGHVQSKTITVPESVDL
ref|YP_079889.1         QVLSDLTNYTSIVLGPRLSENHLKQIQIVPIQPKKAVAILVTNTGHVENKTINFPAEVDL
ref|ZP_02170056.1|      KLLSELTNYTSIVLGPEMFESKLRQIQLIPISDKQAVAIIVTDTGHVENQTVHFPERINP
RAAC00876               NVLSMLTKQTVIVLGPKTDTEKLRKIELIPLGGGRAIAILVTNSGHVETVHVRFSSEMEA
                        :;** **: * *****.   .:*::::::*:  *;**;**:;***:.  :  .. ::

ref|NP_980690.1         SDLEKMVNILNEKLSGVPMSELHNKIFKEIVTVLRGYVHNYDSAIKILDGTFQVP-LSEK
ref|ZP_02257686.1|      SDLEKMVNILNEKLSGVPMSELHNKIFKEIVTVLRGYVHNYDSAIKILDGTFQVP-LSEK
ref|YP_038371.1         SDLEKMVNILNEKLSGVPMSELHNKIFKEIVTVLRGYVHNYDSAIKMLDGTFQVP-LSEK
ref|YP_079889.1         SDLEKLVNILNERLRGVPISELKDRIFKEVVIFLKSHIQNYDTILHALGATLDSSVQTDR
ref|ZP_02170056.1|      DDLEKVVNILNDRLRGVPLYKLNEALSKEIHAVMKQYVNRHEAMLNVFHEVPRQHAREK-
RAAC00876               DDVETLVRVLNDKVVGVPISELRRTLYAELAGELRRTVERFEDAIAVLNEVCQVPEREEA
                        .*:*.:*.:**::: ***.:*.  : *:  ::  :....:  :  .      .

ref|NP_980690.1         IYFGGKANMLSQPEFHDIQKVRSLLTMIDNEAEFYDILRHKQVGIQVKIGRENSSTAMED
ref|ZP_02257686.1|      IYFGGKANMLSQPEFHDIQKVRSLLTMIDNEAEFYDILRHKQVGIQVKIGRENSATAMED
ref|YP_038371.1         IYFGGKANMLSQPEFHDIHKVRSLLTMIDNEAEFYDILRHKQVGIQVKIGRENSATAMED
ref|YP_079889.1         LFFGGKINMLNQPEFHDIDRVKSLLSLIEKEQEILRLFQSTESGITIKIGKENDYEEMEN
ref|ZP_02170056.1|      VYFSGKTNILAQPEFNDVERVRKILNIFEEDQLVSKLFRSDQEGMTIRIGEENHFAPFDD
RAAC00876               VYIGGASNMLAQPEFHDVGKAQPILSLLEQNESISNWFPKAEDGIEVRIGAENAVVELKD
                        :::.*  *:* ****:*: :.: :*.:::::    .   :    : *:  ::** **         :.:

ref|NP_980690.1         CSLISATYSIGEEQVGTIAILGPTRMQYSRVISLLQLFTRQITDGLKK-----
ref|ZP_02257686.1|      CSLISATYSIGEEQLGTIAILGPTRMQYSRVISLLQLFTRQITDGLKK-----
ref|YP_038371.1         CSLISATYSIGEEQLGTIAILGPTRMQYSRVISLLQLFTRQFTDGLKK-----
ref|YP_079889.1         CSLITATYTVGSKQIGSIAVIGPTRMDYSRVVGLLQHVSSDLSKALT------
ref|ZP_02170056.1|      CTIITATYEAGGQYLGTVGILGPTRMEYPRVISIMEYLATDLSKKLS------
RAAC00876               CTVIATTYRLGGVPVGHIGVLGPTRMDYNRVMQILSFTSQALTEFLTRFASSG
                        *::*::**  *   :*   :.::*****:* **: ::.  :  ::. *.
```

```
FIG 129 ref YP_001488458.1|     ------------------------KVTINEVAAYAGVSKSTVSRYINGRTNEISIEKVK
ref YP_080909.1|        ------------------------KVTINEVAAHAGVSKSTVSRYINGKIDAISPKKVK
ref ZP_01665756.1|      ------------------------TIRDVAQQAGVSKSTISRYLNGRYECMSLETRE
RAAC00525               MIAGQDGGGGAPPPFAWERRHSVPKRATIQDVARAAGVSVTTVSRYLNGRYESMSENTRE
ref YP_841318.1|        ------------------------EKLTIQDVADYAGVSKATVSRYLNRGGEQLSADVEA
ref NP_347033.1|        ------------------------KKVVIDDVAKLAGVSKATISRYLNGKFEYMSEKTKD
                                                .* :** **** :*:***:*   : :* .

ref YP_001488458.1|     KIKKAIEELHYRPSQLAQGLKVRKSKVIGFIVADITNPFSVATLRGVEEICDEYGYSIMV
ref YP_080909.1|        SIKKAIEELNYRPSQMAQGLKVKSKVIGFLVADITNPFSVATLRGVEEVCDQYGYSIMV
ref ZP_01665756.1|      RIARVIAELDYRPNAVARSLKQKRTHTVGAIVANILNPFSTSIIRGVEDHCKKHGFNLIL
RAAC00525               KIAAVIAELGYRPNALAKGLKAQRTETVGAIVVNMSYPFCVGFLRAFSRTLSAAGYHLMV
ref YP_841318.1|        RVAAAIRALGYSPSPMAQGLKRGKSRLIGLVVADVSNSFSVAVLRGVEKACRDAGYMVML
ref NP_347033.1|        RIKESIEELNYRPNNIARSLKSNKSKLIGVVIADLTNPFSSIIIKGIGDECKARGYNMVI
                         :    *  * * *. :*:.**  ::. :* ::.::  .*.   ::..    *: :::

ref YP_001488458.1|     CNTDNRPEKEREMLLKLNAHYIEGLIINTTGQNNDILQDFQKDGVPIVLVDRKLSELKVD
ref YP_080909.1|        CNTDNSPEKEREMLHKLNAHYIEGLIINTTGRNNDVLLDLISQDVSIVLVDRKVPGLKID
ref ZP_01665756.1|      CNADDDPVKEREYIEMLTAKQIDGLIINTTGGNN-PLVKEVNASVPVVLIDRKAPEMGLD
RAAC00525               AESEGDAKRERQLIESFVANRVEAIALQTSGANN-DYLEDLAREMPVVLVDRAFALRNAY
ref YP_841318.1|        FNLGNDEQLEREAIRSLSAYRVEGFILHTLGHDAGALADAAQLGKPVVLVDRKVGDAEVD
ref NP_347033.1|        ANSDNDVKQEEEYIKSLLDQRVEGIIVNSTGYNEEFLLSIKERGIPVSMVDRTFCEDKVD
                          :   .    *.: :   :      ::..: :::  * :    . .: ::**

ref YP_001488458.1|     TVTTNNRDITIQLLQQMYEKSYEHIAFFTEPVDGISPREERKEAY-EQTAMSKHK--KPI
ref YP_080909.1|        AVTTNNREVTSQIVNLMYDKGYAQVGLFTEPIKGISPREERASAY-TEIALERNAGGTPL
ref ZP_01665756.1|      TVTVDSDLGARLAIGHLVGLGHRRIAMFTLPCDQVSPRLERVRGYQAALAEYNIPFRPEL
RAAC00525               AIGTNNRDASREIAWQLFDLGYDCVVYLTEDERGIPTRTDRLEGY---LDACRVALREPV
ref YP_841318.1|        LVALDNQTAVQEEAAGHLVEAGYRRLLFISEPIKAISSRNERARAFQAFVAEH-VDTVGGT
ref NP_347033.1|        SVKSNNYDITVETINYLIDAGFNSLCFFTTERLDNIKPRIERERAFIDVCSKRLKKENYNI
                          :  :.           :   ..  :   ::       : .*  :*   .:

ref YP_001488458.1|     IKEIDLKQK---EQLREELVHF-VQTNQQKKAILAANGLLMLKLISELVELGLKIPEDIG
ref YP_080909.1|        VYEADVKDK---ESLLQSV-KSFLEMKEGKKAILGNNGLLMLKIISCLYELGISIPEDVG
ref ZP_01665756.1|      LVETDTQLETVIAKVRELLTRAPG---ERPTAIFGANNLMTMAIVKALKRLGVAIPRDMA
RAAC00525               VMRVRRGDP---ASFREALARVDACARKERTAVYTANGLVLMECYRPLRALGHKVPDAMG
ref YP_841318.1|        VFEAQRGDDDALDEALRALRRGAG---QAPVAVLAANAVISLRVAASAARLGWQLGADLG
ref NP_347033.1|        SVVDYSKAGNLEVNIYKFLNNYSG-----KKAIFAVNGVVLLHTLSAINKLNINVPKDLG
                                 . :.           *:   *  ::        *.    . :.

ref YP_001488458.1|     VAGFDDTEWYKLIGPGITTVAQPSHEMGKAAMQKIKTRLEG---DESAPQTIQLDGEIIV
ref YP_080909.1|        IAGFDDTEWYKLIGPGITTIAQPSHEMGRVAMERIIKRIEG---DESAPQTIQLEAELVL
ref ZP_01665756.1|      VIGFDDWEWAELIDPPITVVAQPVYDMGVKAAAVLIKRIKAGKPPKKPATVVFAPQLVV-
RAAC00525               IATFDQPDWADLVDPPLTCVRQPVEEMGEAAGRIITARLRG---EAVAAEVLVVPSTVVM
ref YP_841318.1|        LIGFDDPEWAALVGPGLSAISQPTDDIGRVATNCLIERLQG---TQLPPRRVLLPGTLVT
ref NP_347033.1|        ICGYDNWGWAALIPPGITTISQPSYEMGSEAAKLVLDRIEG--KASLGAVCKTLSAKLEI
                        :  :*:   *   *: *  ::  **   ::*  *   *:..           .   :

ref YP_001488458.1|     RKS----
ref YP_080909.1|        RQS----
ref ZP_01665756.1|      RASCG--
RAAC00525               RGSTGRG
ref YP_841318.1|        RGSTRR-
ref NP_347033.1|        RGST---
                        * *
```

FIG. 130

```
ref|ZP_02320157.1|        ----------------------------------------------------------------
ref|YP_013918.1|          ----------------------------------------------------------------
ref|NP_470676.1|          ----------------------------------------------------------------
ref|YP_849514.1|          ----------------------------------------------------------------
ref|ZP_02330749.1|        ----------------------------------------------------------------
RAAC01072                 -------------------------------------------------------MGPKGVG ref|ZP_02320157.1|        ----ISKRQQDIYEFIKSEVKEKGYPPSVREIGEAVGLASSSTVHGHLARLEGKGLIRRD
ref|YP_013918.1|          ----ISKRQQDIYEFIKSEVKEKGYPPSVREIGEAVGLASSSTVHGHLARLEGKGLIRRD
ref|NP_470676.1|          ----ISKRQQDIYEFIKSEVKEKGYPPSVREIGEAVGLASSSTVHGHLARLEGKGLIRRD
ref|YP_849514.1|          ----ISKRQQDIYEFIKSEVKEKGYPPSVREIGEAVGLASSSTVHGHLARLEGKGLIRRD
ref|ZP_02330749.1|        ----LSQRQQAILEFIKNEVKEKGYPPSVREIGEAVGLASSSTVHGHLERLEKKGLIRRD
RAAC01072                 TVSGLTARQRAILEFIRKNIREKGYPPSVREIGEAVGLASSSTVHGHLERLQQKGYLRRD
                              :: **: * *:.::**********************.:  :* ref|ZP_02320157.1|        PTKPRAIEILSLEDEAETPN-VVNIPIIGKVTAGMPITAIENIDEYFPLPEYMATGETNV
ref|YP_013918.1|          PTKPRAIEILSLEDEAETPN-VVNIPIIGKVTAGMPITAIENIDEYFPLPEYMAAGETNV
ref|NP_470676.1|          PTKPRAIEILSLEDEAETPN-VVNIPIIGKVTAGMPITAIENIEEYFPLPEYMAAGETNV
ref|YP_849514.1|          PTKPRAIEILSLEDEAETPN-VVNIPIIGKVTAGMPITAIENIEEYFPLPEYMAAGETNV
ref|ZP_02330749.1|        PTKPRAIEILDMDSSSTFSFSVTRVPLIGKVTAGMPITATENIEDYFPLPSHYVG-DHNV
RAAC01072                 PTKPRALELLVDDEE----PGDVVLAPIVGRVTAGLPISALEDIEGYLPLPRDVAKGDE-V
                          ******:*:*   ..     . *.   *::*:**::*  *:*: *:***    . : * ref|ZP_02320157.1|        FMLEIDGESMINAGILDGDKVIVRQQSSAINGEIVVAMTDENEATCKRFYKEANHFRLQP
ref|YP_013918.1|          FMLEIDGESMINAGILDGDKVIVRQQSSAINGEIVVAMTDENEATCKRFYKEANHFRLQP
ref|NP_470676.1|          FMLEIDGESMINAGILDGDKVIVRQQSSAINGEIVVAMTDENEATCKRFYKEANHFRLQP
ref|YP_849514.1|          FMLEIDGESMINAGILDGDKVIVRQQNSAINGEIVVAMTDENEATCKRFYKEANHFRLQP
ref|ZP_02330749.1|        FMLSVLGDSMIETGIHDGDLVIVRQQQTADNGDIVVAMTEDDEATVKRFYKEKDHIRLQP
RAAC01072                 FALRVVGESMINAGILDGDLAIVRRQTSADNGDIVVAMTDEDEATIKRFYREDGRVRLQP
                          * * : *:*:: * .*:* :* :**:::* ****:* .:.**** ref|ZP_02320157.1|        ENDALEPILLNNVTILGKVIGLYRDIR
ref|YP_013918.1|          ENDALEPILLNNVTILGKVIGLYRDIR
ref|NP_470676.1|          ENDALEPIILNNVTILGKVIGLYRDI-
ref|YP_849514.1|          ENDALEPIILNNVTILGKVIGLYRDIR
ref|ZP_02330749.1|        ENSSMAPIILSNVSILGKVIGIFRNI-
RAAC01072                 ENDAMSPLYFPNVTILGKVIGIFRQIR
                          **.:: *: : **:*******::*:*
```

FIG. 131

```
ref|YP_001124617.1|    ------------------------------------------------------------
ref|YP_146331.1|       --------------------------------------------------------DNEQ
ref|YP_849898.1|       ------------------------------------------------------------
ref|NP_471127.1|       ------------------------------------------------------------
ref|NP_465208.1|       ------------------------------------------------------------
RAAC01366              ------------------------------------------------MKGGGDMQA ref|YP_001124617.1|    -KEALDMLKKTGIRITPQRHAILEYLISSMSHPTADEIYKALEGKFPNMSVATVYNNLRV
ref|YP_146331.1|       LKEALDMLKKTGIRITPQRHAILEYLISSMSHPTADEIYKALEGKFPNMSVATVYNNLRV
ref|YP_849898.1|       -KEAVDVLKKTGVRITPQRHAILEFLINSHTHPTADDIYRSLEGNFPNMSVATVYNNLRV
ref|NP_471127.1|       -KEAVDVLKKTGVRITPQRHAILEFLINSHTHPTADDIYRSLEGNFPNMSVATVYNNLRV
ref|NP_465208.1|       -KEAVDVLKKTGVRITPQRHAILEFLINSHTHPTADDIYRALEGNFPNMSVATVYNNLRV
RAAC01366              QKDAVQLLKNAGLRVTPQREAILQFLLDYDGHATVDDIYTSLQDRFPSMSVSTVYNTVKQ
                        *:*:::**::*:*:****.***:*:.    *.*.*:**  :*:..**.***:****.::

ref|YP_001124617.1|    FKEVGLVKELTYGDSSSRFDFVTSNHYHVICEQCGKIVDFHYPALDEVEQLAA--HVTGF
ref|YP_146331.1|       FKEIGLVKELTYGDSSSRFDFVTSNHYHVICEECGKIVDFHYPALDEVEQLAA--HVTGF
ref|YP_849898.1|       FRDAGLIKELSYGDASSRFDFSTSNHYHAICNVCGKIVDFHYPGLDEVEHFAA--HVTGY
ref|NP_471127.1|       FRDAGLIKELSYGDASSRFDFSTSNHYHAICNVCGKIVDFHYPGLDEVEHFAA--HVTGY
ref|NP_465208.1|       FRDAGLIKELSYGDASSRFDFSTSNHYHAICNVCGKIVDFHYPGLDEVEHFAA--HMTGY
RAAC01366              LSQVGLVKEIGVGEGASRFDINVEPHHHLVCTRCGALFDFY---LEEPIQLSVPPEARGF
                        :  : **:**:   *:..****:  .. *:* :*  **  :.**:    *:*  :::.  .  *:

ref|YP_001124617.1|    KVDHHRMEVYGVCPDCQNEK--
ref|YP_146331.1|       KVDHHRMEVYGVCPDCQK----
ref|YP_849898.1|       EIDNHRLEVYGTCPECKEKQIN
ref|NP_471127.1|       EIDNHRLEVYGTCPECKEKQ--
ref|NP_465208.1|       EIDNHRLEVYGICPACKEKQ--
RAAC01
```

FIG. 132

```
ref|YP_077070.1|         ----------------------QRLVAIMKLLSERPGELLPLSFFTERFGAAKSTISED
RAAC01431                MPVCGRLRPRTRAELRRRAMQRHERLIRLTRRLVERPMAPIGISALAEAWGVAKSTLSED
ref|ZP_01666690.1|       ----------------------ERVVALTKLLVDRPHHLFSLGYFSELFGAAKSTISED
ref|YP_814057.1|         ----------------------ERLVDMVKYLLARPHTLIALPFFADRYGAAKSSISED
ref|NP_964223.1|         ----------------------ERLVDMVKYLLARPHTLIALPFFADRYGAAKSSISED
ref|ZP_01173986.1|       ----------------------ERLIDMTNYLLEHPRQLVSLTFFADRYGSAKSSISED
                                               :*::  : . *  :*    .  :  ::: :* * :* ref|YP_077070.1|         LALVKEALEADGSGRLRTHAGAAGGVQYWPLPSREEEQETLLELCRLLSDPGRILPGGFV
RAAC01431                VQLVREVLAEDGAGRVETLVGAQGGVRFVPQVARDRAEAFLWDVARRLASPDRVIAGEFL
ref|ZP_01666690.1|       ILTIKQALQSFGLGTLETVSGAAGGVRYLPQQEAAAINGLLTDLAERLKSADRIIPGGFL
ref|YP_814057.1|         LAILRQTLANDQNGILETVAGAAGGVRYIPFVGKKEATNYLHDLADRIEDPDRILPGNFV
ref|NP_964223.1|         LAILRQTLANDQNGILETVAGAAGGVRYIPFVGKKEATDYLHDLADRIEDPDRILPGNFV
ref|ZP_01173986.1|       LAIIKETFEQRGIGTLQTVPGAAGGVKYSVKVSDDEARPFISGLCEVIASPERLLPGGYL
                          :  :::.:      * :.*  ** ***::            :  :.   : .. *::.*  ::

ref|YP_077070.1|         YMTDLITHPIWSARIGAIMAARFIDAEPDVVLTVETKGIPLALMVARALGLPMVVARREG
RAAC01431                YASDVLGDPDVIDTAGAMVASRFAHAGVEVVVTVETKGIPLAASAARYLHAPLAIVRREQ
ref|ZP_01666690.1|       YMSDILFDSQLMLQIGEVFMTRFQHLAPDCVMTVETKGIPLAFATARAFHVPLVIVRRGS
ref|YP_814057.1|         YLSDILGSPQDLQQIGQLIATKYAYSNVDYVMTIETKGIAIAQAVSRFLNVPFVMVRRRP
ref|NP_964223.1|         YLSDILGSPQDLRQIGQLIATKYAYSNIDYVMTIETKGIALAQAVSRFLNVPFVMVRRRP
ref|ZP_01173986.1|       YMTDILGDPAIVQKAGRVFASAFADADIDVVMTVATKGIPLAYAVGAYLNVPVVIVRRDS
                         * :*::   .       *  :. : :       : *:*: ****.:*   ..  : *...:**

ref|YP_077070.1|         RVTEGPSVTLHYISGS-RRIHTMTVGLRALWRGARVLVVDDFMKAGATARAMVDVAGEMG
RAAC01431                RVTEGASLTTHYVSGSAKRIQTMSLSTRLVPRGARALIVDDFMRAGATARAVAELIGEFG
ref|ZP_01666690.1|       KVTEGPAVSINYVTGSSRRIQTMSLAKRAVPAGARVLIIDDFMKAGGTARGLVDLAQEVG
ref|YP_814057.1|         KITEGSTISVNYVASSSERVEKMELAKRLLPEGSNVLIVDDFMKGGGTLTGMEELVKEFK
ref|NP_964223.1|         KITEGSTISVNYVASSSERVEKMELAKRLLPEGSNVLIVDDFMKGGGTLTGMEELVKEFK
ref|ZP_01173986.1|       RVTEGSTVSINYVSGSAKRIQTMVLSKRSLEEGSKVLIVDDFMKAGGTVNGMISMLEEFK
                         ::***.:::  :*::.*  .*:..*  :. * :    *:..*::****:.*.*   .:  .:   *.

ref|YP_077070.1|         ASVAGVGVFVSTAEPARKQVQRYVSLLTLEQVDEV--ARTVR--------------
RAAC01431                GEVCGTAVFMATSQPAQKMVADYVALLEVGPVRES--GFEVRPNLGALERRVTHVD
ref|ZP_01666690.1|       ARVVGVGVLVATAEPQEKLVEDYVALLILHEVDEHTKKTDIRPAL-----------
ref|YP_814057.1|         GTVAGMCVLCETKYASQKVVDDYQSLIKITEVDRTKKLIKVRP-------------
ref|NP_964223.1|         GTVAGMCVLCETKYASQKVVDDYQSLIKITEV------------------------
ref|ZP_01173986.1|       AHVAGIAVLVEAEKAEERLVDEYLSLVQLADV------------------------
                         . * *  *:   :  . .:  *   * :*:  :   *
```

FIG. 133

```
ref|YP_074599.1|          -MTIRDVARRAGVGVATVSRVLNGTG-YVKAETRERVLAAAAELGYVPSQLARGLVRRLS
RAAC01505                 MVTIRDVARKAGVSVSTVSRVINGSG-YVGEDTERKVLLAMKELNYQPNRIARGLVSRRT
ref|YP_149084.1|          MATIRDVAKRAGVSVATVSRVLNQNG-YVNEETERRVRQAMKELNYKPNEVARALFKKTS
ref|YP_001127265.1        MATIRDVAKRAGVSVATVSRVLNQNG-YVNEETEKRVRRAMKELNYKPSEVARALFKKTS
ref|YP_001661816.1        -VTIKDIAKLANVSITTVSRVINNKSEGVSEETRNRILQLVKELGYQPNAIARGLVTKKT
ref|NP_621898.1|          -VTIKDIARLANVSVTTVSRVINNKPEGVSEETRQKILKLVKELGYQPNAIARGLVTKKT
                            **:*:*:  *.*.::*****:*    *  :*..::    **.* *. :**.*. : :

ref|YP_074599.1|          GTVGLVVPDITNPFFPLITRGVEDAASEAGYTVFLCNTDNDPVLEAQDVRKLREHRVDGI
RAAC01505                 STIGLLIPDVANPFFSEMARGVEDAAIAEGYSVLLCNSDWKSERELMYIDLLKGRWVDGI
ref|YP_149084.1|          KTVGLIVPDITNPFFPELVRAVEDVMNIYDYTVILCNSDEKVEKEREYIEVLKQKYVDGV
ref|YP_001127265.1        KTVGLIVPDITNPFFPELVRAVEDVMNIYDYTVILCNSDEKAEKEREYIEVLKQKYVDGV
ref|YP_001661816.1        KTIGLIIPDISNPFFPDIARGVEDSAHIYGYNVFLCNTDDNLEKESEYINALKEKYVDGI
ref|NP_621898.1|          KTIGLIIPDISNPFFPDIARGVEDSAHIYGYNVFLCNTDDNLEKESEYIRALKEKYVDGI
                          *:**::**::****. :.*.***    .*.*:***:*  .    *  : *: : ***:

ref|YP_074599.1|          IFVG-TTERRELVDQLLADDIPVVVMDRQLEHADVDTVTVDNVAGAQAACRHLIELGHRR
RAAC01505                 VIVG-SRSDSRVIEAAVG-DTPLVIVDRRSSEFRWS-VWTDNRQGAALVVEHLLKMGCSK
ref|YP_149084.1|          ILTTNQFAPEE--VEE--WDVPIVVLDRPLH-ERYPSVVADNYEGARLATRHLYEVGCRR
ref|YP_001127265.1        ILTTNQLTPDE--VDE--WDVPIVVLDRPFN-EKYPSVVVDNYRGARLATRHLYDMGCRR
ref|YP_001661816.1        IFTSSSIPKHEHIMELVKSGIPVIMDRRVDSEDIYGVFLDNYEGGYIATKHLIDLGHKK
ref|NP_621898.1|          IFTSSSIPKHEHIIELVESGIPVVIMDRRVDSENIYGVFLDNYEGGYIATKHLIDLGHEK
                          ::.         .  *:*:** *     *  **  *.  .** ..:*  :

ref|YP_074599.1|          IAHAAGHQSTRTGQDRCQGYRMALEEADIPYDPACVTWGDFTFESGFRVGQVLLGLSPRP
RAAC01505                 IVHIAGPSDSPSAQERRKGYEQAISQAGL---VAIVYEGDFRFASGFEIATMILEGSQRP
ref|YP_149084.1|          IAHIQGPNHVVNAMERFRGYQDEMRALGLG-DRQLVIQGNYQLKQAKE-AVMAALAEHDM
ref|YP_001127265.1        IAHIQGPMYVVNAVERFRGYQDEMMELGIW-EQRLVIQGNYQLKQAKE-AVMAALAQQEI
ref|YP_001661816.1        IACITGPLYTKSAKERLEGYKKALVENGMDVDERLIFEGDYKINSGIIGTEKLLGNNENV
ref|NP_621898.1|          IGCITGPLYTKSAKERLEGYKKALLDSGIKIDEKLIFEGDYKINGGIIGAERLLKDNKDM
                          *   *        .. :* .**.  :   .:    * *::   .         .

ref|YP_074599.1|          TAVFAGNDLIALGVIRAAEEAGLSVPDDLSVVGFDNIQMAALVRPGLTTVRQPAREMGRL
RAAC01505                 DGIFAANDLMAIGVLQAAVKLGVQVPHEVAIVGYDNIPSAGYVSPSLTTVHQPSYQMGVS
ref|YP_149084.1|          DGIFAGNDAMAVGALKAVQQCGLRVPDDIAIIGYDGIPLTEMTTPELSTVSQPIYEMGAM
ref|YP_001127265.1        DGIFAGNDAMAVGALKAVQQCGLRVPDDIAIIGYDGIPLTEMTTPELSTVSQPIYDMGAI
ref|YP_001661816.1        TAIFACNDLMAYGAYKTIRSYGYKIPDDISIVGFDDIQLSQILEPQLTTIKQPAYDMGLA
ref|NP_621898.1|          SAIFACNDLMAYGAYKTIRSFGYKIPDDISVVGFDDIQLSQILEPQLSTIKQPAYDMGLT
                           .:** ** :* *. ::    .  * :*.::::::*:*.*  :    * *:*: ** :**

ref|YP_074599.1|          AMTMLLERIRG---EFSGPGRRHVYPPELIVRGTT---------
RAAC01505                 AFDLLEQFVT---NSGQSARKVKFEPKLVVRDSSLKCPSRNSV
ref|YP_149084.1|          AARILI-KQI---EGKPLEKLHYQLPVQLVVRQST---------
ref|YP_001127265.1        AARILI-KQI---EGKPLEKLHYQLPVQLIVRQST---------
ref|YP_001661816.1        AARMLI-KLVE---GKKLKKKIINFRPQLIIRQST---------
ref|NP_621898.1|          AARMLI-KLIE---GKKLKKKIINFRPQLVIRQST---------
                          *   :*: :       * :*   :*::* ::
```

FIG. 134

```
ref|YP_001661816.1        -----TIKDIAKLANVSITTVSRVINNKSEGVSEETRNRILQLVKELGYQPNAIARGLVT
ref|NP_621898.1|          -----TIKDIARLANVSVTTVSRVINNKPEGVSEETRQKILKLVKELGYQPNAIARGLVT
ref|ZP_01188648.1|        ---MITIYDVAKEAGVSPSTVSRVLNN-YNNVTETTRKKVEAACKKLKYVPNANASSLKK
ref|YP_074599.1|          -----TIRDVARRAGVGVATVSRVLNG-TGYVKAETRERVLAAAABLGYVPSQLARGLVR
ref|YP_147968.1|          ---MASIKDVAKRANVSTATVSRVLRN-AGNVTEETRQRVLEAIEALNYQPNVLGRYLRR
RAAC01078                 MTRMTTMADVAKRAGVSIMTVSRVVNN-SGYVKPSTRQKVLAAMQELNYVP----KGQQS
                             :: *:*: *.*. *****:..   *. **:::        * * * ref|YP_001661816.1        KKTKTIGLIIPDISNPFFPDIARGVEDSAHIYGYNVFLCNTDDNLEKESEYINALKEKYV
ref|NP_621898.1|          KKTKTIGLIIPDISNPFFPDIARGVEDSAHIYGYNVFLCNTDDNLEKESEYIRALKEKYV
ref|ZP_01188648.1|        DNTKTLALIIPDIENPFFISILKGFDDKANKLGYDTILCNTDERLEKEKDYIKMVLKKRI
ref|YP_074599.1|          RLSGTVGLVVPDITNPFFPLITRGVEDAASEAGYTVFLCNTDNDPVLEAQDVRKLREHRV
ref|YP_147968.1|          METETVLVVVPDITNPFFSKVLRGIEAVALEHGYQVLLGDTQNDVRLEEQYLNLLPQRQV
RAAC01078                 SPHDTWMLIVPDITNPFFTFIARGMEDVARKHGFRVFIANTDEDLQKEQEYVQMCLDYQV
                                :::*** ****  : :*.:   *    *:  .:: :*::    * : .   . :

ref|YP_001661816.1        DG--IIFTSSS-IPKHEHIMELVKSGIPIVIMDRRVDSEDIYGVFLDNYEGGYIATKHLI
ref|NP_621898.1|          DG--IIFTSSS-IPKHEHIIELVESGIPVVIMDRRVDSENIYGVFLDNYEGGYIATKHLI
ref|ZP_01188648.1|        DG--VAISTVG-KTS-EHISEFSDRNIPYILLDRKVEGLDADIVCGDNYQGAIDLVNHLI
ref|YP_074599.1|          DG--IIFVGTT--ERRELVDQLLADDIPVVVMDRQLEHADVDTVTVDNVAGAQAACRHLI
ref|YP_147968.1|          DG--MIFLTAR--IRKELVEEMAR-QFPIVLACEYLEGADIPTVSIDNISSARKATEHLI
RAAC01078                 RG--ALVVPVG-DPSRENLVRLTEHQVPFVLIDREIEGLDADLVKGDIRETSRRLVEHLL
                           *        .  *  : .:  .  *  ::  .:: :  *   *     .**:

ref|YP_001661816.1        DLGHKKIACITGPLYTKSAKERLEGYKKALVENGMDVDERLIFEG----DYKINSGIIGT
ref|NP_621898.1|          DLGHEKIGCITGPLYTKSAKERLEGYKKALLDSGIKIDEKLIFEG----DYKINGGIIGA
ref|ZP_01188648.1|        NNGHKDIAMITGPLHVSTSRERFEGYKTALNRAGISVEEDYIKIDYVSQDYSGEKAYEMT
ref|YP_074599.1|          ELGHRRIAHAAGHQSTRTGQDRCQGYRMALEEADIPYDPACVTWG----DFTFESGFRVG
ref|YP_147968.1|          RLGHRRIAHLSGPMNIILSRDRLRGYQQALAQHELEADAALVQEG----DFTYESGYNLT
RAAC01078                 DLGHERIAAVVGPLHSASSRERLDGYRDALLHKGLPVDESLIFTA----PMTRDMDASFV
                          **.*.   *           .::*  **: **    :       :        . .  :

ref|YP_001661816.1        EKLLGNNENVTAIFACNDLMAYGAYKTIRSYGYKIPDDISIVGFDDIQLSQILEPQLTTI
ref|NP_621898.1|          ERLLKDNKDMSAIFACNDLMAYGAYKTIRSFGYKIPDDISVVGFDDIQLSQILEPQLSTI
ref|ZP_01188648.1|        KELLGLNEPPTAIFVANNLMALEVYKALKEEGISVPDDIAIVCFDDLNLIYEIEPFFTVM
ref|YP_074599.1|          QVLLGLSPRPTAVFAGNDLIALGVIRAAEEAGLSVPDDLSVVGFDNIQMAALVRPGLTTV
ref|YP_147968.1|          LKLLALEKPPTAIFAANDEMAIGAIKAVRHRGGRVPDDVAVVGFDDIQMASIFEPSLTTI
RAAC01078                 DALVGRSDAPTALFLGNMFQYAHIVRRLRGLGLSIPHDISVVSFGNTDDLASVDSLATAA
                           *:    .:*:*  *       :    * :*.*:::*  *.: .       .. .:

ref|YP_001661816.1        KQPAYDMGLAAARMLIKLVEGKK--LKK--KIINFRPQLIIRQST-----------
ref|NP_621898.1|          KQPAYDMGLTAARMLIKLIEGKK--LKK--KIINFRPQLVIRQST-----------
ref|ZP_01188648.1|        KQPAYTMGEAAAEILIKRIEMSDNGHRK--RKIVFEPELIIRKSS-----------
ref|YP_074599.1|          RQPAREMGRLAMTMLLERIRGEFSGPGR---RHVYPPELIVRGTT-----------
ref|YP_147968.1|          AQPMFEIGQKAMELLLALIEGT-SARRR---QLVLPDRLVIRDS------------
RAAC01078                 VQPAYNYGSLGAQLLLERIEGVRKTSTR----IVLHSEMVVRSSTAPPPVRMTKKR
                          **    *  .  :*:   :       :      .::::*  :
```

FIG. 135

```
ref|YP_001391734.1     ----------------------------------------------------------------
ref|YP_001254935.1     ----------------------------------------------------------------
ref|YP_001308325.1     ----------------------------------------------------------------
ref|YP_518781.1        ----------------------------------------------------------------
ref|ZP_01171531.1|     ----------------------------------------------------------------
RAAC01972              ---------------------------------------------MRGRSRRPRGLAVREG ref|YP_001391734.1     ---------------------------------EPVDFEDICDLLSDVLACNVYIISRKG
ref|YP_001254935.1     ---------------------------------EPVDFEDICDLLSDVLACNVYIISRKG
ref|YP_001308325.1     ---------------------------------EPVAFQDICTLLSEVLECNVYIISKKG
ref|YP_518781.1        --------------------------------AGHSVDFDEMANVLSESIQSNCYIVGRRG
ref|ZP_01171531.1|     --------------------------------AGKPVNFKEMAETLSEVIEANIFVVSRRG
RAAC01972              TKRRRMPGEGQGDEIVSLLEQVQELGQLLHRSNEQVEFQEVAEFLSRLMQSNVYIVGRKG
                                                         . * *.::.  **   :  .*  :::.:.* ref|YP_001391734.1     KILGSKFYS-GFECEEVREVVLKENRFPDFYNNKLLNVNETLSNSP--NHDK----CVFD
ref|YP_001254935.1     KILGSKFYS-GFECDEVREVVLKENRFPDFYNNKLLNVNETLSNSP--NHDK----CVFD
ref|YP_001308325.1     KVLGYTFGK-DFECEAMKKKVIEDKKFPEDYNKTLLEVNETLSNLP--NEGR----CVFQ
ref|YP_518781.1        KILGYSFMQ-NFGCNTMEDIVVHTERFPESYNEGLLKVTETRSNTT--QVANG---CVFN
ref|ZP_01171531.1|     KLLGFAVNQ-QIENERMKK-MLEDRQFPEEYTKSLFNIQETSSNLD--VESD---YTAFP
RAAC01972              KILGYGVAE-HELTEEWLNIMTREQRFPGDFNKHLLRIEQTIANLTDEQKKP---LYVFS
                       *:       .  .        :   .: .  ..:  :.: *:.: :* :*       .* ref|YP_001391734.1     NLKDCSINNKLSTIVPINGNRERLGTLLLARFDKEFTDEDLILAEYSATIIGLEILRSKQ
ref|YP_001254935.1     NLKDCSINNKLSTIVPINGNRERLGTLLLARFDKEFTDEDLVLAEYSATIIGLEILRSKQ
ref|YP_001308325.1     EIGKCKKVDKLSTIVPIIGSRERLGTLILARFGNPFTDEDLVIVEYSATIVGMEMLRAMQ
ref|YP_518781.1        EKERCHFNNKITTILPILGGGERVGTLVLAKFDQDFSEADLILAEYGATVVGMEILRIKA
ref|ZP_01171531.1|     VENKELFKNGLTTIVPIIGGGERLGTLILARLQEQFHDDDLILGEYGATVVGMEILREKA
RAAC01972              PEENESFRSKHLMITPIIGARERQGTLLFARSQRPFNEDDQILAEYAATVVALEIVHSRQ
                           . * **  *   ** ***::*: . * : * :: **.**:..:*:::

ref|YP_001391734.1     DQIEEEARKKAVVQLAIGTLSYSELEAVEHIFNEL-DGTEGLLVASKIADKVGITRSVIV
ref|YP_001254935.1     DQIEEEARKKAVVQLAIGTLSYSELEAVEHIFNEL-DGTEGLLVASKIADKVGITRSVIV
ref|YP_001308325.1     DEITEDTRKKAVVQLAIGTLSYSELEAVEHIFDEL-NGNEGLLVASKIADKVGITRSVIV
ref|YP_518781.1        ERAEEEARKKAAVQIAVGTLSYSELEAVEHIF-AELGGGDGLLVASKIADRVGITRSVIV
ref|ZP_01171531.1|     EEIEEEARSKAVVQMAISSLSYSELEAIEHIFEEL-NGKEGLLVASKIADRVGITRSVIV
RAAC01972              QQKEEESRQRALAHLAVESLSFSELQAAKYLLDAVRNSPEGIVVSSQIADQHGVTRSVIV
                       :.   *::*.:*  .::*:  ::**:*  ::::    .. :*::*:*:***: *:****** ref|YP_001391734.1     NALRKFESAGVIESRSLGMKGTHIRILNDKLLEELKK----
ref|YP_001254935.1     NALRKFESAGVIESRSLGMKGTHIRILNDKLLEELKK----
ref|YP_001308325.1     NALRKFESAGVIESRSLGMKGTYIRILNEKLIDELKK----
ref|YP_518781.1        NALRKFESAGVIESKSLGMKGTYIRVLNDYLLEELDK----
ref|ZP_01171531.1|     NALRKLESAGVIESRSLGMKGTYIKVLN-------------
RAAC01972              NSIRKLESAGTIESRSLGMKGTHLRILNPYVEEEINRQFER
                       *::**:****.***:******:::**   :: ..       **
```

FIG. 136

```
ref|NP_241876.1|        ----------------LAIIYYSSTGTNYQLAQWAEEAAKEAGAEVKVLKVAETAPDAAI
ref|YP_174035.1|        -----------MANVKTAVIYYSSTGTNYQLAKWAKESAEKEGAEVRLLKFPELAPDAAI
ref|YP_079193.1|        -----------MSNVKLAVVFYSMGGTNYQLAKWAAEGAKEAGADVKVLKVQELAPQSVI
ref|ZP_01169176.1|      -----------LMTVKLAIVYSSTGTNYQMAQWAAEGAKEAGAEATIYKVQELAPESVI
ref|YP_001488917.1|     -----------MENVKLAVIYYSSTGTNYQMAKWAEAGAKEAGAEVKVLKVAELAPEAVV
RAAC00076               MKRETRSGGNTMSNVHLTILYYSATGTNYRMAQIAAEAARELGAEVRVRKVAELAPREVI
                                   :::::**  ****::*:  *   .*.:  **:.  : *.  * **   .:

ref|NP_241876.1|        DSNPAWRAHVDATKDVPAVTLDDLVWADAIMFSIPTRFGNVPSQVKAFLDTTGGLWFEGK
ref|YP_174035.1|        DSNPAWRAHVEATKDVPEVTPDDMEWADSYIFSVPSRFGVLPAQAKQFFDTLGGLWAQGK
ref|YP_079193.1|        EGNEVWKATVDATKDIPVVTSEDIEWADAIIFSTPTRFGNMASQMKQFLDTQGGLWANGK
ref|ZP_01169176.1|      EGVPAWKAHLEETKDVPVVTPDDIAEADAIIFSTPTRFGNMAAQMKQFLDTTGGIWGAGK
ref|YP_001488917.1|     ASNPAWKAHLDETKDIPEVQLSDLEWADAIIFSMPTRFGNLPAQMKQFLDTTGGLWFQGK
RAAC00076               ETSPAWKAHVEATAHVPVATPDDVAWADAVIFSVPSRFGNIPSQMKQFLDTLGPLWAKGL
                          .*:*  ::  *  .:*  .    .*:  : : *:*** :.:*  *  *:** * :*   * ref|NP_241876.1|        LANKVVSAMASASNAHGGQEATVLSLYTTMYHWGAIVAAPGYTAPETFAAGGNPYGTSVT
ref|YP_174035.1|        LANKVVSAMSSASNPHGGQEATILSVYTTMYHWGAIVVAPGYTDQSAFTSGGNPYGTSVT
ref|YP_079193.1|        TVNKVVSAMSSAQNPHGGQEATILSLYTSMMHWGAIIASPGYTDPVLFGAGGNPYGTSVT
ref|ZP_01169176.1|      TVNKVVSGMTSAQNPHGGQEATILSLYTTMYHWGAIVVTPGYSDQSLFPAGGNPYGASVT
ref|YP_001488917.1|     LANKAVSAMTSAQNPNGGQEQTILSLYTTMFHWGAIIAAPGYTDDSLYGAGGNPYGVSVT
RAAC00076               TANKVVSAMSSAQNPHGGQEATILSLYTSMYHWGAIIAAPGFTDASAYASGGNPYGTSVT
                         ...*:**.*.:****  *:::*  ***:.:::     :  :****.* ref|NP_241876.1|        VDQEGNMKEDVKA---AVAHQAKRTIQVAEWVKQG-----
ref|YP_174035.1|        IDQDGNQIEDVEQ---AVKQQAKRTVTVAKAIVTG-----
ref|YP_079193.1|        VDQDGKMIEDVEA---AVKHQAKRTVTVAEWVKKG-----
ref|ZP_01169176.1|      VDQSNEIVGDKDAYKGAIKYQAKRVIGIAESVKNG-----
ref|YP_001488917.1|     VDQNGKIQEDAEA---AAKHQAKRTVNVAEWIKKGQ----
RAAC00076               LSENGEIDPGAQD---AIRHQARRTVTIASWVKQGQAVTV
                        :.:..:    . .   *   **:*.: :*.  :   *
```

FIG. 137

```
ref|ZP_02327651.1|        ---------------------------------------LQIEFEQRRRALI
sp|O32720|SP2AA_PAEPO     ---------------------------------------LQIEMEHHRGVLI
ref|NP_833792.1|          ---------------------------------------LSMQLEVKRDVLC
ref|NP_846529.1|          ---------------------------------------LSMQLEVKRDVLC
ref|YP_001646701.1|       ---------------------------------------LSMHLEVKRDVLC
RAAC02144                 ----------------------MNFLTRPHKERGCRVSVETKLERGIVV
                                                                :.:.  :  .*   :

ref|ZP_02327651.1|        VRLQGELDHHTADMVKTRMEEAIAKGDARNLVLSRDLSFMDSSGLGVIL
sp|O32720|SP2AA_PAEPO     VRLSGELDHHTSDMVRMQMDEAIQRRQCEHIVLSLKNLQFMDSSGLGVIL
ref|NP_833792.1|          VRLEGELDHHTAEELRTKVTDMIETHGVHHIVLSLENLSFMDSSGLGVIL
ref|NP_846529.1|          VRLAGELDHHTAEELRTKVTDMIETHGVHHIVLSLENLSFMDSSGLGVIL
ref|YP_001646701.1|       VRLEGELDHHTAEELRTKVTDMIETHGVHHIILSLENLTFMDSSGLGVIL
RAAC02144                 IELKGELDHHAVEQMRDRIEQQLAEHGYRGLVMSFRNIDFMDSSGLGLIL
                          :.* ******:  :  ::  ::  : :      .  :::*:..:: ********:**

ref|ZP_02327651.1|        GRYKQITGRGGKMIVCDVNPSIYRLFELSGLFKIVAIEDNERKAISSL--
sp|O32720|SP2AA_PAEPO     GRYKLINQKGGEMAVCDVNPPVHRLLDMSGLFKIMPIYDNEVNALTEL--
ref|NP_833792.1|          GRYKHVKGLGGEMVVCAISPPVKRLFEMSGLFKIVRLEESEAHALATL--
ref|NP_846529.1|          GRYKHVKGLGGEMVVCAISPPVKRLFEMSGLFKIVRLEESEAHALATL--
ref|YP_001646701.1|       GRYKHVKGLGGEMVVCAISPPVKRLFEMSGLFKIVRLEESEAHALATL--
RAAC02144                 GRYRSVSEHGGKMALCEVNPTLRRLFEMSGLLKVIPVYDSEEAAVAAILG
                          ***:  :.   **:* :*  :.*.: **:::***:*::  :  :.*    *::  :

ref|ZP_02327651.1|        -
sp|O32720|SP2AA_PAEPO     -
ref|NP_833792.1|          -
ref|NP_846529.1|          -
ref|YP_001646701.1|       -
RAAC02144                 A
```

FIG. 138A

```
ref|YP_001125957.1|    -HRLA---ETMKTVLDAAYEGVVVVDGNGMVREINRAYCQFLGIRREDAIGKHVTEVIEN
ref|YP_147806.1|       -HRLA---ETMKTVLDAAYEGVVVVDEDGVVREINRAYCQFLGIRREEAIGKHVTEVIEN
ref|ZP_01666100.1|     ---------LESAIESMFEGFVAVDKNGYITMMNQAYGEFLGVDAKEVIGRHVTEVIEN
RAAC02439              MHELAASGDVLRLILDSMYEGIVLVDAKGHIVEINQAYLKLLNMERDRVIGRHVTEVIEN
ref|ZP_01695872.1|     MAQTKNTAEILNAVLESAYEGIAVVDENGILIEFNEAYSRFTGIKREDAIGRHVTEVIEN
ref|NP_693661.1|       ------SAEIVEVILESAYEGVAMVDRNGIIVEFNDAYSRFTGVDKKEAIGHPVQEIIEN
                             :. ::: :..  .* :   :*  .: .:  . .: * *:*** ref|YP_001125957.1|    TRLHICVQSGIPERGYIQKIYGQPMVVHRIPIWRDGKVIGAVGMLIFQGVSEVYAIFQRL
ref|YP_147806.1|       TRLHICVQSGIPERGYIQKIYGQPMVVHRISIWRDGKVIGAIGMLIFQGVSEVYEIFRRL
ref|ZP_01666100.1|     TRMHIVAQTGKPEIGEVQRIGKHAVVVTRKPIIQDGEVVGAVGKILFKDVKDFKMLARKL
RAAC02439              TRLHRVVETGIPERGQLQRIRQHDMVVHRIPIWQGGKVVGAIGVLIFESIRDLYEIIERL
ref|ZP_01695872.1|     TNLHVTVKTAIPERGVIQYIQGQAMVVHRIPIWKGGRVVGAIGMLIFEGVSELYQIFERL
ref|NP_693661.1|       TNLHQTVKTGIAERGVIQYIQGQPMVVHRIPVWRNEELVGAIGMLIFEGVTELYQIYDRY
                       *.:*  .::. .* *  :* *   : :** *:..  .::**:*  ::*:.: :.   :

ref|YP_001125957.1|    QELSR----EASRKEKNEAEASKQEAVASAAVGVERIIGRHPTIAAVKQMIRRAARVPST
ref|YP_147806.1|       QELSR----EASRKEKQETEAKPQETAASAPKGIERIIGRHPAIAAVKQMIRRAARVPST
ref|ZP_01666100.1|     NSLQS----ELEY-YKEELRK---VHGGK--YTIESIVGQSEKMEWLKTIAAKAAKGNST
RAAC02439              QEHAP----QVPS-ARPETEQGSEAHQVRWAYRIDDFLGQSRAVLDLRRMARKAAQTPVT
ref|ZP_01695872.1|     QQDSL---SARKE-KTGSKKMPDQAGFT-------QILGTSESISRVKRLARRAARTSAT
ref|NP_693661.1|       QEKKQ-----KMITEKHSRKEDSNPGQPD--NYLEQIIGQSEELTKLKRMTRKVAQTEAT
                       :.                ..                 ::*    :  ::  :.*:   * ref|YP_001125957.1|    VLITGESGTGKEVVARAIHEAGAHADGPFVSVNCAAIPEALLEAELFGYEDGAFTGAKKG
ref|YP_147806.1|       VLITGESGTGKEVVARAIHEAGPHADGPFVSVNCAAIPESLLEAELFGYEDGAFTGAKKG
ref|ZP_01666100.1|     VLILGESGTGKELFAHAIHNASARRHGPPIKVNCAALPESLLESELFGYDEGAFTGARKG
RAAC02439              VLITGESGTGKEVLAQGIHFESNRANGPPISVNCAAIPDSLLEAELFGYDEGAFTGAKRG
ref|ZP_01695872.1|     VLITGESGTGKELFAKSIHQLSTYARGLFITVNCGAIPEPLFESELFGYEEGAFTGAKKG
ref|NP_693661.1|       VLITGDSGTGKELFAKSIHQLSDYKSGPFVCVNCGAIPEQLFESELFGYEDGSFTGAKRG
                       *** *:****** .*:.**  .    * *: ***.*:*: *:*:*****:*:****::* ref|YP_001125957.1|    GKPGKFQLAHGGTLFLDEIGDMPLAMQAKILRVLEEKKVEKVGGLSETEVDVRIIAATNK
ref|YP_147806.1|       GKPGKFQLAHGGTLFLDEIGDMPLAMQAKILRVLEEKKVEKVGGLSGTEVDVRIIAATNK
ref|ZP_01666100.1|     GKPGKIELANGGTFFLDEIGDMTLAMQAKLLRVLQEREIERVGGTKTNKVDVRIIAATNR
RAAC02439              GKPGQIELAHMGTLFLDEIGDMPLSMQAKLLRVLEDRQVQRVGGTVKREVNLRLISATNR
ref|ZP_01695872.1|     GKPGKFELAENGTLFLDEIGELSPAMQTKLLRAIQEKEAERVGGVKYKYKTNVRIVAATNR
ref|NP_693661.1|       GKKGKFKLADNGTLFLDEIGEMPLAMQTKLLRVIQEKEYEKVGGLTKQPLKARVVAATNR
                       ** *::.:**. **:*****::.  :**:*:**.::::: ::***   . *::::***:

ref|YP_001125957.1|    PLEEMVRDGTFREDLFYRLNIIRIHLPPLRERKTDIPALLAHHMERLCRQFGVVSKSFAK
ref|YP_147806.1|       PLEEMVRNGTFREDLFYRLNIIRIHLPPLRERKTDIPALLAYHMERMCRQFGVALKSFTK
ref|ZP_01666100.1|     DLEKMIERGEFRQDLYYRLNIISLHIPPLRERKEDIPLLCTALLKKINVQVQHWVDGVSP
RAAC02439              DLERMVEEGRFREDLYYRLNIIRLHIPPLRERKEDIPLLLAHYLDMTCERLGKPRMHLSS
ref|ZP_01695872.1|     NLEEMVEAGTFRADLYYRLNIIRIHLPPLRERKEDIPGLVSHFLKAFCRRYDLPEKRISS
ref|NP_693661.1|       NLKVMVEEGTFREDLYYRINVIELYIPPLRNRERDIPLLISSYLLTICKKYNMKKKEITP
                        *: *:. * ** **:**:*.*   ::****:*: *** *  :    :         ..:

ref|YP_001125957.1|    EAMEVLINYSWPGNIRELVNVVEWLISMVE--GENIEREHLPAYL-------STIHPSVT
ref|YP_147806.1|       EAMEVLVHYSWPGNVRELVNVVEWLISMVE--GEKVEREHLPSYL-------STVQPAAS
ref|ZP_01666100.1|     EAMELLLAYDWPGNVRELENVLERAVNLMEEDERQILPEHLPPALKK-IHKAKDLDDGLK
RAAC02439              EVVERLLAYDWPGNVRELVHMVEVLVSLC--DSAYVRLDDFPPHLHKLLQERSSRSPAIT
ref|ZP_01695872.1|     EAVAAMMAYGWKGNVRELANTVERLVTLAD--GPEISRGDLPEAIHEAQPAKDIYAESLI
ref|NP_693661.1|       EAMAVLMKYKWYGNIRELINTIEKLVILTE--NDMIDYHHLPNYMKR---EEFTIDNRLS
                       *.:  :: :: *  **:***  :  :  :    .    :*       :
```

FIG. 138B

```
ref|YP_001125957.1|    PMP---------------DGGAN---------IADQWKEIVYQSERERIAAALVAANGNK
ref|YP_147806.1|       SLP---------------NGGVK---------MADRWKEMVYQSERERIAAALVAAGGNK
ref|ZP_01666100.1|     DLA---------------GILCD-------------------TEKQAIYKALEATGGNK
RAAC02439              PSR---------------SPACDAVPGPAVGSPGAGARERMMQVERELIEAALRESGGNK
ref|ZP_01695872.1|     -SRA---------------------------------REAGEAQEKALIIRALKNAGGNK
ref|NP_693661.1|       PIHQ--------------------------------VKQQEHIRESELIRLTLEQTGGNK
                                                        *     *   :*   :.*** ref|YP_001125957.1|    AEAARRLGIHRSTLYEKLKKYG--
ref|YP_147806.1|       AEAARRLGIHRSTLYEKLKKYGL-
ref|ZP_01666100.1|     SKAAKLLGIHRSGFYQKLHKYNI-
RAAC02439              SLAAKRLGVHRSTLYDKIKKLGIL
ref|ZP_01695872.1|     TKAAELLGIHRTTLYQKIKKYNL-
ref|NP_693661.1|       SKAAQKLGIHRTTLYQKLKK----
                       : **. **:**: :*:*::*
```

FIG. 139

```
ref|YP_001488778.1|      ----------------MTFTAQLREETEPLFEAIYQHPFVRGLAEGKLEKKQIIHYVKQ
ref|YP_081277.1|         ----------------MSFSAELRREADPIFEAIFEHPFVLGLASGRLEKEQLIHYVKQ
ref|YP_174256.1|         ----------------MSFTAELRKTADPIYKAIFSHPFVQGIGKGSLPADSLIHYVKQ
ref|YP_804091.1|         ----------------FSARLKAIAQPVLADIENHPFVRGIQAGAVPAAALMVYVEQ
RAAC00944                MGPSRVPLWPPAEEALLMSFSASLIAMSNPILDAILRHPFVRGIAEGNLSKAAAIRYVSQ
ref|YP_711801.1|         ----------------FSARLWASTEPVYEAILRHPFLTGLTDGTLPRAAFAHFVIQ
                                         *:* *   ::*:  *  ***: *:  * :        :* * ref|YP_001488778.1|      DAEYLQAFIKIYAAALSRCTDKEDIAFFHQQIEFVLDSETHPHQNLCRVAGVSYDGLQG-
ref|YP_081277.1|         DYEYLNAFIQIYGIAISKCQNRKDMEMFHEQISFVLDSEVHPHKNLCRAAGVEYETLQG-
ref|YP_174256.1|         DFEYLNTFMQIYGIAISRCENREDMAMFAEQIGFILHSETHPHHNFCKVAGVRYEDLQY-
ref|YP_804091.1|         DTCFLDAFAKVYAGALSKCTTKDQMRFFEEQIRYTLNDEAGAHQILCDIAGQKLSDHQH-
RAAC00944                DQPYLETYLRVFAHAAALAPRHEDVADFHGRMSLLLGGETQAHDNLLRYAGATPHDVEG-
ref|YP_711801.1|         DAHYLRDYARALAVCAAKAPTEDDVRALANDAAEAVAAEQAMHVDLLDALGGPAPGDPAP
                          *   :*   :   . . :    ..::    :      * * :     * ref|YP_001488778.1|      --------APLAPSAHHYIHHMLQVAKEGTLGEMIAVLLPCPWTYWEIGKRMLTDVQPDP
ref|YP_081277.1|         --------YPLAPSAHHYVRHMLTAAHEGTLGEILAVLLPCPWTYWEIGKKLMKDVQPDP
ref|YP_174256.1|         --------EPLAPTAHHYTRHMLDVAHRGSLAEILAVLLPCPWTYQAIGDYLYETFQPKA
ref|YP_804091.1|         --------AKQRPITYLYNEHLFNALRTGDLIDLIAAMLPCPWTYTEISQQI--VDGAAP
RAAC00944                --------QPKLPTLHHYESHLLASAARGDFAELVAAILPCHHVYVEIGQRLEPILEEKP
ref|YP_711801.1|         GGTPPGGVATVAPTTRAYTSYLLATVYGGSPLEGLAAVLPCYWIYARVGARL---LADSSP
                                   *    * ::: * : : :*.:***  * :. :         .

ref|YP_001488778.1|      SHPFYEWITFYG----GLTDSITVELCKRLDQLAEAASEKEKEKMKQHFILSCQLEYKFW
ref|YP_081277.1|         SHPFYDWICFYGN----RTDSITTKFCARLDEWAETAGKAEKEKMKELFLQSCQLEYGFW
ref|YP_174256.1|         NHPFFDWISFYRS---NGEMGVTKQFCKRLDELAAHATEQEKERMQDHFLKSCQLEYSFW
ref|YP_804091.1|         DNPFLPWIEFYQPQPGQIDGSMVKTLFGMVDELAIGLSEERQHEIEQRFLRSCELEYEFW
RAAC00944                DHPFAAWIRFYAD---PGMQDATHRLFAMIDREAAHFSTERARRVEAAFVASCHLEYRFF
ref|YP_711801.1|         DPVYARWIAAYGD---PAFQAVADRVVALTDRVGAFASEPELVRAADHPAVTARYEWMFW
                          .  : ** *        .    . . *. .      .     *  :.. *: *:

ref|YP_001488778.1|      DMAFTVEEW------------
ref|YP_081277.1|         EMAYTVEDW------------
ref|YP_174256.1|         EMAYVKEKW------------
ref|YP_804091.1|         EQAYYQKDW------------
RAAC00944                DMAYRGESWLPKEALSDVSTP
ref|YP_711801.1|         DAAWRRETW------------
                         : *:  : *
```

FIG. 140A

```
ref|NP_646484.1|         ------------------------------------------------------------
ref|YP_001332652.1|      ------------------------------------------------------------
ref|NP_372249.1|         ------------------------------------------------------------
ref|NP_764957.1|         ------------------------------------------------------------
ref|ZP_01695369.1|       ----------------------------------------------------------MI
RAAC02632                ----------------------------------------------------------MF ref|NP_646484.1|         KKILFDVDGVFLSEERCFDVSALTVYELLMDKCYLGLHSHIDWETLT--DNDIQDIRNRI
ref|YP_001332652.1|      KKILFDVDGVFLSEERCFDVSALTVYELLMDKCYLGLHSHIDWETLT--DNDIQDIRNRI
ref|NP_372249.1|         KKILFDVDGIFLSEERCFDVSALTVYELLMDKCYLGLHSHIDWETLT--DNDIQDIRNRI
ref|NP_764957.1|         KAILFDVDGVFLSEERCFDVSAITVAELLSSPDFLNCDIDIHFDGNLTEND-INKIRRNV
ref|ZP_01695369.1|       QTVLFDVDGVLLSEERYFDASGLTVWELIHSGHYLGLAPEQFKTTLTDEE--IRRIRADV
RAAC02632                RTILFDVDGVMLSEERYFDASALTVHELLTSQRFLGLSSVSPAFSPAPAEDAIRAIRRDV
                         : :****** :.***** **.*..:** **:.  :*.        :  *. **  :

ref|NP_646484.1|         FQKDKILNKLKSLGLNSNWDMLFIVFSIHLIDILKKLSHDEIEAFMYQ-----DEPVELK
ref|YP_001332652.1|      FQKDKILNKLKSLGLNSNWDMLFIVFSIHLIDILKKLSHDEIEAFMYQ-----DEPVELK
ref|NP_372249.1|         FQKDKILNKLKSLGLNSNWDMLFIVFSIHLIDILKKLSHDEIEAFMYQ-----DEPVELK
ref|NP_764957.1|         FNNDRILNQLKSLGLNSNWDMLFIVFSIHLIDKAKQLKPSLRDQLLDE-----LLFTKET
ref|ZP_01695369.1|       FQHDEVLRFLKSRGMNANWDMIYLTFTCQLLHLLSQIKEKEAGRIRGW---LASEIGDVT
RAAC02632                FRYDAVLEGLKNIGVNANWDMVYFVFVAEWVAALERAREASEEAVDRARSVLREGFSEAS
                         *. * :*. **. *:*:****:::.*  .:   .:   .        .        ..

ref|NP_646484.1|         LQN---ISTNLADCFNLNEQLPLQFLDNVKVGKNNIYAALEEFATTELHVSDATLFSLKG
ref|YP_001332652.1|      LQN---ISTNLADCFNLNEQLPLQFLDNVKVGKNNIYAALEEFATTELHVSDATLFSLKG
ref|NP_372249.1|         LQN---ISTNLADCFNLNEQLPLQFLDNVKVGKNNIYAALEEFATTELHVSDATLFSLKG
ref|NP_764957.1|         LKE---IAKDLTDKT-INYSLPYDVIASFRNGKDAIYEDLEVYAKNQLELNNTSLFKLKS
ref|ZP_01695369.1|       LHE----MREVLAHYPVE-TDYSIFLNWFAKRPETKQDLLKVLDQLAYEIFGLTDTQLGK
RAAC02632                LRAIGGLLREALPGYVIAWKGYDALYEGASSRSDLMERAREALARYAPEAD---------
                         *:        :          :                  .:

ref|NP_646484.1|         --------ALWTLAQEVYQEWYLGSKLYEDVEKKIARTTFKTGYIYQEIILRPVDEVKVL
ref|YP_001332652.1|      --------ALWTLAQEVYQEWYLGSKLYEDVEKKIARTTFKTGYIYQEIILRPVDEVKVL
ref|NP_372249.1|         --------ALWTLAQEVYQEWYLGSKLYEDVEKKIARTTFKTGYIYQEIILRPVDEVKVL
ref|NP_764957.1|         --------ALWTLAKDIYQEWYLGKALFNQVEYKKDIQDFKKGFIYDEVILKPIEEIQLL
ref|ZP_01695369.1|       ------KGALWSVCEHASQEWYVGDQNIVASTGKPSVQTGKKGFLDEEIPLAEPEKIGAL
RAAC02632                ------AHALWQVGQETFQEWYLGD----AYTGK---ETGKAGFLTSEYPIVDPAAFAAL
                               *  :  :.  **:*.     *      * *::  .*  :    . * ref|NP_646484.1|         LNDLKGAGFELGIATGRPYTETVVPFENLGLLPYFEADFIATASDVLEAENMYPQARPLG
ref|YP_001332652.1|      LNDLKGAGFELGIATGRPYTETVVPFENLGLLPYFEADFIATASDVLEAENMYPQARPLG
ref|NP_372249.1|         LNDLKGAGFELGIATGRPYTETVVPFENLGLLPYFEADFIATASDVLEAENMYPQARPLG
ref|NP_764957.1|         LQNLIEAGYQIAIATGRPRTETIIPFQSLGLKSYFKDEHIVTASEVLLAEKQFPQYQPLG
ref|ZP_01695369.1|       FSFLAEKGLKLGVGTGRPQLETYGPFRALGWLPLFHEEHIVTADDVLKAEEELGGHTPLA
RAAC02632                LADLKAAGVTLGIATGRPEIETRVPLEHFGWLSYFDPARVTNASDVVAAEERVPHARPLS
                         :  *    *  :.:.****  **  *:.:*  .  *. ..:..*.:*: **:     **.

ref|NP_646484.1|         KPNPFSYIAALYGN-NRDKYESYINKQDNIVN-KDDVFIVGDSLADLLSAQKIGATFIGT
ref|YP_001332652.1|      KPNPFSYIAALYGN-NRDKYESYSNKQDNIVN-KDDVFIVGDSLADLLSAQKIGATFIGT
ref|NP_372249.1|         KPNPFSYIAALYGN-NRDKYESYINKQDNIVN-KDDVFIVGDSLADLLSAQKIGATFIGT
ref|NP_764957.1|         KPNPFSYIATLNGN-YNDQYERYATKQEDIVN-KDEVYIVGDSLADLLSAKKIGATFIGT
ref|ZP_01695369.1|       KPNPFTYLLALKGK--NTPARDCT-ECSLPLENGQEILIVGDSLADLLAAQKIGAQFAGI
RAAC02632                KPHPFSYLRSLMGE--ADVEKLLTVELPIPGIRG-EVLVVGDSIADKLAADRLGASFAAV
                         **:**:*: :* *:    .      :       ::.:****:** *:*.::** * .
```

FIG. 140B

```
ref|NP_646484.1|        LTGLKGKDAAGELEAHHADYVINHLGELRGVL------
ref|YP_001332652.1|     LTGLKGKDAAGELEAHHADYVINHLGELRGVL------
ref|NP_372249.1|        LTGLKGKDAAGELEAHHADYVINHLGELRGVL------
ref|NP_764957.1|        LTGLKGKAAHSELVANGADHVVEDITKIRKIL------
ref|ZP_01695369.1|      LTGLSGKEAKAEFEEHGADYIFENVADLKNI-------
RAAC02632               LTGLEGQAARPKFERLGADYILNHVLELRRVLSLASVE
                        ****.*: *   ::     **::.:.: .:: :
```

FIG. 141

```
ref|ZP_02329050.1|         ------VKVADLVRTFKLEVISGEEGLKRTITVADLYRPGLEMAGYFNYHPQERVQLLGK
gb|AAX09759.1|             ------VKVSELVNQFGLEVISGEQGLKRAITVDDLYRPGLEMAGYFEYHPPERVQILGK
ref|YP_148935.1|           ------VRTKDIIEQFQLELVSGAEGIYRPITTSDLSRPGIEMAGYFAYYPAERLQLLGR
ref|YP_001127122.1|        ------VRTKDIIEQFQLELVSGAEGIYRPITTSDLSRPGIEMAGYFAYYPAERLQLLGR
ref|YP_001376898.1|        ------VRTKDLIEQFQLELVSGEEGIHRPIDTSDLSRPGIEMAGFFTYYPADRVQLLGK
RAAC02474                  MANLRGVSVRQLVRDLDLHVFNEDADLDRMIYTRDINRPGLALAGYLRYHPAERVQILGR
                                 *  .::.  :   *.:..    .: * *    *: *** :**:: *:* :*:*:**:

ref|ZP_02329050.1|         TEMSFYETLTGPIRQRRARQLCTSPETPCIIITRGLDIPDEIIEEAAKHHLPVLRSKVAT
gb|AAX09759.1|             TELAFFEMLPEKERKDRMERLCSSDETPCIIVTRSWKVPEELIEISSEKQIPVLRSSMAT
ref|YP_148935.1|           TELSFYETLTPEEKKSRMERLCT-DITPGIIVSRGLEVPPELIEASERQSVPVMRSTMKT
ref|YP_001127122.1|        TELSFYETLTPEEKRARMQRLCT-DITPGIIVSRGLDVPPELIEASERQSVPVMRSTMKT
ref|YP_001376898.1|        TELTFFDTLTNDQKQERMKALCT-EETPCIIVTRNQDVPKELLQASRESGVPLLRSSQTT
RAAC02474                  TELSFLRGLNEKERALRAFAFCSYQQTPCIIITRGDTPPPVLLEEAASRRIPVLGTPMVT
                           **::*   *       :  *   :*:     ::*.   *   :::  :   :*::  :   * ref|ZP_02329050.1|         TILASRLTNYLENKLAPSTTIHGVLVDVYGVGMLITGGSGIGKSETALELVKRGHRLVAD
gb|AAX09759.1|             AILSSRITSFLERKLAPTATIHGVLVDVYGVGMLITGSSGIGKSETALELVKRGHRLIAD
ref|YP_148935.1|           TRLSSRLTNYLESKLAPTTAVHGVLVDVYGVGVLITGKSGVGKSETALELVKRGHRLVAD
ref|YP_001127122.1|        TRLSSRLTNYLESKLAPTTAVHGVLVDVYGVGVLITGKSGVGKSETALELVKRGHRLVAD
ref|YP_001376898.1|        TRLSSRLTNYLEGKLAPTTAVHGVLVDVYGVGVLIIGQSGVGKSETALELVKRGHRLVAD
RAAC02474                  TRLTARISNYLEDKLAPETLQHGVLVDVYGIGILIIGSSGIGKSETGLELIKRGHRLVAD
                           : *::*::..:** ****  :  *********:*:**  * **:***** .***:******:**

ref|ZP_02329050.1|         DAVEIRQTADYVLSGNAPELIRHLLEIRGVGIINVMTLFGAGAVRNEKKISVVVKLETWQ
gb|AAX09759.1|             DAVEIRQTSDNQLHGTAPELIRHLLEIRGVGIINVMTLFGAGSIRNNKRISLVVRLEAWQ
ref|YP_148935.1|           DCVEIRQEDEDTLVGSAPELIEHLLEIRGLGIINMMTLFGAGAVRTHKRISLVVDLELWD
ref|YP_001127122.1|        DCVEIRQEDEDTLIGSAPELIEHLLEIRGLGIINMMTLFGAGAVLPHKRISLVIDLELWD
ref|YP_001376898.1|        DSVEIRQEDEDTLVGSSPDLIEHLLEIRGLGIINVMTLFGAGAVRNYKRITLVINLEIWD
RAAC02474                  DAVVIRQISDDYLVGSAPPLLQNLIEIRGLGVLNAMTLFGAGAVRTHKRISMVVHLEAWR
                           *.* ***    :   * *.:*  *:.:*:****:*::* *******::    *:*::*: ** * ref|ZP_02329050.1|         QDKQYDRLGLDEETTRIIDTDLPLVTIPVRPGRNLAVIIEVAAMNYRLKRMGYNAALQFT
gb|AAX09759.1|             QEKQYDRLGLDEETTRIIDTDVPLVTIPVRPGRNLAVIIEVAAMNFRLKRMGYNAALQFT
ref|YP_148935.1|           PEKQYDRLGLEEEKVKILDTELPKLTIPVRPGRNLAVIVEVAAMNFRLKRLGVNAAEEFS
ref|YP_001127122.1|        PEKQYDRLGLEEEKMKILDIELPRLTIPVRPGRNLAVIVEVAAMNFRLKRMGVNAAEEFS
ref|YP_001376898.1|        QNKNYDRLGLDEEKMKIIDTELTKITLPVRPGRNLAVIIEVAAMNFRLKRMGVNAAQQFS
RAAC02474                  DNHAYDRLGIETETMKILDIELPKVTVPVRPGRNLAVIVEVAAMNFRLKGMGLDAAKQFA
                           ::  *****::  *.  :*:*  ::. :*:***********:******.*** :*  :** :*:

ref|ZP_02329050.1|         NRLTETIA-------
gb|AAX09759.1|             TKLTETIS-------
ref|YP_148935.1|           ARLSDAI--------
ref|YP_001127122.1|        ARLSDAI--------
ref|YP_001376898.1|        ERLMSAI--------
RAAC02474                  AELEQMIAAQSEGSA
                            .*  . *
```

FIG. 142

```
ref|NP_244107.1        MNTTIYDVAREAGVSMATVSRVVNGNPNVKPATRKKVLEAIERLGYRPNAVARGLASKRT
ref|YP_176259.1        MNTTIYDVAREAGVSMATVSRVVNGNPNVKPTTRKKVLEAIERLNYRPNAVARGLASKRT
ref|YP_148663.1        MTVTIYDVAREANVSMATVSRVVNGNPNVKPSTRKKVLEAIERLGYRPNAVARGLASKKT
ref|YP_001126805.1     MTVTIYDVAREANVSMATVSRVVNGNPNVKPSTRKKVLEAIERLGYRPNAVARGLASKKT
ref|ZP_01188060.1|     MKPTIKDVARKANVSVATVSRVLNNQPGYSVETEKKVLEAIDELGYHPNALARGLVGKRT
RAAC00625              MRATIRDVAKAAGVSAATVSRALNRPDLVDPETLERVRKAMEEMSYQPSAIARGLSARRS
                       *  ** ***: *.** *****.:*       . *  ::* :*::..:.*:*.*:**** .:::

ref|NP_244107.1        TTVGVVIPDISSIFFAELARGIEDIATMYKYNIILCNSDQNKEKEIHLINTLLEKQVDGI
ref|YP_176259.1        TTVGVIIPDISSIFFSELARGIEDIATMYKYNIILCNSDQNKDKEIHLINTLLEKQVDGI
ref|YP_148663.1        TTVGVIIPDISSIFFAELARGIEDIATMYKYNIILSNSDQNKEKELHLLNTMLAKQVDGL
ref|YP_001126805.1     TTVGVIIPDISSIFFAELARGIEDIATMYKYNIILSNSDQNKDKELHLLNTMLAKQVDGI
ref|ZP_01188060.1|     KTLGVLIPRISNMVSSQIMNGIEDAAHKNDHSVIICNTDNDGQKTMVYLDVLREKRVDGI
RAAC00625              DTLGLIVPGITDFFFNELYKGIDRASQQYGMKVLLYDSEHSRERAFEGFSILSGYQVSGI
                       *:*::*  *:..:.    :: .**:  :   .: :: :::: .:: ::  :  :*.*:

ref|NP_244107.1        VFMGGEITNEHAEEFKRAHVPVVLAATLDAEK-EIP-SVNIDYKQAAFDAVTYLIEKGHT
ref|YP_176259.1        VFMGGEITEEHAEQFKRAPVPIVLAATLDDEKS-FP-SVNIDYTQAAEDAIQFLIEKGHK
ref|YP_148663.1        LFMGGTITDEHVAEFQKSSVPIVLAATMGPNEIP---SVNIDYEQAAFEAVTYLLEKGNR
ref|YP_001126805.1     LFMGGTITEEHVAEFQKSSVPIVLAATIEPNET-IP-SVNIDYEQAAFEAVTYLLERGNR
ref|ZP_01188060.1|     IVVSEMLTEEYANKLVELKVPVILISTIDETGQFP--HIKVNDEQAAYQATEYLISKGHK
RAAC00625              IFTSKLVTEDYDPILQRVNIPVVLTLTQSAAKTPLT-AFRIDEVRAMFDVVAYLVSRGHR
                       :.. . :*::   :  . :*::*  *        ..::  :*  :. .:*.. :*:

ref|NP_244107.1        SIGMVSGSL-EDPVNGYQKYAGYREALEERGVAFDESMVVIGDYTYDSGIDAM-NVFTK-
ref|YP_176259.1        RIGMLSGSL-EDPINGYQKFAGYRQALQKNNIEFDENLIVIGDYTYDSGMEAM-DAFL--
ref|YP_148663.1        RIVYVTGPT-DDPIN-QRKLAGYRRALEEHGAPYEEELVIEGDNSYDSGLEAYEKITE--
ref|YP_001126805.1     RVAYVTGPT-DDPIN-QRKLAGYRRALEEHGVPYDEELVVEGDNSYDSGLEAYEKIAE--
ref|ZP_01188060.1|     NIAMISGTP-EDMVAGKPRLDGYKKALRENGLPVKEENIVFGDFWFDSGKECMERLLNN-
RAAC00625              QIAMIAGKLWDDRTG-ELRLEGYREGLRHFGIEYCEARVEFGQYRFDDGYQAMQRLLER-
                       :  ::*   :*    :  **:..*...  *   *: :*.*  :.

ref|NP_244107.1        -LEKRP--TAIFVATDEMALGVIHGAQDHGLNIPDDIEVIGFDNTRLATMVRPTLSTVVQ
ref|YP_176259.1        ALDEKP--TALFASNDEMALGVIHGIQDRGYDVPGDIEVLGFDNTRLATMVRPTLTTVVQ
ref|YP_148663.1        -LAERP--TAVFAGTDEMALGIIHSAQDHGGRVPDELEVVGFDNTRLATMVRPRLTTVVQ
ref|YP_001126805.1     -LAERP--TAVFAGTDEMALGIIHSAQDQGVRVPDELEVVGFDNTRLATMVRPRLTTVVQ
ref|ZP_01188060.1|     --NQGI--TAIFVASDEMAAGALSTAYKSGIRVPEDISIIGFDNTQLAEMTIPPLTTVSQ
RAAC00625              -IRDVP-FTAVCTASDEMALGAIRCLNDHGYRVPDDISVMGFDDLPIARMVTPRLTTVAQ
                       .    : ...** * :   . *  :* ::.::***: :* *. * *:** * ref|NP_244107.1        PIYDIGAVSMRLLTKYMNK----EEVSEHI--VELPHRIEFRQSTR---
ref|YP_176259.1        PLYDIGAVSMRLLTKLMNK----EEVDNYT--VTLPHRIESRGSTK---
ref|YP_148663.1        PMYDIGAVAMRLLTKYMNK----EPVDHHI--VVLPHRLEVRESTK---
ref|YP_001126805.1     PMYDIGAVAMRLLTKYMNK----EHVDNHI--VVLPHRLEVRESTK---
ref|ZP_01188060.1|     PFYQMGYKGLKLLLKAI------KGKEVNS--AILPHVIVERETVKKV-
RAAC00625              PFHEIGEEAVKWLIRAASQ----PPSPSEIGDYLLPHRLVERESVRSIS
                       *::::*  .:: * :       ***  :  *   :.:
```

FIG. 143

```
ref|YP_001488326.1        ---------------MVEKTVTIQLKTGLQARPAALFVQEANRFGADIFLEKDGKKVNAKS
ref|ZP_01860336.1|        ---------------MIEQKVEVKLKTGLQARPAALFVQEANRFSSEVFLERNGKKVNAKS
ref|NP_693386.1|          ---------------MVEKLVTVELDTGLQARPAAQFVQEANRFSSHVFLEKDDKKINAKS
ref|NP_834817.1|          ---------------MVQKRVQVSLKNGLQARPAALFVQEANRFHADIFIEKDGKTVNAKS
ref|ZP_01697803.1|        ---------------MIEKQLEVKLKSGLQARPAAQFVQEATRFSSEIFLEKEGRKVNAKS
RAAC00733                 ---------------MVEKVLTVNLPQGLAARPAAEFVKRASSFSSQIRIGKNGHFVDAKS
                                         *::: : :.*   * :.*. *  :.: : ::.: ::*** ref|YP_001488326.1        IMGLMSLAISSGVTITLIADGADEQEAIEALTDFVNQE---
ref|ZP_01860336.1|        IMGLMSLAVSSGTEITLIADGTDEEQAVKHLTEFVQKES--
ref|NP_693386.1|          IMGLMSLAITKGEQIKLIAEGPDEDTAIEHL----------
ref|NP_834817.1|          IMGIMSLAIGTGSMITITTEGSDAEEALEALA---------
ref|ZP_01697803.1|        IMGLMTLAAGHGETVTLSVDGSDEEEAFEHLANYI------
RAAC00733                 VLGVMSMAIARGESVTLQAEGSDAERAVETLAELLSRDTFE
                          ::*:*::*    *   *  :.: .:*.* : *.: *
```

FIG. 144

```
ref|NP_244433.1|        ----MVEKQVEVKLKTGLQARPAALFVQEANRFTSEIFIEKDGKKVNAKSIMGLMSLAIG
ref|YP_001488326.1      ----MVEKTVTIQLKTGLQARPAALFVQEANRFGADIFLEKDGKKVNAKSIMGLMSLAIS
ref|ZP_01171669.1|      ----MVEKQVEVKLRTGLQARPAALFVQEANRFSSDIFLEKDGKKVNAKSIMGLMSLAVS
ref|ZP_01860336.1|      ------------------------FVQEANRFSSEVFLERNGKKVNAKSIMGLMSLAVS
ref|ZP_02327791.1|      ------------------------FVQEANKFSSEIFVEKDEKKVNAKSIMGIMSLAIS
RAAC02466               MVMKMFEKETIVRLRGGLFARAAAKFVQEATRFKSEVFVERDGKTVNAKSIMGVMSLAIP
                                                *****.:*  :::*:*:: *.********:****:

ref|NP_244433.1|        SGSTITLITEGNDEQEAMEALIAFIEKE----
ref|YP_001488326.1      SGVTITLIADGADEQEAIEALTDFVNQE----
ref|ZP_01171669.1|      TGSVVNLVADGSDEEEALEELSQYIQQE----
ref|ZP_01860336.1|      SGTEITLIADGTDEEQAVKHLTEFVQKE----
ref|ZP_02327791.1|      TGTEIYISAEGSDDEQAVNALVSLVSKEEL--
RAAC02466               SGERVIIRASGTDEQAAVHQLTKLIESEELFV
                        :*   :  :.* *:: *:. *    :..*
```

FIG. 145

```
ref YP_001124914.1|    ----------------------------------------------------------------
ref YP_146760.1        ----------------------------------------------------------------
ref YP_001319371.1|    ----------------------------------------------------------------
ref ZP_00742387.1|     ----------------------------------------------------------------
ref ZP_01723416.1|     ----------------------------------------------------------------
RAAC02678              MGVRLRGGRADGGRAHQAVARQVPRGRVSVSHPHRARVGLSPGGERVKERAASRGSDDDF ref YP_001124914.1|    ----------------------------------------------------------------
ref YP_146760.1        ----------------------------------------------------------------
ref YP_001319371.1|    ----------------------------------------------------------------
ref ZP_00742387.1|     ----------------------------------------------------------------
ref ZP_01723416.1|     ----------------------------------------------------------------
RAAC02678              RARHQRWQWREALDRLLWMSCWSFVLLSASYGVVRLMGRALGWRPVPYGQLMIIGGVGVV ref YP_001124914.1|    --------------------------AINRIAKGDF--RVNLQVDWGGR--HHPFAELVT
ref YP_146760.1        --------------------------AINRIAKGDF--RVNLQADWGGR--NHPFAELVT
ref YP_001319371.1|    --------------------------ALESIAKGNF--NVRLDDKFKK---DESFSRLVK
ref ZP_00742387.1|     --------------------------IQKIAKGDFSVKIRNEEKY-----DGEIGVLVK
ref ZP_01723416.1|     --------------------------ALRQMAKGDFNIQ--LDVK-GNK--EDQFGQLIH
RAAC02678              MLALVALLWNALGFDRDDRLFFRILDSLSEIGRGNFSARAMLEVRRGFP--DHPMNQLVL
                                                 :  :.:*:*  .   :         .   :  *:

ref YP_001124914.1|    RINDMAANLQAMEDMRQEFISNVSHEIGSPLTSIRGFARALKNENLSQEQRMHYLDIIET
ref YP_146760.1        RINDMAANLQAMEEMRQEFISNVSHEIGSPLTSIRGFARALKNEDLSREQRLHYLDIIET
ref YP_001319371.1|    SVNMMASGLDQMEKMRQEFISNVSHEIQSPLASIQGFAQLLQNDELSPEERKHYLSIIET
ref ZP_00742387.1|     SINDMTDELNTMEKMRQEFISNVSHEIQSPLTSIKGFARALQDDNLSEEKRKHYLTIIET
ref ZP_01723416.1|     GINHMAVELGELERMRQEFISNVSHEIQSPLTSINGFAKALKNIHLPEEKRQHYLEIIEL
RAAC02678              HVREMAEGLERIEQMRQEFVANVSHEMQTPLTSILGFVKALKSDGLSEGERRHYLDIIEA
                       :.  *:   *   :* ***::*:  ;: .: *:.   *.  :* * * ref YP_001124914.1|    ECVRLSKLSENLLRLAMLDSERYPLHPTSYRLDTQLQTLILHCEPQWAEKDVDMCAVMEK
ref YP_146760.1        ECVRLSKLSENLLRLAMLDSDHYPFHPTSYRLDTQLQTLILHCEPQWAEKELNMCVLFEK
ref YP_001319371.1|    ESKRLSKLSDSLLKLAILESDSMRFEPKAYRLDKQLRNLILACEPQWREKRINMEAFLDE
ref ZP_00742387.1|     ETTRLSKLSQNLLKLTLLESEEYTPERVSYRLDQQLKQIVLNSEPLWAEKEIELDLDLEK
ref ZP_01723416.1|     ESNRLSKISDNLLKLTSLESQHHPFETTTYRLDKQLRNVILALEPNWVAKQLDFDLHLDN
RAAC02678              ESERLSRLADNLLKLTSLESGHHPVTLTRFRLDRQLREVAIACEPLWTEKGLFLDMQVEP
                       *  ***::::.**:*: *:*            :*** **: :  : ** *  * : ..:

ref YP_001124914.1|    VSITADEDLLSQVWLNLIHNAIKFTPKGGTITVQVQRRGEQAIVTISDTGPGIPKHDQPR
ref YP_146760.1        VIITADEDLLSQVWLNLIHNAIKFTPKGGTITIQLQRRGEQAIVTVSDTGPGINEHDQLR
ref YP_001319371.1|    VTITADEDMMSQVWINLIYNSIKFTPEGGSVRVDLNQHGKTIVCKISDTGIGIPEEDQKH
ref ZP_00742387.1|     VHVTADQESMSQVWINLIHNSIKFTPSGGTITIQLKEHETVVEVRICDSGIGISEEQKQH
ref ZP_01723416.1|     ITITADEDLLNQVWMNLLTNSIKFTSDRGAITLTMTQHLDTITIIVQDTGIGLSEEQQMH
RAAC02678              VELEGDEDLLGQVWMNLLSNAIKFTEPGGRIQVRLEKEETGVCVSVADTGIGIRPEDVSR
                       :  :   .*::  :.***:**: *:****    *   :  :   ..       : *:*  *:  .: :

ref YP_001124914.1|    IFERFYKVDKSRHRAAGGSGLGLAIAKQIVDMHHGTISVQSEPGEGATFTVELP------
ref YP_146760.1        IFERFYKADKSRHRAAGGSGLGLSIAKKIVDIHHGIISVQSQPGEGATFTVELP------
ref YP_001319371.1|    IFERFYKADKSRERSKKGGGLGLSITKKIIDMHYGDISVQSKSGTGTTFFTVSLP------
ref ZP_00742387.1|     IFERFYKADSSRNRASGGSGLGLAIVKKVLDLHQGEIKVESEEGKGTEFIVRIP------
ref ZP_01723416.1|     IFERFYKADQSRTAANGGSGLGLAIVKKIIDMHHGTIAVESKLGKFTAFLITLP------
RAAC02678              VFTRFFKADRSRGKP--GNGLGLAIAKRIVEMHRGDISVESEPGRGSTFKVHLPYTQGGR
                       :* **:*.* **   .  *.****:*.*:::::*  * * *:*: *   : *  :  :*
```

FIG. 146

```
ref|YP_001394884.1          --------------------------------------------------------DLMFLST
ref|ZP_01574787.1|          -----------------------------------------EIGTYGDNYLNEHDIAFIND
ref|ZP_02185068.1|          -----------------------------------------ISYMGPTAYSEHDALFIAD
ref|YP_001559227.1          -----------------------------------------ISYYGPYFLSENDFKFLSA
RAAC02507                   MSLRRKIILAFFLTLSIMLVALAFILQAEVHRHFLSVVCPEINSVSPSLTQQIEVHFEQA
ref|YP_517080.1|            --------------------------------------------------------FVSA
                                                                                     * ref|YP_001394884.1          LNR-ILISVGIISLCLALILGVIISGSLSRPILRVIESAEEISKGDYSTRIN-ENSNIIE
ref|ZP_01574787.1|          LYK-LLWAVGLFSLILSLLFGTVMSKRLVSPIARVINTAKSISKGFYSDRIT-EKSNTRE
ref|ZP_02185068.1|          MKN-NLIIVAIVALILSIFFAALVAKKISGPIVRVKDFTREIAKGDY-TSLSPEKTDIKE
ref|YP_001559227.1          LNT-ILVSIGSVSLLFAVYIGWMLARKISGPITKTVKMTTEIAEGNYEIRFS-EHTGTKE
RAAC02507                   LTQSLLWTV-LIFVVATAGVAVLVSRAITQRIFVMQKQALEIARGKWGTTIP--VEGHDE
ref|YP_517080.1|            IYQ-SLLFAGALALIIGILLSYWTSRRLISPLQNLTKAAQRVGEGHLDEHVS---VMTKDE
                            :.   * .: ..    :    ::   :     .:..*      .       * ref|YP_001394884.1          INNLTSTINNLAETLQNQENLRKRLTADVSHELRTPLTTLQSHMEAILDGIWEPTQDRIN
ref|ZP_01574787.1|          INQLTVSINDLAENMEKQETLRRRLTGDVAHELRTPLATLQSHMEAMIDGIWSADSERLK
ref|ZP_02185068.1|          LDELISSVNALSVQLENQQDIRNQLSSDIAHEIRTPLTTLKGSLEAMIDGIWEITDDRLQ
ref|YP_001559227.1          LDALVSSINNLASSLEKQEGIRKQLTSDVSHELRTPLTTIGTHIEAMIEGVWEPTTERLK
RAAC02507                   LSSLANTLNSLSKQLHKQEELRRNLIQDLAHELRTPLTTLRSHIQAFYDGLWEPNRERLY
ref|YP_517080.1|            VGQLAIAFNGMADSLKKQEHLRKQFTADIAHELRTPLTSIRSYIEAFQDGVLPADKENLT
                            :. *   :.*  ::   :.:*:  :*:..:    *::**:****:::     ::*: :*:

ref|YP_001394884.1          SCHGEIMRINRMVNDLEKLAE--YEGENLI----LNKSEFNISEVVKNIMLNFENEYVSK
ref|ZP_01574787.1|          SCHEEIVRISKMVGDLERLAK--YESENIT----LNMDTFDITKLAKRQVQNFETEFLCK
ref|ZP_02185068.1|          SCYEEINRITRLIGSIDKINE--IESHQDS----LNKTSFDLYALAENISSNFEALFVKK
ref|YP_001559227.1          SCYEEINRITNLVKDLEQL---AKVENDNLK----LNITSVNILEVIDTIKDNFETEIYNK
RAAC02507                   SCLEEIQRFEALVTSVERLYEADVAVHAAR----RDLSSADVNQVAQSVIQLFEPRCAEL
ref|YP_517080.1|            IINEEIERLVGLSSDLKDLNVAEMG--ALK----LNFTQVDITELIDKTVNKLIPLIQEK
                              *: *:    :  .:. :              :  ::    :.       :

ref|YP_001394884.1          EI-------DFIFNSRDI--FICADKDKISQIIINLISNALKYTRQGGKVLIQVDNKNEY
ref|ZP_01574787.1|          GL-------ELELTGPSCLVY--ADKDKISQVFVNLLSNALKYTPKGGSVELHIQDNNNF
ref|ZP_02185068.1|          NI-------YYALNGD--PLFITADKDKISQVITNLLSNAVKFTPPEGTITLKIRNEENQ
ref|YP_001559227.1          SL-------DVSVIGTAS--TILVDKERISQVIINLLSNAIKYTPDFGKIVISLEDYETN
RAAC02507                   GIR------LELRTPDVPVWVTARAQHVSQILWNLLDNAVKFTPSGGNIVVEVGHQDGK
ref|YP_517080.1|            GIA------FEWEKP-ASVFIEGDEYHLTRLFYNLIHNAYKFTESNGRISIQMELRQSD
                            :                         ::::::  **: ** *:*   * : :    :

ref|YP_001394884.1          LELIVQDNGQGIPKEDLPYIFERFYRADKSRNRLTGGAGIGLTITKSLVEAHKGKITVES
ref|ZP_01574787.1|          IEISVEDNGLGIPEEDLPYIFERFYRADKSRDRLTGGSGIGLTICKSIVLAHGGDIYAQS
ref|ZP_02185068.1|          ALLTIADTGEGIHPKEINRIFERFYMSDLSRNSFLGGQGIGLSIVKSIIKAHNGTITVKS
ref|YP_001559227.1          LVIQMKDNGIGIPEEELPFIFERFYRADKSRNRRTGGAGIGLAIVKSVVHSHGGKVEVSS
RAAC02507                   PFLSVKDSGVGIPAEEIDNIFERFYRVDKSRDRKTGGSGLGLAIVKQLVELSRGFVQVNS
ref|YP_517080.1|            VRISVCDSGIGIPKEDLPFIFERFYRAEKSRSRETGGTGIGLALVQQITQLHRGTLDVES
                               : *.*   :::   ** : .    ** *:**: :.:    * :  ..* ref|YP_001394884.1          ELNKGTTFKVSIP-
ref|ZP_01574787.1|          NPGKGTKFIFTVPK
ref|ZP_02185068.1|          DYGKGSTFTVILP-
ref|YP_001559227.1          KLETGTVFRVILP-
RAAC02507                   RVGRGSTFTVVWPE
ref|YP_517080.1|            NPGQGSKFTVVLP-
                               *: *  . *
```

FIG. 147A

```
ref|ZP_01667455.1|      MFQRTLRRLSIINSVVFLLIFLTFGAVLYGYVAYRLFDKVDDAMRFKAENFKIVNGRAIL
ref|YP_146183.1|        ------------------------------------------------------------
RAAC00906               MFRKTALRLVLLYTVVFAGILLLFSAVVYAFTDHRVRADEIATMSTAAANLRACRDEQIL
ref|ZP_01515931.1|      ------------------------------------------------------------
ref|YP_001637100.1|     ------------------------------------------------------------
ref|YP_001430381.1|     ------------------------------------------------------------ ref|ZP_01667455.1|      PGRVRFLFDPRIIILVRDSQGRVTSSFPSEVAELERL------------AALASQVDAGK
ref|YP_146183.1|        ------------------------------------------------------------
RAAC00906               PGDR---DDGEASPLHRGHSSGPGPDGDRLLAEVDETREQHLVYVLLSGTRVVLQTPAGS
ref|ZP_01515931.1|      ------------------------------------------------------------
ref|YP_001637100.1|     ------------------------------------------------------------
ref|YP_001430381.1|     ------------------------------------------------------------ ref|ZP_01667455.1|      VHISEVDSHA----------YRLISLPYRYEENVLQTERGPIVVKDVIAVSIV-----DS
ref|YP_146183.1|        ------------------------------------------------------------
RAAC00906               LTASEASIVARDGLGARPRGVSVAGVPYLGMKVELP---RPVRIGDASANAAVILYNRAQ
ref|ZP_01515931.1|      ---------------------------------------------GPAALQLGRVLNDQEQ
ref|YP_001637100.1|     ------------------------------------------------------------
ref|YP_001430381.1|     ------------------------------------------------------------ ref|ZP_01667455.1|      EVALLRNLFMIIVSGLVIGMLIIIMAGYYLARRAMVPIQAAWEKQQQFVADASHELRTPL
ref|YP_146183.1|        ---------------------------MSKRALIPIEEAYERQRQFVADASHELRTPL
RAAC00906               DVAFLRELLTILSVSAGFFAVASAGVGFALASRALRPIRRSFEEQRRFVAHASHELRTPL
ref|ZP_01515931.1|      ---VLYQLLTGLVGFGIVGAVMIGIASWWLAGRALRPABEEAWTRQLRFISSASHELRAPL
ref|YP_001637100.1|     ---------------------------LAGRSLRPABEEAWVRQTRFIASASHELRAPL
ref|YP_001430381.1|     ---------------------------LAGRALRPAQEAWERQQRFIASASHELRAPL
                                                   ::  *::  *  .  ::  .*  :*::  ******:**

ref|ZP_01667455.1|      AVIKSNAELMLRHPDHTIEDESIRVTN-IVREVRRMTRLVADLLTLARADANQSELQLG-
ref|YP_146183.1|        SVVFSSVEALALEEDVMKNDFARRLLDRLREELKRITKLMNDLLTLARADAKNAALELSK
RAAC00906               AVMRLQIDRMFRHPGETILDMSEVIAS-LARETSRLQRLVNDLLTLAKADEGEAVLRLR-
ref|ZP_01515931.1|      TLIRASAEVALRNAKDE--DQRELLTD-VLSESDHMRRLVDDLLTLSRLDSGSLTLQRQ-
ref|YP_001637100.1|     TLIRASAEVALRHADDP--DQRELLSD-VLSESDHMRRLVDDLLTLSRLDSGALVLQRQ-
ref|YP_001430381.1|     TLIRASAEVALRDTPSDTADQYELLGD-ILAESDHMRRLVDDLLTLTRLDSGQLKLVIE-
                         :::    .:       .        *        :  .:    *   ::  :*:  *****::  *       * ref|ZP_01667455.1|      -AVSLSELVDAVSEQFKPLAQLEGHTLTVAVYEQLELVGDRERLYQLLVILLDNAVKYTP
ref|YP_146183.1|        QTFDFRPHAERTFQLVSELAAKKQITMHFHAPEQALVTADPDKLTQLLYILLDNAIKYTP
RAAC00906               -PVDLATIAREAALRFAPLAEEKGVQLRVSAAETP-IVADPDRLLELLSILVDNAIAFTP
ref|ZP_01515931.1|      -PITLNDFLADLHRHVSRLGEERGITITLAQARGT-VIADPDRLRQILLLILIDNALRYTP
ref|YP_001637100.1|     -PVSLPSFLADLHRQVRRLGEEKGIAIQLAPITGT-VLADPDRLRQVLLILIDNALRYTP
ref|YP_001430381.1|     -PVNLADLLSRVHRQVARLGEQRGITIELTTVGGV-VQADAERLQQVLLIALDNALRHTP
                         ..  :             .  *.  .  :  .           :  .*  ::*  ::*  *  :***:  .**

ref|ZP_01667455.1|      PPGHILITGVRQGSHILLTVEDSGQGIPPEDLPRVFDRFYRGDKARSREK--GGTGLGLA
ref|YP_146183.1|        EGGEVTLSIRTEPKQFILSVKDTGIGIPPEDIGRIFDRFYRVDKTRSRQQ--GGHGLGLS
RAAC00906               AGGWVEIDAHASGSAAVLAVRDTGRGIPPEHLPRVFDRFYQADPSRTTR----GAGLGLS
ref|ZP_01515931.1|      TGGTITLNAELAGKQVRISVRDTGCGITPEHLPHLFERFYRADQARNRSSNTNNAGLGLS
ref|YP_001637100.1|     SGGVITIATEPAGKQIRLSVSDNGCGIAPEHLPHLFERFYRVDVARNRSD--GHAGLGLA
ref|YP_001430381.1|     SGGTITLAAAPTGRMVQITVTDTGSGIAPEHLPHIFERFYRADPARGREN--GNAGLGLS
                        *  :  :                ::*  *.*  **.**.:  ::*:***:  *  :*              ****:
```

FIG. 147B

```
ref|ZP_01667455.1|      IAKWIVEKHGGKIWVES--KVGVGTKFSVLLP------------------------
ref|YP_146183.1         IAKWIVEAHGGTIHVQS--QLGQGSEFLVRLP------------------------
RAAC00906               IAKWIAEAHGGQIRIFSPGSHGTGTEVEVRLPQSRSAEPGRGRFARLLAICYKKNSS
ref|ZP_01515931.1|      IAKGLVEAHGGTIGIES--EVNKGT-------------------------------
ref|YP_001637100.1|     IAKGLVEAHSGAIGIES--EVNRGT-------------------------------
ref|YP_001430381.1|     IAKGLVEAMHGRITVTS--ALGAGTTVSVALPQGET--------------------
                        *** :.*   * * : *    . *:
```

FIG. 148

```
ref|YP_005108.1|       --DDGEGIPEEHLPHLFERFYRVDKARDRERGGSGLGLAIVKAILEAHGGEVWVESQVGK
ref|YP_144769.1|       --DDGEGIPEEHLPHLFERFYRVDKARDRERGGSGLGLAIVKAILEAHGGEVWVESQVGK
ref|ZP_01773683.1|     --DSGIGIPEKDLPRLFERFYRVDEARSRDNGGTGLGLSIVKHIVQAHGGTLEVKSEQGK
ref|YP_001157480.1|    VADTGPGIPAQHLPHIFERFYRVDTARDRGNGGSGIGLAIVRAVVSAHGGRVRAENVPGG
RAAC02211              MADNGVGIPKVHHPHVFERFYRVDEARSRAKGGAGLGLAICKAIVEAHGGRMEWESEPGE
ref|YP_001124914.1|    ISDTGPGIPKHDQPRIFERFYKVDKSRHRAAGGSGLGLAIAKQIVDMHHGTISVQSEPGE
                         *  * ***  . *::***:  :*  *   **:*:**:*  :  ::.  *  *   :.  * ref|YP_005108.1|       GTAFSFSLPASGP-----
ref|YP_144769.1|       GTAFSFSLPASGP-----
ref|ZP_01773683.1|     GSVFSFTLPIA-------
ref|YP_001157480.1|    GAMVKVVLPPAG------
RAAC02211              GAVFTVTLPVAGPDGDGA
ref|YP_001124914.1|    GATFTVELPIRGP-----
                       *:  ... **
```

FIG. 149A

```
ref|ZP_00739567.1    ------------------------------------------------------------
ref|NP_830390.1|     ------------------------------------------------------------
ref|ZP_01696335.1    ------------------------------------------------------------
ref|YP_001037228.1|  ------------------------------------------------------------
RAAC01489            MFKRLSLRLTLLTVVLLVVLYSITSLALYGIIRGFVMRSIDFNLRQAAYRVAN-TAVLTG
ref|ZP_01667455.1    ------------------------LYGYVAYRLFDKVDDAMRFKAENFKIVNGRAILPG ref|ZP_00739567.1    ------TWNGKIVKIEGDN--RKFRSIFEENLEKFSPKKLGELQD------IEVQGRYFR
ref|NP_830390.1|     ------TWNGKIVKIEGDN--RKFRSIFEENLESFSPEKLEELQD------IEVQGRYFR
ref|ZP_01696335.1    ------------------------------------------------------------
ref|YP_001037228.1|  ------------------------------------------------------------
RAAC01489            IPSFASTGSPEINFVLADN--GVYTSIADPDLASALENRLNRAVDRPTFFNFTYQGEHYR
ref|ZP_01667455.1    RVRFLF--DPRIIILVRDSQGRVTSSFPSEVAELERLAALASQVDAGKVHISEVDSHAYR ref|ZP_00739567.1    AFSL-----------QKDGEIVQIVRDI---TAEERMLNTLFLILVIGCSIGSLCAIGIG
ref|NP_830390.1|     AFSLQ-----------KDGEIVQIVRDI---TAEEGMLNTLFLILVIGCSIGSLCAIGIG
ref|ZP_01696335.1    --------------------------------------------------------AVIAG
ref|YP_001037228.1|  -------------------YIIVFLDY---TVEEKMYKPLIIISIYIVLLSIVLVFTVS
RAAC01489            VYDLP------IAAGSGGPAYVATILDD---TQTVRAMSDLRSVIVIVGLFGICGATLVG
ref|ZP_01667455.1    LISLPYRYEENVLQTERGPIVVKDVIAVSIVDSEVALLRNLFMIIVSGLVIGMLIIIMAG
                                                                              .

ref|ZP_00739567.1    FFLAGRALVPIQNSWEKQQQFVSDASHELRTPLAVIQSKTDVLFQSPSATIEEKAMDIST
ref|NP_830390.1|     FFLAGRALVPIQSSWEKQQQFVSDASHELRTPLAVIQSKTDVLFQSPSATIEEKAMDIST
ref|ZP_01696335.1    LVLAERALKPIKAAWDKQTQFVSDASHEIRTPLAVIQSRVELLLRKPNETVRDVLQDIST
ref|YP_001037228.1|  FFLANRSIKPIKTSWEKQTAFIADASHELRTPLAVINSNLEIVMENENETVGSQMKWLGN
RAAC01489            FILSDRMLQPIRRAFQRQLEFVADASHELRTPLAVIQSNLGIVMEHTDQTVEENLEWLNN
ref|ZP_01667455.1    YYLARRAMVPIQAAWEKQQQFVADASHELRTPLAVIKSNAELMLRHPDHTIEDESIRVTN
                     *: * : **: ::::*  *::*****:*******:*.   :::.   *: .    :  .

ref|ZP_00739567.1    ISKECRRLSKLVSNLLLLARSDSN-QIEMDKKTFELDKLLEEIVAPYKEIASYQEKEMIL
ref|NP_830390.1|     ISKECRRLSKLVSNLLLLARSDSN-QIEMDKKIFELDKLLEEIVAPYKEIASYQEKEMML
ref|ZP_01696335.1    VLNECRRLTKLVSNLLTLARSDSD-KIEIERKPFYLDELLREIMDHFSELAAIQGKTLIL
ref|YP_001037228.1|  IQSELERMKKLVDDLLFLARADAEDEMPKEY--FDLSRLVHKIYDEFTPLCQKKSLEFLL
RAAC01489            AHGEARRLAKLVQDLLTLARSDSE-RMPVERRPVALNDLLERIHDLYETIAEMRGIELTV
ref|ZP_01667455.1    IVREVRRMTRLVADLLTLARADAN-QSELQLGAVSLSELVDAVSEQFKPLAQLEGHTLTV
                       * .*: :** :** ***:*::   . *. *: .  :. * *   .

ref|ZP_00739567.1    KVERGVSFMGDRERIHQMMVILLLDNAMKYTNEGGHIQIDCTQMSSSIRIQVKDDGIGVKE
ref|NP_830390.1|     KVERGVSFMGDRERIHQMMVILLLDNAMKYTNEGGHIQIDCTQTSSSIRIQVKDDGIGVKE
ref|ZP_01696335.1    KSAPPVTFSGDRDRIHQLIVILLDNAMKYTGDGGKIELACFESKNHVGISVQDNGIGLKE
ref|YP_001037228.1|  DAKDNIVFYGNEFRIKQLITILLDNAIKFTGEGGKIILKLKVHANSIQLSVSDTGEGIAK
RAAC01489            RAEEPLVVLGDRDRLHQLLVILIDNAMKFTDAGGKVEIAATRNRNQAILSVRDTGIGIAK
ref|ZP_01667455.1    AVYEQLELVGDRERLYQLLVILLDNAVKYTPPPGHILITGVRQGSHILLTVEDSGQGIPP
                     :  . *:.  *:  *::.**:***:*:*    *:: :      .     :  *  * *:

ref|ZP_00739567.1    EDIPKLFDRFYQGDKARS---T-SEGAGLGLSIANWIVEKHYGKISVESRW-GNGTCFEV
ref|NP_830390.1|     EDIPKLFDRFYQGDKARS---T-SEGAGLGLSIANWIVEKHYGKISVESKW-GDGTCFEV
ref|ZP_01696335.1    EDREKIFDRFFQVSKSRTK----TESLGLGLSIAKWIVEKHSGKIRVDSK-LGEGTTFTI
ref|YP_001037228.1|  EHIDKIFDRFYRVDKSRSNHG---GSGLGLAIAKCIVNEHKGTIDVFSE-VSRGTEFTV
RAAC01489            EHLERVFDRFYTVDTARS-RHGEAKGTGLGLSIAKWIVEAHGGRISIASEGIGKGTTVRV
ref|ZP_01667455.1    EDLPRVFDRFYRGDKARSR---EKGGTGLGLAIAKWIVEKHGGKIWVESK-VGVGTKFSV
                     *.  ::****:   ..:*:         . ****:**: **: * * : *.  .**  . :
```

FIG. 149B

```
ref|ZP_00739567.1|      IFPKNQK----------------
ref|NP_830390.1|        IFPKNQK----------------
ref|ZP_01696335.1|      TFPKKKRKDA-------------
ref|YP_001037228.1|     SLP--------------------
RAAC01489               ELPLSPKRAAGSDEGDVTAKSEA
ref|ZP_01667455.1|      LLPV-------------------
                         :*
```

FIG. 150A

```
ref|ZP_01697157.1|      --------------------------------IEVSNRLIEKDYDSRVRVNASGELR-Q
ref|ZP_02329946.1|      ------------------------------------------------------------
ref|YP_001212380.1      ------------------------------------------------------------
RAAC02391               MIPFAIGLGVGLAIGALFALWQMSWFRSLRRYLLDAMDAIVQGRYDVRMYEYRSRPAEIA
ref|ZP_00539202.1|      ------------------YSSTKRFLRPIAEATEVLHELSHGNYKSRVYELTAPDESRD
ref|NP_693085.1|        -----------------------------------VDRLIEGNYSARFYNGNSP-EMEE ref|ZP_01697157.1|      LTKA-INNLAHNLKQQMNEIDENEQQLTAVLENMDSGVMLIQTSGRIMLVNRAMEEMTGL
ref|ZP_02329946.1|      --RT-INRMAENLQIQMQHIRENEYRLQGVLENMVSGVMMVDQRGTITLVNRSAEDILGY
ref|YP_001212380.1      --RS-INYLARQLKNNIEDVIAEKNRIKAILSSMSDGVIAMDAWGRMILINPVVEELFRI
RAAC02391               IFRH-FNRMAERIQETLADLSQERDILRHILQNMTTGVIYLRSDGQVQMVNHAAERLFRR
ref|ZP_00539202.1|      LGKS-INLLARNLENASSGEAMQRARLESLIEYMGAGLMLIDEKGYVLLVNRTYREMFNI
ref|NP_693085.1|        LSVK-VNTLARNMSEIAIQEQMQSEQLTTIVDNMQSGLVLIDEKGYVHVVNRKFLEMFGE
                         .* :*..:.                  :   :  ::. *  *::  :   *  : ::*     :

ref|ZP_01697157.1|      SSGELIGKRH------IEAGKSFGLSQLIDRSLKTGERFRDEVHL---YYPKERILDAHI
ref|ZP_02329946.1|      SSHELLNKSY------LDAGFQLEFTALLADAIETHTRVREELML---HFPQEQILEVHV
ref|YP_001212380.1      TMAASRGKNI------LRVIRNYDLEKLLNQALETGRCMQKQIQI---LAPEPRVFQVHV
RAAC02391               PVEQWKDRDH------WTVFRNYQLGSAIDHALLFGTPWSGEFQIRDGVTVAVRLVPISA
ref|ZP_00539202.1|      -YGQSNGQLY------YRVLPNEKMSQVIEDVYLTEKPNRKQSSVRFGLNS--RTFMVSA
ref|NP_693085.1|        EESNYRGHLY------YDVFENENVHETVQKTFLYEETVKKSFVHREGLNKIY--VEVVG
                          .:            .     .   .

ref|ZP_01697157.1|      APYVGESGELR-GVVAVLHDVTETRRLEQIRSEFVANVSHELKTPVTSVKGFAETLLDGA
ref|ZP_02329946.1|      SPIVQGDGQ-RKGVLVVLHDITAVRRLERIRSEFVANVSHELKTPVAAVKGFAETLMAGA
ref|YP_001212380.1      IP-LQNSGAERGGVVALLHDITERKILQEMRSEFVANVSHELRTPLTSIRGFAETLLDGA
RAAC02391               APRMRNKADGRHDVLMLVNDVSEWRRLERMRSDFVANVSHELKTPIAAIRGFAETLLDGD
ref|ZP_00539202.1|      AP-IFGKNGRVQGTTVVFNDITEIKKLEQMRKDFVANVSHELKTPLTSIKGFAETLLDGA
ref|NP_693085.1|        AP-IFNERNMLKGAVLVLYDITELKKLEKMRKDFVANVSHELRTPITSIRGFAETLLDNN
                         *  :     ..   :. *:: :  *:..*.:*********.**.:::.*******:  .

ref|ZP_01697157.1|      MYDEATLREFLKIIYDESDRLHRLISDILDLSRIEQHRILLKMEQLNVVDVVAETVQTMR
ref|ZP_02329946.1|      LEDKEMARSFLQIIYDESDRLNRLIGDILELSKIESKRIPLQFSPVDVESIVENSIQMMK
ref|YP_001212380.1      LEEPDTARRFLEIINSETERLSRLIDELLNLSRLESHKWVPKRQPVNMGELIKRAVAILQ
RAAC02391               VDE-EAREKFLRTIYEESLRMGNLVSDLLELSKLEASDSHVDPVAVDLYEVLVRAVDRVR
ref|ZP_00539202.1|      QDVPEIREQFLNIIHDESERMQTLVEDLLELSRLEQDNYQLETTIVDVTSLLHETATLLQ
ref|NP_693085.1|        ITDPAT-KEFMEIIYKESHRLQLLIEDLLALSRLEREDFRLLIDNYDVRQMVEEILPQLH
                          .*:. *  .*: *:   *: ::* **::*          :: ..:: .     ::

ref|ZP_01697157.1|      KRIEKK--QLELVLPQKRHVMMEADKDRLRQILLNLVTNAIAYTPDKGRIEI------SL
ref|ZP_02329946.1|      AEAEKK--HITLESCVENELYIEADEDRLRQILINLLSNGISYTPEGGRVSIGVEFVPSL
ref|YP_001212380.1      PRAVEKNLAIKINLP-EDLPVVQGDPDMLSQVLLNLIENAVVYTQAGGEVSIS------
ref|NP_693085.1|        PVANEK--EITIELPREQRLHVWAEPDLLQVFLNLLTNAIHYSPPKSRVCVT------
ref|ZP_00539202.1|      RKATEK--QMTIHLETEEEVFIRADLNRLKQVVVNLVANALNYTPNGGNVWIS------
ref|NP_693085.1|        QKAENK--NLTFDLEVPDQLTMRADKDRMKQVLINLIDNSIHYTPSGGDICLA------
                         :*    :          : .:: *:.:**: *.:  *:       . : :

ref|ZP_01697157.1|      IER-ENE-LDLIVSDTGIGISEKDLPRIFERFYRVDKARSRQSGGTGLGLAIVKHLVESY
ref|ZP_02329946.1|      DDNPDNERMRIRISDTGIGIPEKDLPRIFERFYRVDKARSRSSGGTGLGLSIVKHL----
ref|YP_001212380.1      -AAATQDEMKVDVKDNGIGIPPESLSRVFERFYRVDKARSREQGGTGLGLSIVKHIIDA-
RAAC02391               -WDVLVDRVKVHVKDNGIGIPKESLPRVFERFYRVHKDRSRASGGTGLGLAIVKHIVTAL
ref|ZP_00539202.1|      -LEDGEEAVMLRIKDDGIGIHPKEMQRIFERFYRVDKARSRNSGGTGLGLAIVKHII---
ref|NP_693085.1|        -ISEETDVIHFQVKDSGIGMDEKSQTRVFERFYRVDKARSRNTGGTGLGLAIVKHIV---
                            :   :  :.* ***:  :.  *:*******.* ***  *******:****:
```

FIG. 150B

```
ref|ZP_01697157.1|      HGKIRVESEEGKGSTFIVTLPRTQTRP
ref|ZP_02329946.1|      ---------------------------
ref|YP_001212380.1|     ---------------------------
RAAC02391               GGEVGVESEEGKGSDFWFTLSRLDARP
ref|ZP_00539202.1|      ---------------------------
ref|NP_693085.1|        ---------------------------
```

FIG. 151A

```
ref|YP_147095.1|          ---QYLDLFIDESKEHLQAINERLLELEKTPEDMSVVNDIFRSAHTLKGMSATMGFEDLA
ref|YP_001125215.1|       ---QYLDIFIDESKEHLQTINERLLELEQTPGDMALVNEIFRSAHTLKGMSATMGFEDLA
ref|ZP_01171502.1|        ---QYLEVFIEESREHLQAINEHLLELEKNPADLKIINEIFRSAHTLKGMSATMGYEDLA
ref|ZP_01861001.1|        --NQYLEVFIEESKEHLQTCNEQLLELEKNPENLAIVNEIFRSAHTLKGMAATMGYEDLA
ref|YP_001486785.1|       --NQYLDIFLDESREHLQTCNEKLLDLEKNPTDLQLVNDIFRAAHTLKGMSATMGYADMA
RAAC02885                 MHDEYLEAFLAESMENVERLEAFCLTLEREGSKPDLLDEMFRAAHTLKGMSATMGFSKLA
                              :**: *: ** *::    :    * :   .  ::::::*****:**. .:* ref|YP_147095.1|          NLTHQMENVLDGIRNRRLSVTPELLDVIFEAVDHLEAMISSIA-AGGDGTRDVRRTVEQL
ref|YP_001125215.1|       NLTHQLENVLDGIRNQRLIVTPELLDVVFQAVDHLEAMIISIA-SGGDGKRDVGETVEQL
ref|ZP_01171502.1|        RLTHQMENVLDAIRNQKIGVTPELLDTVFLAVDDLEAMVLSIS-EGGDGKRDVSTAVKQL
ref|ZP_01861001.1|        SLTHQMENVLDAIRNSKIQVSSLILDVVFMAVDDLEAMVMSIA-EGGDGKRDVTEIVKKL
ref|YP_001486785.1|       QLTHHLENMFDAIRNEQMIVTPESMDTMFEALDHLEAMVQSIA-EGGDGKRDVTEISKKL
RAAC02885                 ALTHRVEDLLGTLRDERVRLEPRHVDALLLAVDRMRARIQAIGVSAKEPDEPDDDAMDAL
                           ***::*::: .:*: ::  : .  :*.::  *:* ..* : :*..  .  .      * ref|YP_147095.1|          KRIE--QGEMPNKQAAREEPP-----------LEHAYGEFEYHVLEQAKEQGFSVYEIRV
ref|YP_001125215.1|       KRIE--QGEMPNKPTAGEQLP-----------LEHTYGEFEYHVLQQAKDQGFSIYEIRV
ref|ZP_01171502.1|        ELIE--NGQTPLMESRQEAAAAAAAEAEVPAELRSDYDEFERTVLSQSKEQGFDVFEISI
ref|ZP_01861001.1|        ALIE--KGESLDNLQAQSEAAAAVLEAEPSNTHTAQYDQFERTVIEQSKEQGFQCFEISV
ref|YP_001486785.1|       DVTGSHAEAAPSVETADVSAAS---------ANDLDYNEFERTVLDEAREQGFKCYELNV
RAAC02885                 AGAL--RGGADVGGTREEDSKP-----------FANLSDWANRAAAEGKE----LYTVHI
                                                            .:.  ::.::         :  :  :

ref|YP_147095.1|          RLRDDCLLKAARVYMVFEQLNEVGEIVKATPPVE---MLEEEQFDR--EFLVTVVSKAPA
ref|YP_001125215.1|       RLRKDCMLKAARVYMVFEQLNEAGEIVKSTPPAD---MLEEEKFDQ--EFLVTVVSKTPA
ref|ZP_01171502.1|        SLREDCLLKAARVFMVFEVLEKSGEIIKSNPPVD---VLEEEQFDS--AFTVTLVTKEPK
ref|ZP_01861001.1|        SLREDCLLKAARVFMVFEVLEKCGEVIKSVPAVD---VLEEENFDQ--DFLVSIVSKDSQ
ref|YP_001486785.1|       TLSDACLLKAVRVYMIFERLNEAGEVVKTVPNAE---LLESEDFES--EFSISYLSKQPM
RAAC02885                 RLAPDCVMPGVRLAMAYQALKASAILMAAHPAEEN---VMAGQVEATEAFAAVMVAPGEI
                            * *::  ..*: *  ::  *: . ::  *   :      : :  ..:    *   ::

ref|YP_147095.1|          DELQKRLMGISEIDDVKVS-----------MLSSNEPSAES--EKAAAP---QQPAAME
ref|YP_001125215.1|       DELRMRLMSISEIDEVEIA-----------AVTVDEPSAKSGEQDDLEP---PVSTAIG
ref|ZP_01171502.1|        EEIQAKIMKVSEIBKAEIINIDL-------------MPASPAEEEPAPAPGIIQPVEEP-
ref|ZP_01861001.1|        EDIKKKVMKVSEVHKVDVRLVDL-EKGKESDSQITEQPSASTEDATDRVTGKQANVASVP
ref|YP_001486785.1|       DEVKKIVMTISEVEQVEIS----------EVSAFEEASPAEKQEAKPEQEKEEVSVPAA
RAAC02885                 DRVRQGVLDVTDVSSCEVS---------------KVSESHSAPKEDAPRAEQGDAPIE
                          :  ::  ::  ::::  . .:                      :

ref|YP_147095.1|          QAAAVQAEAEAPEKQTAKQATKTIRVNIERLDRLMNLFEELVVDRGRLEQISRELNHAEL
ref|YP_001125215.1|       QVAATQTKAEAAEKLAAKQAGKTIRVNIERLDMLMNLFEELVVDRGRLEQISRDLNHPEL
ref|ZP_01171502.1|        ---KEESRNGAPAKQASSK---TIRVNIERLDILMNLFEELVIDRGRLEQISKELNNQEL
ref|ZP_01861001.1|        VVKKEEKKESAPSKQANTG-NKTIRVNIERLDILMNLFEELVIDRGRLEQISKELNHPEL
ref|YP_001486785.1|       KAPANDAPKANGNNVAAAGGTKTIRVNIDRLDSLMNLFEELVIDRGRLEQIAKELENNEL
RAAC02885                 PRVSRHANGSSPAG-ADLRRDATLRVPVRKVDALMNTLSDLVITKTRLATLVSSADDPAL
                                      .    :        *:** : ::* * :.:: :  **  :  . :.   * ref|YP_147095.1|          TETVERMSRISSDLQTIILNMRMVPVETVFNRFPRMVRQLARELGKKVRLDIIGADTELD
ref|YP_001125215.1|       TETVERMSRISSDLQTIILNMRMVPVETVFNRFPRMVRQLARELGKKVRLDVIGAETELD
ref|ZP_01171502.1|        HETVERMSRISGDLQNIILNMRMVPVETVFNRFPRMVRQLARDLNKKINLEIVGAETELD
ref|ZP_01861001.1|        NETVERMSRISGDLQNIILNMRMVPVETVFNRFPRMIRQLARDLNKKIELEIIGAETELD
ref|YP_001486785.1|       TDTVERMTRISGDLQSIILNMRMVPVETVFNRFPRMIRQLTKELNKKIELIIEGAETELD
RAAC02885                 KEAVERLDRLTGDIQDGLMRLRMVPVETIFHRYPRMMRDLEHRLQREFDFVMTGLDTEMD
                          ::***:  *::.*:*   ::.:*******:*:*****:*:   :  * ::. :  : * :**:*
```

FIG. 151B

```
ref|YP_147095.1|         RTVIDEIGDPLVHLIRNALDHGIEAPDVRVARGKPEEGTVQLRAYHSGNHVFIEIEDDGA
ref|YP_001125215.1|      RTVIDEIGDPLVHLIRNALDHGIEAPDIRVACGKPEEGTVKLRAYHSGNHVFIEIEDDGA
ref|ZP_01171502.1|       RTVIDEIGDPLVHLIRNALDHGVETPEVRKANGKNEEGTVVLKAYHSGNHVFIELIDDGA
ref|ZP_01861001.1|       RTVIDEIGDPLVHLLRNAIDHGIEAPEIRRQNGKPEEGTVTLKAYHSGNHVFIEISDNGG
ref|YP_001486785.1|      RTVIDEIGDPLLHLLRNSLDHGIESPEERVKKGKPEKGTVLLKAYHSGNHVFIEVEDDGG
RAAC02885                RVVLEEMGEVIVHLLRNAVDHGLEPPEARESQGKPRRGIVRLAAYTASGHVYLEVSDDGR
                         *.*::*:*:  :::::***:*.*:  *    ** ..* * *  :..::*: *:* ref|YP_147095.1|         GISREKVLQKAKSRGIVSPQAAEHLNDQQIYELIFAPGFSTAEQVSDISGRGVGLDVVKS
ref|YP_001125215.1|      GISREKVLQKAIDRGIVSAEEAAHLTDQQVYGLIFSPGFSTADRISDISGRGVGLDVVKS
ref|ZP_01171502.1|       GINRDKVLQKAVKNGIITEQAGASLTDKQVYELIFASGFSTADKISDVSGRGVGLDVVKS
ref|ZP_01861001.1|       GISREKVLKKAISQGIVTEESAAALTDRQVYELILASGFSTAETISDISGRGVGLDVVKA
ref|YP_001486785.1|      GINRKKVLEKALERGVITDREAETLEDHQIDSLIFAAGFSTADTISDISGRGVGLDVVKN
RAAC02885                GIDRGRVLETAVAKGWITPEEGAAMSDESVYALLFRPGFSTAERVSDISGRGVGLDAVRE
                         **.* :**:.*  .* ::  . . . : *...: *:: .*****: :**:********.*:

ref|YP_147095.1|         TIESLGGTVSVDSQPGKGSLFSIQLPLTLSIISVLLVQIAEETYAIPLSSIIETALVKKE
ref|YP_001125215.1|      TIQSLGGTVTVDSQPGKGSLFSIQLPLTLSIISVLLVQIAAETYAIPLSSIMETALVKKE
ref|ZP_01171502.1|       TIESLGGTVTIDSQEGKGSTFSIQLPLTLSIISVMLIEVQKEKYAIPLSSIIETAIIKKE
ref|ZP_01861001.1|       TIESLGGSITIDSVLGEGSTFSIQLPLTLSIISVMLVEVEKEKYAIPLSSIIETAIIKKE
ref|YP_001486785.1|      KLESLGGSVSINSTEGQGSLFSIQLPLTLSIISVLLVKLEEETFAIPISSIIETAVIKKS
RAAC02885                KVEALGGQIRLNSVLGAGTTFTIELPLTLAILSALLVSVRGQVFAIPTANVDEVRRVTRD
                         .::.:***  : ::*   *  *:  *:*:*****:*:*..:*:..  :  :*** :.: *. :..

ref|YP_147095.1|         EIFSAHNQPVIDFRGKIVPLVRLKDVFAVP-GVADDGDAVAVVIVRKGEKLAALAVDSFI
ref|YP_001125215.1|      DIFSAHNQPVIDFRGKVVPLVRLKDVFSVP-NASDEGDAVAAVIVRKGEKLAALAVDSFI
ref|ZP_01171502.1|       DIMNAHNQKVIDFRGKVVPLLFLKDVFAVPVHLEEDGY-YSVVIVRKGDKMAGLVVDSFI
ref|ZP_01861001.1|       DILNAHNQKVIDFRGKVVPLLFLEDVFEIPKQEGDDFY--SVVIVRKGDRMAGLVVDSFI
ref|YP_001486785.1|      DILQTHDREVIDFRGKFIVPVVYLKKQFHVP-NANELEEELHIIVVRKGDKLTAFVVDSFI
RAAC02885                DVRHVQERPVFQDSAGIVPIVDLAERLGLG--SRRDAYPQTAVVCRDGKRRLALVVDHVL
                         ::  .:::  *::    .  :**:: * .  :       ::  *.*.:   .:.** .:

ref|YP_147095.1|         GQQEVVLKSLGNYLSSVFAISGATILGDGRVALIIDCNAL----
ref|YP_001125215.1|      GQQEVVLKSLGNYLSSVFAISGATILGDGRVALIIDCNAL----
ref|ZP_01171502.1|       GQQEIVLKSLGGYLNDIFAISGATILGDGQVALIVDCNALIN--
ref|ZP_01861001.1|       GQQEVVLKSLGNYLTDVFAISGATILGDGQVALIVDCNAL----
ref|YP_001486785.1|      GQQEVVLKSLGDYLPNVFAISGATILGDGQVALIVDCNAL----
RAAC02885                DELEIVNKPLGRYLQGVREFAGATILGDGRVSLILDVRSIANPA
                         .: *:* *.** **  .: ::*********:*:**:*  .::
```

FIG. 152

```
ref YP_001125206.1|    -MARILVVDDAAFMRMMIKDILTKNGHEVVAEAADGRQAIEKYKETRPDIVTMDITMPEM
ref ZP_01696550.1|     ----ILIVDDAAFMRMMIKDILTKNGYDVVAEAGDGAQAIEKYKEHRPDLVTMDITMPEV
ref ZP_01860990.1|     MANKILIVDDAAFMRMMIKDILTKNGFEVVGEAADGNQAVEKYKELSPDLVTMDITMPEK
ref NP_243310.1|       --ARILIVDDASFMRMMIKDILTKNGYDVVGEAHDGEQAVEKYKELSPDLVTMDITMPEK
RAAC02876              -MANILVVDDAAFMRMMIKDILTKNGHVVVGEAADGAQAVERYQELRPDLVTMDITMPEV
ref YP_001410204.1|    -MAKVLVVDDAAFMRMMLKDILTKAGHEVVGEAANGVEAVEKYKELKPDVVTMDITMPEM
                         :*:**:*:**** *. . :* :*:*:*:*   :******* ref YP_001125206.1|    DGITALKEIKKIDSNAKVIMCSAMGQQAMVIDAIQAGAKDFVVKPFQADRVIEAINKTL-
ref ZP_01696550.1|     DGISALKEIKKIDPDAKVIMCSAMGQQAMVIDAIQAGAKDFIVKPFQADRVIEAIQKTL-
ref ZP_01860990.1|     DGIAALKEIKSLDANAKIIMCSAMGQQAMVIDAIQAGAKDFIVKPFQADRVIEAIQKAL-
ref NP_243310.1|       DGIAALKDIRAIDPNAKVIMCSAMGQQAMVIDAIQAGAKDFIVKPFQADRVIDAIQKTL-
RAAC02876              DGIEAIKRIRQIDPNARIIVCSAMGQQAMVIEAIQAGAKDFIVKPFQADRVVEAVQKALR
ref YP_001410204.1|    NGIDAIKEIKKFDPNATVIVCSAMGQQAMVIEAIQAGAKDFIVKPFQAARVIEAIQKVLK
                       :** *:* *: .*..* .*:***********:*******.****** **.:*:.*.*
```

FIG 153

```
ref|ZP_01696550.1|      ----------------IEKYKEHRPDLVTMDITMPEVDGISALKEIKKIDPDAKVIMCSA
ref|NP_243310.1|        ----------------VEKYKELSPDLVTMDITMPEKDGIAALKDIRAIDPNAKVIMCSA
ref|ZP_01725653.1|      ----------------VEKYNELKPDLVTMDITMPEMDGIAALKAIKGSDPSATVIMCSA
ref|YP_753552.1|        ----------------IEKYKELKPDLVTMDITMPEMDGIAAVKEIKAVDPAARIIMCSA
ref|YP_001559801.1|     ----------------VERYNETKPDLVMMDITMPEMDGIQALKKIKSVDPNATVIMCSA
RAAC00987               MKLSMKLPTVTKQWSVIRRYQECKPDLVTMDLTMPNVDGIQAIKKIRAIDPDA-------
                                        :.:*:*  **  :*: * *:* *:   ** * ref|ZP_01696550.1|      MGQQAMVIDAIQAGAKDFIVKPFQADRVIEAIQKTL-
ref|NP_243310.1|        MGQQAMVIDAIQAGAKDFIVKPFQADRVIDAIQKTL-
ref|ZP_01725653.1|      MGQQAMVIDAIQAGAKDFIVKPFQADRVIEAIQKAL-
ref|YP_753552.1|        MGQQAMVIDAIQAGAKDFIVKPFQPERVIEAVSKAL-
ref|YP_001559801.1|     MGQQAMVIESIQSGAKDFIVKPFQADRVLEAVKKAI-
RAAC00987               -------------------KPFQIDRVISAVDKALN
                                           ****  :**:.*:.*::
```

FIG. 154A

```
ref YP_148131.1|        ----SVVGKLWFTILLLVSCVLFILSILLIKFLEDYYVQEAENDLTRLATKVAEVMHDYR
ref YP_001126300.1|     ----SVVGKLWFTILLLVSCVLFILTILLIKFFEEYYVQEAENDLTRLATKVAEVMHDYR
ref NP_390192.1|        ----SVVGKLWFTILSLVLIVLFILTVLLLEFIENYHVEEAENDLTQLANKVAVILENHE
ref YP_001487274.1|     ----SVVGKLWLTILFLVLIVLSILTVLLLEFIENYHVEEAKSDLTQMANKVAVILESHD
ref YP_079616.1|        ----SVVGKLWFTILLLVSFVLFILTFFLLEFIENYHVDEAEADLTKLASKVAVIMENHK
RAAC02162               MIPNSIVAKMWLTIVGMVFVIQALLSVLLQQVFNKYIVTREEASLTQLALTIESVLATAT
                            *:*.*:*:**: :*   :  :*:..:* :.::.* * .: .**::* .: ::

ref YP_148131.1|        DEQLARSIAWTLVDNRTKAVIVADESHYWYSPGDAG-LDNMPLSSIRQDRDLRRVLTDGK
ref YP_001126300.1|     DEQLARSIAWTLVDNRSKAIIVADESHYWYSPGEAD-LKDMPLSSIREDSDLRRVLTDQE
ref NP_390192.1|        DQALARSITWELADNLTSIAIIQDEKNHWYSPNDKNRLSSITVEQIQHDKDLNKALKDHK
ref YP_001487274.1|     DQSLARSITSELADKLTSIAIIQEDGLEWYSSEKDGKLPAITKKQIEADSDLNQALKDRK
ref YP_079616.1|        DQETARSITWELADELTSIAVIKNENEYWYSPREHQKVASITLKDIKNDPDLNEALRKHQ
RAAC02162               DRSIKEQVASDIAKRVERATVVYGIP---YTANAALKAAYDAMTPAER-----QALSRGQ
                        *.      ..::    :... :       *:.          .       ..*   :

ref YP_148131.1|        TMKKRLYMPERHPKEKLPRDMIIVGVPMSMPDGSRGAVFIYQSLEAIADATERTKELIFL
ref YP_001126300.1|     TVKKRLYATEWEQNGKPQHDMIIVGVPMSMPDGSRGAVFIYQSLEAIADATEHTKELIFL
ref NP_390192.1|        KVSKRTGLSDTDTDNE----RLIVGVPYEK-DGKKGMVPLSQSLLAVKDTTKHTTRYIFL
ref YP_001487274.1|     KISKRAEPNAGNHKDE----RIVVGVPFEA-NGKKGMVPLSQSLLAVEQTTKHTTRYIFL
ref YP_079616.1|        KVQKRTVIS--NQKND----QLIVGVPYGK-GEDEGMVFLSQSLLAVKDTTQHTTRYILF
RAAC02162               PVTLRGALGKVNRLTV------YVQIPSAR-SPQPGMLAVSQDTSVLDEPLREIRNMVLF
                          :  *    .         * :*     ..  * :   :*.  .:  ..  . .:::

ref YP_148131.1|        AAFIAIVMTTFFAFFLSTRITAPLRKMRQAAFEMARGHFDMKVPILTNDEIGGLAMAFNQ
ref YP_001126300.1|     AAFIAIVMTTFFAFFLSTRITAPLRKMRQAAFEVARGHFDTKVPILTNDEIGGLAMAFNQ
ref NP_390192.1|        AAGIAIVLTTFFAFFLSSRVTYPLRKMREGAQDLAKGKFDTKIPILTQDEIGELATAFNQ
ref YP_001487274.1|     AAGIAIVLTTIFAFFLSTRVTYPLRKMKEGAQDLAKGKFDTKIPILTQDEIGELAIAFNQ
ref YP_079616.1|        AAAIAIVLTTIFAFFLSSRITYPLRKMRQGAQDLAKGKFDTKIPILTQDEIGELAIAFNQ
RAAC02162               DTVLGVILATGFAFVISKNLSRPLVDMTRAAEEMARGHYRQRVRVVTKDEVGRLGHTFNA
                           :.::::* ***.:*..:: ** .* ..* ::*:*::  ::  ::*:**:* *. :**

ref YP_148131.1|        MGRRLQFNINALNQEKEQLASILSSMADGVITFNRDGEILITNPPAERFLQAWYFEQGND
ref YP_001126300.1|     MGRRLQFNINALNQEKEQLASILSSMADGVITFSREGEILITNPPAERFLQAWYFEQGND
ref NP_390192.1|        MGRQLNFHINALNQEKEQLSNILSSMADGVITINIDGTILVTNPPAERFLQAWYYEQNMN
ref YP_001487274.1|     MGKQLTFHITALNQEKEHLSNILSSMADGVITINIDGTILMTNPPAERFLQAWYYEQNMK
ref YP_079616.1|        MGRQLKFHITALNQEKEHLSNILSSMADGVITINIDGTILVTNPPAERFLQAWYYEQNMN
RAAC02162               LARQLAETIEQLSMEREGLQRILSSLQDGVVATDLDGRVVLANPPAKRHLRHLSVAERGI
                        :.::*    *  *.:*  *    ****:  ***:: . .*   :::*****:*.*:    :

ref YP_148131.1|        AEAMAPLPPQVKELFARVVREEKEQSTEVTLQGRTWVILMTPLYGK--TMVRGAVAVLRD
ref YP_001126300.1|     AETMAPLPPQVKELFARVVREEKEQSTEVTIQGRTWVILMTPLYGK--TMVRGAVAVLRD
ref NP_390192.1|        IKEGDNLPPEAKELFQNAVSTEKEQMIEMTLQGRSWVLLMSPLYAE--SHVRGAVAVLRD
ref YP_001487274.1|     IKDGDELPPEARELFHTAVSTEKEQMIEVTLQGRTWVLLMSPLYNQQD--VRGAVAVLRD
ref YP_079616.1|        VKEGHELPPEARELFQNTVSTEKEQMIEMTLQGRTWVLLMSPLYNQ--SHVRGAVAVLRD
RAAC02162               VDE-ERLPDRLMSLWVRVREQQDAVYREDTWDGRTIGITMLPLYETDGTTLRGALCVLRD
                          .   **  . .*:.  .   :.   * * :**:  : * *         :*:.**** ref YP_148131.1|        MTEERRLDKLRKDFIANVSHELRTPIAMLQGYSEAIIDDIAASEKEKKEMAKVIYDESLR
ref YP_001126300.1|     MTEERRLDKLRKDFIANVSHELRTPIAMLQGYSEAIIDDIAASEEEKKEMAKVIYDESLR
ref NP_390192.1|        MTEERRLDKLREDFIANVSHELRTPISMLQGYSEAIVDDIASSEDRKEIAQIIYDESLR
ref YP_001487274.1|     MTEERRLDKLRKDFIANVSHELRTPIAMLQGYSEAIIDDIAGSEEEKKEIAQIIYDESLR
ref YP_079616.1|        MTEERRLDKLRKDFIANVSHELRTPISMLQGYSEAIVDDIASSEEEKKEIAQVIYDESLR
RAAC02162               ITEERRLDRLRKDFIANVSHELRTPLSMLQGYTEALLDDISDDPDMRRELTEIIHDETLR
                        :********:**:************ .*****:**:.**: . .  ::*:::.*:**:**
```

FIG. 154B

```
ref|YP_148131.1|         MGRLVNDLLDLARMEAGHIELEYEQVKLVPYIERVIRKFYGLAK-EKQIELTAEFRDRDI
ref|YP_001126300.1|      MGRLVNDLLDLARMEAGHIELQYEQVELVPYVERVIRKFYGLAK-EKQIELTAEFRDENI
ref|NP_390192.1|         MGRLVNDLLDLARMESGHTGLHYEKINVNEFLEKIIRKFSGVAKEK-NIALDHDISLTEE
ref|YP_001487274.1|      MGRLVNDLLDLARMEAGHITLNLESTDTEELTEKIYRKFLGIAKEK-QVDLTYDIQV-DE
ref|YP_079616.1|         MGRLVNDLLDLARMEAGHISLNVEPVELREFFERVFRKFYGVAGDK-NITLSHNLDLHEA
RAAC02162                MKRLVNDLLNLAQLESGQFKLHFARVDLTQVMRRVARKFQALASDE--DHLTFEVSIPDH
                         * *******:**::*:*:  *.    .   .::.***..:.*   :    *  :.   :

ref|YP_148131.1|         EIAL--DPDRIEQVLTNLIDNAIRHTESGGTVRLIIEPSGDGVTIHVQDSGSGIPEEDLP
ref|YP_001126300.1|      EIAF--DPDRIEQVLTNLIDNAIRHTEAGGTVRLIIERSGDGVTIHVQDSGSGIPEEDLP
ref|NP_390192.1|         EFMF--DEDKMEQVFTNLIDNALRHTSAGGSVSISVHSVKDGLKIDIKDSGSGIPEEDLP
ref|YP_001487274.1|      PHFV-LDPDKMEQVFTNLIDNAIRHTPEGGEVHFSVQSVESGLKMDVKDSGSGIPEEDLP
ref|YP_079616.1|         KFVF--DPDKMEQVLTNLIDNAIRHTNAGGTVHVDVQSAESGLKIAVKDSGSGIPEEDLP
RAAC02162                PVMVDGDEDRLEQVFTNLLDNAFRHTAQG-TIRFELDIRHDYAYVRVADTGSGIPEEDVP
                         .  * *::*:*:*:*  *   : . :.   .  : : *:********:* ref|YP_148131.1|         FVFERFYKADKARTRGRSGTGLGLAIAKNIVEAHKGLITVHSKLNEGTTFSFYLPARGP-
ref|YP_001126300.1|      FVFERFYKADKARTRGRSGTGLGLAIAKNIVETHKGRITVHSKLNEGTTFSFYLPAHGPK
ref|NP_390192.1|         FIFERFYKADKARTRGRAGTGLGLAIVKNIVEAHNGSITVHSRIDKGTTFSFYIP-----
ref|YP_001487274.1|      FIFERFYKADKARTRGRSGTGLGLAIVKNIVEAHQGSIHAHSKAGTGTHFTFYIP-----
ref|YP_079616.1|         FIFERFYKADKARTRGKGGTGLGLAIVKNIVDAHNGSITVHSMLNEGTSFTFYIPRNKQD
RAAC02162                YIFERFYKADKARTRSRSGTGLGLAIARQLVIEHRGEILVESHLGEGTTFTVVLPLASPN
                         :.**********..::.******.::.:*   *.*.*  ..*   ** *:.  :* ref|YP_148131.1|         ---------
ref|YP_001126300.1|      E--------
ref|NP_390192.1|         ---------
ref|YP_001487274.1|      ---------
ref|YP_079616.1|         D--------
RAAC02162                DHGEGESVS
```

FIG. 155

```
ref|YP_955166.1|        -------ILGYLGPNWFASVMGTGIVATAGASLPVHVPGLRGFALVVWVLSALWLLVLIF
ref|YP_001133548.1      ---DRPSILGYLGPNWFASVMGTGIVATAGASLPVHMPGLRGFATAVWVLSALWLVVLIL
ref|YP_907563.1|        -----VEVLGNIGPNWFASVMGTGIVAVAGATLPVHVVGLRAFTQVVWVIAAALLLALIV
ref|ZP_00997175.1|      ------------GPNWFAAVMGTGIVANAVATLPVQVPGLLAFARVVWALDVLLLALILA
ref|YP_829143.1|        --------------NWFASIMGTGIVATAAATLPLQFPGLRTGATVVWALASMLLILLTT
RAAC00012               MGGDGMHIIRQFGVNWFTTVMGIGIVAALTYTSPIHLPFQHAVGEILFIGVNVVFVFAFA
                                      ***::***  ****    :  *::.          ::        :

ref|YP_955166.1|        ATFAHWLRNPVVARSHVRNPQMAHFYGAAPMALLTVGSGALLVGRDLIGERAAVDLAWVL
ref|YP_001133548.1      AMLAHWLRNPTVARGHVRNPTMAHFYGAAPMALLTVGSGALLVGEDLIGARLAVDLAWAL
ref|YP_907563.1|        LVGGHWLRHPTVARSHARNPQMAHFYGAAPMALMTVGADAVLAGGPLIGERLAVDLDWVL
ref|ZP_00997175.1|      ATAVHWVQHHDTARSHLDHPVMSHFYGAPAMALMTVGAGALLVGQPVVGRSVAIDMASAL
ref|YP_829143.1|        ATVVHWIRHRETAQSHHSHPVMAHFYGAPPMALLTVGAGTLLLGKDVLGEQLALGIDTVL
RAAC00012               MWILRWLLTPDAAIDDFRHPGRALFYGAFAMGINVVGNDYFLIGTHMMPKHTAIAISFAI
                         :*:     .*  ..   :*    :  ****  .*.: .**  . .* *  ::     *: :  .:

ref|YP_955166.1|        WTTGTLGALFTAMTIPYLMFTQYRVEPDAAFGGWLMPVVPPMVAAATGSLLIPHMAEGPG
ref|YP_001133548.1      WVAGTLGGLFTAMTIPYLMFTQYRVEPDAAFGGWLMPVVPPMVAAATGSLLIPHMAEGVG
ref|YP_907563.1|        WTAGTIGGLFTAVSIPFLMFTQHRVEPDAAFGGWLMPVVPPMVSAATGALLLPHMPAGSG
ref|ZP_00997175.1|      WVSGTLLGLWTAVAVPVKAFTTHEVAPDAAFGGWLMPVVPPMVSAATGPLLLPHLPAGQW
ref|YP_829143.1|        WVAGTVLGLASAVAVPYLQFTRHQVTQDSAFGGWLMPVVPPMVSASTGALLLPYVPAGQA
RAAC00012               WLAGVAASVFSVIVVPYLLFTEHKVERDETVASWLIPLVPPIVAAATGTNLIPYAG-GPG
                        *  *.    .:  :.:   :*      **   :.*     *  :...**:*:***:*:*:**.  *:*:  * ref|YP_955166.1|        -RATMLYGCYAMFGLSLVASLIIITMVWSRLAHYGTSGTARVPTLWIVLGPLGQSI-TVA
ref|YP_001133548.1      -RATMLYGCYAMFGLSLVASLIIITMVWSRLAHFGTSGTARVPTLWIVLGPLGQSI-TVA
ref|YP_907563.1|        -RETMLYGCYAMFGLSFVASLNIIAMIWSRLVLYGTSGTARVPTLWIVLGPLGQSI-TAA
ref|ZP_00997175.1|      -QLAMQLACTMMFGLTLVASLIVITLIWGRLVHHKVGASAAVPTLWIVLGPLGQSV-TAA
ref|YP_829143.1|        -RLSLLMGCYAMFGLSLLASIIITTLIWNRLAGHKIGAAAAVPTLWIVLGPLGQSI-TAA
RAAC00012               AQFSMTAGIVALFGMTFFLFIMTSALVYSRLVFHRRLSGQEAPTLWIEIGPIGMAMGTFC
                         : ::     .  :**::. :   :  :::.**. .    .***** :**:*  ::  * .

ref|YP_955166.1|        GL-LGTDAAL-AVDA-----RLADGMAVFAVLYGVPVWGFAVLWI---ALAAALT---VR
ref|YP_001133548.1      GL-LGTDAAL-AVDEN----LADGMRVFAVLYGVPVWGFAVLWI---GLATALT---VR
ref|YP_907563.1|        GL-LGAAAATGAVDHE-----LAETMQAFAIIFGVPVWGFAMLWI---ALSTALT---VR
ref|ZP_00997175.1|      HT-LGVAAPTVLPEP------FGSAFTAMGLVFGLPMWGFAMLW---LAIAATVT---LR
ref|YP_829143.1|        NL-LGGNAHLAVSGT------LAQAMEALGVLYGVPVLGFALMW---AALATAIT---IR
RAAC00012               GIPLNAPHVFGPYFG---------GLRDLGAVFSIAMWGVGVWWILLSALYTFLH---LT
                          *.              :  :. ::.:.: *..: *      .:  :    :

ref|YP_955166.1|        TLR---RGMPFALTWWSLTFPVGTFVTGTAQLALHTGL--PAFRYAAAVAYLGLLCTWL-
ref|YP_001133548.1      TLR---RGMPFALTWWSLTFPVGTFVTGTTQLAVHTSL--PAFRYAAAIAYIGLLCTWL-
ref|YP_907563.1|        TLR---RGMPFALTWWSLTFPVGTFVTGTSQLALHTHL--PAFRVAAAAAYAGLLATWV-
ref|ZP_00997175.1|      TAR---SGLPFTLGWWSFTFPAGTVVTGTSGLAAATGA--TFLQFTALALYAGLVLAWA-
ref|YP_829143.1|        TAR---RGLPFSLTWWSFTFPIGTCVTGLTGLAAHTHL--AVFDAMAVAGYTLLVAAWI-
RAAC00012               PKG---DGLPFHLGWWSYVFPIGSFTNGTYALHRLLGH-----PFFAVAGLVQLGILWLC
                         .  *:** * * . *: ..*   *       *    *     * ref|YP_955166.1|        --LVAVRTVRG--GLRGGL-----------------
ref|YP_001133548.1      --LVAVRTLRV--GIGRG------------------
ref|YP_907563.1|        --LVAIRTVRG--SLRGNLL----------------
ref|ZP_00997175.1|      --TVAFRTARG--AWDGRLLR---------------
ref|YP_829143.1|        --IVAARTFHGS-ILQGTLFQ---------------
RAAC00012               FAIVIVRTVHG--VAAGHLIQWRRDHAHRHELKARRA
```

FIG. 156A

```
emb|CAG29823.1|      MTGGEVIRPT GGSGRRGRLR VFIGAAPGVG KTYTMLREAR RLREEGTDVV IGWVETHGRP
ref|NP_923516.1|     ---------- -----RGRLK LYLGYTPGVG KTVRMLQEAR RLRRRGVDLV VGWVETHGRP
ref|ZP_02329377.1|   ---------- -----RGRLK IYLGAVSGSG KTYHMLREAQ SLKENGIDVV LCAVSTLNRP
ref|ZP_02329377.1|   ---------- ----RRGVFK VYIGAAPGVG KTYMLREGN DLARMGIDVI VGLLETHGRR
ref|ZP_02329377.1|   ---------- -----GRLK IYLGAVSGSG KTYHMLREAQ SLKENGIDVV LCAVSTLNRP
RAAC02761            MTGGEVIRPT GGSGRRGRLR VFIGAAPGVG KTYTMLREAR RLREEGTDVV IGWVETHGRP
Clustal Consensus                      *  ::  :::* ..* *    :*..  *  .  *::  :  :.* .* emb|CAG29823.1|      ATEKLLEGLE VIPPRVLKVG QATFEEPDLD AIVARRPEVC VIDELAHTNP PGAMHEKRYE
ref|NP_923516.1|     DTEALLADLE VMAPRQVAYQ GVIIPELDLE AILQRRPATV LIDELAHTNA PGSRHRKRYE
ref|ZP_02329377.1|   ETARQASGLE TIPSIDWTKD GVIQQDLNLV ALVERNPEVV LVDGLAHRNR QGALFPTRLG
ref|ZP_02329377.1|   ETAEQLGNLG MIPRRKIDYR GTTLEEMDTD AIIERAPDVV LVDELAHTNV PGSRHNKRFE
ref|ZP_02329377.1|   ETARQASGLE TIPSIDWTKD GVIQQDLNLV ALVERNPEVV LVDGLAHRNR QGALFPTRLG
RAAC02761            ATEKLLEGLE VIPPRVLKVG QATFEEPDLD AIVARRPEVC VIDELAHTNP PGAMHEKRYE
Clustal Consensus     *        .*            :         :   :   *::  *  *    ::* *** *     *:  . .* emb|CAG29823.1|      DVMYLLDRGI SVMTAFNIQH LESVRDEVQQ QLGIRVREVV PEWFLREADE VTVIDVTPET
ref|NP_923516.1|     DVEVLLDAGV SVMSAMNIQH LESVAEAAGR LIGAVVHETV PDRLLRSAEE VQLVDASPEA
ref|ZP_02329377.1|   DISFLLEKGI SVITTVNVYE LEGVRELARK LAGVEVKTIV PSGTLEMADE VRLIDVTPET
ref|ZP_02329377.1|   DVLDILNAGI SVITTVNVQH LESLNDAVEQ ITGVRVRETV PDSILWMADE VELIDVPPQT
ref|ZP_02329377.1|   DISFLLEKGI SVITTVNVYE LEGVRELARK LAGVEVKTIV PSGTLEMADE VRLIDVTPET
RAAC02761            DVMYLLDRGI SVMTAFNIQH LESVRDEVQQ QLGIRVREVV PEWFLREADE VTVIDVTPET
Clustal Consensus    *:  :*: *: **:::.*: .**.:  . .   *  *:  .*  *.  * *:* * ::*..*::

emb|CAG29823.1|      LRQRLRDGEI YPPEKVDAAL QNFFRVDRLA WLRQMSLRAV ADDVDERLEH SYERRAIPGP
ref|NP_923516.1|     VLERLQRG-- -DAARYIPPG SPFLRRSTLV YLRELALRAV AEVVDADILS --GKNGVAGP
ref|ZP_02329377.1|   ILKRLEEGNL P-----GQKE HHLFLKGNIG VLRELALRLV AEDVNGSLEK YRKSKGLSGP
ref|ZP_02329377.1|   LRQRMKEGRI YSMEKVEQAL GHFFKIGNLI ALRELALREI ADDVDERLES WERKESLRGP
ref|ZP_02329377.1|   ILKRLEEGNL P-----GQKE HHLFLKGNIG VLRELALRLV AEDVNGSLEK YRKSKGLSGP
RAAC02761            LRQRLRDGEI YPPEKVDAAL QNFFRVDRLA WLRQMSLRAV ADDVDERLEH SYERRAIPGP
Clustal Consensus    :  :*:.  *              ::   . :   **:::**   :  *:   *:            ...:  **

emb|CAG29823.1|      VGAKEVVLVC VSHPDRAATL IERGRRMAMR MKGDLHVVYA AETDEDRMTE RARAEVDELR
ref|NP_923516.1|     AGVRERVLAA VSTNPASARI IRRGARIAER LDAELFVAYV ETG--RPLAP PEAQTLQEHR
ref|ZP_02329377.1|   SGAGERILVS TQYHWNGSIY VRRGQQIANR LNGDLYVICF QHTG-KPLSK EQAAFKRSLK
ref|ZP_02329377.1|   WRREETIFVC VKLNDHAERI IRRGFRIAFR LKARWHVAYL HHG----SGM EDEARLKELK
ref|ZP_02329377.1|   SGAGERILVS TQYHWNGSIY VRRGQQIANR LNGDLYVICF QHTG-KPLSK EQAAFKRSLK
RAAC02761            VGAKEVVLVC VSHPDRAATL IERGRRMAMR MKGDLHVVYA AETDEDRMTE RARAEVDELR
Clustal Consensus                 *  ::.. ..   .        :.** ::* *  :..   .*                              . :

emb|CAG29823.1|      RLAEFEGAEW VLEP-KRDRP VGEVILRVAR RVNATQVVLG QPRKGASPRR LMAWHHPVQY
ref|NP_923516.1|     AATEAAAGEF VQLQ-NRD-- VAGALIDFAL QKNITQVIVG ESLR--SPAE ELVRGSVINT
ref|ZP_02329377.1|   KLVDKIGAVF VELPFPGRRK LADSLLDYAM KNSVTRIVLG HSKH--TRIQ ELWQGSIIND
ref|ZP_02329377.1|   GLTERLGGSF EVITGQGKKD PADLLLAKAN EYNSTQMILG KSCS--PSWR DRWQGSLVKR
ref|ZP_02329377.1|   KLVDKIGAVF VELPFPGRRK LADSLLDYAM KNSVTRIVLG HSKH--TRIQ ELWQGSIIND
RAAC02761            RLAEFEGAEW VLEP-KRDRP VGEVILRVAR RVNATQVVLG QPRKGASPRR LMAWHHPVQY
Clustal Consensus      .:   ..  :          .      :   *       . . :*::::*  ..                      ::

emb|CAG29823.1|      LLKHLQYVDL RVVG------ ------WRPL SPAAREQRNW ASERVVRE-- RKLP--GKLT
ref|NP_923516.1|     LLRTTSNIDV LIVGE----- -AESSMVGPL TPVAQPPFA VGCLLVGADS RRAHGCGRHK
ref|ZP_02329377.1|   ILRKMTRTDL FVVADRAERD GERILPAKRK VGTKKAELYR RHSKQEMQKE IEKIRRGVFK
ref|ZP_02329377.1|   LLRGARHMDV LVV------- ---------- ---------- ---------- ----------
ref|ZP_02329377.1|   ILRKMTRTDL FVVA------ ---------- ---------- ---------- ----------
RAAC02761            LLKHLQYVDL RVVG------ ------WRPL SPAAREQRNW ASERVVRE-- RKLP--GKLT
Clustal Consensus    :*:       *:   :*
```

FIG. 156B

```
emb|CAG29823.1|       LYIGAAPGVG KTYRMLQDAE DWKVRGIDVV IGLIETHGRP ETEAQIGDLE RIPKRRIEYG
ref|NP_923516.1|      IYLGAAPGVG KTFAMLQEAE HLEASGIDVV CGVIETHGRA ETAALIENLE VVPKRAIGYQ
ref|ZP_02329377.1|    VYIGAAPGVG KTYTMLREGN DLARMGIDVI VGLLETHGRR ETAEQLGNLG MIPRRKIDYR
ref|ZP_02329377.1|    ---------- ---------- ---------- ---------- ---------- ----------
ref|ZP_02329377.1|    ---------- ---------- ---------- ---------- ---------- ----------
RAAC02761             LYIGAAPGVG KTYRMLQDAE DWKVRGIDVV IGLIETHGRP ETEAQIGDLE RIPKRRIEYG
Clustal Consensus emb|CAG29823.1|       GKVYEEPDLA AILARRPQVV LMDELAHTNA PGSMFKKRYQ DILYLLEHGV DVVSAVNVQH
ref|NP_923516.1|      GRTFLELDVE AVLRRRPAVV LVDELAHTNI AGAGNTKRFQ DVEVLLGAGI DVVSTLNIQH
ref|ZP_02329377.1|    GTTLEEMDTD AIIERAPDVV LVDELAHTNV PGSRHNKRFE DVLDILNAGI SVITTVNVQH
ref|ZP_02329377.1|    ---------- ---------- ---------- ---------- ---------- ----------
ref|ZP_02329377.1|    ---------- ---------- ---------- ---------- ---------- ----------
RAAC02761             GKVYEEPDLA AILARRPQVV LMDELAHTNA PGSMFKKRYQ DILYLLEHGV DVVSAVNVQH
Clustal Consensus emb|CAG29823.1|       LESLKDRVEH ITGATIRERV PDWFVKLASE VKLIDVSPET LVERLLEGKI YPPEKVEQAL
ref|NP_923516.1|      LESLNTLVER TTGVKVRETL PDLVVEAADE VVLVDLPTGE LTQRLREGKI YAQAKVEQAL
ref|ZP_02329377.1|    LESLNDAVEQ ITGVRVRETV PDSILWMADE VELIDVPPQT LRQRMKEGRI YSMEKVEQAL
ref|ZP_02329377.1|    ---------- ---------- ---------- ---------- ---------- ----------
ref|ZP_02329377.1|    ---------- ---------- ---------- ---------- ---------- ----------
RAAC02761             LESLKDRVEH ITGATIRERV PDWFVKLASE VKLIDVSPET LVERLLEGKI YPPEKVEQAL
Clustal Consensus emb|CAG29823.1|       SNFFQLAHLA ALREIALREV ADVVDGRLAP PPPADPE--- -----RILVC VNYRPHSEAL
ref|NP_923516.1|      ANFFRPENLS ALRELALREV ADDCTTRKLE EAAHGPGG-- -----RVLVC INLRPNAEQL
ref|ZP_02329377.1|    GEFFKIGNLI ALRELALREI ADDVDERLES WERKESLRGP WRREETIFVC VKLNDHAERI
ref|ZP_02329377.1|    ---------- ---------- ---------- ---------- ---------- ----------
ref|ZP_02329377.1|    ---------- ---------- ---------- ---------- ---------- ----------
RAAC02761             SNFFQLAHLA ALREIALREV ADVVDGRLAP PPPADPE--- -----RILVC VNYRPHSEAL
Clustal Consensus emb|CAG29823.1|       IRRGWRIADR LQAKLYVLVV QTEFPLSSQS ERDFAAVRDL AEQFGAEFLL RPALHKSVGQ
ref|NP_923516.1|      IRRGARIASR LSAPLVVAEI GAED--DGPT ARAVERLGEL TRQLGGEFIE RPAAANQVPE
ref|ZP_02329377.1|    IRRGFRIAFR LKARWHVAYL HHGSGMEDEA RLKELKGLTE RLGGSFEVIT GQGKKDPADL
ref|ZP_02329377.1|    ---------- ---------- ---------- ---------- ---------- ----------
ref|ZP_02329377.1|    ---------- ---------- ---------- ---------- ---------- ----------
RAAC02761             IRRGWRIADR LQAKLYVLVV QTEFPLSSQS ERDFAAVRDL AEQFGAEFLL RPALHKSVGQ
Clustal Consensus emb|CAG29823.1|       VIVETAESES VSQIVMGQPL NRGLGARFAH RPITYVLNRA EFVDLHIVAY AGRWSQPSA
ref|NP_923516.1|      QIDALAEEQG VTILVMGESR RSRWEKLLHG CVIEQVVRRV RNLDVLIV-- ---------
ref|ZP_02329377.1|    LLAKANEYNS TQMILGKSCS PSWRDRWQGS LVKRLLRGAR HMDVLVV--- ---------
ref|ZP_02329377.1|    ---------- ---------- ---------- ---------- ---------- ---------
ref|ZP_02329377.1|    ---------- ---------- ---------- ---------- ---------- ---------
RAAC02761             VIVETAESES VSQIVMGQPL NRGLGARFAH RPITYVLNRA EFVDLHIVAY AGRWSQPSA
Clustal Consensus
```

FIG. 157

```
ref|YP_897521.1|        MEGKILIVDDQYGIRVLLHEVFQKEGYQTFQAANGFQALDIVKKDNPDLVVLDMKIPGMD
ref|ZP_00744427.1|      MEGKILIVDDQYGIRVLLHEVFQKEGYQTFQAANGFQALDIVKKDNPDLVVLDMKIPGMD
ref|YP_001647908.1|     MEGKILIVDDQYGIRVLLHEVFQKEGYQTFQAANGFQALDIVKKDNPDLVVLDMKIPGMD
ref|YP_001377039.1|     MEGKILIVDDQYGIRVLLHEVFQKEGYQTFQAANGFQALDIVKKDNPDLVILDMKIPGMD
ref|NP_244654.1|        ---KILVVDDQYGIRVLLNEILQKDGYQMFQAANGIQALAIVEEETPDLVLLDMKIPGMD
RAAC00477               MAYKVLVVDDQFGIRVLLHEVLQREGYEVFQASNGPSALSIVEREQPDLVLLDMKIPGMD
                           *:**:****:*::*::: *: . :.: :******* ref|YP_897521.1|        GIEILKHVKEIDESIKVILMTAYGELDMIQEAKDLGALMHFAKPFDIDEIRQAVRNELAV
ref|ZP_00744427.1|      GIEILKHVKEIDESIKVILMTAYGELDMIQEAKDLGALMHFAKPFDIDEIRQAVRNELAV
ref|YP_001647908.1|     GIEILKHVKEIDESIKVILMTAYGELDMIQEAKDLGALMHFAKPFDIDEIRQAVRDQLAV
ref|YP_001377039.1|     GIEILKHVKEINADIKVILMTAYGELDMIQEAKDLGALMHFAKPFDIDEIRQAVRNEI--
ref|NP_244654.1|        GLEILRRIKDMNPNIEVIMMTAYGELNMINEAMQLGAVTHFAKPFDIDDVRAVIAENMKS
RAAC00477               GLEILRNLRKLGVDAKVIMMTAYGELDLIHEAMEMGAVAHFTKPFDIDELRRTVREHLEA
                        *:***:.::.:. . :**:*******::*:** ::**: **:******::* .: :.:

ref|YP_897521.1|        EA---
ref|ZP_00744427.1|      EA---
ref|YP_001647908.1|     EA---
ref|YP_001377039.1|     -----
ref|NP_244654.1|        -----
RAAC00477               RAQAE
```

FIG. 158A

```
ref|YP_848463.1|      MRFFQSVQFKLVIMYLLLIIVAMQVIGAYFVRELEGQLEKNFQNSITNSITLLDYNAREE
ref|ZP_01695448.1|    ---FQSIHFKFVLIYILLIVVAMEIIGVYFINKLENQLETNFKKSIYDQVNVLEYSIEDL
ref|ZP_02169265.1|    ---FKSIHVKIVTIYVLLILIAMQVIGVYFTQQLEDQLVENFYETLDERANLLAYNVQQE
ref|ZP_00539458.1|    ---FKSIQWKLVVIYALLILVAMQVIGVYFVRSLEKQYITNFSKSVEDRAGLVAYNVGKE
ref|NP_694373.1|      ---FRSIQLKFIIIYILLLIIAVQVIGSFFTDRLNEELTRNFKTTVGERVEMLSHNLEQA
RAAC00019             MMRFRSLRVKLVMVYTLLILFAVELIGAYFVQALTSSLVRNQAQTARTQAQLMATLIAPE
                         *:*::  *::  :* **::.*:::**   :*      *      *      :     ::

ref|YP_848463.1|      IIKNSDNSV----KLQNDIRELLVDFSR---ASSNLIEVRIVDEK-GKILGTSNLNNQGI
ref|ZP_01695448.1|    LTKKQNQAA----DITLKVRKVLGDFK-----STDVSEIRLIDAHSGVILGTS-SNDQSI
ref|ZP_02169265.1|    MSRDEDEEE---QSLRVRTDNVLGELFN-----MENAQARVVDQF-SNVVTVTNPEEDIY
ref|ZP_00539458.1|    FDKTGDDEAS-KRQLSESLGQLLSEFSSGSTSRNDILEVQIIDQD-SIIQATSDEDNQSA
ref|NP_694373.1|      FARDRSEESGTIESLEEEIRRIINDINR----GNASTTINVVDNQ-SRVRGTNVLDDQNQ
RAAC00019             LAPGARVSN----SAVSNLLQSVPQFLN--------GTVYVLNQS---GYVMYTTAGGAL
                      :                   . :  ::         :::

ref|YP_848463.1|      VGQKSNDPLVKRTLSLGTTSEDKIYKDESNKNNRVWVNVSSIKNKGEVIGAIYLVADIES
ref|ZP_01695448.1|    VGQKTTEDIVKSVRVTGQP-EDQIYLDKQTG-DRMWVLASPIKANGELIGIIYLVSKIET
ref|ZP_02169265.1|    IGQRTTNFRIIRALG-GSTEEAVLRNENTGHRTRVLAVPVE-TEENQVVGAIYIEASMEE
ref|ZP_00539458.1|    VGQRATNSLIKKAQATSSSRVDTVLDPTTEDKIRIFAVPVTSERTGATTGMIYVRASMES
ref|NP_694373.1|      IGQKLAHPMVRDALLFNSTDDSIFYEKDTDSRVYVYVVKPILGEDN-MAVGAIFYKSSLEE
RAAC00019             VGQKRIDSVATQALLHHTFAQSVRYDP--LSKSHLLAVAVPVTLHGTYLGVLEYVLSIQS
                      :**:                                 :  .          *  :   .::

ref|YP_848463.1|      VYKQVDDITNIFITGTLIAMVITAILGILLSRTITKPIVEMKRQAYAMARGNYSRKVKVY
ref|ZP_01695448.1|    VYRQVQAINQIFMTGTVIAVLVTALLGIITARTISKPLSEIRKQAMAMARGNFARKVKVI
ref|ZP_02169265.1|    IYEQMAQTNQILLTGTMISLVLTAALGIFLSRTITRPIVEMRRQADFLGKGDFSQNVEVY
ref|ZP_00539458.1|    IYSQMQQVTRILATGTVIALVITSILGVLLSRTITRPISDMRRQAIEMRRGNFSRKVKVY
ref|NP_694373.1|      VYGQIEDINNIFLQGSILAITISAIIGILVARTITKPIMEMREQALIMANGDFTQKVNVY
RAAC00019             TYETIHQATTIFYTGSIAVLAIVMILGAIVARALTRPVMEVTRQAEVMARGDFSQRLEAM
                       *   :  .  *:  *::  : :   :*  . :  *::::*:  ::  .**   .  .*:::::.

ref|YP_848463.1|      GVDEIGELADSFNTLTKRVQEAQAMTEGERRKLSSVLAYMTDGVIATDRRGKVILINTPA
ref|ZP_01695448.1|    GNDEIGQLAYSFNHMTKKLQEAQASTEGERRKLDSILTHMTDGVIATDRRGRIILINEPA
ref|ZP_02169265.1|    GDDEIGQLSATFNELTNKLEEAHATTEGERRKLSSVLTHMTDGVIATDREGQIILMNRRA
ref|ZP_00539458.1|    SDDEIGQLARSFNELTDELLEANATTEAERRKLTSVLENMTDGVIATDRTLRVILMNDQA
ref|NP_694373.1|      GRDEIGQLAETFNDLNSRLKHSYATIEEERRKLSSILANMSDGVIATDNDGSVTLMNDAA
RAAC00019             SNDEIGDLVASINHLADELEEAIAANRLEQERLRAVITSMGEGVIVLDSSGQVLMMNRAA
                      . ****:*  ::*  :  ..:  .:    *   .  *:.:*  :::   *  :****. *      :  ::*  * ref|YP_848463.1|      EKML----RVK---HESANGRSIIDVLDIGDSYQFEDLMEVDGSLTMDRSTLDKPYILRA
ref|ZP_01695448.1|    AEML----DVS---RETVLSQPLISVLKIENEHKFDDLLTEQDSVILDFSTEEEPYILRA
ref|ZP_02169265.1|    EELT----GYS---QEEAIGYDLVGMLNLAHFMKLSDLYNMDDPILLDFEHHDEELILEA
ref|ZP_00539458.1|    KDIV----GVD---ESGIVGTNLKDLLALGDDFMIPEDGTMP-PRLLDFSSEDELFLVRA
ref|NP_694373.1|      AKLIGE-------NPEDLIGDSVIDVLHLEGKEIDLSELHSNGSMIIDFSNEDTPFLIRA
RAAC00019             RQMLS----------QAAGGEEEAIRQLELDRLMQG--------DVATGVREVRVIGNT
                       .:         .:            :   :              . :    :  ..:

ref|YP_848463.1|      NFSVI---QRET---GFNNGVIAVLHDITDQEKVDQERRDFVSNVSHELRTPLTSMHSYL
ref|ZP_01695448.1|    NFSVI---QNEA---GFVSGLITVLHDVTEQEKIDMERREFVANVSHELRTPLTTMRSYL
ref|ZP_02169265.1|    NFSVI---EKEN---GRKNGLIAVLHDVTEQERIEQERREFVANVSHELRTPLTSMKSYL
ref|ZP_00539458.1|    FFSPV---KKHS---GPITGMIIVLHDVTEQEQVEQDRREFVANVSHELRTPLTTMRSYL
ref|NP_694373.1|      NFSTVVD-EEEE-----VTGFITVISDVTEQQKMEQERRDFVSNVSHELRTPLTTMKSYL
RAAC00019             IFHVILTSVQRR---GQVDGYVAVVRDVTEQEKLDQARRDFVSNVSHELRTPLTTVKSYL
                       *  :      ..        *  :  *:*:*:::::  **:**:************:::***
```

FIG. 158B

```
ref|YP_848463.1       EALSDGAWEDKEIAPRFLEVTQNET--------ERMIRLVNDLLKLSRMDGGREHLE-KS
ref|ZP_01695448.1|    EALTDGAWKDEKIAPQFLGVTQNET--------ERMIRLVNDLLKLSKMDSKDEHLN-KE
ref|ZP_02169265.1|    EALLDGAVNDSDVAPQFLQVTSNET--------DRMIRLVNDLLQLSKMDARDDHML-MA
ref|ZP_00539458.1|    EALAEGAYQDEELAPRFLETTQNET--------ERMIRLVTDLLQLSKMDSKEYKMN-KV
ref|NP_694373.1       EALSDGAWENKEIAPRFLDVTQKET--------NRMIRMVNDLLQLSKMDSDELPMH-KQ
RAAC00019             EVMRDLGDDEAETKREFLEVIARET--------DRMVRLTRDLLLLSGLDRGGPRSVEMR
                      *.:  :   ..:  .   .  .  .         :**:*:. *   :* ref|YP_848463.1       FVNFTD-FFNHIIDRFEMM-KKETIMFKRHIP-KEPVIIEIDEDKVMQVLDNIISNANKY
ref|ZP_01695448.1|    WVNFVE-FFHHVIDRFEM-AKQQNVTFKRKLP-NTEIFVEIDEDKMTQVLYNIISNALKY
ref|ZP_02169265.1|    EVNIVN-MIHHVIDRFEMSNKQENIQFRRRLPD-VPLSVMGDRDKLVQLLDNMVSNAVKY
ref|ZP_00539458.1|    RFDYIQ-FLNDILDRHDM-TKPERIRFRRKI-MKRKVYIRGDQDKLIQVADNILTNAIKY
ref|NP_694373.1       REEFTS-YLYQVLDRYEMN-KPESIHMEKNIPNTK-AYVWMDRDKITQVLDNVITNAIKY
RAAC00019             AIPVHG-LLEGVVERFQLQAAKQELSRVHLPQRRDVCVYGDEDMVNRVLDNVLSNALKY
                               :   :::*.::          :   :.  .:          :   *.*  :  ::   *:::** **

ref|YP_848463.1       SPDGGRISFYLKKFEDEIEISIADEGLGVPEEDLANVFDRFFRVDKARSREMGGTGLGLA
ref|ZP_01695448.1|    SPEGGQITFKLRELNEKIEVSISDQGVGIPKENVKKIFERFYRVDKARSRKLGGTGLGLA
ref|ZP_02169265.1|    SPEGGVITITLKQEKERLIVSVKDEGVGIPKENLPHVFDRFYRVDKARSRSLGGTGLGLA
ref|ZP_00539458.1|    SPEGGTITVRTMLRAKRIVISIKDEGVGIPKANLQKIFERFYRVDKARARKIGGTGLGLS
ref|NP_694373.1       SPDGGKIRVKLDIRRHYLLVSIQDQGMGIAYDKLDKIFERFYRVDKARNRKLGGTGLGLA
RAAC00019             TPPGGRIEVRADVTAQHVTFIISDTGIGIPPEDLPHVFERFYRVEKGRSRRGGGTGLGLA
                      :* ** * .        .  : .: *  *:*:..   .:  ::*:**:**:*.*  *   *******:

ref|YP_848463.1       IAREVIEAHGGRIWAERNKSKGTVIKFTL--------
ref|ZP_01695448.1|    IAKEMVEMHGGSIWASSKEGKGTTIYFTLPYEPAQED
ref|ZP_02169265.1|    IAKEIVEVHGGHIWVSSDWGKGTTFFFSL--------
ref|ZP_00539458.1|    IAKDVVSAHGGDIWAESEWGRGTTIYFTL--------
ref|NP_694373.1       ITKELVEAHHGQIWAQSSEGKGTTILFTL--------
RAAC00019             LAREMVERMGGEIRMESEPQRGTTVYVTLRRAEEDAV
                      ::::::.    * *   .   .    :**.. ..:*
```

FIG. 159

```
ref|ZP_01169692.1      MDKKILVVDDEKPIADILQFNLKKEGYEVHCAYDGNEALEKVEEVKPDLILLDIMLPQRD
ref|ZP_01695449.1      MDKKILVVDDEKPIADILQFNLTKEGYTVYCAYDGEEALEKVEEVQPDLIVLDIMLPKRD
ref|YP_001127497.1|    MEKRILVVDDEKPIADILQFNLQKEGYEVICAYDGEEALQKVEETMPDLILLDIMLPLKD
ref|YP_149327.1|       MEKRILVVDDEKPIADILQFNLQKEGYEVICAYDGEEALQKVEETMPDLILLDIMLPLKD
ref|YP_534941.1|       ----ILVVDDEKPISDIVKFNLTKEGYDVYTAYDGEEALQQVKEVEPDLILLDLMLPKID
RAAC00020              MPAHILVVEDEEPIANILRFALEREGYRVSCAYDGAEALERWRALQPDLILLDVMLPEVD
                           **::**::*::*  *  :***   *  **  *::  .    **::***  * ref|ZP_01169692.1      GMEVCREVRKKYEMPIIMLTAKDSEIDKVLGLELGADDYVTKPFSNRELIARVKANLRRH
ref|ZP_01695449.1      GMEVCREVRKKYNMPIIMVTAKDSEIDKVLGLELGADDYVTKPFSTRELIARVKANLRRH
ref|YP_001127497.1|    GMEVCREVRKKYDMPIIMLTAKDSEIDKVLGLELGADDYVTKPFSTRELLARVKANLRRH
ref|YP_149327.1|       GMEVCREVRKKYDMPIIMLTAKDSEIDKVLGLELGADDYVTKPFSTRELLARVKANLRRH
ref|YP_534941.1|       GLEVAREVRKTHDMPIIMVTAKDSEIDKVLGLELGADDYVTKPFSNRELVARVKANLRRQ
RAAC00020              GFDVLRAIRQASGVPVIILTAKDDEVDKVLGLELGADDYVTKPFSTRELVARVKANLRRA
                       *::* * :*:    :*:*::****.*:*****************::******* ref|ZP_01169692.1      QQIAAKAGEEEETN-EIAIGSLVIHPDAYVVSKRGETIELTHREFELLHYLAKHIGQVMT
ref|ZP_01695449.1      QQTPAAPGEEEESN-EIAIGSLVIHPDAYVVSKRGETIELTHREFELLHYLAKHIGQVMT
ref|YP_001127497.1|    AQTATQEEEESETN-EIVVGPLVIRPDAYVVQKRGETIELTHREFELLHYLAKHIGQVMT
ref|YP_149327.1|       AQTANQEEGENETN-EIVIGPLVIRPDAYVVQKRGETIELTHREFELLHYLAKHIGQVMT
ref|YP_534941.1|       SAVAAKSSAEDDKNSEITVGDLTIHPEAYTVSKNGQRIELTHREFELLHYLAQHLGQVMT
RAAC00020              SDVLR----EHKENERYVVQDLVIDLAEYTVTKAGPIPLTHREFQVLAVLAAHPGRVFT
                         *  . *  . .:   *.*   *.*   *:  *   *****::*   ** * *:*:* ref|ZP_01169692.1      REHLLQTVWGYDYYGDVRTVDVTVRRLREKIEDNPSHPTWIVTRRGVGYYLRN-
ref|ZP_01695449.1      REHLLETVWGYDYYGDVRTVDVTVRRLREKVEDNPSHPEWIVTRRGVGYYLRN-
ref|YP_001127497.1|    REHLLQTVWGYDYYGDVRTVDVTVRRLREKIEDNPSHPSWIVTRRGVGYYLRN-
ref|YP_149327.1|       REHLLQTVWGYDYYGDVRTVDVTVRRLREKIEDNPSHPNWIVTRRGVGYYLRN-
ref|YP_534941.1|       REHLLQTVWGYDYFGDVRTVDVTVRRLREKIEDNPSRPTWLVTRRGVGYYLRN-
RAAC00020              RDQLVDQVWGSDYVGDTRAVDVTIRRLREKLEPDPSQPRYVLTRRGVGYYVRNE
                       *::*:: *** ** **.*:****:******:* :**:*  :::********:**
```

FIG. 160A

```
gb|EDQ48509.1|        ------------------------------------------------------------
gb|EDQ48476.1|        ------------------------------------------------------------
ref|ZP_01575425.1     ------------------------------------------------------------
RAAC01715             MSFGAETGGFGAFLSRTSAKKDKNDGIYDSPARRDSFIMFREKPFSFLVGREGRANVSVR
ref|ZP_02025790.1     ------------------------------------------------------------
ref|YP_001662047.1|   ------------------------------------------------------------ gb|EDQ48509.1|        ------------------------------------------------------------
gb|EDQ48476.1|        ------------------------------------------------------------
ref|ZP_01575425.1     ------------------------------------------------------------
RAAC01715             MPKKTNVSSSLHAIREVRTSWPSVTWDVLQQHPVELDFREVERALDGVRDRQAWLVVVVR
ref|ZP_02025790.1     ------------------------------------------------------------
ref|YP_001662047.1|   ------------------------------------------------------------ gb|EDQ48509.1|        ------------------------------------------------------------
gb|EDQ48476.1|        ------------------------------------------------------------
ref|ZP_01575425.1     ------------------------------------------------------------
RAAC01715             SSRVVPIYPFLAQIQSAGFDCVHLLSCDAAAYVMTLAAHHPERAMEGFESALARLAADRT
ref|ZP_02025790.1     ------------------------------------------------------------
ref|YP_001662047.1|   ------------------------------------------------------------ gb|EDQ48509.1|        ------------------------------------------------------------
gb|EDQ48476.1|        ------------------------------------------------------------
ref|ZP_01575425.1     ------------------------------------------------------------
RAAC01715             LVGVSSACDEREVVRWWQALMEATAASHWNVFESSAYSQGRRELVPLHEEDRTRLITRAV
ref|ZP_02025790.1     ----------KAASEAITALSLNFYSASHIIAFSRDYIANRNIFPVDISVRLHEYETAI
ref|YP_001662047.1|   ------------------------------------------------------------ gb|EDQ48509.1|        ----------VLECVRQCFERLKEQRAGTGTIVRVCSQLEDMACREVQEYREIRGKEAR-
gb|EDQ48476.1|        ------------------------------------------------------------
ref|ZP_01575425.1     ------------------------------------------------------------
RAAC01715             TQLGDRGYEGIASVVEDLFAQLAERPTKLEDVAELCAQFIMAAVGQRQADGRDRMLQVP-
ref|ZP_02025790.1     LQLN---FKAAKDVVSTLFSNLQSNFTDEASVKNICTQIYLISYRLVMSTYNLPMDEKYV
ref|YP_001662047.1|   ------------------------------------------------------------ gb|EDQ48509.1|        --ARLETQLR----ACMSFSDMEDCFVEAFRSAL---EKVYGLRSEMGGKAVEIVKRWIA
gb|EDQ48476.1|        ---ALR-----------------LIEARDDEK---------KEHTNQVVSRLNRYVE
ref|ZP_01575425.1     -------------------------------------------------INQVRKTIE
RAAC01715             --ISTRQWLRFVAEECPKWWDWRDKLKQALMVVL----GREEAVRTAHSAQIGQVIEIIE
ref|ZP_02025790.1     KMLTESSDIFQLKSIVSDMIN---DLQIQLTQSVK----------KYSSFIEESLNYIK
ref|YP_001662047.1|   -------------------------------------------------IDEAIKLIQ
                                                                          :    . :

gb|EDQ48509.1|        EHY--SEHAELNTLAAMVYLTPSYLSKLFKQETGLTLTEYITDVRLKNAKRLLRTEPNMK
gb|EDQ48476.1|        EHL--DSDLSLTTLSDLVHLNPYYMSRLYKQMTGVNLPDYITDERIKKAKELVV-ESHLK
ref|ZP_01575425.1     ERF--KEQISISTLARDVYLTPTYLCVLFKQVTGTTINDYLTLTRLEKAKK-LLSDPYIK
RAAC01715             RHY--DSDLDVATLASQVFLSPSYLSKRFKSETGMTIREFIVQTRLNKAKDLLLRDFHLK
ref|ZP_02025790.1     EHL--EDDLSLEQIAQHIHINESYFSRTFKKECGNSVISYINNLRINKAKELLATS-NLK
ref|YP_001662047.1|   ENY-SDLNISLNSIAEKLYITPNYLSTLFKSEMGVTFSDYLTACRIEKAKELL-KDVKVK
                       ..    .  .:  ::   :.:.  *:.   :*.  *  .  .::     *:::**   :   . :*
```

FIG. 160B

```
gb|EDQ48509.1|         VHQIGAEVGYADPAYFNKLFKKVVGVTPNEYK-----------------
gb|EDQ48476.1|         MHEICKKVGFESPAYFTRIFKKKTGSTPQEFREK---------------
ref|ZP_01575425.1|     LYDVCYEVGYLSPSYFSRLFKKYTGISPSEYRNVAI--------------
RAAC01715              AYEVGAHVGYPDPTYFNKLFKRQVGLTPKAFRDRAMRQARGFKQEDSRSS
ref|ZP_02025790.1|     TFEISEAVGIHDPAYFSVLFKKNTGMSPKAYRDQ---------------
ref|YP_001662047.1|    IYEVAEAVGYTDQHYFSKVFKNITGFTPKEYREKIL-------------
                        .::    **    .  **. :**. .* :*.  ::
```

FIG. 161A

```
ref|NP_844784.1|        ------------------------------------------------------------
ref|ZP_02259481.1|      ------------------------------------------------------------
ref|YP_894957.1|        ------------------------------------------------------------
ref|NP_978751.1|        ------------------------------------------------------------
ref|ZP_00741477.1|      ------------------------------------------------------------
RAAC01137               ---------------------------------------------------MHRFEPKVR ref|NP_844784.1|        ------------------------------------------------------LPETA
ref|ZP_02259481.1|      ------------------------------------------------------LPETA
ref|YP_894957.1|        ------------------------------------------------------LPETA
ref|NP_978751.1|        ------------------------------------------------------LPETA
ref|ZP_00741477.1|      ------------------------------------------------------LPETA
RAAC01137               TWSRTWRAAAILGWLLAAALLAAVFPAASKEEINRS----------------TLLPASA
                                                                            **  :* ref|NP_844784.1|        MSQQAEALMKKEFPNNAGNPLLVVWYRDGGLQSQDYKLIQDVYKELKASPLKEQSTLPPF
ref|ZP_02259481.1|      MSQQAEALMKKEFPNNAGNPLLVVWYRDGGLQSQDYKLIQDVYKELKASPLKEQSTLPPF
ref|YP_894957.1|        MSQQAEALMKKEFPNNAGNPLLVVWYRDGGLQSQDYKLIQDVYKELKASPLKEQSTLPPF
ref|NP_978751.1|        MSQQAEALMKKEFPNNAGNPLLVVWYRDGGLQSQDYKLIQDVYKELKASPLKEQSTLPPF
ref|ZP_00741477.1|      MSQQAEALMKKEFPNNTGNPLLVVWYRDGGLQSQDYKLIQDVYKELKANPLKEQSTLPPF
RAAC01137               PSQMATARVRDAFPASSGTPAILVFYDPTGISSADWAAIRRTVRELRTHPVTAQTQVPPL
                         ** *  *  ::. **  .:*.*  ::*:*    *:.* *:   *:  .:**::  *: . *:  :**:

ref|NP_844784.1|        DTIPEQVLSKSASKDGTSFVTPVFFNKSAGTDILKENLDDLRNIVNSKVDEDPFKRKIND
ref|ZP_02259481.1|      DTIPEQVLSKSASKDGTSFVTPVFFNKSAGTDILKGNLDDLRKIVNSKVDVDPFKQKISD
ref|YP_894957.1|        DTIPEQVLSKSASKDGTSFVTPVFFNKSAGTDILKGNLDDLRKIVNSKVDVDPFKQKISD
ref|NP_978751.1|        DTIPEQALSKSASKDGTSFVTPVFFNKSAGTDILKGNLDDLRKIVNSKVDVDPFKQKISD
ref|ZP_00741477.1|      DTIPEQVLSKSASKDGTSFVTPVFFNKSAGTDILKGNLEKLEKKVNSKVDEDPFKQKISE
RAAC01137               DALPSGAAARFASDDGKVVSFPVLLRADASQDQLNQAVDEIDQDLRRAVGAGALNLALDR
                        *::*.   . ::  **.**.  . **::. .*. * *:   ::.:  : :.    *.  ..:: ..

ref|NP_844784.1|        AGLHVRLSGPVGIQTDAVSLFSQADVKLLVATVLLVLVLLILLYRSPILAILPLLVVGFA
ref|ZP_02259481.1|      SGLHVRLSGPVGIQTDAVSLFSQADVKLLIATVLLVLVLLILLYRSPILAILPLLVVGFA
ref|YP_894957.1|        SGLHVRLSGPVGIQTDAVSLFSQADVKLLIATVLLVLVLLILLYRSPILAILPLLVVGFA
ref|NP_978751.1|        SGLHVRLSGPVGIQTDAVSLFSQADVKLLVATVLLVLVLLILLYRSPILAILPLLVVGFA
ref|ZP_00741477.1|      SGLHVRLSGPVGIQTDAVSLFSQADVKLLVATVLLVLILLILLYRSPILAILPILVVGFA
RAAC01137               PGLHAYVTGPAGIAVDATHLFQHADLALLIATTLLVLALMIVLYRSPILALVPLVSVGIA
                        .***. ::**.** .**. **.:**: **:**.**** *:*:******::*:: **:*
```

FIG. 161B

```
ref|NP_844784.1|      YGIISPTLGFLADHGWIKVDAQAISIMTVLLFGAGTDYCLFLISRYREYLLEEESKYKAL
ref|ZP_02259481.1|    YGIISPTLGFLADYGWIKVDAQAISIMTVLLFGAGTDYCLFLISRYREYLLEEESKYKAL
ref|YP_894957.1|      YGIISPTLGFLADHGWIKVDAQAISIMTVLLFGAGTDYCLFLISRYREYLLEEESKYKAL
ref|NP_978751.1|      YGIISPTLGFLADHGWIKVDAQAISIMTVLLFGAGTDYCLFLISRYREYLLEEESKYKAL
ref|ZP_00741477.1|    YGIISPTLGFLADHGWIKVDAQAISIMTVLLFGAGTDYCLFLISRYREYLLEEESKYKAL
RAAC01137             YAVVSSLLGAWARYGGLTFDAQTLSILTVLLFGAGTDYCLFLIARYRQELRRHERPIDAL
                      *.::*. **   * :* :..***::**:*****************:***:  *  ..*   .**

ref|NP_844784.1|      QLAIKASGGAIIMSALTVVLGLGTLLLAHYGAFHRFAVPFSVAVFIMGIAALTILPAFLL
ref|ZP_02259481.1|    QLAIKASGGAIIMSALTVVLGLGTLLLAHYGAFHRFAVPFSAAVFIMGIAALTILPAFLL
ref|YP_894957.1|      QLAIKASGGAIIMSALTVVLGLGTLLLAHYGAFHRFAVPFSVAVFIMGIAALTILPALLL
ref|NP_978751.1|      QLAIKASGGAIIMSALTVVLGLGTLLLAHYGAFHRFAVPFSVAVFIMGIAALTILPALLL
ref|ZP_00741477.1|    QLAIKASGGAIIMSALTVVLGLGTLLLAHYGAFHRFAVPFSVAVFIMGIAALTILPALLL
RAAC01137             RAGYKSAAGAILMSGLTVSASLLSLLAARSPSFHEFAIPFSVAVFVMALVAITFVPALIG
                      :  . *::.***:**.***   .* :** *:  :**.**:***.***:*.:.*:*::**::

ref|NP_844784.1|      IFGRTAFFPFIPRTTSMNEELARRKKKVVKVKKSKGAFSKKLGDVVVRRPWTIIMLTVFV
ref|ZP_02259481.1|    IFGRTAFFPFIPRTTSMNEELARRKKKVVKVKKSKGAFSKKLGDVVVRRPWTIIMLTVFV
ref|YP_894957.1|      IFGRAAFFPFVPRTTSMNEELARRKKKVVKVKKSKGAFSKKLGDVVVRRPWTIIMLTVFV
ref|NP_978751.1|      IFGRAAFFPFVPRTTSMNEELARRKKKVVKVKKSKGAFSKKLGDVVVRRPWTIIMLTVFV
ref|ZP_00741477.1|    IFGRIAFFPFIPRTTSMNEEFARKKKRAVKVEKSKGSFSKKLGDVVVRRPWTIIMLTVFV
RAAC01137             SLGRAAFWPRIPRYEPDAPDAGR----------PGRVSRWLGRTAVRRRKPVAVLGSLA
                      :** **:* :**   . : .*          * .*: **  ..***  .: :* :.

ref|NP_844784.1|      LGGLASFVPRIQYTYDLLESFPKDMPSREGFTLISDHFSAGELAPVKVIVDTKGKELPIK
ref|ZP_02259481.1|    LGGLASFVPRIQYTYDLLESFPKDMPSREGFTLISDHFSAGELAPVKVIVDTKGKELPIK
ref|YP_894957.1|      LGGLASFVPRIQYTYDLLESFPKDMPSREGFTLISDHFSAGELAPVKVVVDTKGKELPIK
ref|NP_978751.1|      LGGLASFVPRIQYTYDLLESFPKDMPSREGFTLISDHFSAGELAPVKVVVDTKGKELPMK
ref|ZP_00741477.1|    LGGLASFVPRIQYTYDLLESFPKDMPSREGFTLISDHFSAGELAPVKVVVDTKGKELPIK
RAAC01137             LAACCLALPHVRTSYDLLSSFPADMPSREGYAVLSAHESPGALAPIDVLVEGGSPEGAVR
                      *... .  :*::::  :****.*** ******:::* * *.* ***:.*:*:  . * .::

ref|NP_844784.1|      --EELEKFSFVNTVKDPKEGKENKQIQMYEVSLAENPYSIEALDQIPKLKNSVEKVFKDA
ref|ZP_02259481.1|    --EELEKFSFVNTVKDPKEGKENKQIQMYEVSLAENPYSIEALDQIPKLKNSVEKVFKDA
ref|YP_894957.1|      --EELEKFSFVNTVKDPKEGKENKQIQMYEVSLAENPYSIEALDQIPKLKNSVEKVFKDA
ref|NP_978751.1|      --QELEKFSFVKTVKEPKDGKENKQIKMYEVSLAENPYSIEALDQIPKLKIHVEKVLKDA
ref|ZP_00741477.1|    --QELEKFSFVNTVKEPKEGKENKQIQMYEVSLAENPYSIEALDQIPKLKSNVEKVLKDA
RAAC01137             ---AVQSLAAVEQVH-LVAVRDHAHVALMQVELRTNPYSETAMAALS----SIERAAAKG
                        ::.:: *: *:    ::: ::  : :*.*  ****  *: : .   :*:.. ..

ref|NP_844784.1|      GISNAED-QLWIGGETASLYDTKQITERDEAVIIPVMISIIALLLLVYLRSIVAMIYLIV
ref|ZP_02259481.1|    GISNAED-QLWIGGETASLYDTKQITERDEAIIIPVMISIIALLLLVYLRSIVAMIYLIV
ref|YP_894957.1|      GISNAED-QLWIGGETASLYDTKQITERDEAVIIPVMISIIALLLLVYLRSIVAMIYLIV
ref|NP_978751.1|      GVTKAED-QLWIGGETASLYDTKQITERDEAVIIPVMISIIALLLLVYLRSIVAMIYLIV
ref|ZP_00741477.1|    GIRNTED-QLWIGGETASLYDTKQITERDESVIIPVMISIIALLLLVYLRSVVAMIYLIV
RAAC01137             ASAGGQAAHVFLAGETAAQEDTRAITARDTRVVIPIVVAIGLLLLVYLRSVVAPLYLLA
                      .    :    ::::.****:  **: ** **  ::**:::   *.*********:** :**:.

ref|NP_844784.1|      TVVLSFFSALGAGWLLLHYGMGAPAIQGAIPLYAFVFLVALGEDYNIFMVSEIWKNRKTQ
ref|ZP_02259481.1|    TVVLSFFSALGAGWLLLHYGMGAPAIQGAIPLYAFVFLVALGEDYNIFMVSEIWKNRKTQ
ref|YP_894957.1|      TVVLSFFSALGAGWLLLHYGMGAPAIQGAIPLYAFVFLVALGEDYNIFMVSEIWKNRKTQ
ref|NP_978751.1|      TVVLSFFSALGAGWILLHFGMGAPAIQGAIPLYAFVFLVALGEDYNIFMVSEIWKNRKTQ
ref|ZP_00741477.1|    TVVLSFFSALGAGWILLHYGMGAPAIQGAIPLYAFVFLVALGEDYNIFMVSEIWKNRKTQ
RAAC01137             TIVLSYGAAMGLGWLVIREVLHQPAMQGAIPLYAFVFLVALGEDYNIFMVSRIWEVWRRG
                      *:***: :*:* **::::   :   **:********************::*.**:   :
```

FIG. 161C

```
ref|NP_844784.1|       NHLDAVKNGVIQTGSVITSAGLILAGTFAVLGTLPIQVLVQFGIVTAIGVLLDTFIVRPL
ref|ZP_02259481.1|     NHLDAVKNGVIQTGSVITSAGLILAGTFAVLGTLPIQVLVQFGIVTAIGVLLDTFIVRPL
ref|YP_894957.1|       NHLDAVKNGVIQTGSVITSAGLILAGTFAVLGTLPIQVLVQFGIVTAIGVLLDTFIVRPL
ref|NP_978751.1|       NHLAAVKNGVIQTGSVITSAGLILAGTFAVLGTLPIQVLVQFGIVTAIGVLLDTFIVRPL
ref|ZP_00741477.1|     NHMDAVKNGVIQTGSVITSAGLILAGTFAVLGTLPIQVLVQFGIVTAIGVLLDTFIVRPL
RAAC01137              QADAAVERGVADTASVITSAGLILAGTFAMLASLPIQVLLQFGVVTAIGVLLDTFVVRPW
                       :   :. :*.***************:*.:***:*:**********:* ref|NP_844784.1|       LVPAITVVLGRFAFWP---
ref|ZP_02259481.1|     LVPAITVVLGRFAFWP---
ref|YP_894957.1|       LVPAITVVLGRFAFWP---
ref|NP_978751.1|       LVPAITVVLGRFAFWP---
ref|ZP_00741477.1|     LVPAITVVLGRFAFWP---
RAAC01137              MVPAITALLGDAARWPRRT
                       :*****.:**  * **
```

FIG. 162A

```
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                MAERYAEFVA RFKYGIIAVW ILAVALAHVL LPQLNAIVAE KNTEFLPNSS SVVIASNWLK ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                RVDPARQAGS SAVVAMYNPH GLIAADKAWF TQKLKQVADE KPAYGVKTVT AAYNQSKSVQ ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                NQFFSADRTV EIATIGFPGN DVSKATDASL NQLHQVFQQP PKDAQILFTG DTPIENDNIN ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                ISMDGASKTA GVTIALVLVI LLVVFRSVVA PFLTLLSIGL SYLLTTNLVA VLANVGLPVS ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                TFTDTFLIAI IFGAGTDYSI IVLNRFREEA SRGLAPVDAL ARAMSGVAKT VVYSALTVFL ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                SFATLYFARF GLFRSGVGVA VGLAVTLFAC LTFLPALMMV LGRYVFWPRR NLDGASHKPS ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                RIWDLTGRTA LRHPWWTLAG VLVVLTPIAL SFTDKRTFDP TSDIPTAPSV EGFHVVSKAF ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|ZP_02168855.1|       ---------- ---------- ---------- ---------- ---------- ----------
ref|NP_470526.1|         ---------- ---------- ---------- ---------- ---------- ----------
RAAC03013                GPGKVLPMDV VIDTPDNLRT PEGLATIEQV SEAIAKLPFV QQVQSATRPT GSVIAEFELA ref|ZP_02168855.1|       ---------- ---------- ---------- ---------- ---------- ----------
ref|ZP_02168855.1|       ---------- ---------- ---------- ---------- ---------- ----------
```

FIG. 162B

```
ref|ZP_02168855.1      ---------- ---------- ---------- ---------- ---------- ----------
ref|ZP_02168855.1      ---------- ---------- ---------- ---------- ---------- ----------
ref|NP_470526.1|       ---------- ---------- ---------- ---------- ---------- ----------
RAAC03013              KQNQLAANGL GKVQTGLNQV ASHVGTKSAQ QAANAANTLS SGASALAQAG GKLSQGAAQA ref|ZP_02168855.1      ---------- ---------- ---------- ---------- ---------- ----------
ref|ZP_02168855.1      ---------- ---------- ---------- ---------- ---------- ----------
ref|ZP_02168855.1      ---------- ---------- ---------- ---------- ---------- ----------
ref|ZP_02168855.1      ---------- ---------- ---------- ---------- ---------- ----------
ref|NP_470526.1|       ---------- ---------- ---------- ---------- ---------- ----------
RAAC03013              QEGASKLAAG AQALSSGASR LTQANTQLAS GAAQVAAGSQ QVAQGADKLA TSARSIASGQ ref|ZP_02168855.1      ---------- ---------- ---------- ---------- ---------- ----------
ref|ZP_02168855.1      ---------- ----PDIDQFV REEGQAEAPE GFFSQIAEEL IEEDD-GFGG EEILLVYEQE
ref|ZP_02168855.1      ---------- ---------- ---------- ---------- ---------- ----------
ref|ZP_02168855.1      ---------- ---------- ---------- ---------- ---------- ----------
ref|NP_470526.1|       ---------- ---PPMADLV REKGELKLPD GYPSSLATEM QKKHNPDDKG SAYIAVYTAD
RAAC03013              TALANGAARE AQAAQQLANA IAAWTKAHPA EASDPNWQQI VALAQGNAAG AQQTAKAASQ ref|ZP_02168855.1      ---------- ---------- ---------- ---------- ----DGMAEA RQGASDLSGG
ref|ZP_02168855.1      DGFSSEQKEE IKEVLAGLSE EDHNLPIHAV TGPFDGDMEE ERLISEDGDV LIALVEMDIE
ref|ZP_02168855.1      ---------- ---------- ---------- ---------- ---------- ----------
ref|ZP_02168855.1      ---------- ---------- ---------- ---------- ---------- ----------
ref|NP_470526.1|       HKLTGTELNN IKKSLDSIDK NKDELEVTNV VSSFNQPELK DKFLSKDGKT MVASLTVDDT
RAAC03013              LANGTSQWAN GATSLAEGAG KVAAGASQLA AGSRGAASGA KGLSDGAAQV GQGASSLAQG ref|ZP_02168855.1      LDELQSGHYA LLDGVGEGRN GLENFRKGLR DMLEGTEELN -------EGI GEAEDALRQV
ref|ZP_02168855.1      AHEYADIRNE LQEASQAEGV DHDQTGEAVI NEDVVVSTEE GLVTSTYITV SLVFLVLALV
ref|ZP_02168855.1      ---------- ---------- ---------- ---------- ---------- ----------
ref|ZP_02168855.1      ---------- ---------- ---------- -------TEE GLVTSTYITV SLVFLVLALV
ref|NP_470526.1|       DASVKSIRNA LDKKMDVKGV DTYLTGNKLI QEDVVQGSED GLHKTEGITV VFILVVLFLV
RAAC03013              LNQLSGGARQ LQAGLGKWAA GAAQFSSGLS NAGAGENQLH SALVKLSNGV GTVKTALDET ref|ZP_02168855.1      SKQEENPLEG LFIPNEAF-E EEAFEEAFDQ YV--TPGGQV AGMELLFEED PYSQEAMMIL
ref|ZP_02168855.1      FKSLVSPLVP LLLLGTVYLF SISIVSRLID WVGFPVSNFT QMFVLAVVFG VGTDYCILIM
ref|ZP_02168855.1      ---------- ---------- ---------- ---------- ---------- ----------
ref|ZP_02168855.1      FKSLVSPLVP LLLLGTVYLF SISIVSRLID WVGFPVSNFT QMFVLAVVFG VGTDYCILIM
ref|NP_470526.1|       FRSAVAFFIP LLTVGISYLV AQSTVAFLID IFNFPVSTYT QIFMVCIMFG IGTDYCILLM
RAAC03013              AKAQTSGDPG FYVPASAISS NKSLRQALDS YI--SPDGHV ADIRVTLKSD PYSMTAIQEM ref|ZP_02168855.1      DEVEEVAAFT LRDTPFEDKE MAFSGITSSN RDLRDVSDQD FFVTAAVMLA GIFIALTFLF
ref|ZP_02168855.1      KRFQEEVLKD QTAFQAMLTT MRASKSTVLY SALTGFIGFA TIYLADFDLY QSAVGVAVAV
ref|ZP_02168855.1      ---------- ---------- ---------- ---------- ---------- ----------
ref|ZP_02168855.1      KRFQEEVLKD QTAFQAMLTT MRASKSTVLY SALTGFIGFA TIYLADFDLY QSAVGVAVAV
ref|NP_470526.1|       SRFKEEMGAG LDPRESVHAT YRTAGKTVIY SGVAVLVAFT SLYFVQFDLY RSAVAVGVGI
RAAC03013              PRLETVAQAA FTAAPIHTGQ VGFAGTTPTQ YALNQLSNQD FVRMMALILG SIFLLLVVML ref|ZP_02168855.1      KSLIMPLYVL VSLVLTYIGS MAVAELIFVT ILGYDGIM-- ---WAVPFFS FVLLMALGVD
ref|ZP_02168855.1      LVMMAGIWMV MPAVLALGGV RLFWPGKPGS SNPSNPLWGF IGGLTLRSPK LALVAVALLV
ref|ZP_02168855.1      ---------- ---------- ---------- ---------- --------FS FVLLMALGVD
ref|ZP_02168855.1      LVMMAGIWMV MPAVLALGGV RLFWP----- ---------- ---------- ----------
ref|NP_470526.1|       VVLLAALYTL VPFFMSTLGT HLFWPLNKNI SHKENKVWGA AGKFTFARPW IALLIVAAIT
RAAC03013              RSLIAPLYVI ASLTGTYFVT MACLQFVAVD VMHKAGIS-- ---WTVPFFA LLLLVALGVD
```

FIG. 162C

```
ref ZP_02168855.1|     YSIFLMGRFR EILEEGEEIT IHDAIHIAMK RIGGTVISAA LILGGTFAAM MASGVLTLMQ
ref ZP_02168855.1|     IPFYLFYDDL RSFDNVQEIR GDYDSVKAYE LTEEAFGQGD LFFSTLYLKT DEASWDDEGK
ref ZP_02168855.1|     YSIFLMGRFR EILEEGEEIT IHDAIHIAMK RIGGTVISAA LILGGTFAAM MASGVLTLMQ
ref ZP_02168855.1|     ---------- ---------- ---------- ---------- ---------- ----------
ref NP_470526.1|       LPPILLHTGT ESFNSLDEIS DKYPSKKGFE IVSDSFGAGQ VAPTQVFIEN DDN-MRTTEY
RAAC03013              YSIFLMSRFD EELRRHPELN LRSAMLYAMR QMGNVIFSAA AIMAGTFGSM SVSGVTTLVE ref ZP_02168855.1|     VSTVIMTGLL LYTLVMLPVF VPACMLLLGS WNWWPLGR-- ---------- ----------
ref ZP_02168855.1|     IAHLEQLAMN IEKVEGIRGV RGLNRPDEDV PDEFRIPEQA GILSEGMVEA LDGLDELSDG
ref ZP_02168855.1|     VSTVIMTGLL LYTLVMLPVF VPACMLLGS  WNWWP----- ---------- ----------
ref ZP_02168855.1|     ---------- ---------- ---------- ---------- ---------- ----------
ref NP_470526.1|       IAQIEKISDD LSHLKGIDMV MSASRPAGKR VDDIYIKNQA GQVNDGVGQA TDGVGEVKKG
RAAC03013              IGLSVIIGLA LYALIVLALF VPACTAIVGE AHFWPFRRVP REEQELRLPE ELAAE----- ref ZP_02168855.1|     -------
ref ZP_02168855.1|     I------
ref ZP_02168855.1|     -------
ref ZP_02168855.1|     -------
ref NP_470526.1|       LDSASSE
RAAC03013              -------
```

US 9,957,510 B2

TRANSCRIPTIONAL CONTROL IN *ALICYCLOBACILLUS ACIDOCALDARIUS* AND ASSOCIATED GENES, PROTEINS, AND METHODS

CROSS-REFERENCE TO RELATED APPLICATIONS

This application is a divisional of U.S. patent application Ser. No. 14/920,598, filed Oct. 22, 2015, now U.S. Pat. No. 9,499,824, issued Nov. 22, 2016, which is a divisional of U.S. patent application Ser. No. 14/256,819, filed Apr. 18, 2014, now U.S. Pat. No. 9,187,753, issued Nov. 17, 2015, which is a divisional of U.S. patent application Ser. No. 12/380,008, filed Feb. 20, 2009, now U.S. Pat. No. 8,716,011, issued May 6, 2014, which claims the benefit of the filing date of U.S. Provisional Patent Application Ser. No. 61/030,820, filed Feb. 22, 2008, for "TRANSCRIPTIONAL CONTROL IN *ALICYCLOBACILLUS ACIDOCALDARIUS* AND ASSOCIATED GENES, PROTEINS, AND METHODS," the disclosure of each of which is hereby incorporated herein in its entirety by this reference.

GOVERNMENT RIGHTS

This invention was made with government support under Contract Number DE-AC07-99ID13727 and Contract Number DE-AC07-05ID14517 awarded by the United States Department of Energy. The government has certain rights in the invention.

STATEMENT ACCORDING TO 37 C.F.R. § 1.821(C) OR (E)—SEQUENCE LISTING SUBMITTED AS PDF FILE WITH A REQUEST TO TRANSFER CRF FROM PARENT APPLICATION

Pursuant to 37 C.F.R. § 1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

The present invention relates generally to biotechnology. More specifically, the present invention relates to isolated and/or purified polypeptides and nucleic acid sequences encoding polypeptides from *Alicyclobacillus acidocaldarius* and methods for their use.

BACKGROUND

Bacterial DNA codes for information that regulates transcription of genes into mRNA which codes for proteins or enzymes used for control of growth and processing of energy, carbon and other compounds by the cell. Most of these transcriptional regulators/repressors function to turn on and off genes to minimize expenditure of cellular energy in response to their growth environment (i.e., presence of growth substrate, metals, temperature, etc.).

BRIEF SUMMARY

Embodiments of the invention relate to purified and/or isolated nucleotide sequences of the genome of *Alicyclobacillus acidocaldarius*, or a homologue or fragment thereof. In one embodiment of the invention, the nucleotide sequence is selected from at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or a homologue or fragment thereof. In another embodiment of the invention, the homologue is selected from the group consisting of a nucleotide sequence having at least 80% sequence identity to at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928.

Embodiments of the invention may further relate to an isolated and/or purified nucleic acid sequence comprising a nucleic acid sequence encoding a polypeptide selected from the group consisting of a polypeptide having at least 90% sequence identity to at least one of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

Embodiments of the invention also relate to isolated and/or purified polypeptides coded for by a nucleotide sequence comprising a nucleotide sequence of the genome of *Alicyclobacillus acidocaldarius*, or a homologue or fragment thereof. In one embodiment, the nucleotide sequence comprises a nucleotide sequence selected from the group consisting of a nucleotide sequence having at least 80% sequence identity to at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2860, 2877, 2894, 2911, and 2928.

In another embodiment of the invention, the nucleotide sequence comprises a nucleotide sequence selected from at least one of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2860, 2877, 2894, 2911, and 2928 or a homologue or fragment thereof. In still another embodiment, the polypeptide comprises an amino acid sequence of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927. In yet another embodiment, the polypeptide comprises an amino acid sequence selected from the group consisting of a polypeptide having at least 90% sequence identity to at least one of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

In embodiments of the invention, the polypeptides may be acidophilic and/or thermophilic. In further embodiments, the polypeptides may be glycosylated, pegylated, and/or otherwise post-translationally modified.

Embodiments of methods include placing a recombinant, purified, and/or isolated polypeptide selected from the group consisting of a polypeptide having at least 90% sequence identity to SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in, or replacing a component, of an in-vitro transcription system such as, by way of non-limiting example, a polymerase chain reaction or a reticulocyte lysate transcription/translation system.

Further embodiments of methods include placing a cell producing or encoding a recombinant, purified, and/or isolated nucleotide sequence comprising a nucleotide sequence selected from the group consisting of a nucleotide sequences having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in an environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

These and other aspects of the invention will become apparent to the skilled artisan in view of the teachings contained herein.

BRIEF DESCRIPTION OF THE DRAWINGS

FIG. 1 depicts a sequence alignment (ClustalW) between SEQ ID NO: 1446 (RAAC01465) and ref|ZP_01666866.1|, ref|YP_001039288.1|, ref|YP_001210812.1|, ref|YP_001111548.1|, and ref|ZP_01576004.1| (SEQ ID NOS: 1448-1452), respectively, which all have the function assigned to SEQ ID NO: 1446 in Table 1. Amino acids conserved among all sequences are indicted by a "*" and generally conserved amino acids are indicated by a ":".

FIG. 2 depicts a sequence alignment (ClustalW) between SEQ ID NO: 443 (RAAC00371) and ref|YP_145986.1|, ref|YP_001124263.1|, ref|NP_241028.1|, ref|YP_001210899.1|, and ref|YP_001111617.1| (SEQ ID NOS: 445-449), respectively, which all have the function assigned to SEQ ID NO: 443 in Table 1. Amino acids conserved among all sequences are indicted by a "*" and generally conserved amino acids are indicated by a ":".

FIGS. 3A-3C depict a sequence alignment (ClustalW) (ClustalW) between SEQ ID NO: 477 (RAAC00408) and ref|ZP_02326346.1|, ref|NP_240992.1|, ref|YP_001124230.1|, ref|YP_145951.1|, and ref|YP_173646.1| (SEQ ID NOS: 479-483), respectively, which all have the function assigned to SEQ ID NO: 477 in Table 1. Amino acids conserved among all sequences are indicted by a "*" and generally conserved amino acids are indicated by a ":".

FIGS. 4A-4C depict a sequence alignment (ClustalW) (ClustalW) between SEQ ID NO: 460 (RAAC00407) and ref|ZP_02326345.1|, ref|YP_001124231.1|, ref|NP_240993.1|, ref|YP_145952.1|, and ref|NP_976431.1| (SEQ ID NOS: 462-466), respectively, which all have the function assigned to SEQ ID NO: 460 in Table 1. Amino acids conserved among all sequences are indicted by a "*" and generally conserved amino acids are indicated by a ":".

FIG. 5 depicts a sequence alignment (ClustalW) between SEQ ID NO: 596 (RAAC00480) and ref|NP_244660.1|, ref|ZP_01168478.1|, ref|YP_001127419.1|, ref|ZP_01860921.1|, and ref|NP_693930.1| (SEQ ID NOS: 598-602), respectively, which all have the function assigned to SEQ ID NO: 596 in Table 1. Amino acids conserved among all sequences are indicted by a "*" and generally conserved amino acids are indicated by a ":".

FIG. 6 depicts a sequence alignment (ClustalW) between SEQ ID NO: 307 (RAAC00147) and ref|YP_850042.1|, ref|NP_465351.1|, ref|YP_014447.1|, ref|NP_268055.1|, and ref|NP_471274.1| (SEQ ID NOS: 309-313), respectively, which all have the function assigned to SEQ ID NO: 307 in Table 1. Amino acids conserved among all sequences are indicted by a "*" and generally conserved amino acids are indicated by a ":".

FIG. 7 depicts a sequence alignment (ClustalW) between SEQ ID NO: 1752 (RAAC01826) and ref|YP_074736.1|, ref|YP_074981.1|, ref|YP_001394390.1|, ref|NP_244228.1|, and ref|YP_001275817.1| (SEQ ID NOS: 1754-1758), respectively, which all have the function assigned to SEQ ID NO: 1752 in Table 1. Amino acids conserved among all sequences are indicted by a "*" and generally conserved amino acids are indicated by a ":".

FIG. 8 depicts a sequence alignment (ClustalW) between SEQ ID NO: 868 (RAAC00896) and ref|YP_001126509.1|, ref|YP_148335.1|, ref|ZP_02328521.1|, ref|ZP_01173341.1|, and ref|YP_001376241.1| (SEQ ID NOS: 870-874), respectively, which all have the function assigned to SEQ ID NO: 868 in Table 1. Amino acids conserved among all sequences are indicted by a "*" and generally conserved amino acids are indicated by a ":".

FIG. 9 depicts a sequence alignment (ClustalW) between SEQ ID NO: 256 (RAAC00120) and ref|NP_243422.1|, ref|YP_146980.1|, ref|YP_001125115.1|, ref|ZP_01862300.1|, and ref|ZP_01172495.1| (SEQ ID NOS: 258-262), respectively, which all have the function assigned to SEQ ID NO: 256 in Table 1. Amino acids conserved among all sequences are indicted by a "*" and generally conserved amino acids are indicated by a ":".

FIG. 10 depicts a sequence alignment (ClustalW) between SEQ ID NO: 1956 (RAAC02146) and ref|YP_001126333.1|, gb|AAB81194.1|, ref|YP_148161.1|, pdb|1L0O|C, and ref|YP_001487306.1| (SEQ ID NOS: 1958-1962), respectively, which all have the function assigned to SEQ ID NO: 1956 in Table 1. Amino acids conserved among all sequences are indicted by a "*" and generally conserved amino acids are indicated by a ":".

FIG. 11 depicts a sequence alignment (ClustalW) between SEQ ID NO: 273 (RAAC00121) and ref|ZP_02330758.1|, ref|YP_001212395.1|, ref|YP_001125116.1|, ref|NP_243420.1|, and ref|ZP_01667054.1| (SEQ ID NOS: 275-279), respectively, which all have the function assigned to SEQ ID NO: 273 in Table 1. Amino acids conserved among all sequences are indicted by a "*" and generally conserved amino acids are indicated by a ":".

FIG. 12 depicts a sequence alignment (ClustalW) between SEQ ID NO: 2262 (RAAC02546) and ref|YP_001512033.1|, ref|NP_976421.1|, ref|NP_842661.1|, ref|NP_829995.1|, and ref|YP_001373458.1| (SEQ ID NOS: 2264-2268), respectively, which all have the function assigned to SEQ ID NO: 2262 in Table 1. Amino acids conserved among all sequences are indicted by a "*" and generally conserved amino acids are indicated by a ":".

FIG. 13 depicts a sequence alignment (ClustalW) between SEQ ID NO: 511 (RAAC00418) and ref|YP_077384.1|, ref|YP_001419777.1|, emb|CAA41793.1|, ref|ZP_01173595.1|, and ref|NP_240981.1| (SEQ ID NOS: 513-517), respectively, which all have the function assigned to SEQ ID NO: 511 in Table 1. Amino acids conserved among all sequences are indicted by a "*" and generally conserved amino acids are indicated by a ":".

FIG. 14 depicts a sequence alignment (ClustalW) between SEQ ID NO: 2602 (RAAC02968) and ref|YP_001409756.1|, ref|YP_001485343.1|, ref|YP_181606.1|, ref|NP_976421.1|, and ref|NP_842661.1| (SEQ ID NOS: 2604-2608), respectively, which all have the function assigned to SEQ ID NO: 2602 in Table 1. Amino acids conserved among all sequences are indicted by a "*" and generally conserved amino acids are indicated by a ":".

FIG. 15 depicts a sequence alignment between SEQ ID NO: 2927 (RAAC03263) and RTHT02135, RTHT02135, RBLH00099, RBSB05130, and RCTH01302 (SEQ ID NOS: 2929-2933), respectively, which all have the function assigned to SEQ ID NO: 2927 in Table 1. Amino acids conserved among all sequences are indicted by a "*" and generally conserved amino acids are indicated by a ":".

FIG. 16 depicts a sequence alignment (ClustalW) between SEQ ID NO: 817 (RAAC00856) and ref|YP_001126560.1|, ref|NP_242151.1|, ref|YP_175113.1|, ref|YP_148388.1|, and ref|ZP_01861605.1| (SEQ ID NOS: 819-823), respectively, which all have the function assigned to SEQ ID NO: 817 in Table 1. Amino acids conserved among all sequences are indicted by a "*" and generally conserved amino acids are indicated by a ":".

FIG. 17 depicts a sequence alignment (ClustalW) between SEQ ID NO: 1735 (RAAC01814) and ref|YP_148388.1|, ref|YP_001126560.1|, gb|ABY76244.1|, ref|YP_896655.1|, and ref|NP_980714.1| (SEQ ID NOS: 1737-1741), respectively, which all have the function assigned to SEQ ID NO: 1735 in Table 1. Amino acids conserved among all sequences are indicted by a "*" and generally conserved amino acids are indicated by a ":".

FIG. 18 depicts a sequence alignment (ClustalW) between SEQ ID NO: 2381 (RAAC02673) and ref|YP_001486125.1|, ref|ZP_01696681.1|, ref|NP_388808.1|, ref|NP_830819.1|, and ref|YP_001643827.1| (SEQ ID NOS: 2383-2387), respectively, which all have the function assigned to SEQ ID NO: 2381 in Table 1. Amino acids conserved among all sequences are indicted by a "*" and generally conserved amino acids are indicated by a ":".

FIG. 19 depicts a sequence alignment (ClustalW) between SEQ ID NO: 1905 (RAAC02112) and ref|YP_148250.1|, ref|ZP_01725195.1|, ref|NP_390312.1|, ref|ZP_00538565.1|, and ref|YP_001126420.1| (SEQ ID NOS: 1907-1911), respectively, which all have the function assigned to SEQ ID NO: 1905 in Table 1. Amino acids conserved among all sequences are indicted by a "*" and generally conserved amino acids are indicated by a ":".

FIG. 20 depicts a sequence alignment (ClustalW) between SEQ ID NO: 2568 (RAAC02902) and ref|YP_147113.1|, ref|NP_243282.1|, ref|YP_001125233.1|, ref|YP_175727.1|, and ref|ZP_02330483.1| (SEQ ID NOS: 2570-2574), respectively, which all have the function assigned to SEQ ID NO: 2568 in Table 1. Amino acids conserved among all sequences are indicted by a "*" and generally conserved amino acids are indicated by a ":".

FIG. 21 depicts a sequence alignment (ClustalW) between SEQ ID NO: 494 (RAAC00415) and ref|ZP_01173598.1|, ref|YP_173640.1|, ref|YP_089786.1|, ref|YP_848410.1|, and ref|NP_691027.1| (SEQ ID NOS: 496-500), respectively, which all have the function assigned to SEQ ID NO: 494 in Table 1. Amino acids conserved among all sequences are indicted by a "*" and generally conserved amino acids are indicated by a ":".

FIGS. 22A and 22B depict a sequence alignment (ClustalW) between SEQ ID NO: 562 (RAAC00475) and ref|YP_149235.1|, ref|YP_001127411.1|, ref|YP_001377035.1|, gb|AAU09403.1|, and ref|YP_039325.1| (SEQ ID NOS: 564-568), respectively, which all have the function assigned to SEQ ID NO: 562 in Table 1. Amino acids conserved among all sequences are indicted by a "*" and generally conserved amino acids are indicated by a ":".

FIGS. 23A and 23B depict a sequence alignment (ClustalW) between SEQ ID NO: 2619 (RAAC02984) and ref|ZP_01173129.1|, ref|ZP_01696484.1|, ref|YP_001488275.1|, ref|ZP_02171541.1|, and ref|YP_173520.1| (SEQ ID NOS: 2621-2625), respectively, which all have the function assigned to SEQ ID NO: 2619 in Table 1. Amino acids conserved among all sequences are indicted by a "*" and generally conserved amino acids are indicated by a ":".

FIGS. 24A and 24B depict a sequence alignment (ClustalW) between SEQ ID NO: 2636 (RAAC02994) and ref|NP_244812.1|, ref|ZP_02171541.1|, ref|ZP_01173129.1|, ref|YP_090070.1|, and ref|YP_077660.1| (SEQ ID NOS: 2638-2642), respectively, which all have the function assigned to SEQ ID NO: 2636 in Table 1. Amino acids conserved among all sequences are indicted by a "*" and generally conserved amino acids are indicated by a ":".

FIG. 25 depicts a sequence alignment (ClustalW) between SEQ ID NO: 86 (RAAC00039) and ref|YP_177603.1|, ref|NP_244925.1|, ref|YP_001423363.1|, ref|ZP_02327875.1|, and ref|ZP_02172038.1| (SEQ ID NOS: 88-92), respectively, which all have the function assigned to SEQ ID NO: 86 in Table 1. Amino acids conserved among all sequences are indicted by a "*" and generally conserved amino acids are indicated by a ":".

FIG. 26 depicts a sequence alignment (ClustalW) between SEQ ID NO: 1871 (RAAC02034) and ref|YP_001422137.1|, ref|YP_080133.1|, ref|NP_243941.1|, ref|YP_176156.1|, and ref|YP_001376422.1| (SEQ ID NOS: 1873-1877), respectively, which all have the function assigned to SEQ ID NO: 1871 in Table 1. Amino acids conserved among all sequences are indicted by a "*" and generally conserved amino acids are indicated by a ":".

FIG. 27 depicts a sequence alignment (ClustalW) between SEQ ID NO: 188 (RAAC00092) and ref|ZP_01697682.1|, ref|YP_146960.1|, ref|NP_242122.1|, ref|YP_001125095.1|, and ref|ZP_01860230.1| (SEQ ID NOS: 190-194), respectively, which all have the function assigned to SEQ ID NO: 188 in Table 1. Amino acids conserved among all sequences are indicted by a "*" and generally conserved amino acids are indicated by a ":".

FIG. 28 depicts a sequence alignment (ClustalW) between SEQ ID NO: 2143 (RAAC02454) and ref|YP_001125095.1|, ref|YP_896293.1|, ref|YP_146960.1|, ref|NP_389392.1|, and ref|ZP_02261942.1| (SEQ ID NOS: 2145-2149), respectively, which all have the function assigned to SEQ ID NO: 2143 in Table 1. Amino acids conserved among all sequences are indicted by a "*" and generally conserved amino acids are indicated by a ":".

FIG. 29 depicts a sequence alignment (ClustalW) between SEQ ID NO: 341 (RAAC00212) and ref|YP_752777.1|, ref|YP_001666100.1|, ref|NP_621806.1|, ref|ZP_01666183.1|, and ref|YP_077079.1| (SEQ ID NOS: 343-347), respectively, which all have the function assigned to SEQ ID NO: 341 in Table 1. Amino acids conserved among all sequences are indicted by a "*" and generally conserved amino acids are indicated by a ":".

FIG. 30 depicts a sequence alignment (ClustalW) between SEQ ID NO: 2772 (RAAC03236) and ref|YP_001666100.1|, ref|YP_001317994.1|, ref|NP_621806.1|, ref|YP_001181188.1|, and ref|NP_346951.1| (SEQ ID NOS: 2774-2778), respectively, which all have the function assigned to SEQ ID NO: 2772 in Table 1. Amino acids conserved among all sequences are indicted by a "*" and generally conserved amino acids are indicated by a ":".

FIG. 31 depicts a sequence alignment (ClustalW) between SEQ ID NO: 2296 (RAAC02603) and ref|NP_346951.1|, ref|YP_001181188.1|, ref|YP_001666100.1|, ref|NP_621806.1|, and ref|YP_001317994.1| (SEQ ID NOS: 2298-2302), respectively, which all have the function assigned to SEQ ID NO: 2296 in Table 1. Amino acids conserved among all sequences are indicted by a "*" and generally conserved amino acids are indicated by a ":".

FIG. 32 depicts a sequence alignment (ClustalW) between SEQ ID NO: 324 (RAAC00161) and gb|AAC62407.1|, ref|YP_001374031.1|, ref|NP_830661.1|, ref|YP_037204.1|, and ref|NP_979446.1| (SEQ ID NOS: 326-330), respectively, which all have the function assigned to SEQ ID NO: 324 in Table 1. Amino acids conserved among all sequences are indicted by a "*" and generally conserved amino acids are indicated by a ":".

FIG. 33 depicts a sequence alignment (ClustalW) between SEQ ID NO: 919 (RAAC00923) and ref|YP_001422239.1|, ref|YP_001420593.1|, ref|ZP_01697004.1|, ref|ZP_01170670.1|, and ref|YP_001486165.1| (SEQ ID NOS: 921-925), respectively, which all have the function assigned to SEQ ID NO: 919 in Table 1. Amino acids conserved among all sequences are indicted by a "*" and generally conserved amino acids are indicated by a ":".

FIG. 34 depicts a sequence alignment (ClustalW) between SEQ ID NO: 749 (RAAC00643) and ref|ZP_02330525.1|, ref|NP_623103.1|, ref|ZP_02330045.1|, ref|YP_001665292.1|, and ref|YP_001665293.1| (SEQ ID NOS: 751-755), respectively, which all have the function assigned to SEQ ID NO: 749 in Table 1. Amino acids conserved among all sequences are indicted by a "*" and generally conserved amino acids are indicated by a ":".

FIG. 35 depicts a sequence alignment (ClustalW) between SEQ ID NO: 1361 (RAAC01427) and ref|NP_240926.1|, ref|ZP_02330558.1|, ref|YP_001419725.1|, ref|NP_829946.1|, and ref|NP_842611.1| (SEQ ID NOS: 1363-1367), respectively, which all have the function assigned to SEQ ID NO: 1361 in Table 1. Amino acids conserved among all sequences are indicted by a "*" and generally conserved amino acids are indicated by a ":".

FIG. 36 depicts a sequence alignment (ClustalW) between SEQ ID NO: 426 (RAAC00365) and ref|YP_173696.1|, ref|ZP_02329530.1|, ref|ZP_01696660.1|, ref|NP_241105.1|, and ref|YP_001124272.1| (SEQ ID NOS: 428-432), respectively, which all have the function assigned to SEQ ID NO: 426 in Table 1. Amino acids conserved among all sequences are indicted by a "*" and generally conserved amino acids are indicated by a ":".

FIGS. 37A and 37B depict a sequence alignment (ClustalW) between SEQ ID NO: 1531 (RAAC01563) and ref|ZP_01665476.1|, ref|ZP_02259717.1|, ref|YP_036745.1|, ref|YP_028716.1|, and ref|YP_083969.1| (SEQ ID NOS: 1533-1537), respectively, which all have the function assigned to SEQ ID NO: 1531 in Table 1. Amino acids conserved among all sequences are indicted by a "*" and generally conserved amino acids are indicated by a ":".

FIG. 38 depicts a sequence alignment (ClustalW) between SEQ ID NO: 2806 (RAAC02315) and ref|YP_145847.1|, gb|ABG00342.1|, ref|YP_536482.1|, ref|YP_891181.1|, and ref|YP_799230.1| (SEQ ID NOS: 2808-2812), respectively, which all have the function assigned to SEQ ID NO: 2806 in Table 1. Amino acids conserved among all sequences are indicted by a "*" and generally conserved amino acids are indicated by a ":".

FIG. 39 depicts a sequence alignment (ClustalW) between SEQ ID NO: 103 (RAAC00040) and ref|YP_001423364.1|, ref|NP_391977.1|, ref|YP_001488932.1|, ref|YP_093870.1|, and ref|YP_081433.1| (SEQ ID NOS: 105-109), respectively, which all have the function assigned to SEQ ID NO: 103 in Table 1. Amino acids conserved among all sequences are indicted by a "*" and generally conserved amino acids are indicated by a ":".

FIG. 40 depicts a sequence alignment (ClustalW) between SEQ ID NO: 205 (RAAC00113) and ref|ZP_01697918.1|, ref|YP_001125108.1|, emb|CAJ75583.1|, ref|YP_146973.1|, and ref|ZP_01172488.1| (SEQ ID NOS: 207-211), respectively, which all have the function assigned to SEQ ID NO: 205 in Table 1. Amino acids conserved among all sequences are indicted by a "*" and generally conserved amino acids are indicated by a ":".

FIGS. 41A and 41B depict a sequence alignment (ClustalW) between SEQ ID NO: 222 (RAAC00117) and ref|ZP_02330014.1|, emb|CAJ75587.1|, ref|YP_146977.1|, ref|YP_001125112.1|, and ref|NP_243425.1| (SEQ ID NOS: 224-228), respectively, which all have the function assigned to SEQ ID NO: 222 in Table 1. Amino acids conserved among all sequences are indicted by a "*" and generally conserved amino acids are indicated by a ":".

FIG. 42 depicts a sequence alignment (ClustalW) between SEQ ID NO: 239 (RAAC00118) and ref|YP_078922.1|, ref|YP_001375784.1|, ref|ZP_02171874.1|, ref|YP_001646530.1|, and gb|AAN04557.1| (SEQ ID NOS: 241-245), respectively, which all have the function assigned to SEQ ID NO: 239 in Table 1. Amino acids conserved among all sequences are indicted by a "*" and generally conserved amino acids are indicated by a ":".

FIG. 43 depicts a sequence alignment (ClustalW) between SEQ ID NO: 1344 (RAAC01377) and ref|YP_147952.1|, ref|YP_520670.1|, ref|YP_001395809.1|, ref|YP_001309701.1|, and ref|YP_001643660.1| (SEQ ID NOS: 1346-1350), respectively, which all have the function assigned to SEQ ID NO: 1344 in Table 1. Amino acids conserved among all sequences are indicted by a "*" and generally conserved amino acids are indicated by a ":".

FIGS. 44A and 44B depict a sequence alignment (ClustalW) between SEQ ID NO: 2840 (RAAC02381) and ref|NP_622177.1|, ref|YP_848858.1|, ref|YP_001374688.1|, ref|NP_470039.1|, and ref|ZP_01929325.1| (SEQ ID NOS: 2842-2846), respectively, which all have the function assigned to SEQ ID NO: 2840 in Table 1. Amino acids conserved among all sequences are indicted by a "*" and generally conserved amino acids are indicated by a ":".

FIG. 45 depicts a sequence alignment (ClustalW) between SEQ ID NO: 1038 (RAAC00991) and ref|ZP_02327412.1|, ref|YP_001487207.1|, ref|ZP_01172765.1|, ref|NP_831314.1|, and ref|NP_844008.1| (SEQ ID NOS: 1040-1044), respectively, which all have the function assigned to SEQ ID NO: 1038 in Table 1. Amino acids conserved among all sequences are indicted by a "*" and generally conserved amino acids are indicated by a ":".

FIG. 46 depicts a sequence alignment (ClustalW) between SEQ ID NO: 766 (RAAC00650) and ref|YP_001127183.1|, ref|ZP_02038504.1|, ref|YP_001647987.1|, ref|YP_001377114.1|, and ref|NP_835081.1| (SEQ ID NOS: 768-772), respectively, which all have the function assigned to SEQ ID NO: 766 in Table 1. Amino acids conserved among all sequences are indicted by a "*" and generally conserved amino acids are indicated by a ":".

FIG. 47 depicts a sequence alignment (ClustalW) between SEQ ID NO: 2041 (RAAC02421) and ref|ZP_01721811.1|, ref|NP_241897.1|, ref|YP_001486101.1|, ref|ZP_01170532.1|, and ref|ZP_02327994.1| (SEQ ID NOS: 2043-2047), respectively, which all have the function assigned to SEQ ID NO: 2041 in Table 1. Amino acids conserved among all sequences are indicted by a "*" and generally conserved amino acids are indicated by a ":".

FIGS. 48A and 48B depict a sequence alignment (ClustalW) between SEQ ID NO: 1922 (RAAC02142) and ref|ZP_01860158.1|, ref|YP_148164.1|, ref|NP_242401.1|, ref|YP_001126336.1|, and ref|YP_001421751.1| (SEQ ID NOS: 1924-1928), respectively, which all have the function assigned to SEQ ID NO: 1922 in Table 1. Amino acids conserved among all sequences are indicted by a "*" and generally conserved amino acids are indicated by a ":".

FIGS. 49A and 49B depict a sequence alignment (ClustalW) between SEQ ID NO: 2687 (RAAC03015) and ref|NP_628606.1|, ref|ZP_02061285.1|, ref|NP_824958.1|, emb|CAA04971.1|, and gb|AAC32488.1| (SEQ ID NOS: 2689-2693), respectively, which all have the function assigned to SEQ ID NO: 2687 in Table 1. Amino acids conserved among all sequences are indicted by a "*" and generally conserved amino acids are indicated by a ":".

FIGS. 50A and 50B depict a sequence alignment (ClustalW) between SEQ ID NO: 2517 (RAAC02227) and ref|YP_430213.1|, ref|YP_001212426.1|, ref|YP_001663198.1|, ref|YP_360920.1|, and ref|YP_001665129.1| (SEQ ID NOS: 2519-2523), respectively, which all have the function assigned to SEQ ID NO: 2517 in Table 1. Amino acids conserved among all sequences are indicted by a "*" and generally conserved amino acids are indicated by a ":".

FIG. 51 depicts a sequence alignment (ClustalW) between SEQ ID NO: 834 (RAAC00872) and ref|NP_622598.1|, ref|YP_001320854.1|, ref|YP_001665389.1|, ref|YP_001037463.1|, and ref|YP_001512768.1| (SEQ ID NOS: 836-840), respectively, which all have the function assigned to SEQ ID NO: 834 in Table 1. Amino acids conserved among all sequences are indicted by a "*" and generally conserved amino acids are indicated by a ":".

FIG. 52 depicts a sequence alignment (ClustalW) between SEQ ID NO: 120 (RAAC00045) and ref|ZP_02172045.1|, ref|ZP_01189194.1|, ref|NP_244931.1|, ref|YP_001213468.1|, and ref|YP_358877.1| (SEQ ID NOS: 122-126), respectively, which all have the function assigned to SEQ ID NO: 120 in Table 1. Amino acids conserved among all sequences are indicted by a "*" and generally conserved amino acids are indicated by a ":".

FIGS. 53A and 53B depict a sequence alignment (ClustalW) between SEQ ID NO: 2092 (RAAC02428) and dbj|BAB83769.1|, ref|YP_146913.1|, sp|P11961|ODP2_BACST, ref|ZP_01696305.1|, and ref|YP_001125047.1| (SEQ ID NOS: 2094-2098), respectively, which all have the function assigned to SEQ ID NO: 2092 in Table 1. Amino acids conserved among all sequences are indicted by a "*" and generally conserved amino acids are indicated by a ":".

FIGS. 54A and 54B depict a sequence alignment (ClustalW) between SEQ ID NO: 1650 (RAAC01659) and ref|ZP_02326222.1|, ref|NP_241081.1|, ref|YP_074242.1|, ref|YP_001153408.1|, and ref|NP_560158.1| (SEQ ID NOS: 1652-1656), respectively, which all have the function assigned to SEQ ID NO: 1650 in Table 1. Amino acids conserved among all sequences are indicted by a "*" and generally conserved amino acids are indicated by a ":".

FIG. 55 depicts a sequence alignment (ClustalW) between SEQ ID NO: 1701 (RAAC01745) and ref|YP_001127228.1|, ref|YP_149070.1|, ref|ZP_00539127.1|, ref|ZP_02326224.1|, and ref|NP_241079.1| (SEQ ID NOS: 1703-1707), respectively, which all have the function assigned to SEQ ID NO: 1701 in Table 1. Amino acids conserved among all sequences are indicted by a "*" and generally conserved amino acids are indicated by a ":".

FIG. 56 depicts a sequence alignment (ClustalW) between SEQ ID NO: 1718 (RAAC01746) and ref|YP_149069.1|, ref|YP_001127227.1|, ref|ZP_00539126.1|, ref|YP_001125046.1|, and ref|NP_833691.1| (SEQ ID NOS: 1720-1724), respectively, which all have the function assigned to SEQ ID NO: 1718 in Table 1. Amino acids conserved among all sequences are indicted by a "*" and generally conserved amino acids are indicated by a ":".

FIG. 57 depicts a sequence alignment (ClustalW) between SEQ ID NO: 2058 (RAAC02426) and ref|NP_243521.1|, pdb|1W85|A, sp|P21873|ODPA_BACST, ref|YP_001421036.1|, and ref|YP_146911.1| (SEQ ID NOS: 2060-2064), respectively, which all have the function assigned to SEQ ID NO: 2058 in Table 1. Amino acids conserved among all sequences are indicted by a "*" and generally conserved amino acids are indicated by a ":".

FIG. 58 depicts a sequence alignment (ClustalW) between SEQ ID NO: 2075 (RAAC02427) and ref|ZP_01696304.1|, sp|P21874|ODPB_BACST, ref|YP_001125046.1|, pdb|1W85|B, and ref|YP_146912.1| (SEQ ID NOS: 2077-2081), respectively, which all have the function assigned to SEQ ID NO: 2075 in Table 1. Amino acids conserved among all sequences are indicted by a "*" and generally conserved amino acids are indicated by a ":".

FIG. 59 depicts a sequence alignment (ClustalW) between SEQ ID NO: 1616 (RAAC01657) and ref|ZP_02326224.1|, dbj|BAB40585.1|, ref|NP_241079.1|, ref|YP_001126012.1|, and ref|ZP_01171269.1| (SEQ ID NOS: 1618-1622), respectively, which all have the function assigned to SEQ ID NO: 1616 in Table 1. Amino acids conserved among all sequences are indicted by a "*" and generally conserved amino acids are indicated by a ":".

FIG. 60 depicts a sequence alignment (ClustalW) between SEQ ID NO: 1633 (RAAC01658) and ref|ZP_02326223.1|, ref|NP_241080.1|, dbj|BAB40586.1|, ref|YP_001126011.1|, and ref|NP_693798.1| (SEQ ID NOS: 1635-1639), respectively, which all have the function assigned to SEQ ID NO: 1633 in Table 1. Amino acids conserved among all sequences are indicted by a "*" and generally conserved amino acids are indicated by a ":".

FIGS. 61A and 61B depict a sequence alignment (ClustalW) between SEQ ID NO: 630 (RAAC00484) and ref|YP_001125466.1|, ref|ZP_01697095.1|, ref|YP_147353.1|, ref|ZP_01886631.1|, and ref|YP_077737.1| (SEQ ID NOS: 632-636), respectively, which all have the function assigned to SEQ ID NO: 630 Table 1. Amino acids conserved among all sequences are indicted by a "*" and generally conserved amino acids are indicated by a ":".

FIG. 62 depicts a sequence alignment (ClustalW) between SEQ ID NO: 613 (RAAC00483) and ref|NP_886151.1|, ref|YP_147354.1|, ref|YP_001125467.1|, ref|YP_001420062.1|, and ref|NP_242684.1| (SEQ ID NOS: 615-619), respectively, which all have the function assigned to SEQ ID NO: 613 in Table 1. Amino acids conserved among all sequences are indicted by a "*" and generally conserved amino acids are indicated by a ":".

FIG. 63 depicts a sequence alignment (ClustalW) between SEQ ID NO: 290 (RAAC00134) and ref|ZP_01860800.1|, ref|YP_147000.1|, ref|ZP_01695960.1|, ref|YP_001125127.1|, and ref|YP_806677.1| (SEQ ID NOS: 292-296), respectively, which all have the function assigned to SEQ ID NO: 290 in Table 1. Amino acids conserved among all sequences are indicted by a "*" and generally conserved amino acids are indicated by a ":".

FIG. 64 depicts a sequence alignment (ClustalW) between SEQ ID NO: 358 (RAAC00215) and ref|YP_145879.1|, ref|ZP_01697513.1|, ref|YP_001124157.1|, ref|ZP_01174007.1|, and ref|YP_001642924.1| (SEQ ID NOS: 360-364), respectively, which all have the function assigned to SEQ ID NO: 358 in Table 1. Amino acids conserved among all sequences are indicted by a "*" and generally conserved amino acids are indicated by a ":".

FIG. 65 depicts a sequence alignment (ClustalW) between SEQ ID NO: 2177 (RAAC02164) and ref|YP_359129.1|, ref|ZP_02127016.1|, ref|YP_001540277.1|, pdb|1M2N|A, and pdb|1M2K|A (SEQ ID NOS: 2179-2183), respectively, which all have the function assigned to SEQ ID NO: 2177 in Table 1. Amino acids conserved among all sequences are indicted by a "*" and generally conserved amino acids are indicated by a ":".

FIGS. 66A-66C depict a sequence alignment (ClustalW) between SEQ ID NO: 1395 (RAAC01438) and ref|YP_173587.1|, ref|NP_240935.1|, ref|YP_001373418.1|, ref|YP_892975.1|, and ref|NP_976379.1| (SEQ ID NOS: 1397-1401), respectively, which all have the function assigned to SEQ ID NO: 1395 in Table 1. Amino acids conserved among all sequences are indicted by a "*" and generally conserved amino acids are indicated by a ":".

FIG. 67 depicts a sequence alignment (ClustalW) between SEQ ID NO: 2755 (RAAC03184) and ref|YP_001105447.1|, ref|YP_117520.1|, ref|YP_046943.1|, ref|YP_707186.1|, and ref|YP_001337847.1| (SEQ ID NOS: 2757-2761), respectively, which all have the function assigned to SEQ ID NO: 2755 in Table 1. Amino acids conserved among all sequences are indicted by a "*" and generally conserved amino acids are indicated by a ":".

FIG. 68 depicts a sequence alignment between SEQ ID NO: 2859 (RAAC02740) and ref|NP_391246.1|, ref|YP_001488252.1|, ref|NP_244416.1|, ref|YP_001112264.1|, and ref|YP_430670.1| (SEQ ID NOS: 2861-2865), respectively, which all have the function assigned to SEQ ID NO: 2859 in Table 1. Amino acids conserved among all sequences are indicted by a "*" and generally conserved amino acids are indicated by a ":".

FIG. 69 depicts a sequence alignment between SEQ ID NO: 2893 (RAAC02937) and ref|YP_075413.1|, ref|YP_001662816.1|, ref|YP_001664674.1|, ref|YP_827514.1|, and ref|YP_827514.1| (SEQ ID NOS: 2895-2899), respectively, which all have the function assigned to SEQ ID NO: 2893 in Table 1. Amino acids conserved among all sequences are indicted by a "*" and generally conserved amino acids are indicated by a ":".

FIG. 70 depicts a sequence alignment (ClustalW) between SEQ ID NO: 783 (RAAC00675) and ref|YP_001373772.1|, ref|YP_034761.1|, ref|YP_893335.1|, ref|ZP_00237972.1|, and ref|ZP_02329595.1| (SEQ ID NOS: 785-789), respectively, which all have the function assigned to SEQ ID NO: 783 in Table 1. Amino acids conserved among all sequences are indicted by a "*" and generally conserved amino acids are indicated by a ":".

FIG. 71 depicts a sequence alignment (ClustalW) between SEQ ID NO: 2789 (RAAC02292) and gb|AAB91591.1|, ref|YP_001422657.1|, ref|NP_391247.1|, ref|YP_093160.1|, and ref|NP_391246.1| (SEQ ID NOS: 2791-2795), respectively, which all have the function assigned to SEQ ID NO: 2789 in Table 1. Amino acids conserved among all sequences are indicted by a "*" and generally conserved amino acids are indicated by a ":".

FIG. 72 depicts a sequence alignment (ClustalW) between SEQ ID NO: 1599 (RAAC01655) and ref|ZP_00235680.1|, ref|NP_241278.1|, ref|NP_845841.1|, ref|ZP_02260616.1|, and ref|ZP_02256143.1| (SEQ ID NOS: 1601-1605), respectively, which all have the function assigned to SEQ ID NO: 1599 Table 1. Amino acids conserved among all sequences are indicted by a "*" and generally conserved amino acids are indicated by a ":".

FIG. 73 depicts a sequence alignment (ClustalW) between SEQ ID NO: 545 (RAAC00436) and ref|ZP_02171828.1|, ref|YP_077369.1|, ref|YP_001485328.1|, ref|ZP_02329455.1|, and ref|YP_001419762.1| (SEQ ID NOS: 547-551), respectively, which all have the function assigned to SEQ ID NO: 545 in Table 1. Amino acids conserved among all sequences are indicted by a "*" and generally conserved amino acids are indicated by a ":".

FIG. 74 depicts a sequence alignment (ClustalW) between SEQ ID NO: 1429 (RAAC01464) and ref|YP_001485324.1|, ref|YP_001124204.1|, ref|YP_145925.1|, ref|YP_077366.1|, and ref|NP_829977.1| (SEQ ID NOS: 1431-1435), respectively, which all have the function assigned to SEQ ID NO: 1429 in Table 1. Amino acids conserved among all sequences are indicted by a "*" and generally conserved amino acids are indicated by a ":".

FIG. 75 depicts a sequence alignment (ClustalW) between SEQ ID NO: 698 (RAAC00579) and ref|ZP_01440002.1|, ref|NP_896891.1|, ref|YP_001623237.1|, ref|ZP_01419169.1|, and ref|ZP_01084741.1| (SEQ ID NOS: 700-704), respectively, which all have the function assigned to SEQ ID NO: 698 in Table 1. Amino acids conserved among all sequences are indicted by a "*" and generally conserved amino acids are indicated by a ":".

FIG. 76 depicts a sequence alignment (ClustalW) between SEQ ID NO: 2721 (RAAC03156) and ref|YP_954024.1|, ref|YP_001360254.1|, ref|YP_001156989.1|, ref|ZP_00050136.2|, and ref|YP_591607.1| (SEQ ID NOS: 2723-2727), respectively, which all have the function assigned to SEQ ID NO: 2721 in Table 1. Amino acids conserved among all sequences are indicted by a "*" and generally conserved amino acids are indicated by a ":".

FIG. 77 depicts a sequence alignment (ClustalW) between SEQ ID NO: 715 (RAAC00603) and ref|YP_001309477.1|, ref|YP_001180339.1|, ref|NP_242735.1|, ref|YP_173905.1|, and ref|ZP_00603386.1| (SEQ ID NOS: 717-721), respectively, which all have the function assigned to SEQ ID NO: 715 in Table 1. Amino acids conserved among all sequences are indicted by a "*" and generally conserved amino acids are indicated by a ":".

FIG. 78 depicts a sequence alignment (ClustalW) between SEQ ID NO: 2738 (RAAC03180) and ref|YP_001664041.1|, ref|YP_001210714.1|, ref|NP_242309.1|, ref|ZP_02038515.1|, and ref|YP_085042.1| (SEQ ID NOS: 2740-2744), respectively, which all have the function assigned to SEQ ID NO: 2738 in Table 1. Amino acids conserved among all sequences are indicted by a "*" and generally conserved amino acids are indicated by a ":".

FIG. 79 depicts a sequence alignment (ClustalW) between SEQ ID NO: 2024 (RAAC02417) and ref|NP_469419.1|, ref|ZP_02309926.1|, ref|ZP_01926077.1|, ref|ZP_01941236.1|, and ref|YP_001111866.1| (SEQ ID NOS: 2026-2030), respectively, which all have the function assigned to SEQ ID NO: 2024 in Table 1. Amino acids conserved among all sequences are indicted by a "*" and generally conserved amino acids are indicated by a ":".

FIG. 80 depicts a sequence alignment (ClustalW) between SEQ ID NO: 1786 (RAAC01912) and ref|YP_001103030.1|, ref|YP_001363698.1|, ref|NP_625321.1|, ref|NP_822608.1|, and ref|ZP_00996757.1| (SEQ ID NOS: 1788-1792), respectively, which all have the function assigned to SEQ ID NO: 1786 in Table 1. Amino acids conserved among all sequences are indicted by a "*" and generally conserved amino acids are indicated by a ":".

FIG. 81 depicts a sequence alignment (ClustalW) between SEQ ID NO: 2330 (RAAC02663) and ref|YP_527240.1|, ref|NP_435364.1|, ref|YP_001313948.1|, ref|YP_001169444.1|, and ref|ZP_01509063.1| (SEQ ID NOS: 2332-2336), respectively, which all have the function assigned to SEQ ID NO: 2330 in Table 1. Amino acids conserved among all sequences are indicted by a "*" and generally conserved amino acids are indicated by a ":".

FIG. 82 depicts a sequence alignment (ClustalW) between SEQ ID NO: 1191 (RAAC01158) and ref|YP_077724.1|, ref|YP_643029.1|, ref|YP_174340.1|, ref|YP_001308645.1|, and ref|YP_516602.1| (SEQ ID NOS: 1193-1197), respectively, which all have the function assigned to SEQ ID NO: 1191 in Table 1. Amino acids conserved among all sequences are indicted by a "*" and generally conserved amino acids are indicated by a ":".

FIG. 83 depicts a sequence alignment (ClustalW) between SEQ ID NO: 137 (RAAC00068) and ref|ZP_02328287.1|, ref|YP_001420528.1|, ref|YP_430032.1|, ref|ZP_02082978.1|, and ref|ZP_01962813.1| (SEQ ID NOS: 139-143), respectively, which all have the function assigned to SEQ ID NO: 137 in Table 1. Amino acids conserved among all sequences are indicted by a "*" and generally conserved amino acids are indicated by a ":".

FIG. 84 depicts a sequence alignment (ClustalW) between SEQ ID NO: 1055 (RAAC01035) and ref|YP_642998.1|, ref|NP_822795.1|, emb|CAJ88752.1|, ref|YP_001191149.1|, and ref|YP_752794.1| (SEQ ID NOS: 1057-1061), respectively, which all have the function assigned to SEQ ID NO: 1055 in Table 1. Amino acids conserved among all sequences are indicted by a "*" and generally conserved amino acids are indicated by a ":".

FIG. 85 depicts a sequence alignment (ClustalW) between SEQ ID NO: 1854 (RAAC02031) and ref|YP_148128.1|, ref|YP_001126297.1|, ref|YP_900875.1|, ref|ZP_01662088.1|, and ref|ZP_01697892.1| (SEQ ID NOS: 1856-1860), respectively, which all have the function assigned to SEQ ID NO: 1854 in Table 1. Amino acids conserved among all sequences are indicted by a "*" and generally conserved amino acids are indicated by a ":".

FIG. 86 depicts a sequence alignment (ClustalW) between SEQ ID NO: 2653 (RAAC03005) and ref|YP_001127075.1|, ref|YP_148880.1|, ref|YP_832996.1|, ref|YP_949591.1|, and ref|YP_950253.1| (SEQ ID NOS: 2655-2659), respectively, which all have the function assigned to SEQ ID NO: 2653 in Table 1. Amino acids conserved among all sequences are indicted by a "*" and generally conserved amino acids are indicated by a ":".

FIG. 87 depicts a sequence alignment (ClustalW) between SEQ ID NO: 2160 (RAAC02459) and ref|YP_073926.1|, emb|CAB08003.1|, ref|YP_431134.1|, ref|YP_001422711.1|, and ref|YP_080763.1| (SEQ ID NOS: 2162-2166), respectively, which all have the function assigned to SEQ ID NO: 2160 in Table 1. Amino acids conserved among all sequences are indicted by a "*" and generally conserved amino acids are indicated by a ":".

FIG. 88 depicts a sequence alignment (ClustalW) between SEQ ID NO: 1293 (RAAC01353) and RAAC01353_nuc, ref|YP_147389.1|, ref|NP_243003.1|, ref|YP_001125502.1|, and ref|YP_001665938.1| (SEQ ID NOS: 1294-1298), respectively, which all have the function assigned to SEQ ID NO: 1293 in Table 1. Amino acids conserved among all sequences are indicted by a "*" and generally conserved amino acids are indicated by a ":".

FIG. 89 depicts a sequence alignment (ClustalW) between SEQ ID NO: 2109 (RAAC02432) and ref|ZP_02329176.1|, ref|YP_076367.1|, ref|NP_694155.1|, ref|YP_001126042.1|, and ref|YP_643152.1| (SEQ ID NOS: 2111-2115), respectively, which all have the function assigned to SEQ ID NO: 2109 in Table 1. Amino acids conserved among all sequences are indicted by a "*" and generally conserved amino acids are indicated by a ":".

FIG. 90 depicts a sequence alignment (ClustalW) between SEQ ID NO: 681 (RAAC00570) and emb|CAB65654.1|, ref|YP_001662226.1|, ref|YP_001664166.1|, ref|NP_624096.1|, and ref|ZP_02171282.1| (SEQ ID NOS: 683-687), respectively, which all have the function assigned to SEQ ID NO: 681 in Table 1. Amino acids conserved among all sequences are indicted by a "*" and generally conserved amino acids are indicated by a ":".

FIG. 91 depicts a sequence alignment (ClustalW) between SEQ ID NO: 375 (RAAC00269) and ref|ZP_01188890.1|, ref|ZP_01188246.1|, ref|ZP_01188241.1|, ref|NP_242794.1|, and ref|NP_244559.1| (SEQ ID NOS: 377-381), respectively, which all have the function assigned to SEQ ID NO: 375 in Table 1. Amino acids conserved among all sequences are indicted by a "*" and generally conserved amino acids are indicated by a ":".

FIG. 92 depicts a sequence alignment (ClustalW) between SEQ ID NO: 1837 (RAAC02012) and ref|YP_430255.1|, ref|YP_518526.1|, ref|ZP_01369294.1|, ref|YP_361384.1|, and ref|YP_001213325.1| (SEQ ID NOS: 1839-1843), respectively, which all have the function assigned to SEQ ID NO: 1837 in Table 1. Amino acids conserved among all sequences are indicted by a "*" and generally conserved amino acids are indicated by a ":".

FIG. 93 depicts a sequence alignment (ClustalW) between SEQ ID NO: 1667 (RAAC01701) and ref|NP_691275.1|, ref|NP_354021.1|, ref|YP_174284.1|, ref|ZP_01074644.1|, and ref|NP_772010.1| (SEQ ID NOS: 1669-1673), respectively, which all have the function assigned to SEQ ID NO: 1667 in Table 1. Amino acids conserved among all sequences are indicted by a "*" and generally conserved amino acids are indicated by a ":".

FIG. 94 depicts a sequence alignment (ClustalW) between SEQ ID NO: 936 (RAAC00927) and ref|ZP_02330514.1|, ref|NP_347485.1|, ref|YP_001253394.1|, ref|YP_001308605.1|, and ref|YP_001376921.1| (SEQ ID NOS: 938-942), respectively, which all have the function assigned to SEQ ID NO: 936 in Table 1. Amino acids conserved among all sequences are indicted by a "*" and generally conserved amino acids are indicated by a ":".

FIG. 95 depicts a sequence alignment (ClustalW) between SEQ ID NO: 953 (RAAC00935) and ref|YP_001422559.1|, ref|NP_391166.1|, gb|AAB87745.1|, pdb|1S3J|A, and ref|YP_001643469.1| (SEQ ID NOS: 955-959), respectively, which all have the function assigned to SEQ ID NO: 953 in Table 1. Amino acids conserved among all sequences are indicted by a "*" and generally conserved amino acids are indicated by a ":".

FIG. 96 depicts a sequence alignment (ClustalW) between SEQ ID NO: 1888 (RAAC02041) and ref|NP_693030.1|, ref|YP_001320949.1|, ref|YP_001512727.1|, ref|YP_001126687.1|, and ref|YP_148522.1| (SEQ ID NOS: 1890-1894), respectively, which all have the function assigned to SEQ ID NO: 1888 in Table 1. Amino acids conserved among all sequences are indicted by a "*" and generally conserved amino acids are indicated by a ":".

FIG. 97 depicts a sequence alignment (ClustalW) between SEQ ID NO: 2670 (RAAC02241) and ref|NP_629113.1|, ref|NP_824479.1|, ref|YP_001508494.1|, ref|ZP_01169478.1|, and ref|NP_631123.1| (SEQ ID NOS: 2672-2676), respectively, which all have the function assigned to SEQ ID NO: 2670 in Table 1. Amino acids conserved among all sequences are indicted by a "*" and generally conserved amino acids are indicated by a ":".

FIG. 98 depicts a sequence alignment (ClustalW) between SEQ ID NO: 2347 (RAAC02671) and ref|NP_388620.1|, ref|YP_001420380.1|, ref|YP_090401.1|, ref|YP_077997.1|, and ref|YP_714968.1| (SEQ ID NOS: 2349-2353), respectively, which all have the function assigned to SEQ ID NO: 2347 in Table 1. Amino acids conserved among all sequences are indicted by a "*" and generally conserved amino acids are indicated by a ":".

FIG. 99 depicts a sequence alignment (ClustalW) between SEQ ID NO: 664 (RAAC00549) and ref|YP_427081.1|, ref|YP_001141973.1|, ref|YP_927240.1|, ref|YP_001141729.1|, and ref|YP_856665.1| (SEQ ID NOS: 666-670), respectively, which all have the function assigned to SEQ ID NO: 664 in Table 1. Amino acids conserved among all sequences are indicted by a "*" and generally conserved amino acids are indicated by a ":".

FIG. 100 depicts a sequence alignment (ClustalW) between SEQ ID NO: 1123 (RAAC01080) and dbj|BAA00729.1|, ref|NP_389627.1|, ref|ZP_02328256.1|, ref|NP_833433.1|, and ref|YP_001375615.1| (SEQ ID NOS: 1125-1129), respectively, which all have the function assigned to SEQ ID NO: 1123 in Table 1. Amino acids conserved among all sequences are indicted by a "*" and generally conserved amino acids are indicated by a ":".

FIG. 101 depicts a sequence alignment (ClustalW) between SEQ ID NO: 1140 (RAAC01126) and ref|YP_146517.1|, ref|ZP_00739458.1|, ref|YP_001124699.1|, ref|YP_893832.1|, and ref|NP_830863.1| (SEQ ID NOS: 1142-1146), respectively, which all have the function assigned to SEQ ID NO: 664 in Table 1. Amino acids conserved among all sequences are indicted by a "*" and generally conserved amino acids are indicated by a ":".

FIG. 102 depicts a sequence alignment (ClustalW) between SEQ ID NO: 1174 (RAAC01138) and ref|NP_832103.1|, ref|YP_894956.1|, ref|ZP_02215257.1|, ref|NP_978750.1|, and ref|NP_844783.1| (SEQ ID NOS: 1176-1180), respectively, which all have the function assigned to SEQ ID NO: 1174 in Table 1. Amino acids conserved among all sequences are indicted by a "*" and generally conserved amino acids are indicated by a ":".

FIG. 103 depicts a sequence alignment (ClustalW) between SEQ ID NO: 409 (RAAC00354) and ref|YP_001309939.1|, ref|YP_001643723.1|, ref|YP_079403.1|, ref|YP_001647188.1|, and ref|NP_980994.1| (SEQ ID NOS: 411-415), respectively, which all have the function assigned to SEQ ID NO: 409 in Table 1. Amino acids conserved among all sequences are indicted by a "*" and generally conserved amino acids are indicated by a ":".

FIG. 104 depicts a sequence alignment (ClustalW) between SEQ ID NO: 2415 (RAAC02712) and ref|YP_036650.1|, ref|NP_978853.1|, ref|ZP_01173627.1|, ref|NP_844911.1|, and ref|ZP_02256518.1| (SEQ ID NOS: 2417-2421), respectively, which all have the function assigned to SEQ ID NO: 2415 in Table 1. Amino acids conserved among all sequences are indicted by a "*" and generally conserved amino acids are indicated by a ":".

FIG. 105 depicts a sequence alignment (ClustalW) between SEQ ID NO: 1072 (RAAC01059) and ref|ZP_02327699.1|, ref|YP_001126706.1|, ref|YP_148542.1|, ref|NP_243968.1|, and ref|YP_360433.1| (SEQ ID NOS: 1074-1078), respectively, which all have the function assigned to SEQ ID NO: 1072 in Table 1. Amino acids conserved among all sequences are indicted by a "*" and generally conserved amino acids are indicated by a ":".

FIG. 106 depicts a sequence alignment (ClustalW) between SEQ ID NO: 1565 (RAAC01638) and ref|YP_076316.1|, ref|YP_603589.1|, ref|NP_296097.1|, ref|YP_004584.1|, and ref|YP_144239.1| (SEQ ID NOS: 1567-1571), respectively, which all have the function assigned to SEQ ID NO: 1565 in Table 1. Amino acids conserved among all sequences are indicted by a "*" and generally conserved amino acids are indicated by a ":".

FIG. 107 depicts a sequence alignment (ClustalW) between SEQ ID NO: 1973 (RAAC02161) and ref|YP_148132.1|, ref|YP_001126301.1|, ref|ZP_02330236.1|, ref|NP_242446.1|, and ref|YP_175331.1| (SEQ ID NOS: 1975-1979), respectively, which all have the function assigned to SEQ ID NO: 1973 in Table 1. Amino acids conserved among all sequences are indicted by a "*" and generally conserved amino acids are indicated by a ":".

FIG. 108 depicts a sequence alignment (ClustalW) between SEQ ID NO: 392 (RAAC00349) and ref|YP_430046.1|, ref|YP_358986.1|, ref|YP_001213400.1|, ref|ZP_02330078.1|, and ref|YP_001114520.1| (SEQ ID NOS: 394-398), respectively, which all have the function assigned to SEQ ID NO: 392 in Table 1. Amino acids conserved among all sequences are indicted by a "*" and generally conserved amino acids are indicated by a ":".

FIG. 109 depicts a sequence alignment (ClustalW) between SEQ ID NO: 1327 (RAAC01375) and ref|YP_079987.1|, ref|YP_001634921.1|, ref|YP_290510.1|, ref|YP_001423330.1|, and ref|YP_001422015.1| (SEQ ID NOS: 1329-1333), respectively, which all have the function assigned to SEQ ID NO: 1327 in Table 1. Amino acids conserved among all sequences are indicted by a "*" and generally conserved amino acids are indicated by a ":".

FIG. 110 depicts a sequence alignment (ClustalW) between SEQ ID NO: 18 (RAAC00013) and ref|YP_146744.1|, ref|YP_001647744.1|, ref|NP_981573.1|, ref|ZP_02255842.1|, and ref|YP_897365.1| (SEQ ID NOS: 20-24), respectively, which all have the function assigned to SEQ ID NO: 18 in Table 1. Amino acids conserved among all sequences are indicted by a "*" and generally conserved amino acids are indicated by a ":".

FIG. 111 depicts a sequence alignment (ClustalW) between SEQ ID NO: 1480 (RAAC01493) and ref|YP_075596.1|, ref|YP_430668.1|, ref|YP_590553.1|, ref|YP_478499.1|, and ref|YP_001668480.1| (SEQ ID NOS: 1482-1486), respectively, which all have the function assigned to SEQ ID NO: 1480 in Table 1. Amino acids conserved among all sequences are indicted by a "*" and generally conserved amino acids are indicated by a ":".

FIG. 112 depicts a sequence alignment (ClustalW) between SEQ ID NO: 1582 (RAAC01653) and ref|ZP_00743391.1|, ref|YP_001375561.1|, ref|YP_896056.1|, ref|NP_845992.1|, and ref|ZP_02254866.1| (SEQ ID NOS: 1584-1588), respectively, which all have the function assigned to SEQ ID NO: 1582 in Table 1. Amino acids conserved among all sequences are indicted by a "*" and generally conserved amino acids are indicated by a ":".

FIG. 113 depicts a sequence alignment (ClustalW) between SEQ ID NO: 528 (RAAC00430) and ref|YP_001210836.1|, ref|YP_001111557.1|, ref|YP_001485333.1|, ref|NP_240971.1|, and ref|NP_387969.1| (SEQ ID NOS: 530-534), respectively, which all have the function assigned to SEQ ID NO: 528 in Table 1. Amino acids conserved among all sequences are indicted by a "*" and generally conserved amino acids are indicated by a ":".

FIG. 114 depicts a sequence alignment (ClustalW) between SEQ ID NO: 2823 (RAAC02359) and ref|NP_832076.1|, ref|YP_001645033.1|, ref|NP_844759.1|, ref|YP_001375058.1|, and ref|YP_535778.1| (SEQ ID NOS: 2825-2829), respectively, which all have the function assigned to SEQ ID NO: 2823 in Table 1. Amino acids conserved among all sequences are indicted by a "*" and generally conserved amino acids are indicated by a ":".

FIG. 115 depicts a sequence alignment (ClustalW) between SEQ ID NO: 2279 (RAAC02589) and ref|ZP_00591928.1|, ref|YP_001003150.1|, ref|NP_046614.1|, ref|YP_375842.1|, and ref|YP_001131112.1| (SEQ ID NOS: 2281-2285), respectively, which all have the function assigned to SEQ ID NO: 2279 in Table 1. Amino acids conserved among all sequences are indicted by a "*" and generally conserved amino acids are indicated by a ":".

FIG. 116 depicts a sequence alignment (ClustalW) between SEQ ID NO: 1412 (RAAC01442) and ref|ZP_02170919.1|, ref|YP_535778.1|, ref|ZP_01862118.1|, ref|NP_692713.1|, and ref|YP_359077.1| (SEQ ID NOS: 1414-1418), respectively, which all have the function assigned to SEQ ID NO: 1412 in Table 1. Amino acids conserved among all sequences are indicted by a "*" and generally conserved amino acids are indicated by a ":".

FIG. 117 depicts a sequence alignment (ClustalW) between SEQ ID NO: 69 (RAAC00027) and ref|YP_001213441.1|, ref|NP_244917.1|, ref|YP_001377189.1|, ref YP_149334.1|, and ref|YP_077145.1| (SEQ ID NOS: 71-75), respectively, which all have the function assigned to SEQ ID NO: 69 in Table 1. Amino acids conserved among all sequences are indicted by a "*" and generally conserved amino acids are indicated by a ":".

FIG. 118 depicts a sequence alignment (ClustalW) between SEQ ID NO: 2245 (RAAC02508) and ref|NP_624000.1|, ref|YP_001662406.1|, ref|YP_001664279.1|, ref|YP_001038261.1|, and ref|YP_001394883.1| (SEQ ID NOS: 2247-2251), respectively, which all have the function assigned to SEQ ID NO: 2245 in Table 1. Amino acids conserved among all sequences are indicted by a "*" and generally conserved amino acids are indicated by a ":".

FIG. 119 depicts a sequence alignment (ClustalW) between SEQ ID NO: 885 (RAAC00905) and ref|ZP_00739566.1|, ref|NP_830389.1|, ref|YP_001643379.1|, ref|ZP_00237866.1|, and ref|YP_034830.1| (SEQ ID NOS: 887-891), respectively, which all have the function assigned to SEQ ID NO: 885 in Table 1. Amino acids conserved among all sequences are indicted by a "*" and generally conserved amino acids are indicated by a ":".

FIG. 120 depicts a sequence alignment (ClustalW) between SEQ ID NO: 1769 (RAAC01903) and ref|YP_001244333.1|, emb|CAI44346.1|, ref|ZP_02128221.1|, ref|NP_228001.1|, and ref|ZP_02171167.1| (SEQ ID NOS: 1771-1775), respectively, which all have the function assigned to SEQ ID NO: 1769 in Table 1. Amino acids conserved among all sequences are indicted by a "*" and generally conserved amino acids are indicated by a ":".

FIG. 121 depicts a sequence alignment (ClustalW) between SEQ ID NO: 987 (RAAC00981) and ref|YP_290547.1|, ref|YP_074752.1|, ref|YP_480150.1|, ref|YP_001509772.1|, and ref|NP_627230.1| (SEQ ID NOS: 989-993), respectively, which all have the function assigned to SEQ ID NO: 987 in Table 1. Amino acids conserved among all sequences are indicted by a "*" and generally conserved amino acids are indicated by a ":".

FIGS. 122A and 122B depict a sequence alignment (ClustalW) between SEQ ID NO: 1004 (RAAC00986) and ref YP_001489923.1|, ref|ZP_01964315.1|, ref|NP_937072.1|, ref|NP_762428.1|, and ref|ZP_01847462.1| (SEQ ID NOS: 1006-1010), respectively, which all have the function assigned to SEQ ID NO: 1004 Table 1. Amino acids conserved among all sequences are indicted by a "*" and generally conserved amino acids are indicated by a ":".

FIGS. 123A and 123B depict a sequence alignment (ClustalW) between SEQ ID NO: 2704 (RAAC03031) and ref|ZP_01170738.1|, ref|ZP_00539543.1|, ref|ZP_02168828.1|, ref|ZP_01856429.1|, and ref|YP_001114416.1| (SEQ ID NOS: 2706-2710), respectively, which all have the function assigned to SEQ ID NO: 2704 Table 1. Amino acids conserved among all sequences are indicted by a "*" and generally conserved amino acids are indicated by a ":".

FIG. 124 depicts a sequence alignment (ClustalW) between SEQ ID NO: 1803 (RAAC01956) and pdb|1B4A|A, sp|O31408|ARGR_BACST, ref|ZP_00538558.1|, ref|NP_243643.1|, and ref|YP_001126414.1| (SEQ ID NOS: 1805-1809), respectively, which all have the function assigned to SEQ ID NO: 1803 in Table 1. Amino acids conserved among all sequences are indicted by a "*" and generally conserved amino acids are indicated by a ":".

FIG. 125 depicts a sequence alignment (ClustalW) between SEQ ID NO: 1497 (RAAC01498) and ref|YP_001127098.1|, ref|YP_148912.1|, ref|ZP_01696601.1|, ref|YP_176517.1|, and ref|ZP_01171675.1| (SEQ ID NOS: 1499-1503), respectively, which all have the function assigned to SEQ ID NO: 1497 in Table 1. Amino acids conserved among all sequences are indicted by a "*" and generally conserved amino acids are indicated by a ":".

FIG. 126 depicts a sequence alignment (ClustalW) between SEQ ID NO: 1548 (RAAC01624) and ref|YP_090740.1|, ref|YP_078338.1|, ref|NP_243093.1|, ref|YP_001126180.1|, and ref|YP_001422307.1| (SEQ ID NOS: 1550-1554), respectively, which all have the function assigned to SEQ ID NO: 1548 in Table 1. Amino acids conserved among all sequences are indicted by a "*" and generally conserved amino acids are indicated by a ":".

FIG. 127 depicts a sequence alignment (ClustalW) between SEQ ID NO: 171 (RAAC00077) and ref|ZP_01696173.1|, ref|ZP_02327860.1|, ref|ZP_00539488.1|, ref|NP_694112.1|, and ref|YP_034511.1| (SEQ ID NOS: 173-177), respectively, which all have the function assigned to SEQ ID NO: 171 in Table 1. Amino acids conserved among all sequences are indicted by a "*" and generally conserved amino acids are indicated by a ":".

FIG. 128 depicts a sequence alignment (ClustalW) between SEQ ID NO: 851 (RAAC00876) and ref|ZP_02170056.1|, ref|YP_079889.1|, ref|NP_980690.1|, ref|ZP_02257686.1|, and ref|YP_038371.1| (SEQ ID NOS: 853-857), respectively, which all have the function assigned to SEQ ID NO: 851 in Table 1. Amino acids conserved among all sequences are indicted by a "*" and generally conserved amino acids are indicated by a ":".

FIG. 129 depicts a sequence alignment (ClustalW) between SEQ ID NO: 647 (RAAC00525) and ref|YP_001488458.1|, ref|ZP_01665756.1|, ref|NP_347033.1|, ref|YP_080909.1|, and ref|YP_841318.1| (SEQ ID NOS: 649-653), respectively, which all have the function assigned to SEQ ID NO: 647 in Table 1. Amino acids conserved among all sequences are indicted by a "*" and generally conserved amino acids are indicated by a ":".

FIG. 130 depicts a sequence alignment (ClustalW) between SEQ ID NO: 1089 (RAAC01072) and ref|YP_849514.1|, ref|ZP_02320157.1|, ref|YP_013918.1|, ref|ZP_02330749.1|, and ref|NP_470676.1| (SEQ ID NOS: 1091-1095), respectively, which all have the function assigned to SEQ ID NO: 1089 in Table 1. Amino acids conserved among all sequences are indicted by a "*" and generally conserved amino acids are indicated by a ":".

FIG. 131 depicts a sequence alignment (ClustalW) between SEQ ID NO: 1310 (RAAC01366) and ref|YP_849898.1|, ref|NP_471127.1|, ref|NP_465208.1|, ref|YP_001124617.1|, and ref|YP_146331.1| (SEQ ID NOS: 1312-1316), respectively, which all have the function assigned to SEQ ID NO: 1310 Table 1. Amino acids conserved among all sequences are indicted by a "*" and generally conserved amino acids are indicated by a ":".

FIG. 132 depicts a sequence alignment (ClustalW) between SEQ ID NO: 1378 (RAAC01431) and ref|ZP_01666690.1|, ref|YP_077070.1|, ref|ZP_01173986.1|, ref|YP_814057.1|, and ref|NP_964223.1| (SEQ ID NOS: 1380-1384), respectively, which all have the function assigned to SEQ ID NO: 1378 in Table 1. Amino acids conserved among all sequences are indicted by a "*" and generally conserved amino acids are indicated by a ":".

FIG. 133 depicts a sequence alignment (ClustalW) between SEQ ID NO: 1514 (RAAC01505) and ref|YP_149084.1|, ref|YP_001127265.1|, ref|YP_074599.1|, ref|YP_001661816.1|, and ref|NP_621898.1| (SEQ ID NOS: 1516-1520), respectively, which all have the function assigned to SEQ ID NO: 1514 in Table 1. Amino acids conserved among all sequences are indicted by a "*" and generally conserved amino acids are indicated by a ":".

FIG. 134 depicts a sequence alignment (ClustalW) between SEQ ID NO: 1514 (RAAC01505) and ref|YP_149084.1|, ref|YP_001127265.1|, ref|YP_074599.1|, ref|YP_001661816.1|, and ref|NP_621898.1| (SEQ ID NOS: 1516-1520), respectively, which all have the function assigned to SEQ ID NO: 1514 in Table 1. Amino acids conserved among all sequences are indicted by a "*" and generally conserved amino acids are indicated by a ":".

FIG. 135 depicts a sequence alignment between SEQ ID NO: 1820 (RAAC01972) and ref|ZP_01171531.1|, ref|YP_001391734.1|, ref|YP_001308325.1|, ref|YP_518781.1|, and ref|YP_001254935.1| (SEQ ID NOS: 1822-1826), respectively, which all have the function assigned to SEQ ID NO: 1820 Table 1. Amino acids conserved among all sequences are indicted by a "*" and generally conserved amino acids are indicated by a ":".

FIG. 136 depicts a sequence alignment between SEQ ID NO: 154 (RAAC00076) and ref|YP_001488917.1|, ref|YP_079193.1|, ref|NP_241876.1|, ref|YP_174035.1|, and ref|ZP_01169176.1| (SEQ ID NOS: 156-160), respectively, which all have the function assigned to SEQ ID NO: 154 in Table 1. Amino acids conserved among all sequences are indicted by a "*" and generally conserved amino acids are indicated by a ":".

FIG. 137 depicts a sequence alignment between SEQ ID NO: 1939 (RAAC02144) and ref|ZP_02327651.1|, sp|O32720|SP2AA_PAEPO, ref|NP_833792.1|, ref|NP_846529.1|, and ref|YP_001646701.1| (SEQ ID NOS: 1941-1945), respectively, which all have the function assigned to SEQ ID NO: 1939 in Table 1. Amino acids conserved among all sequences are indicted by a "*" and generally conserved amino acids are indicated by a ":".

FIGS. 138A and 138B depict a sequence alignment between SEQ ID NO: 2126 (RAAC02439) and ref|YP_001125957.1|, ref|YP_147806.1|, ref|ZP_01695872.1|, ref|NP_693661.1|, and ref|ZP_01666100.1| (SEQ ID NOS: 2128-2132), respectively, which all have the function assigned to SEQ ID NO: 2126 Table 1. Amino acids conserved among all sequences are indicted by a "*" and generally conserved amino acids are indicated by a ":".

FIG. 139 depicts a sequence alignment between SEQ ID NO: 970 (RAAC00944) and ref|YP_001488778.1|, ref|YP_174256.1|, ref|YP_081277.1|, ref|YP_711801.1|, and ref|YP_804091.1| (SEQ ID NOS: 972-976), respectively, which all have the function assigned to SEQ ID NO: 970 in Table 1. Amino acids conserved among all sequences are indicted by a "*" and generally conserved amino acids are indicated by a ":".

FIGS. 140A and 140B depict a sequence alignment between SEQ ID NO: 2313 (RAAC02632) and ref|ZP_01695369.1|, ref|NP_764957.1|, ref|NP_646484.1|, ref|YP_001332652.1|, and ref|NP_372249.1| (SEQ ID NOS: 2315-2319), respectively, which all have the function assigned to SEQ ID NO: 2313 in Table 1. Amino acids conserved among all sequences are indicted by a "*" and generally conserved amino acids are indicated by a ":".

FIG. 141 depicts a sequence alignment between SEQ ID NO: 2211 (RAAC02474) and ref|ZP_02329050.1|, ref|YP_148935.1|, gb|AAX09759.1|, ref|YP_001127122.1|, and ref|YP_001376898.1| (SEQ ID NOS: 2213-2217), respectively, which all have the function assigned to SEQ ID NO: 2211 in Table 1. Amino acids conserved among all sequences are indicted by a "*" and generally conserved amino acids are indicated by a ":".

FIG. 142 depicts a sequence alignment between SEQ ID NO: 732 (RAAC00625) and ref|NP_244107.1|, ref|ZP_01188060.1|, ref|YP_176259.1|, ref|YP_148663.1|, and ref|YP_001126805.1| (SEQ ID NOS: 734-738), respectively, which all have the function assigned to SEQ ID NO: 732 in Table 1. Amino acids conserved among all sequences are indicted by a "*" and generally conserved amino acids are indicated by a ":".

FIG. 143 depicts a sequence alignment between SEQ ID NO: 800 (RAAC00733) and ref|ZP_01697803.1|, ref|YP_001488326.1|, ref|ZP_01860336.1|, ref|NP_834817.1|, and ref|NP_693386.1| (SEQ ID NOS: 802-806), respectively, which all have the function assigned to SEQ ID NO: 800 in Table 1. Amino acids conserved among all sequences are indicted by a "*" and generally conserved amino acids are indicated by a ":".

FIG. 144 depicts a sequence alignment between SEQ ID NO: 2194 (RAAC02466) and ref|ZP_01860336.1|, ref|ZP_02327791.1|, ref|NP_244433.1|, ref|ZP_01171669.1|, and ref|YP_001488326.1| (SEQ ID NOS: 2196-2200), respectively, which all have the function assigned to SEQ ID NO: 2194 in Table 1. Amino acids conserved among all sequences are indicted by a "*" and generally conserved amino acids are indicated by a ":".

FIG. 145 depicts a sequence alignment between SEQ ID NO: 2398 (RAAC02678) and ref|YP_001124914.1|, ref|YP_146760.1|, ref|YP_001319371.1|, ref|ZP_01723416.1|, and ref|ZP_00742387.1| (SEQ ID NOS: 2400-2404), respectively, which all have the function assigned to SEQ ID NO: 2398 in Table 1. Amino acids conserved among all sequences are indicted by a "*" and generally conserved amino acids are indicated by a ":".

FIG. 146 depicts a sequence alignment between SEQ ID NO: 2228 (RAAC02507) and ref|YP_517080.1|, ref|ZP_02185068.1|, ref|YP_001394884.1|, ref|ZP_01574787.1|, and ref|YP_001559227.1| (SEQ ID NOS: 2230-2234), respectively, which all have the function assigned to SEQ ID NO: 2228 in Table 1. Amino acids conserved among all sequences are indicted by a "*" and generally conserved amino acids are indicated by a ":".

FIGS. 147A and 147B depict a sequence alignment between SEQ ID NO: 902 (RAAC00906) and ref|ZP_01667455.1|, ref|ZP_01515931.1|, ref|YP_001430381.1|, ref|YP_001637100.1|, and ref|YP_146183.1| (SEQ ID NOS: 904-908), respectively, which all have the function assigned to SEQ ID NO: 902 Table 1. Amino acids conserved among all sequences are indicted by a "*" and generally conserved amino acids are indicated by a ":".

FIG. 148 depicts a sequence alignment between SEQ ID NO: 2364 (RAAC02211) and ref|YP_005108.1|, ref|YP_144769.1|, ref|YP_001124914.1|, ref|YP_001157480.1|, and ref|ZP_01773683.1| (SEQ ID NOS: 2366-2370), respectively, which all have the function assigned to SEQ ID NO: 2364 in Table 1. Amino acids conserved among all sequences are indicted by a "*" and generally conserved amino acids are indicated by a ":".

FIGS. 149A and 149B depict a sequence alignment between SEQ ID NO: 1463 (RAAC01489) and ref|ZP_01696335.1|, ref|ZP_01667455.1|, ref|ZP_00739567.1|, ref|YP_001037228.1|, and ref|NP_830390.1| (SEQ ID NOS: 1465-1469), respectively, which all have the function assigned to SEQ ID NO: 1463 Table 1. Amino acids conserved among all sequences are indicted by a "*" and generally conserved amino acids are indicated by a ":".

FIGS. 150A and 150B depict a sequence alignment between SEQ ID NO: 2007 (RAAC02391) and ref|ZP_01697157.1|, ref|YP_001212380.1|, ref|ZP_00539202.1|, ref|NP_693085.1|, and ref|ZP_02329946.1| (SEQ ID NOS: 2009-2013), respectively, which all have the function assigned to SEQ ID NO: 2007 Table 1. Amino acids conserved among all sequences are indicted by a "*" and generally conserved amino acids are indicated by a ":".

FIGS. 151A and 151B depict a sequence alignment between SEQ ID NO: 2551 (RAAC02885) and ref|YP_147095.1|, ref|ZP_01171502.1|, ref|YP_001125215.1|, ref|YP_001486785.1|, and ref|ZP_01861001.1| (SEQ ID NOS: 2553-2557), respectively, which all have the function assigned to SEQ ID NO: 2551 Table 1. Amino acids conserved among all sequences are indicted by a "*" and generally conserved amino acids are indicated by a ":".

FIG. 152 depicts a sequence alignment between SEQ ID NO: 2534 (RAAC02876) and ref|YP_001125206.1|, ref|ZP_01696550.1|, ref|YP_001410204.1|, ref|ZP_01860990.1|, and ref|NP_243310.1| (SEQ ID NOS: 2536-2540), respectively, which all have the function assigned to SEQ ID NO: 2534 in Table 1. Amino acids conserved among all sequences are indicted by a "*" and generally conserved amino acids are indicated by a ":".

FIG. 153 depicts a sequence alignment between SEQ ID NO: 1021 (RAAC00987) and ref|YP_001559801.1|, ref|ZP_01696550.1|, ref|YP_753552.1|, ref|NP_243310.1|, and ref|ZP_01725653.1| (SEQ ID NOS: 1023-1027), respectively, which all have the function assigned to SEQ ID NO: 1021 in Table 1. Amino acids conserved among all sequences are indicted by a "*" and generally conserved amino acids are indicated by a ":".

FIGS. 154A and 154B depict a sequence alignment between SEQ ID NO: 1990 (RAAC02162) and ref|YP_148131.1|, ref|YP_001126300.1|, ref|YP_079616.1|, ref|NP_390192.1|, and ref|YP_001487274.1| (SEQ ID NOS: 1992-1996), respectively, which all have the function assigned to SEQ ID NO: 1990 Table 1. Amino acids conserved among all sequences are indicted by a "*" and generally conserved amino acids are indicated by a ":".

FIG. 155 depicts a sequence alignment between SEQ ID NO: 1 (RAAC00012) and ref|YP_907563.1|, ref|YP_955166.1|, ref|ZP_00997175.1|, ref|YP_001133548.1|, and ref|YP_829143.1| (SEQ ID NOS: 3-7), respectively, which all have the function assigned to SEQ ID NO: 1 in Table 1. Amino acids conserved among all sequences are indicted by a "*" and generally conserved amino acids are indicated by a ":".

FIGS. 156A and 156B depict a sequence alignment between SEQ ID NO: 2876 (RAAC02761) and emb|CAG29823.1|, ref|NP_923516.1|, ref|ZP_02329377.1|, gb|EAY57526.1|, and ref|YP_149098.1| (SEQ ID NOS: 2878-2882), respectively, which all have the function assigned to SEQ ID NO: 2876 in Table 1. Amino acids conserved among all sequences are indicted by a "*" and generally conserved amino acids are indicated by a ":".

FIG. 157 depicts a sequence alignment between SEQ ID NO: 579 (RAAC00477) and ref|YP_001377039.1|, ref|NP_244654.1|, ref|YP_001647908.1|, ref|YP_897521.1|, and ref|ZP_00744427.1| (SEQ ID NOS: 581-585), respectively, which all have the function assigned to SEQ ID NO: 579 in Table 1. Amino acids conserved among all sequences are indicted by a "*" and generally conserved amino acids are indicated by a ":".

FIGS. 158A and 158B depict a sequence alignment between SEQ ID NO: 35 (RAAC00019) and ref|ZP_02169265.1|, ref|YP_848463.1|, ref|NP_694373.1|, ref|ZP_01695448.1|, and ref|ZP_00539458.1| (SEQ ID NOS: 37-41), respectively, which all have the function assigned to SEQ ID NO: 35 in Table 1. Amino acids conserved among all sequences are indicted by a "*" and generally conserved amino acids are indicated by a ":".

FIG. 159 depicts a sequence alignment between SEQ ID NO: 52 (RAAC00020) and ref|ZP_01169692.1|, ref|ZP_01695449.1|, ref|YP_001127497.1|, ref|YP_149327.1|, and ref|YP_534941.1| (SEQ ID NOS: 54-58), respectively, which all have the function assigned to SEQ ID NO: 52 in Table 1. Amino acids conserved among all sequences are indicted by a "*" and generally conserved amino acids are indicated by a ":".

FIGS. 160A and 160B depict a sequence alignment between SEQ ID NO: 1684 (RAAC01715) and gb|EDQ48509.1|, gb|EDQ48476.1|, ref|ZP_01575425.1|, ref|ZP_02025790.1|, and ref|YP_001662047.1| (SEQ ID NOS: 1686-1690), respectively, which all have the function assigned to SEQ ID NO: 1684 in Table 1. Amino acids conserved among all sequences are indicted by a "*" and generally conserved amino acids are indicated by a ":".

FIGS. 161A-161C depict a sequence alignment between SEQ ID NO: 1157 (RAAC01137) and ref|NP_978751.1|, ref|ZP_00741477.1|, ref|YP_894957.1|, ref|NP_844784.1|, and ref|ZP_02259481.1| (SEQ ID NOS: 1159-1163), respectively, which all have the function assigned to SEQ ID NO: 1157 in Table 1. Amino acids conserved among all sequences are indicted by a "*" and generally conserved amino acids are indicated by a ":".

FIGS. 162A-162C depict a sequence alignment between SEQ ID NO: 2910 (RAAC03013) and ref|ZP_02168855.1|, ref|NP_470526.1|, ref|ZP_02320069.1|, ref|ZP_01927122.1|, and ref|YP_013834.1| (SEQ ID NOS: 2912-2916), respectively, which all have the function assigned to SEQ ID NO: 2910 in Table 1. Amino acids conserved among all sequences are indicted by a "*" and generally conserved amino acids are indicated by a ":".

DETAILED DESCRIPTION

Bacterial DNA codes for information that regulates transcription of genes into mRNA, which codes for proteins or enzymes used for; control of growth, and processing of energy, carbon and other compounds by the cell. Most of these transcriptional regulators/repressors function to turn on and off genes to minimize expenditure of cellular energy in response to their growth environment (i.e., presence of growth substrate, metals, temperature, etc.). This can become a problem related to process development because regulation and control of enzymes for a specific reaction may lead to suboptimal growth or suboptimal production of a desired metabolite (enzyme or compound). The genome of *Alicyclobacillus acidocaldarius* strain ATCC 27009 contains numerous coding sequences for transcriptional regulators and repressors of proteins related to growth, and processing of carbon by the cell. These regulators and repressors may directly affect expression of glycosyl hydrolase and/or esterase enzymes for processing of biomass outside the cell, as well as controlling production of valuable secondary metabolites.

Metabolic engineering through modification (genetic engineering) of these regulatory responses for transcription is one approach for optimization of cellular processes, by way of non-limiting example, *Alicyclobacillus acidocaldarius*. Control of these genes will allow for over-expression of desired pathways (e.g., production of glycosyl hydrolases, organic acids or alcohols), or likewise elimination or causing reduced expression of genes leading to undesired pathways or products (e.g., proteins that control transcription of glycosyl hydrolase genes). Control of these genes, or using them as loci for controlling/optimizing carbon processing in organisms, such as, by way of non-limiting example, the thermoacidophile *Alicyclobacillus acidocaldarius* has not been previously attempted using genes and proteins from *Alicyclobacillus acidocaldarius*; thereby, making use of transcriptional regulators from this source novel.

Embodiments of the invention include genes and associated proteins related to regulation of growth and metabolism of the thermoacidophile *Alicyclobacillus acidocaldarius*. Coding sequences for genes related to these processes were determined from sequence information generated from sequencing the genome of *Alicyclobacillus acidocaldarius*. These genes and proteins may represent targets for metabolic engineering of *Alicyclobacillus acidocaldarius* or other organisms. Non-limiting examples of nucleotide sequences found within the genome of *Alicyclobacillus acidocaldarius*, and amino acids coded thereby, associated with regulation of growth and carbon metabolism are listed in Table 1. Regulators and repressors may be, without limitation, of the following classes: regulators that control growth, including cell division and growth under aerobic and anaerobic conditions; regulators that respond to environmental conditions such as temperature, metal concentration and metabolite concentration; regulators of secondary metabolite pathways such as amino acids, organic acids, alcohols, antibiotics, antibiotic resistance, enzymes related to DNA processing and others; repressors related to carbon processing operons that respond to the presence or absence of organic compounds in the growth environment; signal transduction regulators that control phases of growth and carbon processing; regulators that control the response of *Alicyclobacillus acidocaldarius* to its growth environment allowing movement toward carbon sources or biofilm formation on a carbon source; and others.

Embodiments of the invention relate in part to the gene sequences and/or protein sequences comprising genes and/or proteins of *Alicyclobacillus acidocaldarius*. Genes and proteins included are those which play a role in transcription and transcriptional control. Intracellular enzyme activities may be thermophilic and/or acidophilic in nature and general examples of similar genes are described in the literature. Classes of genes, sequences, enzymes and factors include, but are not limited to, those listed in Table 1.

TABLE 1

Alicyclobacillus acidocaldarius genes related to transcription and transcriptional regulation

| Reference | Gene Sequence | Protein Sequence | Function |
|---|---|---|---|
| RAAC00012 | SEQ ID NO: 2 | SEQ ID NO: 1 | C4-dicarboxylate transport protein |
| RAAC00013 | SEQ ID NO: 19 | SEQ ID NO: 18 | Transcriptional regulators, LysR family |
| RAAC00019 | SEQ ID NO: 36 | SEQ ID NO: 35 | Two-component sensor kinase yycG |
| RAAC00020 | SEQ ID NO: 53 | SEQ ID NO: 52 | Two-component response regulator yycF |
| RAAC00027 | SEQ ID NO: 70 | SEQ ID NO: 69 | Single-strand DNA binding protein |
| RAAC00039 | SEQ ID NO: 87 | SEQ ID NO: 86 | Stage 0 sporulation protein J |
| RAAC00040 | SEQ ID NO: 104 | SEQ ID NO: 103 | Chromosome partitioning protein parA |
| RAAC00045 | SEQ ID NO: 121 | SEQ ID NO: 120 | Jag protein |
| RAAC00068 | SEQ ID NO: 138 | SEQ ID NO: 137 | Transcriptional regulator, GntR family |
| RAAC00076 | SEQ ID NO: 155 | SEQ ID NO: 154 | Trp repressor binding protein |
| RAAC00077 | SEQ ID NO: 172 | SEQ ID NO: 171 | Gluconate operon transcriptional repressor |
| RAAC00092 | SEQ ID NO: 189 | SEQ ID NO: 188 | Prespore specific transcriptional activator rsfA |
| RAAC00113 | SEQ ID NO: 206 | SEQ ID NO: 205 | Cell-division initiation protein DivIB |
| RAAC00117 | SEQ ID NO: 223 | SEQ ID NO: 222 | Cell division protein ftsA |
| RAAC00118 | SEQ ID NO: 240 | SEQ ID NO: 239 | Cell division protein ftsZ |
| RAAC00120 | SEQ ID NO: 257 | SEQ ID NO: 256 | RNA polymerase sigma-E factor |
| RAAC00121 | SEQ ID NO: 274 | SEQ ID NO: 273 | RNA polymerase sigma-G factor |
| RAAC00134 | SEQ ID NO: 291 | SEQ ID NO: 290 | Pyrimidine operon regulatory protein pyrR |
| RAAC00147 | SEQ ID NO: 308 | SEQ ID NO: 307 | DNA-directed RNA polymerase omega chain |
| RAAC00161 | SEQ ID NO: 325 | SEQ ID NO: 324 | Small acid-soluble spore protein |
| RAAC00212 | SEQ ID NO: 342 | SEQ ID NO: 341 | Transcription state regulatory protein abrB |
| RAAC00215 | SEQ ID NO: 359 | SEQ ID NO: 358 | Phosphorelay inhibitor |
| RAAC00269 | SEQ ID NO: 376 | SEQ ID NO: 375 | Transcriptional regulator, LacI family |
| RAAC00349 | SEQ ID NO: 393 | SEQ ID NO: 392 | Transcriptional regulator, AsnC family |
| RAAC00354 | SEQ ID NO: 410 | SEQ ID NO: 409 | Transcriptional regulator, TetR family |
| RAAC00365 | SEQ ID NO: 427 | SEQ ID NO: 426 | N-acetylmuramoyl-L-alanine amidase |
| RAAC00371 | SEQ ID NO: 444 | SEQ ID NO: 443 | DNA-directed RNA polymerase alpha chain |
| RAAC00407 | SEQ ID NO: 461 | SEQ ID NO: 460 | DNA-directed RNA polymerase beta' chain |
| RAAC00408 | SEQ ID NO: 478 | SEQ ID NO: 477 | DNA-directed RNA polymerase beta chain |
| RAAC00415 | SEQ ID NO: 495 | SEQ ID NO: 494 | Transcription antitermination protein nusG |
| RAAC00418 | SEQ ID NO: 512 | SEQ ID NO: 511 | RNA polymerase sigma-H factor |
| RAAC00430 | SEQ ID NO: 529 | SEQ ID NO: 528 | DNA-binding protein |
| RAAC00436 | SEQ ID NO: 546 | SEQ ID NO: 545 | Transcriptional regulator ctsR |
| RAAC00475 | SEQ ID NO: 563 | SEQ ID NO: 562 | Transcription termination factor rho |
| RAAC00477 | SEQ ID NO: 580 | SEQ ID NO: 579 | Sporulation initiation phosphotransferase F |
| RAAC00480 | SEQ ID NO: 597 | SEQ ID NO: 596 | DNA-directed RNA polymerase delta chain |
| RAAC00483 | SEQ ID NO: 614 | SEQ ID NO: 613 | Regulator of kinase autophosphorylation inhibitor |
| RAAC00484 | SEQ ID NO: 631 | SEQ ID NO: 630 | Kinase autophosphorylation inhibitor kipI |
| RAAC00525 | SEQ ID NO: 648 | SEQ ID NO: 647 | Kdg operon repressor |
| RAAC00549 | SEQ ID NO: 665 | SEQ ID NO: 664 | Transcriptional regulator, MerR family |
| RAAC00570 | SEQ ID NO: 682 | SEQ ID NO: 681 | Transcriptional regulator, LacI family |
| RAAC00579 | SEQ ID NO: 699 | SEQ ID NO: 698 | Transcriptional regulator, ArsR family |
| RAAC00603 | SEQ ID NO: 716 | SEQ ID NO: 715 | Transcriptional regulator, ArsR family |
| RAAC00625 | SEQ ID NO: 733 | SEQ ID NO: 732 | Catabolite control protein A |
| RAAC00643 | SEQ ID NO: 750 | SEQ ID NO: 749 | Small acid-soluble spore protein |
| RAAC00650 | SEQ ID NO: 767 | SEQ ID NO: 766 | Glycosyltransferase |
| RAAC00675 | SEQ ID NO: 784 | SEQ ID NO: 783 | Transcriptional regulator |
| RAAC00733 | SEQ ID NO: 801 | SEQ ID NO: 800 | Catabolite repression protein crh |
| RAAC00856 | SEQ ID NO: 818 | SEQ ID NO: 817 | RNA polymerase sigma-K factor |
| RAAC00872 | SEQ ID NO: 835 | SEQ ID NO: 834 | Spore protease |
| RAAC00876 | SEQ ID NO: 852 | SEQ ID NO: 851 | Heat-inducible transcription repressor hrcA |
| RAAC00896 | SEQ ID NO: 869 | SEQ ID NO: 868 | RNA polymerase sigma factor rpoD |
| RAAC00905 | SEQ ID NO: 886 | SEQ ID NO: 885 | Two-component response regulator |
| RAAC00906 | SEQ ID NO: 903 | SEQ ID NO: 902 | Two component system histidine kinase |
| RAAC00923 | SEQ ID NO: 920 | SEQ ID NO: 919 | Small acid-soluble spore protein |
| RAAC00927 | SEQ ID NO: 937 | SEQ ID NO: 936 | Transcriptional regulator, MarR family |
| RAAC00935 | SEQ ID NO: 954 | SEQ ID NO: 953 | Transcriptional regulator, MarR family |
| RAAC00944 | SEQ ID NO: 971 | SEQ ID NO: 970 | Transcriptional activator tenA |
| RAAC00981 | SEQ ID NO: 988 | SEQ ID NO: 987 | Two-component response regulator |
| RAAC00986 | SEQ ID NO: 1005 | SEQ ID NO: 1004 | Two-component response regulator |
| RAAC00987 | SEQ ID NO: 1022 | SEQ ID NO: 1021 | Chemotaxis protein cheY |
| RAAC00991 | SEQ ID NO: 1039 | SEQ ID NO: 1038 | Glycosyltransferase |
| RAAC01035 | SEQ ID NO: 1056 | SEQ ID NO: 1055 | Transcriptional regulator, GntR family |
| RAAC01059 | SEQ ID NO: 1073 | SEQ ID NO: 1072 | Transcriptional regulator, TetR family |
| RAAC01072 | SEQ ID NO: 1090 | SEQ ID NO: 1089 | Repressor LexA |
| RAAC01078 | SEQ ID NO: 1107 | SEQ ID NO: 1106 | Ribose operon repressor |
| RAAC01080 | SEQ ID NO: 1124 | SEQ ID NO: 1123 | Transcriptional regulator, MerR family |
| RAAC01126 | SEQ ID NO: 1141 | SEQ ID NO: 1140 | Transcriptional regulator, TetR family |
| RAAC01137 | SEQ ID NO: 1158 | SEQ ID NO: 1157 | Transporter, MMPL family |
| RAAC01138 | SEQ ID NO: 1175 | SEQ ID NO: 1174 | Transcriptional regulator, TetR family |
| RAAC01158 | SEQ ID NO: 1192 | SEQ ID NO: 1191 | Transcriptional regulator, GntR family |
| RAAC01353 | SEQ ID NO: 1294 | SEQ ID NO: 1293 | Transcriptional regulator, IclR family |
| RAAC01366 | SEQ ID NO: 1311 | SEQ ID NO: 1310 | Peroxide operon regulator |
| RAAC01375 | SEQ ID NO: 1328 | SEQ ID NO: 1327 | Transcriptional regulators, LysR family |
| RAAC01377 | SEQ ID NO: 1345 | SEQ ID NO: 1344 | Glycosyltransferase |
| RAAC01427 | SEQ ID NO: 1362 | SEQ ID NO: 1361 | SspF protein |

TABLE 1-continued

*Alicyclobacillus acidocaldarius* genes related to transcription and transcriptional regulation

| Reference | Gene Sequence | Protein Sequence | Function |
|---|---|---|---|
| RAAC01431 | SEQ ID NO: 1379 | SEQ ID NO: 1378 | Pur operon repressor |
| RAAC01438 | SEQ ID NO: 1396 | SEQ ID NO: 1395 | Transcription-repair coupling factor |
| RAAC01442 | SEQ ID NO: 1413 | SEQ ID NO: 1412 | DNA-binding protein HU |
| RAAC01464 | SEQ ID NO: 1430 | SEQ ID NO: 1429 | Transcriptional regulator, Xre family |
| RAAC01465 | SEQ ID NO: 1447 | SEQ ID NO: 1446 | Transcription elongation factor greA |
| RAAC01489 | SEQ ID NO: 1464 | SEQ ID NO: 1463 | Two component system histidine kinase |
| RAAC01493 | SEQ ID NO: 1481 | SEQ ID NO: 1480 | Transcriptional regulators, LysR family |
| RAAC01498 | SEQ ID NO: 1498 | SEQ ID NO: 1497 | Central glycolytic genes regulator |
| RAAC01505 | SEQ ID NO: 1515 | SEQ ID NO: 1514 | Ribose operon repressor |
| RAAC01563 | SEQ ID NO: 1532 | SEQ ID NO: 1531 | Sporulation kinase D |
| RAAC01624 | SEQ ID NO: 1549 | SEQ ID NO: 1548 | Ebg operon repressor |
| RAAC01638 | SEQ ID NO: 1566 | SEQ ID NO: 1565 | Transcriptional regulator, TetR family |
| RAAC01653 | SEQ ID NO: 1583 | SEQ ID NO: 1582 | Transcriptional regulators, LysR family |
| RAAC01655 | SEQ ID NO: 1600 | SEQ ID NO: 1599 | Transcriptional regulator |
| RAAC01657 | SEQ ID NO: 1617 | SEQ ID NO: 1616 | Pyruvate dehydrogenase (acetyl-transferring) |
| RAAC01658 | SEQ ID NO: 1634 | SEQ ID NO: 1633 | Pyruvate dehydrogenase (acetyl-transferring) |
| RAAC01659 | SEQ ID NO: 1651 | SEQ ID NO: 1650 | Dihydrolipoyllysine-residue acetyltransferase |
| RAAC01701 | SEQ ID NO: 1668 | SEQ ID NO: 1667 | Transcriptional regulator, MarR family |
| RAAC01715 | SEQ ID NO: 1685 | SEQ ID NO: 1684 | Two-component response regulator yesN |
| RAAC01745 | SEQ ID NO: 1702 | SEQ ID NO: 1701 | Pyruvate dehydrogenase (acetyl-transferring) |
| RAAC01746 | SEQ ID NO: 1719 | SEQ ID NO: 1718 | Pyruvate dehydrogenase (acetyl-transferring) |
| RAAC01814 | SEQ ID NO: 1736 | SEQ ID NO: 1735 | RNA polymerase sigma-K factor |
| RAAC01826 | SEQ ID NO: 1753 | SEQ ID NO: 1752 | RNA polymerase ECF-type sigma factor |
| RAAC01903 | SEQ ID NO: 1770 | SEQ ID NO: 1769 | Two-component response regulator |
| RAAC01912 | SEQ ID NO: 1787 | SEQ ID NO: 1786 | Transcriptional regulator, DeoR family |
| RAAC01956 | SEQ ID NO: 1804 | SEQ ID NO: 1803 | Arginine repressor, argR |
| RAAC01972 | SEQ ID NO: 1821 | SEQ ID NO: 1820 | Transcription pleiotropic repressor codY |
| RAAC02012 | SEQ ID NO: 1838 | SEQ ID NO: 1837 | Transcriptional regulator, LytR family |
| RAAC02031 | SEQ ID NO: 1855 | SEQ ID NO: 1854 | Transcriptional regulator, GntR family |
| RAAC02034 | SEQ ID NO: 1872 | SEQ ID NO: 1871 | Germination protein gerE |
| RAAC02041 | SEQ ID NO: 1889 | SEQ ID NO: 1888 | Transcriptional regulator, MarR family |
| RAAC02112 | SEQ ID NO: 1906 | SEQ ID NO: 1905 | N utilization substance protein B |
| RAAC02142 | SEQ ID NO: 1923 | SEQ ID NO: 1922 | Serine-type D-Ala-D-Ala carboxypeptidase |
| RAAC02144 | SEQ ID NO: 1940 | SEQ ID NO: 1939 | Anti-sigma F factor antagonist |
| RAAC02146 | SEQ ID NO: 1957 | SEQ ID NO: 1956 | RNA polymerase sigma-F factor |
| RAAC02161 | SEQ ID NO: 1974 | SEQ ID NO: 1973 | Transcriptional regulatory protein resD |
| RAAC02162 | SEQ ID NO: 1991 | SEQ ID NO: 1990 | Sensor protein resE |
| RAAC02391 | SEQ ID NO: 2008 | SEQ ID NO: 2007 | Phosphate regulon sensor protein phoR |
| RAAC02417 | SEQ ID NO: 2025 | SEQ ID NO: 2024 | Transcriptional regulator, Cro/CI family |
| RAAC02421 | SEQ ID NO: 2042 | SEQ ID NO: 2041 | Glycosyltransferase |
| RAAC02426 | SEQ ID NO: 2059 | SEQ ID NO: 2058 | Pyruvate dehydrogenase (acetyl-transferring) |
| RAAC02427 | SEQ ID NO: 2076 | SEQ ID NO: 2075 | Pyruvate dehydrogenase (acetyl-transferring) |
| RAAC02428 | SEQ ID NO: 2093 | SEQ ID NO: 2092 | Dihydrolipoyllysine-residue acetyltransferase |
| RAAC02432 | SEQ ID NO: 2110 | SEQ ID NO: 2109 | Transcriptional regulator, IclR family |
| RAAC02439 | SEQ ID NO: 2127 | SEQ ID NO: 2126 | Sigma-54-dependent transcriptional activator |
| RAAC02454 | SEQ ID NO: 2144 | SEQ ID NO: 2143 | Prespore specific transcriptional activator rsfA |
| RAAC02459 | SEQ ID NO: 2161 | SEQ ID NO: 2160 | Transcriptional regulator, GntR family |
| RAAC02164 | SEQ ID NO: 2178 | SEQ ID NO: 2177 | SIR2 family protein |
| RAAC02466 | SEQ ID NO: 2195 | SEQ ID NO: 2194 | Catabolite repression protein crh |
| RAAC02474 | SEQ ID NO: 2212 | SEQ ID NO: 2211 | Hpr(ser) Kinase/Phosphatase |
| RAAC02507 | SEQ ID NO: 2229 | SEQ ID NO: 2228 | Two component system histidine kinase |
| RAAC02508 | SEQ ID NO: 2246 | SEQ ID NO: 2245 | Two-component response regulator |
| RAAC02546 | SEQ ID NO: 2263 | SEQ ID NO: 2262 | RNA polymerase sigma-H factor |
| RAAC02589 | SEQ ID NO: 2280 | SEQ ID NO: 2279 | DNA-binding protein HU |
| RAAC02603 | SEQ ID NO: 2297 | SEQ ID NO: 2296 | Transcription state regulatory protein abrB |
| RAAC02632 | SEQ ID NO: 2314 | SEQ ID NO: 2313 | Hpr(ser) Kinase/Phosphatase |
| RAAC02663 | SEQ ID NO: 2331 | SEQ ID NO: 2330 | Transcriptional regulator, GntR family |
| RAAC02671 | SEQ ID NO: 2348 | SEQ ID NO: 2347 | Transcriptional regulator, MerR family |
| RAAC02211 | SEQ ID NO: 2365 | SEQ ID NO: 2364 | Two component system histidine kinase |
| RAAC02673 | SEQ ID NO: 2382 | SEQ ID NO: 2381 | Glycerol uptake operon antiterminator regulatory protein |
| RAAC02678 | SEQ ID NO: 2399 | SEQ ID NO: 2398 | Two component system histidine kinase |
| RAAC02712 | SEQ ID NO: 2416 | SEQ ID NO: 2415 | Transcriptional regulator, TetR family |
| RAAC02227 | SEQ ID NO: 2518 | SEQ ID NO: 2517 | Serine-type D-Ala-D-Ala carboxypeptidase |
| RAAC02876 | SEQ ID NO: 2535 | SEQ ID NO: 2534 | Chemotaxis protein cheY |
| RAAC02885 | SEQ ID NO: 2552 | SEQ ID NO: 2551 | Chemotaxis protein cheA |
| RAAC02902 | SEQ ID NO: 2569 | SEQ ID NO: 2568 | N utilization substance protein A |
| RAAC02968 | SEQ ID NO: 2603 | SEQ ID NO: 2602 | RNA polymerase sigma-H factor |
| RAAC02984 | SEQ ID NO: 2620 | SEQ ID NO: 2619 | Arginine utilization regulatory protein rocR |
| RAAC02994 | SEQ ID NO: 2637 | SEQ ID NO: 2636 | Arginine utilization regulatory protein rocR |
| RAAC03005 | SEQ ID NO: 2654 | SEQ ID NO: 2653 | Transcriptional regulator, GntR family |
| RAAC02241 | SEQ ID NO: 2671 | SEQ ID NO: 2670 | Transcriptional regulator, MarR family |
| RAAC03015 | SEQ ID NO: 2688 | SEQ ID NO: 2687 | Serine-type D-Ala-D-Ala carboxypeptidase |
| RAAC03031 | SEQ ID NO: 2705 | SEQ ID NO: 2704 | Two-component response regulator |
| RAAC03156 | SEQ ID NO: 2722 | SEQ ID NO: 2721 | Transcriptional regulator, ArsR family |
| RAAC03180 | SEQ ID NO: 2739 | SEQ ID NO: 2738 | Transcriptional regulator, Cro/CI family |

TABLE 1-continued

*Alicyclobacillus acidocaldarius* genes related to transcription and transcriptional regulation

| Reference | Gene Sequence | Protein Sequence | Function |
|---|---|---|---|
| RAAC03184 | SEQ ID NO: 2756 | SEQ ID NO: 2755 | Transcriptional regulator |
| RAAC03236 | SEQ ID NO: 2773 | SEQ ID NO: 2772 | Transcription state regulatory protein abrB |
| RAAC02292 | SEQ ID NO: 2790 | SEQ ID NO: 2789 | Transcriptional regulator |
| RAAC02315 | SEQ ID NO: 2807 | SEQ ID NO: 2806 | Chromosome partitioning protein parA |
| RAAC02359 | SEQ ID NO: 2824 | SEQ ID NO: 2823 | DNA-binding protein HU |
| RAAC02381 | SEQ ID NO: 2841 | SEQ ID NO: 2840 | Glycosyltransferase |
| | SEQ ID NO: 2857 | | Catabolite-responsive element |
| | SEQ ID NO: 2858 | | Catabolite responsive element |
| RAAC02740 | SEQ ID NO: 2860 | SEQ ID NO: 2859 | Transcriptional regulator |
| RAAC02761 | SEQ ID NO: 2877 | SEQ ID NO: 2876 | Sensor protein kdpD |
| RAAC02937 | SEQ ID NO: 2894 | SEQ ID NO: 2893 | Transcriptional regulator |
| RAAC03013 | SEQ ID NO: 2911 | SEQ ID NO: 2910 | Transporter, MMPL family |
| RAAC03263 | SEQ ID NO: 2928 | SEQ ID NO: 2927 | RNA polymerase sigma-H factor |

The present invention relates to nucleotides sequences comprising isolated and/or purified nucleotide sequences of the genome of *Alicyclobacillus acidocaldarius* selected from the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments.

The present invention likewise relates to isolated and/or purified nucleotide sequences, characterized in that they comprise at least one of: a) a nucleotide sequence of at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present invention as meaning both a double-stranded or single-stranded DNA in the monomeric and dimeric (so-called in tandem) forms and the transcription products of the DNAs.

Aspects of the invention relate to nucleotide sequences in which it has been possible to isolate, purify or partially purify, starting from separation methods such as, for example, ion-exchange chromatography, by exclusion based on molecular size, or by affinity, or, alternatively, fractionation techniques based on solubility in different solvents, or starting from methods of genetic engineering such as amplification, cloning, and subcloning, it being possible for the sequences of the invention to be carried by vectors.

Isolated and/or purified nucleotide sequence fragment according to the invention will be understood as designating any nucleotide fragment of the genome of *Alicyclobacillus acidocaldarius*, and may include, by way of non-limiting example, a length of at least 8, 12, 20 25, 50, 75, 100, 200, 300, 400, 500, 1000, or more, consecutive nucleotides of the sequence from which it originates.

Specific fragment of an isolated and/or purified nucleotide sequence according to the invention will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

Homologous isolated and/or purified nucleotide sequence in the sense of the present invention is understood as meaning an isolated and/or purified nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequence in the sense of the present invention is understood as meaning a homologous nucleotide sequence having at least one nucleotide sequence of a specific fragment, such as defined above. The "specific" homologous sequences can comprise, for example, the sequences corresponding to the genomic sequence or to the sequences of its fragments representative of variants of the genome of *Alicyclobacillus acidocal-*

*darius*. These specific homologous sequences can thus correspond to variations linked to mutations within strains of *Alicyclobacillus acidocaldarius*, and especially correspond to truncations, substitutions, deletions and/or additions of at least one nucleotide. The homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci.* (U.S.A.) 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well-defined and only one value for the sequence identity between two compared sequences, which value corresponds to the value obtained for the best or optimal alignment.

In the BLAST N or BLAST P "BLAST 2 sequence" software, which is available at the web site ncbi.nlm.nih.gov/gorf/bl2.html, and habitually used by the inventors and in general by the skilled person for comparing and determining the identity between two sequences, gap cost which depends on the sequence length to be compared is directly selected by the software (i.e., 11.2 for substitution matrix BLOSUM-62 for length >85).

Complementary nucleotide sequence of a sequence of the invention is understood as meaning any DNA whose nucleotides are complementary to those of the sequence of the invention, and whose orientation is reversed (antisense sequence).

Hybridization under conditions of stringency with a nucleotide sequence according to the invention is understood as meaning hybridization under conditions of temperature and ionic strength chosen in such a way that they allow the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example, a temperature of 37° C. in the presence of a 2×SSC buffer, respectively require a globally less significant complementarity for the hybridization between the two sequences.

The stringent hybridization conditions described above for a polynucleotide with a size of approximately 350 bases will be adapted by a person skilled in the art for oligonucleotides of greater or smaller size, according to the teachings of Sambrook et al., 1989.

Among the isolated and/or purified nucleotide sequences according to the invention, are those that can be used as a primer or probe in methods allowing the homologous sequences according to the invention to be obtained, these methods, such as the polymerase chain reaction (PCR), nucleic acid cloning, and sequencing, being well known to a person skilled in the art.

Among the isolated and/or purified nucleotide sequences according to the invention, those are again preferred that can be used as a primer or probe in methods allowing the presence of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928, one of their fragments, or one of their variants such as defined below to be diagnosed.

The nucleotide sequence fragments according to the invention can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

Modified nucleotide sequence will be understood as meaning any nucleotide sequence obtained by mutagenesis according to techniques well known to a person skilled in the art, and containing modifications with respect to the normal sequences according to the invention, for example, mutations in the regulatory and/or promoter sequences of polypeptide expression, especially leading to a modification of the rate of expression of the polypeptide or to a modulation of the replicative cycle.

Modified nucleotide sequence will likewise be understood as meaning any nucleotide sequence coding for a modified polypeptide, such as defined below.

The present invention relates to nucleotide sequence comprising isolated and/or purified nucleotide sequences of *Alicyclobacillus acidocaldarius*, characterized in that they are selected from the sequences SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments.

Embodiments of the invention likewise relate to isolated and/or purified nucleotide sequences characterized in that they comprise a nucleotide sequence selected from: a) at least one of a nucleotide sequence of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or one of their fragments; b) a nucleotide sequence of a specific fragment of a sequence such as defined in a); c) a homologous nucleotide sequence having at least 80% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the invention are the nucleotide sequences of SEQ ID NOS: 13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581, 1594-1598, 1611-1615, 1628-1632, 1645-1649, 1662-1666, 1679-1683, 1696-1700, 1713-1717, 1730-1734, 1747-1751, 1764-1768, 1781-1785, 1798-1802, 1815-1819, 1832-1836, 1849-1853, 1866-1870, 1883-1887, 1900-1904, 1917-1921, 1934-1938, 1951-1955, 1968-1972, 1985-1989, 2002-2006, 2019-2023, 2036-2040, 2053-2057, 2070-2074, 2087-2091, 2104-2108, 2121-2125, 2138-2142, 2155-2159, 2172-2176, 2189-2193, 2206-2210, 2223-2227, 2240-2244, 2257-2261, 2274-2278, 2291-2295, 2308-2312, 2325-2329, 2342-2346, 2359-2363, 2376-2380, 2393-2397, 2410-2414, 2427-2431, 2529-2533, 2546-2550, 2563-2567, 2580-2584, 2614-2618, 2631-2635, 2648-2652, 2665-2669, 2682-2686, 2699-2703, 2716-2720, 2733-2737, 2750-2754, 2767-2771, 2784-2788, 2801-2805, 2818-2822, 2835-2839, 2852-2856, 2878-2882, 2888-2892, 2905-2909, 2922-2926, and 2939-2943, or fragments thereof and any isolated and/or purified nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 or fragments thereof. The homologous sequences can comprise, for example, the sequences corresponding to the genomic sequences *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide. As will be apparent to one of ordinary skill in the art, such homologues are easily created and identified using standard techniques and publicly available computer programs such as BLAST. As such, each homologue referenced above should be considered as set forth herein and fully described.

Embodiments of the invention comprise the isolated and/or purified polypeptides coded for by a nucleotide sequence according to the invention, or fragments thereof, whose sequence is represented by a fragment. Amino acid sequences corresponding to the isolated and/or purified polypeptides which can be coded for according to one of the three possible reading frames of at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928.

Embodiments of the invention likewise relate to the isolated and/or purified polypeptides, characterized in that they comprise a polypeptide selected from at least one of the amino acid sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 or one of their fragments.

Among the isolated and/or purified polypeptides, according to embodiments of the invention, are the isolated and/or purified polypeptides of amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2524-2528, 2541-2545, 2558-2562, 2575-2579, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2866-2870, 2883-2887, 2900-2914, 2917-2921, and 2934-2938, or fragments thereof or any other isolated and/or purified polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 or fragments thereof. As will be apparent to one of ordinary skill in the art, such homologues are easily created and identified using standard techniques and publicly available computer programs such as BLAST. As such, each homologue referenced above should be considered as set forth herein and fully described.

Embodiments of the invention also relate to the polypeptides, characterized in that they comprise a polypeptide selected from: a) a specific fragment of at least 5 amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the invention, the isolated and/or purified polypeptides according to the invention may be glycosylated, pegylated, and/or otherwise post-translationally modified. In further embodiments, glycosylation, pegylation, and/or other post-translational modifications may occur in vivo or in vitro and/or may be performed using chemical techniques. In additional embodiments, any glycosylation, pegylation and/or other post-translational modifications may be N-linked or O-linked.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other post-translational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

Aspects of the invention relate to polypeptides that are isolated or obtained by purification from natural sources, or else obtained by genetic recombination, or alternatively by chemical synthesis and that they may thus contain unnatural amino acids, as will be described below.

A "polypeptide fragment" according to the embodiments of the invention is understood as designating a polypeptide containing at least 5 consecutive amino acids, preferably 10 consecutive amino acids or 15 consecutive amino acids.

In the present invention, a specific polypeptide fragment is understood as designating the consecutive polypeptide fragment coded for by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the invention.

"Specific homologous polypeptide" will be understood as designating the homologous polypeptides such as defined above and having a specific fragment of polypeptide according to the invention.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. As will be apparent to one of ordinary skill in the art, such substitutions are easily created and identified using standard molecular biology techniques and publicly available computer programs such as BLAST. As such, each substitution referenced above should be considered as set forth herein and fully described. Examples of such substitutions in the amino acid sequences SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 may include those isolated and/or purified polypeptides of amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2524-2528, 2541-2545, 2558-2562, 2575-2579, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2866-2870, 2883-2887, 2900-2914, 2917-2921, and 2934-2938.

These equivalent amino acids can be determined either by depending on their structural homology with the amino acids, which they substitute, or on results of comparative tests of biological activity between the different polypeptides, which are capable of being carried out.

By way of non-limiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine, etc., the reverse substitutions naturally being envisageable under the same conditions.

In a further embodiment, substitutions are limited to substitutions in amino acids not conserved among other proteins which have similar identified activity. For example, one of ordinary skill in the art may align proteins of the same function in similar organisms and determine which amino acids are generally conserved among proteins of that function. One example of a program that may be used to generate such alignments is available at the website charite.de/bioinf/strap/ in conjunction with the databases provided by the NCBI. Examples of such polypeptides may include, but are not limited to, those found in amino acid sequence SEQ ID NOS: 8-12, 25-29, 42-46, 59-63, 76-80, 93-97, 110-114, 127-131, 144-148, 161-165, 178-182, 195-199, 212-216, 229-233, 246-250, 263-267, 280-284, 297-301, 314-318, 331-335, 348-352, 365-369, 382-386, 399-403, 416-420, 433-437, 450-454, 467-471, 484-488, 501-505, 518-522, 535-539, 552-556, 569-573, 586-590, 603-607, 620-624, 637-641, 654-658, 671-675, 688-692, 705-709, 722-726, 739-743, 756-760, 773-777, 790-794, 807-811, 824-828, 841-845, 858-862, 875-879, 892-896, 909-913, 926-930, 943-947, 960-964, 977-981, 994-998, 1011-1015, 1028-1032, 1045-1049, 1062-1066, 1079-1083, 1096-1100, 1113-1117, 1130-1134, 1147-1151, 1164-1168, 1181-1185, 1198-1202, 1300-1304, 1317-1321, 1334-1338, 1351-1355, 1368-1372, 1385-1389, 1402-1406, 1419-1423, 1436-1440, 1453-1457, 1470-1474, 1487-1491, 1504-1508, 1521-1525, 1538-1542, 1555-1559, 1572-1576, 1589-1593, 1606-1610, 1623-1627, 1640-1644, 1657-1661, 1674-1678, 1691-1695, 1708-1712, 1725-1729, 1742-1746, 1759-1763, 1776-1780, 1793-1797, 1810-1814, 1827-1831, 1844-1848, 1861-1865, 1878-1882, 1895-1899, 1912-1916, 1929-1933, 1946-1950, 1963-1967, 1980-1984, 1997-2001, 2014-2018, 2031-2035, 2048-

2052, 2065-2069, 2082-2086, 2099-2103, 2116-2120, 2133-2137, 2150-2154, 2167-2171, 2184-2188, 2201-2205, 2218-2222, 2235-2239, 2252-2256, 2269-2273, 2286-2290, 2303-2307, 2320-2324, 2337-2341, 2354-2358, 2371-2375, 2388-2392, 2405-2409, 2422-2426, 2524-2528, 2541-2545, 2558-2562, 2575-2579, 2609-2613, 2626-2630, 2643-2647, 2660-2664, 2677-2681, 2694-2698, 2711-2715, 2728-2732, 2745-2749, 2762-2766, 2779-2783, 2796-2800, 2813-2817, 2830-2834, 2847-2851, 2866-2870, 2883-2887, 2900-2914, 2917-2921, and 2934-2938.

Thus, according to one embodiment of the invention, substitutions or mutations may be made at positions that are generally conserved among proteins of that function. In a further embodiment, nucleic acid sequences may be mutated or substituted such that the amino acid they code for is unchanged (degenerate substitutions and/or mutations) and/or mutated or substituted such that any resulting amino acid substitutions or mutations are made at positions that are generally conserved among proteins of that function. Examples of such nucleic acid sequences may include, but are not limited to, those found in are the nucleotide sequences of SEQ ID NOS: 13-17, 30-34, 47-51, 64-68, 81-85, 98-102, 115-119, 132-136, 149-153, 166-170, 183-187, 200-204, 217-221, 234-238, 251-255, 268-272, 285-289, 302-306, 319-323, 336-340, 353-357, 370-374, 387-391, 404-408, 421-425, 438-442, 455-459, 472-476, 489-493, 506-510, 523-527, 540-544, 557-561, 574-578, 591-595, 608-612, 625-629, 642-646, 659-663, 676-680, 693-697, 710-714, 727-731, 744-748, 761-765, 778-782, 795-799, 812-816, 829-833, 846-850, 863-867, 880-884, 897-901, 914-918, 931-935, 948-952, 965-969, 982-986, 999-1003, 1016-1020, 1033-1037, 1050-1054, 1067-1071, 1084-1088, 1101-1105, 1118-1122, 1135-1139, 1152-1156, 1169-1173, 1186-1190, 1203-1207, 1305-1309, 1322-1326, 1339-1343, 1356-1360, 1373-1377, 1390-1394, 1407-1411, 1424-1428, 1441-1445, 1458-1462, 1475-1479, 1492-1496, 1509-1513, 1526-1530, 1543-1547, 1560-1564, 1577-1581, 1594-1598, 1611-1615, 1628-1632, 1645-1649, 1662-1666, 1679-1683, 1696-1700, 1713-1717, 1730-1734, 1747-1751, 1764-1768, 1781-1785, 1798-1802, 1815-1819, 1832-1836, 1849-1853, 1866-1870, 1883-1887, 1900-1904, 1917-1921, 1934-1938, 1951-1955, 1968-1972, 1985-1989, 2002-2006, 2019-2023, 2036-2040, 2053-2057, 2070-2074, 2087-2091, 2104-2108, 2121-2125, 2138-2142, 2155-2159, 2172-2176, 2189-2193, 2206-2210, 2223-2227, 2240-2244, 2257-2261, 2274-2278, 2291-2295, 2308-2312, 2325-2329, 2342-2346, 2359-2363, 2376-2380, 2393-2397, 2410-2414, 2427-2431, 2529-2533, 2546-2550, 2563-2567, 2580-2584, 2614-2618, 2631-2635, 2648-2652, 2665-2669, 2682-2686, 2699-2703, 2716-2720, 2733-2737, 2750-2754, 2767-2771, 2784-2788, 2801-2805, 2818-2822, 2835-2839, 2852-2856, 2878-2882, 2888-2892, 2905-2909, 2922-2926, and 2939-2943 or fragments thereof.

The specific homologous polypeptides likewise correspond to polypeptides coded for by the specific homologous nucleotide sequences such as defined above and thus comprise in the present definition the polypeptides, which are mutated or correspond to variants that can exist in *Alicyclobacillus acidocaldarius*, and which especially correspond to truncations, substitutions, deletions, and/or additions of at least one amino acid residue.

"Specific biologically active fragment of a polypeptide" according to an embodiment of the invention will be understood in particular as designating a specific polypeptide fragment, such as defined above, having at least one of the characteristics of polypeptides according to the invention. In certain embodiments the peptide is capable of behaving as at least one of the types of proteins outlined in Table 1.

The polypeptide fragments according to embodiments of the invention can correspond to isolated or purified fragments naturally present in *Alicyclobacillus acidocaldarius* or correspond to fragments that can be obtained by cleavage of the polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, from hosts transformed by an expression vector according to the invention containing a nucleic acid allowing the expression of the fragments, placed under the control of appropriate regulation and/or expression elements.

"Modified polypeptide" of a polypeptide according to an embodiment of the invention is understood as designating a polypeptide obtained by genetic recombination or by chemical synthesis as will be described below, having at least one modification with respect to the normal sequence. These modifications may or may not be able to bear on amino acids at the origin of specificity, and/or of activity, or at the origin of the structural conformation, localization, and of the capacity of membrane insertion of the polypeptide according to the invention. It will thus be possible to create polypeptides of equivalent, increased, or decreased activity, and of equivalent, narrower, or wider specificity. Among the modified polypeptides, it is necessary to mention the polypeptides in which up to 5 or more amino acids can be modified, truncated at the N- or C-terminal end, or even deleted or added.

The methods allowing the modulations on eukaryotic or prokaryotic cells to be demonstrated are well known to a person of ordinary skill in the art. It is likewise well understood that it will be possible to use the nucleotide sequences coding for the modified polypeptides for the modulations, for example, through vectors according to the invention and described below.

The preceding modified polypeptides can be obtained by using combinatorial chemistry, in which it is possible to systematically vary parts of the polypeptide before testing them on models, cell cultures or microorganisms, for example, to select the compounds that are most active or have the properties sought.

Chemical synthesis likewise has the advantage of being able to use unnatural amino acids, or nonpeptide bonds.

Thus, in order to improve the duration of life of the polypeptides, according to the invention, it may be of interest to use unnatural amino acids, for example, in D form, or else amino acid analogs, especially sulfur-containing forms, for example.

Finally, it will be possible to integrate the structure of the polypeptides according to the invention, its specific or modified homologous forms, into chemical structures of polypeptide type or others. Thus, it may be of interest to provide at the N- and C-terminal ends compounds not recognized by proteases.

The nucleotide sequences coding for a polypeptide according to the invention are likewise part of the invention.

The invention likewise relates to nucleotide sequences utilizable as a primer or probe, characterized in that the sequences are selected from the nucleotide sequences according to the invention.

It is well understood that the present invention, in various embodiments, likewise relates to specific polypeptides of *Alicyclobacillus acidocaldarius*, coded for by nucleotide sequences, capable of being obtained by purification from natural polypeptides, by genetic recombination or by chemical synthesis by procedures well known to a person skilled in the art and such as described in particular below. In the same manner, the labeled or unlabeled mono- or polyclonal antibodies directed against the specific polypeptides coded for by the nucleotide sequences are also encompassed by the invention.

Embodiments of the invention additionally relate to the use of a nucleotide sequence according to the invention as a primer or probe for the detection and/or the amplification of nucleic acid sequences.

The nucleotide sequences according to embodiments of the invention can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially of at least 20 nucleotides.

Other amplification techniques of the target nucleic acid can be advantageously employed as alternatives to PCR.

The nucleotide sequences of the invention, in particular the primers according to the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); and the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al., as well as by Stone et al. in 1996.

In the case where the target polynucleotide to be detected is possibly an RNA, for example, an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the invention also comprise the nucleotide sequences utilizable as a probe or primer according to the invention, characterized in that they are labeled with a radioactive compound or with a nonradioactive compound.

The unlabeled nucleotide sequences can be used directly as probes or primers, although the sequences are generally labeled with a radioactive isotope ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes, which are utilizable for numerous applications.

Examples of nonradioactive labeling of nucleotide sequences are described, for example, in French Patent No. 7810975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The invention, in various embodiments, likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between the capture probe and the target nucleic acid is then detected with the aid of a second probe, a so-called detection probe, labeled with an easily detectable element.

Another aspect of the present invention is a vector for the cloning and/or expression of a sequence, characterized in that it contains a nucleotide sequence according to the invention.

The vectors, according to the invention, characterized in that they contain the elements allowing the integration, expression and/or the secretion of the nucleotide sequences in a determined host cell, are likewise part of the invention.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the invention may be inserted into autonomous replication vectors within the chosen host, or integrated vectors of the chosen host.

Such vectors will be prepared according to the methods currently used by a person skilled in the art, and it will be possible to introduce the clones resulting therefrom into an appropriate host by standard methods, such as, for example, lipofection, electroporation, and thermal shock.

The vectors according to the invention are, for example, vectors of plasmid or viral origin. One example of a vector for the expression of polypeptides of the invention is *Baculovirus*.

These vectors are useful for transforming host cells in order to clone or to express the nucleotide sequences of the invention.

The invention likewise comprises the host cells transformed by a vector according to the invention.

These cells can be obtained by the introduction into host cells of a nucleotide sequence inserted into a vector such as defined above, then the culturing of the cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plants cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example, Sf9 insect cells (Luckow, 1993).

Embodiments of the invention likewise relate to organisms comprising one of the transformed cells according to the invention.

The obtainment of transgenic organisms, according to the invention, of expressing one or more of the genes of *Alicyclobacillus acidocaldarius* or part of the genes may be carried out in, for example, rats, mice, or rabbits according to methods well known to a person skilled in the art, such as by viral or nonviral transfections. It will be possible to obtain the transgenic organisms expressing one or more of the genes by transfection of multiple copies of the genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of the chimeras.

The transformed cells, as well as the transgenic organisms according to the invention, are utilizable in procedures for preparation of recombinant polypeptides.

It is today possible to produce recombinant polypeptides in relatively large quantity by genetic engineering using the cells transformed by expression vectors according to the invention or using transgenic organisms according to the invention.

The procedures for preparation of a polypeptide of the invention in recombinant form, characterized in that they employ a vector and/or a cell transformed by a vector according to the invention and/or a transgenic organism comprising one of the transformed cells according to the invention are themselves comprised in the present invention.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among the procedures for preparation of a polypeptide of the invention in recombinant form, the preparation procedures employing a vector, and/or a cell transformed by the vector and/or a transgenic organism comprising one of the transformed cells, containing a nucleotide sequence according to the invention coding for a polypeptide of *Alicyclobacillus acidocaldarius*.

A variant according to the invention may consist of producing a recombinant polypeptide fused to a "carrier" protein (chimeric protein). The advantage of this system is that it may allow stabilization of and/or a decrease in the proteolysis of the recombinant product, an increase in the solubility in the course of renaturation in vitro and/or a simplification of the purification when the fusion partner has an affinity for a specific ligand.

More particularly, the invention relates to a procedure for preparation of a polypeptide of the invention comprising the following steps: a) culture of transformed cells under conditions allowing the expression of a recombinant polypeptide of a nucleotide sequence according to the invention; b) if need be, recovery of the recombinant polypeptide.

When the procedure for preparation of a polypeptide of the invention employs a transgenic organism according to the invention, the recombinant polypeptide is then extracted from the organism.

The invention also relates to a polypeptide that is capable of being obtained by a procedure of the invention, such as described previously.

The invention also comprises a procedure for preparation of a synthetic polypeptide, characterized in that it uses a sequence of amino acids of polypeptides according to the invention.

The invention likewise relates to a synthetic polypeptide obtained by a procedure according to the invention.

The polypeptides according to the invention can likewise be prepared by techniques that are conventional in the field of the synthesis of peptides. This synthesis can be carried out in homogeneous solution or in solid phase.

For example, recourse can be made to the technique of synthesis in a homogeneous solution described by Houben-Weyl in 1974.

This method of synthesis consists in successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids that are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The invention additionally relates to hybrid polypeptides having at least one polypeptide according to the invention, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the invention in glycosylated, pegylated, and/or otherwise post-translationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the invention, associated with a possibly immunogenic part, in particular, an epitope of the diphtheria toxin, the tetanus toxin, a surface antigen of the hepatitis B virus (Patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

The hybrid nucleotide sequences coding for a hybrid polypeptide as well as the hybrid polypeptides according to the invention characterized in that they are recombinant polypeptides obtained by the expression of the hybrid nucleotide sequences are likewise part of the invention.

The invention likewise comprises the vectors characterized in that they contain one of the hybrid nucleotide sequences. The host cells transformed by the vectors, the transgenic organisms comprising one of the transformed cells as well as the procedures for preparation of recombinant polypeptides using the vectors, the transformed cells and/or the transgenic organisms are, of course, likewise part of the invention.

The polypeptides according to the invention, the antibodies according to the invention described below and the nucleotide sequences according to the invention can advantageously be employed in procedures for the detection and/or identification of *Alicyclobacillus acidocaldarius*, in a sample capable of containing them. These procedures, according to the specificity of the polypeptides, the antibodies and the nucleotide sequences according to the invention that will be used, will in particular be able to detect and/or to identify *Alicyclobacillus acidocaldarius*.

The polypeptides according to the invention can advantageously be employed in a procedure for the detection and/or the identification of *Alicyclobacillus acidocaldarius* in a sample capable of containing them, characterized in that it comprises the following steps: a) contacting of this sample with a polypeptide or one of its fragments according to the invention (under conditions allowing an immunological reaction between the polypeptide and the antibodies possibly present in the biological sample); and b) demonstration of the antigen-antibody complexes possibly formed.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological processes (RIA) or their equivalent.

Thus, the invention likewise relates to the polypeptides according to the invention, labeled with the aid of an adequate label, such as, of the enzymatic, fluorescent or radioactive type.

Such methods comprise, for example, the following steps: deposition of determined quantities of a polypeptide composition according to the invention in the wells of a microtiter plate, introduction into the wells of increasing dilutions of serum, or of a biological sample other than that defined previously, having to be analyzed, incubation of the wells of the microtiter plate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example, at 550 nm, detection, by comparison with a control test, of the quantity of hydrolyzed substrate.

The polypeptides according to the invention allow monoclonal or polyclonal antibodies to be prepared which are characterized in that they specifically recognize the polypeptides according to the invention. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the invention, associated with an adjuvant of the immune response, and then purification of the specific antibodies contained in the serum of the immunized animals on an affinity column on which the polypeptide, which has served as an antigen, has previously been immobilized. The polyclonal antibodies according to the invention can also be prepared by purification, on an affinity column on which a polypeptide according to the invention has previously been immobilized, of the antibodies contained in the serum of an animal immunologically challenged by *Alicyclobacillus acidocaldarius*, or a polypeptide or fragment according to the invention.

The invention likewise relates to mono- or polyclonal antibodies or their fragments, or chimeric antibodies, characterized in that they are capable of specifically recognizing a polypeptide according to the invention.

It will likewise be possible for the antibodies of the invention to be labeled in the same manner as described previously for the nucleic probes of the invention, such as a labeling of enzymatic, fluorescent or radioactive type.

The invention is additionally directed at a procedure for the detection and/or identification of *Alicyclobacillus acidocaldarius* in a sample, characterized in that it comprises the following steps: a) contacting of the sample with a mono- or polyclonal antibody according to the invention (under conditions allowing an immunological reaction between the antibodies and the polypeptides of *Alicyclobacillus acidocaldarius* possibly present in the biological sample); and b) demonstration of the antigen-antibody complex possibly formed.

The present invention likewise relates to a procedure for the detection and/or the identification of *Alicyclobacillus acidocaldarius* in a sample, characterized in that it employs a nucleotide sequence according to the invention.

More particularly, the invention relates to a procedure for the detection and/or the identification of *Alicyclobacillus acidocaldarius* in a sample, characterized in that it contains the following steps: a) if need be, isolation of the DNA from the sample to be analyzed; b) specific amplification of the DNA of the sample with the aid of at least one primer, or a pair of primers, according to the invention; and c) demonstration of the amplification products.

These can be detected, for example, by the technique of molecular hybridization utilizing a nucleic probe according to the invention. This probe will advantageously be labeled with a nonradioactive (cold probe) or radioactive isotope.

For the purposes of the present invention, "DNA of the biological sample" or "DNA contained in the biological sample" will be understood as meaning either the DNA present in the biological sample considered, or possibly the cDNA obtained after the action of an enzyme of reverse transcriptase type on the RNA present in the biological sample.

A further embodiment of the invention comprises a method, characterized in that it comprises the following steps: a) contacting of a nucleotide probe according to the invention with a biological sample, the DNA contained in the biological sample having, if need be, previously been made accessible to hybridization under conditions allowing the hybridization of the nucleotide probe with the DNA of the sample; and b) demonstration of the hybrid formed between the nucleotide probe and the DNA of the biological sample.

The present invention also relates to a procedure according to the invention, characterized in that it comprises the following steps: a) contacting of a nucleotide probe immobilized on a support according to the invention with a biological sample, the DNA of the sample having, if need be, previously been made accessible to hybridization, under conditions allowing the hybridization of the nucleotide probe with the DNA of the sample; b) contacting of the hybrid formed between the nucleotide probe immobilized on a support and the DNA contained in the biological sample, if need be after elimination of the DNA of the biological sample which has not hybridized with the nucleotide probe, with a nucleotide probe labeled according to the invention; and c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the invention.

Embodiments of methods include placing a recombinant, purified, and/or isolated polypeptide selected from the group consisting of a polypeptide having at least 90% sequence identity to SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in, or replacing a component, of an in-vitro transcription system such as, by way of non-limiting example, a polymerase chain reaction or a reticulocyte lysate transcription/translation system.

Further embodiments of methods include placing a cell producing or encoding a recombinant, purified, and/or isolated nucleotide sequence comprising a nucleotide sequence selected from the group consisting of a nucleotide sequence having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 in an environment comprising temperatures at or above about 25, 30, 35, 40, 45, 50, 55, 60, 65, 70, 75, 80, 85, 90, and/or 95 degrees Celsius and/or a pH at, below, and/or above 8, 7, 6, 5, 4, 3, 2, 1, and/or 0.

The present invention provides cells that have been genetically manipulated to have an altered capacity to produce expressed proteins. In particular, the present invention relates to Gram-positive microorganisms, such as *Bacillus* species having enhanced expression of a protein of interest, wherein one or more chromosomal genes have been inactivated, and/or wherein one or more chromosomal genes have been deleted from the *Bacillus* chromosome. In some further embodiments, one or more indigenous chromosomal regions have been deleted from a corresponding wild-type *Bacillus* host chromosome. In further embodiments, the *Bacillus* is an *Alicyclobacillus* sp. or *Alicyclobacillus acidocaldarius*.

In additional embodiments, methods of modulating transcription or transcription or transcriptional control at temperatures at or above about 25, 30, 35, 40, 45, 50, 55, 60, 65, 70, 75, 80, 85, 90, and/or 95 degrees Celsius and/or at a pH at, below, and/or above 8, 7, 6, 5, 4, 3, 2, 1, and/or 0 via a recombinant, purified, and/or isolated nucleotide sequence comprising a nucleotide sequence selected from the group consisting of a nucleotide sequence having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

Further embodiments of the invention may comprise a kit for modulating transcription or transcriptional control, the kit comprising a recombinant, purified, and/or isolated nucleotide sequence comprising a nucleotide sequence selected from the group consisting of a nucleotide sequences having at least 90% sequence identity to at least one of the sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 and/or a recombinant, purified, and/or isolated polypeptide selected from the group consisting of a polypeptide having at least 90% sequence identity to at least one of the sequences of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927.

In embodiments of the invention any one of the isolated and/or purified polypeptides according to the invention may be enzymatically or functionally active at temperatures at or above about 25, 30, 35, 40, 45, 50, 55, 60, 65, 70, 75, 80, 85, 90, and/or 95 degrees Celsius and/or may be enzymatically or functionally active at a pH at, below, and/or above 8, 7, 6, 5, 4, 3, 2, 1, and/or 0. In further embodiments of the invention, glycosylation, pegylation, and/or other post-translational modification may be required for the isolated and/or purified polypeptides according to the invention to be enzymatically or functionally active at a pH at or below 8, 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

The invention is described in additional detail in the following illustrative examples. Although the examples may represent only selected embodiments of the invention, it should be understood that the following examples are illustrative and not limiting.

EXAMPLES

Example 1: Transcription and Transcriptional Control Using Nucleotide and Amino Acid Sequences from *Alicyclobacillus acidocaldarius*

Provided in SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 are a nucleotide sequences isolated from *Alicyclobacillus acidocaldarius* and coding for the polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927. The nucleotide sequences of SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 are placed into expression vectors using techniques standard in the art. The vectors are then provided to cells such as bacteria cells or eukaryotic cells such as Sf9 cells or CHO cells. In conjunction with the normal machinery in present in the cells, the vectors comprising SEQ ID NOS: 2, 19, 36, 53, 70, 87, 104, 121, 138, 155, 172, 189, 206, 223, 240, 257, 274, 291, 308, 325, 342, 359, 376, 393, 410, 427, 444, 461, 478, 495, 512, 529, 546, 563, 580, 597, 614, 631, 648, 665, 682, 699, 716, 733, 750, 767, 784, 801, 818, 835, 852, 869, 886, 903, 920, 937, 954, 971, 988, 1005, 1022, 1039, 1056, 1073, 1090, 1107, 1124, 1141, 1158, 1175, 1192, 1294, 1311, 1328, 1345, 1362, 1379, 1396, 1413, 1430, 1447, 1464, 1481, 1498, 1515, 1532, 1549, 1566, 1583, 1600, 1617, 1634, 1651, 1668, 1685, 1702, 1719, 1736, 1753, 1770, 1787, 1804, 1821, 1838, 1855, 1872, 1889, 1906, 1923, 1940, 1957, 1974, 1991, 2008, 2025, 2042, 2059, 2076, 2093, 2110, 2127, 2144, 2161, 2178, 2195, 2212, 2229, 2246, 2263, 2280, 2297, 2314, 2331, 2348, 2365, 2382, 2399, 2416, 2518, 2535, 2552, 2569, 2603, 2620, 2637, 2654, 2671, 2688, 2705, 2722, 2739, 2756, 2773, 2790, 2807, 2824, 2841, 2857, 2858, 2860, 2877, 2894, 2911, and 2928 produce the polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 are then isolated and/or purified. The isolated and/or purified polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 are then each demonstrated to have one or more of the activities provided in Table 1.

The isolated and/or purified polypeptides of SEQ ID NOS: 1, 18, 35, 52, 69, 86, 103, 120, 137, 154, 171, 188, 205, 222, 239, 256, 273, 290, 307, 324, 341, 358, 375, 392, 409, 426, 443, 460, 477, 494, 511, 528, 545, 562, 579, 596, 613, 630, 647, 664, 681, 698, 715, 732, 749, 766, 783, 800, 817, 834, 851, 868, 885, 902, 819, 936, 953, 970, 987, 1004, 1021, 1038, 1055, 1072, 1089, 1106, 1123, 1140, 1157, 1174, 1191, 1293, 1310, 1327, 1344, 1361, 1378, 1395, 1412, 1429, 1446, 1463, 1480, 1497, 1514, 1531, 1548, 1565, 1582, 1599, 1616, 1633, 1650, 1667, 1684, 1701, 1718, 1735, 1752, 1769, 1786, 1803, 1820, 1837, 1854, 1871, 1888, 1905, 1922, 1939, 1956, 1973, 1990, 2007, 2024, 2041, 2058, 2075, 2092, 2109, 2126, 2143, 2160, 2177, 2194, 2211, 2228, 2245, 2262, 2279, 2296, 2313, 2330, 2347, 2364, 2381, 2398, 2415, 2517, 2534, 2551, 2568, 2602, 2619, 2636, 2653, 2670, 2687, 2704, 2721, 2738, 2755, 2772, 2789, 2806, 2823, 2840, 2859, 2876, 2893, 2910, and 2927 are placed in an extracellular transcription system and are demonstrated to have activity in transcription or modulating transcription.

Example 2: Transcriptional Control Using Catabolite-Responsive Elements from *Alicyclobacillus acidocaldarius*

Provided in SEQ ID NOS: 2857, 2858, 2860, 2877, 2894, 2911, and 2928 are nucleotide sequences isolated from *Alicyclobacillus acidocaldarius*. The nucleotide sequences of SEQ ID NOS: 2857, 2858, 2860, 2877, 2894, 2911, and 2928 are placed into expression vectors and functionally linked to a reporter gene using techniques standard in the art. The vectors are then provided to cells such as bacteria cells or eukaryotic cells such as Sf9 cells or CHO cells. In conjunction with the normal machinery in present in the cells, the vectors comprising SEQ ID NOS: 2857, 2858, 2860, 2877, 2894, 2911, and 2928 attempt to produce the protein coded for by the reporter gene in an environment designed to assay the function of a catabolite-responsive element. The cells are then assayed for the presence or absence and/or level of the reporter gene product. SEQ ID NOS: 2857, 2858, 2860, 2877, 2894, 2911, and 2928 are then each demonstrated to have activity as a catabolite-responsive element.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and that fall within the limits of the appended claims and their legal equivalents.

BIBLIOGRAPHIC REFERENCES

Barany, F., 1991, *PNAS USA,* 88:189-193.
Buckholz, R. G., 1993, Yeast systems for the expression of heterologous gene products, *Curr. Op. Biotechnology* 4:538-542.
Burg, J. L. et al., 1996, *Mol. And Cell. Probes* 10:257-271.
Chu, B. C. F. et al., 1986, *NAR* 14:5591-5603.
Duck, P. et al., 1990, *Biotechniques* 9:142-147.
Edwards, C. P., and Aruffo, A., 1993, Current applications of COS cell based transient expression systems, *Curr. Op. Biotechnology* 4:558-563.
Guateli, J. C. et al., 1990, *PNAS USA* 87:1874-1878.
Houben-Weyl, 1974, in *Methoden der Organischen Chemie,* E. Wunsch ed., Volume 15-I and 15-II, Thieme, Stuttgart.
Innis, M. A. et al., 1990, in *PCR Protocols,* A Guide to Methods and Applications, San Diego, Academic Press.
Kievitis, T. et al., 1991, *J. Virol. Methods* 35:273-286.
Kohler, G. et al., 1975, *Nature* 256(5517):495-497.
Kwoh, D. Y. et al., 1989, *PNAS USA* 86:1173-1177.
Luckow, V. A., 1993, *Baculovirus* systems for the expression of human gene products, *Curr. Op. Biotechnology* 4:564-572.
Matthews, J. A. et al., 1988, *Anal. Biochem.* 169:1-25.
Merrifield, R. D., 1966, *J. Am. Chem. Soc.* 88(21):5051-5052.
Miele, E. A. et al., 1983, *J. Mol. Biol.* 171:281-295.
Olins, P. O., and Lee, S. C., 1993, Recent advances in heterologous gene expression in *E. coli, Curr. Op. Biotechnology* 4:520-525.
Rolfs, A. et al., 1991, In *PCR Topics*. Usage of Polymerase Chain Reaction in Genetic and Infectious Disease, Berlin: Springer-Verlag.
Sambrook, J. et al., 1989, In *Molecular Cloning: A Laboratory Manual,* Cold Spring Harbor, N.Y.: Cold Spring Harbor Laboratory Press.
Sanchez-Pescador, R., 1988, *J. Clin. Microbiol.* 26(10):1934-1938.
Segev D., 1992, in "Non-radioactive Labeling and Detection of Biomolecules," Kessler C. Berlin: Springer-Verlag, New York: 197-205.
Urdea, M. S., 1988, *Nucleic Acids Research* 11:4937-4957.
Walker, G. T. et al., 1992, *NAR* 20:1691-1696.
Walker, G. T. et al., 1992, *PNAS USA* 89:392-396.
White, B. A. et al., 1997, *Methods in Molecular Biology,* 67, Humana Press, Totowa, N.J.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09957510B2). An electronic copy of the "Sequence Listing" will also be available from the USPTO upon request and payment of the fee set forth in 37 CFR 1.19(b)(3).

What is claimed is:

1. An expression vector comprising a nucleic acid encoding a polypeptide having at least 90% sequence identity to SEQ ID NO: 1514 and wherein the polypeptide is a ribose operon repressor.

2. The expression vector of claim 1, wherein the polypeptide is a central glycolytic genes regulator at a temperature at or above 50 degrees Celsius.

3. The expression vector isolated of claim 1, wherein the polypeptide has 100% identity to SEQ ID NO: 1514.

4. The expression vector isolated of claim 1, wherein the nucleic acid has at least 90% identity to SEQ ID NO: 1515.

5. The expression vector isolated of claim 1, wherein the nucleic acid has 100% identity to SEQ ID NO: 1515.

6. A cell comprising the expression vector of claim 1.

7. A method of modulating transcription or transcriptional control at temperatures at or above 25 degrees Celsius, the method comprising providing to a transcriptional system the expression vector of claim 1.

8. The method according to claim 7, wherein providing to a transcriptional system the expression vector of claim 1 occurs at a temperature at or above 50 degrees Celsius.

* * * * *

UNITED STATES PATENT AND TRADEMARK OFFICE
CERTIFICATE OF CORRECTION

PATENT NO. : 9,957,510 B2  
APPLICATION NO. : 15/347936  
DATED : May 1, 2018  
INVENTOR(S) : Brady D. Lee et al.

It is certified that error appears in the above-identified patent and that said Letters Patent is hereby corrected as shown below:

In the Specification  
Column 14, Line 49, change "ref|ZP_00050136.21," to --ref|ZP_00050136.2|,--  
Column 19, Line 60, change "ref YP_149334.1|," to --ref|YP_149334.1|,--  
Column 20, Line 36, change "ref YP_001489923.1|," to --ref|YP_001489923.1|,--

Signed and Sealed this  
Twenty-sixth Day of June, 2018

Andrei Iancu  
*Director of the United States Patent and Trademark Office*